United States Patent
Yoshimoto et al.

(10) Patent No.: US 11,732,307 B2
(45) Date of Patent: Aug. 22, 2023

(54) KIT, DEVICE, AND METHOD FOR DETECTING BLADDER CANCER

(71) Applicants: TORAY INDUSTRIES, INC., Tokyo (JP); NATIONAL CANCER CENTER, Tokyo (JP)

(72) Inventors: Makiko Yoshimoto, Kamakura (JP); Hiroko Sudo, Kamakura (JP); Satoko Kozono, Kamakura (JP); Junpei Kawauchi, Kamakura (JP); Takahiro Ochiya, Tokyo (JP); Hiroyuki Fujimoto, Tokyo (JP); Wataru Usuba, Tokyo (JP); Juntaro Matsuzaki, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 192 days.

(21) Appl. No.: 17/050,134

(22) PCT Filed: Apr. 25, 2019

(86) PCT No.: PCT/JP2019/017536
§ 371 (c)(1),
(2) Date: Oct. 23, 2020

(87) PCT Pub. No.: WO2019/208671
PCT Pub. Date: Oct. 31, 2019

(65) Prior Publication Data
US 2022/0275449 A1    Sep. 1, 2022

(30) Foreign Application Priority Data
Apr. 25, 2018    (JP) .................................. 2018-084416

(51) Int. Cl.
*C12Q 1/6886*    (2018.01)

(52) U.S. Cl.
CPC ..... *C12Q 1/6886* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2013/0084241 A1 | 4/2013 | Adam et al. |
| 2014/0200261 A1 | 7/2014 | Hoge et al. |
| 2014/0206852 A1 | 7/2014 | Hoge et al. |
| 2017/0130273 A1 | 5/2017 | Sudo et al. |
| 2017/0130275 A1 | 5/2017 | Kondou et al. |
| 2017/0130278 A1 | 5/2017 | Sudo et al. |
| 2017/0166975 A1 | 6/2017 | Kondou et al. |

FOREIGN PATENT DOCUMENTS

| | | |
|---|---|---|
| CA | 3 018 048 A1 | 10/2017 |
| EP | 3438284 A1 | 2/2019 |
| JP | 2013-67 A | 1/2013 |
| JP | 2017-38566 A | 2/2017 |
| WO | WO 2005/118806 A2 | 12/2005 |
| WO | WO 2014/152622 A1 | 9/2014 |
| WO | WO 2015/020122 A1 | 2/2015 |
| WO | WO 2015/190591 A1 | 12/2015 |
| WO | WO 2015/194615 A1 | 12/2015 |
| WO | WO 2017/171048 A1 | 10/2017 |

OTHER PUBLICATIONS

Dyrkjot (Cancer Research 2009, 69 (11) Jun. 1, 2009).*
Usuba (Cancer Science 2019, 110:408-419 pub online Nov. 1, 2018).*
Ghorai (Frontiers in Genetics Apr. 2014 vol. 5 article 100).*
Armstrong (Molecular Cancer 2015 14:194).*
De Long et al., "A non-invasive miRNA based assay to detect bladder cancer in cell-free urine". Am J Transl Res, 2015, vol. 7, No. 11, p. 2500-2509.
Du et al., "Cell-free microRNA expression signatures in urine serve as novel noninvasive biomarkers for diagnosis and recurrence prediction of bladder cancer", Oncotarget, 2017, vol. 8, No. 25, p. 40832-40842.
International Search Report, issued in PCT/JP2019/017536, PCT/ISA/210, dated Jul. 23, 2019.
Van Rhijn et al. "Urine Markers for Bladder Cancer Surveillance: A Systematic Review", European Urology, 2005, vol. 47, p. 736-748.
Written Opinion of the International Searching Authority, issued in PCT/JP2019/017536, PCT/ISA/237, dated Jul. 23, 2019.
Lian et al., "Serum microRNAs as predictors of risk for non-muscle invasive bladder cancer," Oncotarget, vol. 9, No. 19, 2018, pp. 14895-14908, 14 pages total.
Partial Supplementary European Search Report far European Application No. 19792965.6, dated Apr. 20, 2022.
Song et al., "Expression Profile Analysis of microRNAs in Prostate Cancer by Next-Generation Sequencing," The Prostate, vol. 75, 2015, pp. 500-516, 17 pages total.
Japanese Office Action for corresponding Japanese Application No. 2020-515545, dated Apr. 25, 2023.

* cited by examiner

*Primary Examiner* — Amanda Haney
(74) *Attorney, Agent, or Firm* — Birch, Stewart, Kolasch & Birch, LLP

(57) ABSTRACT

An embodiment according to the present invention provides a kit or device for detection of bladder cancer, and a method for detecting bladder cancer. An embodiment according to the present invention relates to: a kit or device for detection of bladder cancer, including a nucleic acid(s) capable of specifically binding to an miRNA(s) or a complementary strand(s) thereof in a sample from a subject; and a method for detecting bladder cancer, including measuring the miRNA(s) in vitro.

9 Claims, 28 Drawing Sheets
Specification includes a Sequence Listing.

Fig. 2
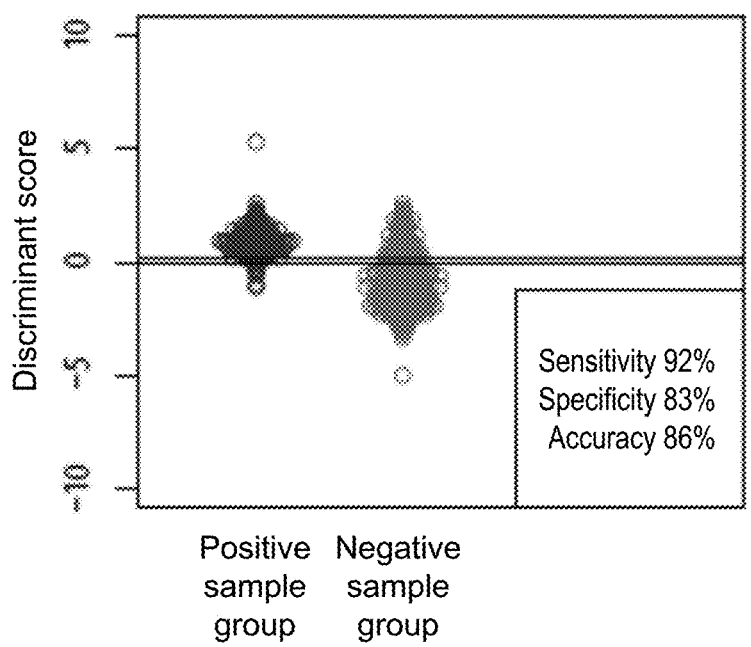
A
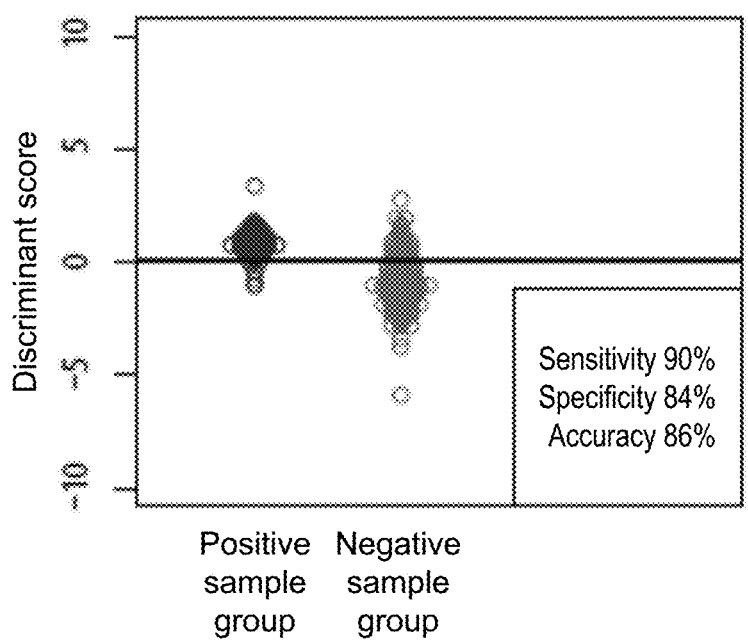
B

Fig. 4A-B
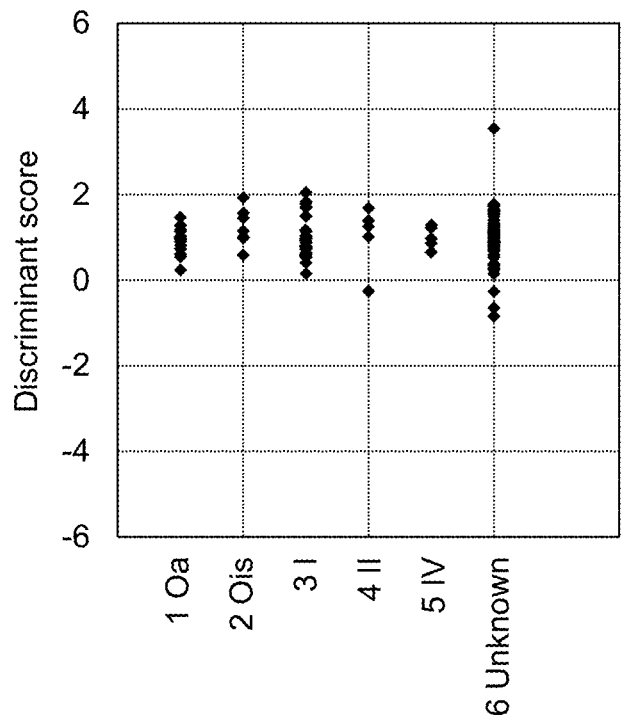
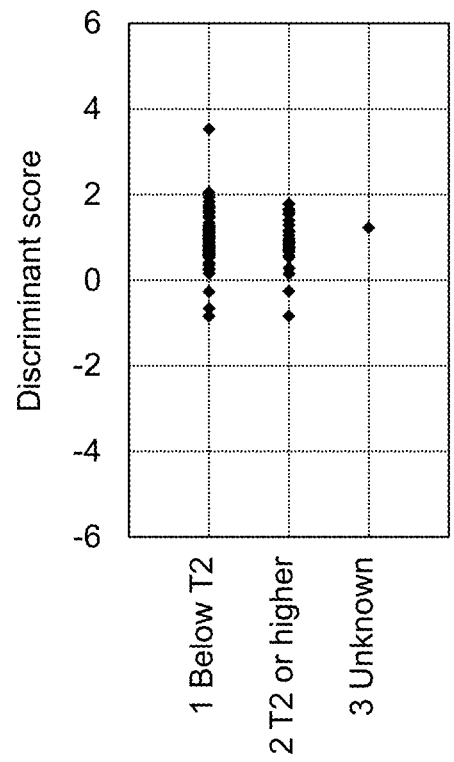

Fig. 4C-D
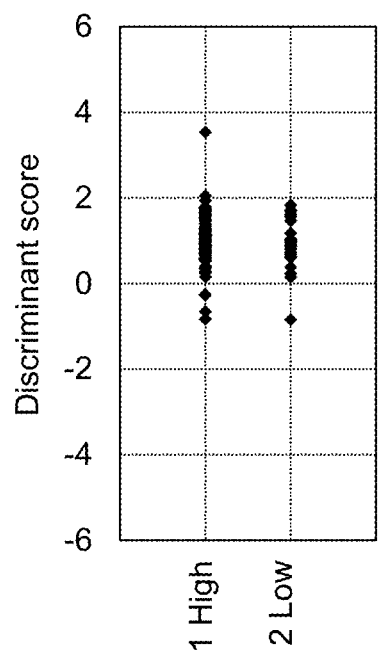
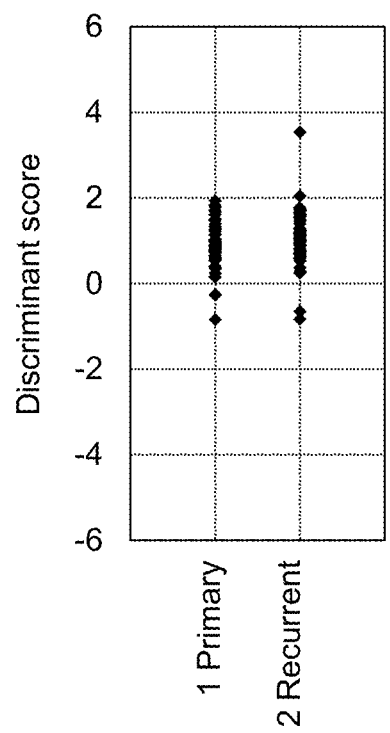

Fig. 5
A
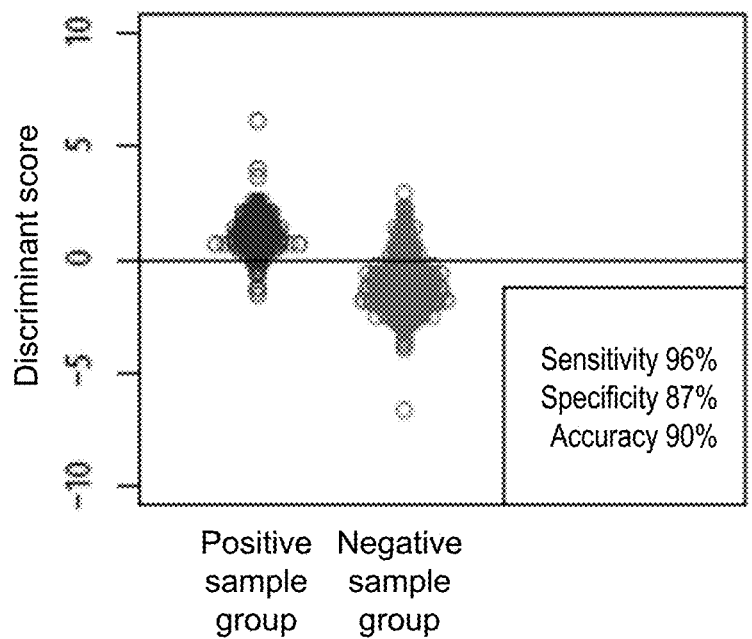
B
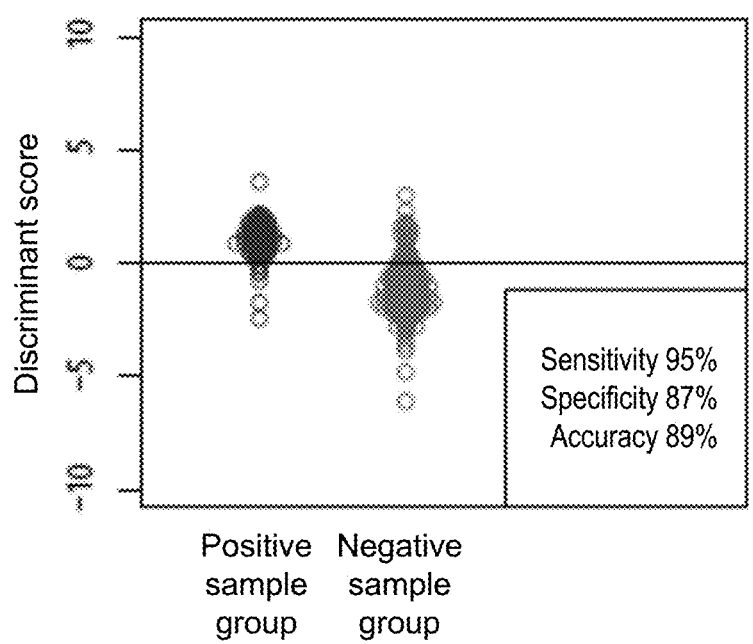

Fig. 7A-B
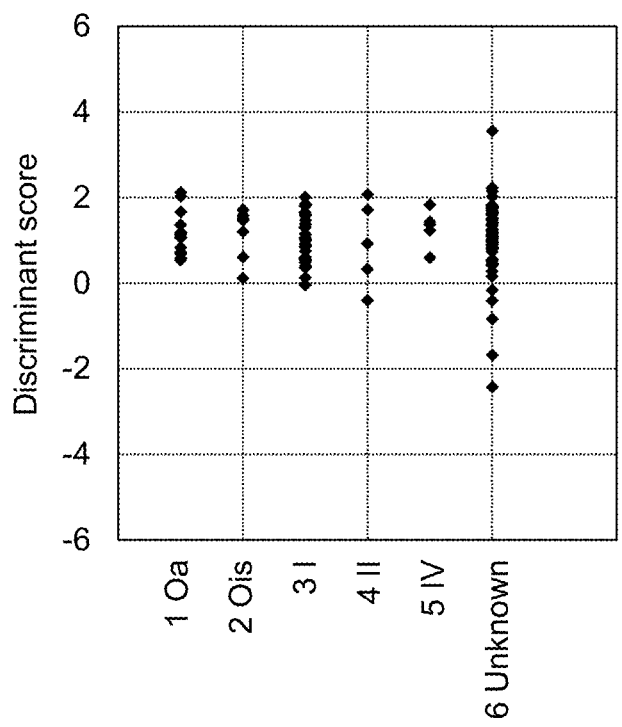
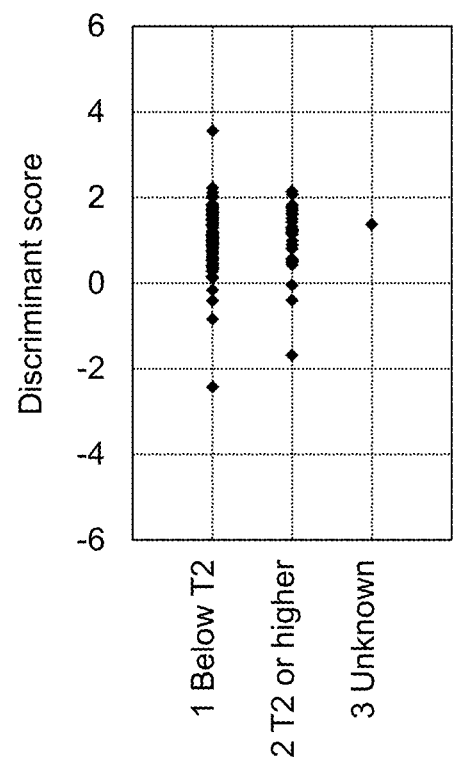

Fig. 7C-D
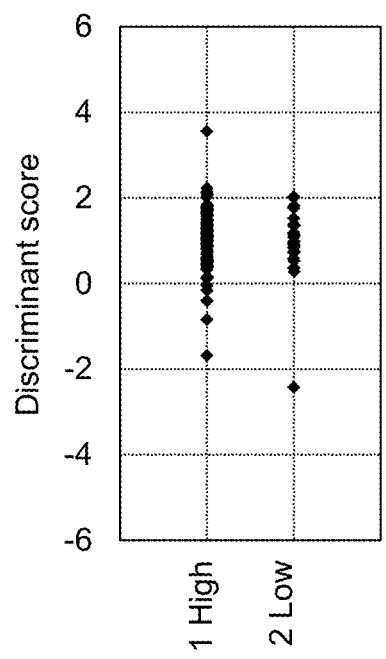
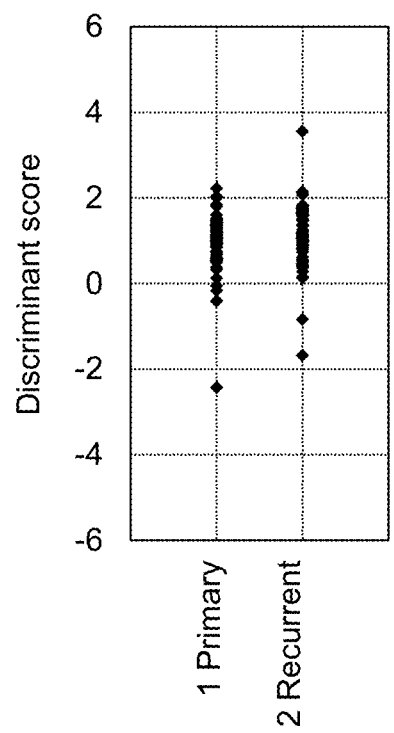

Fig. 8
A
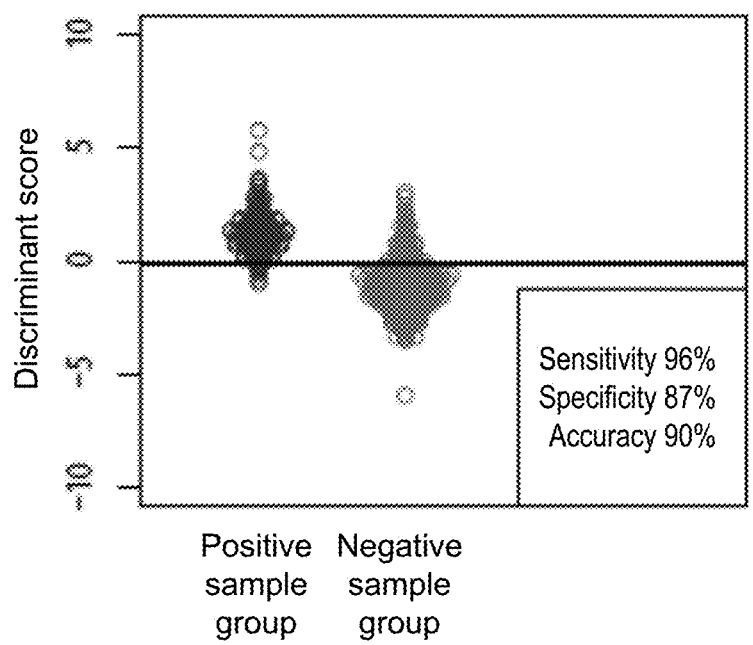
B
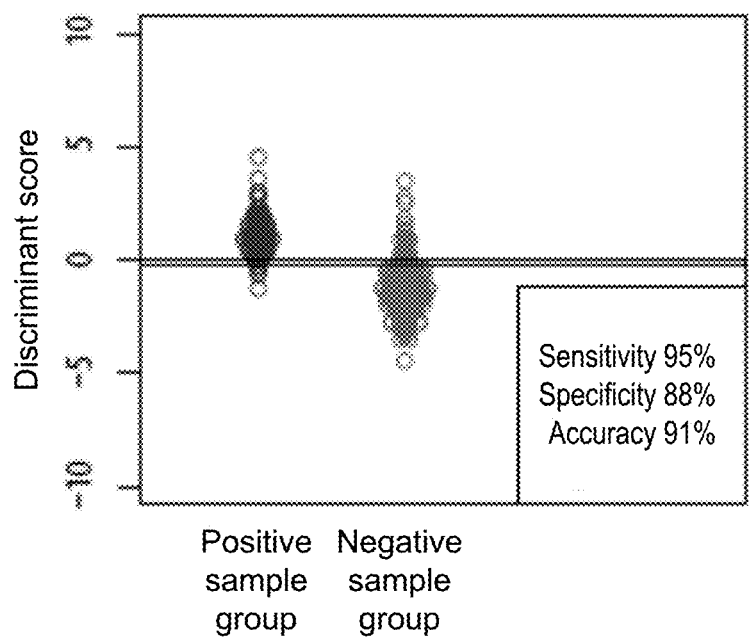

Fig. 10A-B
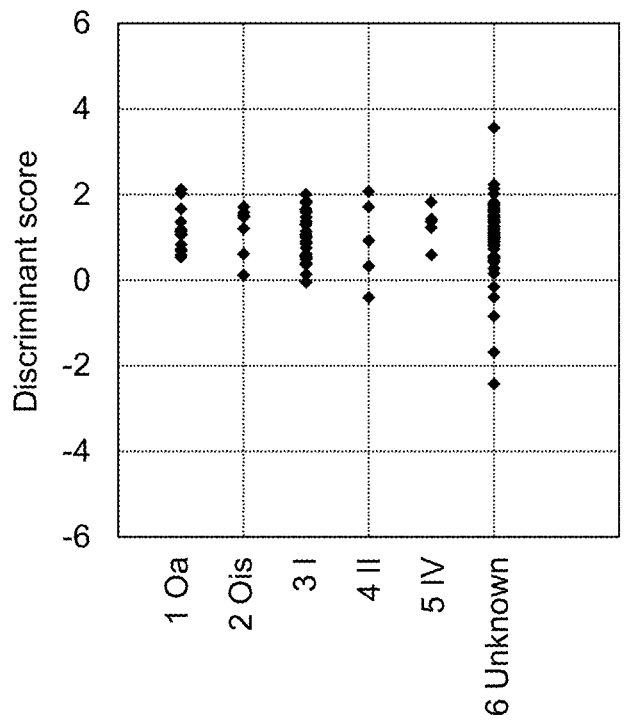
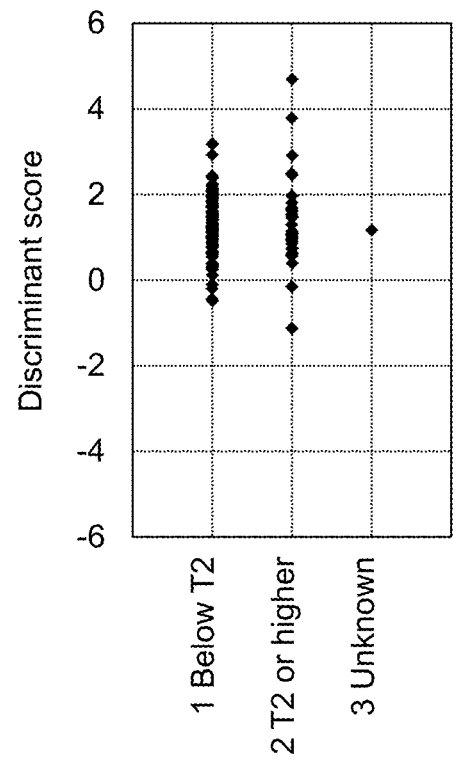

Fig. 10C-D
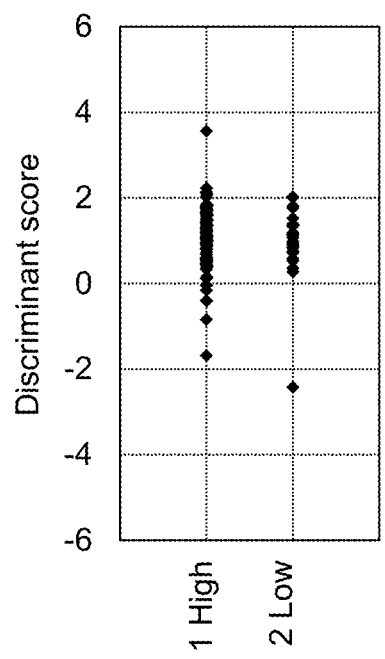
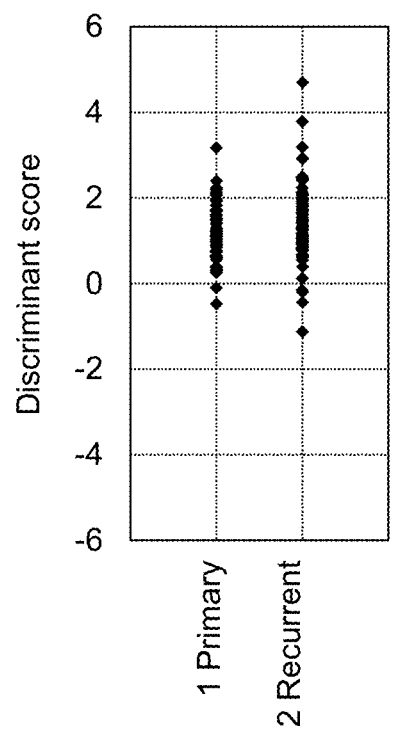

Fig. 11
A
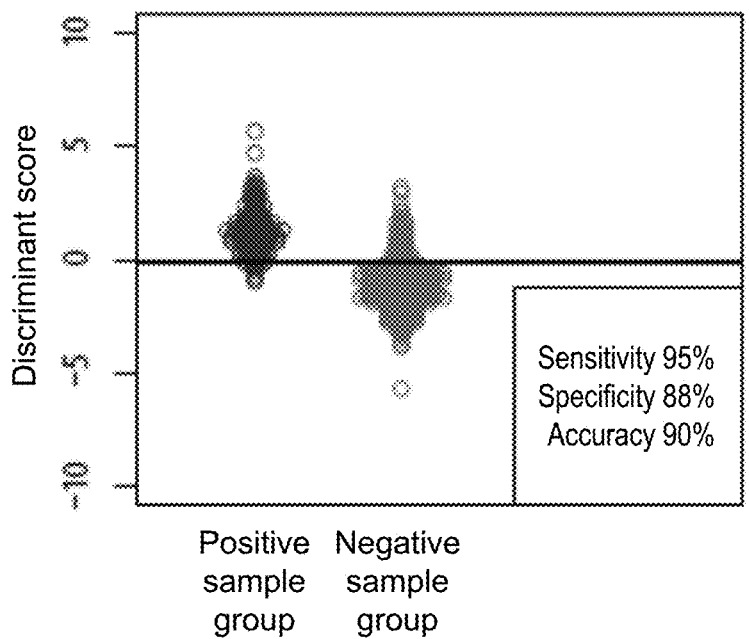
B
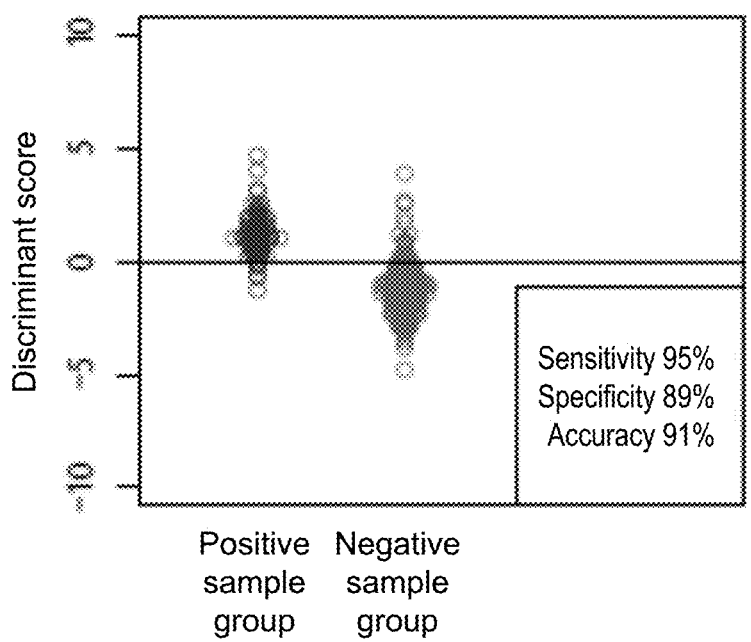

Fig. 13A-B
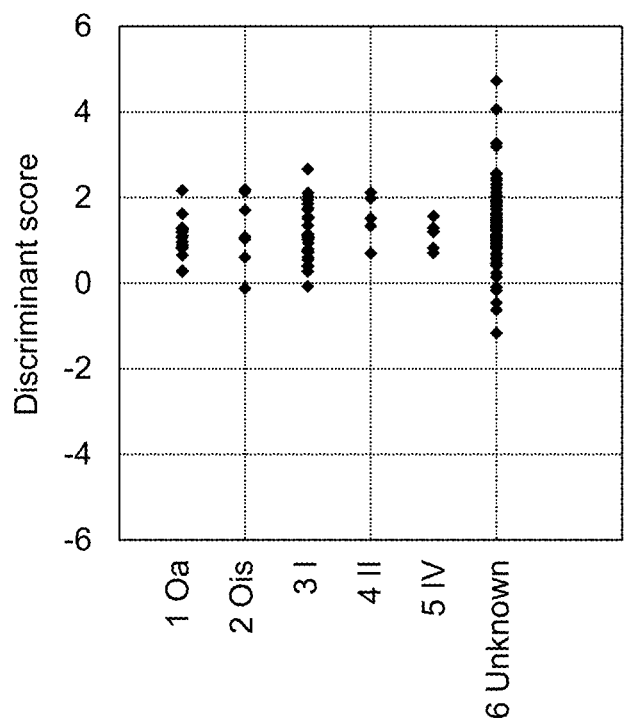
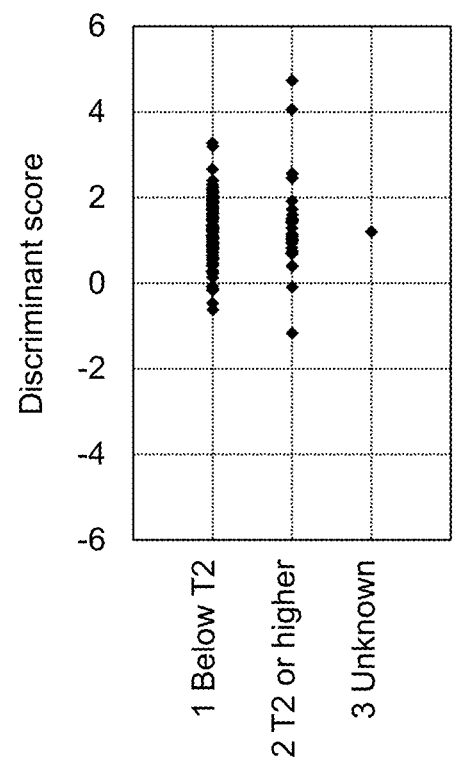

Fig. 13C-D
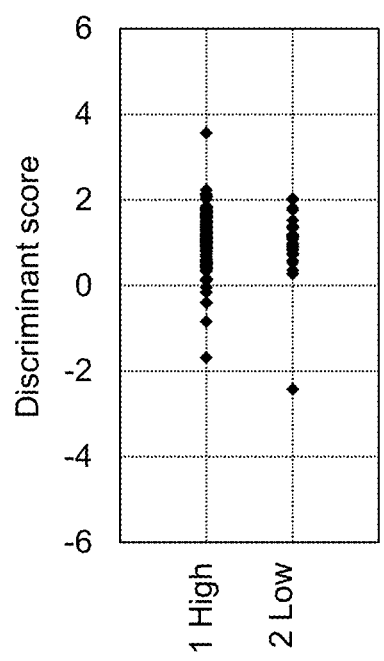
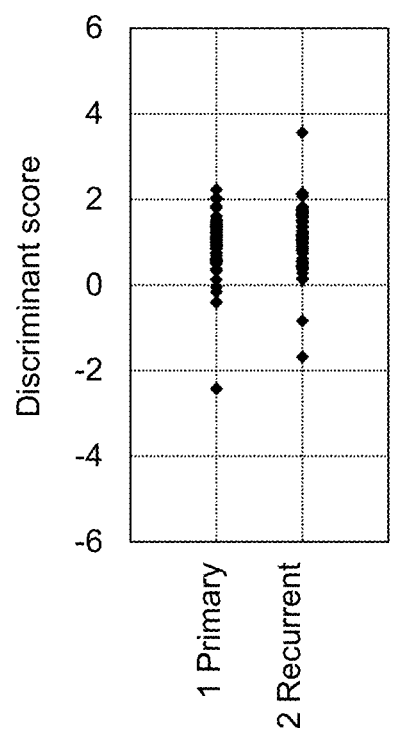

Fig. 15A-B
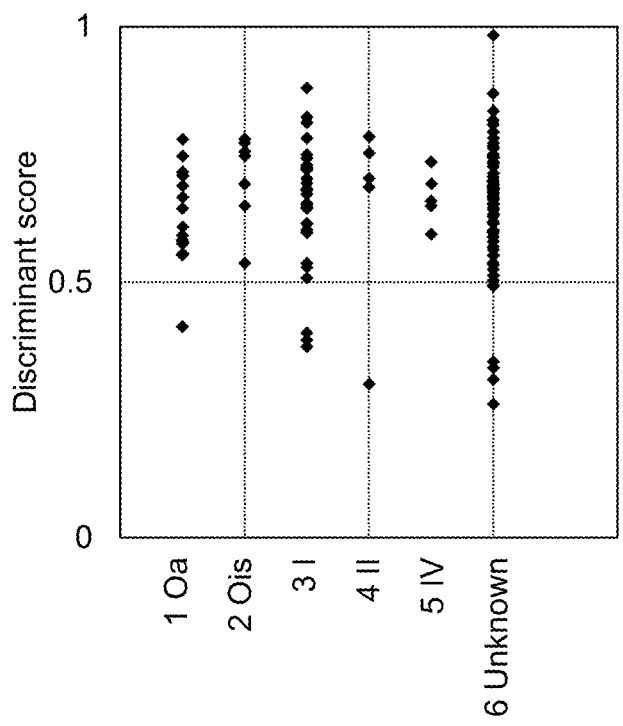
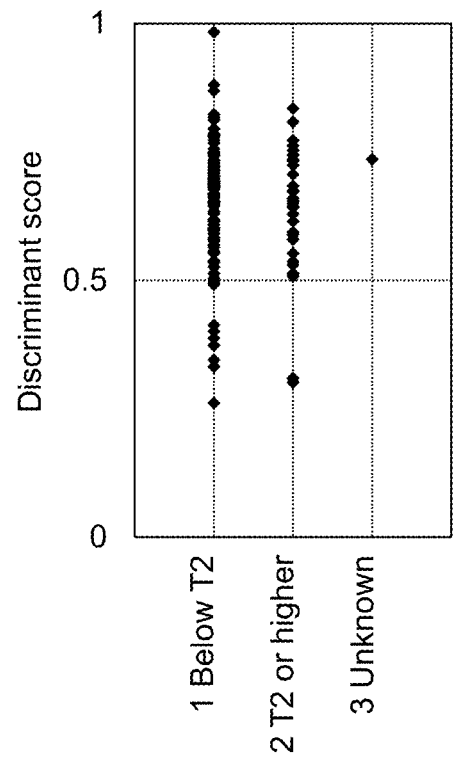

Fig. 15C-D
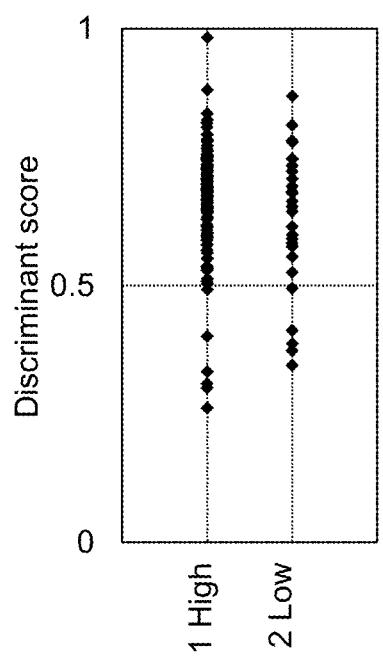
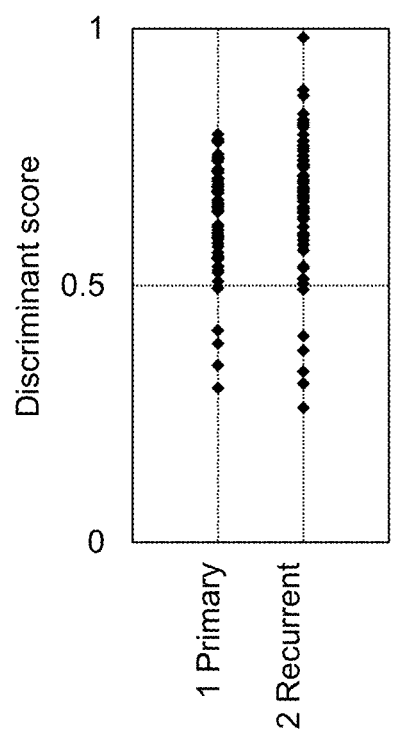

Fig. 17A-B
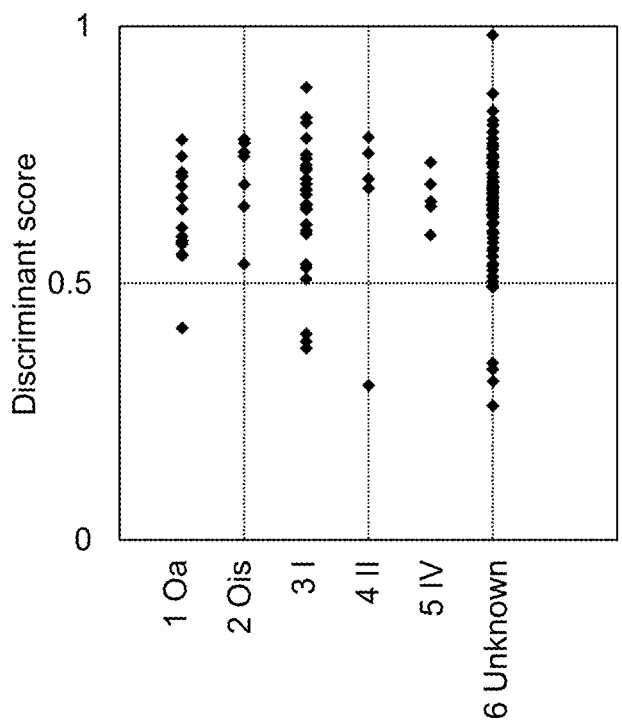
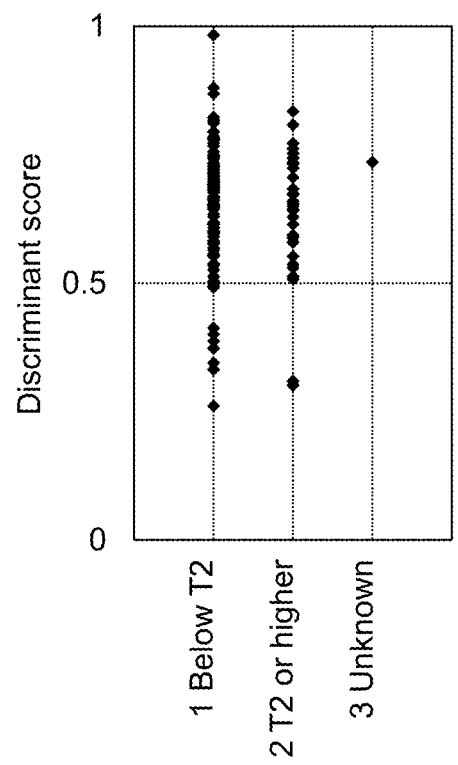

Fig. 17C-D
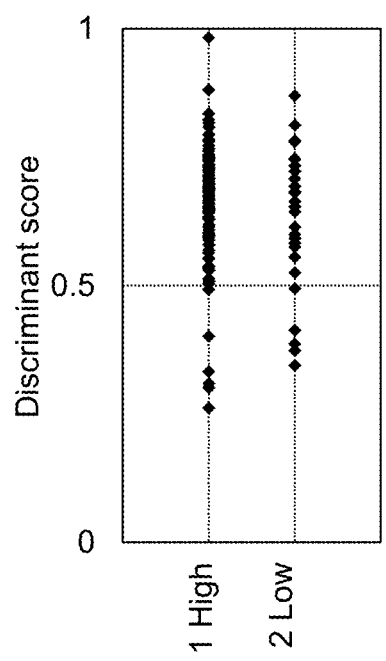
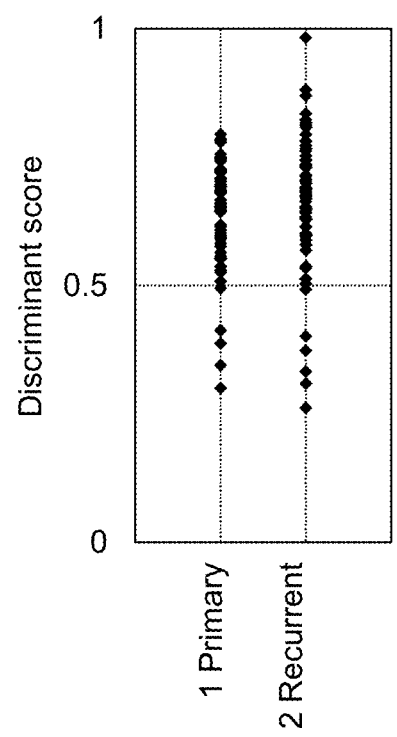

Fig. 19A-B
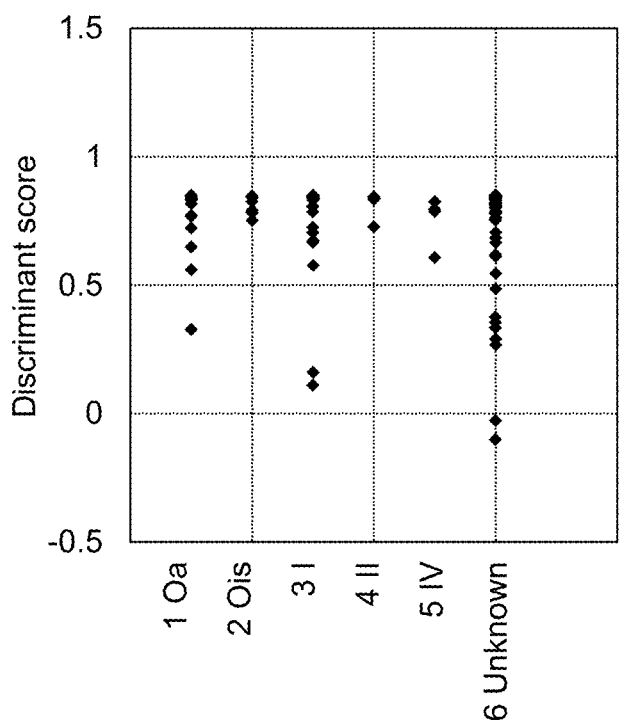
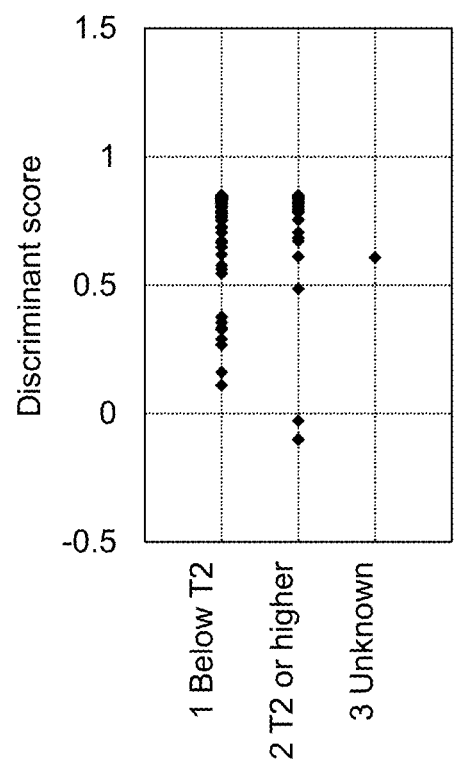

Fig. 19C-D
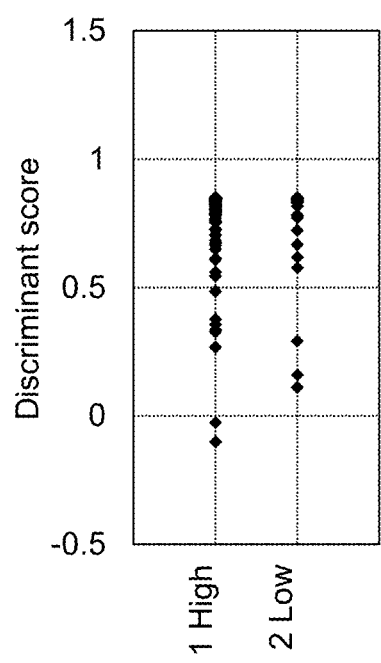
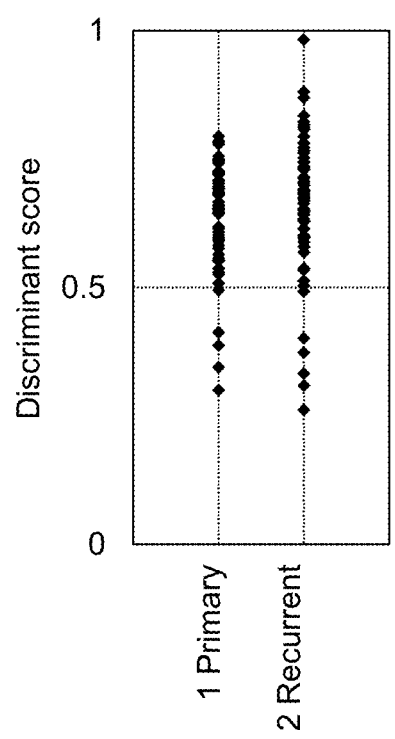

KIT, DEVICE, AND METHOD FOR DETECTING BLADDER CANCER

TECHNICAL FIELD

The present invention relates to a kit or device for detection of bladder cancer, comprising a nucleic acid capable of specifically binding to a specific miRNA or a complementary strand thereof, which is used for examining presence or absence of bladder cancer in a subject, and a method for detecting bladder cancer, comprising measuring the expression level of the miRNA.

BACKGROUND ART

A bladder is an organ in a pelvis and has a role of a kind of a bag for temporarily storing urine produced by a kidney after passing through a renal pelvis and a ureter. When a bladder is stretched due to urine that has accumulated, there is a function of feeling it as a desire to urinate and contracting the muscles to urinate. Inner surface of a bladder is covered with transitional epithelial cells and is highly elastic. It is known that bladder cancer is caused by canceration of the transitional epithelial cells, and the transitional epithelial cancer histologically accounts for 90% of all bladder cancers.

The death rate due to cancer among Japanese in 2008 was 547.7 out of 100,000, and the proportion of bladder cancer among causes of death is increasing year by year due to aging and influx of Western culture. Urothelial cancer including bladder cancer is a urological tumor with the second highest frequency after prostate cancer, and the number of patients in Japan was about 16,000 in 2002 mainly in the elderly. The morbidity is about four times higher in men than in women. It is known that smoking is greatly involved in the development of bladder cancer, and occupational exposure to aromatic amines is another established risk factor. According to the T factor in the TNM classification used to evaluate the degree of invasion, that is, the stage, bladder cancer is classified into three types, in order of increasing invasion: carcinoma in situ (Tis), superficial bladder cancer (Ta and T1), and invasive bladder cancer (T2 or higher). It is known that carcinoma in situ occurs in combination with superficial cancer and invasive cancer, or carcinoma in situ occurs alone. It is also known that carcinoma in situ may be overlooked even in the case of conducting definitive endoscopy since it is scattered in the mucous membrane of the bladder and spreads like crawling. Superficial bladder cancer is a cancer invasion of which remains on the surface of the bladder, that is, the superficial mucosa and the submucosa below and which rarely metastasizes to other organs. However, it is known that superficial bladder cancer tends to recur many times in the bladder, and follow-up examinations are highly important. It is known that invasive bladder cancer develops so as to extend to the muscles of the bladder and even outside the bladder like a root and tends to metastasize. Further, in the histological grade of bladder cancer shown by the High/Low grade, a High-grade bladder cancer is highly malignant and is likely to infiltrate and metastasize at an early stage, and therefore early detection is particularly highly important.

Treatment of bladder cancer is determined in consideration of degree of progression (Terms handling renal pelvis, ureter and bladder cancer, edited by The Japanese Urological Association, The Japanese Society of Pathology, and The Japan Radiological Society, published by KANEHARA & Co., LTD., 2011), metastasis, and general conditions. The standard method for treating bladder cancer is shown in Bladder Cancer Treatment Guidelines, edited by The Japanese Urological Association, 2015 edition, published by Igakutosho-shuppan Ltd. Currently, the most common treatments are surgical resection (transurethral resection of bladder tumor (TUR-BT), total cystectomy), radiation therapy, chemotherapy with anti-cancer agents, and intravesical BCG therapy. For invasive bladder cancer with a TNM classification of T2 or higher, total cystectomy is a standard treatment, and early detection is very important.

Further, the most reliable and common methods for detecting bladder cancer are currently cystoscopy and urine cytology. Cystoscopy is highly invasive, and urine cytology, which detects detached cancer cells microscopically, is a preferable method in view of invasion. However, it is reported that the specificity is about 94%, and the sensitivity is 35% (Non-Patent Literature 1).

Bladder cancer has a high recurrence rate and often recurs within two years. The recurrence rate after treatment is as high as 50 to 80%, and 10 to 25% thereof is detected as progressive invasive cancer into the muscular layer. Therefore, it is important to detect recurrence and treat it at an early stage to prolong patient survival.

Several urinary protein markers are now available as non-invasive clinical testing markers for bladder cancer. These marker tests have higher sensitivity than urine cytology. For example, in the NMP22 test for detecting a specific nuclear matrix protein NuMA, the sensitivity is 47 to 100%, and the specificity is 55 to 98% (Non-Patent Literature 1). Further, in BTAtrak test for detecting a specific complex of basal membrane fragments, the sensitivity is 60 to 83%, and the specificity is 60 to 79% (Non-Patent Literature 1).

Further, there have been reports of markers using gene expression as an index, such as miR-92a-2-5p, miR-150-3p, miR-1207-5p, miR-1202, miR-135a-3p, miR-1914-3p, miR-1469, miR-149-3p, and miR-663a shown in Patent Literature 1, miR-1254, miR-1246, and miR-92a-3p shown in Patent Literature 2, miR-191-5p and miR-940 shown in Non-Patent Literature 2, and miR-423-5p shown in Non-Patent Literature 3.

CITATION LIST

Patent Literature

Patent Literature 1: JP Patent Publication (Kokai) No. 2013-000067
Patent Literature 2: U.S. Patent Application Publication No. 2013/0084241

Non-Patent Literature

Non-Patent Literature 1: Bas W. G. van Rhijin et al., 2005, European Urology 47, pp. 736 to 748
Non-Patent Literature 2: Long J D et al., 2015, Am J Transl Res 7 (11), pp. 2500-2509
Non-Patent Literature 3: Du L et al., 2017, Oncotarget 8 (25), pp. 40832-40842

SUMMARY OF INVENTION

Problem to be Solved by Invention

Among widely used bladder cancer diagnosis methods, urine cytology has a low sensitivity of 35%. This is because there may be cases of low sensitivity depending on the type of sample, such as the case where it is particularly difficult to distinguish Low-grade samples in the High/Low classification of the histological grade, and there is still a problem that urine cytology is not a universal examination due to its high variability among the observers. Although it is said that the sensitivity of cystoendoscopy is as high as 90%, cystoendoscopy is actually a test that depends on the subjectivity of the operator. Differentiation from mucosal inflammation is often subtle, and if unknown, the cancer may be found as a result of having a short follow-up period and having a conclusion on the next cystoscopy, where there is a risk of overlooking. Further, since cystoendoscopy involves transurethral observation without anesthesia, it is painful for the patient. Particularly for men having a penis, the pain is significant, and there is also a problem of the burden of unnecessary tests. The above-mentioned indicators of existing proteins and gene expression have drawbacks such as poor specificity and/or sensitivity, and large variations in the measurement results depending on the timing of the test.

Accordingly, unnecessary additional examinations may be performed due to misclassification of non-bladder cancer patients as bladder cancer patients, or treatment opportunities may be lost by overlooking bladder cancer patients. Thus, a marker capable of determining bladder cancer correctly regardless of stage, degree of invasion, histological grade, or primary/recurrence with high accuracy has been desired. Further, Patent Literature 1 discloses a method for detecting bladder cancer from a urine sample, in which the accuracy was 86% for 36 patients in the validation group (among them, 27 patients had bladder cancer). However, the number of validation samples is insufficient, and a large amount of urine is necessary since the amount of nucleic acid in urine is very small. Therefore, the detection work is complicated and has not been put to practical use.

It is an object of the present invention to provide a disease diagnosis kit or device that is useful for non-invasive diagnosis and treatment of bladder cancer with a small amount of sample, and a method for determining (or detecting) bladder cancer.

Means for Solution to Problem

As a result of diligent studies in order to solve the above problems, the inventors have found genes available as bladder cancer detection markers from blood which can be collected minimally invasively, and that bladder cancer can be significantly detected using the genes, thereby accomplished the present invention.

SUMMARY OF INVENTION

That is, the present invention includes the following aspects.

(1) A kit for detection of bladder cancer, comprising a nucleic acid(s) capable of specifically binding to at least one polynucleotide selected from the following bladder cancer markers; miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-1282-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, or to a complementary strand of the polynucleotide.

(2) The kit according to (1), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

(3) The kit according to (1) or (2), wherein the kit further comprises a nucleic acid(s) capable of specifically binding to at least one polynucleotide selected from the following other bladder cancer markers: miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p and miR-940, or to a complementary strand of the polynucleotide.

(4) The kit according to (3), wherein the nucleic acid(s) is a polynucleotide(s) selected from the group consisting of the following polynucleotides (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (f) to (i).

(5) A device for detection of bladder cancer, comprising a nucleic acid(s) capable of specifically binding to at least one polynucleotide selected from the following bladder cancer markers: miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, or to a complementary strand of the polynucleotide.

(6) The device according to (5), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

(7) The device according to (5) or (6), wherein the device further comprises a nucleic acid(s) capable of specifically binding to at least one polynucleotide selected from the following other bladder cancer markers: miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940, or to a complementary strand of the polynucleotide.

(8) The device according to (7), wherein the nucleic acid(s) is a polynucleotide(s) selected from the group consisting of the following polynucleotides (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (f) to (i).

(9) The device according to any one of (5) to (8), wherein the device is a device for measurement by a hybridization technique.

(10) The device according to (9), wherein the hybridization technique is a nucleic acid array technique.

(11) A method for detecting bladder cancer, comprising: measuring an expression level(s) of at least one polynucleotide selected from the following bladder cancer markers: miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p in a sample from a subject; and evaluating in vitro whether or not the subject has bladder cancer using the measured expression level(s).

(12) The method according to (11), comprising: plugging the gene expression level(s) of the one or more polynucleotide(s) in the sample from the subject into a discriminant formula capable of discriminating the presence or absence of a bladder cancer distinctively, wherein the discriminant formula is created by using gene expression levels in samples from subjects known to have bladder cancer and gene expression levels in samples from subjects having no bladder cancer as training samples; and thereby evaluating whether or not the subject has a bladder cancer.

(13) The method according to (11) or (12), comprising: measuring an expression level(s) of the polynucleotide(s) by using a nucleic acid(s) capable of specifically binding to the polynucleotide(s) or to a complementary strand(s) of the polynucleotide(s), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

(14) The method according to any one of (11) to (13), further comprising: measuring an expression level(s) of at least one polynucleotide selected from the following other bladder cancer markers: miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

(15) The method according to (14), comprising: measuring an expression level(s) of the polynucleotide(s) by using a nucleic acid(s) capable of specifically binding to the polynucleotide(s) or to a complementary strand(s) of the polynucleotide(s), wherein the nucleic acid(s) is a polynucleotide(s) selected from the group consisting of the following polynucleotides (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (f) to (i).

(16) The method according to any one of (11) to (15), comprising: measuring an expression level(s) of target gene (s) in the sample from the subject by using the kit according to any one of (1) to (4) or the device according to any one of (5) to (10), wherein the kit or the device comprises a nucleic acid(s) capable of specifically binding to the polynucleotide(s) or to a complementary strand(s) of the polynucleotide(s).

(17) The method according to any one of (11) to (16), wherein the subject is a human.

(18) The method according to any one of (11) to (17), wherein the sample is blood, serum, or plasma.

DEFINITION OF TERMS

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA, and synthetic RNA. Here, the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, and more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" represented by a particular nucleotide sequence (or SEQ ID NO) but also "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 766 or a nucleotide sequence derived from the nucleotide sequence by the replacement of u with t. Regardless of whether or not there is a difference in functional region, the "gene" can comprise, for example, expression control regions, coding regions, exons, or introns. The "gene" may be contained in a cell or may exist alone after being released from a cell. Alternatively, the "gene" may be in a state enclosed in a vesicle referred to as an exosome.

The term "exosome" used herein is a vesicle that is encapsulated by the lipid bilayer and secreted from a cell. The exosome is derived from a multivesicular endosome and may incorporate biomaterials such as "genes" (e.g., RNA or DNA) or proteins when released to an extracellular environment. The exosome is known to be contained in a body fluid such as blood, serum, plasma, serum, or lymph.

The term "transcript" used herein refers to an RNA synthesized from the DNA sequence of a gene as a template. RNA polymerase binds to a site referred to as a promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a poly A sequence, including expression control regions, coding regions, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, integrated into a protein complex referred to as RISC, and involved in suppression of mRNA translation. The term "miRNA" used herein includes not only a "miRNA" represented by a particular nucleotide sequence (or SEQ ID NO) but also a "miRNA" comprising a precursor of the "miRNA" (pre-miRNA or pri-miRNA) and having biological functions equivalent to miRNAs encoded thereby, such as a "miRNA" encoding a congener (i.e., a homolog or an ortholog), a variant such as a genetic polymorph, and a derivative. Such a "miRNA" encoding a precursor, a congener, a variant, or a derivative can be specifically identified using "miRBase release 21" (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 766. The term "miRNA" used herein may be a gene product of a miR gene. Such a gene product includes a mature miRNA (e.g., a 15- to 25-nucleotide or 19- to 25-nucleotide non-coding RNA involved in suppression of mRNA translation as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

In this context, the "complementary polynucleotide" (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 766 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2 or 3 or more (e.g., 1 to several) nucleotides in a nucleotide sequence represented by a SEQ ID NO, a nucleotide sequence derived from the nucleotide sequence by the replacement of u with t, or a partial sequence thereof; a variant containing the deletion, substitution, addition, or insertion of one or two or more nucleotides in a nucleotide sequence of a precursor RNA (a premature miRNA) of the sequence of any of SEQ ID NOs: 1 to 243, a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, or approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by a well-known technique such as site-directed mutagenesis or mutagenesis using PCR.

The term "percent (%) identity" used herein can be determined with or without an introduced gap, using a protein or gene search system based on BLAST (https://blast.ncbi.nlm.nih.gov/Blast.cgi) or FASTA (http://www.genome.jp/tools/fasta/) (Zheng Zhang et al., 2000, J. Comput. Biol., Vol. 7, p. 203-214; Altschul, S. F et al., 1990, Journal of Molecular Biology, Vol. 215, p. 403-410; and Pearson, W. R et al., 1988, Proc. Natl. Acad. Sci. U.S.A., Vol. 85, p. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur molecule, etc.), PNA (peptide nucleic acid; Nielsen, P. E et al., 1991, Science, Vol. 254, p. 1497-500), and LNA (locked nucleic acid; Obika, S et al., 1998, Tetrahedron Lett., Vol. 39, p. 5401-5404).

As used herein, the "nucleic acid" capable of specifically binding to a polynucleotide selected from the bladder cancer marker miRNAs described above or to a complementary strand of the polynucleotide is a synthesized or prepared nucleic acid and, for example, includes a "nucleic acid probe" or a "primer", and is utilized directly or indirectly for detecting the presence or absence of bladder cancer in a subject, for diagnosing the presence or absence or the severity of bladder cancer, the presence or absence or the degree of amelioration of bladder cancer, or the therapeutic sensitivity of bladder cancer, or for screening for a candidate substance useful in the prevention, amelioration, or treatment of bladder cancer. The "nucleic acid" includes a nucleotide, an oligonucleotide, and a polynucleotide capable of specifically recognizing and binding to a transcript represented by any of SEQ ID NOs: 1 to 766 or a synthetic cDNA nucleic acid thereof, or a complementary strand thereto in vivo, particularly, in a sample such as a body fluid (e.g., blood or urine), in relation to the development of bladder cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosis- or evaluation-support on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. Meanwhile, the "healthy subject" also means such a mammal, which is an animal without cancer to be detected. The healthy subject is preferably a human.

The term "bladder cancer" used herein is a malignant tumor developed in the bladder, and the term encompasses urothelial carcinoma of the renal pelvis and the urinary tract.

The term "P" or "P value" used herein refers to a probability at which a more extreme statistic than that actually calculated from data under null hypothesis is observed in a statistical test. Thus, a smaller "P" or "P value" is regarded as being a more significant difference between subjects to be compared.

The term "sensitivity" used herein means a value of (the number of true positives)/(the number of true positives+the number of false negatives). High sensitivity allows bladder cancer to be detected early, which leads to complete resection of cancer regions or a lowered recurrence rate.

The term "specificity" used herein means a value of (the number of true negatives)/(the number of true negatives+the number of false positives). High specificity prevents needless extra examination for healthy subjects misjudged as being bladder cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subjected to determination, detection, or diagnosis refers to a tissue and a biological material in which the expression of the gene of the present invention varies as bladder cancer develops, as bladder cancer progresses, or as therapeutic effects on bladder cancer are exerted. Specifically, the sample refers to bladder tissue, renal pelvis, urinary tract, lymph node, organs in the vicinity thereof, organs suspected of metastasis, skin, a body fluid such as blood, urine, saliva, sweat, and tissue exudate, serum or plasma prepared from blood, and others such as feces, hair, or the like. The "sample" further refers to a biological sample extracted therefrom, specifically, a gene such as RNA or miRNA.

The term "hsa-miR-6087 gene" or "hsa-miR-6087" used herein includes the hsa-miR-6087 gene (miRBase Accession No. MIMAT0023712) shown in SEQ ID NO: 1, a homolog or an ortholog of a different organism species, and the like. The gene can be obtained by a method described in Yoo J K et al., 2012, Stem Cells Dev., Vol. 21, pp. 2049-2057. Also, "hsa-mir-6087" (miRBase Accession No. MI0020364; SEQ ID NO: 244) having a hairpin-like structure is known as a precursor of "hsa-miR-6087."

The term "hsa-miR-1185-1-3p gene" or "hsa-miR-1185-1-3p" used herein includes the hsa-miR-1185-1-3p gene (miRBase Accession No. MIMAT0022838) shown in SEQ ID NO: 2, a homolog or an ortholog of a different organism species, and the like. The gene can be obtained by a method described in Berezikov E et al., 2006, Genome Res., Vol. 16, pp. 1289-1298. Also, "hsa-mir-1185-1" (miRBase Accession No. MI0003844; SEQ ID NO: 245) having a hairpin-like structure is known as a precursor of "hsa-miR-1185-1-3p."

The term "hsa-miR-1185-2-3p gene" or "hsa-miR-1185-2-3p" used herein includes the hsa-miR-1185-2-3p gene (miRBase Accession No. MIMAT0022713) shown in SEQ ID NO: 3, a homolog or an ortholog of a different organism species, and the like. The gene can be obtained by a method described in Berezikov E et al., 2006, Genome Res., Vol. 16, pp. 1289-1298. Also, "hsa-mir-1185-2" (miRBase Accession No. MI0003821; SEQ ID NO: 246) having a hairpin-like structure is known as a precursor of "hsa-miR-1185-2-3p."

The term "hsa-miR-1193 gene" or "hsa-miR-1193" used herein includes the hsa-miR-1193 gene (miRBase Accession No. MIMAT0015049) shown in SEQ ID NO: 4, a homolog or an ortholog of a different organism species, and the like. The gene can be obtained by a method described in Stark M S et al., 2010, PLoS One, Vol. 5, e9685. Also, "hsa-mir-1193" (miRBase Accession No. MI0014205; SEQ ID NO: 247) having a hairpin-like structure is known as a precursor of "hsa-miR-1193."

The term "hsa-miR-1199-5p gene" or "hsa-miR-1199-5p" used herein includes the hsa-miR-1199-5p gene (miRBase Accession No. MIMAT0031119) shown in SEQ ID NO: 5, a homolog or an ortholog of a different organism species, and the like. The gene can be obtained by a method described in Salvi A et al., 2013, Int. J. Oncol., Vol. 42, pp. 391-402. Also, "hsa-mir-1199" (miRBase Accession No. MI0020340; SEQ ID NO: 248) having a hairpin-like structure is known as a precursor of "hsa-miR-1199-5p."

The term "hsa-miR-1225-5p gene" or "hsa-miR-1225-5p" used herein includes the hsa-miR-1225-5p gene (miRBase Accession No. MIMAT0005572) shown in SEQ ID NO: 6, a homolog or an ortholog of a different organism species, and the like. The gene can be obtained by a method described in Berezikov E et al., 2007, Mol. Cell, Vol. 28, pp. 328-336. Also, "hsa-mir-1225" (miRBase Accession No. MI0006311; SEQ ID NO: 249) having a hairpin-like structure is known as a precursor of "hsa-miR-1225-5p."

The term "hsa-miR-1227-5p gene" or "hsa-miR-1227-5p" used herein includes the hsa-miR-1227-5p gene (miRBase Accession No. MIMAT0022941) shown in SEQ ID NO: 7, a homolog or an ortholog of a different organism species, and the like. The gene can be obtained by a method described in Berezikov E et al., 2007, Mol. Cell, Vol. 28, pp. 328-336. Also, "hsa-mir-1227" (miRBase Accession No. MI0006316; SEQ ID NO: 250) having a hairpin-like structure is known as a precursor of "hsa-miR-1227-5p."

The term "hsa-miR-1228-3p gene" or "hsa-miR-1228-3p" used herein includes the hsa-miR-1228-3p gene (miRBase Accession No. MIMAT0005583) shown in SEQ ID NO: 8, a homolog or an ortholog of a different organism species, and the like. The gene can be obtained by a method described in Berezikov E et al., 2007, Mol. Cell, Vol. 28, pp. 328-336. Also, "hsa-mir-1228" (miRBase Accession No. MI0006318; SEQ ID NO: 251) having a hairpin-like structure is known as a precursor of "hsa-miR-1228-3p."

The term "hsa-miR-1228-5p gene" or "hsa-miR-1228-5p" used herein includes the hsa-miR-1228-5p gene (miRBase Accession No. MIMAT0005582) shown in SEQ ID NO: 9, a homolog or an ortholog of a different organism species, and the like. The gene can be obtained by a method described in Berezikov E et al., 2007, Mol. Cell, Vol. 28, pp. 328-336. Also, "hsa-mir-1228" (miRBase Accession No. MI0006318; SEQ ID NO: 252) having a hairpin-like structure is known as a precursor of "hsa-miR-1228-5p."

The term "hsa-miR-1237-5p gene" or "hsa-miR-1237-5p" used herein includes the hsa-miR-1237-5p gene (miRBase Accession No. MIMAT0022946) shown in SEQ ID NO: 10, a homolog or an ortholog of a different organism species, and the like. The gene can be obtained by a method described in Berezikov E et al., 2007, Mol. Cell, Vol. 28, pp. 328-336. Also, "hsa-mir-1237" (miRBase Accession No. MI0006327; SEQ ID NO: 253) having a hairpin-like structure is known as a precursor of "hsa-miR-1237-5p."

The term "hsa-miR-1238-5p gene" or "hsa-miR-1238-5p" used herein includes the hsa-miR-1238-5p gene (miRBase Accession No. MIMAT0022947) shown in SEQ ID NO: 11, a homolog or an ortholog of a different organism species, and the like. The gene can be obtained by a method described in Berezikov E et al., 2007, Mol. Cell, Vol. 28, pp. 328-336. Also, "hsa-mir-1238" (miRBase Accession No. MI0006328; SEQ ID NO: 254) having a hairpin-like structure is known as a precursor of "hsa-miR-1238-5p."

The term "hsa-miR-1247-3p gene" or "hsa-miR-1247-3p" used herein includes the hsa-miR-1247-3p gene (miRBase Accession No. MIMAT0022721) shown in SEQ ID NO: 12, a homolog or an ortholog of a different organism species, and the like. The gene can be obtained by a method described in Morin R D et al., 2008, Genome Res., Vol. 18, pp. 610-621. Also, "hsa-mir-1247" (miRBase Accession No. MI0006382; SEQ ID NO: 255) having a hairpin-like structure is known as a precursor of "hsa-miR-1247-3p."

The term "hsa-miR-1268a gene" or "hsa-miR-1268a" used herein includes the hsa-miR-1268a gene (miRBase Accession No. MIMAT0005922) shown in SEQ ID NO: 13, a homolog or an ortholog of a different organism species, and the like. The gene can be obtained by a method described in Morin R D et al., 2008, Genome Res., Vol. 18, pp. 610-621. Also, "hsa-mir-1268a" (miRBase Accession No. MI0006405; SEQ ID NO: 256) having a hairpin-like structure is known as a precursor of "hsa-miR-1268a."

The term "hsa-miR-1268b gene" or "hsa-miR-1268b" used herein includes the hsa-miR-1268b gene (miRBase Accession No. MIMAT0018925) shown in SEQ ID NO: 14, a homolog or an ortholog of a different organism species, and the like. The gene can be obtained by a method described in Jima D D et al., 2010, Blood, Vol. 116, e118-e127. Also, "hsa-mir-1268b" (miRBase Accession No. MI0016748; SEQ ID NO: 257) having a hairpin-like structure is known as a precursor of "hsa-miR-1268b."

The term "hsa-miR-1273g-3p gene" or "hsa-miR-1273g-3p" used herein includes the hsa-miR-1273g-3p gene (miRBase Accession No. MIMAT0022742) shown in SEQ ID NO: 15, a homolog or an ortholog of a different organism species, and the like. The gene can be obtained by a method described in Reshmi G et al., 2011, Genomics, Vol. 97, pp. 333-340. Also, "hsa-mir-1273g" (miRBase Accession No. MI0018003; SEQ ID NO: 258) having a hairpin-like structure is known as a precursor of "hsa-miR-1273g-3p."

The term "hsa-miR-128-2-5p gene" or "hsa-miR-128-2-5p" used herein includes the hsa-miR-128-2-5p gene (miRBase Accession No. MIMAT0031095) shown in SEQ ID NO: 16, a homolog or an ortholog of a different organism species, and the like. The gene can be obtained by a method described in Lagos-Quintana M et al., 2002, Curr. Biol., Vol. 12, pp. 735-739. Also, "hsa-mir-128-2" (miRBase Accession No. MI0000727; SEQ ID NO: 259) having a hairpin-like structure is known as a precursor of "hsa-miR-128-2-5p."

The term "hsa-miR-1343-3p gene" or "hsa-miR-1343-3p" used herein includes the hsa-miR-1343-3p gene (miRBase Accession No. MIMAT0019776) shown in SEQ ID NO: 17, a homolog or an ortholog of a different organism species, and the like. The gene can be obtained by a method described in Persson H et al., 2011, Cancer Res., Vol. 71, pp. 78-86. Also, "hsa-mir-1343" (miRBase Accession No. MI0017320; SEQ ID NO: 260) having a hairpin-like structure is known as a precursor of "hsa-miR-1343-3p."

The term "hsa-miR-1343-5p gene" or "hsa-miR-1343-5p" used herein includes the hsa-miR-1343-5p gene (miRBase Accession No. MIMAT0027038) shown in SEQ ID NO: 18, a homolog or an ortholog of a different organism species, and the like. The gene can be obtained by a method described in Persson H et al., 2011, Cancer Res., Vol. 71, pp. 78-86. Also, "hsa-mir-1343" (miRBase Accession No. MI0017320; SEQ ID NO: 261) having a hairpin-like structure is known as a precursor of "hsa-miR-1343-5p."

The term "hsa-miR-1470 gene" or "hsa-miR-1470" used herein includes the hsa-miR-1470 gene (miRBase Accession No. MIMAT0007348) shown in SEQ ID NO: 19, a homolog or an ortholog of a different organism species, and the like. The gene can be obtained by a method described in Kawaji H et al., 2008, BMC Genomics, Vol. 9, p. 157. Also, "hsa-mir-1470" (miRBase Accession No. MI0007075; SEQ ID NO: 262) having a hairpin-like structure is known as a precursor of "hsa-miR-1470."

The term "hsa-miR-17-3p gene" or "hsa-miR-17-3p" used herein includes the hsa-miR-17-3p gene (miRBase Accession No. MIMAT0000071) shown in SEQ ID NO: 20, a homolog or an ortholog of a different organism species, and the like. The gene can be obtained by a method described in Lagos-Quintana M et al., 2001, Science, Vol. 294, pp. 853-858. Also, "hsa-mir-17" (miRBase Accession No. MI0000071; SEQ ID NO: 263) having a hairpin-like structure is known as a precursor of "hsa-miR-17-3p."

The term "hsa-miR-187-5p gene" or "hsa-miR-187-5p" used herein includes the hsa-miR-187-5p gene (miRBase Accession No. MIMAT0004561) shown in SEQ ID NO: 21, a homolog or an ortholog of a different organism species, and the like. The gene can be obtained by a method described in Lim LP et al., 2003, Science, Vol. 299, p. 1540. Also, "hsa-mir-187" (miRBase Accession No. MI0000274; SEQ ID NO: 264) having a hairpin-like structure is known as a precursor of "hsa-miR-187-5p."

The term "hsa-miR-1908-3p gene" or "hsa-miR-1908-3p" used herein includes the hsa-miR-1908-3p gene (miRBase Accession No. MIMAT0026916) shown in SEQ ID NO: 22, a homolog or an ortholog of a different organism species, and the like. The gene can be obtained by a method described in Bar M et al., 2008, Stem Cells, Vol. 26, pp. 2496-2505. Also, "hsa-mir-1908" (miRBase Accession No. MI0008329; SEQ ID NO: 265) having a hairpin-like structure is known as a precursor of "hsa-miR-1908-3p."

The term "hsa-miR-1908-5p gene" or "hsa-miR-1908-5p" used herein includes the hsa-miR-1908-5p gene (miRBase Accession No. MIMAT0007881) shown in SEQ ID NO: 23, a homolog or an ortholog of a different organism species, and the like. The gene can be obtained by a method described in Bar M et al., 2008, Stem Cells, Vol. 26, pp. 2496-2505. Also, "hsa-mir-1908" (miRBase Accession No. MI0008329; SEQ ID NO: 266) having a hairpin-like structure is known as a precursor of "hsa-miR-1908-5p."

The term "hsa-miR-1909-3p gene" or "hsa-miR-1909-3p" used herein includes the hsa-miR-1909-3p gene (miRBase Accession No. MIMAT0007883) shown in SEQ ID NO: 24, a homolog or an ortholog of a different organism species, and the like. The gene can be obtained by a method described in Bar M et al., 2008, Stem Cells, Vol. 26, pp. 2496-2505. Also, "hsa-mir-1909" (miRBase Accession No. MI0008330; SEQ ID NO: 267) having a hairpin-like structure is known as a precursor of "hsa-miR-1909-3p."

The term "hsa-miR-1915-3p gene" or "hsa-miR-1915-3p" used herein includes the hsa-miR-1915-3p gene (miRBase Accession No. MIMAT0007892) shown in SEQ ID NO: 25, a homolog or an ortholog of a different organism species, and the like. The gene can be obtained by a method described in Bar M et al., 2008, Stem Cells, Vol. 26, pp. 2496-2505. Also, "hsa-mir-1915" (miRBase Accession No. MI0008336; SEQ ID NO: 268) having a hairpin-like structure is known as a precursor of "hsa-miR-1915-3p."

The term "hsa-miR-210-5p gene" or "hsa-miR-210-5p" used herein includes the hsa-miR-210-5p gene (miRBase Accession No. MIMAT0026475) shown in SEQ ID NO: 26, a homolog or an ortholog of a different organism species, and the like. The gene can be obtained by a method described in Lim LP et al., 2003, Science, Vol. 299, p. 1540. Also, "hsa-mir-210" (miRBase Accession No. MI0000286;

SEQ ID NO: 269) having a hairpin-like structure is known as a precursor of "hsa-miR-210-5p."

The term "hsa-miR-24-3p gene" or "hsa-miR-24-3p" used herein includes the hsa-miR-24-3p gene (miRBase Accession No. MIMAT0000080) shown in SEQ ID NO: 27, a homolog or an ortholog of a different organism species, and the like. The gene can be obtained by a method described in Lagos-Quintana M et al., 2001, Science, Vol. 294, pp. 853-858. Also, "hsa-mir-24-1" (miRBase Accession No. MI0000080; SEQ ID NO: 472) and "hsa-mir-24-2" (miRBase Accession No. MI0000081; SEQ ID NO: 484) each having a hairpin-like structure are known as precursors of "hsa-miR-24-3p."

The term "hsa-miR-2467-3p gene" or "hsa-miR-2467-3p" used herein includes the hsa-miR-2467-3p gene (miRBase Accession No. MIMAT0019953) shown in SEQ ID NO: 28, a homolog or an ortholog of a different organism species, and the like. The gene can be obtained by a method described in Persson H et al., 2011, Cancer Res., Vol. 71, pp. 78-86. Also, "hsa-mir-2467" (miRBase Accession No. MI0017432; SEQ ID NO: 270) having a hairpin-like structure is known as a precursor of "hsa-miR-2467-3p."

The term "hsa-miR-2861 gene" or "hsa-miR-2861" used herein includes the hsa-miR-2861 gene (miRBase Accession No. MIMAT0013802) shown in SEQ ID NO: 29, a homolog or an ortholog of a different organism species, and the like. The gene can be obtained by a method described in Li H et al., 2009, J. Clin. Invest., Vol. 119, pp. 3666-3677. Also, "hsa-mir-2861" (miRBase Accession No. MI0013006; SEQ ID NO: 271) having a hairpin-like structure is known as a precursor of "hsa-miR-2861."

The term "hsa-miR-296-3p gene" or "hsa-miR-296-3p" used herein includes the hsa-miR-296-3p gene (miRBase Accession No. MIMAT0004679) shown in SEQ ID NO: 30, a homolog or an ortholog of a different organism species, and the like. The gene can be obtained by a method described in Houbaviy H B et al., 2003, Dev. Cell, Vol. 5, pp. 351-358. Also, "hsa-mir-296" (miRBase Accession No. MI0000747; SEQ ID NO: 272) having a hairpin-like structure is known as a precursor of "hsa-miR-296-3p."

The term "hsa-miR-29b-3p gene" or "hsa-miR-29b-3p" used herein includes the hsa-miR-29b-3p gene (miRBase Accession No. MIMAT0000100) shown in SEQ ID NO: 31, a homolog or an ortholog of a different organism species, and the like. The gene can be obtained by a method described in Mourelatos Z et al., 2002, Genes Dev., Vol. 16, pp. 720-728. Also, "hsa-mir-29b-1" (miRBase Accession No. MI0000105; SEQ ID NO: 473) and "hsa-mir-29b-2" (miRBase Accession No. MI0000107; SEQ ID NO: 485) each having a hairpin-like structure are known as precursors of "hsa-miR-29b-3p."

The term "hsa-miR-3131 gene" or "hsa-miR-3131" used herein includes the hsa-miR-3131 gene (miRBase Accession No. MIMAT0014996) shown in SEQ ID NO: 32, a homolog or an ortholog of a different organism species, and the like. The gene can be obtained by a method described in Stark M S et al., 2010, PLoS One, Vol. 5, e9685. Also, "hsa-mir-3131" (miRBase Accession No. MI0014151; SEQ ID NO: 273) having a hairpin-like structure is known as a precursor of "hsa-miR-3131."

The term "hsa-miR-3154 gene" or "hsa-miR-3154" used herein includes the hsa-miR-3154 gene (miRBase Accession No. MIMAT0015028) shown in SEQ ID NO: 33, a homolog or an ortholog of a different organism species, and the like. The gene can be obtained by a method described in Berezikov E et al., 2006, Genome Res., Vol. 16, pp. 1289-1298. Also, "hsa-mir-3154" (miRBase Accession No. MI0014182; SEQ ID NO: 274) having a hairpin-like structure is known as a precursor of "hsa-miR-3154."

The term "hsa-miR-3158-5p gene" or "hsa-miR-3158-5p" used herein includes the hsa-miR-3158-5p gene (miRBase Accession No. MIMAT0019211) shown in SEQ ID NO: 34, a homolog or an ortholog of a different organism species, and the like. The gene can be obtained by a method described in Creighton C J et al., 2010, PLoS One., Vol. 5, e9637. Also, "hsa-mir-3158-1" (miRBase Accession No. MI0014186; SEQ ID NO: 474) and "hsa-mir-3158-2" (miRBase Accession No. MI0014187; SEQ ID NO: 486) each having a hairpin-like structure are known as precursors of "hsa-miR-3158-5p."

The term "hsa-miR-3160-5p gene" or "hsa-miR-3160-5p" used herein includes the hsa-miR-3160-5p gene (miRBase Accession No. MIMAT0019212) shown in SEQ ID NO: 35, a homolog or an ortholog of a different organism species, and the like. The gene can be obtained by a method described in Stark M S et al., 2010, PLoS One, Vol. 5, e9685. Also, "hsa-mir-3160-1" (miRBase Accession No. MI0014189; SEQ ID NO: 475) and "hsa-mir-3160-2" (miRBase Accession No. MI0014190; SEQ ID NO: 487) each having a hairpin-like structure are known as precursors of "hsa-miR-3160-5p."

The term "hsa-miR-3162-5p gene" or "hsa-miR-3162-5p" used herein includes the hsa-miR-3162-5p gene (miRBase Accession No. MIMAT0015036) shown in SEQ ID NO: 36, a homolog or an ortholog of a different organism species, and the like. The gene can be obtained by a method described in Stark M S et al., 2010, PLoS One, Vol. 5, e9685. Also, "hsa-mir-3162" (miRBase Accession No. MI0014192; SEQ ID NO: 275) having a hairpin-like structure is known as a precursor of "hsa-miR-3162-5p."

The term "hsa-miR-3178 gene" or "hsa-miR-3178" used herein includes the hsa-miR-3178 gene (miRBase Accession No. MIMAT0015055) shown in SEQ ID NO: 37, a homolog or an ortholog of a different organism species, and the like. The gene can be obtained by a method described in Stark M S et al., 2010, PLoS One, Vol. 5, e9685. Also, "hsa-mir-3178" (miRBase Accession No. MI0014212; SEQ ID NO: 276) having a hairpin-like structure is known as a precursor of "hsa-miR-3178."

The term "hsa-miR-3180-3p gene" or "hsa-miR-3180-3p" used herein includes the hsa-miR-3180-3p gene (miRBase Accession No. MIMAT0015058) shown in SEQ ID NO: 38, a homolog or an ortholog of a different organism species, and the like. The gene can be obtained by a method described in Creighton C J et al., 2010, PLoS One., Vol. 5, e9637. Also, "hsa-mir-3180-1" (miRBase Accession No. MI0014214; SEQ ID NO: 496), "hsa-mir-3180-2" (miRBase Accession No. MI0014215; SEQ ID NO: 497), and "hsa-mir-3180-3" (miRBase Accession No. MI0014217; SEQ ID NO: 498) each having a hairpin-like structure are known as precursors of "hsa-miR-3180-3p."

The term "hsa-miR-3184-5p gene" or "hsa-miR-3184-5p" used herein includes the hsa-miR-3184-5p gene (miRBase Accession No. MIMAT0015064) shown in SEQ ID NO: 39, a homolog or an ortholog of a different organism species, and the like. The gene can be obtained by a method described in Stark M S et al., 2010, PLoS One, Vol. 5, e9685. Also, "hsa-mir-3184" (miRBase Accession No. MI0014226; SEQ ID NO: 277) having a hairpin-like structure is known as a precursor of "hsa-miR-3184-5p."

The term "hsa-miR-3185 gene" or "hsa-miR-3185" used herein includes the hsa-miR-3185 gene (miRBase Accession No. MIMAT0015065) shown in SEQ ID NO: 40, a homolog or an ortholog of a different organism species, and the like.

The gene can be obtained by a method described in Stark M S et al., 2010, PLoS One, Vol. 5, e9685. Also, "hsa-mir-3185" (miRBase Accession No. MI0014227; SEQ ID NO: 278) having a hairpin-like structure is known as a precursor of "hsa-miR-3185."

The term "hsa-miR-3194-3p gene" or "hsa-miR-3194-3p" used herein includes the hsa-miR-3194-3p gene (miRBase Accession No. MIMAT0019218) shown in SEQ ID NO: 41, a homolog or an ortholog of a different organism species, and the like. The gene can be obtained by a method described in Stark M S et al., 2010, PLoS One, Vol. 5, e9685. Also, "hsa-mir-3194" (miRBase Accession No. MI0014239; SEQ ID NO: 279) having a hairpin-like structure is known as a precursor of "hsa-miR-3194-3p."

The term "hsa-miR-3195 gene" or "hsa-miR-3195" used herein includes the hsa-miR-3195 gene (miRBase Accession No. MIMAT0015079) shown in SEQ ID NO: 42, a homolog or an ortholog of a different organism species, and the like. The gene can be obtained by a method described in Stark M S et al., 2010, PLoS One, Vol. 5, e9685. Also, "hsa-mir-3195" (miRBase Accession No. MI0014240; SEQ ID NO: 280) having a hairpin-like structure is known as a precursor of "hsa-miR-3195."

The term "hsa-miR-3197 gene" or "hsa-miR-3197" used herein includes the hsa-miR-3197 gene (miRBase Accession No. MIMAT0015082) shown in SEQ ID NO: 43, a homolog or an ortholog of a different organism species, and the like. The gene can be obtained by a method described in Stark M S et al., 2010, PLoS One, Vol. 5, e9685. Also, "hsa-mir-3197" (miRBase Accession No. MI0014245; SEQ ID NO: 281) having a hairpin-like structure is known as a precursor of "hsa-miR-3197."

The term "hsa-miR-320a gene" or "hsa-miR-320a" used herein includes the hsa-miR-320a gene (miRBase Accession No. MIMAT0000510) shown in SEQ ID NO: 44, a homolog or an ortholog of a different organism species, and the like. The gene can be obtained by a method described in Michael M Z et al., 2003, Mol. Cancer Res., Vol. 1, pp. 882-891. Also, "hsa-mir-320a" (miRBase Accession No. MI0000542; SEQ ID NO: 282) having a hairpin-like structure is known as a precursor of "hsa-miR-320a."

The term "hsa-miR-320b gene" or "hsa-miR-320b" used herein includes the hsa-miR-320b gene (miRBase Accession No. MIMAT0005792) shown in SEQ ID NO: 45, a homolog or an ortholog of a different organism species, and the like. The gene can be obtained by a method described in Berezikov E et al., 2006, Genome Res., Vol. 16, pp. 1289-1298. Also, "hsa-mir-320b-1" (miRBase Accession No. MI0003776; SEQ ID NO: 476) and "hsa-mir-320b-2" (miRBase Accession No. MI0003839; SEQ ID NO: 488) each having a hairpin-like structure are known as precursors of "hsa-miR-320b."

The term "hsa-miR-328-5p gene" or "hsa-miR-328-5p" used herein includes the hsa-miR-328-5p gene (miRBase Accession No. MIMAT0026486) shown in SEQ ID NO: 46, a homolog or an ortholog of a different organism species, and the like. The gene can be obtained by a method described in Kim J et al., 2004, Proc. Natl. Acad. Sci., U.S.A., Vol. 101, pp. 360-365. Also, "hsa-mir-328" (miRBase Accession No. MI0000804; SEQ ID NO: 283) having a hairpin-like structure is known as a precursor of "hsa-miR-328-5p."

The term "hsa-miR-342-5p gene" or "hsa-miR-342-5p" used herein includes the hsa-miR-342-5p gene (miRBase Accession No. MIMAT0004694) shown in SEQ ID NO: 47, a homolog or an ortholog of a different organism species, and the like. The gene can be obtained by a method described in Kim J et al., 2004, Proc. Natl. Acad. Sci., U.S.A., Vol. 101, pp. 360-365. Also, "hsa-mir-342" (miRBase Accession No. MI0000805; SEQ ID NO: 284) having a hairpin-like structure is known as a precursor of "hsa-miR-342-5p."

The term "hsa-miR-345-3p gene" or "hsa-miR-345-3p" used herein includes the hsa-miR-345-3p gene (miRBase Accession No. MIMAT0022698) shown in SEQ ID NO: 48, a homolog or an ortholog of a different organism species, and the like. The gene can be obtained by a method described in Kim J et al., 2004, Proc. Natl. Acad. Sci., U.S.A., Vol. 101, pp. 360-365. Also, "hsa-mir-345" (miRBase Accession No. MI0000825; SEQ ID NO: 285) having a hairpin-like structure is known as a precursor of "hsa-miR-345-3p."

The term "hsa-miR-3616-3p gene" or "hsa-miR-3616-3p" used herein includes the hsa-miR-3616-3p gene (miRBase Accession No. MIMAT0017996) shown in SEQ ID NO: 49, a homolog or an ortholog of a different organism species, and the like. The gene can be obtained by a method described in Witten D et al., 2010, BMC Biol., Vol. 8, p. 58. Also, "hsa-mir-3616" (miRBase Accession No. MI0016006; SEQ ID NO: 286) having a hairpin-like structure is known as a precursor of "hsa-miR-3616-3p."

The term "hsa-miR-3619-3p gene" or "hsa-miR-3619-3p" used herein includes the hsa-miR-3619-3p gene (miRBase Accession No. MIMAT0019219) shown in SEQ ID NO: 50, a homolog or an ortholog of a different organism species, and the like. The gene can be obtained by a method described in Witten D et al., 2010, BMC Biol., Vol. 8, p. 58. Also, "hsa-mir-3619" (miRBase Accession No. MI0016009; SEQ ID NO: 287) having a hairpin-like structure is known as a precursor of "hsa-miR-3619-3p."

The term "hsa-miR-3620-5p gene" or "hsa-miR-3620-5p" used herein includes the hsa-miR-3620-5p gene (miRBase Accession No. MIMAT0022967) shown in SEQ ID NO: 51, a homolog or an ortholog of a different organism species, and the like. The gene can be obtained by a method described in Witten D et al., 2010, BMC Biol., Vol. 8, p. 58. Also, "hsa-mir-3620" (miRBase Accession No. MI0016011; SEQ ID NO: 288) having a hairpin-like structure is known as a precursor of "hsa-miR-3620-5p."

The term "hsa-miR-3621 gene" or "hsa-miR-3621" used herein includes the hsa-miR-3621 gene (miRBase Accession No. MIMAT0018002) shown in SEQ ID NO: 52, a homolog or an ortholog of a different organism species, and the like. The gene can be obtained by a method described in Witten D et al., 2010, BMC Biol., Vol. 8, p. 58. Also, "hsa-mir-3621" (miRBase Accession No. MI0016012; SEQ ID NO: 289) having a hairpin-like structure is known as a precursor of "hsa-miR-3621."

The term "hsa-miR-3622a-5p gene" or "hsa-miR-3622a-5p" used herein includes the hsa-miR-3622a-5p gene (miRBase Accession No. MIMAT0018003) shown in SEQ ID NO: 53, a homolog or an ortholog of a different organism species, and the like. The gene can be obtained by a method described in Witten D et al., 2010, BMC Biol., Vol. 8, p. 58. Also, "hsa-mir-3622a" (miRBase Accession No. MI0016013; SEQ ID NO: 290) having a hairpin-like structure is known as a precursor of "hsa-miR-3622a-5p."

The term "hsa-miR-3648 gene" or "hsa-miR-3648" used herein includes the hsa-miR-3648 gene (miRBase Accession No. MIMAT0018068) shown in SEQ ID NO: 54, a homolog or an ortholog of a different organism species, and the like. The gene can be obtained by a method described in Meiri E et al., 2010, Nucleic Acids Res., Vol. 38, pp. 6234-6246. Also, "hsa-mir-3648-1" (miRBase Accession No.

MI0016048; SEQ ID NO: 477) and "hsa-mir-3648-2" (miR-Base Accession No. MI0031512; SEQ ID NO: 489) each having a hairpin-like structure are known as precursors of "hsa-miR-3648."

The term "hsa-miR-3652 gene" or "hsa-miR-3652" used herein includes the hsa-miR-3652 gene (miRBase Accession No. MIMAT0018072) shown in SEQ ID NO: 55, a homolog or an ortholog of a different organism species, and the like. The gene can be obtained by a method described in Meiri E et al., 2010, Nucleic Acids Res., Vol. 38, pp. 6234-6246. Also, "hsa-mir-3652" (miRBase Accession No. MI0016052; SEQ ID NO: 291) having a hairpin-like structure is known as a precursor of "hsa-miR-3652."

The term "hsa-miR-3656 gene" or "hsa-miR-3656" used herein includes the hsa-miR-3656 gene (miRBase Accession No. MIMAT0018076) shown in SEQ ID NO: 56, a homolog or an ortholog of a different organism species, and the like. The gene can be obtained by a method described in Meiri E et al., 2010, Nucleic Acids Res., Vol. 38, pp. 6234-6246. Also, "hsa-mir-3656" (miRBase Accession No. MI0016056; SEQ ID NO: 292) having a hairpin-like structure is known as a precursor of "hsa-miR-3656."

The term "hsa-miR-3663-3p gene" or "hsa-miR-3663-3p" used herein includes the hsa-miR-3663-3p gene (miRBase Accession No. MIMAT0018085) shown in SEQ ID NO: 57, a homolog or an ortholog of a different organism species, and the like. The gene can be obtained by a method described in Liao J Y et al., 2010, PLoS One, Vol. 5, e10563. Also, "hsa-mir-3663" (miRBase Accession No. MI0016064; SEQ ID NO: 293) having a hairpin-like structure is known as a precursor of "hsa-miR-3663-3p."

The term "hsa-miR-3679-5p gene" or "hsa-miR-3679-5p" used herein includes the hsa-miR-3679-5p gene (miRBase Accession No. MIMAT0018104) shown in SEQ ID NO: 58, a homolog or an ortholog of a different organism species, and the like. The gene can be obtained by a method described in Creighton C J et al., 2010, PLoS One., Vol. 5, e9637. Also, "hsa-mir-3679" (miRBase Accession No. MI0016080; SEQ ID NO: 294) having a hairpin-like structure is known as a precursor of "hsa-miR-3679-5p."

The term "hsa-miR-371b-5p gene" or "hsa-miR-371b-5p" used herein includes the hsa-miR-371b-5p gene (miRBase Accession No. MIMAT0019892) shown in SEQ ID NO: 59, a homolog or an ortholog of a different organism species, and the like. The gene can be obtained by a method described in Persson H et al., 2011, Cancer Res., Vol. 71, pp. 78-86. Also, "hsa-mir-371b" (miRBase Accession No. MI0017393; SEQ ID NO: 295) having a hairpin-like structure is known as a precursor of "hsa-miR-371b-5p."

The term "hsa-miR-373-5p gene" or "hsa-miR-373-5p" used herein includes the hsa-miR-373-5p gene (miRBase Accession No. MIMAT0000725) shown in SEQ ID NO: 60, a homolog or an ortholog of a different organism species, and the like. The gene can be obtained by a method described in Suh M R et al., 2004, Dev. Biol., Vol. 270, pp. 488-498. Also, "hsa-mir-373" (miRBase Accession No. MI0000781; SEQ ID NO: 296) having a hairpin-like structure is known as a precursor of "hsa-miR-373-5p."

The term "hsa-miR-3917 gene" or "hsa-miR-3917" used herein includes the hsa-miR-3917 gene (miRBase Accession No. MIMAT0018191) shown in SEQ ID NO: 61, a homolog or an ortholog of a different organism species, and the like. The gene can be obtained by a method described in Creighton C J et al., 2010, PLoS One., Vol. 5, e9637. Also, "hsa-mir-3917" (miRBase Accession No. MI0016423; SEQ ID NO: 297) having a hairpin-like structure is known as a precursor of "hsa-miR-3917."

The term "hsa-miR-3940-5p gene" or "hsa-miR-3940-5p" used herein includes the hsa-miR-3940-5p gene (miRBase Accession No. MIMAT0019229) shown in SEQ ID NO: 62, a homolog or an ortholog of a different organism species, and the like. The gene can be obtained by a method described in Liao J Y et al., 2010, PLoS One, Vol. 5, e10563. Also, "hsa-mir-3940" (miRBase Accession No. MI0016597; SEQ ID NO: 298) having a hairpin-like structure is known as a precursor of "hsa-miR-3940-5p."

The term "hsa-miR-3960 gene" or "hsa-miR-3960" used herein includes the hsa-miR-3960 gene (miRBase Accession No. MIMAT0019337) shown in SEQ ID NO: 63, a homolog or an ortholog of a different organism species, and the like. The gene can be obtained by a method described in Hu R et al., 2011, J. Biol. Chem., Vol. 286, pp. 12328-12339. Also, "hsa-mir-3960" (miRBase Accession No. MI0016964; SEQ ID NO: 299) having a hairpin-like structure is known as a precursor of "hsa-miR-3960."

The term "hsa-miR-4258 gene" or "hsa-miR-4258" used herein includes the hsa-miR-4258 gene (miRBase Accession No. MIMAT0016879) shown in SEQ ID NO: 64, a homolog or an ortholog of a different organism species, and the like. The gene can be obtained by a method described in Goff L A et al., 2009, PLoS One, Vol. 4, e7192. Also, "hsa-mir-4258" (miRBase Accession No. MI0015857; SEQ ID NO: 300) having a hairpin-like structure is known as a precursor of "hsa-miR-4258."

The term "hsa-miR-4259 gene" or "hsa-miR-4259" used herein includes the hsa-miR-4259 gene (miRBase Accession No. MIMAT0016880) shown in SEQ ID NO: 65, a homolog or an ortholog of a different organism species, and the like. The gene can be obtained by a method described in Goff L A et al., 2009, PLoS One, Vol. 4, e7192. Also, "hsa-mir-4259" (miRBase Accession No. MI0015858; SEQ ID NO: 301) having a hairpin-like structure is known as a precursor of "hsa-miR-4259."

The term "hsa-miR-4270 gene" or "hsa-miR-4270" used herein includes the hsa-miR-4270 gene (miRBase Accession No. MIMAT0016900) shown in SEQ ID NO: 66, a homolog or an ortholog of a different organism species, and the like. The gene can be obtained by a method described in Goff L A et al., 2009, PLoS One, Vol. 4, e7192. Also, "hsa-mir-4270" (miRBase Accession No. MI0015878; SEQ ID NO: 302) having a hairpin-like structure is known as a precursor of "hsa-miR-4270."

The term "hsa-miR-4286 gene" or "hsa-miR-4286" used herein includes the hsa-miR-4286 gene (miRBase Accession No. MIMAT0016916) shown in SEQ ID NO: 67, a homolog or an ortholog of a different organism species, and the like. The gene can be obtained by a method described in Goff L A et al., 2009, PLoS One, Vol. 4, e7192. Also, "hsa-mir-4286" (miRBase Accession No. MI0015894; SEQ ID NO: 303) having a hairpin-like structure is known as a precursor of "hsa-miR-4286."

The term "hsa-miR-4298 gene" or "hsa-miR-4298" used herein includes the hsa-miR-4298 gene (miRBase Accession No. MIMAT0016852) shown in SEQ ID NO: 68, a homolog or an ortholog of a different organism species, and the like. The gene can be obtained by a method described in Goff L A et al., 2009, PLoS One, Vol. 4, e7192. Also, "hsa-mir-4298" (miRBase Accession No. MI0015830; SEQ ID NO: 304) having a hairpin-like structure is known as a precursor of "hsa-miR-4298."

The term "hsa-miR-4322 gene" or "hsa-miR-4322" used herein includes the hsa-miR-4322 gene (miRBase Accession No. MIMAT0016873) shown in SEQ ID NO: 69, a homolog or an ortholog of a different organism species, and the like.

The gene can be obtained by a method described in Goff L A et al., 2009, PLoS One, Vol. 4, e7192. Also, "hsa-mir-4322" (miRBase Accession No. MI0015851; SEQ ID NO: 305) having a hairpin-like structure is known as a precursor of "hsa-miR-4322."

The term "hsa-miR-4327 gene" or "hsa-miR-4327" used herein includes the hsa-miR-4327 gene (miRBase Accession No. MIMAT0016889) shown in SEQ ID NO: 70, a homolog or an ortholog of a different organism species, and the like. The gene can be obtained by a method described in Goff L A et al., 2009, PLoS One, Vol. 4, e7192. Also, "hsa-mir-4327" (miRBase Accession No. MI0015867; SEQ ID NO: 306) having a hairpin-like structure is known as a precursor of "hsa-miR-4327."

The term "hsa-miR-4417 gene" or "hsa-miR-4417" used herein includes the hsa-miR-4417 gene (miRBase Accession No. MIMAT0018929) shown in SEQ ID NO: 71, a homolog or an ortholog of a different organism species, and the like. The gene can be obtained by a method described in Jima D D et al., 2010, Blood, Vol. 116, e118-e127. Also, "hsa-mir-4417" (miRBase Accession No. MI0016753; SEQ ID NO: 307) having a hairpin-like structure is known as a precursor of "hsa-miR-4417."

The term "hsa-miR-4419b gene" or "hsa-miR-4419b" used herein includes the hsa-miR-4419b gene (miRBase Accession No. MIMAT0019034) shown in SEQ ID NO: 72, a homolog or an ortholog of a different organism species, and the like. The gene can be obtained by a method described in Jima D D et al., 2010, Blood, Vol. 116, e118-e127. Also, "hsa-mir-4419b" (miRBase Accession No. MI0016861; SEQ ID NO: 308) having a hairpin-like structure is known as a precursor of "hsa-miR-4419b."

The term "hsa-miR-4429 gene" or "hsa-miR-4429" used herein includes the hsa-miR-4429 gene (miRBase Accession No. MIMAT0018944) shown in SEQ ID NO: 73, a homolog or an ortholog of a different organism species, and the like. The gene can be obtained by a method described in Jima D D et al., 2010, Blood, Vol. 116, e118-e127. Also, "hsa-mir-4429" (miRBase Accession No. MI0016768; SEQ ID NO: 309) having a hairpin-like structure is known as a precursor of "hsa-miR-4429."

The term "hsa-miR-4430 gene" or "hsa-miR-4430" used herein includes the hsa-miR-4430 gene (miRBase Accession No. MIMAT0018945) shown in SEQ ID NO: 74, a homolog or an ortholog of a different organism species, and the like. The gene can be obtained by a method described in Jima D D et al., 2010, Blood, Vol. 116, e118-e127. Also, "hsa-mir-4430" (miRBase Accession No. MI0016769; SEQ ID NO: 310) having a hairpin-like structure is known as a precursor of "hsa-miR-4430."

The term "hsa-miR-4433a-3p gene" or "hsa-miR-4433a-3p" used herein includes the hsa-miR-4433a-3p gene (miRBase Accession No. MIMAT0018949) shown in SEQ ID NO: 75, a homolog or an ortholog of a different organism species, and the like. The gene can be obtained by a method described in Jima D D et al., 2010, Blood, Vol. 116, e118-e127. Also, "hsa-mir-4433a" (miRBase Accession No. MI0016773; SEQ ID NO: 311) having a hairpin-like structure is known as a precursor of "hsa-miR-4433a-3p."

The term "hsa-miR-4436b-5p gene" or "hsa-miR-4436b-5p" used herein includes the hsa-miR-4436b-5p gene (miRBase Accession No. MIMAT0019940) shown in SEQ ID NO: 76, a homolog or an ortholog of a different organism species, and the like. The gene can be obtained by a method described in Persson H et al., 2011, Cancer Res., Vol. 71, pp. 78-86. Also, "hsa-mir-4436b-1" (miRBase Accession No. MI0017425; SEQ ID NO: 478) and "hsa-mir-4436b-2" (miRBase Accession No. MI0019110; SEQ ID NO: 490) each having a hairpin-like structure are known as precursors of "hsa-miR-4436b-5p."

The term "hsa-miR-4443 gene" or "hsa-miR-4443" used herein includes the hsa-miR-4443 gene (miRBase Accession No. MIMAT0018961) shown in SEQ ID NO: 77, a homolog or an ortholog of a different organism species, and the like. The gene can be obtained by a method described in Jima D D et al., 2010, Blood, Vol. 116, e118-e127. Also, "hsa-mir-4443" (miRBase Accession No. MI0016786; SEQ ID NO: 312) having a hairpin-like structure is known as a precursor of "hsa-miR-4443."

The term "hsa-miR-4446-3p gene" or "hsa-miR-4446-3p" used herein includes the hsa-miR-4446-3p gene (miRBase Accession No. MIMAT0018965) shown in SEQ ID NO: 78, a homolog or an ortholog of a different organism species, and the like. The gene can be obtained by a method described in Jima D D et al., 2010, Blood, Vol. 116, e118-e127. Also, "hsa-mir-4446" (miRBase Accession No. MI0016789; SEQ ID NO: 313) having a hairpin-like structure is known as a precursor of "hsa-miR-4446-3p."

The term "hsa-miR-4447 gene" or "hsa-miR-4447" used herein includes the hsa-miR-4447 gene (miRBase Accession No. MIMAT0018966) shown in SEQ ID NO: 79, a homolog or an ortholog of a different organism species, and the like. The gene can be obtained by a method described in Jima D D et al., 2010, Blood, Vol. 116, e118-e127. Also, "hsa-mir-4447" (miRBase Accession No. MI0016790; SEQ ID NO: 314) having a hairpin-like structure is known as a precursor of "hsa-miR-4447."

The term "hsa-miR-4448 gene" or "hsa-miR-4448" used herein includes the hsa-miR-4448 gene (miRBase Accession No. MIMAT0018967) shown in SEQ ID NO: 80, a homolog or an ortholog of a different organism species, and the like. The gene can be obtained by a method described in Jima D D et al., 2010, Blood, Vol. 116, e118-e127. Also, "hsa-mir-4448" (miRBase Accession No. MI0016791; SEQ ID NO: 315) having a hairpin-like structure is known as a precursor of "hsa-miR-4448."

The term "hsa-miR-4449 gene" or "hsa-miR-4449" used herein includes the hsa-miR-4449 gene (miRBase Accession No. MIMAT0018968) shown in SEQ ID NO: 81, a homolog or an ortholog of a different organism species, and the like. The gene can be obtained by a method described in Jima D D et al., 2010, Blood, Vol. 116, e118-e127. Also, "hsa-mir-4449" (miRBase Accession No. MI0016792; SEQ ID NO: 316) having a hairpin-like structure is known as a precursor of "hsa-miR-4449."

The term "hsa-miR-4454 gene" or "hsa-miR-4454" used herein includes the hsa-miR-4454 gene (miRBase Accession No. MIMAT0018976) shown in SEQ ID NO: 82, a homolog or an ortholog of a different organism species, and the like. The gene can be obtained by a method described in Jima D D et al., 2010, Blood, Vol. 116, e118-e127. Also, "hsa-mir-4454" (miRBase Accession No. MI0016800; SEQ ID NO: 317) having a hairpin-like structure is known as a precursor of "hsa-miR-4454."

The term "hsa-miR-4455 gene" or "hsa-miR-4455" used herein includes the hsa-miR-4455 gene (miRBase Accession No. MIMAT0018977) shown in SEQ ID NO: 83, a homolog or an ortholog of a different organism species, and the like. The gene can be obtained by a method described in Jima D D et al., 2010, Blood, Vol. 116, e118-e127. Also, "hsa-mir-4455" (miRBase Accession No. MI0016801; SEQ ID NO: 318) having a hairpin-like structure is known as a precursor of "hsa-miR-4455."

The term "hsa-miR-4459 gene" or "hsa-miR-4459" used herein includes the hsa-miR-4459 gene (miRBase Accession No. MIMAT0018981) shown in SEQ ID NO: 84, a homolog or an ortholog of a different organism species, and the like. The gene can be obtained by a method described in Jima D D et al., 2010, Blood, Vol. 116, e118-e127. Also, "hsa-mir-4459" (miRBase Accession No. MI0016805; SEQ ID NO: 319) having a hairpin-like structure is known as a precursor of "hsa-miR-4459."

The term "hsa-miR-4462 gene" or "hsa-miR-4462" used herein includes the hsa-miR-4462 gene (miRBase Accession No. MIMAT0018986) shown in SEQ ID NO: 85, a homolog or an ortholog of a different organism species, and the like. The gene can be obtained by a method described in Jima D D et al., 2010, Blood, Vol. 116, e118-e127. Also, "hsa-mir-4462" (miRBase Accession No. MI0016810; SEQ ID NO: 320) having a hairpin-like structure is known as a precursor of "hsa-miR-4462."

The term "hsa-miR-4466 gene" or "hsa-miR-4466" used herein includes the hsa-miR-4466 gene (miRBase Accession No. MIMAT0018993) shown in SEQ ID NO: 86, a homolog or an ortholog of a different organism species, and the like. The gene can be obtained by a method described in Jima D D et al., 2010, Blood, Vol. 116, e118-e127. Also, "hsa-mir-4466" (miRBase Accession No. MI0016817; SEQ ID NO: 321) having a hairpin-like structure is known as a precursor of "hsa-miR-4466."

The term "hsa-miR-4467 gene" or "hsa-miR-4467" used herein includes the hsa-miR-4467 gene (miRBase Accession No. MIMAT0018994) shown in SEQ ID NO: 87, a homolog or an ortholog of a different organism species, and the like. The gene can be obtained by a method described in Jima D D et al., 2010, Blood, Vol. 116, e118-e127. Also, "hsa-mir-4467" (miRBase Accession No. MI0016818; SEQ ID NO: 322) having a hairpin-like structure is known as a precursor of "hsa-miR-4467."

The term "hsa-miR-4480 gene" or "hsa-miR-4480" used herein includes the hsa-miR-4480 gene (miRBase Accession No. MIMAT0019014) shown in SEQ ID NO: 88, a homolog or an ortholog of a different organism species, and the like. The gene can be obtained by a method described in Jima D D et al., 2010, Blood, Vol. 116, e118-e127. Also, "hsa-mir-4480" (miRBase Accession No. MI0016841; SEQ ID NO: 323) having a hairpin-like structure is known as a precursor of "hsa-miR-4480."

The term "hsa-miR-4483 gene" or "hsa-miR-4483" used herein includes the hsa-miR-4483 gene (miRBase Accession No. MIMAT0019017) shown in SEQ ID NO: 89, a homolog or an ortholog of a different organism species, and the like. The gene can be obtained by a method described in Jima D D et al., 2010, Blood, Vol. 116, e118-e127. Also, "hsa-mir-4483" (miRBase Accession No. MI0016844; SEQ ID NO: 324) having a hairpin-like structure is known as a precursor of "hsa-miR-4483."

The term "hsa-miR-4484 gene" or "hsa-miR-4484" used herein includes the hsa-miR-4484 gene (miRBase Accession No. MIMAT0019018) shown in SEQ ID NO: 90, a homolog or an ortholog of a different organism species, and the like. The gene can be obtained by a method described in Jima D D et al., 2010, Blood, Vol. 116, e118-e127. Also, "hsa-mir-4484" (miRBase Accession No. MI0016845; SEQ ID NO: 325) having a hairpin-like structure is known as a precursor of "hsa-miR-4484."

The term "hsa-miR-4485-5p gene" or "hsa-miR-4485-5p" used herein includes the hsa-miR-4485-5p gene (miRBase Accession No. MIMAT0032116) shown in SEQ ID NO: 91, a homolog or an ortholog of a different organism species, and the like. The gene can be obtained by a method described in Jima D D et al., 2010, Blood, Vol. 116, e118-e127. Also, "hsa-mir-4485" (miRBase Accession No. MI0016846; SEQ ID NO: 326) having a hairpin-like structure is known as a precursor of "hsa-miR-4485-5p."

The term "hsa-miR-4488 gene" or "hsa-miR-4488" used herein includes the hsa-miR-4488 gene (miRBase Accession No. MIMAT0019022) shown in SEQ ID NO: 92, a homolog or an ortholog of a different organism species, and the like. The gene can be obtained by a method described in Jima D D et al., 2010, Blood, Vol. 116, e118-e127. Also, "hsa-mir-4488" (miRBase Accession No. MI0016849; SEQ ID NO: 327) having a hairpin-like structure is known as a precursor of "hsa-miR-4488."

The term "hsa-miR-4492 gene" or "hsa-miR-4492" used herein includes the hsa-miR-4492 gene (miRBase Accession No. MIMAT0019027) shown in SEQ ID NO: 93, a homolog or an ortholog of a different organism species, and the like. The gene can be obtained by a method described in Jima D D et al., 2010, Blood, Vol. 116, e118-e127. Also, "hsa-mir-4492" (miRBase Accession No. MI0016854; SEQ ID NO: 328) having a hairpin-like structure is known as a precursor of "hsa-miR-4492."

The term "hsa-miR-4505 gene" or "hsa-miR-4505" used herein includes the hsa-miR-4505 gene (miRBase Accession No. MIMAT0019041) shown in SEQ ID NO: 94, a homolog or an ortholog of a different organism species, and the like. The gene can be obtained by a method described in Jima D D et al., 2010, Blood, Vol. 116, e118-e127. Also, "hsa-mir-4505" (miRBase Accession No. MI0016868; SEQ ID NO: 329) having a hairpin-like structure is known as a precursor of "hsa-miR-4505."

The term "hsa-miR-4515 gene" or "hsa-miR-4515" used herein includes the hsa-miR-4515 gene (miRBase Accession No. MIMAT0019052) shown in SEQ ID NO: 95, a homolog or an ortholog of a different organism species, and the like. The gene can be obtained by a method described in Jima D D et al., 2010, Blood, Vol. 116, e118-e127. Also, "hsa-mir-4515" (miRBase Accession No. MI0016881; SEQ ID NO: 330) having a hairpin-like structure is known as a precursor of "hsa-miR-4515."

The term "hsa-miR-4525 gene" or "hsa-miR-4525" used herein includes the hsa-miR-4525 gene (miRBase Accession No. MIMAT0019064) shown in SEQ ID NO: 96, a homolog or an ortholog of a different organism species, and the like. The gene can be obtained by a method described in Jima D D et al., 2010, Blood, Vol. 116, e118-e127. Also, "hsa-mir-4525" (miRBase Accession No. MI0016892; SEQ ID NO: 331) having a hairpin-like structure is known as a precursor of "hsa-miR-4525."

The term "hsa-miR-4534 gene" or "hsa-miR-4534" used herein includes the hsa-miR-4534 gene (miRBase Accession No. MIMAT0019073) shown in SEQ ID NO: 97, a homolog or an ortholog of a different organism species, and the like. The gene can be obtained by a method described in Jima D D et al., 2010, Blood, Vol. 116, e118-e127. Also, "hsa-mir-4534" (miRBase Accession No. MI0016901; SEQ ID NO: 332) having a hairpin-like structure is known as a precursor of "hsa-miR-4534."

The term "hsa-miR-4535 gene" or "hsa-miR-4535" used herein includes the hsa-miR-4535 gene (miRBase Accession No. MIMAT0019075) shown in SEQ ID NO: 98, a homolog or an ortholog of a different organism species, and the like. The gene can be obtained by a method described in Jima D D et al., 2010, Blood, Vol. 116, e118-e127. Also, "hsa-mir- 4535" (miRBase Accession No. MI0016903; SEQ ID NO: 333) having a hairpin-like structure is known as a precursor of "hsa-miR-4535."

The term "hsa-miR-4633-3p gene" or "hsa-miR-4633-3p" used herein includes the hsa-miR-4633-3p gene (miRBase Accession No. MIMAT0019690) shown in SEQ ID NO: 99, a homolog or an ortholog of a different organism species, and the like. The gene can be obtained by a method described in Persson H et al., 2011, Cancer Res., Vol. 71, pp. 78-86. Also, "hsa-mir-4633" (miRBase Accession No. MI0017260; SEQ ID NO: 334) having a hairpin-like structure is known as a precursor of "hsa-miR-4633-3p."

The term "hsa-miR-4634 gene" or "hsa-miR-4634" used herein includes the hsa-miR-4634 gene (miRBase Accession No. MIMAT0019691) shown in SEQ ID NO: 100, a homolog or an ortholog of a different organism species, and the like. The gene can be obtained by a method described in Persson H et al., 2011, Cancer Res., Vol. 71, pp. 78-86. Also, "hsa-mir-4634" (miRBase Accession No. MI0017261; SEQ ID NO: 335) having a hairpin-like structure is known as a precursor of "hsa-miR-4634."

The term "hsa-miR-4640-5p gene" or "hsa-miR-4640-5p" used herein includes the hsa-miR-4640-5p gene (miRBase Accession No. MIMAT0019699) shown in SEQ ID NO: 101, a homolog or an ortholog of a different organism species, and the like. The gene can be obtained by a method described in Persson H et al., 2011, Cancer Res., Vol. 71, pp. 78-86. Also, "hsa-mir-4640" (miRBase Accession No. MI0017267; SEQ ID NO: 336) having a hairpin-like structure is known as a precursor of "hsa-miR-4640-5p."

The term "hsa-miR-4649-5p gene" or "hsa-miR-4649-5p" used herein includes the hsa-miR-4649-5p gene (miRBase Accession No. MIMAT0019711) shown in SEQ ID NO: 102, a homolog or an ortholog of a different organism species, and the like. The gene can be obtained by a method described in Persson H et al., 2011, Cancer Res., Vol. 71, pp. 78-86. Also, "hsa-mir-4649" (miRBase Accession No. MI0017276; SEQ ID NO: 337) having a hairpin-like structure is known as a precursor of "hsa-miR-4649-5p."

The term "hsa-miR-4651 gene" or "hsa-miR-4651" used herein includes the hsa-miR-4651 gene (miRBase Accession No. MIMAT0019715) shown in SEQ ID NO: 103, a homolog or an ortholog of a different organism species, and the like. The gene can be obtained by a method described in Persson H et al., 2011, Cancer Res., Vol. 71, pp. 78-86. Also, "hsa-mir-4651" (miRBase Accession No. MI0017279; SEQ ID NO: 338) having a hairpin-like structure is known as a precursor of "hsa-miR-4651."

The term "hsa-miR-4652-5p gene" or "hsa-miR-4652-5p" used herein includes the hsa-miR-4652-5p gene (miRBase Accession No. MIMAT0019716) shown in SEQ ID NO: 104, a homolog or an ortholog of a different organism species, and the like. The gene can be obtained by a method described in Persson H et al., 2011, Cancer Res., Vol. 71, pp. 78-86. Also, "hsa-mir-4652" (miRBase Accession No. MI0017280; SEQ ID NO: 339) having a hairpin-like structure is known as a precursor of "hsa-miR-4652-5p."

The term "hsa-miR-4655-5p gene" or "hsa-miR-4655-5p" used herein includes the hsa-miR-4655-5p gene (miRBase Accession No. MIMAT0019721) shown in SEQ ID NO: 105, a homolog or an ortholog of a different organism species, and the like. The gene can be obtained by a method described in Persson H et al., 2011, Cancer Res., Vol. 71, pp. 78-86. Also, "hsa-mir-4655" (miRBase Accession No. MI0017283; SEQ ID NO: 340) having a hairpin-like structure is known as a precursor of "hsa-miR-4655-5p."

The term "hsa-miR-4656 gene" or "hsa-miR-4656" used herein includes the hsa-miR-4656 gene (miRBase Accession No. MIMAT0019723) shown in SEQ ID NO: 106, a homolog or an ortholog of a different organism species, and the like. The gene can be obtained by a method described in Persson H et al., 2011, Cancer Res., Vol. 71, pp. 78-86. Also, "hsa-mir-4656" (miRBase Accession No. MI0017284; SEQ ID NO: 341) having a hairpin-like structure is known as a precursor of "hsa-miR-4656."

The term "hsa-miR-4658 gene" or "hsa-miR-4658" used herein includes the hsa-miR-4658 gene (miRBase Accession No. MIMAT0019725) shown in SEQ ID NO: 107, a homolog or an ortholog of a different organism species, and the like. The gene can be obtained by a method described in Persson H et al., 2011, Cancer Res., Vol. 71, pp. 78-86. Also, "hsa-mir-4658" (miRBase Accession No. MI0017286; SEQ ID NO: 342) having a hairpin-like structure is known as a precursor of "hsa-miR-4658."

The term "hsa-miR-4663 gene" or "hsa-miR-4663" used herein includes the hsa-miR-4663 gene (miRBase Accession No. MIMAT0019735) shown in SEQ ID NO: 108, a homolog or an ortholog of a different organism species, and the like. The gene can be obtained by a method described in Persson H et al., 2011, Cancer Res., Vol. 71, pp. 78-86. Also, "hsa-mir-4663" (miRBase Accession No. MI0017292; SEQ ID NO: 343) having a hairpin-like structure is known as a precursor of "hsa-miR-4663."

The term "hsa-miR-4673 gene" or "hsa-miR-4673" used herein includes the hsa-miR-4673 gene (miRBase Accession No. MIMAT0019755) shown in SEQ ID NO: 109, a homolog or an ortholog of a different organism species, and the like. The gene can be obtained by a method described in Persson H et al., 2011, Cancer Res., Vol. 71, pp. 78-86. Also, "hsa-mir-4673" (miRBase Accession No. MI0017304; SEQ ID NO: 344) having a hairpin-like structure is known as a precursor of "hsa-miR-4673."

The term "hsa-miR-4675 gene" or "hsa-miR-4675" used herein includes the hsa-miR-4675 gene (miRBase Accession No. MIMAT0019757) shown in SEQ ID NO: 110, a homolog or an ortholog of a different organism species, and the like. The gene can be obtained by a method described in Persson H et al., 2011, Cancer Res., Vol. 71, pp. 78-86. Also, "hsa-mir-4675" (miRBase Accession No. MI0017306; SEQ ID NO: 345) having a hairpin-like structure is known as a precursor of "hsa-miR-4675."

The term "hsa-miR-4687-3p gene" or "hsa-miR-4687-3p" used herein includes the hsa-miR-4687-3p gene (miRBase Accession No. MIMAT0019775) shown in SEQ ID NO: 111, a homolog or an ortholog of a different organism species, and the like. The gene can be obtained by a method described in Persson H et al., 2011, Cancer Res., Vol. 71, pp. 78-86. Also, "hsa-mir-4687" (miRBase Accession No. MI0017319; SEQ ID NO: 346) having a hairpin-like structure is known as a precursor of "hsa-miR-4687-3p."

The term "hsa-miR-4687-5p gene" or "hsa-miR-4687-5p" used herein includes the hsa-miR-4687-5p gene (miRBase Accession No. MIMAT0019774) shown in SEQ ID NO: 112, a homolog or an ortholog of a different organism species, and the like. The gene can be obtained by a method described in Persson H et al., 2011, Cancer Res., Vol. 71, pp. 78-86. Also, "hsa-mir-4687" (miRBase Accession No. MI0017319; SEQ ID NO: 347) having a hairpin-like structure is known as a precursor of "hsa-miR-4687-5p."

The term "hsa-miR-4690-5p gene" or "hsa-miR-4690-5p" used herein includes the hsa-miR-4690-5p gene (miRBase Accession No. MIMAT0019779) shown in SEQ ID NO: 113, a homolog or an ortholog of a different organism species, and the like. The gene can be obtained by a method described in Persson H et al., 2011, Cancer Res., Vol. 71, pp. 78-86. Also, "hsa-mir-4690" (miRBase Accession No. MI0017323; SEQ ID NO: 348) having a hairpin-like structure is known as a precursor of "hsa-miR-4690-5p."

The term "hsa-miR-4695-5p gene" or "hsa-miR-4695-5p" used herein includes the hsa-miR-4695-5p gene (miRBase Accession No. MIMAT0019788) shown in SEQ ID NO: 114, a homolog or an ortholog of a different organism species, and the like. The gene can be obtained by a method described in Persson H et al., 2011, Cancer Res., Vol. 71, pp. 78-86. Also, "hsa-mir-4695" (miRBase Accession No. MI0017328; SEQ ID NO: 349) having a hairpin-like structure is known as a precursor of "hsa-miR-4695-5p."

The term "hsa-miR-4697-5p gene" or "hsa-miR-4697-5p" used herein includes the hsa-miR-4697-5p gene (miRBase Accession No. MIMAT0019791) shown in SEQ ID NO: 115, a homolog or an ortholog of a different organism species, and the like. The gene can be obtained by a method described in Persson H et al., 2011, Cancer Res., Vol. 71, pp. 78-86. Also, "hsa-mir-4697" (miRBase Accession No. MI0017330; SEQ ID NO: 350) having a hairpin-like structure is known as a precursor of "hsa-miR-4697-5p."

The term "hsa-miR-4706 gene" or "hsa-miR-4706" used herein includes the hsa-miR-4706 gene (miRBase Accession No. MIMAT0019806) shown in SEQ ID NO: 116, a homolog or an ortholog of a different organism species, and the like. The gene can be obtained by a method described in Persson H et al., 2011, Cancer Res., Vol. 71, pp. 78-86. Also, "hsa-mir-4706" (miRBase Accession No. MI0017339; SEQ ID NO: 351) having a hairpin-like structure is known as a precursor of "hsa-miR-4706."

The term "hsa-miR-4707-3p gene" or "hsa-miR-4707-3p" used herein includes the hsa-miR-4707-3p gene (miRBase Accession No. MIMAT0019808) shown in SEQ ID NO: 117, a homolog or an ortholog of a different organism species, and the like. The gene can be obtained by a method described in Persson H et al., 2011, Cancer Res., Vol. 71, pp. 78-86. Also, "hsa-mir-4707" (miRBase Accession No. MI0017340; SEQ ID NO: 352) having a hairpin-like structure is known as a precursor of "hsa-miR-4707-3p."

The term "hsa-miR-4707-5p gene" or "hsa-miR-4707-5p" used herein includes the hsa-miR-4707-5p gene (miRBase Accession No. MIMAT0019807) shown in SEQ ID NO: 118, a homolog or an ortholog of a different organism species, and the like. The gene can be obtained by a method described in Persson H et al., 2011, Cancer Res., Vol. 71, pp. 78-86. Also, "hsa-mir-4707" (miRBase Accession No. MI0017340; SEQ ID NO: 353) having a hairpin-like structure is known as a precursor of "hsa-miR-4707-5p."

The term "hsa-miR-4708-3p gene" or "hsa-miR-4708-3p" used herein includes the hsa-miR-4708-3p gene (miRBase Accession No. MIMAT0019810) shown in SEQ ID NO: 119, a homolog or an ortholog of a different organism species, and the like. The gene can be obtained by a method described in Persson H et al., 2011, Cancer Res., Vol. 71, pp. 78-86. Also, "hsa-mir-4708" (miRBase Accession No. MI0017341; SEQ ID NO: 354) having a hairpin-like structure is known as a precursor of "hsa-miR-4708-3p."

The term "hsa-miR-4710 gene" or "hsa-miR-4710" used herein includes the hsa-miR-4710 gene (miRBase Accession No. MIMAT0019815) shown in SEQ ID NO: 120, a homolog or an ortholog of a different organism species, and the like. The gene can be obtained by a method described in Persson H et al., 2011, Cancer Res., Vol. 71, pp. 78-86. Also, "hsa-mir-4710" (miRBase Accession No. MI0017344; SEQ ID NO: 355) having a hairpin-like structure is known as a precursor of "hsa-miR-4710."

The term "hsa-miR-4718 gene" or "hsa-miR-4718" used herein includes the hsa-miR-4718 gene (miRBase Accession No. MIMAT0019831) shown in SEQ ID NO: 121, a homolog or an ortholog of a different organism species, and the like. The gene can be obtained by a method described in Persson H et al., 2011, Cancer Res., Vol. 71, pp. 78-86. Also, "hsa-mir-4718" (miRBase Accession No. MI0017353; SEQ ID NO: 356) having a hairpin-like structure is known as a precursor of "hsa-miR-4718."

The term "hsa-miR-4722-5p gene" or "hsa-miR-4722-5p" used herein includes the hsa-miR-4722-5p gene (miRBase Accession No. MIMAT0019836) shown in SEQ ID NO: 122, a homolog or an ortholog of a different organism species, and the like. The gene can be obtained by a method described in Persson H et al., 2011, Cancer Res., Vol. 71, pp. 78-86. Also, "hsa-mir-4722" (miRBase Accession No. MI0017357; SEQ ID NO: 357) having a hairpin-like structure is known as a precursor of "hsa-miR-4722-5p."

The term "hsa-miR-4725-3p gene" or "hsa-miR-4725-3p" used herein includes the hsa-miR-4725-3p gene (miRBase Accession No. MIMAT0019844) shown in SEQ ID NO: 123, a homolog or an ortholog of a different organism species, and the like. The gene can be obtained by a method described in Persson H et al., 2011, Cancer Res., Vol. 71, pp. 78-86. Also, "hsa-mir-4725" (miRBase Accession No. MI0017362; SEQ ID NO: 358) having a hairpin-like structure is known as a precursor of "hsa-miR-4725-3p."

The term "hsa-miR-4726-5p gene" or "hsa-miR-4726-5p" used herein includes the hsa-miR-4726-5p gene (miRBase Accession No. MIMAT0019845) shown in SEQ ID NO: 124, a homolog or an ortholog of a different organism species, and the like. The gene can be obtained by a method described in Persson H et al., 2011, Cancer Res., Vol. 71, pp. 78-86. Also, "hsa-mir-4726" (miRBase Accession No. MI0017363; SEQ ID NO: 359) having a hairpin-like structure is known as a precursor of "hsa-miR-4726-5p."

The term "hsa-miR-4727-3p gene" or "hsa-miR-4727-3p" used herein includes the hsa-miR-4727-3p gene (miRBase Accession No. MIMAT0019848) shown in SEQ ID NO: 125, a homolog or an ortholog of a different organism species, and the like. The gene can be obtained by a method described in Persson H et al., 2011, Cancer Res., Vol. 71, pp. 78-86. Also, "hsa-mir-4727" (miRBase Accession No. MI0017364; SEQ ID NO: 360) having a hairpin-like structure is known as a precursor of "hsa-miR-4727-3p."

The term "hsa-miR-4728-5p gene" or "hsa-miR-4728-5p" used herein includes the hsa-miR-4728-5p gene (miRBase Accession No. MIMAT0019849) shown in SEQ ID NO: 126, a homolog or an ortholog of a different organism species, and the like. The gene can be obtained by a method described in Persson H et al., 2011, Cancer Res., Vol. 71, pp. 78-86. Also, "hsa-mir-4728" (miRBase Accession No. MI0017365; SEQ ID NO: 361) having a hairpin-like structure is known as a precursor of "hsa-miR-4728-5p."

The term "hsa-miR-4731-5p gene" or "hsa-miR-4731-5p" used herein includes the hsa-miR-4731-5p gene (miRBase Accession No. MIMAT0019853) shown in SEQ ID NO: 127, a homolog or an ortholog of a different organism species, and the like. The gene can be obtained by a method described in Persson H et al., 2011, Cancer Res., Vol. 71, pp. 78-86. Also, "hsa-mir-4731" (miRBase Accession No. MI0017368; SEQ ID NO: 362) having a hairpin-like structure is known as a precursor of "hsa-miR-4731-5p."

The term "hsa-miR-4736 gene" or "hsa-miR-4736" used herein includes the hsa-miR-4736 gene (miRBase Accession No. MIMAT0019862) shown in SEQ ID NO: 128, a homolog or an ortholog of a different organism species, and the like. The gene can be obtained by a method described in Persson H et al., 2011, Cancer Res., Vol. 71, pp. 78-86. Also, "hsa-mir-4736" (miRBase Accession No. MI0017373; SEQ ID NO: 363) having a hairpin-like structure is known as a precursor of "hsa-miR-4736."

The term "hsa-miR-4739 gene" or "hsa-miR-4739" used herein includes the hsa-miR-4739 gene (miRBase Accession No. MIMAT0019868) shown in SEQ ID NO: 129, a homolog or an ortholog of a different organism species, and the like. The gene can be obtained by a method described in Persson H et al., 2011, Cancer Res., Vol. 71, pp. 78-86. Also, "hsa-mir-4739" (miRBase Accession No. MI0017377; SEQ ID NO: 364) having a hairpin-like structure is known as a precursor of "hsa-miR-4739."

The term "hsa-miR-4740-5p gene" or "hsa-miR-4740-5p" used herein includes the hsa-miR-4740-5p gene (miRBase Accession No. MIMAT0019869) shown in SEQ ID NO: 130, a homolog or an ortholog of a different organism species, and the like. The gene can be obtained by a method described in Persson H et al., 2011, Cancer Res., Vol. 71, pp. 78-86. Also, "hsa-mir-4740" (miRBase Accession No. MI0017378; SEQ ID NO: 365) having a hairpin-like structure is known as a precursor of "hsa-miR-4740-5p."

The term "hsa-miR-4741 gene" or "hsa-miR-4741" used herein includes the hsa-miR-4741 gene (miRBase Accession No. MIMAT0019871) shown in SEQ ID NO: 131, a homolog or an ortholog of a different organism species, and the like. The gene can be obtained by a method described in Persson H et al., 2011, Cancer Res., Vol. 71, pp. 78-86. Also, "hsa-mir-4741" (miRBase Accession No. MI0017379; SEQ ID NO: 366) having a hairpin-like structure is known as a precursor of "hsa-miR-4741."

The term "hsa-miR-4750-5p gene" or "hsa-miR-4750-5p" used herein includes the hsa-miR-4750-5p gene (miRBase Accession No. MIMAT0019887) shown in SEQ ID NO: 132, a homolog or an ortholog of a different organism species, and the like. The gene can be obtained by a method described in Persson H et al., 2011, Cancer Res., Vol. 71, pp. 78-86. Also, "hsa-mir-4750" (miRBase Accession No. MI0017389; SEQ ID NO: 367) having a hairpin-like structure is known as a precursor of "hsa-miR-4750-5p."

The term "hsa-miR-4755-3p gene" or "hsa-miR-4755-3p" used herein includes the hsa-miR-4755-3p gene (miRBase Accession No. MIMAT0019896) shown in SEQ ID NO: 133, a homolog or an ortholog of a different organism species, and the like. The gene can be obtained by a method described in Persson H et al., 2011, Cancer Res., Vol. 71, pp. 78-86. Also, "hsa-mir-4755" (miRBase Accession No. MI0017395; SEQ ID NO: 368) having a hairpin-like structure is known as a precursor of "hsa-miR-4755-3p."

The term "hsa-miR-4763-3p gene" or "hsa-miR-4763-3p" used herein includes the hsa-miR-4763-3p gene (miRBase Accession No. MIMAT0019913) shown in SEQ ID NO: 134, a homolog or an ortholog of a different organism species, and the like. The gene can be obtained by a method described in Persson H et al., 2011, Cancer Res., Vol. 71, pp. 78-86. Also, "hsa-mir-4763" (miRBase Accession No. MI0017404; SEQ ID NO: 369) having a hairpin-like structure is known as a precursor of "hsa-miR-4763-3p."

The term "hsa-miR-4771 gene" or "hsa-miR-4771" used herein includes the hsa-miR-4771 gene (miRBase Accession No. MIMAT0019925) shown in SEQ ID NO: 135, a homolog or an ortholog of a different organism species, and the like. The gene can be obtained by a method described in Persson H et al., 2011, Cancer Res., Vol. 71, pp. 78-86. Also, "hsa-mir-4771-1" (miRBase Accession No. MI0017412; SEQ ID NO: 479) and "hsa-mir-4771-2" (miRBase Accession No. MI0017413; SEQ ID NO: 491) each having a hairpin-like structure are known as precursors of "hsa-miR-4771."

The term "hsa-miR-4783-3p gene" or "hsa-miR-4783-3p" used herein includes the hsa-miR-4783-3p gene (miRBase Accession No. MIMAT0019947) shown in SEQ ID NO: 136, a homolog or an ortholog of a different organism species, and the like. The gene can be obtained by a method described in Persson H et al., 2011, Cancer Res., Vol. 71, pp. 78-86. Also, "hsa-mir-4783" (miRBase Accession No. MI0017428; SEQ ID NO: 370) having a hairpin-like structure is known as a precursor of "hsa-miR-4783-3p."

The term "hsa-miR-4783-5p gene" or "hsa-miR-4783-5p" used herein includes the hsa-miR-4783-5p gene (miRBase Accession No. MIMAT0019946) shown in SEQ ID NO: 137, a homolog or an ortholog of a different organism species, and the like. The gene can be obtained by a method described in Persson H et al., 2011, Cancer Res., Vol. 71, pp. 78-86. Also, "hsa-mir-4783" (miRBase Accession No. MI0017428; SEQ ID NO: 371) having a hairpin-like structure is known as a precursor of "hsa-miR-4783-5p."

The term "hsa-miR-4787-3p gene" or "hsa-miR-4787-3p" used herein includes the hsa-miR-4787-3p gene (miRBase Accession No. MIMAT0019957) shown in SEQ ID NO: 138, a homolog or an ortholog of a different organism species, and the like. The gene can be obtained by a method described in Persson H et al., 2011, Cancer Res., Vol. 71, pp. 78-86. Also, "hsa-mir-4787" (miRBase Accession No. MI0017434; SEQ ID NO: 372) having a hairpin-like structure is known as a precursor of "hsa-miR-4787-3p."

The term "hsa-miR-4792 gene" or "hsa-miR-4792" used herein includes the hsa-miR-4792 gene (miRBase Accession No. MIMAT0019964) shown in SEQ ID NO: 139, a homolog or an ortholog of a different organism species, and the like. The gene can be obtained by a method described in Persson H et al., 2011, Cancer Res., Vol. 71, pp. 78-86. Also, "hsa-mir-4792" (miRBase Accession No. MI0017439; SEQ ID NO: 373) having a hairpin-like structure is known as a precursor of "hsa-miR-4792."

The term "hsa-miR-498 gene" or "hsa-miR-498" used herein includes the hsa-miR-498 gene (miRBase Accession No. MIMAT0002824) shown in SEQ ID NO: 140, a homolog or an ortholog of a different organism species, and the like. The gene can be obtained by a method described in Bentwich I et al., 2005, Nat. Genet., Vol. 37, pp. 766-770. Also, "hsa-mir-498" (miRBase Accession No. MI0003142; SEQ ID NO: 374) having a hairpin-like structure is known as a precursor of "hsa-miR-498."

The term "hsa-miR-5008-5p gene" or "hsa-miR-5008-5p" used herein includes the hsa-miR-5008-5p gene (miRBase Accession No. MIMAT0021039) shown in SEQ ID NO: 141, a homolog or an ortholog of a different organism species, and the like. The gene can be obtained by a method described in Hansen T B et al., 2011, RNA Biol., Vol. 8, pp. 378-383. Also, "hsa-mir-5008" (miRBase Accession No. MI0017876; SEQ ID NO: 375) having a hairpin-like structure is known as a precursor of "hsa-miR-5008-5p."

The term "hsa-miR-5010-5p gene" or "hsa-miR-5010-5p" used herein includes the hsa-miR-5010-5p gene (miRBase Accession No. MIMAT0021043) shown in SEQ ID NO: 142, a homolog or an ortholog of a different organism species, and the like. The gene can be obtained by a method described in Hansen T B et al., 2011, RNA Biol., Vol. 8, pp. 378-383. Also, "hsa-mir-5010" (miRBase Accession No.

MI0017878; SEQ ID NO: 376) having a hairpin-like structure is known as a precursor of "hsa-miR-5010-5p."

The term "hsa-miR-504-3p gene" or "hsa-miR-504-3p" used herein includes the hsa-miR-504-3p gene (miRBase Accession No. MIMAT0026612) shown in SEQ ID NO: 143, a homolog or an ortholog of a different organism species, and the like. The gene can be obtained by a method described in Bentwich I et al., 2005, Nat. Genet., Vol. 37, pp. 766-770. Also, "hsa-mir-504" (miRBase Accession No. MI0003189; SEQ ID NO: 377) having a hairpin-like structure is known as a precursor of "hsa-miR-504-3p."

The term "hsa-miR-5195-3p gene" or "hsa-miR-5195-3p" used herein includes the hsa-miR-5195-3p gene (miRBase Accession No. MIMAT0021127) shown in SEQ ID NO: 144, a homolog or an ortholog of a different organism species, and the like. The gene can be obtained by a method described in Schotte D et al., 2011, Leukemia, Vol. 25, pp. 1389-1399. Also, "hsa-mir-5195" (miRBase Accession No. MI0018174; SEQ ID NO: 378) having a hairpin-like structure is known as a precursor of "hsa-miR-5195-3p."

The term "hsa-miR-550a-5p gene" or "hsa-miR-550a-5p" used herein includes the hsa-miR-550a-5p gene (miRBase Accession No. MIMAT0004800) shown in SEQ ID NO: 145, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-550a-1" (miRBase Accession No. MI0003600; SEQ ID NO: 480) and "hsa-mir-550a-2" (miRBase Accession No. MI0003601; SEQ ID NO: 492) each having a hairpin-like structure are known as precursors of "hsa-miR-550a-5p."

The term "hsa-miR-5572 gene" or "hsa-miR-5572" used herein includes the hsa-miR-5572 gene (miRBase Accession No. MIMAT0022260) shown in SEQ ID NO: 146, a homolog or an ortholog of a different organism species, and the like. The gene can be obtained by a method described in Tandon M et al., 2012, Oral Dis., Vol. 18, pp. 127-131. Also, "hsa-mir-5572" (miRBase Accession No. MI0019117; SEQ ID NO: 379) having a hairpin-like structure is known as a precursor of "hsa-miR-5572."

The term "hsa-miR-5739 gene" or "hsa-miR-5739" used herein includes the hsa-miR-5739 gene (miRBase Accession No. MIMAT0023116) shown in SEQ ID NO: 147, a homolog or an ortholog of a different organism species, and the like. The gene can be obtained by a method described in Yoo J K et al., 2011, Biochem. Biophys. Res. Commun., Vol. 415, pp. 258-262. Also, "hsa-mir-5739" (miRBase Accession No. MI0019412; SEQ ID NO: 380) having a hairpin-like structure is known as a precursor of "hsa-miR-5739."

The term "hsa-miR-6075 gene" or "hsa-miR-6075" used herein includes the hsa-miR-6075 gene (miRBase Accession No. MIMAT0023700) shown in SEQ ID NO: 148, a homolog or an ortholog of a different organism species, and the like. The gene can be obtained by a method described in Voellenkle C et al., 2012, RNA, Vol. 18, pp. 472-484. Also, "hsa-mir-6075" (miRBase Accession No. MI0020352; SEQ ID NO: 381) having a hairpin-like structure is known as a precursor of "hsa-miR-6075."

The term "hsa-miR-6076 gene" or "hsa-miR-6076" used herein includes the hsa-miR-6076 gene (miRBase Accession No. MIMAT0023701) shown in SEQ ID NO: 149, a homolog or an ortholog of a different organism species, and the like. The gene can be obtained by a method described in Voellenkle C et al., 2012, RNA, Vol. 18, pp. 472-484. Also, "hsa-mir-6076" (miRBase Accession No. MI0020353; SEQ ID NO: 382) having a hairpin-like structure is known as a precursor of "hsa-miR-6076."

The term "hsa-miR-6088 gene" or "hsa-miR-6088" used herein includes the hsa-miR-6088 gene (miRBase Accession No. MIMAT0023713) shown in SEQ ID NO: 150, a homolog or an ortholog of a different organism species, and the like. The gene can be obtained by a method described in Yoo J K et al., 2012, Stem Cells Dev., Vol. 21, pp. 2049-2057. Also, "hsa-mir-6088" (miRBase Accession No. MI0020365; SEQ ID NO: 383) having a hairpin-like structure is known as a precursor of "hsa-miR-6088."

The term "hsa-miR-6124 gene" or "hsa-miR-6124" used herein includes the hsa-miR-6124 gene (miRBase Accession No. MIMAT0024597) shown in SEQ ID NO: 151, a homolog or an ortholog of a different organism species, and the like. The gene can be obtained by a method described in Smith J L et al., 2012, J. Virol., Vol. 86, pp. 5278-5287. Also, "hsa-mir-6124" (miRBase Accession No. MI0021258; SEQ ID NO: 384) having a hairpin-like structure is known as a precursor of "hsa-miR-6124."

The term "hsa-miR-6131 gene" or "hsa-miR-6131" used herein includes the hsa-miR-6131 gene (miRBase Accession No. MIMAT0024615) shown in SEQ ID NO: 152, a homolog or an ortholog of a different organism species, and the like. The gene can be obtained by a method described in Dannemann M et al., 2012, Genome Biol. Evol., Vol. 4, pp. 552-564. Also, "hsa-mir-6131" (miRBase Accession No. MI0021276; SEQ ID NO: 385) having a hairpin-like structure is known as a precursor of "hsa-miR-6131."

The term "hsa-miR-6132 gene" or "hsa-miR-6132" used herein includes the hsa-miR-6132 gene (miRBase Accession No. MIMAT0024616) shown in SEQ ID NO: 153, a homolog or an ortholog of a different organism species, and the like. The gene can be obtained by a method described in Dannemann M et al., 2012, Genome Biol. Evol., Vol. 4, pp. 552-564. Also, "hsa-mir-6132" (miRBase Accession No. MI0021277; SEQ ID NO: 386) having a hairpin-like structure is known as a precursor of "hsa-miR-6132."

The term "hsa-miR-614 gene" or "hsa-miR-614" used herein includes the hsa-miR-614 gene (miRBase Accession No. MIMAT0003282) shown in SEQ ID NO: 154, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-614" (miRBase Accession No. MI0003627; SEQ ID NO: 387) having a hairpin-like structure is known as a precursor of "hsa-miR-614."

The term "hsa-miR-615-5p gene" or "hsa-miR-615-5p" used herein includes the hsa-miR-615-5p gene (miRBase Accession No. MIMAT0004804) shown in SEQ ID NO: 155, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-615" (miRBase Accession No. MI0003628; SEQ ID NO: 388) having a hairpin-like structure is known as a precursor of "hsa-miR-615-5p."

The term "hsa-miR-619-5p gene" or "hsa-miR-619-5p" used herein includes the hsa-miR-619-5p gene (miRBase Accession No. MIMAT0026622) shown in SEQ ID NO: 156, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-619" (miRBase Accession No. MI0003633; SEQ ID NO: 389) having a hairpin-like structure is known as a precursor of "hsa-miR-619-5p."

The term "hsa-miR-642b-3p gene" or "hsa-miR-642b-3p" used herein includes the hsa-miR-642b-3p gene (miRBase Accession No. MIMAT0018444) shown in SEQ ID NO: 157, a homolog or an ortholog of a different organism species, and the like. The gene can be obtained by a method described in Witten D et al., 2010, BMC Biol., Vol. 8, p. 58. Also, "hsa-mir-642b" (miRBase Accession No. MI0016685; SEQ ID NO: 390) having a hairpin-like structure is known as a precursor of "hsa-miR-642b-3p."

The term "hsa-miR-6510-5p gene" or "hsa-miR-6510-5p" used herein includes the hsa-miR-6510-5p gene (miRBase Accession No. MIMAT0025476) shown in SEQ ID NO: 158, a homolog or an ortholog of a different organism species, and the like. The gene can be obtained by a method described in Joyce C E et al., 2011, Hum. Mol. Genet., Vol. 20, pp. 4025-4040. Also, "hsa-mir-6510" (miRBase Accession No. MI0022222; SEQ ID NO: 391) having a hairpin-like structure is known as a precursor of "hsa-miR-6510-5p."

The term "hsa-miR-6511a-5p gene" or "hsa-miR-6511a-5p" used herein includes the hsa-miR-6511a-5p gene (miRBase Accession No. MIMAT0025478) shown in SEQ ID NO: 159, a homolog or an ortholog of a different organism species, and the like. The gene can be obtained by a method described in Joyce C E et al., 2011, Hum. Mol. Genet., Vol. 20, pp. 4025-4040. Also, "hsa-mir-6511a-1" (miRBase Accession No. MI0022223; SEQ ID NO: 499), "hsa-mir-6511a-2" (miRBase Accession No. MI0023564; SEQ ID NO: 501), "hsa-mir-6511a-3" (miRBase Accession No. MI0023565; SEQ ID NO: 503), and "hsa-mir-6511a-4" (miRBase Accession No. MI0023566; SEQ ID NO: 505) each having a hairpin-like structure are known as precursors of "hsa-miR-6511a-5p."

The term "hsa-miR-6515-3p gene" or "hsa-miR-6515-3p" used herein includes the hsa-miR-6515-3p gene (miRBase Accession No. MIMAT0025487) shown in SEQ ID NO: 160, a homolog or an ortholog of a different organism species, and the like. The gene can be obtained by a method described in Joyce C E et al., 2011, Hum. Mol. Genet., Vol. 20, pp. 4025-4040. Also, "hsa-mir-6515" (miRBase Accession No. MI0022227; SEQ ID NO: 392) having a hairpin-like structure is known as a precursor of "hsa-miR-6515-3p."

The term "hsa-miR-6515-5p gene" or "hsa-miR-6515-5p" used herein includes the hsa-miR-6515-5p gene (miRBase Accession No. MIMAT0025486) shown in SEQ ID NO: 161, a homolog or an ortholog of a different organism species, and the like. The gene can be obtained by a method described in Joyce C E et al., 2011, Hum. Mol. Genet., Vol. 20, pp. 4025-4040. Also, "hsa-mir-6515" (miRBase Accession No. MI0022227; SEQ ID NO: 393) having a hairpin-like structure is known as a precursor of "hsa-miR-6515-5p."

The term "hsa-miR-663b gene" or "hsa-miR-663b" used herein includes the hsa-miR-663b gene (miRBase Accession No. MIMAT0005867) shown in SEQ ID NO: 162, a homolog or an ortholog of a different organism species, and the like. The gene can be obtained by a method described in Takada S et al., 2008, Leukemia., Vol. 22, pp. 1274-1278. Also, "hsa-mir-663b" (miRBase Accession No. MI0006336; SEQ ID NO: 394) having a hairpin-like structure is known as a precursor of "hsa-miR-663b."

The term "hsa-miR-6716-5p gene" or "hsa-miR-6716-5p" used herein includes the hsa-miR-6716-5p gene (miRBase Accession No. MIMAT0025844) shown in SEQ ID NO: 163, a homolog or an ortholog of a different organism species, and the like. The gene can be obtained by a method described in Li Y et al., 2012, Gene, Vol. 497, pp. 330-335. Also, "hsa-mir-6716" (miRBase Accession No. MI0022550; SEQ ID NO: 395) having a hairpin-like structure is known as a precursor of "hsa-miR-6716-5p."

The term "hsa-miR-6717-5p gene" or "hsa-miR-6717-5p" used herein includes the hsa-miR-6717-5p gene (miRBase Accession No. MIMAT0025846) shown in SEQ ID NO: 164, a homolog or an ortholog of a different organism species, and the like. The gene can be obtained by a method described in Li Y et al., 2012, Gene, Vol. 497, pp. 330-335. Also, "hsa-mir-6717" (miRBase Accession No. MI0022551; SEQ ID NO: 396) having a hairpin-like structure is known as a precursor of "hsa-miR-6717-5p."

The term "hsa-miR-6722-3p gene" or "hsa-miR-6722-3p" used herein includes the hsa-miR-6722-3p gene (miRBase Accession No. MIMAT0025854) shown in SEQ ID NO: 165, a homolog or an ortholog of a different organism species, and the like. The gene can be obtained by a method described in Li Y et al., 2012, Gene, Vol. 497, pp. 330-335. Also, "hsa-mir-6722" (miRBase Accession No. MI0022557; SEQ ID NO: 397) having a hairpin-like structure is known as a precursor of "hsa-miR-6722-3p."

The term "hsa-miR-6724-5p gene" or "hsa-miR-6724-5p" used herein includes the hsa-miR-6724-5p gene (miRBase Accession No. MIMAT0025856) shown in SEQ ID NO: 166, a homolog or an ortholog of a different organism species, and the like. The gene can be obtained by a method described in Li Y et al., 2012, Gene, Vol. 497, pp. 330-335. Also, "hsa-mir-6724-1" (miRBase Accession No. MI0022559; SEQ ID NO: 500), "hsa-mir-6724-2" (miRBase Accession No. MI0031516; SEQ ID NO: 502), "hsa-mir-6724-3" (miRBase Accession No. MI0031517; SEQ ID NO: 504), and "hsa-mir-6724-4" (miRBase Accession No. MI0031518; SEQ ID NO: 506) each having a hairpin-like structure are known as precursors of "hsa-miR-6724-5p."

The term "hsa-miR-6726-5p gene" or "hsa-miR-6726-5p" used herein includes the hsa-miR-6726-5p gene (miRBase Accession No. MIMAT0027353) shown in SEQ ID NO: 167, a homolog or an ortholog of a different organism species, and the like. The gene can be obtained by a method described in Ladewig E et al., 2012, Genome Res., Vol. 22, pp. 1634-1645. Also, "hsa-mir-6726" (miRBase Accession No. MI0022571; SEQ ID NO: 398) having a hairpin-like structure is known as a precursor of "hsa-miR-6726-5p."

The term "hsa-miR-6737-5p gene" or "hsa-miR-6737-5p" used herein includes the hsa-miR-6737-5p gene (miRBase Accession No. MIMAT0027375) shown in SEQ ID NO: 168, a homolog or an ortholog of a different organism species, and the like. The gene can be obtained by a method described in Ladewig E et al., 2012, Genome Res., Vol. 22, pp. 1634-1645. Also, "hsa-mir-6737" (miRBase Accession No. MI0022582; SEQ ID NO: 399) having a hairpin-like structure is known as a precursor of "hsa-miR-6737-5p."

The term "hsa-miR-6741-5p gene" or "hsa-miR-6741-5p" used herein includes the hsa-miR-6741-5p gene (miRBase Accession No. MIMAT0027383) shown in SEQ ID NO: 169, a homolog or an ortholog of a different organism species, and the like. The gene can be obtained by a method described in Ladewig E et al., 2012, Genome Res., Vol. 22, pp. 1634-1645. Also, "hsa-mir-6741" (miRBase Accession No. MI0022586; SEQ ID NO: 400) having a hairpin-like structure is known as a precursor of "hsa-miR-6741-5p."

The term "hsa-miR-6742-5p gene" or "hsa-miR-6742-5p" used herein includes the hsa-miR-6742-5p gene (miRBase Accession No. MIMAT0027385) shown in SEQ ID NO: 170, a homolog or an ortholog of a different organism species, and the like. The gene can be obtained by a method described in Ladewig E et al., 2012, Genome Res., Vol. 22, pp. 1634-1645. Also, "hsa-mir-6742" (miRBase Accession No. MI0022587; SEQ ID NO: 401) having a hairpin-like structure is known as a precursor of "hsa-miR-6742-5p."

The term "hsa-miR-6743-5p gene" or "hsa-miR-6743-5p" used herein includes the hsa-miR-6743-5p gene (miRBase Accession No. MIMAT0027387) shown in SEQ ID NO: 171, a homolog or an ortholog of a different organism species, and the like. The gene can be obtained by a method described in Ladewig E et al., 2012, Genome Res., Vol. 22, pp. 1634-1645. Also, "hsa-mir-6743" (miRBase Accession No. MI0022588; SEQ ID NO: 402) having a hairpin-like structure is known as a precursor of "hsa-miR-6743-5p."

The term "hsa-miR-6746-5p gene" or "hsa-miR-6746-5p" used herein includes the hsa-miR-6746-5p gene (miRBase Accession No. MIMAT0027392) shown in SEQ ID NO: 172, a homolog or an ortholog of a different organism species, and the like. The gene can be obtained by a method described in Ladewig E et al., 2012, Genome Res., Vol. 22, pp. 1634-1645. Also, "hsa-mir-6746" (miRBase Accession No. MI0022591; SEQ ID NO: 403) having a hairpin-like structure is known as a precursor of "hsa-miR-6746-5p."

The term "hsa-miR-6749-5p gene" or "hsa-miR-6749-5p" used herein includes the hsa-miR-6749-5p gene (miRBase Accession No. MIMAT0027398) shown in SEQ ID NO: 173, a homolog or an ortholog of a different organism species, and the like. The gene can be obtained by a method described in Ladewig E et al., 2012, Genome Res., Vol. 22, pp. 1634-1645. Also, "hsa-mir-6749" (miRBase Accession No. MI0022594; SEQ ID NO: 404) having a hairpin-like structure is known as a precursor of "hsa-miR-6749-5p."

The term "hsa-miR-6760-5p gene" or "hsa-miR-6760-5p" used herein includes the hsa-miR-6760-5p gene (miRBase Accession No. MIMAT0027420) shown in SEQ ID NO: 174, a homolog or an ortholog of a different organism species, and the like. The gene can be obtained by a method described in Ladewig E et al., 2012, Genome Res., Vol. 22, pp. 1634-1645. Also, "hsa-mir-6760" (miRBase Accession No. MI0022605; SEQ ID NO: 405) having a hairpin-like structure is known as a precursor of "hsa-miR-6760-5p."

The term "hsa-miR-6762-5p gene" or "hsa-miR-6762-5p" used herein includes the hsa-miR-6762-5p gene (miRBase Accession No. MIMAT0027424) shown in SEQ ID NO: 175, a homolog or an ortholog of a different organism species, and the like. The gene can be obtained by a method described in Ladewig E et al., 2012, Genome Res., Vol. 22, pp. 1634-1645. Also, "hsa-mir-6762" (miRBase Accession No. MI0022607; SEQ ID NO: 406) having a hairpin-like structure is known as a precursor of "hsa-miR-6762-5p."

The term "hsa-miR-6765-3p gene" or "hsa-miR-6765-3p" used herein includes the hsa-miR-6765-3p gene (miRBase Accession No. MIMAT0027431) shown in SEQ ID NO: 176, a homolog or an ortholog of a different organism species, and the like. The gene can be obtained by a method described in Ladewig E et al., 2012, Genome Res., Vol. 22, pp. 1634-1645. Also, "hsa-mir-6765" (miRBase Accession No. MI0022610; SEQ ID NO: 407) having a hairpin-like structure is known as a precursor of "hsa-miR-6765-3p."

The term "hsa-miR-6765-5p gene" or "hsa-miR-6765-5p" used herein includes the hsa-miR-6765-5p gene (miRBase Accession No. MIMAT0027430) shown in SEQ ID NO: 177, a homolog or an ortholog of a different organism species, and the like. The gene can be obtained by a method described in Ladewig E et al., 2012, Genome Res., Vol. 22, pp. 1634-1645. Also, "hsa-mir-6765" (miRBase Accession No. MI0022610; SEQ ID NO: 408) having a hairpin-like structure is known as a precursor of "hsa-miR-6765-5p."

The term "hsa-miR-6766-3p gene" or "hsa-miR-6766-3p" used herein includes the hsa-miR-6766-3p gene (miRBase Accession No. MIMAT0027433) shown in SEQ ID NO: 178, a homolog or an ortholog of a different organism species, and the like. The gene can be obtained by a method described in Ladewig E et al., 2012, Genome Res., Vol. 22, pp. 1634-1645. Also, "hsa-mir-6766" (miRBase Accession No. MI0022611; SEQ ID NO: 409) having a hairpin-like structure is known as a precursor of "hsa-miR-6766-3p."

The term "hsa-miR-6766-5p gene" or "hsa-miR-6766-5p" used herein includes the hsa-miR-6766-5p gene (miRBase Accession No. MIMAT0027432) shown in SEQ ID NO: 179, a homolog or an ortholog of a different organism species, and the like. The gene can be obtained by a method described in Ladewig E et al., 2012, Genome Res., Vol. 22, pp. 1634-1645. Also, "hsa-mir-6766" (miRBase Accession No. MI0022611; SEQ ID NO: 410) having a hairpin-like structure is known as a precursor of "hsa-miR-6766-5p."

The term "hsa-miR-6771-5p gene" or "hsa-miR-6771-5p" used herein includes the hsa-miR-6771-5p gene (miRBase Accession No. MIMAT0027442) shown in SEQ ID NO: 180, a homolog or an ortholog of a different organism species, and the like. The gene can be obtained by a method described in Ladewig E et al., 2012, Genome Res., Vol. 22, pp. 1634-1645. Also, "hsa-mir-6771" (miRBase Accession No. MI0022616; SEQ ID NO: 411) having a hairpin-like structure is known as a precursor of "hsa-miR-6771-5p."

The term "hsa-miR-6774-5p gene" or "hsa-miR-6774-5p" used herein includes the hsa-miR-6774-5p gene (miRBase Accession No. MIMAT0027448) shown in SEQ ID NO: 181, a homolog or an ortholog of a different organism species, and the like. The gene can be obtained by a method described in Ladewig E et al., 2012, Genome Res., Vol. 22, pp. 1634-1645. Also, "hsa-mir-6774" (miRBase Accession No. MI0022619; SEQ ID NO: 412) having a hairpin-like structure is known as a precursor of "hsa-miR-6774-5p."

The term "hsa-miR-6777-5p gene" or "hsa-miR-6777-5p" used herein includes the hsa-miR-6777-5p gene (miRBase Accession No. MIMAT0027454) shown in SEQ ID NO: 182, a homolog or an ortholog of a different organism species, and the like. The gene can be obtained by a method described in Ladewig E et al., 2012, Genome Res., Vol. 22, pp. 1634-1645. Also, "hsa-mir-6777" (miRBase Accession No. MI0022622; SEQ ID NO: 413) having a hairpin-like structure is known as a precursor of "hsa-miR-6777-5p."

The term "hsa-miR-6778-5p gene" or "hsa-miR-6778-5p" used herein includes the hsa-miR-6778-5p gene (miRBase Accession No. MIMAT0027456) shown in SEQ ID NO: 183, a homolog or an ortholog of a different organism species, and the like. The gene can be obtained by a method described in Ladewig E et al., 2012, Genome Res., Vol. 22, pp. 1634-1645. Also, "hsa-mir-6778" (miRBase Accession No. MI0022623; SEQ ID NO: 414) having a hairpin-like structure is known as a precursor of "hsa-miR-6778-5p."

The term "hsa-miR-6780b-5p gene" or "hsa-miR-6780b-5p" used herein includes the hsa-miR-6780b-5p gene (miRBase Accession No. MIMAT0027572) shown in SEQ ID NO: 184, a homolog or an ortholog of a different organism species, and the like. The gene can be obtained by a method described in Ladewig E et al., 2012, Genome Res., Vol. 22, pp. 1634-1645. Also, "hsa-mir-6780b" (miRBase Accession No. MI0022681; SEQ ID NO: 415) having a hairpin-like structure is known as a precursor of "hsa-miR-6780b-5p."

The term "hsa-miR-6781-5p gene" or "hsa-miR-6781-5p" used herein includes the hsa-miR-6781-5p gene (miRBase Accession No. MIMAT0027462) shown in SEQ ID NO: 185, a homolog or an ortholog of a different organism species, and the like. The gene can be obtained by a method described in Ladewig E et al., 2012, Genome Res., Vol. 22, pp. 1634-1645. Also, "hsa-mir-6781" (miRBase Accession No. MI0022626; SEQ ID NO: 416) having a hairpin-like structure is known as a precursor of "hsa-miR-6781-5p."

The term "hsa-miR-6782-5p gene" or "hsa-miR-6782-5p" used herein includes the hsa-miR-6782-5p gene (miRBase Accession No. MIMAT0027464) shown in SEQ ID NO: 186, a homolog or an ortholog of a different organism species, and the like. The gene can be obtained by a method described in Ladewig E et al., 2012, Genome Res., Vol. 22, pp. 1634-1645. Also, "hsa-mir-6782" (miRBase Accession No. MI0022627; SEQ ID NO: 417) having a hairpin-like structure is known as a precursor of "hsa-miR-6782-5p."

The term "hsa-miR-6784-5p gene" or "hsa-miR-6784-5p" used herein includes the hsa-miR-6784-5p gene (miRBase Accession No. MIMAT0027468) shown in SEQ ID NO: 187, a homolog or an ortholog of a different organism species, and the like. The gene can be obtained by a method described in Ladewig E et al., 2012, Genome Res., Vol. 22, pp. 1634-1645. Also, "hsa-mir-6784" (miRBase Accession No. MI0022629; SEQ ID NO: 418) having a hairpin-like structure is known as a precursor of "hsa-miR-6784-5p."

The term "hsa-miR-6785-5p gene" or "hsa-miR-6785-5p" used herein includes the hsa-miR-6785-5p gene (miRBase Accession No. MIMAT0027470) shown in SEQ ID NO: 188, a homolog or an ortholog of a different organism species, and the like. The gene can be obtained by a method described in Ladewig E et al., 2012, Genome Res., Vol. 22, pp. 1634-1645. Also, "hsa-mir-6785" (miRBase Accession No. MI0022630; SEQ ID NO: 419) having a hairpin-like structure is known as a precursor of "hsa-miR-6785-5p."

The term "hsa-miR-6787-5p gene" or "hsa-miR-6787-5p" used herein includes the hsa-miR-6787-5p gene (miRBase Accession No. MIMAT0027474) shown in SEQ ID NO: 189, a homolog or an ortholog of a different organism species, and the like. The gene can be obtained by a method described in Ladewig E et al., 2012, Genome Res., Vol. 22, pp. 1634-1645. Also, "hsa-mir-6787" (miRBase Accession No. MI0022632; SEQ ID NO: 420) having a hairpin-like structure is known as a precursor of "hsa-miR-6787-5p."

The term "hsa-miR-6789-5p gene" or "hsa-miR-6789-5p" used herein includes the hsa-miR-6789-5p gene (miRBase Accession No. MIMAT0027478) shown in SEQ ID NO: 190, a homolog or an ortholog of a different organism species, and the like. The gene can be obtained by a method described in Ladewig E et al., 2012, Genome Res., Vol. 22, pp. 1634-1645. Also, "hsa-mir-6789" (miRBase Accession No. MI0022634; SEQ ID NO: 421) having a hairpin-like structure is known as a precursor of "hsa-miR-6789-5p."

The term "hsa-miR-6791-5p gene" or "hsa-miR-6791-5p" used herein includes the hsa-miR-6791-5p gene (miRBase Accession No. MIMAT0027482) shown in SEQ ID NO: 191, a homolog or an ortholog of a different organism species, and the like. The gene can be obtained by a method described in Ladewig E et al., 2012, Genome Res., Vol. 22, pp. 1634-1645. Also, "hsa-mir-6791" (miRBase Accession No. MI0022636; SEQ ID NO: 422) having a hairpin-like structure is known as a precursor of "hsa-miR-6791-5p."

The term "hsa-miR-6794-5p gene" or "hsa-miR-6794-5p" used herein includes the hsa-miR-6794-5p gene (miRBase Accession No. MIMAT0027488) shown in SEQ ID NO: 192, a homolog or an ortholog of a different organism species, and the like. The gene can be obtained by a method described in Ladewig E et al., 2012, Genome Res., Vol. 22, pp. 1634-1645. Also, "hsa-mir-6794" (miRBase Accession No. MI0022639; SEQ ID NO: 423) having a hairpin-like structure is known as a precursor of "hsa-miR-6794-5p."

The term "hsa-miR-6800-5p gene" or "hsa-miR-6800-5p" used herein includes the hsa-miR-6800-5p gene (miRBase Accession No. MIMAT0027500) shown in SEQ ID NO: 193, a homolog or an ortholog of a different organism species, and the like. The gene can be obtained by a method described in Ladewig E et al., 2012, Genome Res., Vol. 22, pp. 1634-1645. Also, "hsa-mir-6800" (miRBase Accession No. MI0022645; SEQ ID NO: 424) having a hairpin-like structure is known as a precursor of "hsa-miR-6800-5p."

The term "hsa-miR-6802-5p gene" or "hsa-miR-6802-5p" used herein includes the hsa-miR-6802-5p gene (miRBase Accession No. MIMAT0027504) shown in SEQ ID NO: 194, a homolog or an ortholog of a different organism species, and the like. The gene can be obtained by a method described in Ladewig E et al., 2012, Genome Res., Vol. 22, pp. 1634-1645. Also, "hsa-mir-6802" (miRBase Accession No. MI0022647; SEQ ID NO: 425) having a hairpin-like structure is known as a precursor of "hsa-miR-6802-5p."

The term "hsa-miR-6803-5p gene" or "hsa-miR-6803-5p" used herein includes the hsa-miR-6803-5p gene (miRBase Accession No. MIMAT0027506) shown in SEQ ID NO: 195, a homolog or an ortholog of a different organism species, and the like. The gene can be obtained by a method described in Ladewig E et al., 2012, Genome Res., Vol. 22, pp. 1634-1645. Also, "hsa-mir-6803" (miRBase Accession No. MI0022648; SEQ ID NO: 426) having a hairpin-like structure is known as a precursor of "hsa-miR-6803-5p."

The term "hsa-miR-6812-5p gene" or "hsa-miR-6812-5p" used herein includes the hsa-miR-6812-5p gene (miRBase Accession No. MIMAT0027524) shown in SEQ ID NO: 196, a homolog or an ortholog of a different organism species, and the like. The gene can be obtained by a method described in Ladewig E et al., 2012, Genome Res., Vol. 22, pp. 1634-1645. Also, "hsa-mir-6812" (miRBase Accession No. MI0022657; SEQ ID NO: 427) having a hairpin-like structure is known as a precursor of "hsa-miR-6812-5p."

The term "hsa-miR-6816-5p gene" or "hsa-miR-6816-5p" used herein includes the hsa-miR-6816-5p gene (miRBase Accession No. MIMAT0027532) shown in SEQ ID NO: 197, a homolog or an ortholog of a different organism species, and the like. The gene can be obtained by a method described in Ladewig E et al., 2012, Genome Res., Vol. 22, pp. 1634-1645. Also, "hsa-mir-6816" (miRBase Accession No. MI0022661; SEQ ID NO: 428) having a hairpin-like structure is known as a precursor of "hsa-miR-6816-5p."

The term "hsa-miR-6819-5p gene" or "hsa-miR-6819-5p" used herein includes the hsa-miR-6819-5p gene (miRBase Accession No. MIMAT0027538) shown in SEQ ID NO: 198, a homolog or an ortholog of a different organism species, and the like. The gene can be obtained by a method described in Ladewig E et al., 2012, Genome Res., Vol. 22, pp. 1634-1645. Also, "hsa-mir-6819" (miRBase Accession No. MI0022664; SEQ ID NO: 429) having a hairpin-like structure is known as a precursor of "hsa-miR-6819-5p."

The term "hsa-miR-6821-5p gene" or "hsa-miR-6821-5p" used herein includes the hsa-miR-6821-5p gene (miRBase Accession No. MIMAT0027542) shown in SEQ ID NO: 199, a homolog or an ortholog of a different organism species, and the like. The gene can be obtained by a method described in Ladewig E et al., 2012, Genome Res., Vol. 22, pp. 1634-1645. Also, "hsa-mir-6821" (miRBase Accession No. MI0022666; SEQ ID NO: 430) having a hairpin-like structure is known as a precursor of "hsa-miR-6821-5p."

The term "hsa-miR-6826-5p gene" or "hsa-miR-6826-5p" used herein includes the hsa-miR-6826-5p gene (miRBase Accession No. MIMAT0027552) shown in SEQ ID NO: 200, a homolog or an ortholog of a different organism species, and the like. The gene can be obtained by a method described in Ladewig E et al., 2012, Genome Res., Vol. 22, pp. 1634-1645. Also, "hsa-mir-6826" (miRBase Accession No. MI0022671; SEQ ID NO: 431) having a hairpin-like structure is known as a precursor of "hsa-miR-6826-5p."

The term "hsa-miR-6831-5p gene" or "hsa-miR-6831-5p" used herein includes the hsa-miR-6831-5p gene (miRBase Accession No. MIMAT0027562) shown in SEQ ID NO: 201, a homolog or an ortholog of a different organism species, and the like. The gene can be obtained by a method described in Ladewig E et al., 2012, Genome Res., Vol. 22, pp. 1634-1645. Also, "hsa-mir-6831" (miRBase Accession No. MI0022676; SEQ ID NO: 432) having a hairpin-like structure is known as a precursor of "hsa-miR-6831-5p."

The term "hsa-miR-6836-3p gene" or "hsa-miR-6836-3p" used herein includes the hsa-miR-6836-3p gene (miRBase Accession No. MIMAT0027575) shown in SEQ ID NO: 202, a homolog or an ortholog of a different organism species, and the like. The gene can be obtained by a method described in Ladewig E et al., 2012, Genome Res., Vol. 22, pp. 1634-1645. Also, "hsa-mir-6836" (miRBase Accession No. MI0022682; SEQ ID NO: 433) having a hairpin-like structure is known as a precursor of "hsa-miR-6836-3p."

The term "hsa-miR-6840-3p gene" or "hsa-miR-6840-3p" used herein includes the hsa-miR-6840-3p gene (miRBase Accession No. MIMAT0027583) shown in SEQ ID NO: 203, a homolog or an ortholog of a different organism species, and the like. The gene can be obtained by a method described in Ladewig E et al., 2012, Genome Res., Vol. 22, pp. 1634-1645. Also, "hsa-mir-6840" (miRBase Accession No. MI0022686; SEQ ID NO: 434) having a hairpin-like structure is known as a precursor of "hsa-miR-6840-3p."

The term "hsa-miR-6842-5p gene" or "hsa-miR-6842-5p" used herein includes the hsa-miR-6842-5p gene (miRBase Accession No. MIMAT0027586) shown in SEQ ID NO: 204, a homolog or an ortholog of a different organism species, and the like. The gene can be obtained by a method described in Ladewig E et al., 2012, Genome Res., Vol. 22, pp. 1634-1645. Also, "hsa-mir-6842" (miRBase Accession No. MI0022688; SEQ ID NO: 435) having a hairpin-like structure is known as a precursor of "hsa-miR-6842-5p."

The term "hsa-miR-6850-5p gene" or "hsa-miR-6850-5p" used herein includes the hsa-miR-6850-5p gene (miRBase Accession No. MIMAT0027600) shown in SEQ ID NO: 205, a homolog or an ortholog of a different organism species, and the like. The gene can be obtained by a method described in Ladewig E et al., 2012, Genome Res., Vol. 22, pp. 1634-1645. Also, "hsa-mir-6850" (miRBase Accession No. MI0022696; SEQ ID NO: 436) having a hairpin-like structure is known as a precursor of "hsa-miR-6850-5p."

The term "hsa-miR-6861-5p gene" or "hsa-miR-6861-5p" used herein includes the hsa-miR-6861-5p gene (miRBase Accession No. MIMAT0027623) shown in SEQ ID NO: 206, a homolog or an ortholog of a different organism species, and the like. The gene can be obtained by a method described in Ladewig E et al., 2012, Genome Res., Vol. 22, pp. 1634-1645. Also, "hsa-mir-6861" (miRBase Accession No. MI0022708; SEQ ID NO: 437) having a hairpin-like structure is known as a precursor of "hsa-miR-6861-5p."

The term "hsa-miR-6869-5p gene" or "hsa-miR-6869-5p" used herein includes the hsa-miR-6869-5p gene (miRBase Accession No. MIMAT0027638) shown in SEQ ID NO: 207, a homolog or an ortholog of a different organism species, and the like. The gene can be obtained by a method described in Ladewig E et al., 2012, Genome Res., Vol. 22, pp. 1634-1645. Also, "hsa-mir-6869" (miRBase Accession No. MI0022716; SEQ ID NO: 438) having a hairpin-like structure is known as a precursor of "hsa-miR-6869-5p."

The term "hsa-miR-6870-5p gene" or "hsa-miR-6870-5p" used herein includes the hsa-miR-6870-5p gene (miRBase Accession No. MIMAT0027640) shown in SEQ ID NO: 208, a homolog or an ortholog of a different organism species, and the like. The gene can be obtained by a method described in Ladewig E et al., 2012, Genome Res., Vol. 22, pp. 1634-1645. Also, "hsa-mir-6870" (miRBase Accession No. MI0022717; SEQ ID NO: 439) having a hairpin-like structure is known as a precursor of "hsa-miR-6870-5p."

The term "hsa-miR-6877-5p gene" or "hsa-miR-6877-5p" used herein includes the hsa-miR-6877-5p gene (miRBase Accession No. MIMAT0027654) shown in SEQ ID NO: 209, a homolog or an ortholog of a different organism species, and the like. The gene can be obtained by a method described in Ladewig E et al., 2012, Genome Res., Vol. 22, pp. 1634-1645. Also, "hsa-mir-6877" (miRBase Accession No. MI0022724; SEQ ID NO: 440) having a hairpin-like structure is known as a precursor of "hsa-miR-6877-5p."

The term "hsa-miR-6879-5p gene" or "hsa-miR-6879-5p" used herein includes the hsa-miR-6879-5p gene (miRBase Accession No. MIMAT0027658) shown in SEQ ID NO: 210, a homolog or an ortholog of a different organism species, and the like. The gene can be obtained by a method described in Ladewig E et al., 2012, Genome Res., Vol. 22, pp. 1634-1645. Also, "hsa-mir-6879" (miRBase Accession No. MI0022726; SEQ ID NO: 441) having a hairpin-like structure is known as a precursor of "hsa-miR-6879-5p."

The term "hsa-miR-6880-3p gene" or "hsa-miR-6880-3p" used herein includes the hsa-miR-6880-3p gene (miRBase Accession No. MIMAT0027661) shown in SEQ ID NO: 211, a homolog or an ortholog of a different organism species, and the like. The gene can be obtained by a method described in Ladewig E et al., 2012, Genome Res., Vol. 22, pp. 1634-1645. Also, "hsa-mir-6880" (miRBase Accession No. MI0022727; SEQ ID NO: 442) having a hairpin-like structure is known as a precursor of "hsa-miR-6880-3p."

The term "hsa-miR-6880-5p gene" or "hsa-miR-6880-5p" used herein includes the hsa-miR-6880-5p gene (miRBase Accession No. MIMAT0027660) shown in SEQ ID NO: 212, a homolog or an ortholog of a different organism species, and the like. The gene can be obtained by a method described in Ladewig E et al., 2012, Genome Res., Vol. 22, pp. 1634-1645. Also, "hsa-mir-6880" (miRBase Accession No. MI0022727; SEQ ID NO: 443) having a hairpin-like structure is known as a precursor of "hsa-miR-6880-5p."

The term "hsa-miR-6885-5p gene" or "hsa-miR-6885-5p" used herein includes the hsa-miR-6885-5p gene (miRBase Accession No. MIMAT0027670) shown in SEQ ID NO: 213, a homolog or an ortholog of a different organism species, and the like. The gene can be obtained by a method described in Ladewig E et al., 2012, Genome Res., Vol. 22, pp. 1634-1645. Also, "hsa-mir-6885" (miRBase Accession No. MI0022732; SEQ ID NO: 444) having a hairpin-like structure is known as a precursor of "hsa-miR-6885-5p."

The term "hsa-miR-6887-5p gene" or "hsa-miR-6887-5p" used herein includes the hsa-miR-6887-5p gene (miRBase Accession No. MIMAT0027674) shown in SEQ ID NO: 214, a homolog or an ortholog of a different organism species, and the like. The gene can be obtained by a method described in Ladewig E et al., 2012, Genome Res., Vol. 22, pp. 1634-1645. Also, "hsa-mir-6887" (miRBase Accession No. MI0022734; SEQ ID NO: 445) having a hairpin-like structure is known as a precursor of "hsa-miR-6887-5p."

The term "hsa-miR-7107-5p gene" or "hsa-miR-7107-5p" used herein includes the hsa-miR-7107-5p gene (miRBase Accession No. MIMAT0028111) shown in SEQ ID NO: 215, a homolog or an ortholog of a different organism species, and the like. The gene can be obtained by a method described in Ladewig E et al., 2012, Genome Res., Vol. 22, pp. 1634-1645. Also, "hsa-mir-7107" (miRBase Accession No. MI0022958; SEQ ID NO: 446) having a hairpin-like structure is known as a precursor of "hsa-miR-7107-5p."

The term "hsa-miR-7108-3p gene" or "hsa-miR-7108-3p" used herein includes the hsa-miR-7108-3p gene (miRBase Accession No. MIMAT0028114) shown in SEQ ID NO: 216, a homolog or an ortholog of a different organism species, and the like. The gene can be obtained by a method described in Ladewig E et al., 2012, Genome Res., Vol. 22, pp. 1634-1645. Also, "hsa-mir-7108" (miRBase Accession No. MI0022959; SEQ ID NO: 447) having a hairpin-like structure is known as a precursor of "hsa-miR-7108-3p."

The term "hsa-miR-7109-5p gene" or "hsa-miR-7109-5p" used herein includes the hsa-miR-7109-5p gene (miRBase Accession No. MIMAT0028115) shown in SEQ ID NO: 217, a homolog or an ortholog of a different organism species, and the like. The gene can be obtained by a method described in Ladewig E et al., 2012, Genome Res., Vol. 22, pp. 1634-1645. Also, "hsa-mir-7109" (miRBase Accession No. MI0022960; SEQ ID NO: 448) having a hairpin-like structure is known as a precursor of "hsa-miR-7109-5p."

The term "hsa-miR-711 gene" or "hsa-miR-711" used herein includes the hsa-miR-711 gene (miRBase Accession No. MIMAT0012734) shown in SEQ ID NO: 218, a homolog or an ortholog of a different organism species, and the like. The gene can be obtained by a method described in Artzi S et al., 2008, BMC Bioinformatics, Vol. 9, p. 39. Also, "hsa-mir-711" (miRBase Accession No. MI0012488; SEQ ID NO: 449) having a hairpin-like structure is known as a precursor of "hsa-miR-711."

The term "hsa-miR-7113-3p gene" or "hsa-miR-7113-3p" used herein includes the hsa-miR-7113-3p gene (miRBase Accession No. MIMAT0028124) shown in SEQ ID NO: 219, a homolog or an ortholog of a different organism species, and the like. The gene can be obtained by a method described in Ladewig E et al., 2012, Genome Res., Vol. 22, pp. 1634-1645. Also, "hsa-mir-7113" (miRBase Accession No. MI0022964; SEQ ID NO: 450) having a hairpin-like structure is known as a precursor of "hsa-miR-7113-3p."

The term "hsa-miR-7150 gene" or "hsa-miR-7150" used herein includes the hsa-miR-7150 gene (miRBase Accession No. MIMAT0028211) shown in SEQ ID NO: 220, a homolog or an ortholog of a different organism species, and the like. The gene can be obtained by a method described in Oulas A et al., 2009, Nucleic Acids Res., Vol. 37, pp. 3276-3287. Also, "hsa-mir-7150" (miRBase Accession No. MI0023610; SEQ ID NO: 451) having a hairpin-like structure is known as a precursor of "hsa-miR-7150."

The term "hsa-miR-744-5p gene" or "hsa-miR-744-5p" used herein includes the hsa-miR-744-5p gene (miRBase Accession No. MIMAT0004945) shown in SEQ ID NO: 221, a homolog or an ortholog of a different organism species, and the like. The gene can be obtained by a method described in Berezikov E et al., 2006, Genome Res., Vol. 16, pp. 1289-1298. Also, "hsa-mir-744" (miRBase Accession No. MI0005559; SEQ ID NO: 452) having a hairpin-like structure is known as a precursor of "hsa-miR-744-5p."

The term "hsa-miR-7975 gene" or "hsa-miR-7975" used herein includes the hsa-miR-7975 gene (miRBase Accession No. MIMAT0031178) shown in SEQ ID NO: 222, a homolog or an ortholog of a different organism species, and the like. The gene can be obtained by a method described in Velthut-Meikas A et al., 2013, Mol. Endocrinol., Vol. 27, pp. 1128-1141. Also, "hsa-mir-7975" (miRBase Accession No. MI0025751; SEQ ID NO: 453) having a hairpin-like structure is known as a precursor of "hsa-miR-7975."

The term "hsa-miR-7977 gene" or "hsa-miR-7977" used herein includes the hsa-miR-7977 gene (miRBase Accession No. MIMAT0031180) shown in SEQ ID NO: 223, a homolog or an ortholog of a different organism species, and the like. The gene can be obtained by a method described in Velthut-Meikas A et al., 2013, Mol. Endocrinol., Vol. 27, pp. 1128-1141. Also, "hsa-mir-7977" (miRBase Accession No. MI0025753; SEQ ID NO: 454) having a hairpin-like structure is known as a precursor of "hsa-miR-7977."

The term "hsa-miR-8052 gene" or "hsa-miR-8052" used herein includes the hsa-miR-8052 gene (miRBase Accession No. MIMAT0030979) shown in SEQ ID NO: 224, a homolog or an ortholog of a different organism species, and the like. The gene can be obtained by a method described in Wang H J et al., 2013, Shock, Vol. 39, pp. 480-487. Also, "hsa-mir-8052" (miRBase Accession No. MI0025888; SEQ ID NO: 455) having a hairpin-like structure is known as a precursor of "hsa-miR-8052."

The term "hsa-miR-8069 gene" or "hsa-miR-8069" used herein includes the hsa-miR-8069 gene (miRBase Accession No. MIMAT0030996) shown in SEQ ID NO: 225, a homolog or an ortholog of a different organism species, and the like. The gene can be obtained by a method described in Wang H J et al., 2013, Shock, Vol. 39, pp. 480-487. Also, "hsa-mir-8069-1" (miRBase Accession No. MI0025905; SEQ ID NO: 481) and "hsa-mir-8069-2" (miRBase Accession No. MI0031519; SEQ ID NO: 493) each having a hairpin-like structure are known as precursors of "hsa-miR-8069."

The term "hsa-miR-8073 gene" or "hsa-miR-8073" used herein includes the hsa-miR-8073 gene (miRBase Accession No. MIMAT0031000) shown in SEQ ID NO: 226, a homolog or an ortholog of a different organism species, and the like. The gene can be obtained by a method described in Wang H J et al., 2013, Shock, Vol. 39, pp. 480-487. Also, "hsa-mir-8073" (miRBase Accession No. MI0025909; SEQ ID NO: 456) having a hairpin-like structure is known as a precursor of "hsa-miR-8073."

The term "hsa-miR-887-3p gene" or "hsa-miR-887-3p" used herein includes the hsa-miR-887-3p gene (miRBase Accession No. MIMAT0004951) shown in SEQ ID NO: 227, a homolog or an ortholog of a different organism species, and the like. The gene can be obtained by a method described in Berezikov E et al., 2006, Genome Res., Vol. 16, pp. 1289-1298. Also, "hsa-mir-887" (miRBase Accession No. MI0005562; SEQ ID NO: 457) having a hairpin-like structure is known as a precursor of "hsa-miR-887-3p."

The term "hsa-miR-937-5p gene" or "hsa-miR-937-5p" used herein includes the hsa-miR-937-5p gene (miRBase Accession No. MIMAT0022938) shown in SEQ ID NO: 228, a homolog or an ortholog of a different organism species, and the like. The gene can be obtained by a method described in Lui WO et al., 2007, Cancer Res., Vol. 67, pp. 6031-6043. Also, "hsa-mir-937" (miRBase Accession No. MI0005759; SEQ ID NO: 458) having a hairpin-like structure is known as a precursor of "hsa-miR-937-5p."

The term "hsa-miR-1202 gene" or "hsa-miR-1202" used herein includes the hsa-miR-1202 gene (miRBase Accession No. MIMAT0005865) shown in SEQ ID NO: 229, a homolog or an ortholog of a different organism species, and the like. The gene can be obtained by a method described in Marton S et al., 2008, Leukemia, Vol. 22, pp. 330-338. Also, "hsa-mir-1202" (miRBase Accession No. MI0006334; SEQ ID NO: 459) having a hairpin-like structure is known as a precursor of "hsa-miR-1202."

The term "hsa-miR-1207-5p gene" or "hsa-miR-1207-5p" used herein includes the hsa-miR-1207-5p gene (miRBase Accession No. MIMAT0005871) shown in SEQ ID NO: 230, a homolog or an ortholog of a different organism species, and the like. The gene can be obtained by a method described in Huppi K et al., 2008, Mol. Cancer Res., Vol. 6, pp. 212-221. Also, "hsa-mir-1207" (miRBase Accession No. MI0006340; SEQ ID NO: 460) having a hairpin-like structure is known as a precursor of "hsa-miR-1207-5p."

The term "hsa-miR-1246 gene" or "hsa-miR-1246" used herein includes the hsa-miR-1246 gene (miRBase Accession No. MIMAT0005898) shown in SEQ ID NO: 231, a homolog or an ortholog of a different organism species, and the like. The gene can be obtained by a method described in Morin R D et al., 2008, Genome Res., Vol. 18, pp. 610-621. Also, "hsa-mir-1246" (miRBase Accession No. MI0006381; SEQ ID NO: 461) having a hairpin-like structure is known as a precursor of "hsa-miR-1246."

The term "hsa-miR-1254 gene" or "hsa-miR-1254" used herein includes the hsa-miR-1254 gene (miRBase Accession No. MIMAT0005905) shown in SEQ ID NO: 232, a homolog or an ortholog of a different organism species, and the like. The gene can be obtained by a method described in Morin R D et al., 2008, Genome Res., Vol. 18, pp. 610-621. Also, "hsa-mir-1254-1" (miRBase Accession No. MI0006388; SEQ ID NO: 482) and "hsa-mir-1254-2" (miRBase Accession No. MI0016747; SEQ ID NO: 494) each having a hairpin-like structure are known as precursors of "hsa-miR-1254."

The term "hsa-miR-135a-3p gene" or "hsa-miR-135a-3p" used herein includes the hsa-miR-135a-3p gene (miRBase Accession No. MIMAT0004595) shown in SEQ ID NO: 233, a homolog or an ortholog of a different organism species, and the like. The gene can be obtained by a method described in Lagos-Quintana M et al., 2002, Curr. Biol., Vol. 12, pp. 735-739. Also, "hsa-mir-135a-1" (miRBase Accession No. MI0000452; SEQ ID NO: 462) having a hairpin-like structure is known as a precursor of "hsa-miR-135a-3p."

The term "hsa-miR-1469 gene" or "hsa-miR-1469" used herein includes the hsa-miR-1469 gene (miRBase Accession No. MIMAT0007347) shown in SEQ ID NO: 234, a homolog or an ortholog of a different organism species, and the like. The gene can be obtained by a method described in Kawaji H et al., 2008, BMC Genomics, Vol. 9, p. 157. Also, "hsa-mir-1469" (miRBase Accession No. MI0007074; SEQ ID NO: 463) having a hairpin-like structure is known as a precursor of "hsa-miR-1469."

The term "hsa-miR-149-3p gene" or "hsa-miR-149-3p" used herein includes the hsa-miR-149-3p gene (miRBase Accession No. MIMAT0004609) shown in SEQ ID NO: 235, a homolog or an ortholog of a different organism species, and the like. The gene can be obtained by a method described in Lagos-Quintana M et al., 2002, Curr. Biol., Vol. 12, pp. 735-739. Also, "hsa-mir-149" (miRBase Accession No. MI0000478; SEQ ID NO: 464) having a hairpin-like structure is known as a precursor of "hsa-miR-149-3p."

The term "hsa-miR-150-3p gene" or "hsa-miR-150-3p" used herein includes the hsa-miR-150-3p gene (miRBase Accession No. MIMAT0004610) shown in SEQ ID NO: 236, a homolog or an ortholog of a different organism species, and the like. The gene can be obtained by a method described in Lagos-Quintana M et al., 2002, Curr. Biol., Vol. 12, pp. 735-739. Also, "hsa-mir-150" (miRBase Accession No. MI0000479; SEQ ID NO: 465) having a hairpin-like structure is known as a precursor of "hsa-miR-150-3p."

The term "hsa-miR-1914-3p gene" or "hsa-miR-1914-3p" used herein includes the hsa-miR-1914-3p gene (miRBase Accession No. MIMAT0007890) shown in SEQ ID NO: 237, a homolog or an ortholog of a different organism species, and the like. The gene can be obtained by a method described in Bar M et al., 2008, Stem Cells, Vol. 26, pp. 2496-2505. Also, "hsa-mir-1914" (miRBase Accession No. MI0008335; SEQ ID NO: 466) having a hairpin-like structure is known as a precursor of "hsa-miR-1914-3p."

The term "hsa-miR-191-5p gene" or "hsa-miR-191-5p" used herein includes the hsa-miR-191-5p gene (miRBase Accession No. MIMAT0000440) shown in SEQ ID NO: 238, a homolog or an ortholog of a different organism species, and the like. The gene can be obtained by a method described in Lagos-Quintana M et al., 2003, RNA, Vol. 9, pp. 175-179. Also, "hsa-mir-191" (miRBase Accession No. MI0000465; SEQ ID NO: 467) having a hairpin-like structure is known as a precursor of "hsa-miR-191-5p."

The term "hsa-miR-423-5p gene" or "hsa-miR-423-5p" used herein includes the hsa-miR-423-5p gene (miRBase Accession No. MIMAT0004748) shown in SEQ ID NO: 239, a homolog or an ortholog of a different organism species, and the like. The gene can be obtained by a method described in Kasashima K et al., 2004, Biochem. Biophys. Res. Commun., Vol. 322, pp. 403-410. Also, "hsa-mir-423" (miRBase Accession No. MI0001445; SEQ ID NO: 468) having a hairpin-like structure is known as a precursor of "hsa-miR-423-5p."

The term "hsa-miR-663a gene" or "hsa-miR-663a" used herein includes the hsa-miR-663a gene (miRBase Accession No. MIMAT0003326) shown in SEQ ID NO: 240, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-663a" (miRBase Accession No. MI0003672; SEQ ID NO: 469) having a hairpin-like structure is known as a precursor of "hsa-miR-663a."

The term "hsa-miR-92a-2-5p gene" or "hsa-miR-92a-2-5p" used herein includes the hsa-miR-92a-2-5p gene (miRBase Accession No. MIMAT0004508) shown in SEQ ID NO: 241, a homolog or an ortholog of a different organism species, and the like. The gene can be obtained by a method described in Mourelatos Z et al., 2002, Genes Dev., Vol. 16, pp. 720-728. Also, "hsa-mir-92a-2" (miRBase Accession No. MI0000094; SEQ ID NO: 470) having a hairpin-like structure is known as a precursor of "hsa-miR-92a-2-5p."

The term "hsa-miR-92a-3p gene" or "hsa-miR-92a-3p" used herein includes the hsa-miR-92a-3p gene (miRBase Accession No. MIMAT0000092) shown in SEQ ID NO: 242, a homolog or an ortholog of a different organism species, and the like. The gene can be obtained by a method described in Mourelatos Z et al., 2002, Genes Dev., Vol. 16, pp. 720-728. Also, "hsa-mir-92a-1" (miRBase Accession No. MI0000093; SEQ ID NO: 483) and "hsa-mir-92a-2" (miRBase Accession No. MI0000094; SEQ ID NO: 495) each having a hairpin-like structure are known as precursors of "hsa-miR-92a-3p."

The term "hsa-miR-940 gene" or "hsa-miR-940" used herein includes the hsa-miR-940 gene (miRBase Accession No. MIMAT0004983) shown in SEQ ID NO: 243, a homolog or an ortholog of a different organism species, and the like. The gene can be obtained by a method described in Lui WO et al., 2007, Cancer Res., Vol. 67, pp. 6031-6043. Also, "hsa-mir-940" (miRBase Accession No. MI0005762;

SEQ ID NO: 471) having a hairpin-like structure is known as a precursor of "hsa-miR-940."

A mature miRNA may become a variant due to the sequence cleaved shorter or longer by one to several flanking nucleotides or due to substitution of nucleotides, when it is cleaved as the mature miRNA from its RNA precursor having a hairpin-like structure. This variant is referred to as isomiR (Morin R D et al., 2008, Genome Res., Vol. 18, pp. 610-621). The miRBase Release 21 shows the nucleotide sequences represented by any of SEQ ID NOs: 1 to 243 as well as a large number of the nucleotide sequence variants and fragments represented by any of SEQ ID NOs: 507 to 766, referred to as isomiRs. These variants can also be obtained as miRNAs having a nucleotide sequence represented by any of SEQ ID NOs: 1 to 243. Among the variants of polynucleotides comprising the nucleotide sequence represented by any of SEQ ID NOs: 1, 2, 3, 8, 9, 10, 12, 13, 14, 15, 16, 17, 20, 21, 22, 24, 25, 26, 27, 28, 29, 30, 31, 32, 33, 34, 36, 37, 38, 42, 43, 44, 45, 46, 47, 48, 49, 51, 54, 55, 56, 58, 61, 62, 63, 67, 68, 69, 71, 72, 73, 74, 75, 77, 78, 80, 81, 82, 84, 86, 87, 89, 90, 91, 92, 93, 94, 95, 96, 101, 103, 105, 109, 111, 113, 114, 116, 117, 118, 119, 123, 124, 126, 127, 129, 131, 132, 133, 134, 135, 136, 139, 142, 143, 146, 150, 151, 152, 153, 154, 155, 156, 157, 158, 159, 161, 162, 163, 164, 166, 218, 221, 227, 228, 231, 232, 233, 235, 236, 237, 238, 239, 240, 241, 242, and 243 or a nucleotide sequence derived from any of the nucleotide sequences mentioned above by the replacement of u with t according to the present invention, specific examples of the longest variants registered in the miRBase Release 21 include polynucleotides represented by SEQ ID NOs: 507 to 632. Among the variants of polynucleotides comprising the nucleotide sequence represented by any of SEQ ID NOs: 1, 2, 3, 4, 8, 9, 10, 12, 13, 14, 15, 16, 17, 19, 20, 21, 22, 24, 25, 26, 27, 28, 29, 30, 31, 32, 33, 34, 36, 37, 38, 40, 41, 42, 43, 44, 45, 46, 47, 48, 49, 51, 53, 54, 55, 56, 58, 61, 62, 63, 67, 68, 71, 72, 73, 74, 75, 77, 78, 80, 81, 82, 84, 86, 90, 91, 92, 93, 95, 96, 101, 105, 107, 109, 111, 112, 113, 114, 116, 117, 118, 119, 120, 122, 123, 124, 125, 126, 127, 129, 131, 132, 133, 134, 135, 136, 138, 139, 142, 143, 145, 146, 150, 151, 152, 154, 155, 156, 157, 158, 159, 161, 162, 163, 164, 166, 218, 221, 222, 227, 228, 229, 231, 232, 233, and 235 or a nucleotide sequence derived from any of the nucleotide sequences mentioned above by the replacement of u with t according to the present invention, examples of the shortest variants registered in the miRBase Release 21 include polynucleotides represented by SEQ ID NOs: 633 to 766. In addition to these variants and fragments, a large number of isomiR polynucleotides of SEQ ID NOs: 1 to 243 registered in the miRBase are included. Further examples of polynucleotides each comprising a nucleotide sequence represented by any of SEQ ID NOs: 1 to 243 include precursors thereof, which are polynucleotides each represented by any of SEQ ID NOs: 507 to 766.

The names and miRBase Accession Nos. (registration numbers) of the genes represented by SEQ ID NOs: 1 to 766 are shown in Table 1.

As used herein, the expression "capable of specifically binding" refers to a situation in which the nucleic acid probe or the primer used in the present invention binds to a specific target nucleic acid and it cannot substantially bind to other nucleic acids.

TABLE 1

| SEQ ID NO | Name of gene | MIMAT No. |
|---|---|---|
| 1 | hsa-miR-6087 | MIMAT0023712 |
| 2 | hsa-miR-1185-1-3p | MIMAT0022838 |
| 3 | hsa-miR-1185-2-3p | MIMAT0022713 |
| 4 | hsa-miR-1193 | MIMAT0015049 |
| 5 | hsa-miR-1199-5p | MIMAT0031119 |
| 6 | hsa-miR-1225-5p | MIMAT0005572 |
| 7 | hsa-miR-1227-5p | MIMAT0022941 |
| 8 | hsa-miR-1228-3p | MIMAT0005583 |
| 9 | hsa-miR-1228-5p | MIMAT0005582 |
| 10 | hsa-miR-1237-5p | MIMAT0022946 |
| 11 | hsa-miR-1238-5p | MIMAT0022947 |
| 12 | hsa-miR-1247-3p | MIMAT0022721 |
| 13 | hsa-miR-1268a | MIMAT0005922 |
| 14 | hsa-miR-1268b | MIMAT0018925 |
| 15 | hsa-miR-1273g-3p | MIMAT0022742 |
| 16 | hsa-miR-128-2-5p | MIMAT0031095 |
| 17 | hsa-miR-1343-3p | MIMAT0019776 |
| 18 | hsa-miR-1343-5p | MIMAT0027038 |
| 19 | hsa-miR-1470 | MIMAT0007348 |
| 20 | hsa-miR-17-3p | MIMAT0000071 |
| 21 | hsa-miR-187-5p | MIMAT0004561 |
| 22 | hsa-miR-1908-3p | MIMAT0026916 |
| 23 | hsa-miR-1908-5p | MIMAT0007881 |
| 24 | hsa-miR-1909-3p | MIMAT0007883 |
| 25 | hsa-miR-1915-3p | MIMAT0007892 |
| 26 | hsa-miR-210-5p | MIMAT0026475 |
| 27 | hsa-miR-24-3p | MIMAT0000080 |
| 28 | hsa-miR-2467-3p | MIMAT0019953 |
| 29 | hsa-miR-2861 | MIMAT0013802 |
| 30 | hsa-miR-296-3p | MIMAT0004679 |
| 31 | hsa-miR-29b-3p | MIMAT0000100 |
| 32 | hsa-miR-3131 | MIMAT0014996 |
| 33 | hsa-miR-3154 | MIMAT0015028 |
| 34 | hsa-miR-3158-5p | MIMAT0019211 |
| 35 | hsa-miR-3160-5p | MIMAT0019212 |
| 36 | hsa-miR-3162-5p | MIMAT0015036 |
| 37 | hsa-miR-3178 | MIMAT0015055 |
| 38 | hsa-miR-3180-3p | MIMAT0015058 |
| 39 | hsa-miR-3184-5p | MIMAT0015064 |
| 40 | hsa-miR-3185 | MIMAT0015065 |
| 41 | hsa-miR-3194-3p | MIMAT0019218 |
| 42 | hsa-miR-3195 | MIMAT0015079 |
| 43 | hsa-miR-3197 | MIMAT0015082 |
| 44 | hsa-miR-320a | MIMAT0000510 |
| 45 | hsa-miR-320b | MIMAT0005792 |
| 46 | hsa-miR-328-5p | MIMAT0026486 |
| 47 | hsa-miR-342-5p | MIMAT0004694 |
| 48 | hsa-miR-345-3p | MIMAT0022698 |
| 49 | hsa-miR-3616-3p | MIMAT0017996 |
| 50 | hsa-miR-3619-3p | MIMAT0019219 |
| 51 | hsa-miR-3620-5p | MIMAT0022967 |
| 52 | hsa-miR-3621 | MIMAT0018002 |
| 53 | hsa-miR-3622a-5p | MIMAT0018003 |
| 54 | hsa-miR-3648 | MIMAT0018068 |
| 55 | hsa-miR-3652 | MIMAT0018072 |
| 56 | hsa-miR-3656 | MIMAT0018076 |
| 57 | hsa-miR-3663-3p | MIMAT0018085 |
| 58 | hsa-miR-3679-5p | MIMAT0018104 |
| 59 | hsa-miR-371b-5p | MIMAT0019892 |
| 60 | hsa-miR-373-5p | MIMAT0000725 |
| 61 | hsa-miR-3917 | MIMAT0018191 |
| 62 | hsa-miR-3940-5p | MIMAT0019229 |
| 63 | hsa-miR-3960 | MIMAT0019337 |
| 64 | hsa-miR-4258 | MIMAT0016879 |
| 65 | hsa-miR-4259 | MIMAT0016880 |
| 66 | hsa-miR-4270 | MIMAT0016900 |
| 67 | hsa-miR-4286 | MIMAT0016916 |
| 68 | hsa-miR-4298 | MIMAT0016852 |
| 69 | hsa-miR-4322 | MIMAT0016873 |
| 70 | hsa-miR-4327 | MIMAT0016889 |
| 71 | hsa-miR-4417 | MIMAT0018929 |
| 72 | hsa-miR-4419b | MIMAT0019034 |
| 73 | hsa-miR-4429 | MIMAT0018944 |
| 74 | hsa-miR-4430 | MIMAT0018945 |
| 75 | hsa-miR-4433a-3p | MIMAT0018949 |
| 76 | hsa-miR-4436b-5p | MIMAT0019940 |
| 77 | hsa-miR-4443 | MIMAT0018961 |

TABLE 1-continued

| SEQ ID NO | Name of gene | MIMAT No. |
|---|---|---|
| 78 | hsa-miR-4446-3p | MIMAT0018965 |
| 79 | hsa-miR-4447 | MIMAT0018966 |
| 80 | hsa-miR-4448 | MIMAT0018967 |
| 81 | hsa-miR-4449 | MIMAT0018968 |
| 82 | hsa-miR-4454 | MIMAT0018976 |
| 83 | hsa-miR-4455 | MIMAT0018977 |
| 84 | hsa-miR-4459 | MIMAT0018981 |
| 85 | hsa-miR-4462 | MIMAT0018986 |
| 86 | hsa-miR-4466 | MIMAT0018993 |
| 87 | hsa-miR-4467 | MIMAT0018994 |
| 88 | hsa-miR-4480 | MIMAT0019014 |
| 89 | hsa-miR-4483 | MIMAT0019017 |
| 90 | hsa-miR-4484 | MIMAT0019018 |
| 91 | hsa-miR-4485-5p | MIMAT0032116 |
| 92 | hsa-miR-4488 | MIMAT0019022 |
| 93 | hsa-miR-4492 | MIMAT0019027 |
| 94 | hsa-miR-4505 | MIMAT0019041 |
| 95 | hsa-miR-4515 | MIMAT0019052 |
| 96 | hsa-miR-4525 | MIMAT0019064 |
| 97 | hsa-miR-4534 | MIMAT0019073 |
| 98 | hsa-miR-4535 | MIMAT0019075 |
| 99 | hsa-miR-4633-3p | MIMAT0019690 |
| 100 | hsa-miR-4634 | MIMAT0019691 |
| 101 | hsa-miR-4640-5p | MIMAT0019699 |
| 102 | hsa-miR-4649-5p | MIMAT0019711 |
| 103 | hsa-miR-4651 | MIMAT0019715 |
| 104 | hsa-miR-4652-5p | MIMAT0019716 |
| 105 | hsa-miR-4655-5p | MIMAT0019721 |
| 106 | hsa-miR-4656 | MIMAT0019723 |
| 107 | hsa-miR-4658 | MIMAT0019725 |
| 108 | hsa-miR-4663 | MIMAT0019735 |
| 109 | hsa-miR-4673 | MIMAT0019755 |
| 110 | hsa-miR-4675 | MIMAT0019757 |
| 111 | hsa-miR-4687-3p | MIMAT0019775 |
| 112 | hsa-miR-4687-5p | MIMAT0019774 |
| 113 | hsa-miR-4690-5p | MIMAT0019779 |
| 114 | hsa-miR-4695-5p | MIMAT0019788 |
| 115 | hsa-miR-4697-5p | MIMAT0019791 |
| 116 | hsa-miR-4706 | MIMAT0019806 |
| 117 | hsa-miR-4707-3p | MIMAT0019808 |
| 118 | hsa-miR-4707-5p | MIMAT0019807 |
| 119 | hsa-miR-4708-3p | MIMAT0019810 |
| 120 | hsa-miR-4710 | MIMAT0019815 |
| 121 | hsa-miR-4718 | MIMAT0019831 |
| 122 | hsa-miR-4722-5p | MIMAT0019836 |
| 123 | hsa-miR-4725-3p | MIMAT0019844 |
| 124 | hsa-miR-4726-5p | MIMAT0019845 |
| 125 | hsa-miR-4727-3p | MIMAT0019848 |
| 126 | hsa-miR-4728-5p | MIMAT0019849 |
| 127 | hsa-miR-4731-5p | MIMAT0019853 |
| 128 | hsa-miR-4736 | MIMAT0019862 |
| 129 | hsa-miR-4739 | MIMAT0019868 |
| 130 | hsa-miR-4740-5p | MIMAT0019869 |
| 131 | hsa-miR-4741 | MIMAT0019871 |
| 132 | hsa-miR-4750-5p | MIMAT0019887 |
| 133 | hsa-miR-4755-3p | MIMAT0019896 |
| 134 | hsa-miR-4763-3p | MIMAT0019913 |
| 135 | hsa-miR-4771 | MIMAT0019925 |
| 136 | hsa-miR-4783-3p | MIMAT0019947 |
| 137 | hsa-miR-4783-5p | MIMAT0019946 |
| 138 | hsa-miR-4787-3p | MIMAT0019957 |
| 139 | hsa-miR-4792 | MIMAT0019964 |
| 140 | hsa-miR-498 | MIMAT0002824 |
| 141 | hsa-miR-5008-5p | MIMAT0021039 |
| 142 | hsa-miR-5010-5p | MIMAT0021043 |
| 143 | hsa-miR-504-3p | MIMAT0026612 |
| 144 | hsa-miR-5195-3p | MIMAT0021127 |
| 145 | hsa-miR-550a-5p | MIMAT0004800 |
| 146 | hsa-miR-5572 | MIMAT0022260 |
| 147 | hsa-miR-5739 | MIMAT0023116 |
| 148 | hsa-miR-6075 | MIMAT0023700 |
| 149 | hsa-miR-6076 | MIMAT0023701 |
| 150 | hsa-miR-6088 | MIMAT0023713 |
| 151 | hsa-miR-6124 | MIMAT0024597 |
| 152 | hsa-miR-6131 | MIMAT0024615 |
| 153 | hsa-miR-6132 | MIMAT0024616 |
| 154 | hsa-miR-614 | MIMAT0003282 |
| 155 | hsa-miR-615-5p | MIMAT0004804 |
| 156 | hsa-miR-619-5p | MIMAT0026622 |
| 157 | hsa-miR-642b-3p | MIMAT0018444 |
| 158 | hsa-miR-6510-5p | MIMAT0025476 |
| 159 | hsa-miR-6511a-5p | MIMAT0025478 |
| 160 | hsa-miR-6515-3p | MIMAT0025487 |
| 161 | hsa-miR-6515-5p | MIMAT0025486 |
| 162 | hsa-miR-663b | MIMAT0005867 |
| 163 | hsa-miR-6716-5p | MIMAT0025844 |
| 164 | hsa-miR-6717-5p | MIMAT0025846 |
| 165 | hsa-miR-6722-3p | MIMAT0025854 |
| 166 | hsa-miR-6724-5p | MIMAT0025856 |
| 167 | hsa-miR-6726-5p | MIMAT0027353 |
| 168 | hsa-miR-6737-5p | MIMAT0027375 |
| 169 | hsa-miR-6741-5p | MIMAT0027383 |
| 170 | hsa-miR-6742-5p | MIMAT0027385 |
| 171 | hsa-miR-6743-5p | MIMAT0027387 |
| 172 | hsa-miR-6746-5p | MIMAT0027392 |
| 173 | hsa-miR-6749-5p | MIMAT0027398 |
| 174 | hsa-miR-6760-5p | MIMAT0027420 |
| 175 | hsa-miR-6762-5p | MIMAT0027424 |
| 176 | hsa-miR-6765-3p | MIMAT0027431 |
| 177 | hsa-miR-6765-5p | MIMAT0027430 |
| 178 | hsa-miR-6766-3p | MIMAT0027433 |
| 179 | hsa-miR-6766-5p | MIMAT0027432 |
| 180 | hsa-miR-6771-5p | MIMAT0027442 |
| 181 | hsa-miR-6774-5p | MIMAT0027448 |
| 182 | hsa-miR-6777-5p | MIMAT0027454 |
| 183 | hsa-miR-6778-5p | MIMAT0027456 |
| 184 | hsa-miR-6780b-5p | MIMAT0027572 |
| 185 | hsa-miR-6781-5p | MIMAT0027462 |
| 186 | hsa-miR-6782-5p | MIMAT0027464 |
| 187 | hsa-miR-6784-5p | MIMAT0027468 |
| 188 | hsa-miR-6785-5p | MIMAT0027470 |
| 189 | hsa-miR-6787-5p | MIMAT0027474 |
| 190 | hsa-miR-6789-5p | MIMAT0027478 |
| 191 | hsa-miR-6791-5p | MIMAT0027482 |
| 192 | hsa-miR-6794-5p | MIMAT0027488 |
| 193 | hsa-miR-6800-5p | MIMAT0027500 |
| 194 | hsa-miR-6802-5p | MIMAT0027504 |
| 195 | hsa-miR-6803-5p | MIMAT0027506 |
| 196 | hsa-miR-6812-5p | MIMAT0027524 |
| 197 | hsa-miR-6816-5p | MIMAT0027532 |
| 198 | hsa-miR-6819-5p | MIMAT0027538 |
| 199 | hsa-miR-6821-5p | MIMAT0027542 |
| 200 | hsa-miR-6826-5p | MIMAT0027552 |
| 201 | hsa-miR-6831-5p | MIMAT0027562 |
| 202 | hsa-miR-6836-3p | MIMAT0027575 |
| 203 | hsa-miR-6840-3p | MIMAT0027583 |
| 204 | hsa-miR-6842-5p | MIMAT0027586 |
| 205 | hsa-miR-6850-5p | MIMAT0027600 |
| 206 | hsa-miR-6861-5p | MIMAT0027623 |
| 207 | hsa-miR-6869-5p | MIMAT0027638 |
| 208 | hsa-miR-6870-5p | MIMAT0027640 |
| 209 | hsa-miR-6877-5p | MIMAT0027654 |
| 210 | hsa-miR-6879-5p | MIMAT0027658 |
| 211 | hsa-miR-6880-3p | MIMAT0027661 |
| 212 | hsa-miR-6880-5p | MIMAT0027660 |
| 213 | hsa-miR-6885-5p | MIMAT0027670 |
| 214 | hsa-miR-6887-5p | MIMAT0027674 |
| 215 | hsa-miR-7107-5p | MIMAT0028111 |
| 216 | hsa-miR-7108-3p | MIMAT0028114 |
| 217 | hsa-miR-7109-5p | MIMAT0028115 |
| 218 | hsa-miR-711 | MIMAT0012734 |
| 219 | hsa-miR-7113-3p | MIMAT0028124 |
| 220 | hsa-miR-7150 | MIMAT0028211 |
| 221 | hsa-miR-744-5p | MIMAT0004945 |
| 222 | hsa-miR-7975 | MIMAT0031178 |
| 223 | hsa-miR-7977 | MIMAT0031180 |
| 224 | hsa-miR-8052 | MIMAT0030979 |
| 225 | hsa-miR-8069 | MIMAT0030996 |
| 226 | hsa-miR-8073 | MIMAT0031000 |
| 227 | hsa-miR-887-3p | MIMAT0004951 |
| 228 | hsa-miR-937-5p | MIMAT0022938 |
| 229 | hsa-miR-1202 | MIMAT0005865 |
| 230 | hsa-miR-1207-5p | MIMAT0005871 |
| 231 | hsa-miR-1246 | MIMAT0005898 |

TABLE 1-continued

| SEQ ID NO | Name of gene | MIMAT No. |
|---|---|---|
| 232 | hsa-miR-1254 | MIMAT0005905 |
| 233 | hsa-miR-135a-3p | MIMAT0004595 |
| 234 | hsa-miR-1469 | MIMAT0007347 |
| 235 | hsa-miR-149-3p | MIMAT0004609 |
| 236 | hsa-miR-150-3p | MIMAT0004610 |
| 237 | hsa-miR-1914-3p | MIMAT0007890 |
| 238 | hsa-miR-191-5p | MIMAT0000440 |
| 239 | hsa-miR-423-5p | MIMAT0004748 |
| 240 | hsa-miR-663a | MIMAT0003326 |
| 241 | hsa-miR-92a-2-5p | MIMAT0004508 |
| 242 | hsa-miR-92a-3p | MIMAT0000092 |
| 243 | hsa-miR-940 | MIMAT0004983 |
| 244 | hsa-mir-6087 | MI0020364 |
| 245 | hsa-mir-1185-1 | MI0003844 |
| 246 | hsa-mir-1185-2 | MI0003821 |
| 247 | hsa-mir-1193 | MI0014205 |
| 248 | hsa-mir-1199 | MI0020340 |
| 249 | hsa-mir-1225 | MI0006311 |
| 250 | hsa-mir-1227 | MI0006316 |
| 251 | hsa-mir-1228 | MI0006318 |
| 252 | hsa-mir-1228 | MI0006318 |
| 253 | hsa-mir-1237 | MI0006327 |
| 254 | hsa-mir-1238 | MI0006328 |
| 255 | hsa-mir-1247 | MI0006382 |
| 256 | hsa-mir-1268a | MI0006405 |
| 257 | hsa-mir-1268b | MI0016748 |
| 258 | hsa-mir-1273g | MI0018003 |
| 259 | hsa-mir-128-2 | MI0000727 |
| 260 | hsa-mir-1343 | MI0017320 |
| 261 | hsa-mir-1343 | MI0017320 |
| 262 | hsa-mir-1470 | MI0007075 |
| 263 | hsa-mir-17 | MI0000071 |
| 264 | hsa-mir-187 | MI0000274 |
| 265 | hsa-mir-1908 | MI0008329 |
| 266 | hsa-mir-1908 | MI0008329 |
| 267 | hsa-mir-1909 | MI0008330 |
| 268 | hsa-mir-1915 | MI0008336 |
| 269 | hsa-mir-210 | MI0000286 |
| 270 | hsa-mir-2467 | MI0017432 |
| 271 | hsa-mir-2861 | MI0013006 |
| 272 | hsa-mir-296 | MI0000747 |
| 273 | hsa-mir-3131 | MI0014151 |
| 274 | hsa-mir-3154 | MI0014182 |
| 275 | hsa-mir-3162 | MI0014192 |
| 276 | hsa-mir-3178 | MI0014212 |
| 277 | hsa-mir-3184 | MI0014226 |
| 278 | hsa-mir-3185 | MI0014227 |
| 279 | hsa-mir-3194 | MI0014239 |
| 280 | hsa-mir-3195 | MI0014240 |
| 281 | hsa-mir-3197 | MI0014245 |
| 282 | hsa-mir-320a | MI0000542 |
| 283 | hsa-mir-328 | MI0000804 |
| 284 | hsa-mir-342 | MI0000805 |
| 285 | hsa-mir-345 | MI0000825 |
| 286 | hsa-mir-3616 | MI0016006 |
| 287 | hsa-mir-3619 | MI0016009 |
| 288 | hsa-mir-3620 | MI0016011 |
| 289 | hsa-mir-3621 | MI0016012 |
| 290 | hsa-mir-3622a | MI0016013 |
| 291 | hsa-mir-3652 | MI0016052 |
| 292 | hsa-mir-3656 | MI0016056 |
| 293 | hsa-mir-3663 | MI0016064 |
| 294 | hsa-mir-3679 | MI0016080 |
| 295 | hsa-mir-371b | MI0017393 |
| 296 | hsa-mir-373 | MI0000781 |
| 297 | hsa-mir-3917 | MI0016423 |
| 298 | hsa-mir-3940 | MI0016597 |
| 299 | hsa-mir-3960 | MI0016964 |
| 300 | hsa-mir-4258 | MI0015857 |
| 301 | hsa-mir-4259 | MI0015858 |
| 302 | hsa-mir-4270 | MI0015878 |
| 303 | hsa-mir-4286 | MI0015894 |
| 304 | hsa-mir-4298 | MI0015830 |
| 305 | hsa-mir-4322 | MI0015851 |
| 306 | hsa-mir-4327 | MI0015867 |
| 307 | hsa-mir-4417 | MI0016753 |
| 308 | hsa-mir-4419b | MI0016861 |
| 309 | hsa-mir-4429 | MI0016768 |
| 310 | hsa-mir-4430 | MI0016769 |
| 311 | hsa-mir-4433a | MI0016773 |
| 312 | hsa-mir-4443 | MI0016786 |
| 313 | hsa-mir-4446 | MI0016789 |
| 314 | hsa-mir-4447 | MI0016790 |
| 315 | hsa-mir-4448 | MI0016791 |
| 316 | hsa-mir-4449 | MI0016792 |
| 317 | hsa-mir-4454 | MI0016800 |
| 318 | hsa-mir-4455 | MI0016801 |
| 319 | hsa-mir-4459 | MI0016805 |
| 320 | hsa-mir-4462 | MI0016810 |
| 321 | hsa-mir-4466 | MI0016817 |
| 322 | hsa-mir-4467 | MI0016818 |
| 323 | hsa-mir-4480 | MI0016841 |
| 324 | hsa-mir-4483 | MI0016844 |
| 325 | hsa-mir-4484 | MI0016845 |
| 326 | hsa-mir-4485 | MI0016846 |
| 327 | hsa-mir-4488 | MI0016849 |
| 328 | hsa-mir-4492 | MI0016854 |
| 329 | hsa-mir-4505 | MI0016868 |
| 330 | hsa-mir-4515 | MI0016881 |
| 331 | hsa-mir-4525 | MI0016892 |
| 332 | hsa-mir-4534 | MI0016901 |
| 333 | hsa-mir-4535 | MI0016903 |
| 334 | hsa-mir-4633 | MI0017260 |
| 335 | hsa-mir-4634 | MI0017261 |
| 336 | hsa-mir-4640 | MI0017267 |
| 337 | hsa-mir-4649 | MI0017276 |
| 338 | hsa-mir-4651 | MI0017279 |
| 339 | hsa-mir-4652 | MI0017280 |
| 340 | hsa-mir-4655 | MI0017283 |
| 341 | hsa-mir-4656 | MI0017284 |
| 342 | hsa-mir-4658 | MI0017286 |
| 343 | hsa-mir-4663 | MI0017292 |
| 344 | hsa-mir-4673 | MI0017304 |
| 345 | hsa-mir-4675 | MI0017306 |
| 346 | hsa-mir-4687 | MI0017319 |
| 347 | hsa-mir-4687 | MI0017319 |
| 348 | hsa-mir-4690 | MI0017323 |
| 349 | hsa-mir-4695 | MI0017328 |
| 350 | hsa-mir-4697 | MI0017330 |
| 351 | hsa-mir-4706 | MI0017339 |
| 352 | hsa-mir-4707 | MI0017340 |
| 353 | hsa-mir-4707 | MI0017340 |
| 354 | hsa-mir-4708 | MI0017341 |
| 355 | hsa-mir-4710 | MI0017344 |
| 356 | hsa-mir-4718 | MI0017353 |
| 357 | hsa-mir-4722 | MI0017357 |
| 358 | hsa-mir-4725 | MI0017362 |
| 359 | hsa-mir-4726 | MI0017363 |
| 360 | hsa-mir-4727 | MI0017364 |
| 361 | hsa-mir-4728 | MI0017365 |
| 362 | hsa-mir-4731 | MI0017368 |
| 363 | hsa-mir-4736 | MI0017373 |
| 364 | hsa-mir-4739 | MI0017377 |
| 365 | hsa-mir-4740 | MI0017378 |
| 366 | hsa-mir-4741 | MI0017379 |
| 367 | hsa-mir-4750 | MI0017389 |
| 368 | hsa-mir-4755 | MI0017395 |
| 369 | hsa-mir-4763 | MI0017404 |
| 370 | hsa-mir-4783 | MI0017428 |
| 371 | hsa-mir-4783 | MI0017428 |
| 372 | hsa-mir-4787 | MI0017434 |
| 373 | hsa-mir-4792 | MI0017439 |
| 374 | hsa-mir-498 | MI0003142 |
| 375 | hsa-mir-5008 | MI0017876 |
| 376 | hsa-mir-5010 | MI0017878 |
| 377 | hsa-mir-504 | MI0003189 |
| 378 | hsa-mir-5195 | MI0018174 |
| 379 | hsa-mir-5572 | MI0019117 |
| 380 | hsa-mir-5739 | MI0019412 |
| 381 | hsa-mir-6075 | MI0020352 |
| 382 | hsa-mir-6076 | MI0020353 |
| 383 | hsa-mir-6088 | MI0020365 |
| 384 | hsa-mir-6124 | MI0021258 |
| 385 | hsa-mir-6131 | MI0021276 |

TABLE 1-continued

| SEQ ID NO | Name of gene | MIMAT No. |
|---|---|---|
| 386 | hsa-mir-6132 | MI0021277 |
| 387 | hsa-mir-614 | MI0003627 |
| 388 | hsa-mir-615 | MI0003628 |
| 389 | hsa-mir-619 | MI0003633 |
| 390 | hsa-mir-642b | MI0016685 |
| 391 | hsa-mir-6510 | MI0022222 |
| 392 | hsa-mir-6515 | MI0022227 |
| 393 | hsa-mir-6515 | MI0022227 |
| 394 | hsa-mir-663b | MI0006336 |
| 395 | hsa-mir-6716 | MI0022550 |
| 396 | hsa-mir-6717 | MI0022551 |
| 397 | hsa-mir-6722 | MI0022557 |
| 398 | hsa-mir-6726 | MI0022571 |
| 399 | hsa-mir-6737 | MI0022582 |
| 400 | hsa-mir-6741 | MI0022586 |
| 401 | hsa-mir-6742 | MI0022587 |
| 402 | hsa-mir-6743 | MI0022588 |
| 403 | hsa-mir-6746 | MI0022591 |
| 404 | hsa-mir-6749 | MI0022594 |
| 405 | hsa-mir-6760 | MI0022605 |
| 406 | hsa-mir-6762 | MI0022607 |
| 407 | hsa-mir-6765 | MI0022610 |
| 408 | hsa-mir-6765 | MI0022610 |
| 409 | hsa-mir-6766 | MI0022611 |
| 410 | hsa-mir-6766 | MI0022611 |
| 411 | hsa-mir-6771 | MI0022616 |
| 412 | hsa-mir-6774 | MI0022619 |
| 413 | hsa-mir-6777 | MI0022622 |
| 414 | hsa-mir-6778 | MI0022623 |
| 415 | hsa-mir-6780b | MI0022681 |
| 416 | hsa-mir-6781 | MI0022626 |
| 417 | hsa-mir-6782 | MI0022627 |
| 418 | hsa-mir-6784 | MI0022629 |
| 419 | hsa-mir-6785 | MI0022630 |
| 420 | hsa-mir-6787 | MI0022632 |
| 421 | hsa-mir-6789 | MI0022634 |
| 422 | hsa-mir-6791 | MI0022636 |
| 423 | hsa-mir-6794 | MI0022639 |
| 424 | hsa-mir-6800 | MI0022645 |
| 425 | hsa-mir-6802 | MI0022647 |
| 426 | hsa-mir-6803 | MI0022648 |
| 427 | hsa-mir-6812 | MI0022657 |
| 428 | hsa-mir-6816 | MI0022661 |
| 429 | hsa-mir-6819 | MI0022664 |
| 430 | hsa-mir-6821 | MI0022666 |
| 431 | hsa-mir-6826 | MI0022671 |
| 432 | hsa-mir-6831 | MI0022676 |
| 433 | hsa-mir-6836 | MI0022682 |
| 434 | hsa-mir-6840 | MI0022686 |
| 435 | hsa-mir-6842 | MI0022688 |
| 436 | hsa-mir-6850 | MI0022696 |
| 437 | hsa-mir-6861 | MI0022708 |
| 438 | hsa-mir-6869 | MI0022716 |
| 439 | hsa-mir-6870 | MI0022717 |
| 440 | hsa-mir-6877 | MI0022724 |
| 441 | hsa-mir-6879 | MI0022726 |
| 442 | hsa-mir-6880 | MI0022727 |
| 443 | hsa-mir-6880 | MI0022727 |
| 444 | hsa-mir-6885 | MI0022732 |
| 445 | hsa-mir-6887 | MI0022734 |
| 446 | hsa-mir-7107 | MI0022958 |
| 447 | hsa-mir-7108 | MI0022959 |
| 448 | hsa-mir-7109 | MI0022960 |
| 449 | hsa-mir-711 | MI0012488 |
| 450 | hsa-mir-7113 | MI0022964 |
| 451 | hsa-mir-7150 | MI0023610 |
| 452 | hsa-mir-744 | MI0005559 |
| 453 | hsa-mir-7975 | MI0025751 |
| 454 | hsa-mir-7977 | MI0025753 |
| 455 | hsa-mir-8052 | MI0025888 |
| 456 | hsa-mir-8073 | MI0025909 |
| 457 | hsa-mir-887 | MI0005562 |
| 458 | hsa-mir-937 | MI0005759 |
| 459 | hsa-mir-1202 | MI0006334 |
| 460 | hsa-mir-1207 | MI0006340 |
| 461 | hsa-mir-1246 | MI0006381 |
| 462 | hsa-mir-135a-1 | MI0000452 |
| 463 | hsa-mir-1469 | MI0007074 |
| 464 | hsa-mir-149 | MI0000478 |
| 465 | hsa-mir-150 | MI0000479 |
| 466 | hsa-mir-1914 | MI0008335 |
| 467 | hsa-mir-191 | MI0000465 |
| 468 | hsa-mir-423 | MI0001445 |
| 469 | hsa-mir-663a | MI0003672 |
| 470 | hsa-mir-92a-2 | MI0000094 |
| 471 | hsa-mir-940 | MI0005762 |
| 472 | hsa-mir-24-1 | MI0000080 |
| 473 | hsa-mir-29b-1 | MI0000105 |
| 474 | hsa-mir-3158-1 | MI0014186 |
| 475 | hsa-mir-3160-1 | MI0014189 |
| 476 | hsa-mir-320b-1 | MI0003776 |
| 477 | hsa-mir-3648-1 | MI0016048 |
| 478 | hsa-mir-4436b-1 | MI0017425 |
| 479 | hsa-mir-4771-1 | MI0017412 |
| 480 | hsa-mir-550a-1 | MI0003600 |
| 481 | hsa-mir-8069-1 | MI0025905 |
| 482 | hsa-mir-1254-1 | MI0006388 |
| 483 | hsa-mir-92a-1 | MI0000093 |
| 484 | hsa-mir-24-2 | MI0000081 |
| 485 | hsa-mir-29b-2 | MI0000107 |
| 486 | hsa-mir-3158-2 | MI0014187 |
| 487 | hsa-mir-3160-2 | MI0014190 |
| 488 | hsa-mir-320b-2 | MI0003839 |
| 489 | hsa-mir-3648-2 | MI0031512 |
| 490 | hsa-mir-4436b-2 | MI0019110 |
| 491 | hsa-mir-4771-2 | MI0017413 |
| 492 | hsa-mir-550a-2 | MI0003601 |
| 493 | hsa-mir-8069-2 | MI0031519 |
| 494 | hsa-mir-1254-2 | MI0016747 |
| 495 | hsa-mir-92a-2 | MI0000094 |
| 496 | hsa-mir-3180-1 | MI0014214 |
| 497 | hsa-mir-3180-2 | MI0014215 |
| 498 | hsa-mir-3180-3 | MI0014217 |
| 499 | hsa-mir-6511a-1 | MI0022223 |
| 500 | hsa-mir-6724-1 | MI0022559 |
| 501 | hsa-mir-6511a-2 | MI0023564 |
| 502 | hsa-mir-6724-2 | MI0031516 |
| 503 | hsa-mir-6511a-3 | MI0023565 |
| 504 | hsa-mir-6724-3 | MI0031517 |
| 505 | hsa-mir-6511a-4 | MI0023566 |
| 506 | hsa-mir-6724-4 | MI0031518 |
| 507 | isomiR example 1 of SEQ ID NO: 1 | — |
| 508 | isomiR example 2 of SEQ ID NO: 2 | — |
| 509 | isomiR example 3 of SEQ ID NO: 3 | — |
| 510 | isomiR example 4 of SEQ ID NO: 8 | — |
| 511 | isomiR example 5 of SEQ ID NO: 9 | — |
| 512 | isomiR example 6 of SEQ ID NO: 10 | — |
| 513 | isomiR example 7 of SEQ ID NO: 12 | — |
| 514 | isomiR example 8 of SEQ ID NO: 13 | — |
| 515 | isomiR example 9 of SEQ ID NO: 14 | — |
| 516 | isomiR example 10 of SEQ ID NO: 15 | — |
| 517 | isomiR example 11 of SEQ ID NO: 16 | — |
| 518 | isomiR example 12 of SEQ ID NO: 17 | — |
| 519 | isomiR example 13 of SEQ ID NO: 20 | — |
| 520 | isomiR example 14 of SEQ ID NO: 21 | — |
| 521 | isomiR example 15 of SEQ ID NO: 22 | — |
| 522 | isomiR example 16 of SEQ ID NO: 24 | — |
| 523 | isomiR example 17 of SEQ ID NO: 25 | — |
| 524 | isomiR example 18 of SEQ ID NO: 26 | — |
| 525 | isomiR example 19 of SEQ ID NO: 27 | — |
| 526 | isomiR example 20 of SEQ ID NO: 28 | — |
| 527 | isomiR example 21 of SEQ ID NO: 29 | — |
| 528 | isomiR example 22 of SEQ ID NO: 30 | — |
| 529 | isomiR example 23 of SEQ ID NO: 31 | — |
| 530 | isomiR example 24 of SEQ ID NO: 32 | — |
| 531 | isomiR example 25 of SEQ ID NO: 33 | — |
| 532 | isomiR example 26 of SEQ ID NO: 34 | — |
| 533 | isomiR example 27 of SEQ ID NO: 36 | — |
| 534 | isomiR example 28 of SEQ ID NO: 37 | — |
| 535 | isomiR example 29 of SEQ ID NO: 38 | — |
| 536 | isomiR example 30 of SEQ ID NO: 42 | — |
| 537 | isomiR example 31 of SEQ ID NO: 43 | — |
| 538 | isomiR example 32 of SEQ ID NO: 44 | — |
| 539 | isomiR example 33 of SEQ ID NO: 45 | — |

TABLE 1-continued

| SEQ ID NO | Name of gene | MIMAT No. |
|---|---|---|
| 540 | isomiR example 34 of SEQ ID NO: 46 | — |
| 541 | isomiR example 35 of SEQ ID NO: 47 | — |
| 542 | isomiR example 36 of SEQ ID NO: 48 | — |
| 543 | isomiR example 37 of SEQ ID NO: 49 | — |
| 544 | isomiR example 38 of SEQ ID NO: 51 | — |
| 545 | isomiR example 39 of SEQ ID NO: 54 | — |
| 546 | isomiR example 40 of SEQ ID NO: 55 | — |
| 547 | isomiR example 41 of SEQ ID NO: 56 | — |
| 548 | isomiR example 42 of SEQ ID NO: 58 | — |
| 549 | isomiR example 43 of SEQ ID NO: 61 | — |
| 550 | isomiR example 44 of SEQ ID NO: 62 | — |
| 551 | isomiR example 45 of SEQ ID NO: 63 | — |
| 552 | isomiR example 46 of SEQ ID NO: 67 | — |
| 553 | isomiR example 47 of SEQ ID NO: 68 | — |
| 554 | isomiR example 48 of SEQ ID NO: 69 | — |
| 555 | isomiR example 49 of SEQ ID NO: 71 | — |
| 556 | isomiR example 50 of SEQ ID NO: 72 | — |
| 557 | isomiR example 51 of SEQ ID NO: 73 | — |
| 558 | isomiR example 52 of SEQ ID NO: 74 | — |
| 559 | isomiR example 53 of SEQ ID NO: 75 | — |
| 560 | isomiR example 54 of SEQ ID NO: 77 | — |
| 561 | isomiR example 55 of SEQ ID NO: 78 | — |
| 562 | isomiR example 56 of SEQ ID NO: 80 | — |
| 563 | isomiR example 57 of SEQ ID NO: 81 | — |
| 564 | isomiR example 58 of SEQ ID NO: 82 | — |
| 565 | isomiR example 59 of SEQ ID NO: 84 | — |
| 566 | isomiR example 60 of SEQ ID NO: 86 | — |
| 567 | isomiR example 61 of SEQ ID NO: 87 | — |
| 568 | isomiR example 62 of SEQ ID NO: 89 | — |
| 569 | isomiR example 63 of SEQ ID NO: 90 | — |
| 570 | isomiR example 64 of SEQ ID NO: 91 | — |
| 571 | isomiR example 65 of SEQ ID NO: 92 | — |
| 572 | isomiR example 66 of SEQ ID NO: 93 | — |
| 573 | isomiR example 67 of SEQ ID NO: 94 | — |
| 574 | isomiR example 68 of SEQ ID NO: 95 | — |
| 575 | isomiR example 69 of SEQ ID NO: 96 | — |
| 576 | isomiR example 70 of SEQ ID NO: 101 | — |
| 577 | isomiR example 71 of SEQ ID NO: 103 | — |
| 578 | isomiR example 72 of SEQ ID NO: 105 | — |
| 579 | isomiR example 73 of SEQ ID NO: 109 | — |
| 580 | isomiR example 74 of SEQ ID NO: 111 | — |
| 581 | isomiR example 75 of SEQ ID NO: 113 | — |
| 582 | isomiR example 76 of SEQ ID NO: 114 | — |
| 583 | isomiR example 77 of SEQ ID NO: 116 | — |
| 584 | isomiR example 78 of SEQ ID NO: 117 | — |
| 585 | isomiR example 79 of SEQ ID NO: 118 | — |
| 586 | isomiR example 80 of SEQ ID NO: 119 | — |
| 587 | isomiR example 81 of SEQ ID NO: 123 | — |
| 588 | isomiR example 82 of SEQ ID NO: 124 | — |
| 589 | isomiR example 83 of SEQ ID NO: 126 | — |
| 590 | isomiR example 84 of SEQ ID NO: 127 | — |
| 591 | isomiR example 85 of SEQ ID NO: 129 | — |
| 592 | isomiR example 86 of SEQ ID NO: 131 | — |
| 593 | isomiR example 87 of SEQ ID NO: 132 | — |
| 594 | isomiR example 88 of SEQ ID NO: 133 | — |
| 595 | isomiR example 89 of SEQ ID NO: 134 | — |
| 596 | isomiR example 90 of SEQ ID NO: 135 | — |
| 597 | isomiR example 91 of SEQ ID NO: 136 | — |
| 598 | isomiR example 92 of SEQ ID NO: 139 | — |
| 599 | isomiR example 93 of SEQ ID NO: 142 | — |
| 600 | isomiR example 94 of SEQ ID NO: 143 | — |
| 601 | isomiR example 95 of SEQ ID NO: 146 | — |
| 602 | isomiR example 96 of SEQ ID NO: 150 | — |
| 603 | isomiR example 97 of SEQ ID NO: 151 | — |
| 604 | isomiR example 98 of SEQ ID NO: 152 | — |
| 605 | isomiR example 99 of SEQ ID NO: 153 | — |
| 606 | isomiR example 100 of SEQ ID NO: 154 | — |
| 607 | isomiR example 101 of SEQ ID NO: 155 | — |
| 608 | isomiR example 102 of SEQ ID NO: 156 | — |
| 609 | isomiR example 103 of SEQ ID NO: 157 | — |
| 610 | isomiR example 104 of SEQ ID NO: 158 | — |
| 611 | isomiR example 105 of SEQ ID NO: 159 | — |
| 612 | isomiR example 106 of SEQ ID NO: 161 | — |
| 613 | isomiR example 107 of SEQ ID NO: 162 | — |
| 614 | isomiR example 108 of SEQ ID NO: 163 | — |
| 615 | isomiR example 109 of SEQ ID NO: 164 | — |
| 616 | isomiR example 110 of SEQ ID NO: 166 | — |
| 617 | isomiR example 111 of SEQ ID NO: 218 | — |
| 618 | isomiR example 112 of SEQ ID NO: 221 | — |
| 619 | isomiR example 113 of SEQ ID NO: 227 | — |
| 620 | isomiR example 114 of SEQ ID NO: 228 | — |
| 621 | isomiR example 115 of SEQ ID NO: 231 | — |
| 622 | isomiR example 116 of SEQ ID NO: 232 | — |
| 623 | isomiR example 117 of SEQ ID NO: 233 | — |
| 624 | isomiR example 118 of SEQ ID NO: 235 | — |
| 625 | isomiR example 119 of SEQ ID NO: 236 | — |
| 626 | isomiR example 120 of SEQ ID NO: 237 | — |
| 627 | isomiR example 121 of SEQ ID NO: 238 | — |
| 628 | isomiR example 122 of SEQ ID NO: 239 | — |
| 629 | isomiR example 123 of SEQ ID NO: 240 | — |
| 630 | isomiR example 124 of SEQ ID NO: 241 | — |
| 631 | isomiR example 125 of SEQ ID NO: 242 | — |
| 632 | isomiR example 126 of SEQ ID NO: 243 | — |
| 633 | isomiR example 1 of SEQ ID NO: 1 | — |
| 634 | isomiR example 2 of SEQ ID NO: 2 | — |
| 635 | isomiR example 3 of SEQ ID NO: 3 | — |
| 636 | isomiR example 4 of SEQ ID NO: 4 | — |
| 637 | isomiR example 5 of SEQ ID NO: 8 | — |
| 638 | isomiR example 6 of SEQ ID NO: 9 | — |
| 639 | isomiR example 7 of SEQ ID NO: 10 | — |
| 640 | isomiR example 8 of SEQ ID NO: 12 | — |
| 641 | isomiR example 9 of SEQ ID NO: 13 | — |
| 642 | isomiR example 10 of SEQ ID NO: 14 | — |
| 643 | isomiR example 11 of SEQ ID NO: 15 | — |
| 644 | isomiR example 12 of SEQ ID NO: 16 | — |
| 645 | isomiR example 13 of SEQ ID NO: 17 | — |
| 646 | isomiR example 14 of SEQ ID NO: 19 | — |
| 647 | isomiR example 15 of SEQ ID NO: 20 | — |
| 648 | isomiR example 16 of SEQ ID NO: 21 | — |
| 649 | isomiR example 17 of SEQ ID NO: 22 | — |
| 650 | isomiR example 18 of SEQ ID NO: 24 | — |
| 651 | isomiR example 19 of SEQ ID NO: 25 | — |
| 652 | isomiR example 20 of SEQ ID NO: 26 | — |
| 653 | isomiR example 21 of SEQ ID NO: 27 | — |
| 654 | isomiR example 22 of SEQ ID NO: 28 | — |
| 655 | isomiR example 23 of SEQ ID NO: 29 | — |
| 656 | isomiR example 24 of SEQ ID NO: 30 | — |
| 657 | isomiR example 25 of SEQ ID NO: 31 | — |
| 658 | isomiR example 26 of SEQ ID NO: 32 | — |
| 659 | isomiR example 27 of SEQ ID NO: 33 | — |
| 660 | isomiR example 28 of SEQ ID NO: 34 | — |
| 661 | isomiR example 29 of SEQ ID NO: 36 | — |
| 662 | isomiR example 30 of SEQ ID NO: 37 | — |
| 663 | isomiR example 31 of SEQ ID NO: 38 | — |
| 664 | isomiR example 32 of SEQ ID NO: 40 | — |
| 665 | isomiR example 33 of SEQ ID NO: 41 | — |
| 666 | isomiR example 34 of SEQ ID NO: 42 | — |
| 667 | isomiR example 35 of SEQ ID NO: 43 | — |
| 668 | isomiR example 36 of SEQ ID NO: 44 | — |
| 669 | isomiR example 37 of SEQ ID NO: 45 | — |
| 670 | isomiR example 38 of SEQ ID NO: 46 | — |
| 671 | isomiR example 39 of SEQ ID NO: 47 | — |
| 672 | isomiR example 40 of SEQ ID NO: 48 | — |
| 673 | isomiR example 41 of SEQ ID NO: 49 | — |
| 674 | isomiR example 42 of SEQ ID NO: 51 | — |
| 675 | isomiR example 43 of SEQ ID NO: 53 | — |
| 676 | isomiR example 44 of SEQ ID NO: 54 | — |
| 677 | isomiR example 45 of SEQ ID NO: 55 | — |
| 678 | isomiR example 46 of SEQ ID NO: 56 | — |
| 679 | isomiR example 47 of SEQ ID NO: 58 | — |
| 680 | isomiR example 48 of SEQ ID NO: 61 | — |
| 681 | isomiR example 49 of SEQ ID NO: 62 | — |
| 682 | isomiR example 50 of SEQ ID NO: 63 | — |
| 683 | isomiR example 51 of SEQ ID NO: 67 | — |
| 684 | isomiR example 52 of SEQ ID NO: 68 | — |
| 685 | isomiR example 53 of SEQ ID NO: 71 | — |
| 686 | isomiR example 54 of SEQ ID NO: 72 | — |
| 687 | isomiR example 55 of SEQ ID NO: 73 | — |
| 688 | isomiR example 56 of SEQ ID NO: 74 | — |
| 689 | isomiR example 57 of SEQ ID NO: 75 | — |
| 690 | isomiR example 58 of SEQ ID NO: 77 | — |
| 691 | isomiR example 59 of SEQ ID NO: 78 | — |
| 692 | isomiR example 60 of SEQ ID NO: 80 | — |
| 693 | isomiR example 61 of SEQ ID NO: 81 | — |

TABLE 1-continued

| SEQ ID NO | Name of gene | MIMAT No. |
|---|---|---|
| 694 | isomiR example 62 of SEQ ID NO: 82 | — |
| 695 | isomiR example 63 of SEQ ID NO: 84 | — |
| 696 | isomiR example 64 of SEQ ID NO: 86 | — |
| 697 | isomiR example 65 of SEQ ID NO: 90 | — |
| 698 | isomiR example 66 of SEQ ID NO: 91 | — |
| 699 | isomiR example 67 of SEQ ID NO: 92 | — |
| 700 | isomiR example 68 of SEQ ID NO: 93 | — |
| 701 | isomiR example 69 of SEQ ID NO: 95 | — |
| 702 | isomiR example 70 of SEQ ID NO: 96 | — |
| 703 | isomiR example 71 of SEQ ID NO: 101 | — |
| 704 | isomiR example 72 of SEQ ID NO: 105 | — |
| 705 | isomiR example 73 of SEQ ID NO: 107 | — |
| 706 | isomiR example 74 of SEQ ID NO: 109 | — |
| 707 | isomiR example 75 of SEQ ID NO: 111 | — |
| 708 | isomiR example 76 of SEQ ID NO: 112 | — |
| 709 | isomiR example 77 of SEQ ID NO: 113 | — |
| 710 | isomiR example 78 of SEQ ID NO: 114 | — |
| 711 | isomiR example 79 of SEQ ID NO: 116 | — |
| 712 | isomiR example 80 of SEQ ID NO: 117 | — |
| 713 | isomiR example 81 of SEQ ID NO: 118 | — |
| 714 | isomiR example 82 of SEQ ID NO: 119 | — |
| 715 | isomiR example 83 of SEQ ID NO: 120 | — |
| 716 | isomiR example 84 of SEQ ID NO: 122 | — |
| 717 | isomiR example 85 of SEQ ID NO: 123 | — |
| 718 | isomiR example 86 of SEQ ID NO: 124 | — |
| 719 | isomiR example 87 of SEQ ID NO: 125 | — |
| 720 | isomiR example 88 of SEQ ID NO: 126 | — |
| 721 | isomiR example 89 of SEQ ID NO: 127 | — |
| 722 | isomiR example 90 of SEQ ID NO: 129 | — |
| 723 | isomiR example 91 of SEQ ID NO: 131 | — |
| 724 | isomiR example 92 of SEQ ID NO: 132 | — |
| 725 | isomiR example 93 of SEQ ID NO: 133 | — |
| 726 | isomiR example 94 of SEQ ID NO: 134 | — |
| 727 | isomiR example 95 of SEQ ID NO: 135 | — |
| 728 | isomiR example 96 of SEQ ID NO: 136 | — |
| 729 | isomiR example 97 of SEQ ID NO: 138 | — |
| 730 | isomiR example 98 of SEQ ID NO: 139 | — |
| 731 | isomiR example 99 of SEQ ID NO: 142 | — |
| 732 | isomiR example 100 of SEQ ID NO: 143 | — |
| 733 | isomiR example 101 of SEQ ID NO: 145 | — |
| 734 | isomiR example 102 of SEQ ID NO: 146 | — |
| 735 | isomiR example 103 of SEQ ID NO: 150 | — |
| 736 | isomiR example 104 of SEQ ID NO: 151 | — |
| 737 | isomiR example 105 of SEQ ID NO: 152 | — |
| 738 | isomiR example 106 of SEQ ID NO: 154 | — |
| 739 | isomiR example 107 of SEQ ID NO: 155 | — |
| 740 | isomiR example 108 of SEQ ID NO: 156 | — |
| 741 | isomiR example 109 of SEQ ID NO: 157 | — |
| 742 | isomiR example 110 of SEQ ID NO: 158 | — |
| 743 | isomiR example 111 of SEQ ID NO: 159 | — |
| 744 | isomiR example 112 of SEQ ID NO: 161 | — |
| 745 | isomiR example 113 of SEQ ID NO: 162 | — |
| 746 | isomiR example 114 of SEQ ID NO: 163 | — |
| 747 | isomiR example 115 of SEQ ID NO: 164 | — |
| 748 | isomiR example 116 of SEQ ID NO: 166 | — |
| 749 | isomiR example 117 of SEQ ID NO: 218 | — |
| 750 | isomiR example 118 of SEQ ID NO: 221 | — |
| 751 | isomiR example 119 of SEQ ID NO: 222 | — |
| 752 | isomiR example 120 of SEQ ID NO: 227 | — |
| 753 | isomiR example 121 of SEQ ID NO: 228 | — |
| 754 | isomiR example 122 of SEQ ID NO: 229 | — |
| 755 | isomiR example 123 of SEQ ID NO: 231 | — |
| 756 | isomiR example 124 of SEQ ID NO: 232 | — |
| 757 | isomiR example 125 of SEQ ID NO: 233 | — |
| 758 | isomiR example 126 of SEQ ID NO: 235 | — |
| 759 | isomiR example 127 of SEQ ID NO: 236 | — |
| 760 | isomiR example 128 of SEQ ID NO: 237 | — |
| 761 | isomiR example 129 of SEQ ID NO: 238 | — |
| 762 | isomiR example 130 of SEQ ID NO: 239 | — |
| 763 | isomiR example 131 of SEQ ID NO: 240 | — |
| 764 | isomiR example 132 of SEQ ID NO: 241 | — |
| 765 | isomiR example 133 of SEQ ID NO: 242 | — |
| 766 | isomiR example 134 of SEQ ID NO: 243 | — |

The present specification encompasses the contents disclosed in Japanese Patent Application No. 2018-084416 from which the present application claims priority.

Advantageous Effect of Invention

The present invention enables easy detection of bladder cancer with high accuracy. For example, whether or not a subject has bladder cancer can be detected easily with the use of the measured expression level(s) of one or several miRNAs in the blood, serum, and/or plasma that can be collected less invasively from the subject as an indicator(s).

BRIEF DESCRIPTION OF THE DRAWINGS

FIG. 2 shows plots of discriminant scores in a training cohort (A) and a validation cohort (B) obtained by a discriminant formula for 1 miRNA.

FIG. 4A and FIG. 4B show plots of discriminant scores in validation cohorts according to the stage (A) and according to the depth of intramural invasion (B) obtained by a discriminant formula for 1 miRNA.

FIG. 4C and FIG. 4D show plots of discriminant scores in validation cohorts according to the histologic tumor grade (C) and primary/recurrence (D) obtained by a discriminant formula for 1 miRNA.

FIG. 5 shows plots of discriminant scores in a training cohort (A) and a validation cohort (B) obtained by a discriminant formula for 3 miRNAs.

FIG. 7A and FIG. 7B show plots of discriminant scores in validation cohorts according to the stage (A) and according to the depth of intramural invasion (B) obtained by a discriminant formula for 3 miRNAs.

FIG. 7C and FIG. 7D show plots of discriminant scores in validation cohorts according to the histologic tumor grade (C) and primary/recurrence (D) obtained by a discriminant formula for 3 miRNAs.

FIG. 8 shows plots of discriminant scores in a training cohort (A) and a validation cohort (B) obtained by a discriminant formula for 4 miRNAs.

FIG. 10A and FIG. 10B show plots of discriminant scores in validation cohorts according to the stage (A) and according to the depth of intramural invasion (B) obtained by a discriminant formula for 4 miRNAs.

FIG. 10C and FIG. 10D show plots of discriminant scores in validation cohorts according to the histologic tumor grade (C) and primary/recurrence (D) obtained by a discriminant formula for 4 miRNAs.

FIG. 11 shows plots of discriminant scores in a training cohort (A) and a validation cohort (B) obtained by a discriminant formula for 5 miRNAs.

FIG. 13A and FIG. 13B show plots of discriminant scores in validation cohorts according to the stage (A) and according to the depth of intramural invasion (B) obtained by a discriminant formula for 5 miRNAs.

FIG. 13C and FIG. 13D show plots of discriminant scores in validation cohorts according to the histologic tumor grade (C) and primary/recurrence (D) obtained by a discriminant formula for 5 miRNAs.

FIG. 15A and FIG. 15B show plots of discriminant scores in validation cohorts according to the stage (A) and according to the depth of intramural invasion (B) obtained by a discriminant formula for 3 miRNAs.

FIG. 15C and FIG. 15D show plots of discriminant scores in validation cohorts according to the histologic tumor grade (C) and primary/recurrence (D) obtained by a discriminant formula for 3 miRNAs.

FIG. 17A and FIG. 17B show plots of discriminant scores in validation cohorts according to the stage (A) and according to the depth of intramural invasion (B) obtained by a discriminant formula for 10 miRNAs.

FIG. 17C and FIG. 17D show plots of discriminant scores in validation cohorts according to the histologic tumor grade (C) and primary/recurrence (D) obtained by a discriminant formula for 10 miRNAs.

FIG. 19A and FIG. 19B show plots of discriminant scores in validation cohorts according to the stage (A) and according to the depth of intramural invasion (B) obtained by a discriminant formula for 104 miRNAs.

FIG. 19C and FIG. 19D show plots of discriminant scores in validation cohorts according to the histologic tumor grade (C) and primary/recurrence (D) obtained by a discriminant formula for 104 miRNAs.

DESCRIPTION OF EMBODIMENTS

Figure 1:
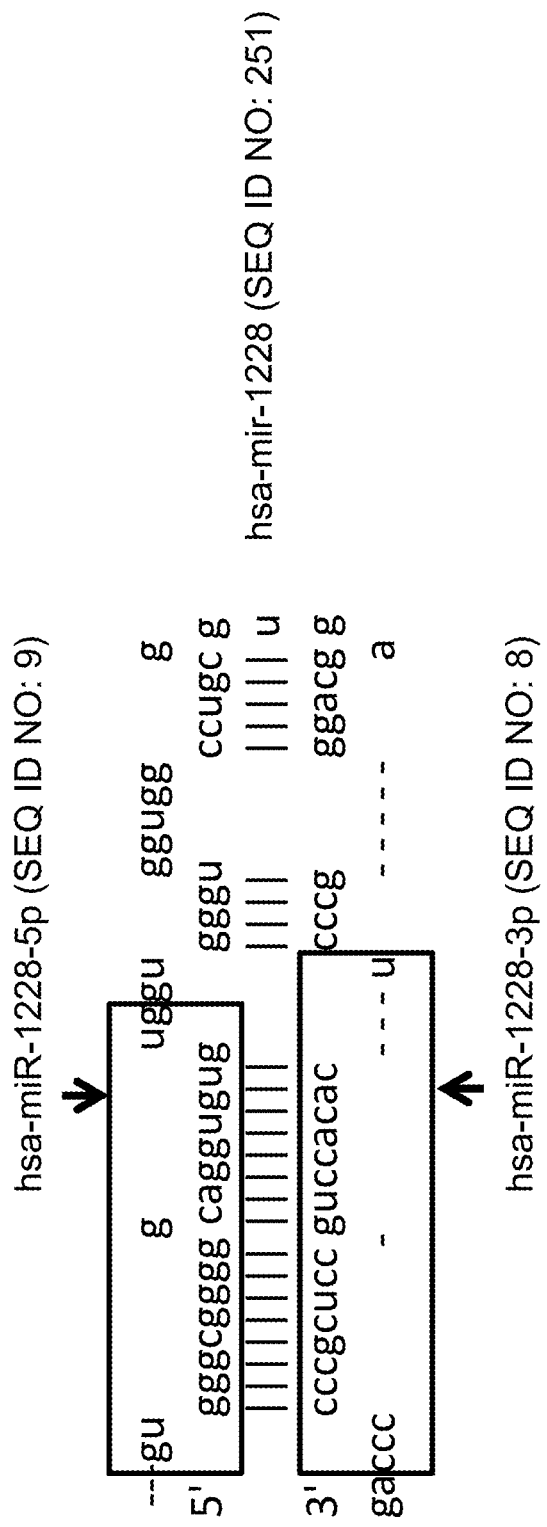
FIG. 1 illustrates the relationship between the nucleotide sequences of hsa-miR-1228-5p represented by SEQ ID NO: 9 and hsa-miR-1228-3p represented by SEQ ID NO: 8, which are generated from a precursor hsa-mir-1228 represented by SEQ ID NO: 251.

Hereinafter, the present invention will be further described in detail.

1. Target Nucleic acid(s) for Bladder Cancer

The major target nucleic acids as bladder cancer markers for detecting bladder cancer or the presence and/or absence of bladder cancer cells by using the nucleic acid probes or primers for detection of bladder cancer as defined above according to the present invention include at least one miRNA selected from the group consisting of miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p. Further, it is possible to preferably use, as target nucleic acid(s), other bladder cancer markers that can be combined with these miRNAs, specifically at least one miRNA selected from the group consisting of miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

Examples of the above miRNAs include any human gene containing any nucleotide sequence represented by any of SEQ ID NOs: 1 to 243 (i.e., respective miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, miR-937-5p, miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, miR-940), any congener thereof, any transcript thereof, and any variant or derivative thereof. Here, the gene, congener, transcript, variant, and derivative are as defined above.

Preferable target nucleic acid(s) is any human gene containing any nucleotide sequence represented by any of SEQ ID NOs: 1 to 243 or any transcript thereof, and more preferably is the corresponding transcript, namely miRNA and any precursor RNA such as pri-miRNA or pre-miRNA thereof.

The 1st target gene is the hsa-miR-6087 gene, a congener thereof, a transcript thereof, or a variant or derivative thereof. None of the previously known reports show that change in the expression of the gene or the transcript thereof can serve as a marker for bladder cancer.

The 2nd target gene is the hsa-miR-1185-1-3p gene, a congener thereof, a transcript thereof, or a derivative thereof. None of the previously known reports show that change in the expression of the gene or the transcript thereof can serve as a marker for bladder cancer.

The 3rd target gene is the hsa-miR-1185-2-3p gene, a congener thereof, a transcript thereof, or a variant or derivative thereof. None of the previously known reports show that change in the expression of the gene or the transcript thereof can serve as a marker for bladder cancer.

The 4th target gene is the hsa-miR-1193 gene, a congener thereof, a transcript thereof, or a variant or derivative thereof. None of the previously known reports show that change in the expression of the gene or the transcript thereof can serve as a marker for bladder cancer.

The 5th target gene is the hsa-miR-1199-5p gene, a congener thereof, a transcript thereof, or a variant or derivative thereof. None of the previously known reports show that change in the expression of the gene or the transcript thereof can serve as a marker for bladder cancer.

The 6th target gene is the hsa-miR-1225-5p gene, a congener thereof, a transcript thereof, or a variant or derivative thereof. None of the previously known reports show that change in the expression of the gene or the transcript thereof can serve as a marker for bladder cancer.

The 7th target gene is the hsa-miR-1227-5p gene, a congener thereof, a transcript thereof, or a variant or derivative thereof. None of the previously known reports show that change in the expression of the gene or the transcript thereof can serve as a marker for bladder cancer.

The 8th target gene is the hsa-miR-1228-3p gene, a congener thereof, a transcript thereof, or a variant or derivative thereof. None of the previously known reports show that change in the expression of the gene or the transcript thereof can serve as a marker for bladder cancer.

The 9th target gene is the hsa-miR-1228-5p gene, a congener thereof, a transcript thereof, or a variant or derivative thereof. None of the previously known reports show that change in the expression of the gene or the transcript thereof can serve as a marker for bladder cancer.

The 10th target gene is the hsa-miR-1237-5p gene, a congener thereof, a transcript thereof, or a variant or derivative thereof. None of the previously known reports show that change in the expression of the gene or the transcript thereof can serve as a marker for bladder cancer.

The 11th target gene is the hsa-miR-1238-5p gene, a congener thereof, a transcript thereof, or a variant or derivative thereof. None of the previously known reports show that change in the expression of the gene or the transcript thereof can serve as a marker for bladder cancer.

The 12th target gene is the hsa-miR-1247-3p gene, a congener thereof, a transcript thereof, or a variant or derivative thereof. None of the previously known reports show that change in the expression of the gene or the transcript thereof can serve as a marker for bladder cancer.

The 13th target gene is the hsa-miR-1268a gene, a congener thereof, a transcript thereof, or a variant or derivative thereof. None of the previously known reports show that change in the expression of the gene or the transcript thereof can serve as a marker for bladder cancer.

The 14th target gene is the hsa-miR-1268b gene, a congener thereof, a transcript thereof, or a variant or derivative thereof. None of the previously known reports show that change in the expression of the gene or the transcript thereof can serve as a marker for bladder cancer.

The 15th target gene is the hsa-miR-1273g-3p gene, a congener thereof, a transcript thereof, or a variant or derivative thereof. None of the previously known reports show that change in the expression of the gene or the transcript thereof can serve as a marker for bladder cancer.

The 16th target gene is the hsa-miR-128-2-5p gene, a congener thereof, a transcript thereof, or a variant or derivative thereof. None of the previously known reports show that change in the expression of the gene or the transcript thereof can serve as a marker for bladder cancer.

The 17th target gene is the hsa-miR-1343-3p gene, a congener thereof, a transcript thereof, or a variant or derivative thereof. None of the previously known reports show that change in the expression of the gene or the transcript thereof can serve as a marker for bladder cancer.

The 18th target gene is the hsa-miR-1343-5p gene, a congener thereof, a transcript thereof, or a variant or derivative thereof. None of the previously known reports show that change in the expression of the gene or the transcript thereof can serve as a marker for bladder cancer.

The 19th target gene is the hsa-miR-1470 gene, a congener thereof, a transcript thereof, or a variant or derivative thereof. None of the previously known reports show that change in the expression of the gene or the transcript thereof can serve as a marker for bladder cancer.

The 20th target gene is the hsa-miR-17-3p gene, a congener thereof, a transcript thereof, or a variant or derivative thereof. None of the previously known reports show that change in the expression of the gene or the transcript thereof can serve as a marker for bladder cancer.

The 21st target gene is the hsa-miR-187-5p gene, a congener thereof, a transcript thereof, or a variant or derivative thereof. None of the previously known reports show that change in the expression of the gene or the transcript thereof can serve as a marker for bladder cancer.

The 22nd target gene is the hsa-miR-1908-3p gene, a congener thereof, a transcript thereof, or a variant or derivative thereof. None of the previously known reports show that change in the expression of the gene or the transcript thereof can serve as a marker for bladder cancer.

The 23rd target gene is the hsa-miR-1908-5p gene, a congener thereof, a transcript thereof, or a variant or derivative thereof. None of the previously known reports show that change in the expression of the gene or the transcript thereof can serve as a marker for bladder cancer.

The 24th target gene is the hsa-miR-1909-3p gene, a congener thereof, a transcript thereof, or a variant or derivative thereof. None of the previously known reports show that change in the expression of the gene or the transcript thereof can serve as a marker for bladder cancer.

The 25th target gene is the hsa-miR-1915-3p gene, a congener thereof, a transcript thereof, or a variant or derivative thereof. None of the previously known reports show that change in the expression of the gene or the transcript thereof can serve as a marker for bladder cancer.

The 26th target gene is the hsa-miR-210-5p gene, a congener thereof, a transcript thereof, or a variant or derivative thereof. None of the previously known reports show that change in the expression of the gene or the transcript thereof can serve as a marker for bladder cancer.

The 27th target gene is the hsa-miR-24-3p gene, a congener thereof, a transcript thereof, or a variant or derivative thereof. None of the previously known reports show that change in the expression of the gene or the transcript thereof can serve as a marker for bladder cancer.

The 28th target gene is the hsa-miR-2467-3p gene, a congener thereof, a transcript thereof, or a variant or derivative thereof. None of the previously known reports show that change in the expression of the gene or the transcript thereof can serve as a marker for bladder cancer.

The 29th target gene is the hsa-miR-2861 gene, a congener thereof, a transcript thereof, or a variant or derivative thereof. None of the previously known reports show that change in the expression of the gene or the transcript thereof can serve as a marker for bladder cancer.

The 30th target gene is the hsa-miR-296-3p gene, a congener thereof, a transcript thereof, or a variant or derivative thereof. None of the previously known reports show that change in the expression of the gene or the transcript thereof can serve as a marker for bladder cancer.

The 31st target gene is the hsa-miR-29b-3p gene, a congener thereof, a transcript thereof, or a variant or derivative thereof. None of the previously known reports show that change in the expression of the gene or the transcript thereof can serve as a marker for bladder cancer.

The 32nd target gene is the hsa-miR-3131 gene, a congener thereof, a transcript thereof, or a variant or derivative thereof. None of the previously known reports show that change in the expression of the gene or the transcript thereof can serve as a marker for bladder cancer.

The 33rd target gene is the hsa-miR-3154 gene, a congener thereof, a transcript thereof, or a variant or derivative thereof. None of the previously known reports show that change in the expression of the gene or the transcript thereof can serve as a marker for bladder cancer.

The 34th target gene is the hsa-miR-3158-5p gene, a congener thereof, a transcript thereof, or a variant or derivative thereof. None of the previously known reports show that change in the expression of the gene or the transcript thereof can serve as a marker for bladder cancer.

The 35th target gene is the hsa-miR-3160-5p gene, a congener thereof, a transcript thereof, or a variant or derivative thereof. None of the previously known reports show that change in the expression of the gene or the transcript thereof can serve as a marker for bladder cancer.

The 36th target gene is the hsa-miR-3162-5p gene, a congener thereof, a transcript thereof, or a variant or derivative thereof. None of the previously known reports show that change in the expression of the gene or the transcript thereof can serve as a marker for bladder cancer.

The 37th target gene is the hsa-miR-3178 gene, a congener thereof, a transcript thereof, or a variant or derivative thereof. None of the previously known reports show that change in the expression of the gene or the transcript thereof can serve as a marker for bladder cancer.

The 38th target gene is the hsa-miR-3180-3p gene, a congener thereof, a transcript thereof, or a variant or derivative thereof. None of the previously known reports show that change in the expression of the gene or the transcript thereof can serve as a marker for bladder cancer.

The 39th target gene is the hsa-miR-3184-5p gene, a congener thereof, a transcript thereof, or a variant or derivative thereof. None of the previously known reports show that change in the expression of the gene or the transcript thereof can serve as a marker for bladder cancer.

The 40th target gene is the hsa-miR-3185 gene, a congener thereof, a transcript thereof, or a variant or derivative thereof. None of the previously known reports show that change in the expression of the gene or the transcript thereof can serve as a marker for bladder cancer.

The 41st target gene is the hsa-miR-3194-3p gene, a congener thereof, a transcript thereof, or a variant or derivative thereof. None of the previously known reports show that change in the expression of the gene or the transcript thereof can serve as a marker for bladder cancer.

The 42nd target gene is the hsa-miR-3195 gene, a congener thereof, a transcript thereof, or a variant or derivative thereof. None of the previously known reports show that change in the expression of the gene or the transcript thereof can serve as a marker for bladder cancer.

The 43rd target gene is the hsa-miR-3197 gene, a congener thereof, a transcript thereof, or a variant or derivative thereof. None of the previously known reports show that change in the expression of the gene or the transcript thereof can serve as a marker for bladder cancer.

The 44th target gene is the hsa-miR-320a gene, a congener thereof, a transcript thereof, or a variant or derivative thereof. None of the previously known reports show that change in the expression of the gene or the transcript thereof can serve as a marker for bladder cancer.

The 45th target gene is the hsa-miR-320b gene, a congener thereof, a transcript thereof, or a variant or derivative thereof. None of the previously known reports show that change in the expression of the gene or the transcript thereof can serve as a marker for bladder cancer.

The 46th target gene is the hsa-miR-328-5p gene, a congener thereof, a transcript thereof, or a variant or derivative thereof. None of the previously known reports show that change in the expression of the gene or the transcript thereof can serve as a marker for bladder cancer.

The 47th target gene is the hsa-miR-342-5p gene, a congener thereof, a transcript thereof, or a variant or derivative thereof. None of the previously known reports show that change in the expression of the gene or the transcript thereof can serve as a marker for bladder cancer.

The 48th target gene is the hsa-miR-345-3p gene, a congener thereof, a transcript thereof, or a variant or derivative thereof. None of the previously known reports show that change in the expression of the gene or the transcript thereof can serve as a marker for bladder cancer.

The 49th target gene is the hsa-miR-3616-3p gene, a congener thereof, a transcript thereof, or a variant or derivative thereof. None of the previously known reports show that change in the expression of the gene or the transcript thereof can serve as a marker for bladder cancer.

The 50th target gene is the hsa-miR-3619-3p gene, a congener thereof, a transcript thereof, or a variant or derivative thereof. None of the previously known reports show that change in the expression of the gene or the transcript thereof can serve as a marker for bladder cancer.

The 51st target gene is the hsa-miR-3620-5p gene, a congener thereof, a transcript thereof, or a variant or derivative thereof. None of the previously known reports show that change in the expression of the gene or the transcript thereof can serve as a marker for bladder cancer.

The 52nd target gene is the hsa-miR-3621 gene, a congener thereof, a transcript thereof, or a variant or derivative thereof. None of the previously known reports show that change in the expression of the gene or the transcript thereof can serve as a marker for bladder cancer.

The 53rd target gene is the hsa-miR-3622a-5p gene, a congener thereof, a transcript thereof, or a variant or derivative thereof. None of the previously known reports show that change in the expression of the gene or the transcript thereof can serve as a marker for bladder cancer.

The 54th target gene is the hsa-miR-3648 gene, a congener thereof, a transcript thereof, or a variant or derivative thereof. None of the previously known reports show that change in the expression of the gene or the transcript thereof can serve as a marker for bladder cancer.

The 55th target gene is the hsa-miR-3652 gene, a congener thereof, a transcript thereof, or a variant or derivative thereof. None of the previously known reports show that change in the expression of the gene or the transcript thereof can serve as a marker for bladder cancer.

The 56th target gene is the hsa-miR-3656 gene, a congener thereof, a transcript thereof, or a variant or derivative thereof. None of the previously known reports show that change in the expression of the gene or the transcript thereof can serve as a marker for bladder cancer.

The 57th target gene is the hsa-miR-3663-3p gene, a congener thereof, a transcript thereof, or a variant or derivative thereof. None of the previously known reports show that change in the expression of the gene or the transcript thereof can serve as a marker for bladder cancer.

The 58th target gene is the hsa-miR-3679-5p gene, a congener thereof, a transcript thereof, or a variant or derivative thereof. None of the previously known reports show that change in the expression of the gene or the transcript thereof can serve as a marker for bladder cancer.

The 59th target gene is the hsa-miR-371b-5p gene, a congener thereof, a transcript thereof, or a variant or derivative thereof. None of the previously known reports show that change in the expression of the gene or the transcript thereof can serve as a marker for bladder cancer.

The 60th target gene is the hsa-miR-373-5p gene, a congener thereof, a transcript thereof, or a variant or derivative thereof. None of the previously known reports show that change in the expression of the gene or the transcript thereof can serve as a marker for bladder cancer.

The 61st target gene is the hsa-miR-3917 gene, a congener thereof, a transcript thereof, or a variant or derivative thereof. None of the previously known reports show that change in the expression of the gene or the transcript thereof can serve as a marker for bladder cancer.

The 62nd target gene is the hsa-miR-3940-5p gene, a congener thereof, a transcript thereof, or a variant or derivative thereof. None of the previously known reports show that change in the expression of the gene or the transcript thereof can serve as a marker for bladder cancer.

The 63rd target gene is the hsa-miR-3960 gene, a congener thereof, a transcript thereof, or a variant or derivative thereof. None of the previously known reports show that change in the expression of the gene or the transcript thereof can serve as a marker for bladder cancer.

The 64th target gene is the hsa-miR-4258 gene, a congener thereof, a transcript thereof, or a variant or derivative thereof. None of the previously known reports show that change in the expression of the gene or the transcript thereof can serve as a marker for bladder cancer.

The 65th target gene is the hsa-miR-4259 gene, a congener thereof, a transcript thereof, or a variant or derivative thereof. None of the previously known reports show that change in the expression of the gene or the transcript thereof can serve as a marker for bladder cancer.

The 66th target gene is the hsa-miR-4270 gene, a congener thereof, a transcript thereof, or a variant or derivative thereof. None of the previously known reports show that change in the expression of the gene or the transcript thereof can serve as a marker for bladder cancer.

The 67th target gene is the hsa-miR-4286 gene, a congener thereof, a transcript thereof, or a variant or derivative thereof. None of the previously known reports show that change in the expression of the gene or the transcript thereof can serve as a marker for bladder cancer.

The 68th target gene is the hsa-miR-4298 gene, a congener thereof, a transcript thereof, or a variant or derivative thereof. None of the previously known reports show that change in the expression of the gene or the transcript thereof can serve as a marker for bladder cancer.

The 69th target gene is the hsa-miR-4322 gene, a congener thereof, a transcript thereof, or a variant or derivative thereof. None of the previously known reports show that change in the expression of the gene or the transcript thereof can serve as a marker for bladder cancer.

The 70th target gene is the hsa-miR-4327 gene, a congener thereof, a transcript thereof, or a variant or derivative thereof. None of the previously known reports show that change in the expression of the gene or the transcript thereof can serve as a marker for bladder cancer.

The 71st target gene is the hsa-miR-4417 gene, a congener thereof, a transcript thereof, or a variant or derivative thereof. None of the previously known reports show that change in the expression of the gene or the transcript thereof can serve as a marker for bladder cancer.

The 72nd target gene is the hsa-miR-4419b gene, a congener thereof, a transcript thereof, or a variant or derivative thereof. None of the previously known reports show that change in the expression of the gene or the transcript thereof can serve as a marker for bladder cancer.

The 73rd target gene is the hsa-miR-4429 gene, a congener thereof, a transcript thereof, or a variant or derivative thereof. None of the previously known reports show that change in the expression of the gene or the transcript thereof can serve as a marker for bladder cancer.

The 74th target gene is the hsa-miR-4430 gene, a congener thereof, a transcript thereof, or a variant or derivative thereof. None of the previously known reports show that change in the expression of the gene or the transcript thereof can serve as a marker for bladder cancer.

The 75th target gene is the hsa-miR-4433a-3p gene, a congener thereof, a transcript thereof, or a variant or derivative thereof. None of the previously known reports show that change in the expression of the gene or the transcript thereof can serve as a marker for bladder cancer.

The 76th target gene is the hsa-miR-4436b-5p gene, a congener thereof, a transcript thereof, or a variant or derivative thereof. None of the previously known reports show that change in the expression of the gene or the transcript thereof can serve as a marker for bladder cancer.

The 77th target gene is the hsa-miR-4443 gene, a congener thereof, a transcript thereof, or a variant or derivative thereof. None of the previously known reports show that change in the expression of the gene or the transcript thereof can serve as a marker for bladder cancer.

The 78th target gene is the hsa-miR-4446-3p gene, a congener thereof, a transcript thereof, or a variant or derivative thereof. None of the previously known reports show that change in the expression of the gene or the transcript thereof can serve as a marker for bladder cancer.

The 79th target gene is the hsa-miR-4447 gene, a congener thereof, a transcript thereof, or a variant or derivative thereof. None of the previously known reports show that change in the expression of the gene or the transcript thereof can serve as a marker for bladder cancer.

The 80th target gene is the hsa-miR-4448 gene, a congener thereof, a transcript thereof, or a variant or derivative thereof. None of the previously known reports show that change in the expression of the gene or the transcript thereof can serve as a marker for bladder cancer.

The 81st target gene is the hsa-miR-4449 gene, a congener thereof, a transcript thereof, or a variant or derivative thereof. None of the previously known reports show that change in the expression of the gene or the transcript thereof can serve as a marker for bladder cancer.

The 82nd target gene is the hsa-miR-4454 gene, a congener thereof, a transcript thereof, or a variant or derivative thereof. None of the previously known reports show that change in the expression of the gene or the transcript thereof can serve as a marker for bladder cancer.

The 83rd target gene is the hsa-miR-4455 gene, a congener thereof, a transcript thereof, or a variant or derivative thereof. None of the previously known reports show that change in the expression of the gene or the transcript thereof can serve as a marker for bladder cancer.

The 84th target gene is the hsa-miR-4459 gene, a congener thereof, a transcript thereof, or a variant or derivative thereof. None of the previously known reports show that change in the expression of the gene or the transcript thereof can serve as a marker for bladder cancer.

The 85th target gene is the hsa-miR-4462 gene, a congener thereof, a transcript thereof, or a variant or derivative thereof. None of the previously known reports show that change in the expression of the gene or the transcript thereof can serve as a marker for bladder cancer.

The 86th target gene is the hsa-miR-4466 gene, a congener thereof, a transcript thereof, or a variant or derivative thereof. None of the previously known reports show that change in the expression of the gene or the transcript thereof can serve as a marker for bladder cancer.

The 87th target gene is the hsa-miR-4467 gene, a congener thereof, a transcript thereof, or a variant or derivative thereof. None of the previously known reports show that change in the expression of the gene or the transcript thereof can serve as a marker for bladder cancer.

The 88th target gene is the hsa-miR-4480 gene, a congener thereof, a transcript thereof, or a variant or derivative thereof. None of the previously known reports show that change in the expression of the gene or the transcript thereof can serve as a marker for bladder cancer.

The 89th target gene is the hsa-miR-4483 gene, a congener thereof, a transcript thereof, or a variant or derivative thereof. None of the previously known reports show that change in the expression of the gene or the transcript thereof can serve as a marker for bladder cancer.

The 90th target gene is the hsa-miR-4484 gene, a congener thereof, a transcript thereof, or a variant or derivative thereof. None of the previously known reports show that change in the expression of the gene or the transcript thereof can serve as a marker for bladder cancer.

The 91st target gene is the hsa-miR-4485-5p gene, a congener thereof, a transcript thereof, or a variant or derivative thereof. None of the previously known reports show that change in the expression of the gene or the transcript thereof can serve as a marker for bladder cancer.

The 92nd target gene is the hsa-miR-4488 gene, a congener thereof, a transcript thereof, or a variant or derivative thereof. None of the previously known reports show that change in the expression of the gene or the transcript thereof can serve as a marker for bladder cancer.

The 93rd target gene is the hsa-miR-4492 gene, a congener thereof, a transcript thereof, or a variant or derivative thereof. None of the previously known reports show that change in the expression of the gene or the transcript thereof can serve as a marker for bladder cancer.

The 94th target gene is the hsa-miR-4505 gene, a congener thereof, a transcript thereof, or a variant or derivative thereof. None of the previously known reports show that change in the expression of the gene or the transcript thereof can serve as a marker for bladder cancer.

The 95th target gene is the hsa-miR-4515 gene, a congener thereof, a transcript thereof, or a variant or derivative thereof. None of the previously known reports show that change in the expression of the gene or the transcript thereof can serve as a marker for bladder cancer.

The 96th target gene is the hsa-miR-4525 gene, a congener thereof, a transcript thereof, or a variant or derivative thereof. None of the previously known reports show that change in the expression of the gene or the transcript thereof can serve as a marker for bladder cancer.

The 97th target gene is the hsa-miR-4534 gene, a congener thereof, a transcript thereof, or a variant or derivative thereof. None of the previously known reports show that change in the expression of the gene or the transcript thereof can serve as a marker for bladder cancer.

The 98th target gene is the hsa-miR-4535 gene, a congener thereof, a transcript thereof, or a variant or derivative thereof. None of the previously known reports show that change in the expression of the gene or the transcript thereof can serve as a marker for bladder cancer.

The 99th target gene is the hsa-miR-4633-3p gene, a congener thereof, a transcript thereof, or a variant or derivative thereof. None of the previously known reports show that change in the expression of the gene or the transcript thereof can serve as a marker for bladder cancer.

The 100th target gene is the hsa-miR-4634 gene, a congener thereof, a transcript thereof, or a variant or derivative thereof. None of the previously known reports show that change in the expression of the gene or the transcript thereof can serve as a marker for bladder cancer.

The 101st target gene is the hsa-miR-4640-5p gene, a congener thereof, a transcript thereof, or a variant or derivative thereof. None of the previously known reports show that change in the expression of the gene or the transcript thereof can serve as a marker for bladder cancer.

The 102nd target gene is the hsa-miR-4649-5p gene, a congener thereof, a transcript thereof, or a variant or derivative thereof. None of the previously known reports show that change in the expression of the gene or the transcript thereof can serve as a marker for bladder cancer.

The 103rd target gene is the hsa-miR-4651 gene, a congener thereof, a transcript thereof, or a variant or derivative thereof. None of the previously known reports show that change in the expression of the gene or the transcript thereof can serve as a marker for bladder cancer.

The 104th target gene is the hsa-miR-4652-5p gene, a congener thereof, a transcript thereof, or a variant or derivative thereof. None of the previously known reports show that change in the expression of the gene or the transcript thereof can serve as a marker for bladder cancer.

The 105th target gene is the hsa-miR-4655-5p gene, a congener thereof, a transcript thereof, or a variant or derivative thereof. None of the previously known reports show that change in the expression of the gene or the transcript thereof can serve as a marker for bladder cancer.

The 106th target gene is the hsa-miR-4656 gene, a congener thereof, a transcript thereof, or a variant or derivative thereof. None of the previously known reports show that change in the expression of the gene or the transcript thereof can serve as a marker for bladder cancer.

The 107th target gene is the hsa-miR-4658 gene, a congener thereof, a transcript thereof, or a variant or derivative thereof. None of the previously known reports show that change in the expression of the gene or the transcript thereof can serve as a marker for bladder cancer.

The 108th target gene is the hsa-miR-4663 gene, a congener thereof, a transcript thereof, or a variant or derivative thereof. None of the previously known reports show that change in the expression of the gene or the transcript thereof can serve as a marker for bladder cancer.

The 109th target gene is the hsa-miR-4673 gene, a congener thereof, a transcript thereof, or a variant or derivative thereof. None of the previously known reports show that change in the expression of the gene or the transcript thereof can serve as a marker for bladder cancer.

The 110th target gene is the hsa-miR-4675 gene, a congener thereof, a transcript thereof, or a variant or derivative thereof. None of the previously known reports show that change in the expression of the gene or the transcript thereof can serve as a marker for bladder cancer.

The 111th target gene is the hsa-miR-4687-3p gene, a congener thereof, a transcript thereof, or a variant or derivative thereof. None of the previously known reports show that change in the expression of the gene or the transcript thereof can serve as a marker for bladder cancer.

The 112th target gene is the hsa-miR-4687-5p gene, a congener thereof, a transcript thereof, or a variant or derivative thereof. None of the previously known reports show that change in the expression of the gene or the transcript thereof can serve as a marker for bladder cancer.

The 113th target gene is the hsa-miR-4690-5p gene, a congener thereof, a transcript thereof, or a variant or derivative thereof. None of the previously known reports show that change in the expression of the gene or the transcript thereof can serve as a marker for bladder cancer.

The 114th target gene is the hsa-miR-4695-5p gene, a congener thereof, a transcript thereof, or a variant or derivative thereof. None of the previously known reports show that change in the expression of the gene or the transcript thereof can serve as a marker for bladder cancer.

The 115th target gene is the hsa-miR-4697-5p gene, a congener thereof, a transcript thereof, or a variant or derivative thereof. None of the previously known reports show that change in the expression of the gene or the transcript thereof can serve as a marker for bladder cancer.

The 116th target gene is the hsa-miR-4706 gene, a congener thereof, a transcript thereof, or a variant or derivative thereof. None of the previously known reports show that change in the expression of the gene or the transcript thereof can serve as a marker for bladder cancer.

The 117th target gene is the hsa-miR-4707-3p gene, a congener thereof, a transcript thereof, or a variant or derivative thereof. None of the previously known reports show that change in the expression of the gene or the transcript thereof can serve as a marker for bladder cancer.

The 118th target gene is the hsa-miR-4707-5p gene, a congener thereof, a transcript thereof, or a variant or derivative thereof. None of the previously known reports show that change in the expression of the gene or the transcript thereof can serve as a marker for bladder cancer.

The 119th target gene is the hsa-miR-4708-3p gene, a congener thereof, a transcript thereof, or a variant or derivative thereof. None of the previously known reports show that change in the expression of the gene or the transcript thereof can serve as a marker for bladder cancer.

The 120th target gene is the hsa-miR-4710 gene, a congener thereof, a transcript thereof, or a variant or derivative thereof. None of the previously known reports show that change in the expression of the gene or the transcript thereof can serve as a marker for bladder cancer.

The 121st target gene is the hsa-miR-4718 gene, a congener thereof, a transcript thereof, or a variant or derivative thereof. None of the previously known reports show that change in the expression of the gene or the transcript thereof can serve as a marker for bladder cancer.

The 122nd target gene is the hsa-miR-4722-5p gene, a congener thereof, a transcript thereof, or a variant or derivative thereof. None of the previously known reports show that change in the expression of the gene or the transcript thereof can serve as a marker for bladder cancer.

The 123rd target gene is the hsa-miR-4725-3p gene, a congener thereof, a transcript thereof, or a variant or derivative thereof. None of the previously known reports show that change in the expression of the gene or the transcript thereof can serve as a marker for bladder cancer.

The 124th target gene is the hsa-miR-4726-5p gene, a congener thereof, a transcript thereof, or a variant or derivative thereof. None of the previously known reports show that change in the expression of the gene or the transcript thereof can serve as a marker for bladder cancer.

The 125th target gene is the hsa-miR-4727-3p gene, a congener thereof, a transcript thereof, or a variant or derivative thereof. None of the previously known reports show that change in the expression of the gene or the transcript thereof can serve as a marker for bladder cancer.

The 126th target gene is the hsa-miR-4728-5p gene, a congener thereof, a transcript thereof, or a variant or derivative thereof. None of the previously known reports show that change in the expression of the gene or the transcript thereof can serve as a marker for bladder cancer.

The 127th target gene is the hsa-miR-4731-5p gene, a congener thereof, a transcript thereof, or a variant or derivative thereof. None of the previously known reports show that change in the expression of the gene or the transcript thereof can serve as a marker for bladder cancer.

The 128th target gene is the hsa-miR-4736 gene, a congener thereof, a transcript thereof, or a variant or derivative thereof. None of the previously known reports show that change in the expression of the gene or the transcript thereof can serve as a marker for bladder cancer.

The 129th target gene is the hsa-miR-4739 gene, a congener thereof, a transcript thereof, or a variant or derivative thereof. None of the previously known reports show that change in the expression of the gene or the transcript thereof can serve as a marker for bladder cancer.

The 130th target gene is the hsa-miR-4740-5p gene, a congener thereof, a transcript thereof, or a variant or derivative thereof. None of the previously known reports show that change in the expression of the gene or the transcript thereof can serve as a marker for bladder cancer.

The 131st target gene is the hsa-miR-4741 gene, a congener thereof, a transcript thereof, or a variant or derivative thereof. None of the previously known reports show that change in the expression of the gene or the transcript thereof can serve as a marker for bladder cancer.

The 132nd target gene is the hsa-miR-4750-5p gene, a congener thereof, a transcript thereof, or a variant or derivative thereof. None of the previously known reports show that change in the expression of the gene or the transcript thereof can serve as a marker for bladder cancer.

The 133rd target gene is the hsa-miR-4755-3p gene, a congener thereof, a transcript thereof, or a variant or derivative thereof. None of the previously known reports show that change in the expression of the gene or the transcript thereof can serve as a marker for bladder cancer.

The 134th target gene is the hsa-miR-4763-3p gene, a congener thereof, a transcript thereof, or a variant or derivative thereof. None of the previously known reports show that change in the expression of the gene or the transcript thereof can serve as a marker for bladder cancer.

The 135th target gene is the hsa-miR-4771 gene, a congener thereof, a transcript thereof, or a variant or derivative thereof. None of the previously known reports show that change in the expression of the gene or the transcript thereof can serve as a marker for bladder cancer.

The 136th target gene is the hsa-miR-4783-3p gene, a congener thereof, a transcript thereof, or a variant or derivative thereof. None of the previously known reports show that change in the expression of the gene or the transcript thereof can serve as a marker for bladder cancer.

The 137th target gene is the hsa-miR-4783-5p gene, a congener thereof, a transcript thereof, or a variant or derivative thereof. None of the previously known reports show that change in the expression of the gene or the transcript thereof can serve as a marker for bladder cancer.

The 138th target gene is the hsa-miR-4787-3p gene, a congener thereof, a transcript thereof, or a variant or derivative thereof. None of the previously known reports show that change in the expression of the gene or the transcript thereof can serve as a marker for bladder cancer.

The 139th target gene is the hsa-miR-4792 gene, a congener thereof, a transcript thereof, or a variant or derivative thereof. None of the previously known reports show that change in the expression of the gene or the transcript thereof can serve as a marker for bladder cancer.

The 140th target gene is the hsa-miR-498 gene, a congener thereof, a transcript thereof, or a variant or derivative thereof. None of the previously known reports show that change in the expression of the gene or the transcript thereof can serve as a marker for bladder cancer.

The 141st target gene is the hsa-miR-5008-5p gene, a congener thereof, a transcript thereof, or a variant or derivative thereof. None of the previously known reports show that change in the expression of the gene or the transcript thereof can serve as a marker for bladder cancer.

The 142nd target gene is the hsa-miR-5010-5p gene, a congener thereof, a transcript thereof, or a variant or derivative thereof. None of the previously known reports show that change in the expression of the gene or the transcript thereof can serve as a marker for bladder cancer.

The 143rd target gene is the hsa-miR-504-3p gene, a congener thereof, a transcript thereof, or a variant or derivative thereof. None of the previously known reports show that change in the expression of the gene or the transcript thereof can serve as a marker for bladder cancer.

The 144th target gene is the hsa-miR-5195-3p gene, a congener thereof, a transcript thereof, or a variant or derivative thereof. None of the previously known reports show that change in the expression of the gene or the transcript thereof can serve as a marker for bladder cancer.

The 145th target gene is the hsa-miR-550a-5p gene, a congener thereof, a transcript thereof, or a variant or derivative thereof. None of the previously known reports show that change in the expression of the gene or the transcript thereof can serve as a marker for bladder cancer.

The 146th target gene is the hsa-miR-5572 gene, a congener thereof, a transcript thereof, or a variant or derivative thereof. None of the previously known reports show that change in the expression of the gene or the transcript thereof can serve as a marker for bladder cancer.

The 147th target gene is the hsa-miR-5739 gene, a congener thereof, a transcript thereof, or a variant or derivative thereof. None of the previously known reports show that change in the expression of the gene or the transcript thereof can serve as a marker for bladder cancer.

The 148th target gene is the hsa-miR-6075 gene, a congener thereof, a transcript thereof, or a variant or derivative thereof. None of the previously known reports show that change in the expression of the gene or the transcript thereof can serve as a marker for bladder cancer.

The 149th target gene is the hsa-miR-6076 gene, a congener thereof, a transcript thereof, or a variant or derivative thereof. None of the previously known reports show that change in the expression of the gene or the transcript thereof can serve as a marker for bladder cancer.

The 150th target gene is the hsa-miR-6088 gene, a congener thereof, a transcript thereof, or a variant or derivative thereof. None of the previously known reports show that change in the expression of the gene or the transcript thereof can serve as a marker for bladder cancer.

The 151st target gene is the hsa-miR-6124 gene, a congener thereof, a transcript thereof, or a variant or derivative thereof. None of the previously known reports show that change in the expression of the gene or the transcript thereof can serve as a marker for bladder cancer.

The 152nd target gene is the hsa-miR-6131 gene, a congener thereof, a transcript thereof, or a variant or derivative thereof. None of the previously known reports show that change in the expression of the gene or the transcript thereof can serve as a marker for bladder cancer.

The 153rd target gene is the hsa-miR-6132 gene, a congener thereof, a transcript thereof, or a variant or derivative thereof. None of the previously known reports show that change in the expression of the gene or the transcript thereof can serve as a marker for bladder cancer.

The 154th target gene is the hsa-miR-614 gene, a congener thereof, a transcript thereof, or a variant or derivative thereof. None of the previously known reports show that change in the expression of the gene or the transcript thereof can serve as a marker for bladder cancer.

The 155th target gene is the hsa-miR-615-5p gene, a congener thereof, a transcript thereof, or a variant or derivative thereof. None of the previously known reports show that change in the expression of the gene or the transcript thereof can serve as a marker for bladder cancer.

The 156th target gene is the hsa-miR-619-5p gene, a congener thereof, a transcript thereof, or a variant or derivative thereof. None of the previously known reports show that change in the expression of the gene or the transcript thereof can serve as a marker for bladder cancer.

The 157th target gene is the hsa-miR-642b-3p gene, a congener thereof, a transcript thereof, or a variant or derivative thereof. None of the previously known reports show that change in the expression of the gene or the transcript thereof can serve as a marker for bladder cancer.

The 158th target gene is the hsa-miR-6510-5p gene, a congener thereof, a transcript thereof, or a variant or derivative thereof. None of the previously known reports show that change in the expression of the gene or the transcript thereof can serve as a marker for bladder cancer.

The 159th target gene is the hsa-miR-6511a-5p gene, a congener thereof, a transcript thereof, or a variant or derivative thereof. None of the previously known reports show that change in the expression of the gene or the transcript thereof can serve as a marker for bladder cancer.

The 160th target gene is the hsa-miR-6515-3p gene, a congener thereof, a transcript thereof, or a variant or derivative thereof. None of the previously known reports show that change in the expression of the gene or the transcript thereof can serve as a marker for bladder cancer.

The 161st target gene is the hsa-miR-6515-5p gene, a congener thereof, a transcript thereof, or a variant or derivative thereof. None of the previously known reports show that change in the expression of the gene or the transcript thereof can serve as a marker for bladder cancer.

The 162nd target gene is the hsa-miR-663b gene, a congener thereof, a transcript thereof, or a variant or derivative thereof. None of the previously known reports show that change in the expression of the gene or the transcript thereof can serve as a marker for bladder cancer.

The 163rd target gene is the hsa-miR-6716-5p gene, a congener thereof, a transcript thereof, or a variant or derivative thereof. None of the previously known reports show that change in the expression of the gene or the transcript thereof can serve as a marker for bladder cancer.

The 164th target gene is the hsa-miR-6717-5p gene, a congener thereof, a transcript thereof, or a variant or derivative thereof. None of the previously known reports show that change in the expression of the gene or the transcript thereof can serve as a marker for bladder cancer.

The 165th target gene is the hsa-miR-6722-3p gene, a congener thereof, a transcript thereof, or a variant or derivative thereof. None of the previously known reports show that change in the expression of the gene or the transcript thereof can serve as a marker for bladder cancer.

The 166th target gene is the hsa-miR-6724-5p gene, a congener thereof, a transcript thereof, or a variant or derivative thereof. None of the previously known reports show that change in the expression of the gene or the transcript thereof can serve as a marker for bladder cancer.

The 167th target gene is the hsa-miR-6726-5p gene, a congener thereof, a transcript thereof, or a variant or derivative thereof. None of the previously known reports show that change in the expression of the gene or the transcript thereof can serve as a marker for bladder cancer.

The 168th target gene is the hsa-miR-6737-5p gene, a congener thereof, a transcript thereof, or a variant or derivative thereof. None of the previously known reports show that change in the expression of the gene or the transcript thereof can serve as a marker for bladder cancer.

The 169th target gene is the hsa-miR-6741-5p gene, a congener thereof, a transcript thereof, or a variant or derivative thereof. None of the previously known reports show that change in the expression of the gene or the transcript thereof can serve as a marker for bladder cancer.

The 170th target gene is the hsa-miR-6742-5p gene, a congener thereof, a transcript thereof, or a variant or derivative thereof. None of the previously known reports show that change in the expression of the gene or the transcript thereof can serve as a marker for bladder cancer.

The 171st target gene is the hsa-miR-6743-5p gene, a congener thereof, a transcript thereof, or a variant or derivative thereof. None of the previously known reports show that change in the expression of the gene or the transcript thereof can serve as a marker for bladder cancer.

The 172nd target gene is the hsa-miR-6746-5p gene, a congener thereof, a transcript thereof, or a variant or derivative thereof. None of the previously known reports show that change in the expression of the gene or the transcript thereof can serve as a marker for bladder cancer.

The 173rd target gene is the hsa-miR-6749-5p gene, a congener thereof, a transcript thereof, or a variant or derivative thereof. None of the previously known reports show that change in the expression of the gene or the transcript thereof can serve as a marker for bladder cancer.

The 174th target gene is the hsa-miR-6760-5p gene, a congener thereof, a transcript thereof, or a variant or derivative thereof. None of the previously known reports show that change in the expression of the gene or the transcript thereof can serve as a marker for bladder cancer.

The 175th target gene is the hsa-miR-6762-5p gene, a congener thereof, a transcript thereof, or a variant or derivative thereof. None of the previously known reports show that change in the expression of the gene or the transcript thereof can serve as a marker for bladder cancer.

The 176th target gene is the hsa-miR-6765-3p gene, a congener thereof, a transcript thereof, or a variant or derivative thereof. None of the previously known reports show that change in the expression of the gene or the transcript thereof can serve as a marker for bladder cancer.

The 177th target gene is the hsa-miR-6765-5p gene, a congener thereof, a transcript thereof, or a variant or derivative thereof. None of the previously known reports show that change in the expression of the gene or the transcript thereof can serve as a marker for bladder cancer.

The 178th target gene is the hsa-miR-6766-3p gene, a congener thereof, a transcript thereof, or a variant or derivative thereof. None of the previously known reports show that change in the expression of the gene or the transcript thereof can serve as a marker for bladder cancer.

The 179th target gene is the hsa-miR-6766-5p gene, a congener thereof, a transcript thereof, or a variant or derivative thereof. None of the previously known reports show that change in the expression of the gene or the transcript thereof can serve as a marker for bladder cancer.

The 180th target gene is the hsa-miR-6771-5p gene, a congener thereof, a transcript thereof, or a variant or derivative thereof. None of the previously known reports show that change in the expression of the gene or the transcript thereof can serve as a marker for bladder cancer.

The 181st target gene is the hsa-miR-6774-5p gene, a congener thereof, a transcript thereof, or a variant or derivative thereof. None of the previously known reports show that change in the expression of the gene or the transcript thereof can serve as a marker for bladder cancer.

The 182nd target gene is the hsa-miR-6777-5p gene, a congener thereof, a transcript thereof, or a variant or derivative thereof. None of the previously known reports show that change in the expression of the gene or the transcript thereof can serve as a marker for bladder cancer.

The 183rd target gene is the hsa-miR-6778-5p gene, a congener thereof, a transcript thereof, or a variant or derivative thereof. None of the previously known reports show that change in the expression of the gene or the transcript thereof can serve as a marker for bladder cancer.

The 184th target gene is the hsa-miR-6780b-5p gene, a congener thereof, a transcript thereof, or a variant or derivative thereof. None of the previously known reports show that change in the expression of the gene or the transcript thereof can serve as a marker for bladder cancer.

The 185th target gene is the hsa-miR-6781-5p gene, a congener thereof, a transcript thereof, or a variant or derivative thereof. None of the previously known reports show that change in the expression of the gene or the transcript thereof can serve as a marker for bladder cancer.

The 186th target gene is the hsa-miR-6782-5p gene, a congener thereof, a transcript thereof, or a variant or derivative thereof. None of the previously known reports show that change in the expression of the gene or the transcript thereof can serve as a marker for bladder cancer.

The 187th target gene is the hsa-miR-6784-5p gene, a congener thereof, a transcript thereof, or a variant or derivative thereof. None of the previously known reports show that change in the expression of the gene or the transcript thereof can serve as a marker for bladder cancer.

The 188th target gene is the hsa-miR-6785-5p gene, a congener thereof, a transcript thereof, or a variant or derivative thereof. None of the previously known reports show that change in the expression of the gene or the transcript thereof can serve as a marker for bladder cancer.

The 189th target gene is the hsa-miR-6787-5p gene, a congener thereof, a transcript thereof, or a variant or derivative thereof. None of the previously known reports show that change in the expression of the gene or the transcript thereof can serve as a marker for bladder cancer.

The 190th target gene is the hsa-miR-6789-5p gene, a congener thereof, a transcript thereof, or a variant or derivative thereof. None of the previously known reports show that change in the expression of the gene or the transcript thereof can serve as a marker for bladder cancer.

The 191st target gene is the hsa-miR-6791-5p gene, a congener thereof, a transcript thereof, or a variant or derivative thereof. None of the previously known reports show that change in the expression of the gene or the transcript thereof can serve as a marker for bladder cancer.

The 192nd target gene is the hsa-miR-6794-5p gene, a congener thereof, a transcript thereof, or a variant or derivative thereof. None of the previously known reports show that change in the expression of the gene or the transcript thereof can serve as a marker for bladder cancer.

The 193rd target gene is the hsa-miR-6800-5p gene, a congener thereof, a transcript thereof, or a variant or derivative thereof. None of the previously known reports show that change in the expression of the gene or the transcript thereof can serve as a marker for bladder cancer.

The 194th target gene is the hsa-miR-6802-5p gene, a congener thereof, a transcript thereof, or a variant or derivative thereof. None of the previously known reports show that change in the expression of the gene or the transcript thereof can serve as a marker for bladder cancer.

The 195th target gene is the hsa-miR-6803-5p gene, a congener thereof, a transcript thereof, or a variant or derivative thereof. None of the previously known reports show that change in the expression of the gene or the transcript thereof can serve as a marker for bladder cancer.

The 196th target gene is the hsa-miR-6812-5p gene, a congener thereof, a transcript thereof, or a variant or derivative thereof. None of the previously known reports show that change in the expression of the gene or the transcript thereof can serve as a marker for bladder cancer.

The 197th target gene is the hsa-miR-6816-5p gene, a congener thereof, a transcript thereof, or a variant or derivative thereof. None of the previously known reports show that change in the expression of the gene or the transcript thereof can serve as a marker for bladder cancer.

The 198th target gene is the hsa-miR-6819-5p gene, a congener thereof, a transcript thereof, or a variant or derivative thereof. None of the previously known reports show that change in the expression of the gene or the transcript thereof can serve as a marker for bladder cancer.

The 199th target gene is the hsa-miR-6821-5p gene, a congener thereof, a transcript thereof, or a variant or derivative thereof. None of the previously known reports show that change in the expression of the gene or the transcript thereof can serve as a marker for bladder cancer.

The 200th target gene is the hsa-miR-6826-5p gene, a congener thereof, a transcript thereof, or a variant or derivative thereof. None of the previously known reports show that change in the expression of the gene or the transcript thereof can serve as a marker for bladder cancer.

The 201st target gene is the hsa-miR-6831-5p gene, a congener thereof, a transcript thereof, or a variant or derivative thereof. None of the previously known reports show that change in the expression of the gene or the transcript thereof can serve as a marker for bladder cancer.

The 202nd target gene is the hsa-miR-6836-3p gene, a congener thereof, a transcript thereof, or a variant or derivative thereof. None of the previously known reports show that change in the expression of the gene or the transcript thereof can serve as a marker for bladder cancer.

The 203rd target gene is the hsa-miR-6840-3p gene, a congener thereof, a transcript thereof, or a variant or derivative thereof. None of the previously known reports show that change in the expression of the gene or the transcript thereof can serve as a marker for bladder cancer.

The 204th target gene is the hsa-miR-6842-5p gene, a congener thereof, a transcript thereof, or a variant or derivative thereof. None of the previously known reports show that change in the expression of the gene or the transcript thereof can serve as a marker for bladder cancer.

The 205th target gene is the hsa-miR-6850-5p gene, a congener thereof, a transcript thereof, or a variant or derivative thereof. None of the previously known reports show that change in the expression of the gene or the transcript thereof can serve as a marker for bladder cancer.

The 206th target gene is the hsa-miR-6861-5p gene, a congener thereof, a transcript thereof, or a variant or derivative thereof. None of the previously known reports show that change in the expression of the gene or the transcript thereof can serve as a marker for bladder cancer.

The 207th target gene is the hsa-miR-6869-5p gene, a congener thereof, a transcript thereof, or a variant or derivative thereof. None of the previously known reports show that change in the expression of the gene or the transcript thereof can serve as a marker for bladder cancer.

The 208th target gene is the hsa-miR-6870-5p gene, a congener thereof, a transcript thereof, or a variant or derivative thereof. None of the previously known reports show that change in the expression of the gene or the transcript thereof can serve as a marker for bladder cancer.

The 209th target gene is the hsa-miR-6877-5p gene, a congener thereof, a transcript thereof, or a variant or derivative thereof. None of the previously known reports show that change in the expression of the gene or the transcript thereof can serve as a marker for bladder cancer.

The 210th target gene is the hsa-miR-6879-5p gene, a congener thereof, a transcript thereof, or a variant or derivative thereof. None of the previously known reports show that change in the expression of the gene or the transcript thereof can serve as a marker for bladder cancer.

The 211st target gene is the hsa-miR-6880-3p gene, a congener thereof, a transcript thereof, or a variant or derivative thereof. None of the previously known reports show that change in the expression of the gene or the transcript thereof can serve as a marker for bladder cancer.

The 212nd target gene is the hsa-miR-6880-5p gene, a congener thereof, a transcript thereof, or a variant or derivative thereof. None of the previously known reports show that change in the expression of the gene or the transcript thereof can serve as a marker for bladder cancer.

The 213rd target gene is the hsa-miR-6885-5p gene, a congener thereof, a transcript thereof, or a variant or derivative thereof. None of the previously known reports show that change in the expression of the gene or the transcript thereof can serve as a marker for bladder cancer.

The 214th target gene is the hsa-miR-6887-5p gene, a congener thereof, a transcript thereof, or a variant or derivative thereof. None of the previously known reports show that change in the expression of the gene or the transcript thereof can serve as a marker for bladder cancer.

The 215th target gene is the hsa-miR-7107-5p gene, a congener thereof, a transcript thereof, or a variant or derivative thereof. None of the previously known reports show that change in the expression of the gene or the transcript thereof can serve as a marker for bladder cancer.

The 216th target gene is the hsa-miR-7108-3p gene, a congener thereof, a transcript thereof, or a variant or derivative thereof. None of the previously known reports show that change in the expression of the gene or the transcript thereof can serve as a marker for bladder cancer.

The 217th target gene is the hsa-miR-7109-5p gene, a congener thereof, a transcript thereof, or a variant or derivative thereof. None of the previously known reports show that change in the expression of the gene or the transcript thereof can serve as a marker for bladder cancer.

The 218th target gene is the hsa-miR-711 gene, a congener thereof, a transcript thereof, or a variant or derivative thereof. None of the previously known reports show that change in the expression of the gene or the transcript thereof can serve as a marker for bladder cancer.

The 219th target gene is the hsa-miR-7113-3p gene, a congener thereof, a transcript thereof, or a variant or derivative thereof. None of the previously known reports show that change in the expression of the gene or the transcript thereof can serve as a marker for bladder cancer.

The 220th target gene is the hsa-miR-7150 gene, a congener thereof, a transcript thereof, or a variant or derivative thereof. None of the previously known reports show that change in the expression of the gene or the transcript thereof can serve as a marker for bladder cancer.

The 221st target gene is the hsa-miR-744-5p gene, a congener thereof, a transcript thereof, or a variant or derivative thereof. None of the previously known reports show that change in the expression of the gene or the transcript thereof can serve as a marker for bladder cancer.

The 222nd target gene is the hsa-miR-7975 gene, a congener thereof, a transcript thereof, or a variant or derivative thereof. None of the previously known reports show that change in the expression of the gene or the transcript thereof can serve as a marker for bladder cancer.

The 223rd target gene is the hsa-miR-7977 gene, a congener thereof, a transcript thereof, or a variant or derivative thereof. None of the previously known reports show that change in the expression of the gene or the transcript thereof can serve as a marker for bladder cancer.

The 224th target gene is the hsa-miR-8052 gene, a congener thereof, a transcript thereof, or a variant or derivative thereof. None of the previously known reports show that change in the expression of the gene or the transcript thereof can serve as a marker for bladder cancer.

The 225th target gene is the hsa-miR-8069 gene, a congener thereof, a transcript thereof, or a variant or derivative thereof. None of the previously known reports show that change in the expression of the gene or the transcript thereof can serve as a marker for bladder cancer.

The 226th target gene is the hsa-miR-8073 gene, a congener thereof, a transcript thereof, or a variant or derivative thereof. None of the previously known reports show that change in the expression of the gene or the transcript thereof can serve as a marker for bladder cancer.

The 227th target gene is the hsa-miR-887-3p gene, a congener thereof, a transcript thereof, or a variant or derivative thereof. None of the previously known reports show that change in the expression of the gene or the transcript thereof can serve as a marker for bladder cancer.

The 228th target gene is the hsa-miR-937-5p gene, a congener thereof, a transcript thereof, or a variant or derivative thereof. None of the previously known reports show that change in the expression of the gene or the transcript thereof can serve as a marker for bladder cancer.

The 229th target gene is the miR-1202 gene, a congener thereof, a transcript thereof, or a variant or derivative thereof. The previously known report shows that change in the expression of the gene or the transcript thereof can serve as a marker for bladder cancer (Patent Literature 1).

The 230th target gene is the miR-1207-5p gene, a congener thereof, a transcript thereof, or a variant or derivative thereof. The previously known report shows that change in the expression of the gene or the transcript thereof can serve as a marker for bladder cancer (Patent Literature 1).

The 231st target gene is the miR-1246 gene, a congener thereof, a transcript thereof, or a variant or derivative thereof. The previously known report shows that change in the expression of the gene or the transcript thereof can serve as a marker for bladder cancer (Patent Literature 2).

The 232nd target gene is the miR-1254 gene, a congener thereof, a transcript thereof, or a variant or derivative thereof. The previously known report shows that change in the expression of the gene or the transcript thereof can serve as a marker for bladder cancer (Patent Literature 2).

The 233rd target gene is the miR-135a-3p gene, a congener thereof, a transcript thereof, or a variant or derivative thereof. The previously known report shows that change in the expression of the gene or the transcript thereof can serve as a marker for bladder cancer (Patent Literature 1).

The 234th target gene is the miR-1469 gene, a congener thereof, a transcript thereof, or a variant or derivative thereof. The previously known report shows that change in the expression of the gene or the transcript thereof can serve as a marker for bladder cancer (Patent Literature 1).

The 235th target gene is the miR-149-3p gene, a congener thereof, a transcript thereof, or a variant or derivative thereof. The previously known report shows that change in the expression of the gene or the transcript thereof can serve as a marker for bladder cancer (Patent Literature 1).

The 236th target gene is the miR-150-3p gene, a congener thereof, a transcript thereof, or a variant or derivative thereof. The previously known report shows that change in the expression of the gene or the transcript thereof can serve as a marker for bladder cancer (Patent Literature 1).

The 237th target gene is the miR-1914-3p gene, a congener thereof, a transcript thereof, or a variant or derivative thereof. The previously known report shows that change in the expression of the gene or the transcript thereof can serve as a marker for bladder cancer (Patent Literature 1).

The 238th target gene is the miR-191-5p gene, a congener thereof, a transcript thereof, or a variant or derivative thereof. The previously known report shows that change in the expression of the gene or the transcript thereof can serve as a marker for bladder cancer (Non Patent Literature 2).

The 239th target gene is the miR-423-5p gene, a congener thereof, a transcript thereof, or a variant or derivative thereof. The previously known report shows that change in the expression of the gene or the transcript thereof can serve as a marker for bladder cancer (Non Patent Literature 3).

The 240th target gene is the miR-663a gene, a congener thereof, a transcript thereof, or a variant or derivative thereof. The previously known report shows that change in the expression of the gene or the transcript thereof can serve as a marker for bladder cancer (Patent Literature 1).

The 241st target gene is the miR-92a-2-5p gene, a congener thereof, a transcript thereof, or a variant or derivative thereof. The previously known report shows that change in the expression of the gene or the transcript thereof can serve as a marker for bladder cancer (Patent Literature 1).

The 242nd target gene is the miR-92a-3p gene, a congener thereof, a transcript thereof, or a variant or derivative thereof. The previously known report shows that change in the expression of the gene or the transcript thereof can serve as a marker for bladder cancer (Patent Literature 2).

The 243rd target gene is the miR-940 gene, a congener thereof, a transcript thereof, or a variant or derivative thereof. The previously known report shows that change in the expression of the gene or the transcript thereof can serve as a marker for bladder cancer (Non Patent Literature 2).

In one aspect, the present invention relates to a marker(s) for detecting bladder cancer or diagnosing bladder cancer, which comprises at least one selected from the above target nucleic acid(s).

In one aspect, the present invention relates to use of at least one selected from the above target nucleic acid(s) for detecting bladder cancer or diagnosing bladder cancer.

2. Nucleic acid Probe(s) or Primer(s) for Detection of Bladder Cancer

A nucleic acid probe(s) or primer(s) capable of being used for detection of bladder cancer or diagnosis of bladder cancer according to the present invention enable(s) qualitative and/or quantitative measurement of the presence, expression level(s), or abundance of the following target nucleic acid(s) for bladder cancer: human-derived miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-5p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, or miR-937-5p, or any combination thereof, any congener thereof, any transcript thereof, or any variant or derivative thereof.

The expression level(s) of the above target nucleic acid(s) in subjects having bladder cancer may be increased or decreased (hereinafter, also referred to as an "increase/decrease"), depending on the kind(s) of the target nucleic acid(s), than healthy subjects, benign disease patients and subjects having a cancer other than bladder cancer. Thus, a kit or device of the present invention can be effectively used for detection of bladder cancer by measuring the expression level(s) of the above target nucleic acid(s) in body fluid derived from a subject (e.g., a human) suspected of having bladder cancer and in body fluids derived from healthy subjects, benign disease patients and patients with a cancer other than bladder cancer and then comparing the expression level(s) therebetween.

A nucleic acid probe(s) or primer(s) capable of being used in the present invention is a nucleic acid probe(s) capable of specifically binding to a polynucleotide(s) consisting of a nucleotide sequence(s) represented by at least one selected from SEQ ID NOs: 1 to 228 or to a complementary strand(s) of the polynucleotide(s), or a primer(s) for amplifying a polynucleotide(s) consisting of a nucleotide sequence(s) represented by at least one selected from SEQ ID NOs: 1 to 228.

The nucleic acid probes or primers capable of being used in the present invention may further comprise a nucleic acid probe(s) capable of specifically binding to a polynucleotide(s) consisting of a nucleotide sequence(s) represented by at least one selected from SEQ ID NOs: 229 to 243 or to a complementary strand(s) of the polynucleotide(s), or a primer(s) for amplifying a polynucleotide(s) consisting of a nucleotide sequence(s) represented by at least one selected from SEQ ID NOs: 229 to 243.

In a preferred embodiment of the method of the present invention, the above nucleic acid probe(s) or primer(s) includes any combination of one or more polynucleotides selected from a group of polynucleotides comprising a nucleotide sequence(s) represented by any of SEQ ID NOs: 1 to 766 and a nucleotide sequence(s) derived from the nucleotide sequence(s) by the replacement of u with t and a group of polynucleotides complementary thereto, a group of polynucleotides hybridizing under stringent conditions (described below) to DNA comprising a nucleotide sequence(s) complementary to the former nucleotide sequence(s) and a group of polynucleotides complementary thereto, and a group of polynucleotides comprising 15 or more, preferably 17 or more consecutive nucleotides in the nucleotide sequence(s) of these polynucleotide groups. These polynucleotides can be used as nucleic acid probes and primers for detecting target nucleic acids, namely the above bladder cancer markers.

Further, specific examples of the nucleic acid probe(s) or primer(s) capable of being used in the present invention include one or more polynucleotides selected from the group consisting of any of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

In addition to at least one polynucleotide selected from any of the above polynucleotides (a) to (e), the nucleic acid probe(s) or primer(s) capable of being used in the present invention can further comprise a polynucleotide represented by any of the following (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (f) to (i).

The above polynucleotides or fragments thereof used in the present invention may each be DNA or RNA.

The above polynucleotide(s) capable of being used in the present invention may be prepared using a general technique such as DNA recombination technology, a PCR method, or a method using an automated DNA/RNA synthesizer.

As the DNA recombination technology or the PCR method, it is possible to use techniques described in, for instance, Ausubel et al., Current Protocols in Molecular Biology, John Willey & Sons, US(1993); and Sambrook et al., Molecular Cloning A Laboratory Manual, Cold Spring Harbor Laboratory Press, US (1989).

The human-derived miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR- 320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, miR-937-5p, miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940, which are represented by SEQ ID NOs: 1 to 243, are known, and methods for obtaining them are also known, as described above. Therefore, a polynucleotide that can be used as a nucleic acid probe or a primer in the present invention can be produced via cloning the gene.

Such a nucleic acid probe(s) or primer(s) may be chemically synthesized using an automated DNA synthesizer. A phosphoramidite process is commonly used for this synthesis, and this process can be used to automatically synthesize a single-stranded DNA with up to about 100 nucleotides in length. The automated DNA synthesizer is commercially available from, for instance, Polygen, Inc., ABI, Inc., or Applied BioSystems, Inc.

Alternatively, a polynucleotide(s) of the present invention may be prepared by cDNA cloning. For the cDNA cloning technology, a microRNA Cloning Kit Wako, for instance, can be utilized.

The sequence of a nucleic acid probe or primer for detection of a polynucleotide consisting of a nucleotide sequence represented by any of SEQ ID NOs: 1 to 243 is not present in vivo as an miRNA or any precursor thereof. For instance, the nucleotide sequences represented by SEQ ID NO: 9 and SEQ ID NO: 8 are generated from the precursor represented by SEQ ID NO: 251. This precursor has a hairpin-like structure as shown in FIG. 1, and the nucleotide sequences represented by SEQ ID NO: 9 and SEQ ID NO: 8 have mismatch sequences therebetween. Accordingly, a nucleotide sequence perfectly complementary to the nucleotide sequence represented by SEQ ID NO: 9 or SEQ ID NO: 8 is not naturally occurring in vivo. Thus, the nucleic acid probe(s) or primer(s) for detecting a nucleotide sequence represented by any of SEQ ID NOs: 1 to 243 may have an artificial nucleotide sequence not present in vivo.

3. Kit or Device for Detection of Bladder Cancer

The present invention provides a kit or device for detection of bladder cancer, comprising one or more polynucleotide(s) (which may include any variant(s), fragment(s), or derivative(s)) capable of being used as a nucleic acid probe(s) or primer(s) for measuring a target nucleic acid(s) as a bladder cancer marker(s) in the present invention.

A target nucleic acid(s) as a bladder cancer marker(s) according to the present invention is preferably selected from the following group A.

Group A:
miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p.

An additional target nucleic acid(s) capable of being optionally used for the measurement is preferably selected from the following group B.

Group B:
miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

A kit or device of the present invention comprises a nucleic acid(s) capable of specifically binding to the above target nucleic acid(s) as bladder cancer marker(s), preferably, one or more polynucleotides selected from the polynucleotides described in Section 2 above or a variant thereof.

Specifically, a kit or device of the present invention may comprise at least one of a polynucleotide comprising (or consisting of) a nucleotide sequence represented by any of SEQ ID NOs: 1 to 228 or a nucleotide sequence derived from the nucleotide sequence by the replacement of u with t or a polynucleotide comprising (or consisting of) a complementary sequence thereof, or a polynucleotide hybridizing under stringent conditions to any of the polynucleotides, or a variant or fragment thereof comprising 15 or more consecutive nucleotides of any of the polynucleotide sequences.

A kit or device of the present invention may further comprise one or more of a polynucleotide comprising (or consisting of) a nucleotide sequence represented by any of SEQ ID NOs: 229 to 243 or a nucleotide sequence derived from the nucleotide sequence by the replacement of u with t or a polynucleotide comprising (or consisting of) a complementary sequence thereof, or a polynucleotide hybridizing under stringent conditions to any of the polynucleotides, or a variant or fragment thereof comprising 15 or more consecutive nucleotides of any of the polynucleotide sequences.

A fragment(s) that can be comprised in a kit or device of the present invention may be, for instance, one or more polynucleotides and preferably two or more polynucleotides selected from the group consisting of the following (1) and (2):

(1) a polynucleotide comprising 15 or more consecutive nucleotides in a nucleotide sequence derived from the nucleotide sequence represented by any of SEQ ID NOs: 1 to 228 by the replacement of u with t or in a complementary sequence thereof; and (2) a polynucleotide comprising 15 or more consecutive nucleotides in a nucleotide sequence derived from the nucleotide sequence represented by any of SEQ ID NOs: 229 to 243 by the replacement of u with t or in a complementary sequence thereof.

In a preferred embodiment, the polynucleotide is a polynucleotide consisting of a nucleotide sequence represented by any of SEQ ID NOs: 1 to 228 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising 15 or more, preferably 17 or more, and more preferably 19 or more consecutive nucleotides of any of the polynucleotides.

In addition, in a preferred embodiment, the polynucleotide is a polynucleotide consisting of a nucleotide sequence represented by any of SEQ ID NOs: 229 to 243 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising 15 or more, preferably 17 or more, and more preferably 19 or more consecutive nucleotides of any of the polynucleotides.

In a preferred embodiment, the fragment may be a polynucleotide comprising 15 or more, preferably 17 or more, and more preferably 19 or more consecutive nucleotides.

In the present invention, the size of the polynucleotide fragment is represented by the number of nucleotides in a range of, for instance, from 15 to less than the total number of consecutive nucleotides in the nucleotide sequence of each polynucleotide, from 17 to less than the total number of nucleotides in the sequence, or from 19 to less than the total number of nucleotides in the sequence.

Specific examples of the above polynucleotide(s) as target nucleic acid(s) in a kit or device of the present invention include 1 or a combination of 2, 3, 4, 5, 6, 7, 8, 9, 10, or more of the above polynucleotides consisting of nucleotide sequences represented by SEQ ID NOs: 1 to 243 listed in above Table 1. This is just an example and all the other various possible combinations are included in the present invention.

Examples of a combination of target nucleic acids in a kit or device for discriminating between bladder cancer patients and subjects without bladder cancer such as healthy subjects, benign bone and soft tissue tumor and benign breast disease patients, and patients with a cancer other than bladder cancer in the present invention include a combination of two or more of the above polynucleotides consisting of nucleotide sequences represented by SEQ ID NOs listed in Table 1. Specifically, any two or more of the above polynucleotides consisting of nucleotide sequences represented by SEQ ID NOs: 1 to 243 can be combined. Among them, at least one of the newly found polynucleotides consisting of nucleotide sequences represented by SEQ ID NOs: 1 to 228 is preferably selected. In particular, a combination comprising at least one polynucleotide selected from the group consisting of polynucleotides described in any of Tables 20 to 22, further desirably the group consisting of polynucleotides described in Table 23, is more preferred.

The following shows 253 non-limiting examples listed in Table 7-Nos. 1 to 11, Tables 13 to 16, and Table 26-Nos. 2 to 9, which are shown later in Examples, as a polynucleotide comprising a nucleotide sequence represented by SEQ ID NO: 1 (miR-6087) or a complementary sequence thereof, or a combination comprising the polynucleotide (the tables show 256 discriminants).

A kit or device of the present invention may comprise, in addition to the above-described polynucleotide(s) in the present invention (which may include any variant(s), fragment(s), or derivative(s)), a polynucleotide(s) known to be able to detect bladder cancer or a polynucleotide(s) that will be discovered in the future.

The kit or device of the present invention may be used in combination with, in addition to the above-described polynucleotides according to the present invention, an antibody (or antibodies) for measuring a known marker(s) for detection of bladder cancer, such as NMP22 test to detect nuclear matrix protein NuMA, or BTAtrak test to detect a specific basement membrane fragment complex.

These polynucleotides, or variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention may be a device for measuring a cancer marker(s), in which nucleic acids such as the above-described polynucleotide(s), variant(s), derivative(s), or fragment(s) thereof according to the present invention are, for instance, bonded or attached onto a solid phase. Examples of the material for the solid phase include plastics, paper, glass, and silicone. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or device of the present invention comprises nucleic acids capable of specifically binding to at least one, preferably at least two, more preferably at least three, most preferably at least five to all polynucleotides selected from the above-mentioned bladder cancer marker miRNAs of the group A, or to a complementary strand(s) of the polynucleotide(s), respectively. The kit or device of the present invention can optionally further comprise nucleic acids capable of specifically binding to at least one, preferably at least two, more preferably at least three, most preferably at least five to all polynucleotides selected from the above-mentioned bladder cancer marker miRNAs of the group B, or to a complementary strand(s) of the polynucleotide(s), respectively.

The kit or device of the present invention can be used for detecting bladder cancer as described in Section 4 below.

4. Method for Detecting Bladder Cancer

The present invention further relates to a method for detecting bladder cancer, comprising measuring, in vitro, 1 or more (e.g., expression profile(s)) of expression levels of bladder cancer-derived genes represented by miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, and optionally expression levels of bladder cancer-derived genes represented by miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940 in a sample; and evaluating in vitro whether or not a subject has bladder cancer using the measured expression level(s) (and optionally a control expression level(s) in a healthy subject(s) as likewise measured). In the method, it is possible to determine that a subject has bladder cancer by using the expression level(s) of the above-mentioned genes in a sample from a subject suspected of having bladder cancer and control expression levels of the genes in samples from subjects without bladder cancer, if there is a difference in the expression level(s) of the target nucleic acid(s) in the samples (e.g., when comparing the expression level(s) between the subjects), in which the sample(s) may be, for instance, blood, serum, plasma or the like collected from the subject suspected of having bladder cancer and subjects without bladder cancer.

The above-mentioned method of the present invention enables less-invasive, highly sensitive and specific early diagnosis of bladder cancer. This allows for an early treatment and improvement in prognosis and further makes it possible to monitor exacerbation of the disease and monitor effectiveness of surgical, radiotherapeutic, and chemotherapeutic treatment.

For the method for extracting the bladder cancer-derived gene(s) from the sample such as blood, serum, or plasma according to the present invention, it is particularly preferred to add a reagent for RNA extraction in 3D-Gene (registered trademark) RNA extraction reagent from liquid sample kit (Toray Industries, Inc., Japan) for preparation of a sample. Alternatively, a general acidic phenol method (acid guanidinium-phenol-chloroform (AGPC)) may be used, or Trizol (registered trademark) (Life Technologies Corp.) may be used. Alternatively, for preparation of a sample, a reagent for RNA extraction containing acidic phenol, such as Trizol (Life Technologies Corp.) or Isogen (Nippon Gene Co., Ltd., Japan) may be added. Alternatively, a kit such as miRNeasy (registered trademark) Mini Kit (Qiagen N.V.) may be used. However, the method according to the present invention is not limited thereto.

The present invention also provides use of a bladder cancer-derived miRNA gene(s) in a sample from a subject for in vitro detection of an expression product(s) thereof.

A technique to be used for carrying out the method of the present invention is not limited and, for instance, the kit or device of the present invention (comprising the above nucleic acid(s) capable of being used in the present invention) as described in the above Section 3 may be used for carrying out the method. In the method of the present invention, the kit or device described above comprising a single polynucleotide or any possible combination of polynucleotides that can be used in the present invention as described above, can be used.

In the detection or (genetic) diagnosis of bladder cancer according to the present invention, a polynucleotide(s) contained in the kit or device of the present invention can be used as a probe(s) or a primer(s). In the case of using the polynucleotide(s) as a primer(s), TaqMan (registered trademark) MicroRNA Assays from Life Technologies Corp., miScript PCR System from Qiagen N.V., or the like can be used. However, the method according to the present invention is not limited thereto.

In the method of the present invention, measurement of the gene expression levels can be performed according to a routine technique of a method known in the art for specifically detecting particular genes, for example, a hybridization technique such as Northern blot, Southern blot, in situ hybridization, Northern hybridization, or Southern hybridization; a quantitative amplification technique such as quantitative RT-PCR; or a method with a next-generation sequencer. A body fluid such as blood, serum, plasma, or urine from a subject is collected as a sample to be assayed depending on the type of the detection method to be used. Alternatively, total RNA prepared from such a body fluid by the method described above may be used, and various polynucleotides including cDNA prepared from the RNA may be used.

The method of the present invention is useful for the diagnosis of bladder cancer or the detection of the presence or absence of bladder cancer. Specifically, the detection of bladder cancer according to the present invention can be performed by detecting in vitro an expression level(s) of a gene(s) which is detected using the nucleic acid probe(s) or the primer(s) contained in the kit or the device according to the present invention, in a sample such as blood, serum, plasma, or urine from a subject suspected of having bladder cancer. If the expression level(s) of a polynucleotide(s) consisting of a nucleotide sequence(s) represented by at least one of SEQ ID NOs: 1 to 228 and optionally a nucleotide sequence(s) represented by one or more of SEQ ID NOs: 229 to 243 in a sample such as blood, serum, plasma, or urine of a subject suspected of having bladder cancer, is statistically significantly higher compared to an expression level(s) thereof in a sample such as blood, serum, or plasma, or urine of a subject without bladder cancer, the former subject can be evaluated as having bladder cancer.

Regarding the method of the present invention, the method for detecting the absence of bladder cancer or the presence of bladder cancer for a sample from a subject comprises collecting a body fluid such as blood, serum, plasma, or urine of the subject, and measuring the expression level(s) of the target gene(s) (or target nucleic acid(s)) contained therein using one or more polynucleotides (including variant(s), fragment(s), or derivative(s)) selected from the groups of polynucleotides according to the present invention, thereby evaluating the presence or absence of bladder cancer or detecting bladder cancer. The method for detecting bladder cancer according to the present invention can also be used to evaluate or diagnose, for example, the presence or absence of amelioration of the disease or the degree of amelioration thereof in a bladder cancer patient when a bladder cancer-related therapeutic drug which is known in the art or on a development stage (including gemcitabine, a platinum-containing drug (cisplatin/carboplatin), paclitaxel, methotrexate, vinblastine, adriamycin, cisplatin, taxane (docetaxel), ifosfamide, other platinum-containing drugs (nedaplatin), and combination drugs thereof, as non-limiting examples) is administered to the patient for treatment or amelioration of the disease.

The method of the present invention may comprise, for example, the following steps (a), (b), and (c):

(a) contacting in vitro a sample from a subject with a polynucleotide(s) contained in a kit or device of the present invention;

(b) measuring an expression level(s) of target nucleic acid(s) in the sample using the polynucleotide(s) as a nucleic acid probe(s) or primer(s); and (c) evaluating the presence or absence of bladder cancer (cells) in the subject on the basis of the measurement results in step (b).

In one embodiment, the present invention provides a method for detecting bladder cancer, comprising measuring an expression level(s) of a target nucleic acid(s) in a sample from a subject using a nucleic acid(s) capable of specifically binding to at least one, preferably at least two polynucleotides selected from miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, or to a complementary strand(s) of the polynucleotide(s); and evaluating in vitro whether or not the subject has bladder cancer by using the measured expression level(s) and a control expression level(s) in a subject(s) without bladder cancer as likewise measured.

The term "evaluating" as used herein is evaluation support based on results of in vitro examination, not physician's judgment.

As described above, in the method of the present invention, specifically, miR-6087 is hsa-miR-6087, miR-1185-1-3p is hsa-miR-1185-1-3p, miR-1185-2-3p is hsa-miR-1185-2-3p, miR-1193 is hsa-miR-1193, miR-1199-5p is hsa-miR-1199-5p, miR-1225-5p is hsa-miR-1225-5p, miR-1227-5p is hsa-miR-1227-5p, miR-1228-3p is hsa-miR-1228-3p, miR-1228-5p is hsa-miR-1228-5p, miR-1237-5p is hsa-miR-1237-5p, miR-1238-5p is hsa-miR-1238-5p, miR-1247-3p is hsa-miR-1247-3p, miR-1268a is hsa-miR-1268a, miR-1268b is hsa-miR-1268b, miR-1273g-3p is hsa-miR-1273g-3p, miR-128-2-5p is hsa-miR-128-2-5p, miR-1343-3p is hsa-miR-1343-3p, miR-1343-5p is hsa-miR-1343-5p, miR-1470 is hsa-miR-1470, miR-17-3p is hsa-miR-17-3p, miR-187-5p is hsa-miR-187-5p, miR-1908-3p is hsa-miR-1908-3p, miR-1908-5p is hsa-miR-1908-5p, miR-1909-3p is hsa-miR-1909-3p, miR-1915-3p is hsa-miR-1915-3p, miR-210-5p is hsa-miR-210-5p, miR-24-3p is hsa-miR-24-3p, miR-2467-3p is hsa-miR-2467-3p, miR-2861 is hsa-miR-2861, miR-296-3p is hsa-miR-296-3p, miR-29b-3p is hsa-miR-29b-3p, miR-3131 is hsa-miR-3131, miR-3154 is hsa-miR-3154, miR-3158-5p is hsa-miR-3158-5p, miR-3160-5p is hsa-miR-3160-5p, miR-3162-5p is hsa-miR-3162-5p, miR-3178 is hsa-miR-3178, miR-3180-3p is hsa-miR-3180-3p, miR-3184-5p is hsa-miR-3184-5p, miR-3185 is hsa-miR-3185, miR-3194-3p is hsa-miR-3194-3p, miR-3195 is hsa-miR-3195, miR-3197 is hsa-miR-3197, miR-320a is hsa-miR-320a, miR-320b is hsa-miR-320b, miR-328-5p is hsa-miR-328-5p, miR-342-5p is hsa-miR-342-5p, miR-345-3p is hsa-miR-345-3p, miR-3616-3p is hsa-miR-3616-3p, miR-3619-3p is hsa-miR-3619-3p, miR-3620-5p is hsa-miR-3620-5p, miR-3621 is hsa-miR-3621, miR-3622a-5p is hsa-miR-3622a-5p, miR-3648 is hsa-miR-3648, miR-3652 is hsa-miR-3652, miR-3656 is hsa-miR-3656, miR-3663-3p is hsa-miR-3663-3p, miR-3679-5p is hsa-miR-3679-5p, miR-371b-5p is hsa-miR-371b-5p, miR-373-5p is hsa-miR-373-5p, miR-3917 is hsa-miR-3917, miR-3940-5p is hsa-miR-3940-5p, miR-3960 is hsa-miR-3960, miR-4258 is hsa-miR-4258, miR-4259 is hsa-miR-4259, miR-4270 is hsa-miR-4270, miR-4286 is hsa-miR-4286, miR-4298 is hsa-miR-4298, miR-4322 is hsa-miR-4322, miR-4327 is hsa-miR-4327, miR-4417 is hsa-miR-4417, miR-4419b is hsa-miR-4419b, miR-4429 is hsa-miR-4429, miR-4430 is hsa-miR-4430, miR-4433a-3p is hsa-miR-4433a-3p, miR-4436b-5p is hsa-miR-4436b-5p, miR-4443 is hsa-miR-4443, miR-4446-3p is hsa-miR-4446-3p, miR-4447 is hsa-miR-4447, miR-4448 is hsa-miR-4448, miR-4449 is hsa-miR-4449, miR-4454 is hsa-miR-4454, miR-4455 is hsa-miR-4455, miR-4459 is hsa-miR-4459, miR-4462 is hsa-miR-4462, miR-4466 is hsa-miR-4466, miR-4467 is hsa-miR-4467, miR-4480 is hsa-miR-4480, miR-4483 is hsa-miR-4483, miR-4484 is hsa-miR-4484, miR-4485-5p is hsa-miR-4485-5p, miR-4488 is hsa-miR-4488, miR-4492 is hsa-miR-4492, miR-4505 is hsa-miR-4505, miR-4515 is hsa-miR-4515, miR-4525 is hsa-miR-4525, miR-4534 is hsa-miR-4534, miR-4535 is hsa-miR-4535, miR-4633-3p is hsa-miR-4633-3p, miR-4634 is hsa-miR-4634, miR-4640-5p is hsa-miR-4640-5p, miR-4649-5p is hsa-miR-4649-5p, miR-4651 is hsa-miR-4651, miR-4652-5p is hsa-miR-4652-5p, miR-4655-5p is hsa-miR-4655-5p, miR-4656 is hsa-miR-4656, miR-4658 is hsa-miR-4658, miR-4663 is hsa-miR-4663, miR-4673 is hsa-miR-4673, miR-4675 is hsa-miR-4675, miR-4687-3p is hsa-miR-4687-3p, miR-4687-5p is hsa-miR-4687-5p, miR-4690-5p is hsa-miR-4690-5p, miR-4695-5p is hsa-miR-4695-5p, miR-4697-5p is hsa-miR-4697-5p, miR-4706 is hsa-miR-4706, miR-4707-3p is hsa-miR-4707-3p, miR-4707-5p is hsa-miR-4707-5p, miR-4708-3p is hsa-miR-4708-3p, miR-4710 is hsa-miR-4710, miR-4718 is hsa-miR-4718, miR-4722-5p is hsa-miR-4722-5p, miR-4725-3p is hsa-miR-4725-3p, miR-4726-5p is hsa-miR-4726-5p, miR-4727-3p is hsa-miR-4727-3p, miR-4728-5p is hsa-miR-4728-5p, miR-4731-5p is hsa-miR-4731-5p, miR-4736 is hsa-miR-4736, miR-4739 is hsa-miR-4739, miR-4740-5p is hsa-miR-4740-5p, miR-4741 is hsa-miR-4741, miR-4750-5p is hsa-miR-4750-5p, miR-4755-3p is hsa-miR-4755-3p, miR-4763-3p is hsa-miR-4763-3p, miR-4771 is hsa-miR-4771, miR-4783-3p is hsa-miR-4783-3p, miR-4783-5p is hsa-miR-4783-5p, miR-4787-3p is hsa-miR-4787-3p, miR-4792 is hsa-miR-4792, miR-498 is hsa-miR-498, miR-5008-5p is hsa-miR-5008-5p, miR-5010-5p is hsa-miR-5010-5p, miR-504-3p is hsa-miR-504-3p, miR-5195-3p is hsa-miR-5195-3p, miR-550a-5p is hsa-miR-550a-5p, miR-5572 is hsa-miR-5572, miR-5739 is hsa-miR-5739, miR-6075 is hsa-miR-6075, miR-6076 is hsa-miR-6076, miR-6088 is hsa-miR-6088, miR-6124 is hsa-miR-6124, miR-6131 is hsa-miR-6131, miR-6132 is hsa-miR-6132, miR-614 is hsa-miR-614, miR-615-5p is hsa-miR-615-5p, miR-619-5p is hsa-miR-619-5p, miR-642b-3p is hsa-miR-642b-3p, miR-6510-5p is hsa-miR-6510-5p, miR-6511a-5p is hsa-miR-6511a-5p, miR-6515-3p is hsa-miR-6515-3p, miR-6515-5p is hsa-miR-6515-5p, miR-663b is hsa-miR-663b, miR-6716-5p is hsa-miR-6716-5p, miR-6717-5p is hsa-miR-6717-5p, miR-6722-3p is hsa-miR-6722-3p, miR-6724-5p is hsa-miR-6724-5p, miR-6726-5p is hsa-miR-6726-5p, miR-6737-5p is hsa-miR-6737-5p, miR-6741-5p is hsa-miR-6741-5p, miR-6742-5p is hsa-miR-6742-5p, miR-6743-5p is hsa-miR-6743-5p, miR-6746-5p is hsa-miR-6746-5p, miR-6749-5p is hsa-miR-6749-5p, miR-6760-5p is hsa-miR-6760-5p, miR-6762-5p is hsa-miR-6762-5p, miR-6765-3p is hsa-miR-6765-3p, miR-6765-5p is hsa-miR-6765-5p, miR-6766-3p is hsa-miR-6766-3p, miR-6766-5p is hsa-miR-6766-5p, miR-6771-5p is hsa-miR-6771-5p, miR-6774-5p is hsa-miR-6774-5p, miR-6777-5p is hsa-miR-6777-5p, miR-6778-5p is hsa-miR-6778-5p, miR-6780b-5p is hsa-miR-6780b-5p, miR-6781-5p is hsa-miR-6781-5p, miR-6782-5p is hsa-miR-6782-5p, miR-6784-5p is hsa-miR-6784-5p, miR-6785-5p is hsa-miR-6785-5p, miR-6787-5p is hsa-miR-6787-5p, miR-6789-5p is hsa-miR-6789-5p, miR-6791-5p is hsa-miR-6791-5p, miR-6794-5p is hsa-miR-6794-5p, miR-6800-5p is hsa-miR-6800-5p, miR-6802-5p is hsa-miR-6802-5p, miR-6803-5p is hsa-miR-6803-5p, miR-6812-5p is hsa-miR-6812-5p, miR-6816-5p is hsa-miR-6816-5p, miR-6819-5p is hsa-miR-6819-5p, miR-6821-5p is hsa-miR-6821-5p, miR-6826-5p is hsa-miR-6826-5p, miR-6831-5p is hsa-miR-6831-5p, miR-6836-3p is hsa-miR-6836-3p, miR-6840-3p is hsa-miR-6840-3p, miR-6842-5p is hsa-miR-6842-5p, miR-6850-5p is hsa-miR-6850-5p, miR-6861-5p is hsa-miR-6861-5p, miR-6869-5p is hsa-miR-6869-5p, miR-6870-5p is hsa-miR-6870-5p, miR-6877-5p is hsa-miR-6877-5p, miR-6879-5p is hsa-miR-6879-5p, miR-6880-3p is hsa-miR-6880-3p, miR-6880-5p is hsa-miR-6880-5p, miR-6885-5p is hsa-miR-6885-5p, miR-6887-5p is hsa-miR-6887-5p, miR-7107-5p is hsa-miR-7107-5p, miR-7108-3p is hsa-miR-7108-3p, miR-7109-5p is hsa-miR-7109-5p, miR-711 is hsa-miR-711, miR-7113-3p is hsa-miR-7113-3p, miR-7150 is hsa-miR-7150, miR-744-5p is hsa-miR-744-5p, miR-7975 is hsa-miR-7975, miR-7977 is hsa-miR-7977, miR-8052 is hsa-miR-8052, miR-8069 is hsa-miR-8069, miR-8073 is hsa-miR-8073, miR-887-3p is hsa-miR-887-3p, and miR-937-5p is hsa-miR-937-5p.

In addition, in one embodiment, a nucleic acid(s) (specifically, a probe(s) or primer(s)) in the method of the present invention, is selected from polynucleotides shown in any of the following group (a) to (e):
(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 228;
(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and
(e) a polynucleotide hybridizing under stringent conditions to any of the polynucleotides (a) to (d).

In the method of the present invention, further, the expression level(s) of at least one polynucleotide selected from miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940 can be measured.

Specifically, miR-1202 is hsa-miR-1202, miR-1207-5p is hsa-miR-1207-5p, miR-1246 is hsa-miR-1246, miR-1254 is hsa-miR-1254, miR-135a-3p is hsa-miR-135a-3p, miR-1469 is hsa-miR-1469, miR-149-3p is hsa-miR-149-3p, miR-150-3p is hsa-miR-150-3p, miR-1914-3p is hsa-miR-1914-3p, miR-191-5p is hsa-miR-191-5p, miR-423-5p is hsa-miR-423-5p, miR-663a is hsa-miR-663a, miR-92a-2-5p is hsa-miR-92a-2-5p, miR-92a-3p is hsa-miR-92a-3p, and miR-940 is hsa-miR-940.

Further, in one embodiment, the expression level(s) of the polynucleotide(s) are measured by using nucleic acid(s) capable of specifically binding to the polynucleotide(s) or to the complementary strand(s) of the polynucleotide(s), and the nucleic acid(s) are polynucleotide(s) selected from the following polynucleotides (f) to (j):
(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 229 to 243;
(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and
(j) a polynucleotide hybridizing under stringent conditions to any of the polynucleotides (f) to (i).

Examples of the sample used in the method of the present invention can include samples prepared from living tissues (preferably bladder tissues or renal pelvis or urinary tract tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse, or a rat, without any limitation, and is preferably a human.

The steps of the method of the present invention can be changed depending on the type of the sample to be measured.

In the case of using RNA as an analyte, the method for detecting bladder cancer (cells) can comprise, for example, the following steps (a), (b), and (c):
(a) binding RNA prepared from a sample from a subject (wherein, for example, the 3' end of the RNA may be polyadenylated for quantitative RT-PCR in step (b) or any sequence may be added to one or both ends of the RNA by ligation, etc.) or a complementary polynucleotides (cDNA) transcribed from the RNA to a polynucleotide(s) in the kit of the present invention;
(b) measuring the sample-derived RNA or the cDNA synthesized from the RNA, which has been bound to the polynucleotide(s), by hybridization using the polynucleotide (s) as a nucleic acid probe(s) or by quantitative RT-PCR using the polynucleotide(s) as a primer(s); and (c) evaluating the presence or absence of bladder cancer (or bladder cancer-derived gene(s)) on the basis of the measurement results of step (b).

For example, various hybridization methods can be used for measuring the expression level(s) of a target gene(s) according to the present invention. For example, Northern blot, Southern blot, DNA chip analysis, in situ hybridization, Northern hybridization, or Southern hybridization can be used as such a hybridization method. PCR such as quantitative RT-PCR or next-generation sequencing can also be used in combination with a hybridization method, or as an alternative thereof.

In the case of using the Northern blot, the presence or absence of expression of each gene or the expression level thereof in the RNA can be detected or measured by using, for example, the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the living tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by using, for example, the primer(s) that can be used in the present invention. Specific examples thereof can include a method which comprises recovering the living tissue-derived RNA from a subject, polyadenylating the 3'-end, preparing cDNAs from the polyadenylated RNA according to a routine method, and performing PCR according to a routine method by hybridizing a pair of primers (consisting of a positive strand and a reverse strand each binding to the cDNA) which could be contained in the kit or device for detection of the present invention with the cDNA such that the region of each target gene marker can be amplified with the cDNA as a template, to detect the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like according to a routine method and hybridizing the single-stranded or double-stranded DNA with a labeled nucleic acid probe for detection.

In the case of using the nucleic acid array analysis, an RNA chip or a DNA chip in which the kit or device for detection in the present invention is attached as nucleic acid probes (single-stranded or double-stranded) to a substrate (solid phase), for example, is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene (registered trademark) Human miRNA Oligo chip (Toray Industries, Inc., Japan) can be used as the DNA chip, though the DNA chip is not limited thereto.

Examples of the measurement using the DNA chip can include, but are not limited to, a method of detecting and measuring a signal derived from the label on the kit or device for detection using an image detector (examples thereof can include Typhoon 9410 (GE Healthcare) and 3D-Gene (registered trademark) scanner (Toray Industries, Inc., Japan)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2)") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95% homology to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCl, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan (registered trademark) MicroRNA Assays (Life Technologies Corp.), LNA (registered trademark)-based MicroRNA PCR (Exiqon), or Ncode (registered trademark) miRNA qRT-PCR kit (Invitrogen Corp.) may be used.

In the method of the present invention, measurement of the gene expression level(s) may be performed with a sequencer, in addition to hybridization methods described above. In use of a sequencer, any of DNA sequencers of the first generation based on Sanger method, the second generation with shorter read size, and the third generation with longer read size can be used (herein referred to as "next-generation sequencer", including sequencers of the second generation and the third generation). For example, a commercially available measurement kit specially designed for measuring miRNA using Miseq, Hiseq, or NexSeq (Illumina, Inc.); Ion Proton, Ion PGM, or Ion S5/S5 XL (Thermo Fisher Scientific Inc.); PacBio RS II or Sequel (Pacific Biosciences of California, Inc.); MinION (Oxford Nanopore Technologies Ltd.) exemplified in use of a Nanopore sequencer; or the like may be used.

Next-generation sequencing is a method of obtaining sequence information using a next-generation sequencer, and characterized by being capable of simultaneously performing a huge number of sequencing reactions compared to Sanger method (e.g., Rick Kamps et al., Int. J. Mol. Sci., 2017, 18(2), p. 308 and Int. Neurourol. J., 2016, 20 (Suppl.2), S76-83). Examples of next-generation sequencing steps for miRNA include, but not limited to, the following steps: at first, adaptor sequences having predetermined nucleotide sequences are attached, and all RNAs are reverse-transcribed into cDNAs before or after attachment of the sequences. After the reverse transcription, cDNAs derived from specific target miRNAs may be amplified or concentrated by PCR or the like or with a probe or the like, for analyzing the target miRNA before sequencing steps. Subsequent sequencing steps varies in detail depending on the type of a next-generation sequencer, but typically, a sequencing reaction is performed by linking to a substrate via an adaptor sequence and further using the adaptor sequence as a priming site. See details of the sequencing reaction, for example, in Rick Kamps et al. (see supra). Finally, the data are outputted. This step provides a collection of sequence information (reads) obtained by the sequencing reaction. For example, next-generation sequencing can identify a target miRNA(s) based on the sequence information, and measure the expression level thereof based on the number of reads having the sequences of the target miRNA(s).

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene(s) having a gene expression level of $2^6$, preferably $2^8$, more preferably $2^{10}$ or larger in 20% or more, preferably 50% or more, more preferably 80% or more of the number of measurement samples can be selected as the analyte(s). Examples of the normalization of the gene expression level include, but are not limited to, global normalization and quantile normalization (Bolstad, B. M. et al., 2003, Bioinformatics, Vol. 19, p. 185-193).

The present invention also provides a method for detecting bladder cancer (or assisting the detection thereof) in a subject, comprising measuring a target genes or gene expression levels in a sample from the subject; and assigning the expression levels of the target genes in the sample from the subject to a discriminant (discriminant function), which is prepared using gene expression levels of a sample(s) from a subject(s) (or a patient(s)) known to have bladder cancer and a sample(s) from a subject(s) without bladder cancer, as a training sample(s), and which can distinguishably discriminate the presence or absence of bladder cancer, thereby evaluating the presence or absence of bladder cancer.

Specifically, the present invention further provides the method comprising a first step of measuring in vitro expression levels of target genes, which are known to determine or evaluate whether a subject has bladder cancer and/or not, in a plurality of samples; a second step of preparing a discriminant using the measurement values of the expression levels of the target genes obtained in the first step as training samples; a third step of measuring in vitro the expression levels of the target genes in a sample from the subject in the same manner as in the first step; and a fourth step of assigning the measurement values of the expression levels of the target genes obtained in the third step to the discriminant obtained in the second step, and determining or evaluating whether or not the subject has bladder cancer on the basis of the results obtained from the discriminant. The above target genes are those that can be detected, for example, by the polynucleotides, the polynucleotides contained in the kit or chip, and variants thereof or fragments thereof.

The discriminant herein can be prepared by use of any discriminant analysis method, based on which a discriminant that distinguishably discriminates the presence or absence of bladder cancer can be prepared, such as Fisher's discriminant analysis, nonlinear discriminant analysis based on the Mahalanobis' distance, neural network, Support Vector Machine (SVM), logistic regression analysis (especially, logistic regression analysis using the LASSO (Least Absolute Shrinkage and Selection Operator)), k-nearest neighbor method, or decision tree, though the analysis method is not limited to these specific examples.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and $w_0$ represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, a type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this formula, μ represents an average input, $n_g$ represents the number of data belonging to class g, and $μ_g$ represents an average input of the data belonging to class g. The numerator and the denominator are the interclass variance and the intraclass variance, respectively, when each of data is projected in the direction of the vector w. Discriminant coefficient wi is determined by maximizing this ratio (Takafumi Kanamori et al., "Pattern Recognition", KYORITSU SHUPPAN CO., LTD. (Tokyo, Japan) (2009); Richard O. et al., Pattern Classification, Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)}$$

$$\text{subject to } \mu = \sum_{i=1}^{n} \frac{x_i}{n}, \mu_g = \sum_{i: u_i = g}^{n} \frac{x_i}{n_g}$$

Formula 2

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1}(x - \mu)\}^{\frac{1}{2}}$$

Formula 3

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, an RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a group of bladder cancer patients and a group of subjects without bladder cancer. A bladder tissue test can be used as a reference of determining whether or not a subject has bladder cancer.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_{a} \frac{1}{2} a^T Q a - e^T a$$

$$\text{subject to } y^T a = 0, 0 \le a_i \le C, i = 1, \ldots, l,$$

Formula 4

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

$$f(x) = \text{sgn}\left(\sum_{i=1}^{l} y_i a_i K(x_i, x) + b\right)$$

Formula 5

For example, an RBF kernel defined by Formula 6 can be used as the kernel function. In this formula, x represents a support vector, and y represents a kernel parameter for adjusting the complexity of the hyperplane.

$$K(x_i, x_j) = \exp(-r \|x_i - x_j\|^2), r < 0$$

Formula 6

Logistic regression is a multivariate analysis method in which one category variable (binary variable) is used as an objective variable to predict the probability of occurrence by using multiple explanatory variables, and is expressed in the following formula 7.

$$\log it(\text{prob}(y_i = 1)) = \beta_0 + \Sigma_{j=1}^{P} \beta_j \chi_j$$

Formula 7

The LASSO (Least Absolute Shrinkage and Selection Operator) method is one of techniques for selecting and adjusting variables when multiple observed variables are present, and was proposed by Tibshirani (Tibshirani R., 1996, J R Stat Soc Ser B, vol. 58, p 267-88). The LASSO method is characterized in that when regression coefficients are estimated, penalties are imposed, so that overfitting to a model is reduced and some of the regression coefficients are then estimated as 0. In logistic regression using the LASSO method, regression coefficients are estimated so as to maximize a log-likelihood function expressed in Formula 8.

$$\frac{1}{N}\sum_{i=1}^{N}\left(y_i(\beta_0 + x_j^T\beta) - \log\left(1 + e^{(\beta_0 + x_j^T\beta)}\right)\right) - \lambda\sum_{j=1}^{p}|\beta_j| \quad \text{Formula 8}$$

The value y of the discriminant formula obtained in analysis by the LASSO method is assigned to the logistic function represented by the following formula 9, and the group to which the subject belongs can be determined on the basis of the obtained value.

Exp(y)/(1+exp(y))   Formula 9

In addition to these methods, an approach such as neural network, k-nearest neighbor method, decision tree, or logistic regression analysis can be selected as a method for determining or evaluating whether or not the sample derived from the subject contains bladder cancer.

The method of the present invention can comprise, for example, the following steps (a), (b), and (c):

(a) measuring an expression level(s) of a target gene(s) in samples already known to be from bladder cancer patients and to be from subjects without bladder cancer, using polynucleotide(s), a kit, or a DNA chip for detection according to the present invention;

(b) preparing the discriminants of Formulas 1 to 3, 5 and 6 described above from the measurement values of the expression level(s) measured in step (a); and (c) measuring an expression level(s) of the target gene(s) in a sample from a subject using the polynucleotide(s), the kit, or the DNA chip for diagnosis (detection) according to the present invention, and assigning the obtained measurement value(s) to the discriminants prepared in step (b), and determining or evaluating whether or not the subject has bladder cancer on the basis of the obtained results, or evaluating the expression level(s) derived from a bladder cancer patient by comparison with a control from a subject (s) without bladder cancer.

In this context, in the discriminants of Formulas 1 to 3, 5 and 6, x represents an explanatory variable and includes a value obtained by measuring a polynucleotide(s) selected from the polynucleotides described in Section 2 above, or a fragment thereof. Specifically, the explanatory variable of the present invention for discriminating between a bladder cancer patient(s) and subject(s) without bladder cancer is a gene expression level(s) selected from, for example, the following (1) and (2):

(1) gene expression level(s) in sera of a bladder cancer patient and a subject without bladder cancer as measured by any DNA comprising 15 or more consecutive nucleotides in the nucleotide sequence represented by any of SEQ ID NOs: 1 to 228 or in a complementary sequence thereof; and (2) gene expression level(s) in sera of a bladder cancer patient and a subject without bladder cancer as measured by any DNA comprising 15 or more consecutive nucleotides in the nucleotide sequence represented by any of SEQ ID NOs: 229 to 243 or in a complementary sequence thereof.

As described above, for the method for determining or evaluating whether or not a subject has bladder cancer using a sample from the subject, it is necessary to use a discriminant employing one or more gene expression levels as an explanatory variable(s). In particular, for enhancing the accuracy of the discriminant using a single gene expression level alone, it is necessary to use a gene having a clear difference in the expression level between two groups consisting of a group of bladder cancer patients and a group of subjects with normal cognitive functions, in a discriminant.

Specifically, the gene that is used for an explanatory variable of a discriminant is preferably determined as follows. First, using comprehensive gene expression levels of a group of bladder cancer patients and comprehensive gene expression levels of a group of test subjects without bladder cancer, both of which are in a training cohort, as a data set, the degree of difference in the expression level of each gene between the two groups is obtained by use of, for example, the P value of a parametric analysis such as t-test, the P value of a nonparametric analysis such as the Mann-Whitney's U test or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a group of bladder cancer patients and gene expression levels of a group of test subjects without bladder cancer may be calculated to select a gene that is used for an explanatory variable in a discriminant. Alternatively, ROC curves may be prepared using gene expression levels of a group of bladder cancer patients and a group of test subjects without bladder cancer, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). To the discriminant, the gene expression level of another independent bladder cancer patient or a test subject without bladder cancer is assigned as an explanatory variable to calculate discrimination results of the group to which the independent bladder cancer patient or the test subject without bladder cancer belongs. Specifically, the gene set for diagnosis found and the discriminant constructed using the gene set for diagnosis can be evaluated in an independent sample cohort to find more universal gene set for diagnosis that can detect bladder cancer and a more universal method for discriminating bladder cancer.

In preparing a discriminant using expression levels of a plurality of genes as an explanatory variable, it is not necessary to select a gene having a clear difference in expression level between the group of bladder cancer patients and the group of test subjects without bladder cancer as described above. Specifically, if expression levels of a plurality of genes are used in combination even though the expression levels of individual genes do not clearly differ, a discriminant having high discriminant performance can be obtained, as the case may be. Because of this, it is possible to utilize a method of directly searching for a discriminant having high discriminant performance without beforehand selecting the gene to be employed in the discriminant.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminant using a newly prepared sample cohort for evaluation of the performance of the discriminant.

The present invention provides a polynucleotide(s) for diagnosis or detection of a disease as being useful for diagnosing and treating bladder cancer, a method for detecting bladder cancer using the polynucleotide(s), and a kit and device for detecting bladder cancer, comprising the polynucleotide(s). In particular, existing diagnosis might cause needless extra examination for non-bladder cancer patients misjudged as being bladder cancer patients, or loss of treatment opportunities because of oversight of bladder cancer patients. By contrast, according to the present invention, bladder cancer can be accurately determined in a non-invasive manner and in a small amount of a sample, irrespective of stage, the degree of infiltration, histological grade, and primary/recurrent tumor. Specifically, the present invention provides a kit or device for diagnosis of a disease useful in diagnosis and treatment of bladder cancer from highly accurate bladder cancer markers, and a method for determining (or detecting) bladder cancer.

A gene set for diagnosis may be set as, for instance, any combination selected from one or two or more of the above polynucleotides based on a nucleotide sequence(s) represented by any of SEQ ID NOs: 1 to 228 as described above, and optionally further comprising one or two or more of the above polynucleotide based on a nucleotide sequence(s) represented by any of SEQ ID NOs: 229 to 243. Then, a discriminant is constructed using the expression levels of the gene set for diagnosis in samples from patients diagnosed with bladder cancer as a result of tissue diagnosis and samples from subjects without bladder cancer. As a result, whether or not a subject, from which an unknown sample is provided, has bladder cancer can be discriminated with 96% accuracy at the highest by measuring expression levels of the gene set for diagnosis in the unknown sample.

The kit and the method, etc. of the present invention can detect bladder cancer with good sensitivity and therefore enables bladder cancer to be detected early. As a result, early treatment is achieved, probably leading to drastic improvement in survival rate. Furthermore, it becomes possible to avoid losing treatment opportunities because of oversight of bladder cancer patients, or carrying out needless extra examination for non-bladder cancer patients misjudged as being bladder cancer patients, due to high variability found among observers of urinary cytology or different results based on the subjective views of operators of bladder endoscopy.

EXAMPLES

The present invention is described further specifically with reference to Examples below. However, the scope of the present invention is not intended to be limited by these Examples.

Reference Example

<Collection of Samples>

Sera were collected using VENOJECT II vacuum blood collecting tube VP-AS109K63 (Terumo Corp. (Japan)) from a total of 1,303 people (Table 2) including 392 bladder cancer patients, 50 lung cancer patients, 50 colorectal cancer patients, 50 esophageal cancer patients, 50 stomach cancer patients, 50 liver cancer patients, 50 biliary tract cancer patients, 50 pancreatic cancer patients, 50 prostate cancer patients, 50 breast cancer patients, 50 ovarian cancer patients, 11 uterine sarcoma patients, 50 malignant brain tumor patients, 50 malignant bone and soft tissue tumor patients, 50 benign bone and soft tissue tumor patients, 28 benign breast disease patients, 28 benign ovarian tumor patients, 50 benign prostate disease patients, 18 uterine fibroid patients, 26 benign brain tumor patients, and 100 healthy subjects after obtainment of informed consent.

For the stage of the bladder cancer patients, 57 people were in stage 0a, 10 people were in stage 0 is, 121 people were in stage I, 15 people were in stage II, 2 people were in stage III, 14 people were in stage IV, and 97 people were unknown. For the T classification that shows the depth of in-wall invasion of the primary tumor in the TNM classification, 300 people were of below T2, 90 people were of T2 or higher, and 2 people were unknown. For the histological grade of bladder cancer, 315 people were in the High grade, and 77 people were in the Low grade. Further, 178 patients had the primary bladder cancer, and 214 patients had recurrence (Table 3).

<Extraction of Total RNA>

Total RNA was obtained, using a reagent for RNA extraction in 3D-Gene (registered trademark) RNA extraction reagent from liquid sample kit (Toray Industries, Inc., Japan) according to the protocol provided by the manufacturer, from 300 µL of the serum sample obtained from each of the total of 1,303 people.

<Measurement of Gene Expression Level> miRNA in the total RNA, which was obtained from the serum sample of each of the total of 1,303 people was fluorescently labeled by use of 3D-Gene (registered trademark) miRNA Labeling kit (Toray Industries, Inc.) according to the protocol provided by the manufacturer. The oligo DNA chip used was 3D-Gene (registered trademark) Human miRNA Oligo chip (Toray Industries, Inc.) with attached probes having sequences complementary to 2,565 miRNAs among the miRNAs registered in miRBase Release 21.

Hybridization under stringent conditions and washing following the hybridization were performed according to the protocol provided by the manufacturer. The DNA chip was scanned using 3D-Gene (registered trademark) scanner (Toray Industries, Inc.) to obtain images. Fluorescence intensity was digitized using 3D-Gene (registered trademark) Extraction (Toray Industries, Inc.). The digitized fluorescence intensity was converted to a logarithmic value having a base of 2 and used as a gene expression level, from which a blank value was subtracted. A missing value was replaced with a signal value 0.1. As a result, the comprehensive gene expression levels of the miRNAs in the sera were obtained for the above 1,303 people.

Samples to be used for discriminant analysis (Examples 1, 2, and 3) of bladder cancer were extracted as follows. In the following description, benign bone and soft tissue tumor, benign breast disease, benign ovarian tumor, prostate benign disease, uterine fibroid, and benign brain tumor patients are collectively referred to as "benign disease patients", and lung cancer, colorectal cancer, esophageal cancer, stomach cancer, liver cancer, biliary tract cancer, pancreatic cancer, prostate cancer, breast cancer, ovarian cancer, uterine sarcoma, malignant brain tumor, and malignant bone and soft tissue tumor patients are collectively referred to as "patients of cancers other than bladder cancer" (Table 2). First, 392 bladder cancer patients were assigned to a positive sample group, and a total of 911 people including 611 cancer patients other than the aforementioned bladder cancer patients, 200 benign disease patients, and 100 healthy subjects were assigned to a negative sample group (Table 2). ⅔ of the samples of each group were sorted into a training cohort, and rest ⅓ of the samples were sorted into a validation cohort (Table 4). That is, 261 bladder cancer patients, 408 patients of cancers other than bladder cancer, 133 benign disease patients, and 67 healthy subjects were assigned to a training cohort, and 131 bladder cancer patients, 203 patients of cancers other than bladder cancer, 67 benign disease patients, and 33 healthy subjects were assigned to a validation cohort (Table 4).

The samples to be used for discriminant analysis (Example 4) of bladder cancer patients of T2 or higher and bladder cancer patients of below T2 in the TNM classification were extracted as follows. First, 90 bladder cancer patients of below T2 were assigned to a positive sample group, and 300 bladder cancer patients of T2 or higher were assigned to a negative sample group. Further, 58 bladder cancer patients of below T2 and 137 bladder cancer patients of T2 or higher were sorted into a training cohort, and 32 bladder cancer patients of below T2 and 163 bladder cancer patients of T2 or higher were sorted into a validation cohort (Table 5).

Calculation and statistical analysis using the digitized gene expression levels of the miRNAs were carried out using R language 3.3.1 (R Core Team (2016). R: A language and environment for statistical computing. R Foundation for Statistical Computing, Vienna, Austria. URL https://www.R-project.org/.) and MASS package 7.3.45 (Venables, W. N. & Ripley, B. D. (2002) Modern Applied Statistics with S. Fourth Edition. Springer, New York. ISBN 0-387-95457-0).

TABLE 2

| Generic term | Disease type of subjects | Number of samples | Total |
|---|---|---|---|
| Bladder cancer patients | Bladder cancer patients | 392 | 392 |
| Other cancer patients | Lung cancer patients | 50 | 611 |
| | Colorectal cancer patients | 50 | |
| | Esophageal cancer patients | 50 | |
| | Stomach cancer patients | 50 | |
| | Liver cancer patients | 50 | |
| | Biliary tract cancer patients | 50 | |
| | Pancreatic cancer patients | 50 | |
| | Prostate cancer patients | 50 | |
| | Breast cancer patients | 50 | |
| | Ovarian cancer patients | 50 | |
| | Uterine sarcoma cancer | 11 | |
| | Malignant brain tumor patients | 50 | |
| | Malignant bone and soft tissue tumor patients | 50 | |
| Benign disease patients | Benign bone and soft tissue tumor patients | 50 | 200 |
| | Benign breast disease patients | 28 | |
| | Benign ovarian tumor patients | 28 | |
| | Prostatic hypertrophy patients | 50 | |
| | Uterine fibroid patients | 18 | |
| | Benign brain tumor patients | 26 | |
| Heathy subjects | Healthy subjects | 100 | 100 |
| Total | | | 1303 |

TABLE 3

| Generic term | Class | Number of Samples |
|---|---|---|
| Bladder cancer stage | 0a | 57 |
| | 0is | 10 |
| | I | 121 |
| | II | 15 |
| | III | 2 |
| | IV | 14 |
| | Unknown | 97 |
| Bladder cancer T classification | Below T2 | 300 |
| | T2 or higher | 90 |
| | Unknown | 2 |
| Histological grade of bladder cancer | High grade | 315 |
| | Low grade | 77 |
| Bladder cancer Primary/Recurrent | Primary | 178 |
| | Recurrent | 214 |

TABLE 4

| Generic term | Training cohort | Validation cohort | Total |
|---|---|---|---|
| Bladder cancer patients (Positive group) | 261 | 131 | 392 |
| Other cancer patients (Negative Group) | 408 | 203 | 611 |
| Benign disease patients (Negative group) | 133 | 67 | 200 |
| Healthy subjects (Negative group) | 67 | 33 | 100 |
| Total | 869 | 434 | 1303 |

TABLE 5

| T classification | Training cohort | Validation cohort | Total |
|---|---|---|---|
| Below T2 (Positive group) | 58 | 32 | 90 |
| T2 or higher (Negative group) | 137 | 163 | 300 |
| Total | 195 | 195 | 390 |

Example 1

<Discriminant Analysis of Bladder Cancer with 1 or Combination of 2 to 5 miRNAs>

In this Example, discriminant formulas with 1 to 5 gene markers were created using a training cohort (Table 4) including bladder cancer patients and subjects without bladder cancer, and then the discriminant performance was evaluated in a validation cohort (Table 4). Genes to be used for the top 50 discriminant formulas ranked by the discriminant performance with each of 1 to 5 markers, that is, a total of 250 discriminant formulas were extracted to obtain 149 gene markers capable of detecting bladder cancer (Table 6).

Specifically, first, miRNA expression levels in the training cohort and the validation cohort obtained in the above Reference Example were together normalized in accordance with global normalization. Further, in order to acquire more reliable diagnostic markers, only 384 genes with a gene expression level of $2^6$ or larger in 50% or more of the samples were analyzed in either the positive sample group (bladder cancer patients) or the negative sample group (patients of cancers other than bladder cancer, benign disease patients, and healthy subjects).

Next, Fisher's discriminant analysis was performed on the measured values of the expression levels of one or a combination of two to five genes out of the aforementioned 384 genes, to construct discriminant formulas for discriminating the presence or absence of bladder cancer. At this time, discriminant formulas with high discriminant performance were searched for by a modified greedy algorithm. Further, the above-prepared discriminant formulas were used to calculate the accuracy, the sensitivity, and the specificity in the validation cohort. Then, the discriminant performance was validated in independent samples. The results for each number of genes used for discrimination are shown below.

Example 1-1

As a result of the above, the top 50 formulas ranked by the discrimination performance were obtained with number of gene 1. The discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Table 7-1. The genes included in these discriminant formulas were selected as diagnostic markers capable of discriminating between bladder cancer patients and subjects without bladder cancer.

Figure 3:
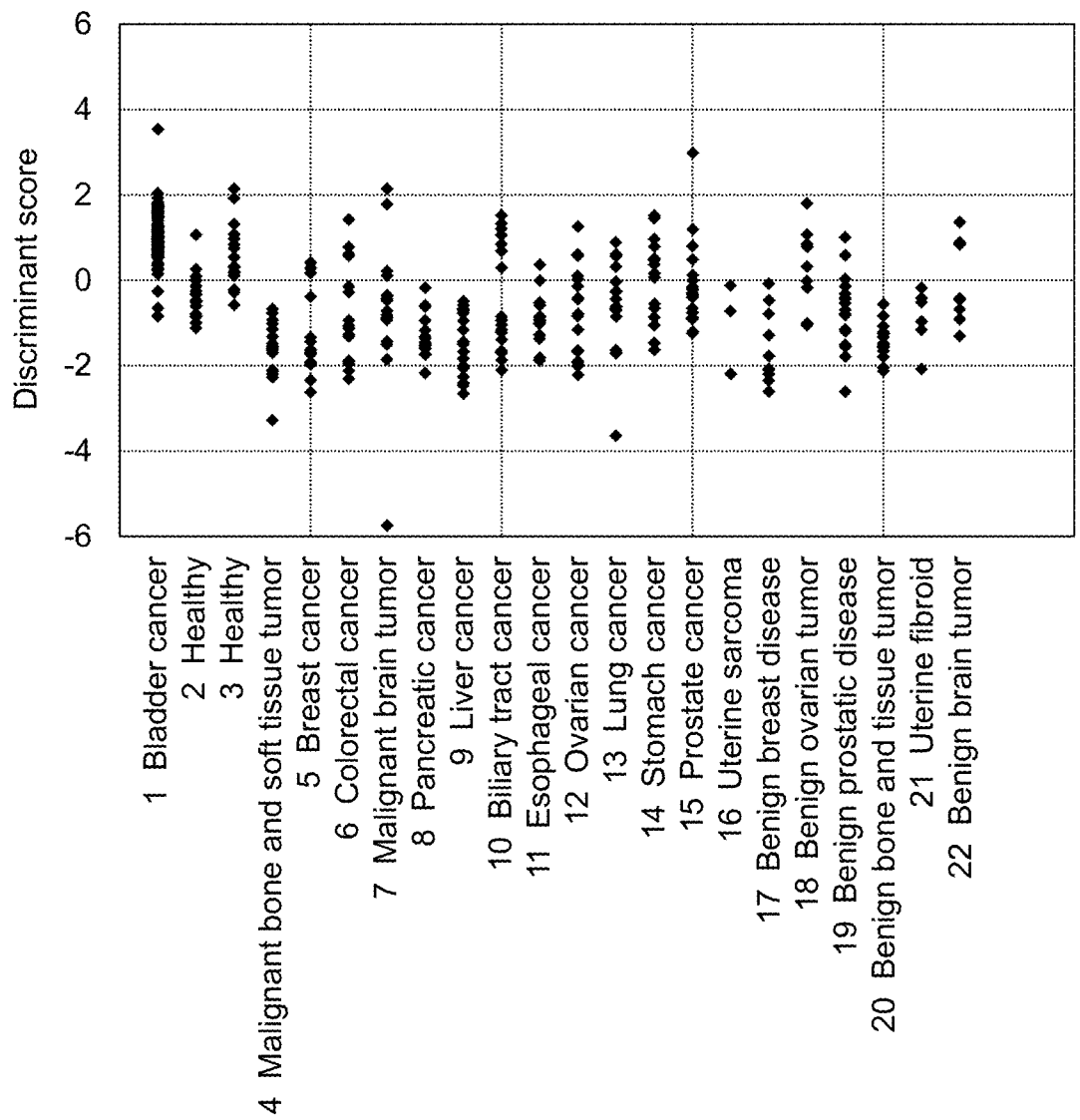
FIG. 3 shows plots of discriminant scores in validation cohorts according to the disease type obtained by a discriminant formula for 1 miRNA.

Measured values were plugged into the discriminant formula shown in No. 1 of Table 7-2 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 2A. The vertical axis of the figure represents the discriminant scores. As compared to the threshold 0.19, higher scores were determined as having bladder cancer, and lower scores were determined as not having bladder cancer. These results could be reproduced also in the validation cohort (FIG. 2B). Further, the discriminant scores in the validation cohort were plotted for each disease type, thereby showing that bladder cancer was significantly separated regardless of the disease type, in FIG. 3. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 4A to D). The vertical axis of the figure represents the discriminant scores. As compared to the threshold 0, higher scores were determined as having bladder cancer, and lower scores were determined as not having bladder cancer.

Example 1-2

As a result of the above, the top 50 formulas ranked by the discriminant performance were obtained with number of gene combination 2. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 8-1 and 8-2. The genes included in these discriminant formulas were selected as diagnostic markers capable of discriminating between bladder cancer patients and subjects without bladder cancer. The accuracy was 84% to 89%, and the sensitivity to discriminate bladder cancer was 86% to 96%, showing extremely high discrimination performance (Table 8-2). The discriminant formulas and the thresholds for discrimination with number of gene combination 2 are shown in Table 8-3.

Example 1-3

As a result of the above, the top 50 formulas ranked by the discriminant performance were obtained with number of gene combination 3. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 9-1 and 9-2. The genes included in these discriminant formulas were selected as diagnostic markers capable of discriminating between bladder cancer patients and subjects without bladder cancer.

Figure 6:
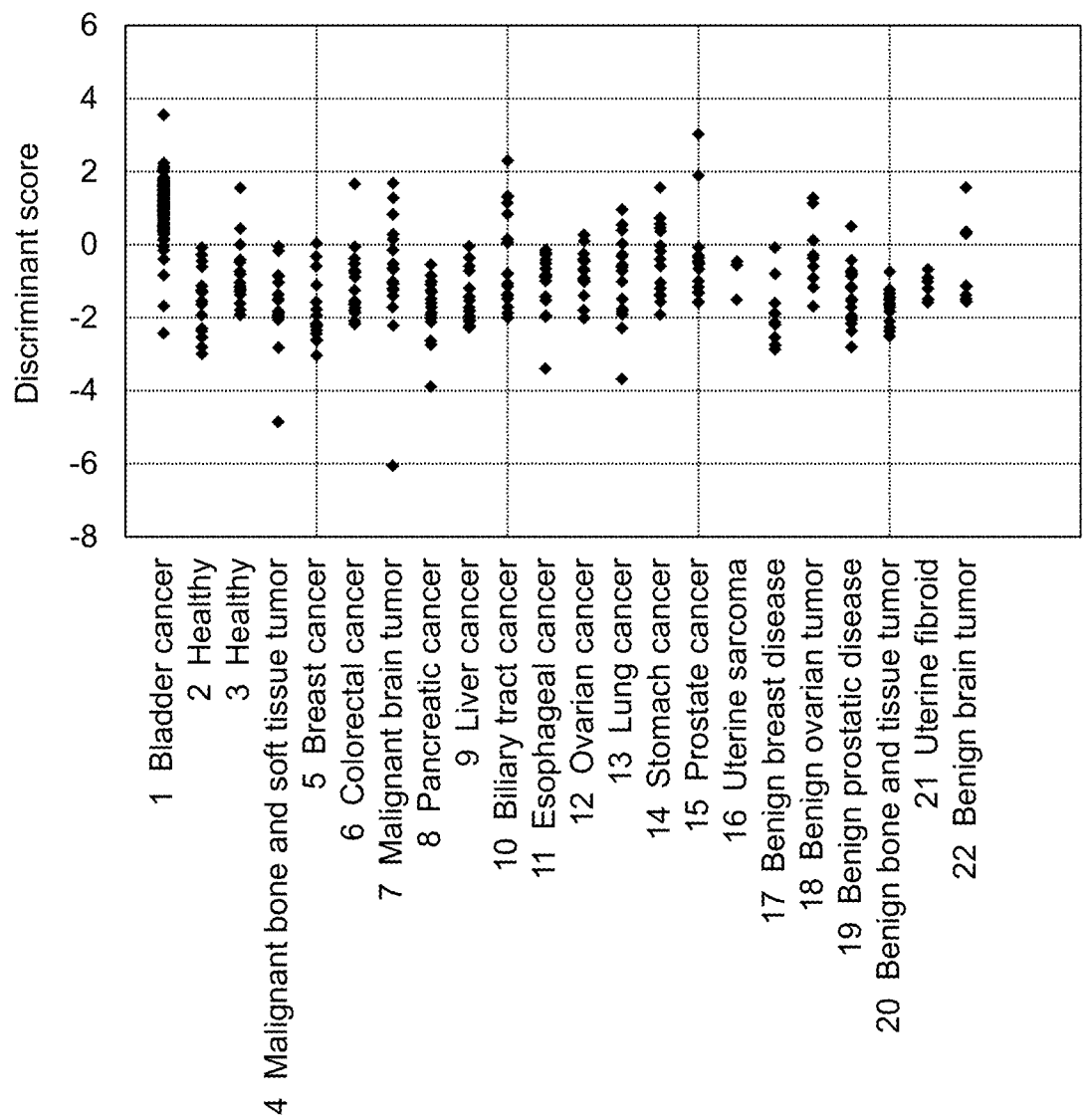
FIG. 6 shows plots of discriminant scores in validation cohorts according to the disease type obtained by a discriminant formula for 3 miRNAs.

Measured values were plugged into the discriminant formula shown in No. 1 of Table 9-3 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 5A. The vertical axis of the figure represents the discriminant scores. As compared to the threshold −0.03, higher scores were determined as having bladder cancer, and lower scores were determined as not having bladder cancer. These results could be reproduced also in the validation cohort (FIG. 5B). Further, the discriminant scores in the validation cohort were plotted for each disease type, thereby showing that bladder cancer was significantly separated regardless of the disease type, in FIG. 6. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 7A to D). The vertical axis of the figure represents the discriminant scores. As compared to the threshold 0, higher scores were determined as having bladder cancer, and lower scores were determined as not having bladder cancer.

Example 1-4

As a result of the above, the top 50 formulas ranked by the discriminant performance were obtained with number of gene combination 4. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 10-1 and 10-2. The genes included in these discriminant formulas were selected as diagnostic markers capable of discriminating between bladder cancer patients and subjects without bladder cancer.

Figure 9:
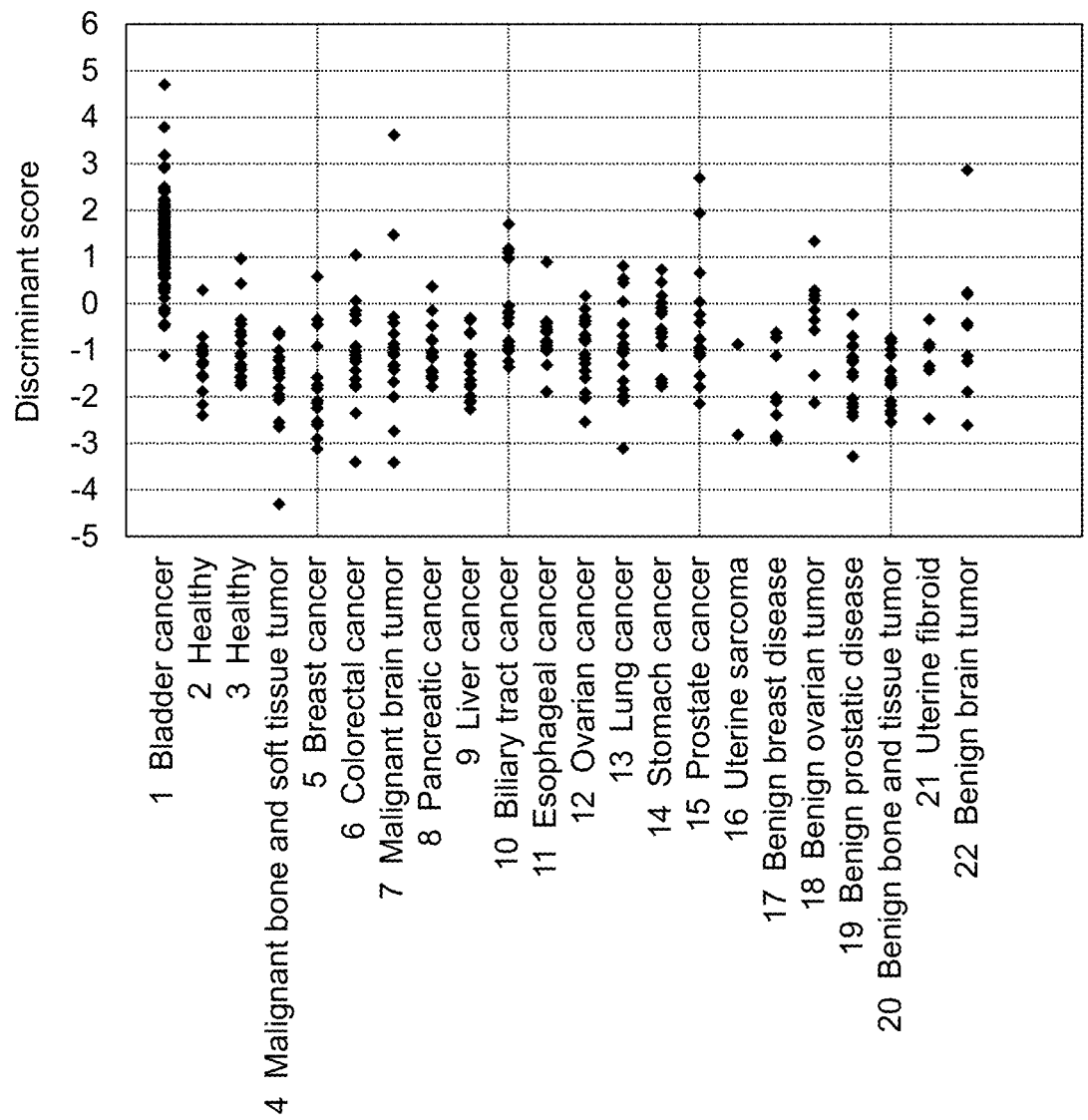
FIG. 9 shows plots of discriminant scores in validation cohorts according to the disease type obtained by a discriminant formula for 4 miRNAs.

Measured values were plugged into the discriminant formula shown in No. 1 of Table 10-3 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 8A. The vertical axis of the figure represents the discriminant scores. As compared to the threshold −0.18, higher scores were determined as having bladder cancer, and lower scores were determined as not having bladder cancer. These results could be reproduced also in the validation cohort (FIG. 8B). Further, the discriminant scores in the validation cohort were plotted for each disease type, thereby showing that bladder cancer was significantly separated regardless of the disease type, in FIG. 9. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 10A to D). The vertical axis of the figure represents the discriminant scores. As compared to the threshold 0, higher scores were determined as having bladder cancer, and lower scores were determined as not having bladder cancer.

Example 1-5

As a result of the above, the top 50 formulas ranked by the discriminant performance were obtained with number of gene combination 5. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 11-1 and 11-2. The genes included in these discriminant formulas were selected as diagnostic markers capable of discriminating between bladder cancer patients and subjects without bladder cancer.

Figure 12:
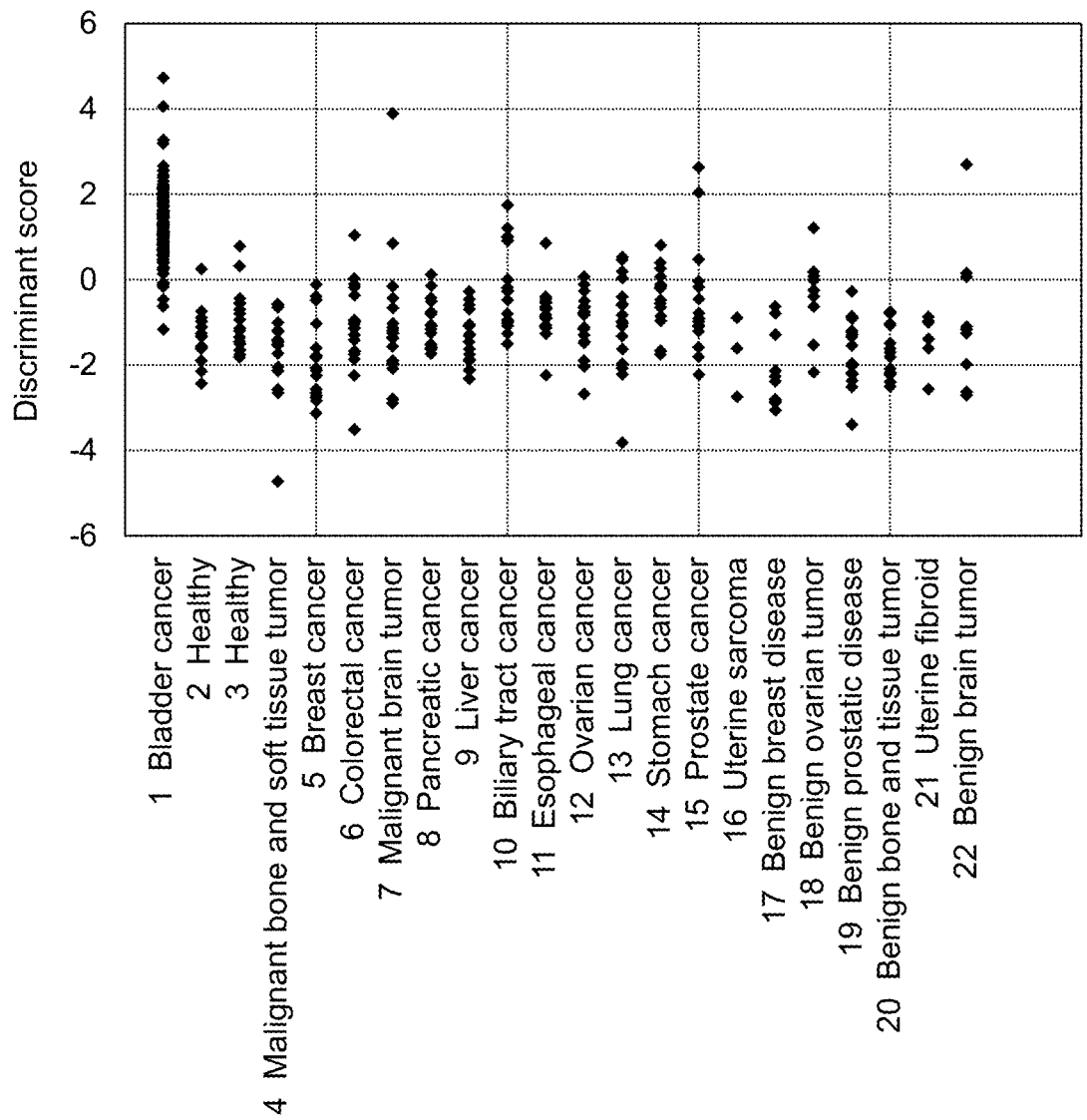
FIG. 12 shows plots of discriminant scores in validation cohorts according to the disease type obtained by a discriminant formula for 5 miRNAs.

Measured values were plugged into the discriminant formula shown in No. 1 of Table 11-3 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 11A. The vertical axis of the figure represents the discriminant scores. As compared to the threshold −0.12, higher scores were determined as having bladder cancer, and lower scores were determined as not having bladder cancer. These results could be reproduced also in the validation cohort (FIG. 11B). Further, the discriminant scores in the validation cohort were plotted for each disease type, thereby showing that bladder cancer was significantly separated regardless of the disease type, in FIG. 12. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 13A to D). The vertical axis of the figure represents the discriminant scores. As compared to the threshold 0, higher scores were determined as having bladder cancer, and lower scores were determined as not having bladder cancer.

From the above, it can be said that the polynucleotides, shown in Tables 6 to 11, which are obtained in Examples 1-1 to 1-5 are a gene group capable of specifically discriminating bladder cancer patients from any of patients of cancers other than bladder cancer, benign disease patients, and healthy subjects. Further, it was demonstrated that higher discriminant performance for bladder cancer can be obtained in the case of combining a plurality of polynucleotides than in the case of using a polynucleotide alone or a smaller number of polynucleotides. Here, the combinations of the plurality of polynucleotides that can be used for detection of bladder cancer are not limited to the above combinations, and the plurality of polynucleotides may be used in any combination.

That is, as shown in the above Example 1, one or a combination of two, three, four, or five polynucleotides can exhibit discriminant performance equal to or higher than the existing bladder cancer markers among all the polynucleotides consisting of the nucleotide sequences represented by Nos. 1 to 149 of Table 6, and they are excellent bladder cancer diagnostic markers that can detect any bladder cancer described in the aforementioned Reference Example, regardless of stage, depth of in-wall invasion, histological grade, and the primary or recurrence.

TABLE 6

| No. | Name of miRNA | SEQ ID NO |
|---|---|---|
| 1 | hsa-miR-1185-1-3p | 2 |
| 2 | hsa-miR-1185-2-3p | 3 |
| 3 | hsa-miR-1228-3p | 8 |
| 4 | hsa-miR-1228-5p | 9 |
| 5 | hsa-miR-1238-5p | 11 |
| 6 | hsa-miR-1247-3p | 12 |
| 7 | hsa-miR-1268a | 13 |
| 8 | hsa-miR-1268b | 14 |
| 9 | hsa-miR-1273g-3p | 15 |
| 10 | hsa-miR-1343-3p | 17 |
| 11 | hsa-miR-1343-5p | 18 |
| 12 | hsa-miR-135a-3p | 233 |
| 13 | hsa-miR-1469 | 234 |
| 14 | hsa-miR-17-3p | 20 |
| 15 | hsa-miR-187-5p | 21 |
| 16 | hsa-miR-1909-3p | 24 |
| 17 | hsa-miR-191-5p | 238 |

TABLE 6-continued

| No. | Name of miRNA | SEQ ID NO |
|---|---|---|
| 18 | hsa-miR-210-5p | 26 |
| 19 | hsa-miR-2467-3p | 28 |
| 20 | hsa-miR-3131 | 32 |
| 21 | hsa-miR-3160-5p | 35 |
| 22 | hsa-miR-3178 | 37 |
| 23 | hsa-miR-3180-3p | 38 |
| 24 | hsa-miR-3185 | 40 |
| 25 | hsa-miR-3194-3p | 41 |
| 26 | hsa-miR-3195 | 42 |
| 27 | hsa-miR-320a | 44 |
| 28 | hsa-miR-320b | 45 |
| 29 | hsa-miR-328-5p | 46 |
| 30 | hsa-miR-345-3p | 48 |
| 31 | hsa-miR-3616-3p | 49 |
| 32 | hsa-miR-3619-3p | 50 |
| 33 | hsa-miR-3620-5p | 51 |
| 34 | hsa-miR-3621 | 52 |
| 35 | hsa-miR-3622a-5p | 53 |
| 36 | hsa-miR-3648 | 54 |
| 37 | hsa-miR-3656 | 56 |
| 38 | hsa-miR-3679-5p | 58 |
| 39 | hsa-miR-371b-5p | 59 |
| 40 | hsa-miR-3940-5p | 62 |
| 41 | hsa-miR-4258 | 64 |
| 42 | hsa-miR-4327 | 70 |
| 43 | hsa-miR-4417 | 71 |
| 44 | hsa-miR-4419b | 72 |
| 45 | hsa-miR-4430 | 74 |
| 46 | hsa-miR-4436b-5p | 76 |
| 47 | hsa-miR-4443 | 77 |
| 48 | hsa-miR-4446-3p | 78 |
| 49 | hsa-miR-4449 | 81 |
| 50 | hsa-miR-4455 | 83 |
| 51 | hsa-miR-4459 | 84 |
| 52 | hsa-miR-4462 | 85 |
| 53 | hsa-miR-4466 | 86 |
| 54 | hsa-miR-4467 | 87 |
| 55 | hsa-miR-4480 | 88 |
| 56 | hsa-miR-4483 | 89 |
| 57 | hsa-miR-4485-5p | 91 |
| 58 | hsa-miR-4488 | 92 |
| 59 | hsa-miR-4492 | 93 |
| 60 | hsa-miR-4505 | 94 |
| 61 | hsa-miR-4525 | 96 |
| 62 | hsa-miR-4535 | 98 |
| 63 | hsa-miR-4651 | 103 |
| 64 | hsa-miR-4652-5p | 104 |
| 65 | hsa-miR-4658 | 107 |
| 66 | hsa-miR-4663 | 108 |
| 67 | hsa-miR-4673 | 109 |
| 68 | hsa-miR-4675 | 110 |
| 69 | hsa-miR-4687-3p | 111 |
| 70 | hsa-miR-4687-5p | 112 |
| 71 | hsa-miR-4690-5p | 113 |
| 72 | hsa-miR-4697-5p | 115 |
| 73 | hsa-miR-4706 | 116 |
| 74 | hsa-miR-4707-3p | 117 |
| 75 | hsa-miR-4707-5p | 118 |
| 76 | hsa-miR-4708-3p | 119 |
| 77 | hsa-miR-4718 | 121 |
| 78 | hsa-miR-4722-5p | 122 |
| 79 | hsa-miR-4725-3p | 123 |
| 80 | hsa-miR-4726-5p | 124 |
| 81 | hsa-miR-4727-3p | 125 |
| 82 | hsa-miR-4728-5p | 126 |
| 83 | hsa-miR-4731-5p | 127 |
| 84 | hsa-miR-4736 | 128 |
| 85 | hsa-miR-4739 | 129 |
| 86 | hsa-miR-4740-5p | 130 |
| 87 | hsa-miR-4741 | 131 |
| 88 | hsa-miR-4750-5p | 132 |
| 89 | hsa-miR-4755-3p | 133 |
| 90 | hsa-miR-4763-3p | 134 |
| 91 | hsa-miR-4771 | 135 |
| 92 | hsa-miR-4787-3p | 138 |
| 93 | hsa-miR-4792 | 139 |
| 94 | hsa-miR-5008-5p | 141 |
| 95 | hsa-miR-5010-5p | 142 |
| 96 | hsa-miR-504-3p | 143 |
| 97 | hsa-miR-550a-5p | 145 |
| 98 | hsa-miR-5572 | 146 |
| 99 | hsa-miR-6075 | 148 |
| 100 | hsa-miR-6076 | 149 |
| 101 | hsa-miR-6087 | 1 |
| 102 | hsa-miR-6088 | 150 |
| 103 | hsa-miR-6132 | 153 |
| 104 | hsa-miR-615-5p | 155 |
| 105 | hsa-miR-619-5p | 156 |
| 106 | hsa-miR-6511a-5p | 159 |
| 107 | hsa-miR-6515-3p | 160 |
| 108 | hsa-miR-663a | 240 |
| 109 | hsa-miR-6716-5p | 163 |
| 110 | hsa-miR-6717-5p | 164 |
| 111 | hsa-miR-6724-5p | 166 |
| 112 | hsa-miR-6737-5p | 168 |
| 113 | hsa-miR-6741-5p | 169 |
| 114 | hsa-miR-6742-5p | 170 |
| 115 | hsa-miR-6743-5p | 171 |
| 116 | hsa-miR-6760-5p | 174 |
| 117 | hsa-miR-6765-5p | 177 |
| 118 | hsa-miR-6766-5p | 179 |
| 119 | hsa-miR-6777-5p | 182 |
| 120 | hsa-miR-6780b-5p | 184 |
| 121 | hsa-miR-6781-5p | 185 |
| 122 | hsa-miR-6784-5p | 187 |
| 123 | hsa-miR-6787-5p | 189 |
| 124 | hsa-miR-6789-5p | 190 |
| 125 | hsa-miR-6791-5p | 191 |
| 126 | hsa-miR-6794-5p | 192 |
| 127 | hsa-miR-6800-5p | 193 |
| 128 | hsa-miR-6802-5p | 194 |
| 129 | hsa-miR-6803-5p | 195 |
| 130 | hsa-miR-6819-5p | 198 |
| 131 | hsa-miR-6821-5p | 199 |
| 132 | hsa-miR-6842-5p | 204 |
| 133 | hsa-miR-6850-5p | 205 |
| 134 | hsa-miR-6861-5p | 206 |
| 135 | hsa-miR-6870-5p | 208 |
| 136 | hsa-miR-6877-5p | 209 |
| 137 | hsa-miR-6880-5p | 212 |
| 138 | hsa-miR-6885-5p | 213 |
| 139 | hsa-miR-7107-5p | 215 |
| 140 | hsa-miR-7108-3p | 216 |
| 141 | hsa-miR-7113-3p | 219 |
| 142 | hsa-miR-7150 | 220 |
| 143 | hsa-miR-744-5p | 221 |
| 144 | hsa-miR-7975 | 222 |
| 145 | hsa-miR-8052 | 224 |
| 146 | hsa-miR-8069 | 225 |
| 147 | hsa-miR-8073 | 226 |
| 148 | hsa-miR-887-3p | 227 |
| 149 | hsa-miR-937-5p | 228 |

TABLE 7-1

| No. | Number of miRNA marker 1 | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| 1 | 1 | hsa-miR-6087 | 1 | 0.92 | 0.83 | 0.86 | 0.90 | 0.90 | 0.84 | 0.86 | 0.91 |
| 2 | 1 | hsa-miR-6088 | 150 | 0.93 | 0.67 | 0.75 | 0.80 | 0.91 | 0.62 | 0.71 | 0.78 |
| 3 | 1 | hsa-miR-4652-5p | 104 | 0.81 | 0.82 | 0.82 | 0.87 | 0.77 | 0.84 | 0.82 | 0.88 |
| 4 | 1 | hsa-miR-615-5p | 155 | 0.77 | 0.73 | 0.74 | 0.81 | 0.76 | 0.78 | 0.78 | 0.83 |
| 5 | 1 | hsa-miR-6819-5p | 198 | 0.74 | 0.72 | 0.73 | 0.78 | 0.73 | 0.70 | 0.71 | 0.78 |
| 6 | 1 | hsa-miR-6877-5p | 209 | 0.85 | 0.59 | 0.67 | 0.77 | 0.85 | 0.58 | 0.66 | 0.77 |
| 7 | 1 | hsa-miR-8073 | 226 | 0.82 | 0.62 | 0.68 | 0.76 | 0.83 | 0.62 | 0.68 | 0.78 |
| 8 | 1 | hsa-miR-4687-3p | 111 | 0.68 | 0.75 | 0.73 | 0.76 | 0.69 | 0.78 | 0.75 | 0.76 |
| 9 | 1 | hsa-miR-4658 | 107 | 0.79 | 0.70 | 0.73 | 0.80 | 0.79 | 0.69 | 0.72 | 0.80 |
| 10 | 1 | hsa-miR-6076 | 149 | 0.83 | 0.59 | 0.66 | 0.74 | 0.76 | 0.53 | 0.60 | 0.70 |
| 11 | 1 | hsa-miR-6777-5p | 182 | 0.86 | 0.57 | 0.65 | 0.74 | 0.82 | 0.53 | 0.62 | 0.73 |
| 12 | 1 | hsa-miR-6724-5p | 166 | 0.82 | 0.58 | 0.65 | 0.75 | 0.81 | 0.58 | 0.65 | 0.75 |
| 13 | 1 | hsa-miR-3194-3p | 41 | 0.80 | 0.63 | 0.68 | 0.78 | 0.76 | 0.61 | 0.66 | 0.76 |
| 14 | 1 | hsa-miR-4436b-5p | 76 | 0.67 | 0.74 | 0.72 | 0.78 | 0.65 | 0.74 | 0.71 | 0.75 |
| 15 | 1 | hsa-miR-187-5p | 21 | 0.88 | 0.53 | 0.63 | 0.72 | 0.88 | 0.56 | 0.65 | 0.73 |
| 16 | 1 | hsa-miR-17-3p | 20 | 0.75 | 0.70 | 0.71 | 0.78 | 0.71 | 0.71 | 0.71 | 0.77 |
| 17 | 1 | hsa-miR-4750-5p | 132 | 0.80 | 0.62 | 0.67 | 0.75 | 0.85 | 0.66 | 0.72 | 0.79 |
| 18 | 1 | hsa-miR-4727-3p | 125 | 0.80 | 0.64 | 0.69 | 0.78 | 0.72 | 0.64 | 0.67 | 0.76 |
| 19 | 1 | hsa-miR-4728-5p | 126 | 0.59 | 0.81 | 0.74 | 0.74 | 0.50 | 0.81 | 0.71 | 0.75 |
| 20 | 1 | hsa-miR-6741-5p | 169 | 0.79 | 0.60 | 0.65 | 0.72 | 0.79 | 0.58 | 0.65 | 0.74 |
| 21 | 1 | hsa-miR-6717-5p | 164 | 0.88 | 0.52 | 0.63 | 0.74 | 0.84 | 0.50 | 0.60 | 0.74 |
| 22 | 1 | hsa-miR-4480 | 88 | 0.70 | 0.69 | 0.70 | 0.75 | 0.67 | 0.69 | 0.69 | 0.75 |
| 23 | 1 | hsa-miR-3160-5p | 35 | 0.77 | 0.61 | 0.66 | 0.77 | 0.76 | 0.59 | 0.64 | 0.77 |
| 24 | 1 | hsa-miR-4663 | 108 | 0.66 | 0.79 | 0.75 | 0.78 | 0.63 | 0.78 | 0.73 | 0.76 |
| 25 | 1 | hsa-miR-4417 | 71 | 0.78 | 0.60 | 0.65 | 0.73 | 0.73 | 0.64 | 0.67 | 0.75 |
| 26 | 1 | hsa-miR-1228-5p | 9 | 0.83 | 0.55 | 0.64 | 0.73 | 0.75 | 0.56 | 0.62 | 0.71 |
| 27 | 1 | hsa-miR-4483 | 89 | 0.67 | 0.72 | 0.70 | 0.74 | 0.65 | 0.74 | 0.71 | 0.74 |
| 28 | 1 | hsa-miR-3619-3p | 50 | 0.74 | 0.62 | 0.65 | 0.74 | 0.73 | 0.62 | 0.65 | 0.74 |
| 29 | 1 | hsa-miR-1343-3p | 17 | 0.91 | 0.49 | 0.61 | 0.67 | 0.90 | 0.51 | 0.63 | 0.68 |
| 30 | 1 | hsa-miR-6075 | 148 | 0.90 | 0.48 | 0.61 | 0.74 | 0.88 | 0.44 | 0.57 | 0.72 |
| 31 | 1 | hsa-miR-320b | 45 | 0.76 | 0.61 | 0.65 | 0.73 | 0.73 | 0.59 | 0.63 | 0.73 |
| 32 | 1 | hsa-miR-4718 | 121 | 0.83 | 0.54 | 0.62 | 0.70 | 0.82 | 0.52 | 0.61 | 0.70 |
| 33 | 1 | hsa-miR-4740-5p | 130 | 0.80 | 0.57 | 0.64 | 0.71 | 0.79 | 0.55 | 0.62 | 0.71 |
| 34 | 1 | hsa-miR-2467-3p | 28 | 0.69 | 0.67 | 0.68 | 0.74 | 0.68 | 0.64 | 0.65 | 0.72 |
| 35 | 1 | hsa-miR-4455 | 83 | 0.76 | 0.60 | 0.65 | 0.72 | 0.76 | 0.59 | 0.64 | 0.68 |
| 36 | 1 | hsa-miR-5572 | 146 | 0.75 | 0.61 | 0.65 | 0.74 | 0.64 | 0.61 | 0.62 | 0.68 |
| 37 | 1 | hsa-miR-4755-3p | 133 | 0.72 | 0.63 | 0.66 | 0.73 | 0.68 | 0.63 | 0.64 | 0.71 |
| 38 | 1 | hsa-miR-6760-5p | 174 | 0.93 | 0.43 | 0.58 | 0.69 | 0.90 | 0.41 | 0.56 | 0.68 |
| 39 | 1 | hsa-miR-3648 | 54 | 0.71 | 0.64 | 0.66 | 0.71 | 0.65 | 0.68 | 0.67 | 0.71 |
| 40 | 1 | hsa-miR-4525 | 96 | 0.89 | 0.47 | 0.59 | 0.73 | 0.86 | 0.50 | 0.61 | 0.74 |
| 41 | 1 | hsa-miR-371b-5p | 59 | 0.79 | 0.60 | 0.65 | 0.73 | 0.66 | 0.61 | 0.63 | 0.67 |
| 42 | 1 | hsa-miR-3622a-5p | 53 | 0.79 | 0.54 | 0.62 | 0.68 | 0.77 | 0.55 | 0.62 | 0.69 |
| 43 | 1 | hsa-miR-744-5p | 221 | 0.71 | 0.60 | 0.64 | 0.69 | 0.61 | 0.56 | 0.58 | 0.65 |
| 44 | 1 | hsa-miR-320a | 44 | 0.72 | 0.62 | 0.65 | 0.69 | 0.67 | 0.60 | 0.62 | 0.68 |
| 45 | 1 | hsa-miR-1247-3p | 12 | 0.81 | 0.51 | 0.60 | 0.68 | 0.79 | 0.51 | 0.59 | 0.70 |
| 46 | 1 | hsa-miR-4708-3p | 119 | 0.82 | 0.51 | 0.61 | 0.68 | 0.84 | 0.47 | 0.58 | 0.69 |
| 47 | 1 | hsa-miR-1238-5p | 11 | 0.86 | 0.46 | 0.58 | 0.66 | 0.88 | 0.45 | 0.58 | 0.68 |
| 48 | 1 | hsa-miR-3620-5p | 51 | 0.77 | 0.56 | 0.62 | 0.68 | 0.75 | 0.53 | 0.59 | 0.70 |
| 49 | 1 | hsa-miR-6803-5p | 195 | 0.72 | 0.63 | 0.65 | 0.70 | 0.68 | 0.60 | 0.62 | 0.70 |
| 50 | 1 | hsa-miR-6766-5p | 179 | 0.64 | 0.67 | 0.66 | 0.71 | 0.68 | 0.71 | 0.70 | 0.75 |

TABLE 7-2

| No. | Number of miRNA | Discriminant formula | Threshold |
|---|---|---|---|
| 1 | 1 | (−2.38622)*hsa-miR-6087 + 28.2057 | 0.19 |
| 2 | 1 | (−1.84282)*hsa-miR-6088 + 20.7857 | −0.29 |
| 3 | 1 | (0.428954)*hsa-miR-4652-5p − 1.99672 | 0.28 |
| 4 | 1 | (0.94437)*hsa-miR-615-5p − 6.18452 | 0.12 |
| 5 | 1 | (1.59298)*hsa-miR-6819-5p − 13.1034 | 0.04 |
| 6 | 1 | (1.26097)*hsa-miR-6877-5p − 10.0907 | −0.21 |
| 7 | 1 | (0.973077)*hsa-miR-8073 − 7.95996 | −0.02 |
| 8 | 1 | (−2.02839)*hsa-miR-4687-3p + 18.5307 | 0.10 |
| 9 | 1 | (0.459695)*hsa-miR-4658 − 2.221 | 0.14 |
| 10 | 1 | (1.31297)*hsa-miR-6076 − 10.3287 | −0.16 |
| 11 | 1 | (0.650895)*hsa-miR-6777-5p − 4.31556 | −0.04 |
| 12 | 1 | (2.5334)*hsa-miR-6724-5p − 26.8774 | −0.17 |
| 13 | 1 | (0.473015)*hsa-miR-3194-3p − 3.91032 | −0.06 |
| 14 | 1 | (0.862895)*hsa-miR-4436b-5p − 5.38183 | 0.18 |
| 15 | 1 | (0.958701)*hsa-miR-187-5p − 8.01195 | −0.20 |
| 16 | 1 | (0.464258)*hsa-miR-17-3p − 2.73158 | 0.23 |
| 17 | 1 | (0.863932)*hsa-miR-4750-5p − 5.86918 | 0.00 |
| 18 | 1 | (0.558605)*hsa-miR-4727-3p − 3.40207 | 0.09 |
| 19 | 1 | (−1.13719)*hsa-miR-4728-5p + 8.17743 | 0.18 |
| 20 | 1 | (1.22441)*hsa-miR-6741-5p − 9.85847 | −0.12 |
| 21 | 1 | (0.598595)*hsa-miR-6717-5p − 4.6341 | −0.06 |
| 22 | 1 | (0.432884)*hsa-miR-4480 − 2.72905 | 0.22 |
| 23 | 1 | (0.454592)*hsa-miR-3160-5p − 3.59088 | −0.20 |
| 24 | 1 | (0.437205)*hsa-miR-4663 − 2.3675 | 0.33 |
| 25 | 1 | (2.29198)*hsa-miR-4417 − 19.4685 | −0.07 |
| 26 | 1 | (−2.46304)*hsa-miR-1228-5p + 27.0668 | −0.12 |
| 27 | 1 | (0.529784)*hsa-miR-4483 − 3.04293 | 0.16 |
| 28 | 1 | (1.08677)*hsa-miR-3619-3p − 9.38089 | −0.21 |
| 29 | 1 | (0.901987)*hsa-miR-1343-3p − 7.36719 | −0.37 |
| 30 | 1 | (1.70213)*hsa-miR-6075 − 15.1524 | −0.50 |
| 31 | 1 | (0.619655)*hsa-miR-320b − 3.83811 | 0.08 |
| 32 | 1 | (0.491734)*hsa-miR-4718 − 4.11397 | −0.10 |

TABLE 7-2-continued

| No. | Number of miRNA | Discriminant formula | Threshold |
|---|---|---|---|
| 33 | 1 | (0.543442)*hsa-miR-4740-5p − 3.44558 | −0.06 |
| 34 | 1 | (0.566603)*hsa-miR-2467-3p − 5.23727 | 0.11 |
| 35 | 1 | (0.496896)*hsa-miR-4455 − 2.69782 | 0.04 |
| 36 | 1 | (0.78147)*hsa-miR-5572 − 4.96372 | 0.05 |
| 37 | 1 | (0.384157)*hsa-miR-4755-3p − 2.12762 | 0.14 |
| 38 | 1 | (0.482362)*hsa-miR-6760-5p − 2.59313 | −0.31 |
| 39 | 1 | (1.71731)*hsa-miR-3648 − 22.6417 | 0.07 |
| 40 | 1 | (0.618585)*hsa-miR-4525 − 6.85074 | −0.48 |
| 41 | 1 | (0.621671)*hsa-miR-371b-5p − 3.40467 | 0.11 |
| 42 | 1 | (0.69848)*hsa-miR-3622a-5p − 4.36254 | −0.02 |
| 43 | 1 | (1.34494)*hsa-miR-744-5p − 12.1875 | 0.00 |
| 44 | 1 | (0.86288)*hsa-miR-320a − 5.99984 | 0.04 |
| 45 | 1 | (1.11344)*hsa-miR-1247-3p − 7.96563 | −0.15 |
| 46 | 1 | (0.590382)*hsa-miR-4708-3p − 4.90478 | −0.21 |
| 47 | 1 | (0.892678)*hsa-miR-1238-5p − 6.81907 | −0.20 |
| 48 | 1 | (−1.68137)*hsa-miR-3620-5p − F12.8603 | −0.25 |
| 49 | 1 | (−4.57263)*hsa-miR-6803-5p + 49.8649 | −0.05 |
| 50 | 1 | (0.95846)*hsa-miR-6766-5p − 6.48535 | 0.19 |

TABLE 8-1

| No. | Number of miRNA | miRNA marker 1 | SEQ ID NO | miRNA marker 2 | SEQ ID NO |
|---|---|---|---|---|---|
| 1 | 2 | hsa-miR-6087 | 1 | hsa-miR-744-5p | 221 |
| 2 | 2 | hsa-miR-6087 | 1 | hsa-miR-4652-5p | 104 |
| 3 | 2 | hsa-miR-6087 | 1 | hsa-miR-6132 | 153 |
| 4 | 2 | hsa-miR-6087 | 1 | hsa-miR-4787-3p | 138 |
| 5 | 2 | hsa-miR-6087 | 1 | hsa-miR-1185-1-3p | 2 |
| 6 | 2 | hsa-miR-6087 | 1 | hsa-miR-4436b-5p | 76 |
| 7 | 2 | hsa-miR-6087 | 1 | hsa-miR-6789-5p | 190 |
| 8 | 2 | hsa-miR-6087 | 1 | hsa-miR-6784-5p | 187 |
| 9 | 2 | hsa-miR-6087 | 1 | hsa-miR-3160-5p | 35 |
| 10 | 2 | hsa-miR-6087 | 1 | hsa-miR-6800-5p | 193 |
| 11 | 2 | hsa-miR-6087 | 1 | hsa-miR-615-5p | 155 |
| 12 | 2 | hsa-miR-6087 | 1 | hsa-miR-1343-5p | 18 |
| 13 | 2 | hsa-miR-6087 | 1 | hsa-miR-1228-5p | 9 |
| 14 | 2 | hsa-miR-6087 | 1 | hsa-miR-6724-5p | 166 |
| 15 | 2 | hsa-miR-6087 | 1 | hsa-miR-4417 | 71 |
| 16 | 2 | hsa-miR-6087 | 1 | hsa-miR-6781-5p | 185 |
| 17 | 2 | hsa-miR-6087 | 1 | hsa-miR-3648 | 54 |
| 18 | 2 | hsa-miR-6087 | 1 | hsa-miR-937-5p | 228 |
| 19 | 2 | hsa-miR-6087 | 1 | hsa-miR-4258 | 64 |
| 20 | 2 | hsa-miR-6087 | 1 | hsa-miR-4466 | 86 |
| 21 | 2 | hsa-miR-6087 | 1 | hsa-miR-187-5p | 21 |
| 22 | 2 | hsa-miR-6087 | 1 | hsa-miR-4740-5p | 130 |
| 23 | 2 | hsa-miR-6087 | 1 | hsa-miR-4697-5p | 115 |
| 24 | 2 | hsa-miR-6087 | 1 | hsa-miR-320b | 45 |
| 25 | 2 | hsa-miR-6087 | 1 | hsa-miR-3656 | 56 |
| 26 | 2 | hsa-miR-6087 | 1 | hsa-miR-4706 | 116 |
| 27 | 2 | hsa-miR-6087 | 1 | hsa-miR-4727-3p | 125 |
| 28 | 2 | hsa-miR-6087 | 1 | hsa-miR-619-5p | 156 |
| 29 | 2 | hsa-miR-6087 | 1 | hsa-miR-663a | 240 |
| 30 | 2 | hsa-miR-6087 | 1 | hsa-miR-320a | 44 |
| 31 | 2 | hsa-miR-6087 | 1 | hsa-miR-6861-5p | 206 |
| 32 | 2 | hsa-miR-6087 | 1 | hsa-miR-6075 | 148 |
| 33 | 2 | hsa-miR-6087 | 1 | hsa-miR-4690-5p | 113 |
| 34 | 2 | hsa-miR-6087 | 1 | hsa-miR-4673 | 109 |
| 35 | 2 | hsa-miR-6087 | 1 | hsa-miR-17-3p | 20 |
| 36 | 2 | hsa-miR-6087 | 1 | hsa-miR-135a-3p | 233 |
| 37 | 2 | hsa-miR-6087 | 1 | hsa-miR-4327 | 70 |
| 38 | 2 | hsa-miR-6087 | 1 | hsa-miR-3195 | 42 |
| 39 | 2 | hsa-miR-6087 | 1 | hsa-miR-4771 | 135 |
| 40 | 2 | hsa-miR-6087 | 1 | hsa-miR-6885-5p | 213 |
| 41 | 2 | hsa-miR-6087 | 1 | hsa-miR-3194-3p | 41 |
| 42 | 2 | hsa-miR-6087 | 1 | hsa-miR-4535 | 98 |
| 43 | 2 | hsa-miR-6087 | 1 | hsa-miR-4736 | 128 |
| 44 | 2 | hsa-miR-6087 | 1 | hsa-miR-4718 | 121 |
| 45 | 2 | hsa-miR-6087 | 1 | hsa-miR-6511a-5p | 159 |
| 46 | 2 | hsa-miR-6087 | 1 | hsa-miR-4663 | 108 |
| 47 | 2 | hsa-miR-6087 | 1 | hsa-miR-550a-5p | 145 |
| 48 | 2 | hsa-miR-6087 | 1 | hsa-miR-4467 | 87 |
| 49 | 2 | hsa-miR-6087 | 1 | hsa-miR-3621 | 52 |
| 50 | 2 | hsa-miR-6087 | 1 | hsa-miR-1185-2-3p | 3 |

TABLE 8-2

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 1 | 0.95 | 0.82 | 0.86 | 0.93 | 0.93 | 0.84 | 0.86 | 0.93 |
| 2 | 0.93 | 0.88 | 0.89 | 0.94 | 0.92 | 0.88 | 0.89 | 0.94 |
| 3 | 0.95 | 0.80 | 0.84 | 0.93 | 0.92 | 0.83 | 0.85 | 0.92 |
| 4 | 0.96 | 0.81 | 0.86 | 0.92 | 0.95 | 0.83 | 0.87 | 0.93 |
| 5 | 0.93 | 0.82 | 0.86 | 0.92 | 0.92 | 0.85 | 0.87 | 0.94 |
| 6 | 0.95 | 0.82 | 0.86 | 0.93 | 0.93 | 0.82 | 0.85 | 0.93 |
| 7 | 0.94 | 0.80 | 0.84 | 0.91 | 0.95 | 0.82 | 0.86 | 0.92 |
| 8 | 0.92 | 0.84 | 0.86 | 0.92 | 0.89 | 0.83 | 0.85 | 0.93 |
| 9 | 0.95 | 0.82 | 0.86 | 0.92 | 0.94 | 0.83 | 0.86 | 0.93 |
| 10 | 0.94 | 0.80 | 0.84 | 0.91 | 0.95 | 0.81 | 0.85 | 0.91 |
| 11 | 0.92 | 0.84 | 0.86 | 0.92 | 0.90 | 0.83 | 0.85 | 0.92 |
| 12 | 0.94 | 0.80 | 0.84 | 0.90 | 0.95 | 0.80 | 0.85 | 0.92 |
| 13 | 0.95 | 0.81 | 0.85 | 0.92 | 0.94 | 0.83 | 0.86 | 0.92 |
| 14 | 0.91 | 0.87 | 0.88 | 0.93 | 0.92 | 0.88 | 0.89 | 0.94 |
| 15 | 0.92 | 0.84 | 0.86 | 0.91 | 0.92 | 0.85 | 0.87 | 0.93 |
| 16 | 0.95 | 0.82 | 0.86 | 0.92 | 0.94 | 0.83 | 0.86 | 0.93 |
| 17 | 0.94 | 0.83 | 0.86 | 0.91 | 0.95 | 0.85 | 0.88 | 0.92 |
| 18 | 0.93 | 0.83 | 0.86 | 0.91 | 0.92 | 0.83 | 0.86 | 0.92 |
| 19 | 0.93 | 0.84 | 0.86 | 0.91 | 0.93 | 0.84 | 0.87 | 0.92 |
| 20 | 0.95 | 0.80 | 0.84 | 0.90 | 0.95 | 0.81 | 0.85 | 0.91 |
| 21 | 0.92 | 0.83 | 0.86 | 0.91 | 0.92 | 0.85 | 0.87 | 0.92 |
| 22 | 0.96 | 0.80 | 0.85 | 0.92 | 0.92 | 0.83 | 0.86 | 0.92 |
| 23 | 0.95 | 0.81 | 0.85 | 0.91 | 0.94 | 0.83 | 0.86 | 0.91 |
| 24 | 0.93 | 0.83 | 0.86 | 0.92 | 0.93 | 0.85 | 0.87 | 0.94 |
| 25 | 0.95 | 0.80 | 0.84 | 0.90 | 0.95 | 0.81 | 0.85 | 0.91 |
| 26 | 0.94 | 0.80 | 0.85 | 0.91 | 0.93 | 0.82 | 0.85 | 0.92 |
| 27 | 0.91 | 0.86 | 0.87 | 0.92 | 0.86 | 0.87 | 0.87 | 0.93 |
| 28 | 0.93 | 0.82 | 0.85 | 0.90 | 0.94 | 0.82 | 0.85 | 0.91 |
| 29 | 0.93 | 0.83 | 0.86 | 0.92 | 0.93 | 0.83 | 0.86 | 0.92 |
| 30 | 0.96 | 0.80 | 0.85 | 0.92 | 0.93 | 0.83 | 0.86 | 0.92 |
| 31 | 0.93 | 0.81 | 0.85 | 0.90 | 0.91 | 0.83 | 0.85 | 0.91 |
| 32 | 0.97 | 0.81 | 0.86 | 0.92 | 0.93 | 0.80 | 0.84 | 0.93 |
| 33 | 0.95 | 0.81 | 0.85 | 0.90 | 0.93 | 0.82 | 0.85 | 0.91 |
| 34 | 0.92 | 0.83 | 0.85 | 0.90 | 0.91 | 0.84 | 0.86 | 0.91 |
| 35 | 0.94 | 0.85 | 0.87 | 0.93 | 0.93 | 0.85 | 0.88 | 0.93 |
| 36 | 0.93 | 0.82 | 0.85 | 0.90 | 0.92 | 0.82 | 0.85 | 0.91 |
| 37 | 0.93 | 0.81 | 0.85 | 0.92 | 0.90 | 0.83 | 0.85 | 0.92 |
| 38 | 0.93 | 0.82 | 0.85 | 0.90 | 0.94 | 0.84 | 0.87 | 0.91 |
| 39 | 0.94 | 0.82 | 0.85 | 0.92 | 0.91 | 0.84 | 0.86 | 0.93 |
| 40 | 0.92 | 0.83 | 0.85 | 0.90 | 0.92 | 0.83 | 0.86 | 0.91 |
| 41 | 0.95 | 0.83 | 0.86 | 0.92 | 0.93 | 0.82 | 0.85 | 0.93 |
| 42 | 0.94 | 0.82 | 0.85 | 0.90 | 0.90 | 0.82 | 0.85 | 0.91 |
| 43 | 0.96 | 0.78 | 0.83 | 0.91 | 0.95 | 0.80 | 0.84 | 0.92 |
| 44 | 0.97 | 0.80 | 0.85 | 0.92 | 0.96 | 0.81 | 0.85 | 0.92 |
| 45 | 0.93 | 0.82 | 0.85 | 0.91 | 0.90 | 0.82 | 0.85 | 0.91 |
| 46 | 0.92 | 0.84 | 0.86 | 0.92 | 0.89 | 0.85 | 0.86 | 0.92 |
| 47 | 0.93 | 0.82 | 0.85 | 0.90 | 0.92 | 0.82 | 0.85 | 0.91 |
| 48 | 0.96 | 0.80 | 0.85 | 0.91 | 0.93 | 0.80 | 0.84 | 0.92 |
| 49 | 0.91 | 0.85 | 0.87 | 0.92 | 0.88 | 0.87 | 0.88 | 0.93 |
| 50 | 0.92 | 0.84 | 0.87 | 0.92 | 0.92 | 0.86 | 0.88 | 0.94 |

TABLE 8-3

| No. | Number of miRNA | Discriminant Formula | Threshold |
|---|---|---|---|
| 1 | 2 | (−2.3378)*hsa-miR-6087 + (0.775187)*hsa-miR-744-5p + 20.6087 | −0.06 |
| 2 | 2 | (−1.82014)*hsa-miR-6087 + (0.263623)*hsa-miR-4652-5p + 20.2873 | 0.13 |
| 3 | 2 | (−2.342)*hsa-miR-6087 + (0.747161)*hsa-miR-6132 + 20.6239 | −0.10 |
| 4 | 2 | (−2.26977)*hsa-miR-6087 + (0.328067)*hsa-miR-4787-3p + 24.4629 | 0.02 |
| 5 | 2 | (−2.4398)*hsa-miR-6087 + (0.350141)*hsa-miR-1185-1-3p + 25.8489 | −0.02 |
| 6 | 2 | (−2.14971)*hsa-miR-6087 + (0.396847)*hsa-miR-4436b-5p + 22.935 | 0.02 |
| 7 | 2 | (−2.31319)*hsa-miR-6087 + (0.485485)*hsa-miR-6789-5p + 22.458 | −0.04 |
| 8 | 2 | (−2.31658)*hsa-miR-6087 + (−0.820454)*hsa-miR-6784-5p + 36.7072 | 0.17 |
| 9 | 2 | (−2.02565)*hsa-miR-6087 + (0.200577)*hsa-miR-3160-5p + 22.3592 | 0.04 |
| 10 | 2 | (−2.43999)*hsa-miR-6087 + (−0.400246)*hsa-miR-6800-5p + 31.9611 | 0.04 |
| 11 | 2 | (−2.11937)*hsa-miR-6087 + (0.336707)*hsa-miR-615-5p + 22.8464 | 0.19 |
| 12 | 2 | (−2.42752)*hsa-miR-6087 + (−0.796893)*hsa-miR-1343-5p + 36.5499 | 0.03 |
| 13 | 2 | (−2.154)*hsa-miR-6087 + (−1.03009)*hsa-miR-1228-5p + 36.7806 | 0.01 |
| 14 | 2 | (−2.14819)*hsa-miR-6087 + (1.1839)*hsa-miR-6724-5p + 12.8318 | 0.23 |
| 15 | 2 | (−2.26)*hsa-miR-6087 + (0.704186)*hsa-miR-4417 + 20.7322 | 0.18 |
| 16 | 2 | (−2.41441)*hsa-miR-6087 + (−1.20586)*hsa-miR-6781-5p + 40.3148 | −0.04 |
| 17 | 2 | (−2.20958)*hsa-miR-6087 + (0.618185)*hsa-miR-3648 + 17.9673 | 0.11 |
| 18 | 2 | (−2.46326)*hsa-miR-6087 + (−0.426017)*hsa-miR-937-5p + 32.6143 | 0.14 |
| 19 | 2 | (−2.37713)*hsa-miR-6087 + (0.352818)*hsa-miR-4258 + 24.5397 | 0.03 |
| 20 | 2 | (−2.32734)*hsa-miR-6087 + (0.611001)*hsa-miR-4466 + 19.6562 | 0.02 |
| 21 | 2 | (−2.25165)*hsa-miR-6087 + (0.222992)*hsa-miR-187-5p + 24.7515 | 0.18 |
| 22 | 2 | (−2.20735)*hsa-miR-6087 + (0.206616)*hsa-miR-4740-5p + 24.7814 | −0.03 |
| 23 | 2 | (−2.32967)*hsa-miR-6087 + (0.548334)*hsa-miR-4697-5p + 22.7714 | −0.01 |
| 24 | 2 | (−2.24507)*hsa-miR-6087 + (0.283037)*hsa-miR-320b + 24.784 | 0.13 |
| 25 | 2 | (−2.46034)*hsa-miR-6087 + (0.960217)*hsa-miR-3656 + 17.8857 | −0.01 |
| 26 | 2 | (−2.24352)*hsa-miR-6087 + (0.361123)*hsa-miR-4706 + 23.4592 | 0.04 |
| 27 | 2 | (−2.13576)*hsa-miR-6087 + (0.236818)*hsa-miR-4727-3p + 23.8029 | 0.26 |
| 28 | 2 | (−2.33994)*hsa-miR-6087 + (0.101029)*hsa-miR-619-5p + 26.8946 | 0.12 |
| 29 | 2 | (−2.33399)*hsa-miR-6087 + (0.585351)*hsa-miR-663a + 20.4173 | 0.05 |
| 30 | 2 | (−2.27949)*hsa-miR-6087 + (0.349853)*hsa-miR-320a + 24.5114 | 0.00 |
| 31 | 2 | (−2.32151)*hsa-miR-6087 + (0.225774)*hsa-miR-6861-5p + 25.6592 | 0.14 |
| 32 | 2 | (−2.12657)*hsa-miR-6087 + (0.759356)*hsa-miR-6075 + 18.3767 | −0.04 |
| 33 | 2 | (−2.34965)*hsa-miR-6087 + (0.20625)*hsa-miR-4690-5p + 26.3628 | 0.10 |
| 34 | 2 | (−2.34461)*hsa-miR-6087 + (0.108729)*hsa-miR-4673 + 27.0938 | 0.17 |
| 35 | 2 | (−2.14934)*hsa-miR-6087 + (0.229327)*hsa-miR-17-3p + 24.0564 | 0.16 |
| 36 | 2 | (−2.36577)*hsa-miR-6087 + (0.0426866)*hsa-miR-135a-3p + 27.7126 | 0.11 |
| 37 | 2 | (−2.43661)*hsa-miR-6087 + (0.746709)*hsa-miR-4327 + 21.855 | 0.00 |
| 38 | 2 | (−2.38999)*hsa-miR-6087 + (0.161276)*hsa-miR-3195 + 26.9159 | 0.14 |
| 39 | 2 | (−2.26696)*hsa-miR-6087 + (0.174565)*hsa-miR-4771 + 25.809 | 0.04 |
| 40 | 2 | (−2.44165)*hsa-miR-6087 + (0.216791)*hsa-miR-6885-5p + 26.3871 | 0.19 |
| 41 | 2 | (−2.06725)*hsa-miR-6087 + (0.200306)*hsa-miR-3194-3p + 22.7794 | 0.03 |
| 42 | 2 | (−2.33398)*hsa-miR-6087 + (0.0943401)*hsa-miR-4535 + 27.0762 | 0.08 |
| 43 | 2 | (−2.30908)*hsa-miR-6087 + (0.228957)*hsa-miR-4736 + 25.7017 | −0.11 |
| 44 | 2 | (−2.22306)*hsa-miR-6087 + (0.174636)*hsa-miR-4718 + 24.816 | −0.04 |
| 45 | 2 | (−2.31893)*hsa-miR-6087 + (0.320313)*hsa-miR-6511a-5p + 24.9405 | 0.11 |
| 46 | 2 | (−2.12785)*hsa-miR-6087 + (0.203709)*hsa-miR-4663 + 24.0486 | 0.10 |
| 47 | 2 | (−2.38066)*hsa-miR-6087 + (0.0856268)*hsa-miR-550a-5p + 27.607 | 0.12 |
| 48 | 2 | (−2.27785)*hsa-miR-6087 + (0.666284)*hsa-miR-4467 + 19.8945 | −0.06 |
| 49 | 2 | (−2.33358)*hsa-miR-6087 + (−0.824656)*hsa-miR-3621 + 36.9712 | 0.25 |
| 50 | 2 | (−2.43195)*hsa-miR-6087 + (0.283136)*hsa-miR-1185-2-3p + 26.4884 | 0.10 |

TABLE 9-1

| No. | Number of miRNA | miRNA marker 1 | SEQ ID NO | miRNA marker 2 | SEQ ID NO | miRNA marker 3 | SEQ ID NO |
|---|---|---|---|---|---|---|---|
| 1 | 3 | hsa-miR-6087 | 1 | hsa-miR-744-5p | 221 | hsa-miR-4725-3p | 123 |
| 2 | 3 | hsa-miR-6087 | 1 | hsa-miR-6132 | 153 | hsa-miR-4725-3p | 123 |
| 3 | 3 | hsa-miR-6087 | 1 | hsa-miR-744-5p | 221 | hsa-miR-1268b | 14 |
| 4 | 3 | hsa-miR-6087 | 1 | hsa-miR-6724-5p | 166 | hsa-miR-3940-5p | 62 |
| 5 | 3 | hsa-miR-6087 | 1 | hsa-miR-4652-5p | 104 | hsa-miR-4728-5p | 126 |
| 6 | 3 | hsa-miR-6087 | 1 | hsa-miR-1185-1-3p | 2 | hsa-miR-4728-5p | 126 |
| 7 | 3 | hsa-miR-6087 | 1 | hsa-miR-1185-2-3p | 3 | hsa-miR-4728-5p | 126 |
| 8 | 3 | hsa-miR-6087 | 1 | hsa-miR-4652-5p | 104 | hsa-miR-6724-5p | 166 |
| 9 | 3 | hsa-miR-6087 | 1 | hsa-miR-6724-5p | 166 | hsa-miR-8069 | 225 |
| 10 | 3 | hsa-miR-6087 | 1 | hsa-miR-6724-5p | 166 | hsa-miR-6781-5p | 185 |
| 11 | 3 | hsa-miR-6087 | 1 | hsa-miR-4652-5p | 104 | hsa-miR-6781-5p | 185 |
| 12 | 3 | hsa-miR-6087 | 1 | hsa-miR-6784-5p | 187 | hsa-miR-4728-5p | 126 |
| 13 | 3 | hsa-miR-6087 | 1 | hsa-miR-744-5p | 221 | hsa-miR-6781-5p | 185 |
| 14 | 3 | hsa-miR-6087 | 1 | hsa-miR-4652-5p | 104 | hsa-miR-6794-5p | 192 |
| 15 | 3 | hsa-miR-6087 | 1 | hsa-miR-1185-1-3p | 2 | hsa-miR-6781-5p | 185 |
| 16 | 3 | hsa-miR-6087 | 1 | hsa-miR-6724-5p | 166 | hsa-miR-3621 | 52 |
| 17 | 3 | hsa-miR-6087 | 1 | hsa-miR-6781-5p | 185 | hsa-miR-6075 | 148 |

TABLE 9-1-continued

| No. | Number of miRNA | miRNA marker 1 | SEQ ID NO | miRNA marker 2 | SEQ ID NO | miRNA marker 3 | SEQ ID NO |
|---|---|---|---|---|---|---|---|
| 18 | 3 | hsa-miR-6087 | 1 | hsa-miR-1185-1-3p | 2 | hsa-miR-6724-5p | 166 |
| 19 | 3 | hsa-miR-6087 | 1 | hsa-miR-6789-5p | 190 | hsa-miR-3940-5p | 62 |
| 20 | 3 | hsa-miR-6087 | 1 | hsa-miR-3160-5p | 35 | hsa-miR-4728-5p | 126 |
| 21 | 3 | hsa-miR-6087 | 1 | hsa-miR-6781-5p | 185 | hsa-miR-4492 | 93 |
| 22 | 3 | hsa-miR-6087 | 1 | hsa-miR-6781-5p | 185 | hsa-miR-4327 | 70 |
| 23 | 3 | hsa-miR-6087 | 1 | hsa-miR-4327 | 70 | hsa-miR-1268b | 14 |
| 24 | 3 | hsa-miR-6087 | 1 | hsa-miR-744-5p | 221 | hsa-miR-3679-5p | 58 |
| 25 | 3 | hsa-miR-6087 | 1 | hsa-miR-6132 | 153 | hsa-miR-4739 | 129 |
| 26 | 3 | hsa-miR-6087 | 1 | hsa-miR-744-5p | 221 | hsa-miR-6765-5p | 177 |
| 27 | 3 | hsa-miR-6087 | 1 | hsa-miR-6784-5p | 187 | hsa-miR-6724-5p | 166 |
| 28 | 3 | hsa-miR-6087 | 1 | hsa-miR-744-5p | 221 | hsa-miR-4505 | 94 |
| 29 | 3 | hsa-miR-6087 | 1 | hsa-miR-6781-5p | 185 | hsa-miR-6780b-5p | 184 |
| 30 | 3 | hsa-miR-6087 | 1 | hsa-miR-744-5p | 221 | hsa-miR-4728-5p | 126 |
| 31 | 3 | hsa-miR-6087 | 1 | hsa-miR-744-5p | 221 | hsa-miR-4739 | 129 |
| 32 | 3 | hsa-miR-6087 | 1 | hsa-miR-6724-5p | 166 | hsa-miR-4446-3p | 78 |
| 33 | 3 | hsa-miR-6087 | 1 | hsa-miR-6075 | 148 | hsa-miR-4741 | 131 |
| 34 | 3 | hsa-miR-6087 | 1 | hsa-miR-744-5p | 221 | hsa-miR-4459 | 84 |
| 35 | 3 | hsa-miR-6087 | 1 | hsa-miR-6132 | 153 | hsa-miR-6781-5p | 185 |
| 36 | 3 | hsa-miR-6087 | 1 | hsa-miR-6132 | 153 | hsa-miR-1268b | 14 |
| 37 | 3 | hsa-miR-6087 | 1 | hsa-miR-6781-5p | 185 | hsa-miR-4707-5p | 118 |
| 38 | 3 | hsa-miR-6087 | 1 | hsa-miR-320a | 44 | hsa-miR-4728-5p | 126 |
| 39 | 3 | hsa-miR-6087 | 1 | hsa-miR-4652-5p | 104 | hsa-miR-6800-5p | 193 |
| 40 | 3 | hsa-miR-6087 | 1 | hsa-miR-4652-5p | 104 | hsa-miR-937-5p | 228 |
| 41 | 3 | hsa-miR-6087 | 1 | hsa-miR-663a | 240 | hsa-miR-4728-5p | 126 |
| 42 | 3 | hsa-miR-6087 | 1 | hsa-miR-744-5p | 221 | hsa-miR-5572 | 146 |
| 43 | 3 | hsa-miR-6087 | 1 | hsa-miR-744-5p | 221 | hsa-miR-7113-3p | 219 |
| 44 | 3 | hsa-miR-6087 | 1 | hsa-miR-4436b-5p | 76 | hsa-miR-6724-5p | 166 |
| 45 | 3 | hsa-miR-6087 | 1 | hsa-miR-6724-5p | 166 | hsa-miR-4658 | 107 |
| 46 | 3 | hsa-miR-6087 | 1 | hsa-miR-6724-5p | 166 | hsa-miR-6850-5p | 205 |
| 47 | 3 | hsa-miR-6087 | 1 | hsa-miR-4467 | 87 | hsa-miR-4741 | 131 |
| 48 | 3 | hsa-miR-6087 | 1 | hsa-miR-744-5p | 221 | hsa-miR-345-3p | 48 |
| 49 | 3 | hsa-miR-6087 | 1 | hsa-miR-744-5p | 221 | hsa-miR-4652-5p | 104 |
| 50 | 3 | hsa-miR-6087 | 1 | hsa-miR-744-5p | 221 | hsa-miR-615-5p | 155 |

TABLE 9-2

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 1 | 0.96 | 0.87 | 0.90 | 0.95 | 0.95 | 0.87 | 0.89 | 0.94 |
| 2 | 0.97 | 0.84 | 0.88 | 0.95 | 0.95 | 0.85 | 0.88 | 0.93 |
| 3 | 0.93 | 0.88 | 0.90 | 0.94 | 0.92 | 0.89 | 0.90 | 0.95 |
| 4 | 0.95 | 0.88 | 0.90 | 0.95 | 0.94 | 0.86 | 0.89 | 0.95 |
| 5 | 0.93 | 0.88 | 0.90 | 0.94 | 0.92 | 0.90 | 0.91 | 0.95 |
| 6 | 0.94 | 0.86 | 0.88 | 0.94 | 0.94 | 0.88 | 0.90 | 0.96 |
| 7 | 0.93 | 0.86 | 0.88 | 0.94 | 0.94 | 0.88 | 0.90 | 0.95 |
| 8 | 0.94 | 0.88 | 0.90 | 0.95 | 0.92 | 0.87 | 0.89 | 0.95 |
| 9 | 0.96 | 0.87 | 0.90 | 0.95 | 0.95 | 0.85 | 0.88 | 0.96 |
| 10 | 0.94 | 0.88 | 0.90 | 0.95 | 0.93 | 0.85 | 0.88 | 0.95 |
| 11 | 0.96 | 0.86 | 0.89 | 0.94 | 0.92 | 0.86 | 0.88 | 0.95 |
| 12 | 0.93 | 0.86 | 0.88 | 0.93 | 0.92 | 0.86 | 0.88 | 0.94 |
| 13 | 0.95 | 0.89 | 0.91 | 0.95 | 0.90 | 0.89 | 0.89 | 0.95 |
| 14 | 0.95 | 0.88 | 0.90 | 0.94 | 0.93 | 0.88 | 0.90 | 0.95 |
| 15 | 0.95 | 0.83 | 0.87 | 0.94 | 0.94 | 0.85 | 0.88 | 0.95 |
| 16 | 0.97 | 0.85 | 0.89 | 0.95 | 0.95 | 0.84 | 0.88 | 0.96 |
| 17 | 0.95 | 0.89 | 0.91 | 0.95 | 0.91 | 0.89 | 0.90 | 0.95 |
| 18 | 0.96 | 0.85 | 0.88 | 0.95 | 0.94 | 0.86 | 0.88 | 0.96 |
| 19 | 0.93 | 0.86 | 0.88 | 0.93 | 0.95 | 0.85 | 0.88 | 0.94 |
| 20 | 0.97 | 0.82 | 0.86 | 0.93 | 0.95 | 0.82 | 0.86 | 0.94 |
| 21 | 0.94 | 0.86 | 0.88 | 0.94 | 0.94 | 0.85 | 0.88 | 0.94 |
| 22 | 0.97 | 0.84 | 0.88 | 0.94 | 0.92 | 0.84 | 0.87 | 0.94 |
| 23 | 0.97 | 0.82 | 0.87 | 0.93 | 0.97 | 0.84 | 0.88 | 0.95 |
| 24 | 0.95 | 0.82 | 0.86 | 0.94 | 0.94 | 0.83 | 0.86 | 0.93 |
| 25 | 0.93 | 0.83 | 0.86 | 0.93 | 0.91 | 0.85 | 0.87 | 0.93 |
| 26 | 0.95 | 0.85 | 0.88 | 0.94 | 0.92 | 0.88 | 0.89 | 0.93 |
| 27 | 0.98 | 0.83 | 0.87 | 0.94 | 0.97 | 0.81 | 0.86 | 0.95 |
| 28 | 0.96 | 0.84 | 0.88 | 0.94 | 0.95 | 0.84 | 0.87 | 0.94 |
| 29 | 0.96 | 0.86 | 0.89 | 0.94 | 0.92 | 0.86 | 0.88 | 0.95 |
| 30 | 0.95 | 0.85 | 0.88 | 0.94 | 0.95 | 0.87 | 0.90 | 0.94 |
| 31 | 0.97 | 0.81 | 0.86 | 0.94 | 0.95 | 0.81 | 0.85 | 0.94 |
| 32 | 0.95 | 0.84 | 0.87 | 0.93 | 0.93 | 0.84 | 0.87 | 0.93 |
| 33 | 0.97 | 0.86 | 0.89 | 0.95 | 0.96 | 0.84 | 0.88 | 0.95 |
| 34 | 0.94 | 0.86 | 0.88 | 0.94 | 0.94 | 0.86 | 0.88 | 0.94 |
| 35 | 0.95 | 0.89 | 0.90 | 0.95 | 0.90 | 0.90 | 0.90 | 0.94 |
| 36 | 0.96 | 0.85 | 0.88 | 0.94 | 0.94 | 0.87 | 0.89 | 0.95 |
| 37 | 0.92 | 0.86 | 0.88 | 0.94 | 0.92 | 0.87 | 0.88 | 0.95 |
| 38 | 0.95 | 0.84 | 0.87 | 0.93 | 0.95 | 0.86 | 0.89 | 0.95 |
| 39 | 0.96 | 0.86 | 0.89 | 0.94 | 0.92 | 0.88 | 0.89 | 0.94 |
| 40 | 0.95 | 0.88 | 0.90 | 0.94 | 0.92 | 0.91 | 0.91 | 0.95 |
| 41 | 0.95 | 0.82 | 0.86 | 0.93 | 0.97 | 0.84 | 0.88 | 0.93 |
| 42 | 0.95 | 0.83 | 0.87 | 0.94 | 0.92 | 0.85 | 0.87 | 0.93 |
| 43 | 0.95 | 0.83 | 0.87 | 0.94 | 0.92 | 0.85 | 0.87 | 0.94 |
| 44 | 0.95 | 0.86 | 0.88 | 0.94 | 0.94 | 0.86 | 0.88 | 0.95 |
| 45 | 0.96 | 0.86 | 0.89 | 0.95 | 0.92 | 0.86 | 0.88 | 0.95 |
| 46 | 0.95 | 0.86 | 0.88 | 0.94 | 0.92 | 0.87 | 0.88 | 0.95 |
| 47 | 0.92 | 0.88 | 0.89 | 0.95 | 0.91 | 0.88 | 0.89 | 0.94 |
| 48 | 0.93 | 0.84 | 0.87 | 0.94 | 0.91 | 0.85 | 0.87 | 0.93 |
| 49 | 0.94 | 0.88 | 0.90 | 0.95 | 0.90 | 0.90 | 0.90 | 0.95 |
| 50 | 0.90 | 0.87 | 0.88 | 0.94 | 0.89 | 0.88 | 0.88 | 0.94 |

TABLE 9-3

| No. | Number of miRNA | Discriminant formula | Threshold |
|---|---|---|---|
| 1 | 3 | (−1.99429)*hsa-miR-6087 + (1.10184)*hsa-miR-744-5p + (−1.10459)*hsa-miR-4725-3p + 23.8798 | −0.03 |
| 2 | 3 | (−1.95975)*hsa-miR-6087 + (1.16604)*hsa-miR-6132 + (−1.212)*hsa-miR-4725-3p + 23.4404 | −0.10 |
| 3 | 3 | (−2.20223)*hsa-miR-6087 + (0.876146)*hsa-miR-744-5p + (−1.10579)*hsa-miR-1268b + 28.7048 | 0.16 |
| 4 | 3 | (−2.05498)*hsa-miR-6087 + (1.23027)*hsa-miR-6724-5p + (−1.08782)*hsa-miR-3940-5p + 23.2838 | 0.13 |
| 5 | 3 | (−1.71841)*hsa-miR-6087 + (0.254835)*hsa-miR-4652-5p + (−0.351324)*hsa-miR-4728-5p + 21.6521 | 0.03 |
| 6 | 3 | (−2.26328)*hsa-miR-6087 + (0.405936)*hsa-miR-1185-1-3p + (−0.511144)*hsa-miR-4728-5p + 26.9615 | −0.05 |
| 7 | 3 | (−2.25177)*hsa-miR-6087 + (0.333345)*hsa-miR-1185-2-3p + (−0.514305)*hsa-miR-4728-5p + 27.6565 | 0.02 |
| 8 | 3 | (−1.7257)*hsa-miR-6087 + (0.239087)*hsa-miR-4652-5p + (0.927038)*hsa-miR-6724-5p + 9.45011 | 0.00 |
| 9 | 3 | (−2.06705)*hsa-miR-6087 + (1.74117)*hsa-miR-6724-5p + (−1.23589)*hsa-miR-8069 + 20.967 | −0.03 |
| 10 | 3 | (−2.20222)*hsa-miR-6087 + (1.33728)*hsa-miR-6724-5p + (−1.35299)*hsa-miR-6781-5p + 25.0559 | 0.03 |
| 11 | 3 | (−1.94646)*hsa-miR-6087 + (0.229418)*hsa-miR-4652-5p + (−0.851585)*hsa-miR-6781-5p + 30.2559 | −0.08 |
| 12 | 3 | (−2.10541)*hsa-miR-6087 + (−1.00455)*hsa-miR-6784-5p + (−0.533517)*hsa-miR-4728-5p + 40.1399 | 0.04 |
| 13 | 3 | (−2.41529)*hsa-miR-6087 + (0.747096)*hsa-miR-744-5p + (−1.13803)*hsa-miR-6781-5p + 32.8928 | 0.24 |
| 14 | 3 | (−1.90118)*hsa-miR-6087 + (0.273655)*hsa-miR-4652-5p + (−0.493469)*hsa-miR-6794-5p + 25.3093 | 0.09 |
| 15 | 3 | (−2.46815)*hsa-miR-6087 + (0.272974)*hsa-miR-1185-1-3p + (−0.980892)*hsa-miR-6781-5p + 36.422 | −0.07 |
| 16 | 3 | (−2.08205)*hsa-miR-6087 + (1.39686)*hsa-miR-6724-5p + (−1.02557)*hsa-miR-3621 + 21.4656 | −0.04 |
| 17 | 3 | (−2.16206)*hsa-miR-6087 + (−1.4256)*hsa-miR-6781-5p + (0.918977)*hsa-miR-6075 + 31.2971 | 0.14 |
| 18 | 3 | (−2.24404)*hsa-miR-6087 + (0.312892)*hsa-miR-1185-1-3p + (1.06503)*hsa-miR-6724-5p + 12.5539 | −0.06 |
| 19 | 3 | (−2.18147)*hsa-miR-6087 + (0.606087)*hsa-miR-6789-5p + (−1.12732)*hsa-miR-3940-5p + 32.1707 | 0.13 |
| 20 | 3 | (−1.83371)*hsa-miR-6087 + (0.213355)*hsa-miR-3160-5p + (−0.448532)*hsa-miR-4728-5p + 23.2149 | −0.22 |
| 21 | 3 | (−2.31805)*hsa-miR-6087 + (−1.46265)*hsa-miR-6781-5p + (0.800432)*hsa-miR-4492 + 33.0483 | 0.04 |
| 22 | 3 | (−2.50024)*hsa-miR-6087 + (−1.25889)*hsa-miR-6781-5p + (0.793953)*hsa-miR-4327 + 34.4615 | −0.08 |
| 23 | 3 | (−2.29625)*hsa-miR-6087 + (0.983807)*hsa-miR-4327 + (−1.19416)*hsa-miR-1268b + 29.4518 | −0.11 |
| 24 | 3 | (−2.30569)*hsa-miR-6087 + (0.839797)*hsa-miR-744-5p + (−0.188923)*hsa-miR-3679-5p + 21.0264 | −0.04 |
| 25 | 3 | (−2.19577)*hsa-miR-6087 + (0.808307)*hsa-miR-6132 + (−0.748748)*hsa-miR-4739 + 26.7689 | 0.01 |
| 26 | 3 | (−2.26014)*hsa-miR-6087 + (0.766578)*hsa-miR-744-5p + (−0.758695)*hsa-miR-6765-5p + 27.5472 | 0.11 |
| 27 | 3 | (−2.10725)*hsa-miR-6087 + (−0.819804)*hsa-miR-6784-5p + (1.1845)*hsa-miR-6724-5p + 21.6589 | −0.16 |
| 28 | 3 | (−2.25504)*hsa-miR-6087 + (1.18918)*hsa-miR-744-5p + (−0.677675)*hsa-miR-4505 + 22.5733 | −0.09 |
| 29 | 3 | (−2.39575)*hsa-miR-6087 + (−1.29)*hsa-miR-6781-5p + (0.857779)*hsa-miR-6780b-5p + 31.9168 | −0.01 |
| 30 | 3 | (−2.21584)*hsa-miR-6087 + (0.73478)*hsa-miR-744-5p + (−0.342334)*hsa-miR-4728-5p + 21.995 | −0.02 |
| 31 | 3 | (−2.21866)*hsa-miR-6087 + (0.799549)*hsa-miR-744-5p + (−0.618661)*hsa-miR-4739 + 25.9626 | −0.19 |
| 32 | 3 | (−2.12377)*hsa-miR-6087 + (1.19662)*hsa-miR-6724-5p + (−0.281989)*hsa-miR-4446-3p + 14.4302 | 0.05 |
| 33 | 3 | (−2.06861)*hsa-miR-6087 + (1.22127)*hsa-miR-6075 + (−1.5794)*hsa-miR-4741 + 28.0564 | −0.06 |
| 34 | 3 | (−2.32205)*hsa-miR-6087 + (0.932446)*hsa-miR-744-5p + (−0.658096)*hsa-miR-4459 + 25.0285 | 0.02 |
| 35 | 3 | (−2.42163)*hsa-miR-6087 + (0.767833)*hsa-miR-6132 + (−1.24265)*hsa-miR-6781-5p + 33.5051 | 0.26 |
| 36 | 3 | (−2.18388)*hsa-miR-6087 + (0.920148)*hsa-miR-6132 + (−1.25728)*hsa-miR-1268b + 29.1879 | 0.01 |
| 37 | 3 | (−2.37789)*hsa-miR-6087 + (−1.34381)*hsa-miR-6781-5p + (0.71287)*hsa-miR-4707-5p + 35.2893 | 0.09 |
| 38 | 3 | (−2.06926)*hsa-miR-6087 + (0.416135)*hsa-miR-320a + (−0.505606)*hsa-miR-4728-5p + 25.2014 | −0.05 |

TABLE 9-3-continued

| No. | Number of miRNA | Discriminant formula | Threshold |
|---|---|---|---|
| 39 | 3 | (−1.89615)*hsa-miR-6087 + (0.25591)*hsa-miR-4652-5p + (−0.317328)*hsa-miR-6800-5p + 23.6953 | 0.07 |
| 40 | 3 | (−1.91797)*hsa-miR-6087 + (0.261947)*hsa-miR-4652-5p + (−0.401191)*hsa-miR-937-5p + 24.7457 | 0.18 |
| 41 | 3 | (−2.17785)*hsa-miR-6087 + (0.582019)*hsa-miR-663a + (−0.406427)*hsa-miR-4728-5p + 21.5351 | −0.16 |
| 42 | 3 | (−2.23659)*hsa-miR-6087 + (0.742371)*hsa-miR-744-5p + (0.122665)*hsa-miR-5572 + 18.9306 | −0.06 |
| 43 | 3 | (−2.30309)*hsa-miR-6087 + (0.760621)*hsa-miR-744-5p + (0.206772)*hsa-miR-7113-3p + 19.0906 | −0.09 |
| 44 | 3 | (−2.00392)*hsa-miR-6087 + (0.335315)*hsa-miR-4436b-5p + (1.0084)*hsa-miR-6724-5p + 10.8971 | 0.10 |
| 45 | 3 | (−1.90126)*hsa-miR-6087 + (1.00918)*hsa-miR-6724-5p + (0.198648)*hsa-miR-4658 + 10.807 | 0.04 |
| 46 | 3 | (−2.1512)*hsa-miR-6087 + (1.72053)*hsa-miR-6724-5p + (−1.06042)*hsa-miR-6850-5p + 18.9069 | 0.06 |
| 47 | 3 | (−2.26287)*hsa-miR-6087 + (1.4033)*hsa-miR-4467 + (−1.81767)*hsa-miR-4741 + 28.6016 | 0.21 |
| 48 | 3 | (−2.27347)*hsa-miR-6087 + (0.769294)*hsa-miR-744-5p + (0.11717)*hsa-miR-345-3p + 19.2282 | −0.02 |
| 49 | 3 | (−1.94211)*hsa-miR-6087 + (0.532517)*hsa-miR-744-5p + (0.207835)*hsa-miR-4652-5p + 17.1632 | 0.07 |
| 50 | 3 | (−2.17617)*hsa-miR-6087 + (0.709611)*hsa-miR-744-5p + (0.226255)*hsa-miR-615-5p + 17.8108 | 0.15 |

TABLE 10-1

| No. | Number of miRNA | miRNA marker 1 | SEQ ID NO | miRNA marker 2 | SEQ ID NO | miRNA marker 3 | SEQ ID NO | miRNA marker 4 | SEQ ID NO |
|---|---|---|---|---|---|---|---|---|---|
| 1 | 4 | hsa-miR-6087 | 1 | hsa-miR-1185-1-3p | 2 | hsa-miR-4728-5p | 126 | hsa-miR-6802-5p | 194 |
| 2 | 4 | hsa-miR-6087 | 1 | hsa-miR-4652-5p | 104 | hsa-miR-4728-5p | 126 | hsa-miR-6819-5p | 198 |
| 3 | 4 | hsa-miR-6087 | 1 | hsa-miR-1185-1-3p | 2 | hsa-miR-4728-5p | 126 | hsa-miR-3648 | 54 |
| 4 | 4 | hsa-miR-6087 | 1 | hsa-miR-1185-1-3p | 2 | hsa-miR-4728-5p | 126 | hsa-miR-6075 | 148 |
| 5 | 4 | hsa-miR-6087 | 1 | hsa-miR-1185-2-3p | 3 | hsa-miR-4728-5p | 126 | hsa-miR-6802-5p | 194 |
| 6 | 4 | hsa-miR-6087 | 1 | hsa-miR-1185-1-3p | 2 | hsa-miR-4728-5p | 126 | hsa-miR-3160-5p | 35 |
| 7 | 4 | hsa-miR-6087 | 1 | hsa-miR-744-5p | 221 | hsa-miR-4725-3p | 123 | hsa-miR-4726-5p | 124 |
| 8 | 4 | hsa-miR-6087 | 1 | hsa-miR-1185-1-3p | 2 | hsa-miR-4728-5p | 126 | hsa-miR-4706 | 116 |
| 9 | 4 | hsa-miR-6087 | 1 | hsa-miR-1185-2-3p | 3 | hsa-miR-4728-5p | 126 | hsa-miR-3160-5p | 35 |
| 10 | 4 | hsa-miR-6087 | 1 | hsa-miR-744-5p | 221 | hsa-miR-4725-3p | 123 | hsa-miR-7113-3p | 219 |
| 11 | 4 | hsa-miR-6087 | 1 | hsa-miR-1185-1-3p | 2 | hsa-miR-4728-5p | 126 | hsa-miR-6787-5p | 189 |
| 12 | 4 | hsa-miR-6087 | 1 | hsa-miR-744-5p | 221 | hsa-miR-4725-3p | 123 | hsa-miR-6717-5p | 164 |
| 13 | 4 | hsa-miR-6087 | 1 | hsa-miR-744-5p | 221 | hsa-miR-4725-3p | 123 | hsa-miR-4485-5p | 91 |
| 14 | 4 | hsa-miR-6087 | 1 | hsa-miR-744-5p | 221 | hsa-miR-4725-3p | 123 | hsa-miR-1343-5p | 18 |
| 15 | 4 | hsa-miR-6087 | 1 | hsa-miR-6724-5p | 166 | hsa-miR-6781-5p | 185 | hsa-miR-4727-3p | 125 |
| 16 | 4 | hsa-miR-6087 | 1 | hsa-miR-744-5p | 221 | hsa-miR-4725-3p | 123 | hsa-miR-4652-5p | 104 |
| 17 | 4 | hsa-miR-6087 | 1 | hsa-miR-744-5p | 221 | hsa-miR-4725-3p | 123 | hsa-miR-4449 | 81 |
| 18 | 4 | hsa-miR-6087 | 1 | hsa-miR-744-5p | 221 | hsa-miR-4725-3p | 123 | hsa-miR-1185-2-3p | 3 |
| 19 | 4 | hsa-miR-6087 | 1 | hsa-miR-1185-1-3p | 2 | hsa-miR-4728-5p | 126 | hsa-miR-1273g-3p | 15 |
| 20 | 4 | hsa-miR-6087 | 1 | hsa-miR-6784-5p | 187 | hsa-miR-4728-5p | 126 | hsa-miR-6802-5p | 194 |
| 21 | 4 | hsa-miR-6087 | 1 | hsa-miR-4652-5p | 104 | hsa-miR-6794-5p | 192 | hsa-miR-6802-5p | 194 |

TABLE 10-1-continued

| No. | Number of miRNA | miRNA marker 1 | SEQ ID NO | miRNA marker 2 | SEQ ID NO | miRNA marker 3 | SEQ ID NO | miRNA marker 4 | SEQ ID NO |
|---|---|---|---|---|---|---|---|---|---|
| 22 | 4 | hsa-miR-6087 | 1 | hsa-miR-744-5p | 221 | hsa-miR-4725-3p | 123 | hsa-miR-345-3p | 48 |
| 23 | 4 | hsa-miR-6087 | 1 | hsa-miR-744-5p | 221 | hsa-miR-4725-3p | 123 | hsa-miR-5010-5p | 142 |
| 24 | 4 | hsa-miR-6087 | 1 | hsa-miR-744-5p | 221 | hsa-miR-4725-3p | 123 | hsa-miR-5572 | 146 |
| 25 | 4 | hsa-miR-6087 | 1 | hsa-miR-744-5p | 221 | hsa-miR-4725-3p | 123 | hsa-miR-371b-5p | 59 |
| 26 | 4 | hsa-miR-6087 | 1 | hsa-miR-744-5p | 221 | hsa-miR-4725-3p | 123 | hsa-miR-4419b | 72 |
| 27 | 4 | hsa-miR-6087 | 1 | hsa-miR-744-5p | 221 | hsa-miR-4725-3p | 123 | hsa-miR-191-5p | 238 |
| 28 | 4 | hsa-miR-6087 | 1 | hsa-miR-6132 | 153 | hsa-miR-4725-3p | 123 | hsa-miR-4652-5p | 104 |
| 29 | 4 | hsa-miR-6087 | 1 | hsa-miR-744-5p | 221 | hsa-miR-4725-3p | 123 | hsa-miR-7108-3p | 216 |
| 30 | 4 | hsa-miR-6087 | 1 | hsa-miR-1185-1-3p | 2 | hsa-miR-4728-5p | 126 | hsa-miR-1228-3p | 8 |
| 31 | 4 | hsa-miR-6087 | 1 | hsa-miR-744-5p | 221 | hsa-miR-4725-3p | 123 | hsa-miR-3616-3p | 49 |
| 32 | 4 | hsa-miR-6087 | 1 | hsa-miR-744-5p | 221 | hsa-miR-4725-3p | 123 | hsa-miR-4462 | 85 |
| 33 | 4 | hsa-miR-6087 | 1 | hsa-miR-744-5p | 221 | hsa-miR-4725-3p | 123 | hsa-miR-8052 | 224 |
| 34 | 4 | hsa-miR-6087 | 1 | hsa-miR-744-5p | 221 | hsa-miR-4725-3p | 123 | hsa-miR-7975 | 222 |
| 35 | 4 | hsa-miR-6087 | 1 | hsa-miR-744-5p | 221 | hsa-miR-4725-3p | 123 | hsa-miR-3622a-5p | 53 |
| 36 | 4 | hsa-miR-6087 | 1 | hsa-miR-744-5p | 221 | hsa-miR-4725-3p | 123 | hsa-miR-6870-5p | 208 |
| 37 | 4 | hsa-miR-6087 | 1 | hsa-miR-744-5p | 221 | hsa-miR-4725-3p | 123 | hsa-miR-4731-5p | 127 |
| 38 | 4 | hsa-miR-6087 | 1 | hsa-miR-744-5p | 221 | hsa-miR-4725-3p | 123 | hsa-miR-4690-5p | 113 |
| 39 | 4 | hsa-miR-6087 | 1 | hsa-miR-744-5p | 221 | hsa-miR-4725-3p | 123 | hsa-miR-3178 | 37 |
| 40 | 4 | hsa-miR-6087 | 1 | hsa-miR-744-5p | 221 | hsa-miR-4725-3p | 123 | hsa-miR-6716-5p | 163 |
| 41 | 4 | hsa-miR-6087 | 1 | hsa-miR-744-5p | 221 | hsa-miR-4725-3p | 123 | hsa-miR-6842-5p | 204 |
| 42 | 4 | hsa-miR-6087 | 1 | hsa-miR-744-5p | 221 | hsa-miR-4725-3p | 123 | hsa-miR-4430 | 74 |
| 43 | 4 | hsa-miR-6087 | 1 | hsa-miR-744-5p | 221 | hsa-miR-4725-3p | 123 | hsa-miR-6742-5p | 170 |
| 44 | 4 | hsa-miR-6087 | 1 | hsa-miR-1185-1-3p | 2 | hsa-miR-4728-5p | 126 | hsa-miR-8073 | 226 |
| 45 | 4 | hsa-miR-6087 | 1 | hsa-miR-1185-1-3p | 2 | hsa-miR-4728-5p | 126 | hsa-miR-3194-3p | 41 |
| 46 | 4 | hsa-miR-6087 | 1 | hsa-miR-1185-2-3p | 3 | hsa-miR-4728-5p | 126 | hsa-miR-4436b-5p | 76 |
| 47 | 4 | hsa-miR-6087 | 1 | hsa-miR-6724-5p | 166 | hsa-miR-8069 | 225 | hsa-miR-4488 | 92 |
| 48 | 4 | hsa-miR-6087 | 1 | hsa-miR-744-5p | 221 | hsa-miR-4725-3p | 123 | hsa-miR-5008-5p | 141 |
| 49 | 4 | hsa-miR-6087 | 1 | hsa-miR-744-5p | 221 | hsa-miR-4725-3p | 123 | hsa-miR-1268a | 13 |
| 50 | 4 | hsa-miR-6087 | 1 | hsa-miR-6784-5p | 187 | hsa-miR-4728-5p | 126 | hsa-miR-6819-5p | 198 |

TABLE 10-2

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 1 | 0.96 | 0.87 | 0.90 | 0.95 | 0.95 | 0.88 | 0.91 | 0.96 |
| 2 | 0.92 | 0.92 | 0.92 | 0.95 | 0.89 | 0.94 | 0.92 | 0.96 |
| 3 | 0.95 | 0.86 | 0.89 | 0.95 | 0.93 | 0.90 | 0.91 | 0.96 |
| 4 | 0.98 | 0.84 | 0.88 | 0.95 | 0.94 | 0.85 | 0.88 | 0.96 |
| 5 | 0.97 | 0.86 | 0.89 | 0.95 | 0.96 | 0.88 | 0.91 | 0.96 |
| 6 | 0.94 | 0.89 | 0.91 | 0.95 | 0.94 | 0.91 | 0.92 | 0.96 |
| 7 | 0.92 | 0.90 | 0.91 | 0.95 | 0.91 | 0.92 | 0.91 | 0.94 |
| 8 | 0.94 | 0.88 | 0.90 | 0.95 | 0.92 | 0.91 | 0.92 | 0.96 |
| 9 | 0.94 | 0.89 | 0.90 | 0.95 | 0.93 | 0.91 | 0.92 | 0.96 |
| 10 | 0.95 | 0.89 | 0.91 | 0.95 | 0.95 | 0.89 | 0.91 | 0.94 |
| 11 | 0.98 | 0.84 | 0.88 | 0.95 | 0.96 | 0.86 | 0.89 | 0.96 |
| 12 | 0.97 | 0.88 | 0.91 | 0.95 | 0.95 | 0.88 | 0.90 | 0.95 |

TABLE 10-2-continued

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 13 | 0.93 | 0.90 | 0.91 | 0.95 | 0.92 | 0.91 | 0.91 | 0.94 |
| 14 | 0.95 | 0.90 | 0.91 | 0.95 | 0.93 | 0.89 | 0.90 | 0.94 |
| 15 | 0.97 | 0.88 | 0.91 | 0.95 | 0.93 | 0.87 | 0.89 | 0.96 |
| 16 | 0.94 | 0.92 | 0.93 | 0.95 | 0.94 | 0.92 | 0.93 | 0.95 |
| 17 | 0.95 | 0.88 | 0.90 | 0.95 | 0.94 | 0.87 | 0.89 | 0.94 |
| 18 | 0.93 | 0.90 | 0.91 | 0.96 | 0.92 | 0.91 | 0.92 | 0.95 |
| 19 | 0.96 | 0.87 | 0.90 | 0.95 | 0.92 | 0.88 | 0.89 | 0.96 |
| 20 | 0.97 | 0.84 | 0.88 | 0.94 | 0.97 | 0.84 | 0.88 | 0.95 |
| 21 | 0.96 | 0.89 | 0.91 | 0.95 | 0.94 | 0.88 | 0.90 | 0.96 |
| 22 | 0.95 | 0.88 | 0.90 | 0.95 | 0.94 | 0.89 | 0.91 | 0.94 |
| 23 | 0.96 | 0.87 | 0.90 | 0.95 | 0.95 | 0.87 | 0.89 | 0.94 |
| 24 | 0.95 | 0.88 | 0.90 | 0.95 | 0.94 | 0.89 | 0.90 | 0.94 |
| 25 | 0.93 | 0.90 | 0.91 | 0.95 | 0.91 | 0.91 | 0.91 | 0.94 |
| 26 | 0.94 | 0.89 | 0.91 | 0.95 | 0.92 | 0.89 | 0.90 | 0.94 |
| 27 | 0.95 | 0.88 | 0.90 | 0.95 | 0.94 | 0.89 | 0.90 | 0.94 |
| 28 | 0.95 | 0.91 | 0.92 | 0.96 | 0.92 | 0.90 | 0.91 | 0.95 |
| 29 | 0.96 | 0.87 | 0.90 | 0.95 | 0.95 | 0.87 | 0.89 | 0.94 |
| 30 | 0.93 | 0.88 | 0.89 | 0.94 | 0.92 | 0.90 | 0.91 | 0.96 |
| 31 | 0.94 | 0.89 | 0.91 | 0.95 | 0.93 | 0.90 | 0.91 | 0.94 |
| 32 | 0.94 | 0.89 | 0.91 | 0.95 | 0.93 | 0.90 | 0.91 | 0.94 |
| 33 | 0.96 | 0.87 | 0.90 | 0.95 | 0.95 | 0.86 | 0.89 | 0.94 |
| 34 | 0.94 | 0.89 | 0.91 | 0.95 | 0.92 | 0.89 | 0.90 | 0.94 |
| 35 | 0.93 | 0.90 | 0.91 | 0.95 | 0.92 | 0.90 | 0.91 | 0.94 |
| 36 | 0.93 | 0.89 | 0.90 | 0.95 | 0.92 | 0.90 | 0.91 | 0.94 |
| 37 | 0.95 | 0.88 | 0.90 | 0.95 | 0.95 | 0.88 | 0.90 | 0.94 |
| 38 | 0.96 | 0.87 | 0.90 | 0.95 | 0.95 | 0.87 | 0.89 | 0.94 |
| 39 | 0.93 | 0.90 | 0.91 | 0.95 | 0.92 | 0.90 | 0.90 | 0.94 |
| 40 | 0.94 | 0.89 | 0.90 | 0.95 | 0.92 | 0.90 | 0.91 | 0.94 |
| 41 | 0.94 | 0.89 | 0.91 | 0.95 | 0.92 | 0.90 | 0.91 | 0.94 |
| 42 | 0.93 | 0.89 | 0.91 | 0.95 | 0.92 | 0.90 | 0.91 | 0.94 |
| 43 | 0.93 | 0.90 | 0.91 | 0.95 | 0.92 | 0.91 | 0.91 | 0.95 |
| 44 | 0.98 | 0.85 | 0.89 | 0.95 | 0.95 | 0.87 | 0.89 | 0.97 |
| 45 | 0.95 | 0.86 | 0.89 | 0.95 | 0.95 | 0.88 | 0.91 | 0.96 |
| 46 | 0.94 | 0.90 | 0.91 | 0.96 | 0.95 | 0.89 | 0.91 | 0.96 |
| 47 | 0.92 | 0.91 | 0.91 | 0.95 | 0.90 | 0.93 | 0.92 | 0.96 |
| 48 | 0.93 | 0.90 | 0.91 | 0.95 | 0.92 | 0.90 | 0.91 | 0.94 |
| 49 | 0.97 | 0.89 | 0.91 | 0.95 | 0.95 | 0.89 | 0.91 | 0.95 |
| 50 | 0.93 | 0.89 | 0.90 | 0.95 | 0.92 | 0.91 | 0.91 | 0.95 |

TABLE 10-3

| No. | Number of miRNA | Discriminant formula | Threshold |
|---|---|---|---|
| 1 | 4 | (−2.0149)*hsa-miR-6087 + (0.323769)*hsa-miR-1185-1-3p + (−0.67387)*hsa-miR-4728-5p + (0.794577)*hsa-miR-6802-5p + 18.5481 | −0.18 |
| 2 | 4 | (−1.40552)*hsa-miR-6087 + (0.197504)*hsa-miR-4652-5p + (−0.649251)*hsa-miR-4728-5p + (0.783379)*hsa-miR-6819-5p + 13.919 | 0.17 |
| 3 | 4 | (−2.1643)*hsa-miR-6087 + (0.390224)*hsa-miR-1185-1-3p + (−0.466874)*hsa-miR-4728-5p + (0.472791)*hsa-miR-3648 + 19.374 | −0.06 |
| 4 | 4 | (−2.11818)*hsa-miR-6087 + (0.349681)*hsa-miR-1185-1-3p + (−0.463979)*hsa-miR-4728-5p + (0.520867)*hsa-miR-6075 + 20.7509 | −0.25 |
| 5 | 4 | (−2.00356)*hsa-miR-6087 + (0.258483)*hsa-miR-1185-2-3p + (−0.672779)*hsa-miR-4728-5p + (0.790807)*hsa-miR-6802-5p + 19.1448 | −0.15 |
| 6 | 4 | (−1.96362)*hsa-miR-6087 + (0.358349)*hsa-miR-1185-1-3p + (−0.535871)*hsa-miR-4728-5p + (0.179607)*hsa-miR-3160-5p + 22.5849 | 0.04 |
| 7 | 4 | (−1.95533)*hsa-miR-6087 + (1.10331)*hsa-miR-744-5p + (−1.0978)*hsa-miR-4725-3p + (0.128777)*hsa-miR-4726-5p + 22.4395 | 0.29 |
| 8 | 4 | (−2.10911)*hsa-miR-6087 + (0.376593)*hsa-miR-1185-1-3p + (−0.566764)*hsa-miR-4728-5p + (0.372519)*hsa-miR-4706 + 22.6335 | 0.06 |
| 9 | 4 | (−1.93996)*hsa-miR-6087 + (0.302274)*hsa-miR-1185-2-3p + (−0.543072)*hsa-miR-4728-5p + (0.188689)*hsa-miR-3160-5p + 22.935 | 0.08 |
| 10 | 4 | (−1.98851)*hsa-miR-6087 + (1.07518)*hsa-miR-744-5p + (−1.04895)*hsa-miR-4725-3p + (0.172295)*hsa-miR-7113-3p + 22.5015 | 0.09 |
| 11 | 4 | (−2.11179)*hsa-miR-6087 + (0.457627)*hsa-miR-1185-1-3p + (−0.655672)*hsa-miR-4728-5p + (0.463185)*hsa-miR-6787-5p + 21.4526 | −0.27 |
| 12 | 4 | (−1.84615)*hsa-miR-6087 + (1.03905)*hsa-miR-744-5p + (−1.15205)*hsa-miR-4725-3p + (0.158937)*hsa-miR-6717-5p + 21.9096 | −0.04 |
| 13 | 4 | (−1.96137)*hsa-miR-6087 + (1.08997)*hsa-miR-744-5p + (−1.13739)*hsa-miR-4725-3p + (0.152475)*hsa-miR-4485-5p + 22.9711 | 0.18 |
| 14 | 4 | (−2.06413)*hsa-miR-6087 + (1.08096)*hsa-miR-744-5p + (−1.02828)*hsa-miR-4725-3p + (−0.583887)*hsa-miR-1343-5p + 29.9398 | 0.19 |
| 15 | 4 | (−2.05106)*hsa-miR-6087 + (1.29598)*hsa-miR-6724-5p + (−1.23117)*hsa-miR-6781-5p + (0.18212)*hsa-miR-4727-3p + 21.4087 | −0.03 |
| 16 | 4 | (−1.72137)*hsa-miR-6087 + (0.842266)*hsa-miR-744-5p + (−0.925472)*hsa-miR-4725-3p + (0.182057)*hsa-miR-4652-5p + 20.4898 | 0.19 |
| 17 | 4 | (−1.96551)*hsa-miR-6087 + (1.09951)*hsa-miR-744-5p + (−1.1063)*hsa-miR-4725-3p + (0.111752)*hsa-miR-4449 + 22.8233 | 0.03 |
| 18 | 4 | (−2.0773)*hsa-miR-6087 + (0.992603)*hsa-miR-744-5p + (−1.0199)*hsa-miR-4725-3p + (0.164433)*hsa-miR-1185-2-3p + 23.7506 | 0.18 |
| 19 | 4 | (−2.15523)*hsa-miR-6087 + (0.385474)*hsa-miR-1185-1-3p + (−0.580318)*hsa-miR-4728-5p + (0.252073)*hsa-miR-1273g-3p + 24.2168 | −0.04 |
| 20 | 4 | (−1.93441)*hsa-miR-6087 + (−0.645629)*hsa-miR-6784-5p + (−0.641236)*hsa-miR-4728-5p + (0.665862)*hsa-miR-6802-5p + 28.6551 | −0.20 |
| 21 | 4 | (−1.90895)*hsa-miR-6087 + (0.224641)*hsa-miR-4652-5p + (−0.861494)*hsa-miR-6794-5p + (0.776175)*hsa-miR-6802-5p + 21.5158 | 0.02 |
| 22 | 4 | (−1.92887)*hsa-miR-6087 + (1.0991)*hsa-miR-744-5p + (−1.11187)*hsa-miR-4725-3p + (0.121799)*hsa-miR-345-3p + 22.4989 | 0.05 |
| 23 | 4 | (−1.97061)*hsa-miR-6087 + (1.08863)*hsa-miR-744-5p + (−1.10606)*hsa-miR-4725-3p + (0.0346128)*hsa-miR-5010-5p + 23.5291 | −0.05 |

TABLE 10-3-continued

| No. | Number of miRNA | Discriminant formula | Threshold |
|---|---|---|---|
| 24 | 4 | (−1.90062)*hsa-miR-6087 + (1.06991)*hsa-miR-744-5p + (−1.1006)*hsa-miR-4725-3p + (0.118253)*hsa-miR-5572 + 22.2737 | 0.01 |
| 25 | 4 | (−1.905)*hsa-miR-6087 + (1.05114)*hsa-miR-744-5p + (−1.07868)*hsa-miR-4725-3p + (0.129274)*hsa-miR-371b-5p + 22.3343 | 0.19 |
| 26 | 4 | (−1.9188)*hsa-miR-6087 + (1.09374)*hsa-miR-744-5p + (−1.1391)*hsa-miR-4725-3p + (0.115326)*hsa-miR-4419b + 22.5689 | 0.15 |
| 27 | 4 | (−1.94067)*hsa-miR-6087 + (1.06815)*hsa-miR-744-5p + (−1.13252)*hsa-miR-4725-3p + (0.061833)*hsa-miR-191-5p + 23.4299 | 0.11 |
| 28 | 4 | (−1.66398)*hsa-miR-6087 + (0.90838)*hsa-miR-6132 + (−1.02495)*hsa-miR-4725-3p + (0.196746)*hsa-miR-4652-5p + 19.7201 | 0.07 |
| 29 | 4 | (−1.98976)*hsa-miR-6087 + (1.12912)*hsa-miR-744-5p + (−1.07893)*hsa-miR-4725-3p + (−0.120496)*hsa-miR-7108-3p + 24.0674 | −0.01 |
| 30 | 4 | (−2.23129)*hsa-miR-6087 + (0.375189)*hsa-miR-1185-1-3p + (−0.539722)*hsa-miR-4728-5p + (0.205572)*hsa-miR-1228-3p + 25.6132 | 0.05 |
| 31 | 4 | (−1.96604)*hsa-miR-6087 + (1.0816)*hsa-miR-744-5p + (−1.09015)*hsa-miR-4725-3p + (0.0752526)*hsa-miR-3616-3p + 23.1811 | 0.16 |
| 32 | 4 | (−1.87322)*hsa-miR-6087 + (1.10377)*hsa-miR-744-5p + (−1.12827)*hsa-miR-4725-3p + (0.106985)*hsa-miR-4462 + 22.063 | 0.12 |
| 33 | 4 | (−1.95782)*hsa-miR-6087 + (1.09779)*hsa-miR-744-5p + (−1.11868)*hsa-miR-4725-3p + (0.0622539)*hsa-miR-8052 + 23.2555 | −0.03 |
| 34 | 4 | (−1.95102)*hsa-miR-6087 + (1.07133)*hsa-miR-744-5p + (−1.13485)*hsa-miR-4725-3p + (0.0958191)*hsa-miR-7975 + 23.0654 | 0.16 |
| 35 | 4 | (−1.9509)*hsa-miR-6087 + (1.09922)*hsa-miR-744-5p + (−1.10474)*hsa-miR-4725-3p + (0.0526832)*hsa-miR-3622a-5p + 23.063 | 0.22 |
| 36 | 4 | (−1.96398)*hsa-miR-6087 + (1.13043)*hsa-miR-744-5p + (−1.15968)*hsa-miR-4725-3p + (0.112344)*hsa-miR-6870-5p + 22.9913 | 0.18 |
| 37 | 4 | (−1.99762)*hsa-miR-6087 + (1.08842)*hsa-miR-744-5p + (−1.0774)*hsa-miR-4725-3p + (0.0998503)*hsa-miR-4731-5p + 23.1902 | 0.00 |
| 38 | 4 | (−1.98872)*hsa-miR-6087 + (1.07852)*hsa-miR-744-5p + (−1.09525)*hsa-miR-4725-3p + (0.07478)*hsa-miR-4690-5p + 23.4267 | −0.04 |
| 39 | 4 | (−2.01272)*hsa-miR-6087 + (1.10487)*hsa-miR-744-5p + (−1.06224)*hsa-miR-4725-3p + (−0.147672)*hsa-miR-3178 + 25.4006 | 0.23 |
| 40 | 4 | (−1.99883)*hsa-miR-6087 + (1.11898)*hsa-miR-744-5p + (−1.09769)*hsa-miR-4725-3p + (0.053479)*hsa-miR-6716-5p + 23.3919 | 0.17 |
| 41 | 4 | (−1.95042)*hsa-miR-6087 + (1.11027)*hsa-miR-744-5p + (−1.10857)*hsa-miR-4725-3p + (0.0671621)*hsa-miR-6842-5p + 22.9281 | 0.15 |
| 42 | 4 | (−1.95428)*hsa-miR-6087 + (1.07352)*hsa-miR-744-5p + (−1.10378)*hsa-miR-4725-3p + (0.0861418)*hsa-miR-4430 + 23.0763 | 0.16 |
| 43 | 4 | (−1.98382)*hsa-miR-6087 + (1.11616)*hsa-miR-744-5p + (−1.03253)*hsa-miR-4725-3p + (0.100572)*hsa-miR-6742-5p + 22.4181 | 0.20 |
| 44 | 4 | (−2.00783)*hsa-miR-6087 + (0.364586)*hsa-miR-1185-1-3p + (−0.551076)*hsa-miR-4728-5p + (0.363576)*hsa-miR-8073 + 21.6081 | −0.20 |
| 45 | 4 | (−2.03251)*hsa-miR-6087 + (0.362574)*hsa-miR-1185-1-3p + (−0.50181)*hsa-miR-4728-5p + (0.162155)*hsa-miR-3194-3p + 23.1964 | −0.13 |
| 46 | 4 | (−2.03272)*hsa-miR-6087 + (0.263552)*hsa-miR-1185-2-3p + (−0.583117)*hsa-miR-4728-5p + (0.376584)*hsa-miR-4436b-5p + 23.77 | 0.01 |
| 47 | 4 | (−2.31168)*hsa-miR-6087 + (1.65372)*hsa-miR-6724-5p + (−1.45426)*hsa-miR-8069 + (0.6299)*hsa-miR-4488 + 19.1417 | 0.42 |
| 48 | 4 | (−1.96801)*hsa-miR-6087 + (1.09607)*hsa-miR-744-5p + (−1.10798)*hsa-miR-4725-3p + (0.102001)*hsa-miR-5008-5p + 23 | 0.19 |
| 49 | 4 | (−1.98495)*hsa-miR-6087 + (1.15587)*hsa-miR-744-5p + (−0.964683)*hsa-miR-4725-3p + (−0.701227)*hsa-miR-1268a + 29.4282 | 0.08 |
| 50 | 4 | (−1.61855)*hsa-miR-6087 + (−0.771761)*hsa-miR-6784-5p + (−0.84099)*hsa-miR-4728-5p + (0.929218)*hsa-miR-6819-5p + 26.3069 | 0.02 |

TABLE 11-1

| No. | Number of miRNA | miRNA marker 1 | SEQ ID NO | miRNA marker 2 | SEQ ID NO | miRNA marker 3 | SEQ ID NO | miRNA marker 4 | SEQ ID NO | miRNA marker 5 | SEQ ID NO |
|---|---|---|---|---|---|---|---|---|---|---|---|
| 1 | 5 | hsa-miR-6087 | 1 | hsa-miR-1185-1-3p | 2 | hsa-miR-4728-5p | 126 | hsa-miR-6802-5p | 194 | hsa-miR-6716-5p | 163 |
| 2 | 5 | hsa-miR-6087 | 1 | hsa-miR-1185-1-3p | 2 | hsa-miR-4728-5p | 126 | hsa-miR-6802-5p | 194 | hsa-miR-210-5p | 26 |
| 3 | 5 | hsa-miR-6087 | 1 | hsa-miR-1185-1-3p | 2 | hsa-miR-4728-5p | 126 | hsa-miR-6802-5p | 194 | hsa-miR-4535 | 98 |
| 4 | 5 | hsa-miR-6087 | 1 | hsa-miR-1185-1-3p | 2 | hsa-miR-4728-5p | 126 | hsa-miR-6802-5p | 194 | hsa-miR-6794-5p | 192 |
| 5 | 5 | hsa-miR-6087 | 1 | hsa-miR-1185-1-3p | 2 | hsa-miR-4728-5p | 126 | hsa-miR-6802-5p | 194 | hsa-miR-3185 | 40 |
| 6 | 5 | hsa-miR-6087 | 1 | hsa-miR-744-5p | 221 | hsa-miR-4725-3p | 123 | hsa-miR-4652-5p | 104 | hsa-miR-6780b-5p | 184 |

TABLE 11-1-continued

| No. | Number of miRNA | miRNA marker 1 | SEQ ID NO | miRNA marker 2 | SEQ ID NO | miRNA marker 3 | SEQ ID NO | miRNA marker 4 | SEQ ID NO | miRNA marker 5 | SEQ ID NO |
|---|---|---|---|---|---|---|---|---|---|---|---|
| 7 | 5 | hsa-miR-6087 | 1 | hsa-miR-1185-1-3p | 2 | hsa-miR-4728-5p | 126 | hsa-miR-6802-5p | 194 | hsa-miR-3648 | 54 |
| 8 | 5 | hsa-miR-6087 | 1 | hsa-miR-1185-1-3p | 2 | hsa-miR-4728-5p | 126 | hsa-miR-6802-5p | 194 | hsa-miR-6737-5p | 168 |
| 9 | 5 | hsa-miR-6087 | 1 | hsa-miR-1185-1-3p | 2 | hsa-miR-4728-5p | 126 | hsa-miR-6802-5p | 194 | hsa-miR-4725-3p | 123 |
| 10 | 5 | hsa-miR-6087 | 1 | hsa-miR-1185-1-3p | 2 | hsa-miR-4728-5p | 126 | hsa-miR-6802-5p | 194 | hsa-miR-7150 | 220 |
| 11 | 5 | hsa-miR-6087 | 1 | hsa-miR-1185-1-3p | 2 | hsa-miR-4728-5p | 126 | hsa-miR-6802-5p | 194 | hsa-miR-7107-5p | 215 |
| 12 | 5 | hsa-miR-6087 | 1 | hsa-miR-1185-2-3p | 3 | hsa-miR-4728-5p | 126 | hsa-miR-6802-5p | 194 | hsa-miR-5008-5p | 141 |
| 13 | 5 | hsa-miR-6087 | 1 | hsa-miR-744-5p | 221 | hsa-miR-4725-3p | 123 | hsa-miR-6717-5p | 164 | hsa-miR-4728-5p | 126 |
| 14 | 5 | hsa-miR-6087 | 1 | hsa-miR-1185-1-3p | 2 | hsa-miR-4728-5p | 126 | hsa-miR-6802-5p | 194 | hsa-miR-4436b-5p | 76 |
| 15 | 5 | hsa-miR-6087 | 1 | hsa-miR-1185-1-3p | 2 | hsa-miR-4728-5p | 126 | hsa-miR-6802-5p | 194 | hsa-miR-4707-3p | 117 |
| 16 | 5 | hsa-miR-6087 | 1 | hsa-miR-1185-1-3p | 2 | hsa-miR-4728-5p | 126 | hsa-miR-6802-5p | 194 | hsa-miR-4651 | 103 |
| 17 | 5 | hsa-miR-6087 | 1 | hsa-miR-1185-1-3p | 2 | hsa-miR-4728-5p | 126 | hsa-miR-6802-5p | 194 | hsa-miR-887-3p | 227 |
| 18 | 5 | hsa-miR-6087 | 1 | hsa-miR-1185-1-3p | 2 | hsa-miR-4728-5p | 126 | hsa-miR-6802-5p | 194 | hsa-miR-328-5p | 46 |
| 19 | 5 | hsa-miR-6087 | 1 | hsa-miR-1185-1-3p | 2 | hsa-miR-4728-5p | 126 | hsa-miR-6802-5p | 194 | hsa-miR-6821-5p | 199 |
| 20 | 5 | hsa-miR-6087 | 1 | hsa-miR-1185-1-3p | 2 | hsa-miR-4728-5p | 126 | hsa-miR-6802-5p | 194 | hsa-miR-4726-5p | 124 |
| 21 | 5 | hsa-miR-6087 | 1 | hsa-miR-1185-1-3p | 2 | hsa-miR-4728-5p | 126 | hsa-miR-6802-5p | 194 | hsa-miR-4792 | 139 |
| 22 | 5 | hsa-miR-6087 | 1 | hsa-miR-1185-1-3p | 2 | hsa-miR-4728-5p | 126 | hsa-miR-6802-5p | 194 | hsa-miR-3619-3p | 50 |
| 23 | 5 | hsa-miR-6087 | 1 | hsa-miR-4652-5p | 104 | hsa-miR-4728-5p | 126 | hsa-miR-6819-5p | 198 | hsa-miR-4687-5p | 112 |
| 24 | 5 | hsa-miR-6087 | 1 | hsa-miR-1185-1-3p | 2 | hsa-miR-4728-5p | 126 | hsa-miR-6802-5p | 194 | hsa-miR-3131 | 32 |
| 25 | 5 | hsa-miR-6087 | 1 | hsa-miR-1185-1-3p | 2 | hsa-miR-4728-5p | 126 | hsa-miR-6802-5p | 194 | hsa-miR-4675 | 110 |
| 26 | 5 | hsa-miR-6087 | 1 | hsa-miR-1185-1-3p | 2 | hsa-miR-4728-5p | 126 | hsa-miR-6802-5p | 194 | hsa-miR-6777-5p | 182 |
| 27 | 5 | hsa-miR-6087 | 1 | hsa-miR-4652-5p | 104 | hsa-miR-4728-5p | 126 | hsa-miR-6819-5p | 198 | hsa-miR-3940-5p | 62 |
| 28 | 5 | hsa-miR-6087 | 1 | hsa-miR-1185-2-3p | 3 | hsa-miR-4728-5p | 126 | hsa-miR-6802-5p | 194 | hsa-miR-1228-3p | 8 |
| 29 | 5 | hsa-miR-6087 | 1 | hsa-miR-1185-2-3p | 3 | hsa-miR-4728-5p | 126 | hsa-miR-6802-5p | 194 | hsa-miR-4258 | 64 |
| 30 | 5 | hsa-miR-6087 | 1 | hsa-miR-1185-1-3p | 2 | hsa-miR-4728-5p | 126 | hsa-miR-6802-5p | 194 | hsa-miR-504-3p | 143 |
| 31 | 5 | hsa-miR-6087 | 1 | hsa-miR-1185-1-3p | 2 | hsa-miR-4728-5p | 126 | hsa-miR-6802-5p | 194 | hsa-miR-3180-3p | 38 |
| 32 | 5 | hsa-miR-6087 | 1 | hsa-miR-1185-1-3p | 2 | hsa-miR-4728-5p | 126 | hsa-miR-6802-5p | 194 | hsa-miR-4722-5p | 122 |
| 33 | 5 | hsa-miR-6087 | 1 | hsa-miR-1185-1-3p | 2 | hsa-miR-4728-5p | 126 | hsa-miR-6802-5p | 194 | hsa-miR-7113-3p | 219 |
| 34 | 5 | hsa-miR-6087 | 1 | hsa-miR-1185-1-3p | 2 | hsa-miR-4728-5p | 126 | hsa-miR-6802-5p | 194 | hsa-miR-6880-5p | 212 |
| 35 | 5 | hsa-miR-6087 | 1 | hsa-miR-1185-1-3p | 2 | hsa-miR-4728-5p | 126 | hsa-miR-6802-5p | 194 | hsa-miR-4763-3p | 134 |
| 36 | 5 | hsa-miR-6087 | 1 | hsa-miR-1185-1-3p | 2 | hsa-miR-4728-5p | 126 | hsa-miR-6802-5p | 194 | hsa-miR-6515-3p | 160 |
| 37 | 5 | hsa-miR-6087 | 1 | hsa-miR-1185-1-3p | 2 | hsa-miR-4728-5p | 126 | hsa-miR-6802-5p | 194 | hsa-miR-6803-5p | 195 |
| 38 | 5 | hsa-miR-6087 | 1 | hsa-miR-1185-1-3p | 2 | hsa-miR-4728-5p | 126 | hsa-miR-6802-5p | 194 | hsa-miR-1909-3p | 24 |
| 39 | 5 | hsa-miR-6087 | 1 | hsa-miR-1185-1-3p | 2 | hsa-miR-4728-5p | 126 | hsa-miR-6075 | 148 | hsa-miR-4466 | 86 |
| 40 | 5 | hsa-miR-6087 | 1 | hsa-miR-1185-2-3p | 3 | hsa-miR-4728-5p | 126 | hsa-miR-6802-5p | 194 | hsa-miR-6794-5p | 192 |
| 41 | 5 | hsa-miR-6087 | 1 | hsa-miR-1185-1-3p | 2 | hsa-miR-4728-5p | 126 | hsa-miR-3160-5p | 35 | hsa-miR-4443 | 77 |
| 42 | 5 | hsa-miR-6087 | 1 | hsa-miR-1185-1-3p | 2 | hsa-miR-4728-5p | 126 | hsa-miR-3160-5p | 35 | hsa-miR-4726-5p | 124 |
| 43 | 5 | hsa-miR-6087 | 1 | hsa-miR-744-5p | 221 | hsa-miR-4725-3p | 123 | hsa-miR-1268a | 13 | hsa-miR-6780b-5p | 184 |
| 44 | 5 | hsa-miR-6087 | 1 | hsa-miR-1185-1-3p | 2 | hsa-miR-4728-5p | 126 | hsa-miR-6802-5p | 194 | hsa-miR-1228-3p | 8 |

TABLE 11-1-continued

| No. | Number of miRNA | miRNA marker 1 | SEQ ID NO | miRNA marker 2 | SEQ ID NO | miRNA marker 3 | SEQ ID NO | miRNA marker 4 | SEQ ID NO | miRNA marker 5 | SEQ ID NO |
|---|---|---|---|---|---|---|---|---|---|---|---|
| 45 | 5 | hsa-miR-6087 | 1 | hsa-miR-1185-1-3p | 2 | hsa-miR-4728-5p | 126 | hsa-miR-6802-5p | 194 | hsa-miR-6743-5p | 171 |
| 46 | 5 | hsa-miR-6087 | 1 | hsa-miR-1185-1-3p | 2 | hsa-miR-4728-5p | 126 | hsa-miR-6802-5p | 194 | hsa-miR-6791-5p | 191 |
| 47 | 5 | hsa-miR-6087 | 1 | hsa-miR-4652-5p | 104 | hsa-miR-4728-5p | 126 | hsa-miR-6819-5p | 198 | hsa-miR-1469 | 234 |
| 48 | 5 | hsa-miR-6087 | 1 | hsa-miR-1185-2-3p | 3 | hsa-miR-4728-5p | 126 | hsa-miR-6802-5p | 194 | hsa-miR-4535 | 98 |
| 49 | 5 | hsa-miR-6087 | 1 | hsa-miR-6784-5p | 187 | hsa-miR-4728-5p | 126 | hsa-miR-6819-5p | 198 | hsa-miR-3160-5p | 35 |
| 50 | 5 | hsa-miR-6087 | 1 | hsa-miR-1185-1-3p | 2 | hsa-miR-4728-5p | 126 | hsa-miR-6802-5p | 194 | hsa-miR-4525 | 96 |

TABLE 11-2

| No. | Training cohort Sensitivity | Training cohort Specificity | Training cohort Accuracy | Training cohort AUC | Validation cohort Sensitivity | Validation cohort Specificity | Validation cohort Accuracy | Validation cohort AUC |
|---|---|---|---|---|---|---|---|---|
| 1 | 0.95 | 0.88 | 0.90 | 0.95 | 0.95 | 0.89 | 0.91 | 0.96 |
| 2 | 0.93 | 0.89 | 0.90 | 0.96 | 0.94 | 0.90 | 0.91 | 0.96 |
| 3 | 0.97 | 0.87 | 0.90 | 0.95 | 0.95 | 0.89 | 0.91 | 0.96 |
| 4 | 0.97 | 0.86 | 0.90 | 0.96 | 0.97 | 0.88 | 0.91 | 0.96 |
| 5 | 0.97 | 0.86 | 0.90 | 0.96 | 0.95 | 0.88 | 0.91 | 0.96 |
| 6 | 0.95 | 0.90 | 0.92 | 0.96 | 0.94 | 0.91 | 0.92 | 0.95 |
| 7 | 0.96 | 0.88 | 0.90 | 0.96 | 0.95 | 0.91 | 0.92 | 0.96 |
| 8 | 0.97 | 0.87 | 0.90 | 0.95 | 0.95 | 0.88 | 0.90 | 0.96 |
| 9 | 0.96 | 0.88 | 0.90 | 0.95 | 0.94 | 0.90 | 0.91 | 0.96 |
| 10 | 0.97 | 0.85 | 0.89 | 0.96 | 0.97 | 0.88 | 0.91 | 0.96 |
| 11 | 0.97 | 0.87 | 0.90 | 0.96 | 0.95 | 0.87 | 0.90 | 0.96 |
| 12 | 0.97 | 0.85 | 0.89 | 0.95 | 0.95 | 0.86 | 0.89 | 0.96 |
| 13 | 0.97 | 0.88 | 0.90 | 0.96 | 0.97 | 0.88 | 0.91 | 0.95 |
| 14 | 0.92 | 0.92 | 0.92 | 0.96 | 0.92 | 0.94 | 0.93 | 0.97 |
| 15 | 0.95 | 0.88 | 0.90 | 0.95 | 0.95 | 0.89 | 0.91 | 0.96 |
| 16 | 0.97 | 0.87 | 0.90 | 0.95 | 0.95 | 0.88 | 0.91 | 0.96 |
| 17 | 0.96 | 0.87 | 0.90 | 0.95 | 0.95 | 0.89 | 0.91 | 0.96 |
| 18 | 0.96 | 0.87 | 0.90 | 0.95 | 0.95 | 0.89 | 0.91 | 0.96 |
| 19 | 0.97 | 0.87 | 0.90 | 0.95 | 0.95 | 0.88 | 0.91 | 0.96 |
| 20 | 0.96 | 0.87 | 0.90 | 0.96 | 0.95 | 0.89 | 0.91 | 0.96 |
| 21 | 0.96 | 0.87 | 0.90 | 0.95 | 0.95 | 0.88 | 0.90 | 0.96 |
| 22 | 0.97 | 0.86 | 0.90 | 0.96 | 0.96 | 0.88 | 0.91 | 0.96 |
| 23 | 0.93 | 0.91 | 0.92 | 0.95 | 0.89 | 0.93 | 0.92 | 0.96 |
| 24 | 0.95 | 0.89 | 0.91 | 0.96 | 0.95 | 0.90 | 0.92 | 0.96 |
| 25 | 0.95 | 0.88 | 0.90 | 0.96 | 0.95 | 0.89 | 0.91 | 0.97 |
| 26 | 0.95 | 0.89 | 0.91 | 0.96 | 0.95 | 0.91 | 0.92 | 0.96 |
| 27 | 0.94 | 0.91 | 0.92 | 0.96 | 0.92 | 0.91 | 0.91 | 0.96 |
| 28 | 0.94 | 0.89 | 0.90 | 0.95 | 0.94 | 0.90 | 0.91 | 0.96 |
| 29 | 0.97 | 0.86 | 0.89 | 0.95 | 0.98 | 0.87 | 0.91 | 0.96 |
| 30 | 0.96 | 0.87 | 0.90 | 0.95 | 0.95 | 0.89 | 0.91 | 0.96 |
| 31 | 0.96 | 0.87 | 0.90 | 0.95 | 0.95 | 0.89 | 0.91 | 0.96 |
| 32 | 0.96 | 0.87 | 0.90 | 0.95 | 0.95 | 0.89 | 0.91 | 0.96 |
| 33 | 0.96 | 0.89 | 0.91 | 0.96 | 0.95 | 0.90 | 0.91 | 0.96 |
| 34 | 0.96 | 0.87 | 0.90 | 0.95 | 0.95 | 0.89 | 0.91 | 0.96 |
| 35 | 0.96 | 0.87 | 0.90 | 0.95 | 0.95 | 0.89 | 0.91 | 0.96 |
| 36 | 0.96 | 0.88 | 0.90 | 0.95 | 0.94 | 0.89 | 0.91 | 0.96 |
| 37 | 0.95 | 0.88 | 0.90 | 0.96 | 0.95 | 0.90 | 0.92 | 0.96 |
| 38 | 0.95 | 0.88 | 0.90 | 0.95 | 0.96 | 0.89 | 0.91 | 0.96 |
| 39 | 0.97 | 0.85 | 0.88 | 0.95 | 0.94 | 0.86 | 0.88 | 0.96 |
| 40 | 0.97 | 0.87 | 0.90 | 0.96 | 0.96 | 0.88 | 0.91 | 0.96 |
| 41 | 0.94 | 0.89 | 0.90 | 0.95 | 0.94 | 0.91 | 0.92 | 0.96 |
| 42 | 0.94 | 0.90 | 0.91 | 0.95 | 0.92 | 0.91 | 0.92 | 0.96 |
| 43 | 0.97 | 0.89 | 0.91 | 0.96 | 0.95 | 0.89 | 0.91 | 0.95 |
| 44 | 0.95 | 0.89 | 0.91 | 0.95 | 0.95 | 0.89 | 0.91 | 0.96 |
| 45 | 0.95 | 0.88 | 0.90 | 0.95 | 0.95 | 0.90 | 0.92 | 0.96 |
| 46 | 0.95 | 0.88 | 0.90 | 0.95 | 0.95 | 0.90 | 0.91 | 0.96 |
| 47 | 0.95 | 0.88 | 0.91 | 0.95 | 0.92 | 0.89 | 0.90 | 0.96 |
| 48 | 0.96 | 0.87 | 0.90 | 0.95 | 0.96 | 0.88 | 0.91 | 0.96 |
| 49 | 0.97 | 0.87 | 0.90 | 0.95 | 0.95 | 0.88 | 0.90 | 0.96 |
| 50 | 0.95 | 0.88 | 0.90 | 0.95 | 0.95 | 0.90 | 0.92 | 0.96 |

TABLE 11-3

| No. | Number of miRNA | Discriminant formula | Threshold |
|---|---|---|---|
| 1 | 5 | (−1.97574)*hsa-miR-6087 + (0.306682)*hsa-miR-1185-1-3p + (−0.751539)*hsa-miR-4728-5p + (0.85344)*hsa-miR-6802-5p + (0.113938)*hsa-miR-6716-5p + 17.5594 | −0.12 |
| 2 | 5 | (−1.95531)*hsa-miR-6087 + (0.305415)*hsa-miR-1185-1-3p + (−0.699384)*hsa-miR-4728-5p + (0.795001)*hsa-miR-6802-5p + (0.137688)*hsa-miR-210-5p + 17.4154 | −0.03 |
| 3 | 5 | (−1.9726)*hsa-miR-6087 + (0.310345)*hsa-miR-1185-1-3p + (−0.697798)*hsa-miR-4728-5p + (0.77435)*hsa-miR-6802-5p + (0.0755933)*hsa-miR-4535 + 18.1116 | −0.16 |
| 4 | 5 | (−2.06728)*hsa-miR-6087 + (0.266954)*hsa-miR-1185-1-3p + (−0.578422)*hsa-miR-4728-5p + (1.00387)*hsa-miR-6802-5p + (−0.398203)*hsa-miR-6794-5p + 20.3473 | −0.15 |
| 5 | 5 | (−1.99673)*hsa-miR-6087 + (0.325411)*hsa-miR-1185-1-3p + (−0.697755)*hsa-miR-4728-5p + (0.761716)*hsa-miR-6802-5p + (0.188115)*hsa-miR-3185 + 17.264 | −0.21 |
| 6 | 5 | (−1.59922)*hsa-miR-6087 + (0.534051)*hsa-miR-744-5p + (−1.3171)*hsa-miR-4725-3p + (0.177022)*hsa-miR-4652-5p + (0.778345)*hsa-miR-6780b-5p + 17.3455 | 0.01 |

TABLE 11-3-continued

| No. | Number of miRNA | Discriminant formula | Threshold |
|---|---|---|---|
| 7 | 5 | (−1.97309)*hsa-miR-6087 + (0.321776)*hsa-miR-1185-1-3p + (−0.625091)*hsa-miR-4728-5p + (0.709608)*hsa-miR-6802-5p + (0.343782)*hsa-miR-3648 + 13.9735 | −0.05 |
| 8 | 5 | (−1.97998)*hsa-miR-6087 + (0.323851)*hsa-miR-1185-1-3p + (−0.702005)*hsa-miR-4728-5p + (0.784423)*hsa-miR-6802-5p + (0.059042)*hsa-miR-6737-5p + 18.0372 | −0.20 |
| 9 | 5 | (−1.94003)*hsa-miR-6087 + (0.325896)*hsa-miR-1185-1-3p + (−0.664139)*hsa-miR-4728-5p + (0.812215)*hsa-miR-6802-5p + (−0.240379)*hsa-miR-4725-3p + 19.6515 | −0.10 |
| 10 | 5 | (−2.00009)*hsa-miR-6087 + (0.305759)*hsa-miR-1185-1-3p + (−0.747234)*hsa-miR-4728-5p + (0.837692)*hsa-miR-6802-5p + (0.176885)*hsa-miR-7150 + 17.2507 | −0.28 |
| 11 | 5 | (−2.00482)*hsa-miR-6087 + (0.308847)*hsa-miR-1185-1-3p + (−0.720592)*hsa-miR-4728-5p + (0.737035)*hsa-miR-6802-5p + (0.217932)*hsa-miR-7107-5p + 17.7126 | −0.21 |
| 12 | 5 | (−1.96891)*hsa-miR-6087 + (0.236715)*hsa-miR-1185-2-3p + (−0.705818)*hsa-miR-4728-5p + (0.768652)*hsa-miR-6802-5p + (0.0835383)*hsa-miR-5008-5p + 18.8164 | −0.27 |
| 13 | 5 | (−1.69769)*hsa-miR-6087 + (0.916917)*hsa-miR-744-5p + (−1.00804)*hsa-miR-4725-3p + (0.234518)*hsa-miR-6717-5p + (−0.410221)*hsa-miR-4728-5p + 22.2844 | −0.17 |
| 14 | 5 | (−1.87799)*hsa-miR-6087 + (0.265005)*hsa-miR-1185-1-3p + (−0.708512)*hsa-miR-4728-5p + (0.668649)*hsa-miR-6802-5p + (0.317351)*hsa-miR-4436b-5p + 16.8662 | 0.20 |
| 15 | 5 | (−1.99172)*hsa-miR-6087 + (0.321678)*hsa-miR-1185-1-3p + (−0.669179)*hsa-miR-4728-5p + (0.779088)*hsa-miR-6802-5p + (0.074244)*hsa-miR-4707-3p + 17.9105 | −0.12 |
| 16 | 5 | (−2.00388)*hsa-miR-6087 + (0.323378)*hsa-miR-1185-1-3p + (−0.673168)*hsa-miR-4728-5p + (0.78929)*hsa-miR-6802-5p + (−0.109544)*hsa-miR-4651 + 19.6303 | −0.19 |
| 17 | 5 | (−2.02979)*hsa-miR-6087 + (0.330996)*hsa-miR-1185-1-3p + (−0.662212)*hsa-miR-4728-5p + (0.775558)*hsa-miR-6802-5p + (−0.0412224)*hsa-miR-887-3p + 19.0101 | −0.17 |
| 18 | 5 | (−2.04222)*hsa-miR-6087 + (0.317481)*hsa-miR-1185-1-3p + (−0.677187)*hsa-miR-4728-5p + (0.774711)*hsa-miR-6802-5p + (0.202952)*hsa-miR-328-5p + 16.8114 | −0.16 |
| 19 | 5 | (−2.02548)*hsa-miR-6087 + (0.325294)*hsa-miR-1185-1-3p + (−0.674895)*hsa-miR-4728-5p + (0.742323)*hsa-miR-6802-5p + (0.156362)*hsa-miR-6821-5p + 17.6787 | −0.19 |
| 20 | 5 | (−1.92431)*hsa-miR-6087 + (0.291659)*hsa-miR-1185-1-3p + (−0.756296)*hsa-miR-4728-5p + (0.765434)*hsa-miR-6802-5p + (0.186329)*hsa-miR-4726-5p + 17.3067 | −0.17 |
| 21 | 5 | (−1.98946)*hsa-miR-6087 + (0.325845)*hsa-miR-1185-1-3p + (−0.684016)*hsa-miR-4728-5p + (0.826354)*hsa-miR-6802-5p + (0.05751)*hsa-miR-4792 + 17.6798 | −0.18 |
| 22 | 5 | (−1.89148)*hsa-miR-6087 + (0.336172)*hsa-miR-1185-1-3p + (−0.687883)*hsa-miR-4728-5p + (0.645637)*hsa-miR-6802-5p + (0.186098)*hsa-miR-3619-3p + 16.8553 | −0.27 |
| 23 | 5 | (−1.41316)*hsa-miR-6087 + (0.182772)*hsa-miR-4652-5p + (−0.663791)*hsa-miR-4728-5p + (0.770082)*hsa-miR-6819-5p + (0.194503)*hsa-miR-4687-5p + 12.9808 | 0.10 |
| 24 | 5 | (−2.10385)*hsa-miR-6087 + (0.370769)*hsa-miR-1185-1-3p + (−0.607674)*hsa-miR-4728-5p + (0.946825)*hsa-miR-6802-5p + (−0.194202)*hsa-miR-3131 + 18.8205 | −0.03 |
| 25 | 5 | (−2.0706)*hsa-miR-6087 + (0.309769)*hsa-miR-1185-1-3p + (−0.678072)*hsa-miR-4728-5p + (0.659069)*hsa-miR-6802-5p + (0.249079)*hsa-miR-4675 + 18.541 | −0.04 |
| 26 | 5 | (−1.81895)*hsa-miR-6087 + (0.313368)*hsa-miR-1185-1-3p + (−0.763737)*hsa-miR-4728-5p + (0.697988)*hsa-miR-6802-5p + (0.169695)*hsa-miR-6777-5p + 16.7353 | −0.07 |
| 27 | 5 | (−1.45369)*hsa-miR-6087 + (0.159876)*hsa-miR-4652-5p + (−0.705944)*hsa-miR-4728-5p + (0.721583)*hsa-miR-6819-5p + (−0.761116)*hsa-miR-3940-5p + 24.0074 | 0.06 |
| 28 | 5 | (−1.97697)*hsa-miR-6087 + (0.239286)*hsa-miR-1185-2-3p + (−0.70536)*hsa-miR-4728-5p + (0.772623)*hsa-miR-6802-5p + (0.2396)*hsa-miR-1228-3p + 17.7097 | 0.01 |
| 29 | 5 | (−2.0355)*hsa-miR-6087 + (0.243538)*hsa-miR-1185-2-3p + (−0.648754)*hsa-miR-4728-5p + (0.708539)*hsa-miR-6802-5p + (0.132378)*hsa-miR-4258 + 18.8945 | −0.24 |
| 30 | 5 | (−1.98344)*hsa-miR-6087 + (0.284183)*hsa-miR-1185-1-3p + (−0.694576)*hsa-miR-4728-5p + (0.797829)*hsa-miR-6802-5p + (0.0759208)*hsa-miR-504-3p + 18.1452 | −0.14 |
| 31 | 5 | (−2.02868)*hsa-miR-6087 + (0.330511)*hsa-miR-1185-1-3p + (−0.682904)*hsa-miR-4728-5p + (0.822105)*hsa-miR-6802-5p + (−0.162048)*hsa-miR-3180-3p + 19.9246 | −0.14 |

TABLE 11-3-continued

| No. | Number of miRNA | Discriminant formula | Threshold |
|---|---|---|---|
| 32 | 5 | (−2.0024)*hsa-miR-6087 + (0.322011)*hsa-miR-1185-1-3p + (−0.701753)*hsa-miR-4728-5p + (0.720378)*hsa-miR-6802-5p + (0.13329)*hsa-miR-4722-5p + 18.4141 | −0.18 |
| 33 | 5 | (−1.96098)*hsa-miR-6087 + (0.284886)*hsa-miR-1185-1-3p + (−0.702706)*hsa-miR-4728-5p + (0.828885)*hsa-miR-6802-5p + (0.205399)*hsa-miR-7113-3p + 16.9012 | −0.11 |
| 34 | 5 | (−2.04675)*hsa-miR-6087 + (0.323234)*hsa-miR-1185-1-3p + (−0.647756)*hsa-miR-4728-5p + (0.803638)*hsa-miR-6802-5p + (−0.0639364)*hsa-miR-6880-5p + 19.1036 | −0.16 |
| 35 | 5 | (−2.01715)*hsa-miR-6087 + (0.324)*hsa-miR-1185-1-3p + (−0.675007)*hsa-miR-4728-5p + (0.784036)*hsa-miR-6802-5p + (0.0823888)*hsa-miR-4763-3p + 17.9 | −0.18 |
| 36 | 5 | (−1.98234)*hsa-miR-6087 + (0.293383)*hsa-miR-1185-1-3p + (−0.717769)*hsa-miR-4728-5p + (0.774551)*hsa-miR-6802-5p + (0.143503)*hsa-miR-6515-3p + 17.8861 | −0.16 |
| 37 | 5 | (−1.92198)*hsa-miR-6087 + (0.323857)*hsa-miR-1185-1-3p + (−0.671473)*hsa-miR-4728-5p + (0.77788)*hsa-miR-6802-5p + (−0.706715)*hsa-miR-6803-5p + 25.293 | −0.04 |
| 38 | 5 | (−2.01752)*hsa-miR-6087 + (0.305205)*hsa-miR-1185-1-3p + (−0.687511)*hsa-miR-4728-5p + (0.751667)*hsa-miR-6802-5p + (−0.441716)*hsa-miR-1909-3p + 23.0425 | −0.15 |
| 39 | 5 | (−2.1145)*hsa-miR-6087 + (0.346492)*hsa-miR-1185-1-3p + (−0.477369)*hsa-miR-4728-5p + (0.541762)*hsa-miR-6075 + (−0.100607)*hsa-miR-4466 + 21.938 | −0.23 |
| 40 | 5 | (−2.0679)*hsa-miR-6087 + (0.210868)*hsa-miR-1185-2-3p + (−0.564075)*hsa-miR-4728-5p + (1.0277)*hsa-miR-6802-5p + (−0.456643)*hsa-miR-6794-5p + 21.1161 | −0.21 |
| 41 | 5 | (−1.90504)*hsa-miR-6087 + (0.317204)*hsa-miR-1185-1-3p + (−0.60802)*hsa-miR-4728-5p + (0.183053)*hsa-miR-3160-5p + (0.161124)*hsa-miR-4443 + 21.6641 | 0.07 |
| 42 | 5 | (−1.88621)*hsa-miR-6087 + (0.328477)*hsa-miR-1185-1-3p + (−0.615267)*hsa-miR-4728-5p + (0.171483)*hsa-miR-3160-5p + (0.169775)*hsa-miR-4726-5p + 21.3692 | 0.08 |
| 43 | 5 | (−1.83671)*hsa-miR-6087 + (0.801734)*hsa-miR-744-5p + (−1.39458)*hsa-miR-4725-3p + (−0.705307)*hsa-miR-1268a + (0.87047)*hsa-miR-6780b-5p + 25.8016 | 0.03 |
| 44 | 5 | (−1.99054)*hsa-miR-6087 + (0.297474)*hsa-miR-1185-1-3p + (−0.697922)*hsa-miR-4728-5p + (0.785747)*hsa-miR-6802-5p + (0.183654)*hsa-miR-1228-3p + 17.4544 | −0.08 |
| 45 | 5 | (−2.05119)*hsa-miR-6087 + (0.333116)*hsa-miR-1185-1-3p + (−0.674012)*hsa-miR-4728-5p + (0.87884)*hsa-miR-6802-5p + (−0.280392)*hsa-miR-6743-5p + 20.9727 | −0.02 |
| 46 | 5 | (−2.04448)*hsa-miR-6087 + (0.312895)*hsa-miR-1185-1-3p + (−0.683115)*hsa-miR-4728-5p + (0.845636)*hsa-miR-6802-5p + (−0.304078)*hsa-miR-6791-5p + 21.4743 | −0.06 |
| 47 | 5 | (−1.47528)*hsa-miR-6087 + (0.177635)*hsa-miR-4652-5p + (−0.649714)*hsa-miR-4728-5p + (0.778168)*hsa-miR-6819-5p + (0.280624)*hsa-miR-1469 + 11.5525 | −0.14 |
| 48 | 5 | (−1.96453)*hsa-miR-6087 + (0.244369)*hsa-miR-1185-2-3p + (−0.692974)*hsa-miR-4728-5p + (0.777289)*hsa-miR-6802-5p + (0.0659214)*hsa-miR-4535 + 18.7085 | −0.15 |
| 49 | 5 | (−1.51864)*hsa-miR-6087 + (−0.628049)*hsa-miR-6784-5p + (−0.813322)*hsa-miR-4728-5p + (0.846001)*hsa-miR-6819-5p + (0.0984264)*hsa-miR-3160-5p + 23.2007 | −0.18 |
| 50 | 5 | (−1.97887)*hsa-miR-6087 + (0.321602)*hsa-miR-1185-1-3p + (−0.655373)*hsa-miR-4728-5p + (0.697661)*hsa-miR-6802-5p + (0.0656159)*hsa-miR-4525 + 18.1775 | −0.07 |

Example 2

<Discriminant Analysis of Bladder Cancer with 1 or Combination of 2 to 104 miRNAs>

In this Example, discriminant formulas with 1 to 104 gene markers were created using a training cohort (Table 4) including bladder cancer patients, patients of cancers other than bladder cancer, benign disease patient, and healthy subjects, to evaluate the discriminant performance in a validation cohort (Table 4). Genes used for discriminant formulas combining up to 104 genes and exhibiting high discriminant accuracy were extracted to obtain gene markers capable of detecting bladder cancer (Table 12).

Specifically, first, miRNA expression levels in the training cohort and the validation cohort obtained in the above Reference Example were together normalized in accordance with global normalization. Further, in order to acquire more reliable diagnostic markers, only 384 genes with a gene expression level of $2^6$ or larger in 50% or more of the samples were analyzed in either the positive sample group (bladder cancer patients) or the negative sample group (patients of cancers other than bladder cancer, benign disease patients, and healthy subjects).

Next, logistic regression analysis was performed from the measured values of the expression levels of the above 384 genes by the LASSO method, and discriminant formulas with one to a combination of a plurality of miRNAs were created, to construct discriminant formulas with a combination of 104 genes for discriminating the presence or absence of bladder cancer with high accuracy. Further, the discriminant formulas were used to calculate the accuracy, the sensitivity, and the specificity in the validation cohort. Then, the discriminant performance was validated in independent samples. Details are shown below for each number of genes used for discrimination.

Example 2-1

As a result of the above, a discriminant formula with a combination of three genes and its threshold (determining positive or negative, where values equal to or higher than the threshold are positive), the sensitivity, specificity, accuracy, and AUC in the training cohort and the validation cohort, and the genes used for the discriminant formula are shown in Tables 13-1 and 13-2. The genes included in these discriminant formulas were selected as diagnostic markers capable of discriminating between bladder cancer patients and subjects without bladder cancer.

Figure 14:
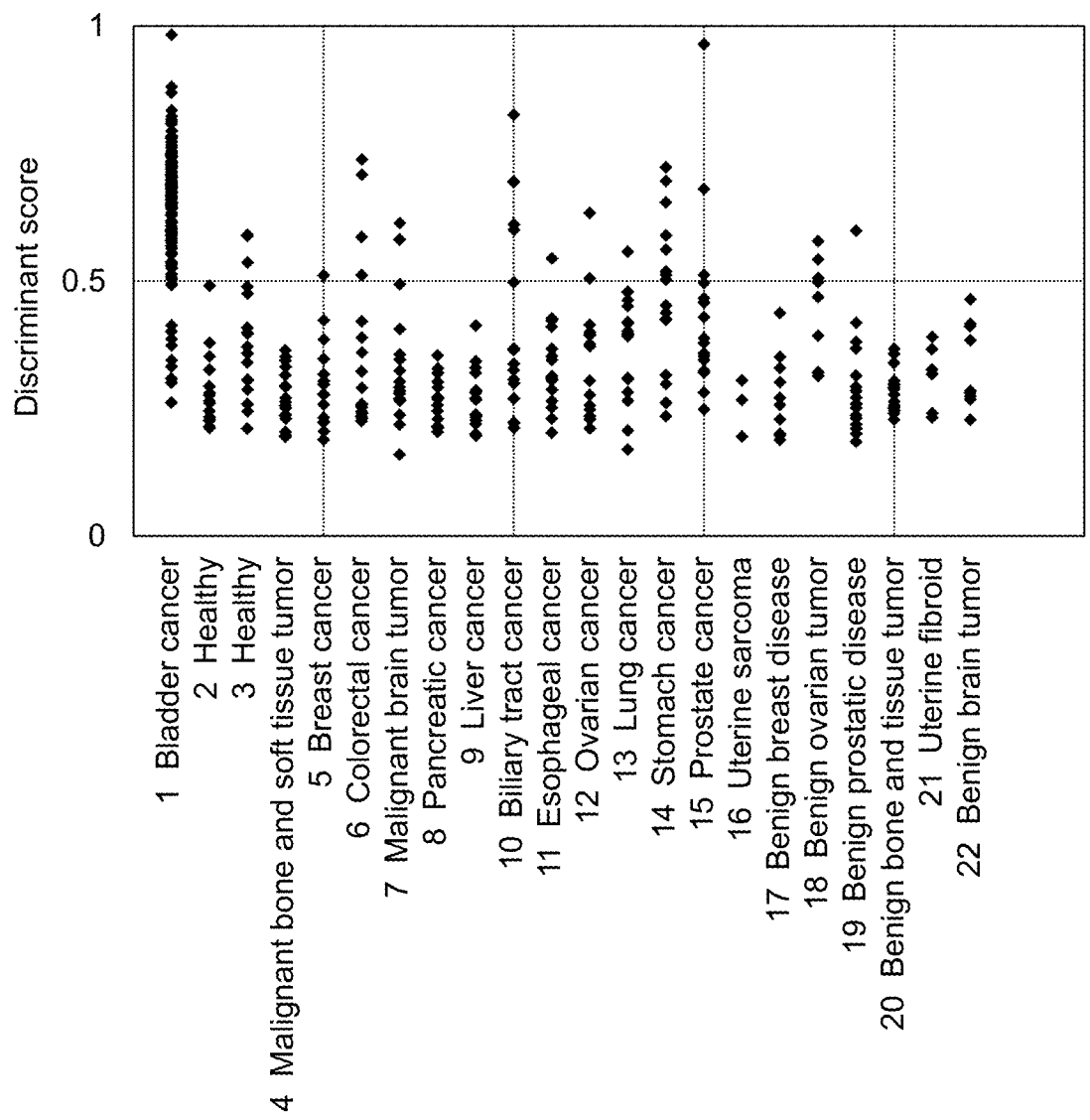
FIG. 14 shows plots of discriminant scores in validation cohorts according to the disease type obtained by a discriminant formula for 3 miRNAs.

Measured values were plugged into the discriminant formula in Table 13-3 to obtain y, the values obtained by substituting y in Formula 9 were plotted as discriminant scores for each disease type in the validation cohort, thereby showing that bladder cancer was significantly separated regardless of the disease type, in FIG. 14. The vertical axis of the figure represents the discriminant scores. As compared to the threshold 0.5, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 15A to D). The vertical axis of the figure represents the discriminant scores. As compared to the threshold 0.5, higher scores were determined as having bladder cancer, and lower scores were determined as not having bladder cancer.

Example 2-2

Figure 16:
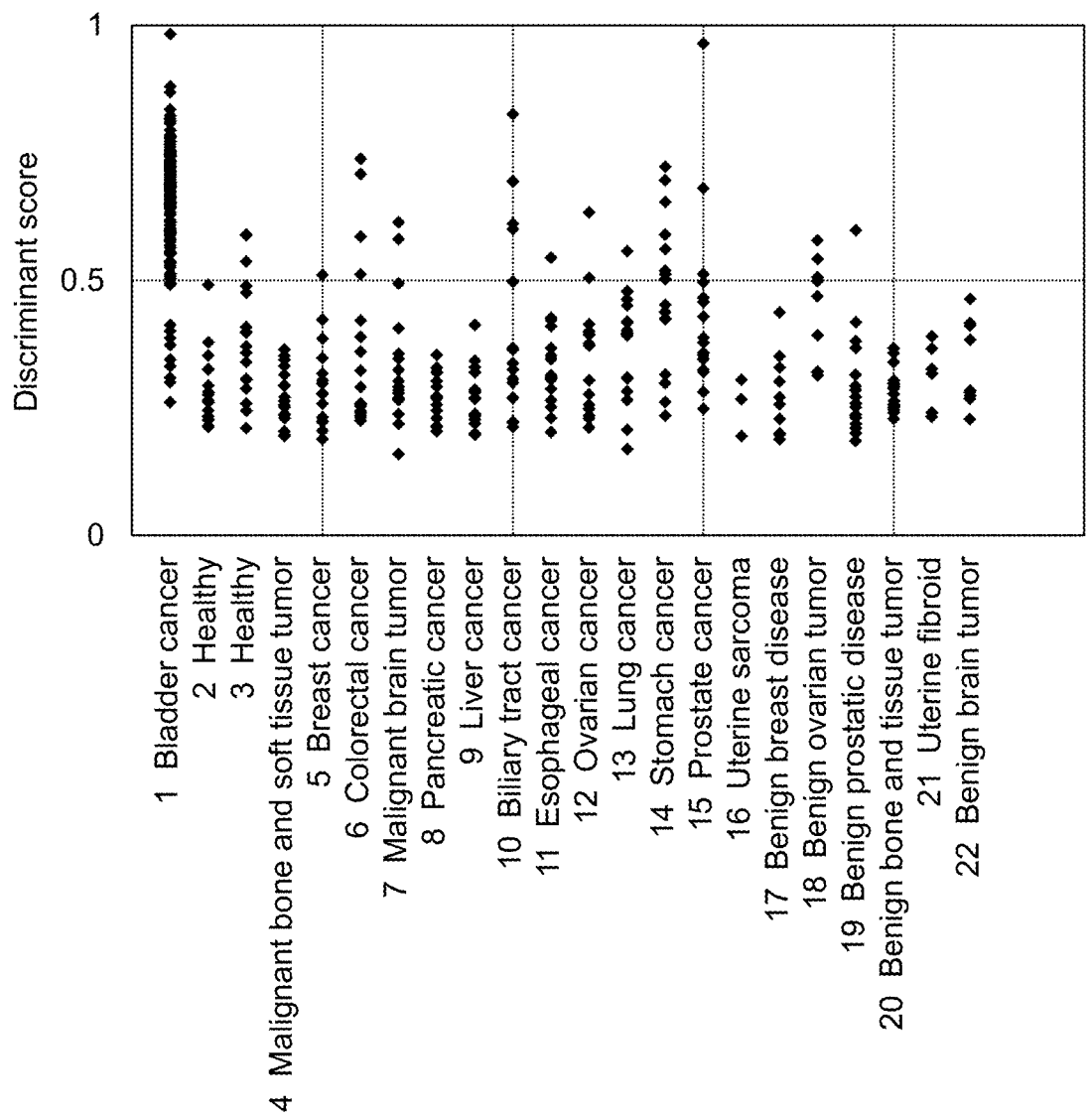
FIG. 16 shows plots of discriminant scores in validation cohorts according to the disease type obtained by a discriminant formula for 10 miRNAs.

As a result of the above, a discriminant formula with a combination of ten genes and its threshold (determining positive or negative, where values equal to or higher than the threshold are positive), the sensitivity, specificity, accuracy, and AUC in the training cohort and the validation cohort, and the genes used for the discriminant formula are shown in Table 14-1. The genes included in these discriminant formulas were selected as diagnostic markers capable of discriminating between bladder cancer patients and subjects without bladder cancer. Measured values were plugged into the discriminant formula in Table 14-2 to obtain y, the values obtained by substituting y in Formula 9 were plotted as discriminant scores for each disease type in the validation cohort, thereby showing that bladder cancer was significantly separated regardless of the disease type, in FIG. 16. The vertical axis of the figure represents the discriminant scores. As compared to the threshold 0.5, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 17A to D). The vertical axis of the figure represents the discriminant scores. As compared to the threshold 0.5, higher scores were determined as having bladder cancer, and lower scores were determined as not having bladder cancer.

Example 2-3

As a result of the above, a discriminant formula with a combination of 104 genes and its threshold (determining positive or negative, where values equal to or higher than the threshold are positive), the sensitivity, specificity, accuracy, and AUC in the training cohort and the validation cohort, and the genes used for the discriminant formula are shown in Table 15-1. The genes included in these discriminant formula were selected as diagnostic markers capable of discriminating between bladder cancer patients and subjects without bladder cancer.

Figure 18:
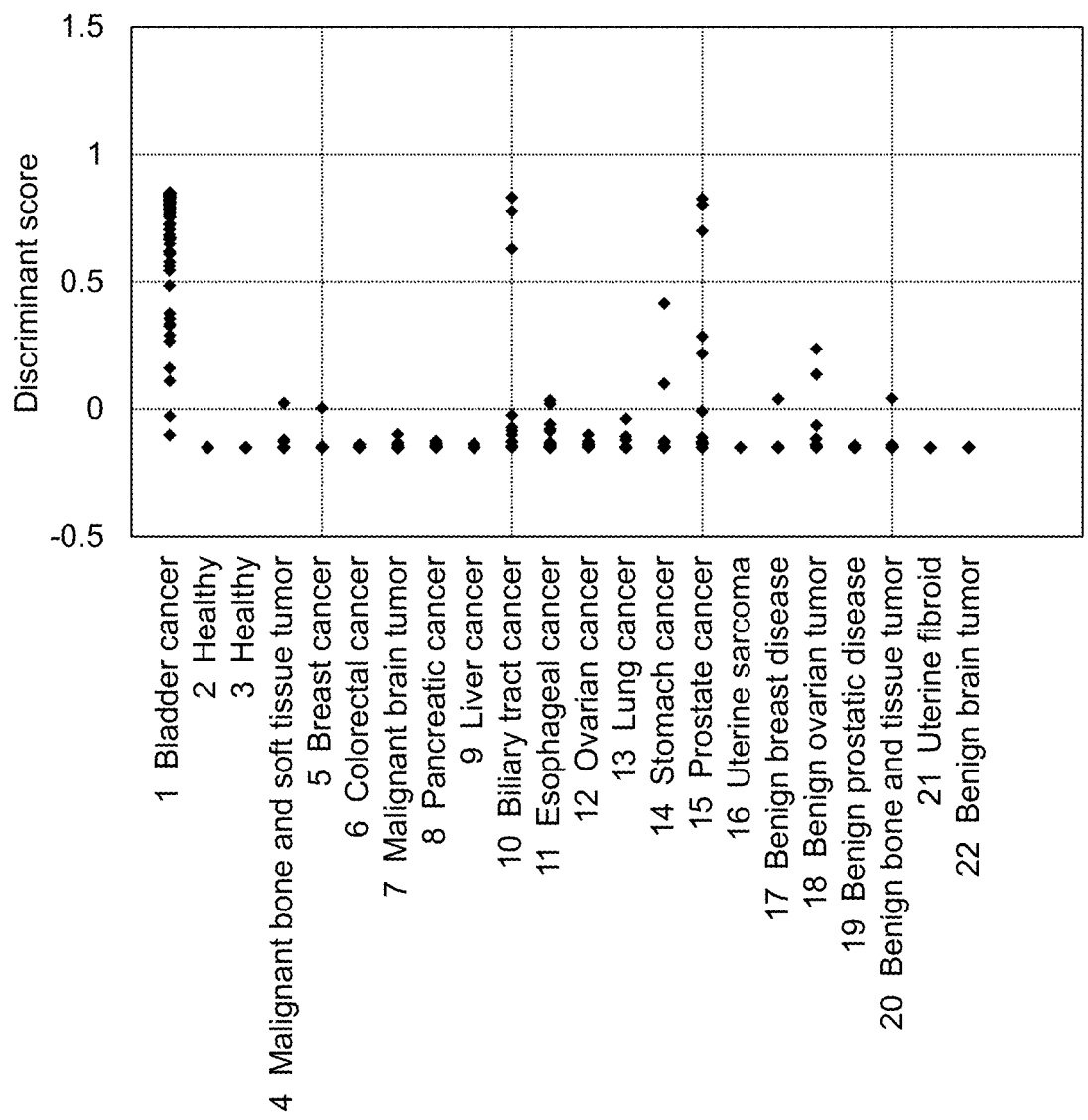
FIG. 18 shows plots of discriminant scores in validation cohorts according to the disease type obtained by a discriminant formula for 104 miRNAs.

Measured values were plugged into the discriminant formula in Table 15-2 to obtain y, the values obtained by substituting y in Formula 9 were plotted as discriminant scores for each disease type in the validation cohort, thereby showing that bladder cancer was significantly separated regardless of the disease type, in FIG. 18. The vertical axis of the figure represents the discriminant scores. As compared to the threshold 0.5, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 19A to D). The vertical axis of the figure represents the discriminant scores. As compared to the threshold 0.5, higher scores were determined as having bladder cancer, and lower scores were determined as not having bladder cancer.

Example 2-4

As a result of the above, discriminant formulas with 1 or a combination of 2 to 103 genes and their thresholds (determining positive or negative, where values equal to or higher than the thresholds are positive), the sensitivity, specificity, accuracy, and AUC in the training cohort and the validation cohort, and the genes used for the discriminant formulas are shown in Table 16-1. The genes included in these discriminant formulas were selected as diagnostic markers capable of discriminating between bladder cancer patients and subjects without bladder cancer. The discriminant formulas and their thresholds for performing discrimination with 1 or a combination of 2 to 104 genes are shown in Table 16-2 (the 104 genes in combination are shown in Table 15-1, as described above).

From the above, it was demonstrated that higher discriminant performance for bladder cancer can be obtained in the case of combining a plurality of genes than in the case of using each gene represented by Nos. 1 to 119 in Table 12 alone. The genes included in these discriminant formulas were selected as diagnostic markers capable of discriminating between bladder cancer patients and subjects without bladder cancer.

TABLE 12

| No. | Name of miRNA | SEQ ID NO |
|---|---|---|
| 1 | hsa-miR-1185-1-3p | 2 |
| 2 | hsa-miR-1185-2-3p | 3 |
| 3 | hsa-miR-1193 | 4 |

TABLE 12-continued

| No. | Name of miRNA | SEQ ID NO |
|---|---|---|
| 4 | hsa-miR-1207-5p | 230 |
| 5 | hsa-miR-1225-5p | 6 |
| 6 | hsa-miR-1227-5p | 7 |
| 7 | hsa-miR-1228-5p | 9 |
| 8 | hsa-miR-1237-5p | 10 |
| 9 | hsa-miR-1246 | 231 |
| 10 | hsa-miR-128-2-5p | 16 |
| 11 | hsa-miR-1343-3p | 17 |
| 12 | hsa-miR-1343-5p | 18 |
| 13 | hsa-miR-149-3p | 235 |
| 14 | hsa-miR-150-3p | 236 |
| 15 | hsa-miR-1908-3p | 22 |
| 16 | hsa-miR-1908-5p | 23 |
| 17 | hsa-miR-1914-3p | 237 |
| 18 | hsa-miR-296-3p | 30 |
| 19 | hsa-miR-29b-3p | 31 |
| 20 | hsa-miR-3154 | 33 |
| 21 | hsa-miR-3158-5p | 34 |
| 22 | hsa-miR-3160-5p | 35 |
| 23 | hsa-miR-3195 | 42 |
| 24 | hsa-miR-3197 | 43 |
| 25 | hsa-miR-328-5p | 46 |
| 26 | hsa-miR-342-5p | 47 |
| 27 | hsa-miR-3619-3p | 50 |
| 28 | hsa-miR-3621 | 52 |
| 29 | hsa-miR-3648 | 54 |
| 30 | hsa-miR-3652 | 55 |
| 31 | hsa-miR-3663-3p | 57 |
| 32 | hsa-miR-371b-5p | 59 |
| 33 | hsa-miR-373-5p | 60 |
| 34 | hsa-miR-3917 | 61 |
| 35 | hsa-miR-3940-5p | 62 |
| 36 | hsa-miR-423-5p | 239 |
| 37 | hsa-miR-4270 | 66 |
| 38 | hsa-miR-4298 | 68 |
| 39 | hsa-miR-4322 | 69 |
| 40 | hsa-miR-4433a-3p | 75 |
| 41 | hsa-miR-4436b-5p | 76 |
| 42 | hsa-miR-4447 | 79 |
| 43 | hsa-miR-4448 | 80 |
| 44 | hsa-miR-4455 | 83 |
| 45 | hsa-miR-4467 | 87 |
| 46 | hsa-miR-4484 | 90 |
| 47 | hsa-miR-4534 | 97 |
| 48 | hsa-miR-4640-5p | 101 |
| 49 | hsa-miR-4649-5p | 102 |
| 50 | hsa-miR-4652-5p | 104 |
| 51 | hsa-miR-4655-5p | 105 |
| 52 | hsa-miR-4658 | 107 |
| 53 | hsa-miR-4663 | 108 |
| 54 | hsa-miR-4675 | 110 |
| 55 | hsa-miR-4687-3p | 111 |
| 56 | hsa-miR-4695-5p | 114 |
| 57 | hsa-miR-4710 | 120 |
| 58 | hsa-miR-4725-3p | 123 |
| 59 | hsa-miR-4728-5p | 126 |
| 60 | hsa-miR-4739 | 129 |
| 61 | hsa-miR-4741 | 131 |
| 62 | hsa-miR-4750-5p | 132 |
| 63 | hsa-miR-4763-3p | 134 |
| 64 | hsa-miR-4771 | 135 |
| 65 | hsa-miR-4783-3p | 136 |
| 66 | hsa-miR-498 | 140 |
| 67 | hsa-miR-5195-3p | 144 |
| 68 | hsa-miR-5739 | 147 |
| 69 | hsa-miR-6075 | 148 |
| 70 | hsa-miR-6087 | 1 |
| 71 | hsa-miR-6088 | 150 |
| 72 | hsa-miR-6124 | 151 |
| 73 | hsa-miR-6132 | 153 |
| 74 | hsa-miR-615-5p | 155 |
| 75 | hsa-miR-642b-3p | 157 |
| 76 | hsa-miR-6510-5p | 158 |
| 77 | hsa-miR-663a | 240 |
| 78 | hsa-miR-6716-5p | 163 |
| 79 | hsa-miR-6717-5p | 164 |
| 80 | hsa-miR-6722-3p | 165 |
| 81 | hsa-miR-6724-5p | 166 |
| 82 | hsa-miR-6726-5p | 167 |
| 83 | hsa-miR-6741-5p | 169 |
| 84 | hsa-miR-6749-5p | 173 |
| 85 | hsa-miR-6760-5p | 174 |
| 86 | hsa-miR-6762-5p | 175 |
| 87 | hsa-miR-6765-3p | 176 |
| 88 | hsa-miR-6766-3p | 178 |
| 89 | hsa-miR-6771-5p | 180 |
| 90 | hsa-miR-6774-5p | 181 |
| 91 | hsa-miR-6777-5p | 182 |
| 92 | hsa-miR-6778-5p | 183 |
| 93 | hsa-miR-6780b-5p | 184 |
| 94 | hsa-miR-6781-5p | 185 |
| 95 | hsa-miR-6782-5p | 186 |
| 96 | hsa-miR-6785-5p | 188 |
| 97 | hsa-miR-6791-5p | 191 |
| 98 | hsa-miR-6794-5p | 192 |
| 99 | hsa-miR-6800-5p | 193 |
| 100 | hsa-miR-6803-5p | 195 |
| 101 | hsa-miR-6812-5p | 196 |
| 102 | hsa-miR-6816-5p | 197 |
| 103 | hsa-miR-6819-5p | 198 |
| 104 | hsa-miR-6826-5p | 200 |
| 105 | hsa-miR-6836-3p | 202 |
| 106 | hsa-miR-6840-3p | 203 |
| 107 | hsa-miR-6869-5p | 207 |
| 108 | hsa-miR-6879-5p | 210 |
| 109 | hsa-miR-6880-3p | 211 |
| 110 | hsa-miR-7107-5p | 215 |
| 111 | hsa-miR-7108-3p | 216 |
| 112 | hsa-miR-711 | 218 |
| 113 | hsa-miR-744-5p | 221 |
| 114 | hsa-miR-8073 | 226 |
| 115 | hsa-miR-887-3p | 227 |
| 116 | hsa-miR-92a-2-5p | 241 |
| 117 | hsa-miR-92a-3p | 242 |
| 118 | hsa-miR-937-5p | 228 |
| 119 | hsa-miR-940 | 243 |

TABLE 13-1

| Number of miRNA | miRNA marker 1 | SEQ ID NO | miRNA marker 2 | SEQ ID NO | miRNA marker 3 | SEQ ID NO |
|---|---|---|---|---|---|---|
| 3 | hsa-miR-4652-5p | 104 | hsa-miR-6087 | 1 | hsa-miR-6724-5p | 166 |

TABLE 13-2

| Number of miRNA | Training cohort | | | | Validation cohort | | | |
|---|---|---|---|---|---|---|---|---|
| | Sensitivity | Specificity | Accuracy | AUC | Sensitivity | Specificity | Accuracy | AUC |
| 3 | 0.93 | 0.88 | 0.89 | 0.94 | 0.92 | 0.89 | 0.90 | 0.94 |

TABLE 13-3

| Number of miRNA | Discriminant formula | Threshold |
|---|---|---|
| 3 | (0.16644)*hsa-miR-4652-5p + (−1.41622)*hsa-miR-6087 + (0.02095)*hsa-miR-6724-5p + 15.02714 | 0.36 |

TABLE 14-1

| Number of miRNA | miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| 10 | hsa-miR-4658 | 107 | 0.94 | 0.90 | 0.91 | 0.95 | 0.92 | 0.92 | 0.92 | 0.96 |
| | hsa-miR-4436b-5p | 76 | | | | | | | | |
| | hsa-miR-4652-5p | 104 | | | | | | | | |
| | hsa-miR-4728-5p | 126 | | | | | | | | |
| | hsa-miR-6087 | 1 | | | | | | | | |
| | hsa-miR-3160-5p | 35 | | | | | | | | |
| | hsa-miR-6724-5p | 166 | | | | | | | | |
| | hsa-miR-3940-5p | 62 | | | | | | | | |
| | hsa-miR-744-5p | 221 | | | | | | | | |
| | hsa-miR-6781-5p | 185 | | | | | | | | |

TABLE 14-2

| Number of miRNA | Discriminant formula | Threshold |
|---|---|---|
| 10 | (0.01504)*hsa-miR-4658 + (0.01562)*hsa-miR-4436b-5p + (0.20522)*hsa-miR-4652-5p + (−0.01556)*hsa-miR-4728-5p + (−1.8352)*hsa-miR-6087 + (0.02667)*hsa-miR-3160-5p + (0.43956)*hsa-miR-6724-5p + (−0.07772)*hsa-miR-3940-5p + (0.03616)*hsa-miR-744-5p + (−0.07753)*hsa-miR-6781-5p + 16.37274 | 0.38 |

TABLE 15-1

| Number of miRNA | miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| 104 | hsa-miR-498 | 140 | 1.00 | 1.00 | 1.00 | 1.00 | 0.92 | 0.98 | 0.96 | 0.99 |
| | hsa-miR-4658 | 107 | | | | | | | | |
| | hsa-miR-6717-5p | 164 | | | | | | | | |
| | hsa-miR-8073 | 226 | | | | | | | | |
| | hsa-miR-92a-3p | 242 | | | | | | | | |
| | hsa-miR-3652 | 55 | | | | | | | | |
| | hsa-miR-6836-3p | 202 | | | | | | | | |
| | hsa-miR-1193 | 4 | | | | | | | | |
| | hsa-miR-4436b-5p | 76 | | | | | | | | |
| | hsa-miR-6812-5p | 196 | | | | | | | | |
| | hsa-miR-4663 | 108 | | | | | | | | |
| | hsa-miR-4652-5p | 104 | | | | | | | | |
| | hsa-miR-1343-5p | 18 | | | | | | | | |
| | hsa-miR-1246 | 231 | | | | | | | | |

TABLE 15-1-continued

| Number of miRNA miRNA marker | SEQ ID NO | Training cohort | | | | Validation cohort | | | |
|---|---|---|---|---|---|---|---|---|---|
| | | Sensitivity | Specificity | Accuracy | AUC | Sensitivity | Specificity | Accuracy | AUC |
| hsa-miR-4448 | 80 | | | | | | | | |
| hsa-miR-6722-3p | 165 | | | | | | | | |
| hsa-miR-6826-5p | 200 | | | | | | | | |
| hsa-miR-29b-3p | 31 | | | | | | | | |
| hsa-miR-1908-5p | 23 | | | | | | | | |
| hsa-miR-6840-3p | 203 | | | | | | | | |
| hsa-miR-3197 | 43 | | | | | | | | |
| hsa-miR-371b-5p | 59 | | | | | | | | |
| hsa-miR-4433a-3p | 75 | | | | | | | | |
| hsa-miR-4534 | 97 | | | | | | | | |
| hsa-miR-6816-5p | 197 | | | | | | | | |
| hsa-miR-6800-5p | 193 | | | | | | | | |
| hsa-miR-150-3p | 236 | | | | | | | | |
| hsa-miR-296-3p | 30 | | | | | | | | |
| hsa-miR-4771 | 135 | | | | | | | | |
| hsa-miR-1908-3p | 22 | | | | | | | | |
| hsa-miR-4298 | 68 | | | | | | | | |
| hsa-miR-6774-5p | 181 | | | | | | | | |
| hsa-miR-615-5p | 155 | | | | | | | | |
| hsa-miR-4741 | 131 | | | | | | | | |
| hsa-miR-1227-5p | 7 | | | | | | | | |
| hsa-miR-1185-1-3p | 2 | | | | | | | | |
| hsa-miR-6765-3p | 176 | | | | | | | | |
| hsa-miR-6741-5p | 169 | | | | | | | | |
| hsa-miR-5739 | 147 | | | | | | | | |
| hsa-miR-373-5p | 60 | | | | | | | | |
| hsa-miR-663a | 240 | | | | | | | | |
| hsa-miR-1228-5p | 9 | | | | | | | | |
| hsa-miR-642b-3p | 157 | | | | | | | | |
| hsa-miR-4728-5p | 126 | | | | | | | | |
| hsa-miR-937-5p | 228 | | | | | | | | |
| hsa-miR-887-3p | 227 | | | | | | | | |
| hsa-miR-6124 | 151 | | | | | | | | |
| hsa-miR-6075 | 148 | | | | | | | | |
| hsa-miR-6778-5p | 183 | | | | | | | | |
| hsa-miR-6762-5p | 175 | | | | | | | | |
| hsa-miR-4484 | 90 | | | | | | | | |
| hsa-miR-6087 | 1 | | | | | | | | |
| hsa-miR-6760-5p | 174 | | | | | | | | |
| hsa-miR-1237-5p | 10 | | | | | | | | |
| hsa-miR-711 | 218 | | | | | | | | |
| hsa-miR-4270 | 66 | | | | | | | | |
| hsa-miR-4710 | 120 | | | | | | | | |
| hsa-miR-5195-3p | 144 | | | | | | | | |
| hsa-miR-128-2-5p | 16 | | | | | | | | |
| hsa-miR-149-3p | 235 | | | | | | | | |
| hsa-miR-1914-3p | 237 | | | | | | | | |
| hsa-miR-4763-3p | 134 | | | | | | | | |
| hsa-miR-6726-5p | 167 | | | | | | | | |
| hsa-miR-1207-5p | 230 | | | | | | | | |
| hsa-miR-4675 | 110 | | | | | | | | |
| hsa-miR-328-5p | 46 | | | | | | | | |
| hsa-miR-6716-5p | 163 | | | | | | | | |
| hsa-miR-4455 | 83 | | | | | | | | |
| hsa-miR-3619-3p | 50 | | | | | | | | |
| hsa-miR-3160-5p | 35 | | | | | | | | |
| hsa-miR-6724-5p | 166 | | | | | | | | |
| hsa-miR-423-5p | 239 | | | | | | | | |
| hsa-miR-92a-2-5p | 241 | | | | | | | | |
| hsa-miR-4447 | 79 | | | | | | | | |
| hsa-miR-3621 | 52 | | | | | | | | |
| hsa-miR-4739 | 129 | | | | | | | | |
| hsa-miR-6132 | 153 | | | | | | | | |
| hsa-miR-6791-5p | 191 | | | | | | | | |
| hsa-miR-4725-3p | 123 | | | | | | | | |
| hsa-miR-3158-5p | 34 | | | | | | | | |
| hsa-miR-6766-3p | 178 | | | | | | | | |
| hsa-miR-6879-5p | 210 | | | | | | | | |
| hsa-miR-940 | 243 | | | | | | | | |
| hsa-miR-4750-5p | 132 | | | | | | | | |
| hsa-miR-3154 | 33 | | | | | | | | |
| hsa-miR-3663-3p | 57 | | | | | | | | |
| hsa-miR-4655-5p | 105 | | | | | | | | |
| hsa-miR-4649-5p | 102 | | | | | | | | |
| hsa-miR-4640-5p | 101 | | | | | | | | |

TABLE 15-1-continued

| Number of miRNA miRNA marker | SEQ ID NO | Training cohort | | | | Validation cohort | | | |
|---|---|---|---|---|---|---|---|---|---|
| | | Sensitivity | Specificity | Accuracy | AUC | Sensitivity | Specificity | Accuracy | AUC |
| hsa-miR-4783-3p | 136 | | | | | | | | |
| hsa-miR-6869-5p | 207 | | | | | | | | |
| hsa-miR-1343-3p | 17 | | | | | | | | |
| hsa-miR-6771-5p | 180 | | | | | | | | |
| hsa-miR-7108-3p | 216 | | | | | | | | |
| hsa-miR-3195 | 42 | | | | | | | | |
| hsa-miR-4687-3p | 111 | | | | | | | | |
| hsa-miR-1185-2-3p | 3 | | | | | | | | |
| hsa-miR-1225-5p | 6 | | | | | | | | |
| hsa-miR-4322 | 69 | | | | | | | | |
| hsa-miR-6088 | 150 | | | | | | | | |
| hsa-miR-6785-5p | 188 | | | | | | | | |
| hsa-miR-6777-5p | 182 | | | | | | | | |
| hsa-miR-4695-5p | 114 | | | | | | | | |
| hsa-miR-6880-3p | 211 | | | | | | | | |

TABLE 15-2

| Number of miRNA | Discriminant formula | Threshold |
|---|---|---|
| 104 | (−0.142443)*hsa-miR-498 + (0.343385)*hsa-miR-4658 + (0.431962)*hsa-miR-6717-5p + (0.002511)*hsa-miR-8073 + (−0.337601)*hsa-miR-92a-3p + (−0.029308)*hsa-miR-3652 + (−0.106071)*hsa-miR-6836-3p + (0.006541)*hsa-miR-1193 + (0.875478)*hsa-miR-4436b-5p + (−0.168653)*hsa-miR-6812-5p + (0.053152)*hsa-miR-4663 + (0.1271)*hsa-miR-4652-5p + (−0.591585)*hsa-miR-1343-5p + (0.083892)*hsa-miR-1246 + (−0.216299)*hsa-miR-4448 + (0.733901)*hsa-miR-6722-3p + (−0.137186)*hsa-miR-6826-5p + (0.036726)*hsa-miR-29b-3p + (2.472847)*hsa-miR-1908-5p + (−0.089103)*hsa-miR-6840-3p + (−1.496956)*hsa-miR-3197 + (0.336997)*hsa-miR-371b-5p + (0.239512)*hsa-miR-4433a-3p + (−0.478043)*hsa-miR-4534 + (0.099419)*hsa-miR-6816-5p + (−0.531065)*hsa-miR-6800-5p + (−0.259498)*hsa-miR-150-3p + (−0.449811)*hsa-miR-296-3p + (0.096368)*hsa-miR-4771 + (−0.038915)*hsa-miR-1908-3p + (−0.083576)*hsa-miR-4298 + (0.128277)*hsa-miR-6774-5p + (0.014162)*hsa-miR-615-5p + (−0.162203)*hsa-miR-4741 + (1.37632)*hsa-miR-1227-5p + (0.203311)*hsa-miR-1185-1-3p + (0.2478)*hsa-miR-6765-3p + (0.659776)*hsa-miR-6741-5p + (−0.422742)*hsa-miR-5739 + (−0.062029)*hsa-miR-373-5p + (0.417561)*hsa-miR-663a + (−3.034528)*hsa-miR-1228-5p + (0.156515)*hsa-miR-642b-3p + (−0.296177)*hsa-miR-4728-5p + (−0.798202)*hsa-miR-937-5p + (−0.004472)*hsa-miR-887-3p + (0.524208)*hsa-miR-6124 + (0.169608)*hsa-miR-6075 + (−0.183942)*hsa-miR-6778-5p + (−0.117397)*hsa-miR-6762-5p + (−0.458025)*hsa-miR-4484 + (−3.409511)*hsa-miR-6087 + (0.076078)*hsa-miR-6760-5p + (0.488415)*hsa-miR-1237-5p + (−0.034753)*hsa-miR-711 + (−0.380955)*hsa-miR-4270 + (−0.292588)*hsa-miR-4710 + (0.830594)*hsa-miR-5195-3p + (0.674073)*hsa-miR-128-2-5p + (−0.603804)*hsa-miR-149-3p + (−0.440067)*hsa-miR-1914-3p + (0.573642)*hsa-miR-4763-3p + (0.088688)*hsa-miR-6726-5p + (−0.007254)*hsa-miR-1207-5p + (0.614477)*hsa-miR-4675 + (0.216859)*hsa-miR-328-5p + (−0.069761)*hsa-miR-6716-5p + (0.381322)*hsa-miR-4455 + (0.748721)*hsa-miR-3619-3p + (0.045501)*hsa-miR-3160-5p + (2.573042)*hsa-miR-6724-5p + (−0.17771)*hsa-miR-423-5p + (0.011489)*hsa-miR-92a-2-5p + (−0.344767)*hsa-miR-4447 + (−1.078043)*hsa-miR-3621 + (0.794977)*hsa-miR-4739 + (0.368263)*hsa-miR-6132 + (−2.288217)*hsa-miR-6791-5p + (−1.158644)*hsa-miR-4725-3p + (−0.156604)*hsa-miR-3158-5p + (−0.254161)*hsa-miR-6766-3p + (−0.305986)*hsa-miR-6879-5p + (−0.236762)*hsa-miR-940 + (0.414075)*hsa-miR-4750-5p + (−0.071799)*hsa-miR-3154 + (0.996824)*hsa-miR-3663-3p + (−0.282559)*hsa-miR-4655-5p + (−1.520084)*hsa-miR-4649-5p + (−0.48277)*hsa-miR-4640-5p + (0.064498)*hsa-miR-4783-3p + (0.472275)*hsa-miR-6869-5p + (−0.955611)*hsa-miR-1343-3p + (−0.204386)*hsa-miR-6771-5p + (−0.12549)*hsa-miR-7108-3p + (−0.487461)*hsa-miR-3195 + (0.872821)*hsa-miR-4687-3p + (0.203465)*hsa-miR-1185-2-3p + (−0.087519)*hsa-miR-1225-5p + (−0.01442)*hsa-miR-4322 + (−0.583521)*hsa-miR-6088 + (1.301175)*hsa-miR-6785-5p + (0.27416)*hsa-miR-6777-5p + (−0.307199)*hsa-miR-4695-5p + (−0.11423)*hsa-miR-6880-3p + 39.943135 | 0.65 |

TABLE 16-1

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| 1 | 1 | hsa-miR-6087 | 1 | 0.92 | 0.83 | 0.86 | 0.90 | 0.90 | 0.84 | 0.86 | 0.91 |
| 2 | 2 | hsa-miR-4652-5p | 104 | 0.94 | 0.83 | 0.86 | 0.92 | 0.94 | 0.84 | 0.87 | 0.93 |
| | | hsa-miR-6087 | 1 | | | | | | | | |
| 3 | 3 | hsa-miR-4652-5p | 104 | 0.93 | 0.88 | 0.89 | 0.94 | 0.92 | 0.89 | 0.90 | 0.94 |
| | | hsa-miR-6087 | 1 | | | | | | | | |
| | | hsa-miR-6724-5p | 166 | | | | | | | | |
| 4 | 4 | hsa-miR-4652-5p | 104 | 0.95 | 0.87 | 0.90 | 0.94 | 0.93 | 0.88 | 0.89 | 0.94 |
| | | hsa-miR-6087 | 1 | | | | | | | | |
| | | hsa-miR-3160-5p | 35 | | | | | | | | |
| | | hsa-miR-6724-5p | 166 | | | | | | | | |
| 5 | 5 | hsa-miR-4658 | 107 | 0.94 | 0.89 | 0.91 | 0.94 | 0.92 | 0.90 | 0.91 | 0.95 |
| | | hsa-miR-4652-5p | 104 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| 6 | 7 | hsa-miR-4658 | 107 | 0.95 | 0.89 | 0.91 | 0.95 | 0.92 | 0.89 | 0.90 | 0.95 |
| | | hsa-miR-4652-5p | 104 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| 7 | 10 | hsa-miR-4658 | 107 | 0.94 | 0.90 | 0.91 | 0.95 | 0.92 | 0.92 | 0.92 | 0.96 |
| | | hsa-miR-4436b-5p | 76 | | | | | | | | |
| | | hsa-miR-4652-5p | 104 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 8 | 11 | hsa-miR-4658 | 107 | 0.95 | 0.91 | 0.92 | 0.96 | 0.92 | 0.91 | 0.91 | 0.96 |
| | | hsa-miR-4436b-5p | 76 | | | | | | | | |
| | | hsa-miR-4652-5p | 104 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 9 | 12 | hsa-miR-4658 | 107 | 0.95 | 0.91 | 0.92 | 0.96 | 0.93 | 0.92 | 0.92 | 0.97 |
| | | hsa-miR-4436b-5p | 76 | | | | | | | | |
| | | hsa-miR-4652-5p | 104 | | | | | | | | |
| | | hsa-miR-371b-5p | 59 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 10 | 13 | hsa-miR-4658 | 107 | 0.95 | 0.92 | 0.93 | 0.97 | 0.92 | 0.93 | 0.93 | 0.97 |
| | | hsa-miR-4436b-5p | 76 | | | | | | | | |
| | | hsa-miR-4652-5p | 104 | | | | | | | | |
| | | hsa-miR-371b-5p | 59 | | | | | | | | |
| | | hsa-miR-615-5p | 155 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 11 | 15 | hsa-miR-4658 | 107 | 0.95 | 0.93 | 0.93 | 0.97 | 0.92 | 0.93 | 0.93 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-371b-5p | 59 | | | | | | | | |
| | | hsa-miR-615-5p | 155 | | | | | | | | |
| | | hsa-miR-4741 | 131 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| 12 | 19 | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| | | hsa-miR-4658 | 107 | 0.96 | 0.91 | 0.93 | 0.97 | 0.93 | 0.91 | 0.92 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-615-5p | 155 | | | | | | | | |
| | | hsa-miR-4741 | 131 | | | | | | | | |
| 13 | 20 | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| | | hsa-miR-4658 | 107 | 0.97 | 0.91 | 0.93 | 0.97 | 0.94 | 0.91 | 0.92 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-615-5p | 155 | | | | | | | | |
| | | hsa-miR-4741 | 131 | | | | | | | | |
| 14 | 21 | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| | | hsa-miR-4658 | 107 | 0.94 | 0.94 | 0.94 | 0.98 | 0.91 | 0.94 | 0.93 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| 15 | 24 | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| | | hsa-miR-4658 | 107 | 0.95 | 0.94 | 0.94 | 0.98 | 0.92 | 0.94 | 0.94 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 16 | 25 | hsa-miR-4658 | 107 | 0.96 | 0.94 | 0.94 | 0.98 | 0.92 | 0.94 | 0.93 | 0.98 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 17 | 26 | hsa-miR-4658 | 107 | 0.96 | 0.94 | 0.94 | 0.98 | 0.92 | 0.94 | 0.94 | 0.98 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| 18 | 29 | hsa-miR-4658 | 107 | 0.96 | 0.94 | 0.95 | 0.98 | 0.94 | 0.94 | 0.94 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-371b-5p | 59 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7107-5p | 215 | | | | | | | | |
| 19 | 31 | hsa-miR-4658 | 107 | 0.96 | 0.94 | 0.95 | 0.98 | 0.95 | 0.94 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7107-5p | 215 | | | | | | | | |
| 20 | 32 | hsa-miR-4658 | 107 | 0.97 | 0.94 | 0.95 | 0.99 | 0.95 | 0.94 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7107-5p | 215 | | | | | | | | |
| 21 | 34 | hsa-miR-4658 | 107 | 0.97 | 0.95 | 0.95 | 0.99 | 0.95 | 0.95 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7108-3p | 216 | | | | | | | | |
| | | hsa-miR-7107-5p | 215 | | | | | | | | |
| 22 | 35 | hsa-miR-4658 | 107 | 0.95 | 0.96 | 0.96 | 0.99 | 0.93 | 0.96 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |

TABLE 16-1-continued

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-6879-5p | 210 | | | | | | | | |
| | | hsa-miR-6781-5p | 185 | | | | | | | | |
| | | hsa-miR-7108-3p | 216 | | | | | | | | |
| | | hsa-miR-7107-5p | 215 | | | | | | | | |
| 23 | 40 | hsa-miR-4658 | 107 | 0.98 | 0.95 | 0.96 | 0.99 | 0.95 | 0.94 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-3917 | 61 | | | | | | | | |
| | | hsa-miR-7108-3p | 216 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 24 | 43 | hsa-miR-4658 | 107 | 0.98 | 0.95 | 0.96 | 0.99 | 0.95 | 0.95 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-4710 | 120 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-7108-3p | 216 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 25 | 46 | hsa-miR-498 | 140 | 0.98 | 0.96 | 0.96 | 0.99 | 0.95 | 0.95 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 26 | 50 | hsa-miR-498 | 140 | 0.98 | 0.96 | 0.97 | 0.99 | 0.95 | 0.95 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 27 | 56 | hsa-miR-498 | 140 | 0.98 | 0.96 | 0.97 | 0.99 | 0.95 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 28 | 60 | hsa-miR-498 | 140 | 0.98 | 0.98 | 0.98 | 0.99 | 0.94 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| 29 | 61 | hsa-miR-498 | 140 | 0.99 | 0.97 | 0.98 | 0.99 | 0.94 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 30 | 62 | hsa-miR-498 | 140 | 0.99 | 0.98 | 0.98 | 1.00 | 0.94 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |

TABLE 16-1-continued

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 31 | 65 | hsa-miR-498 | 140 | 0.98 | 0.99 | 0.99 | 1.00 | 0.92 | 0.97 | 0.96 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-4771 | 135 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 32 | 71 | hsa-miR-498 | 140 | 0.98 | 0.99 | 0.99 | 1.00 | 0.92 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 33 | 75 | hsa-miR-498 | 140 | 0.99 | 0.99 | 0.99 | 1.00 | 0.94 | 0.97 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-29b-3p | 31 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-711 | 218 | | | | | | | | |
| | | hsa-miR-4710 | 120 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 34 | 77 | hsa-miR-498 | 140 | 0.99 | 0.99 | 0.99 | 1.00 | 0.94 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-29b-3p | 31 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-711 | 218 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 35 | 78 | hsa-miR-498 | 140 | 1.00 | 0.99 | 0.99 | 1.00 | 0.94 | 0.97 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-6780b-5p | 184 | | | | | | | | |
| | | hsa-miR-6722-3p | 165 | | | | | | | | |
| | | hsa-miR-29b-3p | 31 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 36 | 85 | hsa-miR-498 | 140 | 1.00 | 0.99 | 0.99 | 1.00 | 0.95 | 0.97 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4649-5p | 102 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 37 | 87 | hsa-miR-498 | 140 | 1.00 | 1.00 | 1.00 | 1.00 | 0.93 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-6836-3p | 202 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4649-5p | 102 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 38 | 89 | hsa-miR-498 | 140 | 1.00 | 1.00 | 1.00 | 1.00 | 0.94 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-6836-3p | 202 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |

TABLE 16-1-continued

| No. | Number of miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| | hsa-miR-29b-3p | 31 | | | | | | | | |
| | hsa-miR-1908-5p | 23 | | | | | | | | |
| | hsa-miR-6840-3p | 203 | | | | | | | | |
| | hsa-miR-3197 | 43 | | | | | | | | |
| | hsa-miR-371b-5p | 59 | | | | | | | | |
| | hsa-miR-4433a-3p | 75 | | | | | | | | |
| | hsa-miR-4534 | 97 | | | | | | | | |
| | hsa-miR-6800-5p | 193 | | | | | | | | |
| | hsa-miR-150-3p | 236 | | | | | | | | |
| | hsa-miR-296-3p | 30 | | | | | | | | |
| | hsa-miR-4771 | 135 | | | | | | | | |
| | hsa-miR-4298 | 68 | | | | | | | | |
| | hsa-miR-6782-5p | 186 | | | | | | | | |
| | hsa-miR-6510-5p | 158 | | | | | | | | |
| | hsa-miR-4741 | 131 | | | | | | | | |
| | hsa-miR-1227-5p | 7 | | | | | | | | |
| | hsa-miR-1185-1-3p | 2 | | | | | | | | |
| | hsa-miR-6765-3p | 176 | | | | | | | | |
| | hsa-miR-6741-5p | 169 | | | | | | | | |
| | hsa-miR-5739 | 147 | | | | | | | | |
| | hsa-miR-373-5p | 60 | | | | | | | | |
| | hsa-miR-663a | 240 | | | | | | | | |
| | hsa-miR-1228-5p | 9 | | | | | | | | |
| | hsa-miR-4728-5p | 126 | | | | | | | | |
| | hsa-miR-937-5p | 228 | | | | | | | | |
| | hsa-miR-887-3p | 227 | | | | | | | | |
| | hsa-miR-6124 | 151 | | | | | | | | |
| | hsa-miR-6075 | 148 | | | | | | | | |
| | hsa-miR-6794-5p | 192 | | | | | | | | |
| | hsa-miR-6778-5p | 183 | | | | | | | | |
| | hsa-miR-4484 | 90 | | | | | | | | |
| | hsa-miR-6087 | 1 | | | | | | | | |
| | hsa-miR-6760-5p | 174 | | | | | | | | |
| | hsa-miR-1237-5p | 10 | | | | | | | | |
| | hsa-miR-711 | 218 | | | | | | | | |
| | hsa-miR-4270 | 66 | | | | | | | | |
| | hsa-miR-4710 | 120 | | | | | | | | |
| | hsa-miR-5195-3p | 144 | | | | | | | | |
| | hsa-miR-149-3p | 235 | | | | | | | | |
| | hsa-miR-1914-3p | 237 | | | | | | | | |
| | hsa-miR-4675 | 110 | | | | | | | | |
| | hsa-miR-328-5p | 46 | | | | | | | | |
| | hsa-miR-4455 | 83 | | | | | | | | |
| | hsa-miR-3619-3p | 50 | | | | | | | | |
| | hsa-miR-3160-5p | 35 | | | | | | | | |
| | hsa-miR-6724-5p | 166 | | | | | | | | |
| | hsa-miR-6803-5p | 195 | | | | | | | | |
| | hsa-miR-423-5p | 239 | | | | | | | | |
| | hsa-miR-4447 | 79 | | | | | | | | |
| | hsa-miR-3621 | 52 | | | | | | | | |
| | hsa-miR-6132 | 153 | | | | | | | | |
| | hsa-miR-6791-5p | 191 | | | | | | | | |
| | hsa-miR-4725-3p | 123 | | | | | | | | |
| | hsa-miR-3158-5p | 34 | | | | | | | | |
| | hsa-miR-6766-3p | 178 | | | | | | | | |
| | hsa-miR-6879-5p | 210 | | | | | | | | |
| | hsa-miR-940 | 243 | | | | | | | | |
| | hsa-miR-4750-5p | 132 | | | | | | | | |
| | hsa-miR-3154 | 33 | | | | | | | | |
| | hsa-miR-3917 | 61 | | | | | | | | |
| | hsa-miR-3663-3p | 57 | | | | | | | | |
| | hsa-miR-4649-5p | 102 | | | | | | | | |
| | hsa-miR-4640-5p | 101 | | | | | | | | |
| | hsa-miR-6749-5p | 173 | | | | | | | | |
| | hsa-miR-6869-5p | 207 | | | | | | | | |
| | hsa-miR-1343-3p | 17 | | | | | | | | |
| | hsa-miR-6771-5p | 180 | | | | | | | | |
| | hsa-miR-7108-3p | 216 | | | | | | | | |
| | hsa-miR-4687-3p | 111 | | | | | | | | |
| | hsa-miR-1185-2-3p | 3 | | | | | | | | |
| | hsa-miR-6088 | 150 | | | | | | | | |
| | hsa-miR-6785-5p | 188 | | | | | | | | |
| | hsa-miR-6777-5p | 182 | | | | | | | | |
| | hsa-miR-4695-5p | 114 | | | | | | | | |
| | hsa-miR-6880-3p | 211 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| 39 | 91 | hsa-miR-498 | 140 | 1.00 | 1.00 | 1.00 | 1.00 | 0.94 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 40 | 92 | hsa-miR-498 | 140 | 1.00 | 1.00 | 1.00 | 1.00 | 0.93 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-4675 | 110 | | | | | | | | |
| | | hsa-miR-328-5p | 46 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 41 | 96 | hsa-miR-498 | 140 | 1.00 | 1.00 | 1.00 | 1.00 | 0.93 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-3652 | 55 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-1246 | 231 | | | | | | | | |
| | | hsa-miR-4448 | 80 | | | | | | | | |
| | | hsa-miR-6722-3p | 165 | | | | | | | | |
| | | hsa-miR-6826-5p | 200 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-1225-5p | 6 | | | | | | | | |
| | | hsa-miR-4322 | 69 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 42 | 101 | hsa-miR-498 | 140 | 1.00 | 1.00 | 1.00 | 1.00 | 0.92 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-3652 | 55 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-1246 | 231 | | | | | | | | |
| | | hsa-miR-4448 | 80 | | | | | | | | |
| | | hsa-miR-6722-3p | 165 | | | | | | | | |
| | | hsa-miR-6826-5p | 200 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6774-5p | 181 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-6762-5p | 175 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-128-2-5p | 16 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-1207-5p | 230 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-3195 | 42 | | | | | | | | |
| | | hsa-miR-4687-3p | 111 | | | | | | | | |
| | | hsa-miR-1185-2-3p | 3 | | | | | | | | |
| | | hsa-miR-1225-5p | 6 | | | | | | | | |
| | | hsa-miR-4322 | 69 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 43 | 103 | hsa-miR-498 | 140 | 1.00 | 1.00 | 1.00 | 1.00 | 0.92 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-3652 | 55 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-1246 | 231 | | | | | | | | |
| | | hsa-miR-4448 | 80 | | | | | | | | |
| | | hsa-miR-6722-3p | 165 | | | | | | | | |
| | | hsa-miR-6826-5p | 200 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-1908-3p | 22 | | | | | | | | |
| | | hsa-miR-4298 | 68 | | | | | | | | |
| | | hsa-miR-6782-5p | 186 | | | | | | | | |
| | | hsa-miR-6774-5p | 181 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-6762-5p | 175 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-128-2-5p | 16 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-1207-5p | 230 | | | | | | | | |
| | | hsa-miR-4675 | 110 | | | | | | | | |
| | | hsa-miR-328-5p | 46 | | | | | | | | |
| | | hsa-miR-6716-5p | 163 | | | | | | | | |
| | | hsa-miR-4455 | 83 | | | | | | | | |
| | | hsa-miR-3619-3p | 50 | | | | | | | | |

TABLE 16-1-continued

| No. | Number of miRNA | miRNA marker | SEQ ID NO | Training cohort Sensitivity | Specificity | Accuracy | AUC | Validation cohort Sensitivity | Specificity | Accuracy | AUC |
|---|---|---|---|---|---|---|---|---|---|---|---|
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-3195 | 42 | | | | | | | | |
| | | hsa-miR-4687-3p | 111 | | | | | | | | |
| | | hsa-miR-1185-2-3p | 3 | | | | | | | | |
| | | hsa-miR-1225-5p | 6 | | | | | | | | |
| | | hsa-miR-4322 | 69 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |

TABLE 16-2

| No. | Number of miRNA | Discriminant formula | Threshold |
|---|---|---|---|
| 1 | 1 | (−0.2257)*hsa-miR-6087 + 1.8523 | 0.31 |
| 2 | 2 | (0.0164)*hsa-miR-4652-5p + (−0.5961)*hsa-miR-6087 + 6.1988 | 0.32 |
| 3 | 3 | (0.16644)*hsa-miR-4652-5p + (−1.41622)*hsa-miR-6087 + (0.02095)*hsa-miR-6724-5p + 15.02714 | 0.36 |
| 4 | 4 | (0.1808861)*hsa-miR-4652-5p + (−1.5070947)*hsa-miR-6087 + (0.0007174)*hsa-miR-3160-5p + (0.1207611)*hsa-miR-6724-5p + 14.9701037 | 0.35 |
| 5 | 5 | (0.002311)*hsa-miR-4658 + (0.202102)*hsa-miR-4652-5p + (−1.666837)*hsa-miR-6087 + (0.019725)*hsa-miR-3160-5p + (0.296171)*hsa-miR-6724-5p + 14.733283 | 0.37 |
| 6 | 7 | (0.009276)*hsa-miR-4658 + (0.20617)*hsa-miR-4652-5p + (−1.751108)*hsa-miR-6087 + (0.024037)*hsa-miR-3160-5p + (0.378666)*hsa-miR-6724-5p + (−0.051277)*hsa-miR-3940-5p + (0.011812)*hsa-miR-744-5p + 15.225552 | 0.36 |
| 7 | 10 | (0.01504)*hsa-miR-4658 + (0.01562)*hsa-miR-4436b-5p + (0.20522)*hsa-miR-4652-5p + (−0.01556)*hsa-miR-4728-5p + (−1.8352)*hsa-miR-6087 + (0.02667)*hsa-miR-3160-5p + (0.43956)*hsa-miR-6724-5p + (−0.07772)*hsa-miR-3940-5p + (0.03616)*hsa-miR-744-5p + (−0.07753)*hsa-miR-6781-5p + 16.37274 | 0.38 |
| 8 | 11 | (0.03167)*hsa-miR-4658 + (0.09435)*hsa-miR-4436b-5p + (0.19419)*hsa-miR-4652-5p + (0.01619)*hsa-miR-1185-1-3p + (−0.11191)*hsa-miR-4728-5p + (−2.06954)*hsa-miR-6087 + (0.03364)*hsa-miR-3160-5p + (0.56712)*hsa-miR-6724-5p + (−0.14439)*hsa-miR-3940-5p + (0.10593)*hsa-miR-744-5p + (−0.32248)*hsa-miR-6781-5p + 20.26016 | 0.36 |
| 9 | 12 | (0.03713)*hsa-miR-4658 + (0.11667)*hsa-miR-4436b-5p + (0.189004)*hsa-miR-4652-5p + (0.005898)*hsa-miR-371b-5p + (0.039419)*hsa-miR-1185-1-3p + (−0.146518)*hsa-miR-4728-5p + (−2.150252)*hsa-miR-6087 + (0.035932)*hsa-miR-3160-5p + (0.608954)*hsa-miR-6724-5p + (−0.168797)*hsa-miR-3940-5p + (0.121841)*hsa-miR-744-5p + (−0.385564)*hsa-miR-6781-5p + 21.366641 | 0.37 |
| 10 | 13 | (0.0429991)*hsa-miR-4658 + (0.1381963)*hsa-miR-4436b-5p + (0.1833864)*hsa-miR-4652-5p + (0.0179274)*hsa-miR-371b-5p + (0.0001277)*hsa-miR-615-5p + (0.0616732)*hsa-miR-1185-1-3p + (−0.1811192)*hsa-miR-4728-5p + (−2.2275877)*hsa-miR-6087 + (0.0377038)*hsa-miR-3160-5p + (0.6494946)*hsa-miR-6724-5p + (−0.1937249)*hsa-miR-3940-5p + (0.1366046)*hsa-miR-744-5p + (−0.4462679)*hsa-miR-6781-5p + 22.4212387 | 0.39 |

TABLE 16-2-continued

| No. | Number of miRNA | Discriminant formula | Threshold |
|---|---|---|---|
| 11 | 15 | (0.04868)*hsa-miR-4658 + (0.1596)*hsa-miR-4436b-5p + (0.01008)*hsa-miR-3648 + (0.17694)*hsa-miR-4652-5p + (0.02936)*hsa-miR-371b-5p + (0.01377)*hsa-miR-615-5p + (−0.03414)*hsa-miR-4741 + (0.08073)*hsa-miR-1185-1-3p + (−0.2158)*hsa-miR-4728-5p + (−2.29949)*hsa-miR-6087 + (0.0386)*hsa-miR-3160-5p + (0.67766)*hsa-miR-6724-5p + (−0.20413)*hsa-miR-3940-5p + (0.15988)*hsa-miR-744-5p + (−0.49283)*hsa-miR-6781-5p + 23.30088 | 0.40 |
| 12 | 19 | (0.0545478)*hsa-miR-4658 + (0.1795112)*hsa-miR-4436b-5p + (0.048759)*hsa-miR-3648 + (0.1692288)*hsa-miR-4652-5p + (−0.0684148)*hsa-miR-3197 + (0.0431115)*hsa-miR-371b-5p + (0.0302838)*hsa-miR-615-5p + (−0.1288749)*hsa-miR-4741 + (0.1008699)*hsa-miR-1185-1-3p + (−0.2404256)*hsa-miR-4728-5p + (−2.360469)*hsa-miR-6087 + (0.0404386)*hsa-miR-3160-5p + (0.6919792)*hsa-miR-6724-5p + (0.0004152)*hsa-miR-6819-5p + (−0.1806119)*hsa-miR-3940-5p + (0.0194496)*hsa-miR-6132 + (0.1868626)*hsa-miR-744-5p + (−0.0039427)*hsa-miR-4725-3p + (−0.4901648)*hsa-miR-6781-5p + 23.9287144 | 0.33 |
| 13 | 20 | (0.06046)*hsa-miR-4658 + (0.19475)*hsa-miR-4436b-5p + (0.09219)*hsa-miR-3648 + (0.16051)*hsa-miR-4652-5p + (−0.14362)*hsa-miR-3197 + (0.05679)*hsa-miR-371b-5p + (0.04647)*hsa-miR-615-5p + (−0.20246)*hsa-miR-4741 + (0.11951)*hsa-miR-1185-1-3p + (−0.01352)*hsa-miR-1228-5p + (−0.26292)*hsa-miR-4728-5p + (−2.39084)*hsa-miR-6087 + (0.04249)*hsa-miR-3160-5p + (0.70554)*hsa-miR-6724-5p + (0.0217)*hsa-miR-6819-5p + (−0.15258)*hsa-miR-3940-5p + (0.09549)*hsa-miR-6132 + (0.17448)*hsa-miR-744-5p + (−0.06463)*hsa-miR-4725-3p + (−0.47787)*hsa-miR-6781-5p + 24.23126 | 0.31 |
| 14 | 21 | (0.066135)*hsa-miR-4658 + (0.210367)*hsa-miR-4436b-5p + (0.136069)*hsa-miR-3648 + (0.151755)*hsa-miR-4652-5p + (−0.217055)*hsa-miR-3197 + (0.070549)*hsa-miR-371b-5p + (−0.001876)*hsa-miR-4298 + (0.061013)*hsa-miR-615-5p + (−0.263946)*hsa-miR-4741 + (0.139502)*hsa-miR-1185-1-3p + (−0.046762)*hsa-miR-1228-5p + (−0.285675)*hsa-miR-4728-5p + (−2.418102)*hsa-miR-6087 + (0.044076)*hsa-miR-3160-5p + (0.719969)*hsa-miR-6724-5p + (0.043873)*hsa-miR-6819-5p + (−0.124564)*hsa-miR-3940-5p + (0.182436)*hsa-miR-6132 + (0.148256)*hsa-miR-744-5p + (−0.128576)*hsa-miR-4725-3p + (−0.465727)*hsa-miR-6781-5p + 24.630655 | 0.42 |
| 15 | 24 | (0.07227)*hsa-miR-4658 + (0.225563)*hsa-miR-4436b-5p + (0.17854)*hsa-miR-3648 + (0.143323)*hsa-miR-4652-5p + (−0.283779)*hsa-miR-3197 + (0.084485)*hsa-miR-371b-5p + (−0.008989)*hsa-miR-4298 + (0.073689)*hsa-miR-615-5p + (−0.314832)*hsa-miR-4741 + (0.158462)*hsa-miR-1185-1-3p + (−0.083694)*hsa-miR-1228-5p + (−0.30272)*hsa-miR-4728-5p + (−0.012772)*hsa-miR-6794-5p + (−2.449261)*hsa-miR-6087 + (−0.003903)*hsa-miR-1914-3p + (0.001884)*hsa-miR-4455 + (0.045298)*hsa-miR-3160-5p + (0.733649)*hsa-miR-6724-5p + (0.068992)*hsa-miR-6819-5p + (−0.106286)*hsa-miR-3940-5p + (0.270347)*hsa-miR-6132 + (0.115944)*hsa-miR-744-5p + (−0.189204)*hsa-miR-4725-3p + (−0.45218)*hsa-miR-6781-5p + 25.200838 | 0.40 |
| 16 | 25 | (0.078288)*hsa-miR-4658 + (0.234354)*hsa-miR-4436b-5p + (0.223491)*hsa-miR-3648 + (0.13527)*hsa-miR-4652-5p + (−0.325939)*hsa-miR-3197 + (0.09817)*hsa-miR-371b-5p + (−0.009864)*hsa-miR-4298 + (0.087172)*hsa-miR-615-5p + (−0.33558)*hsa-miR-4741 + (0.173811)*hsa-miR-1185-1-3p + (−0.128776)*hsa-miR-1228-5p + (−0.311676)*hsa-miR-4728-5p + (−0.053572)*hsa-miR-6794-5p + (−2.490183)*hsa-miR-6087 + (−0.054436)*hsa-miR-1914-3p + (0.010721)*hsa-miR-4455 + (0.046006)*hsa-miR-3160-5p + (0.750534)*hsa-miR-6724-5p + (0.103104)*hsa-miR-6819-5p + (−0.106925)*hsa-miR-3940-5p + (−0.019416)*hsa-miR-3621 + (0.355495)*hsa-miR-6132 + (0.073636)*hsa-miR-744-5p + (−0.237701)*hsa-miR-4725-3p + (−0.429229)*hsa-miR-6781-5p + 26.170495 | 0.39 |
| 17 | 26 | (0.083783)*hsa-miR-4658 + (0.243613)*hsa-miR-4436b-5p + (0.269101)*hsa-miR-3648 + (0.127433)*hsa-miR-4652-5p + (−0.368851)*hsa-miR-3197 + (0.112057)*hsa-miR-371b-5p + (−0.010206)*hsa-miR-4298 + (0.100065)*hsa-miR-615-5p + (−0.350807)*hsa-miR-4741 + (0.188858)*hsa-miR-1185-1-3p + (−0.176919)*hsa-miR-1228-5p + (−0.32006)*hsa-miR-4728-5p + (−0.093763)*hsa-miR-6794-5p + (−2.53136)*hsa-miR-6087 + (−0.103708)*hsa-miR-1914-3p + (0.019746)*hsa-miR-4455 + (0.046344)*hsa-miR-3160-5p + (0.769953)*hsa-miR-6724-5p + (0.138504)*hsa-miR-6819-5p + (−0.102495)*hsa-miR-3940-5p + (−0.048051)*hsa-miR-3621 + (0.437372)*hsa-miR-6132 + (0.032543)*hsa-miR-744-5p + (−0.284094)*hsa-miR-4725-3p + (−0.006409)*hsa-miR-6879-5p + (−0.404277)*hsa-miR-6781-5p + 27.158162 | 0.37 |
| 18 | 29 | (0.087755)*hsa-miR-4658 + (0.005605)*hsa-miR-6717-5p + (0.249795)*hsa-miR-4436b-5p + (0.310768)*hsa-miR-3648 + (0.118877)*hsa-miR-4652-5p + (−0.047254)*hsa-miR-1343-5p + (−0.403849)*hsa-miR-3197 + (0.127993)*hsa-miR-371b-5p + (−0.010857)*hsa-miR-150-3p + (−0.010423)*hsa-miR-4298 + (0.11002)*hsa-miR-615-5p + (−0.35805)*hsa-miR-4741 + (0.205029)*hsa-miR-1185-1-3p + (−0.209555)*hsa-miR-1228-5p + (−0.326719)*hsa-miR-4728-5p + (−0.130857)*hsa-miR-6794-5p + (−2.574218)*hsa-miR-6087 + (−0.142216)*hsa-miR-1914-3p + (0.030074)*hsa-miR-4455 + (0.045325)*hsa-miR-3160-5p + (0.795003)*hsa-miR-6724-5p + (0.180288)*hsa-miR-6819-5p + (−0.093405)*hsa-miR-3940-5p + (−0.084781)*hsa-miR-3621 + (0.516536)*hsa-miR-6132 + (−0.321449)*hsa-miR-4725-3p + (−0.061921)*hsa-miR-6879-5p + (−0.350956)*hsa-miR-6781-5p + (0.010576)*hsa-miR-7107-5p + 28.17408 | 0.37 |

TABLE 16-2-continued

| No. | Number of miRNA | Discriminant formula | Threshold |
|---|---|---|---|
| 19 | 31 | (0.09131)*hsa-miR-4658 + (0.02516)*hsa-miR-6717-5p + (0.25587)*hsa-miR-4436b-5p + (0.34611)*hsa-miR-3648 + (0.11032)*hsa-miR-4652-5p + (−0.12588)*hsa-miR-1343-5p + (−0.45686)*hsa-miR-3197 + (0.14448)*hsa-miR-371b-5p + (−0.03123)*hsa-miR-150-3p + (−0.01034)*hsa-miR-4298 + (0.11806)*hsa-miR-615-5p + (−0.3519)*hsa-miR-4741 + (0.21967)*hsa-miR-1185-1-3p + (−0.21585)*hsa-miR-1228-5p + (−0.32729)*hsa-miR-4728-5p + (−0.04138)*hsa-miR-937-5p + (−0.14605)*hsa-miR-6794-5p + (−2.61942)*hsa-miR-6087 + (−0.17232)*hsa-miR-1914-3p + (0.04136)*hsa-miR-4455 + (0.04466)*hsa-miR-3160-5p + (0.82488)*hsa-miR-6724-5p + (0.20759)*hsa-miR-6819-5p + (−0.08453)*hsa-miR-3940-5p + (−0.11768)*hsa-miR-3621 + (0.55873)*hsa-miR-6132 + (−0.02947)*hsa-miR-6791-5p + (−0.36678)*hsa-miR-4725-3p + (−0.11332)*hsa-miR-6879-5p + (−0.28255)*hsa-miR-6781-5p + (0.04109)*hsa-miR-7107-5p + 29.49037 | 0.38 |
| 20 | 32 | (0.094791)*hsa-miR-4658 + (0.048625)*hsa-miR-6717-5p + (0.264267)*hsa-miR-4436b-5p + (0.380769)*hsa-miR-3648 + (0.10237)*hsa-miR-4652-5p + (−0.189993)*hsa-miR-1343-5p + (−0.514811)*hsa-miR-3197 + (0.161137)*hsa-miR-371b-5p + (−0.001127)*hsa-miR-4534 + (−0.051676)*hsa-miR-150-3p + (−0.009346)*hsa-miR-4298 + (0.124758)*hsa-miR-615-5p + (−0.338756)*hsa-miR-4741 + (0.232869)*hsa-miR-1185-1-3p + (−0.227344)*hsa-miR-1228-5p + (−0.323966)*hsa-miR-4728-5p + (−0.101405)*hsa-miR-937-5p + (−0.152489)*hsa-miR-6794-5p + (−2.667492)*hsa-miR-6087 + (−0.198581)*hsa-miR-1914-3p + (0.052818)*hsa-miR-4455 + (0.044682)*hsa-miR-3160-5p + (0.854099)*hsa-miR-6724-5p + (0.234472)*hsa-miR-6819-5p + (−0.073706)*hsa-miR-3940-5p + (−0.148964)*hsa-miR-3621 + (0.603871)*hsa-miR-6132 + (−0.100126)*hsa-miR-6791-5p + (−0.413578)*hsa-miR-4725-3p + (−0.155446)*hsa-miR-6879-5p + (−0.207971)*hsa-miR-6781-5p + (0.065701)*hsa-miR-7107-5p + 30.991858 | 0.36 |
| 21 | 34 | (0.10002)*hsa-miR-4658 + (0.07199)*hsa-miR-6717-5p + (0.27417)*hsa-miR-4436b-5p + (0.41365)*hsa-miR-3648 + (0.09473)*hsa-miR-4652-5p + (−0.24021)*hsa-miR-1343-5p + (−0.55453)*hsa-miR-3197 + (0.17548)*hsa-miR-371b-5p + (−0.01999)*hsa-miR-4534 + (−0.07048)*hsa-miR-150-3p + (−0.00682)*hsa-miR-4298 + (0.12988)*hsa-miR-615-5p + (−0.33497)*hsa-miR-4741 + (0.2437)*hsa-miR-1185-1-3p + (−0.24377)*hsa-miR-1228-5p + (−0.32132)*hsa-miR-4728-5p + (−0.16401)*hsa-miR-937-5p + (−0.15936)*hsa-miR-6794-5p + (−2.71298)*hsa-miR-6087 + (−0.2154)*hsa-miR-1914-3p + (0.01945)*hsa-miR-328-5p + (0.0661)*hsa-miR-4455 + (0.04892)*hsa-miR-3160-5p + (0.88757)*hsa-miR-6724-5p + (0.261)*hsa-miR-6819-5p + (−0.0618)*hsa-miR-3940-5p + (−0.17201)*hsa-miR-3621 + (0.65157)*hsa-miR-6132 + (−0.16978)*hsa-miR-6791-5p + (−0.46802)*hsa-miR-4725-3p + (−0.18535)*hsa-miR-6879-5p + (−0.1364)*hsa-miR-6781-5p + (−0.02025)*hsa-miR-7108-3p + (0.08954)*hsa-miR-7107-5p + 32.08743 | 0.38 |
| 22 | 35 | (0.106228)*hsa-miR-4658 + (0.092222)*hsa-miR-6717-5p + (0.284732)*hsa-miR-4436b-5p + (0.439982)*hsa-miR-3648 + (0.087768)*hsa-miR-4652-5p + (−0.288995)*hsa-miR-1343-5p + (−0.591559)*hsa-miR-3197 + (0.191085)*hsa-miR-371b-5p + (−0.043247)*hsa-miR-4534 + (−0.088277)*hsa-miR-150-3p + (−0.004687)*hsa-miR-4298 + (0.133882)*hsa-miR-615-5p + (−0.318195)*hsa-miR-4741 + (0.250237)*hsa-miR-1185-1-3p + (−0.291289)*hsa-miR-1228-5p + (−0.320973)*hsa-miR-4728-5p + (−0.219894)*hsa-miR-937-5p + (−0.171833)*hsa-miR-6794-5p + (−2.756634)*hsa-miR-6087 + (−0.234623)*hsa-miR-1914-3p + (0.132945)*hsa-miR-328-5p + (0.080522)*hsa-miR-4455 + (0.022315)*hsa-miR-3619-3p + (0.04827)*hsa-miR-3160-5p + (0.929673)*hsa-miR-6724-5p + (0.278857)*hsa-miR-6819-5p + (−0.038975)*hsa-miR-3940-5p + (−0.202026)*hsa-miR-3621 + (0.694335)*hsa-miR-6132 + (−0.237541)*hsa-miR-6791-5p + (−0.521173)*hsa-miR-4725-3p + (−0.216801)*hsa-miR-6879-5p + (−0.064791)*hsa-miR-6781-5p + (−0.044588)*hsa-miR-7108-3p + (0.115002)*hsa-miR-7107-5p + 32.284424 | 0.44 |
| 23 | 40 | (0.111973)*hsa-miR-4658 + (0.108513)*hsa-miR-6717-5p + (0.294888)*hsa-miR-4436b-5p + (0.460115)*hsa-miR-3648 + (0.082018)*hsa-miR-4652-5p + (−0.334555)*hsa-miR-1343-5p + (0.026567)*hsa-miR-6780b-5p + (−0.631472)*hsa-miR-3197 + (0.20582)*hsa-miR-371b-5p + (−0.06753)*hsa-miR-4534 + (−0.107515)*hsa-miR-150-3p + (−0.001806)*hsa-miR-4298 + (0.133652)*hsa-miR-615-5p + (−0.294458)*hsa-miR-4741 + (0.257498)*hsa-miR-1185-1-3p + (0.01499)*hsa-miR-6741-5p + (−0.343534)*hsa-miR-1228-5p + (−0.326044)*hsa-miR-4728-5p + (−0.268281)*hsa-miR-937-5p + (−0.188276)*hsa-miR-6794-5p + (−2.77578)*hsa-miR-6087 + (−0.25326)*hsa-miR-1914-3p + (0.253644)*hsa-miR-328-5p + (0.093434)*hsa-miR-4455 + (0.050867)*hsa-miR-3619-3p + (0.046344)*hsa-miR-3160-5p + (0.96627)*hsa-miR-6724-5p + (0.290969)*hsa-miR-6819-5p + (−0.050563)*hsa-miR-6803-5p + (−0.004193)*hsa-miR-3940-5p + (−0.233693)*hsa-miR-3621 + (0.723891)*hsa-miR-6132 + (−0.2858)*hsa-miR-6791-5p + (−0.573832)*hsa-miR-4725-3p + (−0.249571)*hsa-miR-6879-5p + (−0.015465)*hsa-miR-3917 + (−0.068567)*hsa-miR-7108-3p + (0.014349)*hsa-miR-6777-5p + (0.140758)*hsa-miR-7107-5p + (−0.014775)*hsa-miR-4695-5p + 32.49695 | 0.34 |
| 24 | 43 | (0.1182475)*hsa-miR-4658 + (0.1197803)*hsa-miR-6717-5p + (0.3060598)*hsa-miR-4436b-5p + (0.4666125)*hsa-miR-3648 + (0.0768109)*hsa-miR-4652-5p + (−0.3660127)*hsa-miR-1343-5p + (0.0779078)*hsa-miR-6780b-5p + (−0.6794313)*hsa-miR-3197 + (0.2182454)*hsa-miR-371b-5p + (−0.0872664)*hsa-miR-4534 + (−0.1263997)*hsa-miR-150-3p + (−0.0009949)*hsa-miR-4298 + (0.129891)*hsa-miR-615-5p + (−0.2532054)*hsa-miR- | 0.34 |

TABLE 16-2-continued

| No. | Number of miRNA | Discriminant formula | Threshold |
|---|---|---|---|
|  |  | 4741 + (0.265776)*hsa-miR-1185-1-3p + (0.0488473)*hsa-miR-6741-5p + (0.013876)*hsa-miR-663a + (−0.3824752)*hsa-miR-1228-5p + (−0.3356264)*hsa-miR-4728-5p + (−0.3169805)*hsa-miR-937-5p + (−0.2061267)*hsa-miR-6794-5p + (−2.7881773)*hsa-miR-6087 + (−0.0105542)*hsa-miR-4710 + (−0.277651)*hsa-miR-1914-3p + (0.3577039)*hsa-miR-328-5p + (0.1079767)*hsa-miR-4455 + (0.0793174)*hsa-miR-3619-3p + (0.0456678)*hsa-miR-3160-5p + (0.9874969)*hsa-miR-6724-5p + (0.2962764)*hsa-miR-6819-5p + (−0.1051374)*hsa-miR-6803-5p + (−0.002844)*hsa-miR-423-5p + (−0.2295274)*hsa-miR-3621 + (0.7297914)*hsa-miR-6132 + (−0.2860436)*hsa-miR-6791-5p + (−0.6332234)*hsa-miR-4725-3p + (−0.2612573)*hsa-miR-6879-5p + (0.001209)*hsa-miR-4750-5p + (−0.037947)*hsa-miR-3917 + (−0.0908195)*hsa-miR-7108-3p + (0.0324727)*hsa-miR-6777-5p + (0.1729576)*hsa-miR-7107-5p + (−0.0517144)*hsa-miR-4695-5p + 32.856908 |  |
| 25 | 46 | (−0.005352)*hsa-miR-498 + (0.132232)*hsa-miR-4658 + (0.130356)*hsa-miR-6717-5p + (0.325461)*hsa-miR-4436b-5p + (0.478366)*hsa-miR-3648 + (0.06741)*hsa-miR-4652-5p + (−0.41825)*hsa-miR-1343-5p + (0.190918)*hsa-miR-6780b-5p + (−0.785808)*hsa-miR-3197 + (0.239585)*hsa-miR-371b-5p + (−0.11711)*hsa-miR-4534 + (−0.160321)*hsa-miR-150-3p + (0.006674)*hsa-miR-6510-5p + (0.118254)*hsa-miR-615-5p + (−0.188815)*hsa-miR-4741 + (0.286654)*hsa-miR-1185-1-3p + (0.118796)*hsa-miR-6741-5p + (0.064285)*hsa-miR-663a + (−0.493968)*hsa-miR-1228-5p + (−0.370209)*hsa-miR-4728-5p + (−0.398178)*hsa-miR-937-5p + (−0.256312)*hsa-miR-6794-5p + (−2.807161)*hsa-miR-6087 + (0.005674)*hsa-miR-6760-5p + (−0.054083)*hsa-miR-4710 + (−0.315825)*hsa-miR-1914-3p + (0.571768)*hsa-miR-328-5p + (0.141972)*hsa-miR-4455 + (0.122801)*hsa-miR-3619-3p + (0.049254)*hsa-miR-3160-5p + (1.036085)*hsa-miR-6724-5p + (0.274732)*hsa-miR-6819-5p + (−0.179594)*hsa-miR-6803-5p + (−0.040321)*hsa-miR-423-5p + (−0.228042)*hsa-miR-3621 + (0.719533)*hsa-miR-6132 + (−0.282126)*hsa-miR-6791-5p + (−0.746826)*hsa-miR-4725-3p + (−0.279081)*hsa-miR-6879-5p + (0.030356)*hsa-miR-4750-5p + (−0.077094)*hsa-miR-3917 + (−0.134091)*hsa-miR-7108-3p + (0.041245)*hsa-miR-6785-5p + (0.061812)*hsa-miR-6777-5p + (0.213941)*hsa-miR-7107-5p + (−0.096421)*hsa-miR-4695-5p + 33.494632 | 0.37 |
| 26 | 50 | (−0.016183)*hsa-miR-498 + (0.140525)*hsa-miR-4658 + (0.138752)*hsa-miR-6717-5p + (0.335968)*hsa-miR-4436b-5p + (0.487273)*hsa-miR-3648 + (0.064953)*hsa-miR-4652-5p + (−0.432112)*hsa-miR-1343-5p + (0.235363)*hsa-miR-6780b-5p + (−0.850973)*hsa-miR-3197 + (0.248658)*hsa-miR-371b-5p + (−0.126924)*hsa-miR-4534 + (−0.174476)*hsa-miR-150-3p + (0.010062)*hsa-miR-6510-5p + (0.107952)*hsa-miR-615-5p + (−0.185519)*hsa-miR-4741 + (0.29531)*hsa-miR-1185-1-3p + (0.142125)*hsa-miR-6741-5p + (0.109416)*hsa-miR-663a + (−0.582482)*hsa-miR-1228-5p + (−0.387859)*hsa-miR-4728-5p + (−0.428943)*hsa-miR-937-5p + (−0.284587)*hsa-miR-6794-5p + (−2.807321)*hsa-miR-6087 + (0.012353)*hsa-miR-6760-5p + (−0.076258)*hsa-miR-4710 + (−0.313368)*hsa-miR-1914-3p + (0.003603)*hsa-miR-4675 + (0.661524)*hsa-miR-328-5p + (0.159843)*hsa-miR-4455 + (0.141437)*hsa-miR-3619-3p + (0.051031)*hsa-miR-3160-5p + (1.074899)*hsa-miR-6724-5p + (0.263537)*hsa-miR-6819-5p + (−0.214544)*hsa-miR-6803-5p + (−0.062736)*hsa-miR-423-5p + (−0.24758)*hsa-miR-3621 + (0.705093)*hsa-miR-6132 + (−0.258836)*hsa-miR-6791-5p + (−0.803341)*hsa-miR-4725-3p + (−0.266875)*hsa-miR-6879-5p + (0.03866)*hsa-miR-4750-5p + (−0.091571)*hsa-miR-3917 + (−0.005156)*hsa-miR-4640-5p + (0.013879)*hsa-miR-6869-5p + (−0.043434)*hsa-miR-1343-3p + (−0.150872)*hsa-miR-7108-3p + (0.092865)*hsa-miR-6785-5p + (0.076104)*hsa-miR-6777-5p + (0.210867)*hsa-miR-7107-5p + (−0.113818)*hsa-miR-4695-5p + 34.071261 | 0.37 |
| 27 | 56 | (−0.025128)*hsa-miR-498 + (0.150279)*hsa-miR-4658 + (0.146413)*hsa-miR-6717-5p + (0.346091)*hsa-miR-4436b-5p + (0.488747)*hsa-miR-3648 + (0.001855)*hsa-miR-4663 + (0.063758)*hsa-miR-4652-5p + (−0.432884)*hsa-miR-1343-5p + (0.261209)*hsa-miR-6780b-5p + (−0.909694)*hsa-miR-3197 + (0.257419)*hsa-miR-371b-5p + (−0.13728)*hsa-miR-4534 + (−0.029983)*hsa-miR-6800-5p + (−0.185616)*hsa-miR-150-3p + (0.010955)*hsa-miR-6510-5p + (0.090225)*hsa-miR-615-5p + (−0.173508)*hsa-miR-4741 + (0.297756)*hsa-miR-1185-1-3p + (0.019795)*hsa-miR-6765-3p + (0.160016)*hsa-miR-6741-5p + (0.151585)*hsa-miR-663a + (−0.678957)*hsa-miR-1228-5p + (−0.403793)*hsa-miR-4728-5p + (−0.453454)*hsa-miR-937-5p + (−0.30722)*hsa-miR-6794-5p + (0.006827)*hsa-miR-4467 + (−2.812003)*hsa-miR-6087 + (0.02017)*hsa-miR-6760-5p + (−0.099839)*hsa-miR-4710 + (−0.317017)*hsa-miR-1914-3p + (0.017153)*hsa-miR-4675 + (0.718407)*hsa-miR-328-5p + (0.17689)*hsa-miR-4455 + (0.161061)*hsa-miR-3619-3p + (0.051338)*hsa-miR-3160-5p + (1.118925)*hsa-miR-6724-5p + (0.253304)*hsa-miR-6819-5p + (−0.246149)*hsa-miR-6803-5p + (−0.08142)*hsa-miR-423-5p + (−0.280917)*hsa-miR-3621 + (0.683385)*hsa-miR-6132 + (−0.236794)*hsa-miR-6791-5p + (−0.851365)*hsa-miR-4725-3p + (−0.251738)*hsa-miR-6879-5p + (0.047986)*hsa-miR-4750-5p + (−0.102195)*hsa-miR-3917 + (0.013753)*hsa-miR-3663-3p + (−0.018254)*hsa-miR-4640-5p + (0.031663)*hsa-miR-6869-5p + (−0.109953)*hsa-miR-1343-3p + (−0.163764)*hsa-miR-7108-3p + (0.15356)*hsa-miR-6785-5p + (0.094727)*hsa-miR- | 0.40 |

TABLE 16-2-continued

| No. | Number of miRNA | Discriminant formula | Threshold |
|---|---|---|---|
| | | 6777-5p + (0.216418)*hsa-miR-7107-5p + (−0.128751)*hsa-miR-4695-5p + (−0.01156)*hsa-miR-6880-3p + 35.063631 | |
| 28 | 60 | (−0.033476)*hsa-miR-498 + (0.160482)*hsa-miR-4658 + (0.153174)*hsa-miR-6717-5p + (0.357836)*hsa-miR-4436b-5p + (0.491196)*hsa-miR-3648 + (0.006556)*hsa-miR-4663 + (0.06228)*hsa-miR-4652-5p + (−0.429191)*hsa-miR-1343-5p + (0.262843)*hsa-miR-6780b-5p + (−0.965673)*hsa-miR-3197 + (0.264128)*hsa-miR-371b-5p + (−0.149303)*hsa-miR-4534 + (−0.065688)*hsa-miR-6800-5p + (−0.195996)*hsa-miR-150-3p + (0.0131)*hsa-miR-6510-5p + (0.072706)*hsa-miR-615-5p + (−0.167745)*hsa-miR-4741 + (0.299395)*hsa-miR-1185-1-3p + (0.043399)*hsa-miR-6765-3p + (0.172159)*hsa-miR-6741-5p + (0.190925)*hsa-miR-663a + (−0.779519)*hsa-miR-1228-5p + (−0.416551)*hsa-miR-4728-5p + (−0.477394)*hsa-miR-937-5p + (0.002656)*hsa-miR-6124 + (−0.330452)*hsa-miR-6794-5p + (0.04873)*hsa-miR-4467 + (−2.827049)*hsa-miR-6087 + (0.028353)*hsa-miR-6760-5p + (−0.123965)*hsa-miR-4710 + (−0.004636)*hsa-miR-149-3p + (−0.322782)*hsa-miR-1914-3p + (0.033272)*hsa-miR-4675 + (0.769227)*hsa-miR-328-5p + (0.191889)*hsa-miR-4455 + (0.178119)*hsa-miR-3619-3p + (0.052353)*hsa-miR-3160-5p + (1.159867)*hsa-miR-6724-5p + (0.245814)*hsa-miR-6819-5p + (−0.283498)*hsa-miR-6803-5p + (−0.0966)*hsa-miR-423-5p + (−0.31385)*hsa-miR-3621 + (0.658198)*hsa-miR-6132 + (−0.228957)*hsa-miR-6791-5p + (−0.891201)*hsa-miR-4725-3p + (−0.001459)*hsa-miR-3158-5p + (−0.229001)*hsa-miR-6879-5p + (0.058559)*hsa-miR-4750-5p + (−0.002053)*hsa-miR-3154 + (−0.110177)*hsa-miR-3917 + (0.029693)*hsa-miR-3663-3p + (−0.028108)*hsa-miR-4640-5p + (0.046381)*hsa-miR-6869-5p + (−0.174581)*hsa-miR-1343-3p + (−0.176201)*hsa-miR-7108-3p + (0.218288)*hsa-miR-6785-5p + (0.112388)*hsa-miR-6777-5p + (0.219305)*hsa-miR-7107-5p + (−0.149239)*hsa-miR-4695-5p + (−0.024099)*hsa-miR-6880-3p + 36.341327 | 0.45 |
| 29 | 61 | (−0.041249)*hsa-miR-498 + (0.170449)*hsa-miR-4658 + (0.166117)*hsa-miR-6717-5p + (0.370018)*hsa-miR-4436b-5p + (0.493019)*hsa-miR-3648 + (0.011021)*hsa-miR-4663 + (0.060933)*hsa-miR-4652-5p + (−0.410439)*hsa-miR-1343-5p + (0.263795)*hsa-miR-6780b-5p + (−1.026295)*hsa-miR-3197 + (0.269733)*hsa-miR-371b-5p + (−0.162985)*hsa-miR-4534 + (−0.107377)*hsa-miR-6800-5p + (−0.205333)*hsa-miR-150-3p + (0.017645)*hsa-miR-6510-5p + (0.056041)*hsa-miR-615-5p + (−0.151309)*hsa-miR-4741 + (0.303372)*hsa-miR-1185-1-3p + (0.067986)*hsa-miR-6765-3p + (0.182823)*hsa-miR-6741-5p + (0.226446)*hsa-miR-663a + (−0.871093)*hsa-miR-1228-5p + (−0.430688)*hsa-miR-4728-5p + (−0.502611)*hsa-miR-937-5p + (0.014189)*hsa-miR-6124 + (−0.350623)*hsa-miR-6794-5p + (0.080354)*hsa-miR-4467 + (−2.849998)*hsa-miR-6087 + (0.035229)*hsa-miR-6760-5p + (−0.145723)*hsa-miR-4710 + (−0.116882)*hsa-miR-149-3p + (−0.324402)*hsa-miR-1914-3p + (0.053016)*hsa-miR-4675 + (0.82584)*hsa-miR-328-5p + (0.207109)*hsa-miR-4455 + (0.201113)*hsa-miR-3619-3p + (0.051902)*hsa-miR-3160-5p + (1.199124)*hsa-miR-6724-5p + (0.236232)*hsa-miR-6819-5p + (−0.340769)*hsa-miR-6803-5p + (−0.106507)*hsa-miR-423-5p + (−0.004904)*hsa-miR-4447 + (−0.353785)*hsa-miR-3621 + (0.640129)*hsa-miR-6132 + (−0.214828)*hsa-miR-6791-5p + (−0.928244)*hsa-miR-4725-3p + (−0.00906)*hsa-miR-3158-5p + (−0.201734)*hsa-miR-6879-5p + (0.070328)*hsa-miR-4750-5p + (−0.005114)*hsa-miR-3154 + (−0.115259)*hsa-miR-3917 + (0.041601)*hsa-miR-3663-3p + (−0.035124)*hsa-miR-4640-5p + (0.050827)*hsa-miR-6869-5p + (−0.235473)*hsa-miR-1343-3p + (−0.188808)*hsa-miR-7108-3p + (0.277703)*hsa-miR-6785-5p + (0.128857)*hsa-miR-6777-5p + (0.217732)*hsa-miR-7107-5p + (−0.170371)*hsa-miR-4695-5p + (−0.034768)*hsa-miR-6880-3p + 38.711879 | 0.42 |
| 30 | 62 | (−0.054116)*hsa-miR-498 + (0.180716)*hsa-miR-4658 + (0.177206)*hsa-miR-6717-5p + (0.386132)*hsa-miR-4436b-5p + (0.493623)*hsa-miR-3648 + (0.014476)*hsa-miR-4663 + (0.060374)*hsa-miR-4652-5p + (−0.402066)*hsa-miR-1343-5p + (0.27385)*hsa-miR-6780b-5p + (−1.081641)*hsa-miR-3197 + (0.276823)*hsa-miR-371b-5p + (−0.174718)*hsa-miR-4534 + (−0.148936)*hsa-miR-6800-5p + (−0.21214)*hsa-miR-150-3p + (0.019785)*hsa-miR-6510-5p + (0.038992)*hsa-miR-615-5p + (−0.13442)*hsa-miR-4741 + (0.307253)*hsa-miR-1185-1-3p + (0.090045)*hsa-miR-6765-3p + (0.194432)*hsa-miR-6741-5p + (0.253275)*hsa-miR-663a + (−0.960451)*hsa-miR-1228-5p + (−0.450253)*hsa-miR-4728-5p + (−0.520849)*hsa-miR-937-5p + (0.030634)*hsa-miR-6124 + (−0.362679)*hsa-miR-6794-5p + (0.114534)*hsa-miR-4467 + (−2.879717)*hsa-miR-6087 + (0.042176)*hsa-miR-6760-5p + (−0.166598)*hsa-miR-4710 + (0.029749)*hsa-miR-5195-3p + (−0.21547)*hsa-miR-149-3p + (−0.330451)*hsa-miR-1914-3p + (0.066854)*hsa-miR-4675 + (0.873268)*hsa-miR-328-5p + (0.221817)*hsa-miR-4455 + (0.224266)*hsa-miR-3619-3p + (0.050875)*hsa-miR-3160-5p + (1.242654)*hsa-miR-6724-5p + (0.216904)*hsa-miR-6819-5p + (−0.386273)*hsa-miR-6803-5p + (−0.115325)*hsa-miR-423-5p + (−0.026966)*hsa-miR-4447 + (−0.388486)*hsa-miR-3621 + (0.627783)*hsa-miR-6132 + (−0.213112)*hsa-miR-6791-5p + (−0.973223)*hsa-miR-4725-3p + (−0.017547)*hsa-miR-3158-5p + (−0.178927)*hsa-miR-6879-5p + (0.085963)*hsa-miR-4750-5p + (−0.009668)*hsa-miR-3154 + | 0.41 |

TABLE 16-2-continued

| No. | Number of miRNA | Discriminant formula | Threshold |
|---|---|---|---|
| | | (−0.121832)*hsa-miR-3917 + (0.05462)*hsa-miR-3663-3p + (−0.036924)*hsa-miR-4640-5p + (0.048531)*hsa-miR-6869-5p + (−0.292652)*hsa-miR-1343-3p + (−0.198013)*hsa-miR-7108-3p + (0.339604)*hsa-miR-6785-5p + (0.145972)*hsa-miR-6777-5p + (0.213095)*hsa-miR-7107-5p + (−0.183618)*hsa-miR-4695-5p + (−0.044321)*hsa-miR-6880-3p + 40.9535 | |
| 31 | 65 | (−0.0706564)*hsa-miR-498 + (0.1901728)*hsa-miR-4658 + (0.1869807)*hsa-miR-6717-5p + (0.4053566)*hsa-miR-4436b-5p + (0.4935334)*hsa-miR-3648 + (0.0168284)*hsa-miR-4663 + (0.0602181)*hsa-miR-4652-5p + (−0.3935623)*hsa-miR-1343-5p + (0.2874051)*hsa-miR-6780b-5p + (−1.1322383)*hsa-miR-3197 + (0.2843696)*hsa-miR-371b-5p + (−0.1882854)*hsa-miR-4534 + (−0.1937783)*hsa-miR-6800-5p + (−0.2187614)*hsa-miR-150-3p + (0.0073898)*hsa-miR-4771 + (0.0219823)*hsa-miR-6510-5p + (0.0249733)*hsa-miR-615-5p + (−0.1161974)*hsa-miR-4741 + (0.3109583)*hsa-miR-1185-1-3p + (0.1092951)*hsa-miR-6765-3p + (0.2048061)*hsa-miR-6741-5p + (−0.0058854)*hsa-miR-373-5p + (0.2752621)*hsa-miR-663a + (−1.0452884)*hsa-miR-1228-5p + (−0.4710701)*hsa-miR-4728-5p + (−0.5343161)*hsa-miR-937-5p + (−0.0008246)*hsa-miR-887-3p + (0.0487656)*hsa-miR-6124 + (−0.3731047)*hsa-miR-6794-5p + (0.1482058)*hsa-miR-4467 + (−2.9164623)*hsa-miR-6087 + (0.0480848)*hsa-miR-6760-5p + (−0.1878837)*hsa-miR-4710 + (0.074284)*hsa-miR-5195-3p + (−0.3036474)*hsa-miR-149-3p + (−0.3348046)*hsa-miR-1914-3p + (0.0772677)*hsa-miR-4675 + (0.9181764)*hsa-miR-328-5p + (0.2342347)*hsa-miR-4455 + (0.2465187)*hsa-miR-3619-3p + (0.0487489)*hsa-miR-3160-5p + (1.2896106)*hsa-miR-6724-5p + (0.1918112)*hsa-miR-6819-5p + (−0.4281541)*hsa-miR-6803-5p + (−0.1229311)*hsa-miR-423-5p + (−0.050782)*hsa-miR-4447 + (−0.4205827)*hsa-miR-3621 + (0.6191909)*hsa-miR-6132 + (−0.2207379)*hsa-miR-6791-5p + (−1.0221646)*hsa-miR-4725-3p + (−0.0260544)*hsa-miR-3158-5p + (−0.1572461)*hsa-miR-6879-5p + (0.1033496)*hsa-miR-4750-5p + (−0.0157931)*hsa-miR-3154 + (−0.1265015)*hsa-miR-3917 + (0.0684396)*hsa-miR-3663-3p + (−0.0388714)*hsa-miR-4640-5p + (0.0424731)*hsa-miR-6869-5p + (−0.3483934)*hsa-miR-1343-3p + (−0.2046679)*hsa-miR-7108-3p + (0.403265)*hsa-miR-6785-5p + (0.1652951)*hsa-miR-6777-5p + (0.2032236)*hsa-miR-7107-5p + (−0.1940787)*hsa-miR-4695-5p + (−0.0544247)*hsa-miR-6880-3p + 43.1328323 | 0.51 |
| 32 | 71 | (−0.087897)*hsa-miR-498 + (0.198892)*hsa-miR-4658 + (0.202208)*hsa-miR-6717-5p + (−0.01578)*hsa-miR-92a-3p + (0.429092)*hsa-miR-4436b-5p + (0.490161)*hsa-miR-3648 + (0.020375)*hsa-miR-4663 + (0.060216)*hsa-miR-4652-5p + (−0.403015)*hsa-miR-1343-5p + (0.305822)*hsa-miR-6780b-5p + (−0.003598)*hsa-miR-4448 + (−1.179904)*hsa-miR-3197 + (0.290834)*hsa-miR-371b-5p + (0.012247)*hsa-miR-4433a-3p + (−0.202324)*hsa-miR-4534 + (−0.233942)*hsa-miR-6800-5p + (−0.226403)*hsa-miR-150-3p + (0.01761)*hsa-miR-4771 + (0.003451)*hsa-miR-6782-5p + (0.026282)*hsa-miR-6510-5p + (0.009447)*hsa-miR-615-5p + (−0.085224)*hsa-miR-4741 + (0.312998)*hsa-miR-1185-1-3p + (0.126507)*hsa-miR-6765-3p + (0.208904)*hsa-miR-6741-5p + (−0.015006)*hsa-miR-373-5p + (0.314371)*hsa-miR-663a + (−1.124148)*hsa-miR-1228-5p + (−0.488472)*hsa-miR-4728-5p + (−0.546588)*hsa-miR-937-5p + (−0.005277)*hsa-miR-887-3p + (0.071211)*hsa-miR-6124 + (0.047877)*hsa-miR-6075 + (−0.387583)*hsa-miR-6794-5p + (0.140566)*hsa-miR-4467 + (−2.964722)*hsa-miR-6087 + (0.054865)*hsa-miR-6760-5p + (−0.2064)*hsa-miR-4710 + (0.11468)*hsa-miR-5195-3p + (−0.39274)*hsa-miR-149-3p + (−0.335697)*hsa-miR-1914-3p + (0.089891)*hsa-miR-4675 + (0.958668)*hsa-miR-328-5p + (0.246056)*hsa-miR-4455 + (0.270054)*hsa-miR-3619-3p + (0.04527)*hsa-miR-3160-5p + (1.336406)*hsa-miR-6724-5p + (0.143639)*hsa-miR-6819-5p + (−0.427856)*hsa-miR-6803-5p + (−0.125715)*hsa-miR-423-5p + (−0.075233)*hsa-miR-4447 + (−0.44821)*hsa-miR-3621 + (0.6037)*hsa-miR-6132 + (−0.23944)*hsa-miR-6791-5p + (−1.067383)*hsa-miR-4725-3p + (−0.032637)*hsa-miR-3158-5p + (−0.143252)*hsa-miR-6879-5p + (0.121177)*hsa-miR-4750-5p + (−0.023571)*hsa-miR-3154 + (−0.128874)*hsa-miR-3917 + (0.083554)*hsa-miR-3663-3p + (−0.040135)*hsa-miR-4640-5p + (−0.029186)*hsa-miR-6749-5p + (0.037319)*hsa-miR-6869-5p + (−0.398115)*hsa-miR-1343-3p + (−0.208272)*hsa-miR-7108-3p + (0.47369)*hsa-miR-6785-5p + (0.184781)*hsa-miR-6777-5p + (0.185309)*hsa-miR-7107-5p + (−0.205072)*hsa-miR-4695-5p + (−0.065419)*hsa-miR-6880-3p + 45.273324 | 0.52 |
| 33 | 75 | (−0.1059352)*hsa-miR-498 + (0.2063018)*hsa-miR-4658 + (0.2215912)*hsa-miR-6717-5p + (−0.0298688)*hsa-miR-92a-3p + (0.4583753)*hsa-miR-4436b-5p + (0.483301)*hsa-miR-3648 + (0.0242259)*hsa-miR-4663 + (0.0604766)*hsa-miR-4652-5p + (−0.4425081)*hsa-miR-1343-5p + (0.309457)*hsa-miR-6780b-5p + (−0.0173718)*hsa-miR-4448 + (0.0013542)*hsa-miR-29b-3p + (−1.2151182)*hsa-miR-3197 + (0.2981005)*hsa-miR-371b-5p + (0.0190017)*hsa-miR-4433a-3p + (−0.2110239)*hsa-miR-4534 + (−0.2813926)*hsa-miR-6800-5p + (−0.2327499)*hsa-miR-150-3p + (0.026306)*hsa-miR-4771 + (0.0169428)*hsa-miR-6782-5p + (0.0279943)*hsa-miR-6510-5p + (−0.0577194)*hsa-miR-4741 + (0.3161462)*hsa-miR-1185-1-3p + (0.1408323)*hsa-miR-6765-3p + (0.2085074)*hsa-miR-6741-5p + (−0.0246274)*hsa-miR-373- | 0.47 |

TABLE 16-2-continued

| No. | Number of miRNA | Discriminant formula | Threshold |
|---|---|---|---|
| | | 5p + (0.3624389)*hsa-miR-663a + (−1.2041074)*hsa-miR-1228-5p + (−0.4910598)*hsa-miR-4728-5p + (−0.5566172)*hsa-miR-937-5p + (−0.0124466)*hsa-miR-887-3p + (0.0992655)*hsa-miR-6124 + (0.094522)*hsa-miR-6075 + (−0.3922484)*hsa-miR-6794-5p + (−0.014239)*hsa-miR-6778-5p + (0.1304415)*hsa-miR-4467 + (−0.0036718)*hsa-miR-4484 + (−2.9988301)*hsa-miR-6087 + (0.0599382)*hsa-miR-6760-5p + (−0.0001349)*hsa-miR-711 + (−0.2208925)*hsa-miR-4710 + (0.1507497)*hsa-miR-5195-3p + (−0A831057)*hsa-miR-149-3p + (−0.3419503)*hsa-miR-1914-3p + (0.1010775)*hsa-miR-4675 + (1.0016789)*hsa-miR-328-5p + (0.2573836)*hsa-miR-4455 + (0.2951085)*hsa-miR-3619-3p + (0.0427975)*hsa-miR-3160-5p + (1.3967438)*hsa-miR-6724-5p + (0.0905735)*hsa-miR-6819-5p + (−0.3985998)*hsa-miR-6803-5p + (−0.1262088)*hsa-miR-423-5p + (−0.0974308)*hsa-miR-4447 + (−0.4666724)*hsa-miR-3621 + (0.5846443)*hsa-miR-6132 + (−0.2716118)*hsa-miR-6791-5p + (−1.1000198)*hsa-miR-4725-3p + (−0.0399952)*hsa-miR-3158-5p + (−0.1353441)*hsa-miR-6879-5p + (0.1381561)*hsa-miR-4750-5p + (−0.0307913)*hsa-miR-3154 + (−0.128336)*hsa-miR-3917 + (0.1073239)*hsa-miR-3663-3p + (−0.0382458)*hsa-miR-4640-5p + (−0.0837819)*hsa-miR-6749-5p + (0.0397535)*hsa-miR-6869-5p + (−0.4512182)*hsa-miR-1343-3p + (−0.2102807)*hsa-miR-7108-3p + (−0.0399303)*hsa-miR-6088 + (0.5473916)*hsa-miR-6785-5p + (0.201801)*hsa-miR-6777-5p + (0.1708449)*hsa-miR-7107-5p + (−0.2136614)*hsa-miR-4695-5p + (−0.0752741)*hsa-miR-6880-3p + 47.5111149 | |
| 34 | 77 | (−0.1209)*hsa-miR-498 + (0.213408)*hsa-miR-4658 + (0.24116)*hsa-miR-6717-5p + (−0.044149)*hsa-miR-92a-3p + (0.483209)*hsa-miR-4436b-5p + (0.475983)*hsa-miR-3648 + (0.02733)*hsa-miR-4663 + (0.062769)*hsa-miR-4652-5p + (−0.450408)*hsa-miR-1343-5p + (0.323437)*hsa-miR-6780b-5p + (−0.032802)*hsa-miR-4448 + (0.006279)*hsa-miR-29b-3p + (−1.226251)*hsa-miR-3197 + (0.303712)*hsa-miR-371b-5p + (0.032248)*hsa-miR-4433a-3p + (−0.220094)*hsa-miR-4534 + (−0.318783)*hsa-miR-6800-5p + (−0.237086)*hsa-miR-150-3p + (−0.031189)*hsa-miR-296-3p + (0.034403)*hsa-miR-4771 + (0.022256)*hsa-miR-6782-5p + (0.031466)*hsa-miR-6510-5p + (−0.021855)*hsa-miR-4741 + (0.324482)*hsa-miR-1185-1-3p + (0.158538)*hsa-miR-6765-3p + (0.210632)*hsa-miR-6741-5p + (−0.033007)*hsa-miR-373-5p + (0.400391)*hsa-miR-663a + (−1.298882)*hsa-miR-1228-5p + (−0.485454)*hsa-miR-4728-5p + (−0.57533)*hsa-miR-937-5p + (−0.023379)*hsa-miR-887-3p + (0.134703)*hsa-miR-6124 + (0.132219)*hsa-miR-6075 + (−0.388436)*hsa-miR-6794-5p + (−0.032443)*hsa-miR-6778-5p + (0.11668)*hsa-miR-4467 + (−0.068978)*hsa-miR-4484 + (−3.031394)*hsa-miR-6087 + (0.062717)*hsa-miR-6760-5p + (−0.002455)*hsa-miR-711 + (−0.232653)*hsa-miR-4710 + (0.179487)*hsa-miR-5195-3p + (−0.563043)*hsa-miR-149-3p + (−0.354414)*hsa-miR-1914-3p + (0.114788)*hsa-miR-4675 + (1.015657)*hsa-miR-328-5p + (0.265782)*hsa-miR-4455 + (0.323327)*hsa-miR-3619-3p + (0.041269)*hsa-miR-3160-5p + (1.451381)*hsa-miR-6724-5p + (0.046169)*hsa-miR-6819-5p + (−0.364269)*hsa-miR-6803-5p + (−0.128832)*hsa-miR-423-5p + (−0.115745)*hsa-miR-4447 + (−0.481969)*hsa-miR-3621 + (0.583038)*hsa-miR-6132 + (−0.313497)*hsa-miR-6791-5p + (−1.115343)*hsa-miR-4725-3p + (−0.044796)*hsa-miR-3158-5p + (−0.002015)*hsa-miR-6766-3p + (−0.126645)*hsa-miR-6879-5p + (0.157733)*hsa-miR-4750-5p + (−0.038586)*hsa-miR-3154 + (−0.128243)*hsa-miR-3917 + (0.14884)*hsa-miR-3663-3p + (−0.049227)*hsa-miR-4640-5p + (−0.133682)*hsa-miR-6749-5p + (0.040222)*hsa-miR-6869-5p + (−0.507848)*hsa-miR-1343-3p + (−0.208462)*hsa-miR-7108-3p + (−0.08765)*hsa-miR-6088 + (0.621228)*hsa-miR-6785-5p + (0.221408)*hsa-miR-6777-5p + (0.15388)*hsa-miR-7107-5p + (−0.216837)*hsa-miR-4695-5p + (−0.083832)*hsa-miR-6880-3p + 49.825891 | 0.48 |
| 35 | 78 | (−0.134198)*hsa-miR-498 + (0.219152)*hsa-miR-4658 + (0.25441)*hsa-miR-6717-5p + (−0.05957)*hsa-miR-92a-3p + (0.513433)*hsa-miR-4436b-5p + (0.448752)*hsa-miR-3648 + (0.030009)*hsa-miR-4663 + (0.066355)*hsa-miR-4652-5p + (−0.466497)*hsa-miR-1343-5p + (0.329188)*hsa-miR-6780b-5p + (−0.045734)*hsa-miR-4448 + (0.035283)*hsa-miR-6722-3p + (0.01013)*hsa-miR-29b-3p + (−1.236716)*hsa-miR-3197 + (0.309181)*hsa-miR-371b-5p + (0.046528)*hsa-miR-4433a-3p + (−0.233746)*hsa-miR-4534 + (−0.352501)*hsa-miR-6800-5p + (−0.238099)*hsa-miR-150-3p + (−0.070535)*hsa-miR-296-3p + (0.043098)*hsa-miR-4771 + (0.024703)*hsa-miR-6782-5p + (0.032974)*hsa-miR-6510-5p + (−0.022481)*hsa-miR-4741 + (0.080601)*hsa-miR-1227-5p + (0.335657)*hsa-miR-1185-1-3p + (0.173929)*hsa-miR-6765-3p + (0.218937)*hsa-miR-6741-5p + (−0.040529)*hsa-miR-373-5p + (0.444955)*hsa-miR-663a + (−1.384992)*hsa-miR-1228-5p + (−0.470094)*hsa-miR-4728-5p + (−0.614166)*hsa-miR-937-5p + (−0.032715)*hsa-miR-887-3p + (0.176516)*hsa-miR-6124 + (0.172498)*hsa-miR-6075 + (−0.369372)*hsa-miR-6794-5p + (−0.053036)*hsa-miR-6778-5p + (0.110957)*hsa-miR-4467 + (−0.120431)*hsa-miR-4484 + (−3.051244)*hsa-miR-6087 + (0.067061)*hsa-miR-6760-5p + (−0.008193)*hsa-miR-711 + (−0.241365)*hsa-miR-4710 + (0.215809)*hsa-miR-5195-3p + (−0.641022)*hsa-miR-149-3p + (−0.362125)*hsa-miR-1914-3p + (0.119243)*hsa-miR-4675 + (1.01775)*hsa-miR-328-5p + (0.273058)*hsa-miR-4455 + (0.354655)*hsa-miR-3619- | 0.45 |

TABLE 16-2-continued

| No. | Number of miRNA | Discriminant formula | Threshold |
|---|---|---|---|
| | | 3p + (0.040135)*hsa-miR-3160-5p + (1.499939)*hsa-miR-6724-5p + (−0.341082)*hsa-miR-6803-5p + (−0.131566)*hsa-miR-423-5p + (−0.136544)*hsa-miR-4447 + (−0.522359)*hsa-miR-3621 + (0.582169)*hsa-miR-6132 + (−0.363936)*hsa-miR-6791-5p + (−1.121977)*hsa-miR-4725-3p + (−0.050657)*hsa-miR-3158-5p + (−0.020979)*hsa-miR-6766-3p + (−0.115331)*hsa-miR-6879-5p + (0.176442)*hsa-miR-4750-5p + (−0.044578)*hsa-miR-3154 + (−0.124778)*hsa-miR-3917 + (0.20127)*hsa-miR-3663-3p + (−0.075031)*hsa-miR-4640-5p + (−0.176008)*hsa-miR-6749-5p + (0.046517)*hsa-miR-6869-5p + (−0.558776)*hsa-miR-1343-3p + (−0.203898)*hsa-miR-7108-3p + (−0.149234)*hsa-miR-6088 + (0.697578)*hsa-miR-6785-5p + (0.240261)*hsa-miR-6777-5p + (0.132853)*hsa-miR-7107-5p + (−0.219847)*hsa-miR-4695-5p + (−0.086883)*hsa-miR-6880-3p + 51.681384 | |
| 36 | 85 | (−0.14581)*hsa-miR-498 + (0.22531)*hsa-miR-4658 + (0.26419)*hsa-miR-6717-5p + (−0.07407)*hsa-miR-92a-3p + (0.54527)*hsa-miR-4436b-5p + (0.41413)*hsa-miR-3648 + (0.03236)*hsa-miR-4663 + (0.06965)*hsa-miR-4652-5p + (−0.4972)*hsa-miR-1343-5p + (0.30052)*hsa-miR-6780b-5p + (−0.05883)*hsa-miR-4448 + (0.09166)*hsa-miR-6722-3p + (0.01424)*hsa-miR-29b-3p + (0.10705)*hsa-miR-1908-5p + (−1.25898)*hsa-miR-3197 + (0.31433)*hsa-miR-371b-5p + (0.05736)*hsa-miR-4433a-3p + (−0.24959)*hsa-miR-4534 + (−0.38816)*hsa-miR-6800-5p + (−0.23476)*hsa-miR-150-3p + (−0.11246)*hsa-miR-296-3p + (0.04962)*hsa-miR-4771 + (0.02654)*hsa-miR-6782-5p + (0.03949)*hsa-miR-6510-5p + (−0.02485)*hsa-miR-4741 + (0.19194)*hsa-miR-1227-5p + (0.33412)*hsa-miR-1185-1-3p + (0.18485)*hsa-miR-6765-3p + (0.23938)*hsa-miR-6741-5p + (−0.03201)*hsa-miR-5739 + (−0.05082)*hsa-miR-373-5p + (0.4906)*hsa-miR-663a + (−1.48305)*hsa-miR-1228-5p + (−0.45347)*hsa-miR-4728-5p + (−0.64025)*hsa-miR-937-5p + (−0.04413)*hsa-miR-887-3p + (0.21688)*hsa-miR-6124 + (0.19479)*hsa-miR-6075 + (−0.33283)*hsa-miR-6794-5p + (−0.07324)*hsa-miR-6778-5p + (0.08666)*hsa-miR-4467 + (−0.1629)*hsa-miR-4484 + (−3.06046)*hsa-miR-6087 + (0.07204)*hsa-miR-6760-5p + (0.03884)*hsa-miR-1237-5p + (−0.01918)*hsa-miR-711 + (−0.24672)*hsa-miR-4710 + (0.26189)*hsa-miR-5195-3p + (−0.69246)*hsa-miR-149-3p + (−0.35773)*hsa-miR-1914-3p + (0.14506)*hsa-miR-4675 + (1.01069)*hsa-miR-328-5p + (0.27932)*hsa-miR-4455 + (0.38713)*hsa-miR-3619-3p + (0.03944)*hsa-miR-3160-5p + (1.53864)*hsa-miR-6724-5p + (−0.29601)*hsa-miR-6803-5p + (−0.1311)*hsa-miR-423-5p + (−0.15862)*hsa-miR-4447 + (−0.57986)*hsa-miR-3621 + (0.57873)*hsa-miR-6132 + (−0.44709)*hsa-miR-6791-5p + (−1.1283)*hsa-miR-4725-3p + (−0.05643)*hsa-miR-3158-5p + (−0.04547)*hsa-miR-6766-3p + (−0.09137)*hsa-miR-6879-5p + (−0.01029)*hsa-miR-940 + (0.18806)*hsa-miR-4750-5p + (−0.04859)*hsa-miR-3154 + (−0.11845)*hsa-miR-3917 + (0.25958)*hsa-miR-3663-3p + (−0.04819)*hsa-miR-4649-5p + (−0.12029)*hsa-miR-4640-5p + (−0.18232)*hsa-miR-6749-5p + (0.07005)*hsa-miR-6869-5p + (−0.61778)*hsa-miR-1343-3p + (−0.19783)*hsa-miR-7108-3p + (0.00869)*hsa-miR-4687-3p + (0.01173)*hsa-miR-1185-2-3p + (−0.19174)*hsa-miR-6088 + (0.76322)*hsa-miR-6785-5p + (0.25584)*hsa-miR-6777-5p + (0.09129)*hsa-miR-7107-5p + (−0.22627)*hsa-miR-4695-5p + (−0.08794)*hsa-miR-6880-3p + 51.88496 | 0.43 |
| 37 | 87 | (−0.157453)*hsa-miR-498 + (0.230367)*hsa-miR-4658 + (0.274585)*hsa-miR-6717-5p + (−0.09043)*hsa-miR-92a-3p + (−0.005947)*hsa-miR-6836-3p + (0.576699)*hsa-miR-4436b-5p + (0.375451)*hsa-miR-3648 + (0.033773)*hsa-miR-4663 + (0.074679)*hsa-miR-4652-5p + (−0.531107)*hsa-miR-1343-5p + (0.236115)*hsa-miR-6780b-5p + (−0.072783)*hsa-miR-4448 + (0.15246)*hsa-miR-6722-3p + (0.021538)*hsa-miR-29b-3p + (0.364676)*hsa-miR-1908-5p + (−1.294776)*hsa-miR-3197 + (0.319799)*hsa-miR-371b-5p + (0.053034)*hsa-miR-4433a-3p + (−0.26573)*hsa-miR-4534 + (−0.414734)*hsa-miR-6800-5p + (−0.227724)*hsa-miR-150-3p + (−0.158597)*hsa-miR-296-3p + (0.054483)*hsa-miR-4771 + (0.025565)*hsa-miR-6782-5p + (0.05238)*hsa-miR-6510-5p + (−0.02941)*hsa-miR-4741 + (0.345658)*hsa-miR-1227-5p + (0.312279)*hsa-miR-1185-1-3p + (0.182437)*hsa-miR-6765-3p + (0.287615)*hsa-miR-6741-5p + (−0.060375)*hsa-miR-5739 + (−0.06654)*hsa-miR-373-5p + (0.543806)*hsa-miR-663a + (−1.608171)*hsa-miR-1228-5p + (−0.440689)*hsa-miR-4728-5p + (−0.664403)*hsa-miR-937-5p + (−0.056281)*hsa-miR-887-3p + (0.25376)*hsa-miR-6124 + (0.187633)*hsa-miR-6075 + (−0.288564)*hsa-miR-6794-5p + (−0.091126)*hsa-miR-6778-5p + (0.032068)*hsa-miR-4467 + (−0.187941)*hsa-miR-4484 + (−3.0713)*hsa-miR-6087 + (0.074614)*hsa-miR-6760-5p + (0.097126)*hsa-miR-1237-5p + (−0.041877)*hsa-miR-711 + (−0.248759)*hsa-miR-4710 + (0.329991)*hsa-miR-5195-3p + (−0.737533)*hsa-miR-149-3p + (−0.344625)*hsa-miR-1914-3p + (0.213601)*hsa-miR-4675 + (0.934153)*hsa-miR-328-5p + (0.286295)*hsa-miR-4455 + (0.424054)*hsa-miR-3619-3p + (0.037511)*hsa-miR-3160-5p + (1.575866)*hsa-miR-6724-5p + (−0.190876)*hsa-miR-6803-5p + (−0.131426)*hsa-miR-423-5p + (−0.182603)*hsa-miR-4447 + (−0.652914)*hsa-miR-3621 + (0.574844)*hsa-miR-6132 + (−0.575516)*hsa-miR-6791-5p + (−1.130357)*hsa-miR-4725-3p + (−0.06239)*hsa-miR-3158-5p + (−0.074748)*hsa-miR-6766-3p + (−0.062363)*hsa-miR-6879-5p + (−0.040747)*hsa-miR-940 + (0.201293)*hsa-miR-4750-5p + (−0.055379)*hsa-miR-3154 + (−0.100101)*hsa-miR-3917 + (0.329357)*hsa-miR-3663-3p + (−0.187888)*hsa-miR-4649-5p + (−0.186714)*hsa-miR-4640-5p + (−0.125967)*hsa-miR-6749-5p + (0.118941)*hsa-miR-6869-5p + (−0.669133)*hsa-miR-1343-3p + (−0.028094)*hsa-miR-6771-5p + (−0.188447)*hsa-miR-7108-3p + (0.088046)*hsa- | 0.52 |

TABLE 16-2-continued

| No. | Number of miRNA | Discriminant formula | Threshold |
|---|---|---|---|
| | | miR-4687-3p + (0.038875)*hsa-miR-1185-2-3p + (−0.202863)*hsa-miR-6088 + (0.821338)*hsa-miR-6785-5p + (0.267602)*hsa-miR-6777-5p + (0.035056)*hsa-miR-7107-5p + (−0.238509)*hsa-miR-4695-5p + (−0.091764)*hsa-miR-6880-3p + 50.550809 | |
| 38 | 89 | (−0.168014)*hsa-miR-498 + (0.236947)*hsa-miR-4658 + (0.287021)*hsa-miR-6717-5p + (−0.107595)*hsa-miR-92a-3p + (−0.00643)*hsa-miR-342-5p + (−0.03917)*hsa-miR-6836-3p + (0.611779)*hsa-miR-4436b-5p + (0.349007)*hsa-miR-3648 + (0.034525)*hsa-miR-4663 + (0.081912)*hsa-miR-4652-5p + (−0.532693)*hsa-miR-1343-5p + (0.152994)*hsa-miR-6780b-5p + (−0.086875)*hsa-miR-4448 + (0.209604)*hsa-miR-6722-3p + (0.028549)*hsa-miR-29b-3p + (0.610171)*hsa-miR-1908-5p + (−0.034301)*hsa-miR-6840-3p + (−1.309847)*hsa-miR-3197 + (0.327547)*hsa-miR-371b-5p + (0.046607)*hsa-miR-4433a-3p + (−0.280802)*hsa-miR-4534 + (−0.427755)*hsa-miR-6800-5p + (−0.222417)*hsa-miR-150-3p + (−0.201041)*hsa-miR-296-3p + (0.058103)*hsa-miR-4771 + (−0.003334)*hsa-miR-4298 + (0.023981)*hsa-miR-6782-5p + (0.057966)*hsa-miR-6510-5p + (−0.044703)*hsa-miR-4741 + (0.529786)*hsa-miR-1227-5p + (0.292578)*hsa-miR-1185-1-3p + (0.178845)*hsa-miR-6765-3p + (0.326475)*hsa-miR-6741-5p + (−0.085267)*hsa-miR-5739 + (−0.075257)*hsa-miR-373-5p + (0.591609)*hsa-miR-663a + (−1.7456)*hsa-miR-1228-5p + (−0.425981)*hsa-miR-4728-5p + (−0.695132)*hsa-miR-937-5p + (−0.066892)*hsa-miR-887-3p + (0.293603)*hsa-miR-6124 + (0.170181)*hsa-miR-6075 + (−0.235506)*hsa-miR-6794-5p + (−0.106995)*hsa-miR-6778-5p + (−0.212924)*hsa-miR-4484 + (−3.076951)*hsa-miR-6087 + (0.073772)*hsa-miR-6760-5p + (0.163007)*hsa-miR-1237-5p + (−0.05604)*hsa-miR-711 + (−0.012622)*hsa-miR-4270 + (−0.252449)*hsa-miR-4710 + (0.401782)*hsa-miR-5195-3p + (−0.759878)*hsa-miR-149-3p + (−0.332393)*hsa-miR-1914-3p + (0.286273)*hsa-miR-4675 + (0.81901)*hsa-miR-328-5p + (0.293622)*hsa-miR-4455 + (0.456444)*hsa-miR-3619-3p + (0.038412)*hsa-miR-3160-5p + (1.623949)*hsa-miR-6724-5p + (−0.08646)*hsa-miR-6803-5p + (−0.129925)*hsa-miR-423-5p + (−0.20693)*hsa-miR-4447 + (−0.720175)*hsa-miR-3621 + (0.568054)*hsa-miR-6132 + (−0.69889)*hsa-miR-6791-5p + (−1.129294)*hsa-miR-4725-3p + (−0.068503)*hsa-miR-3158-5p + (−0.103414)*hsa-miR-6766-3p + (−0.029883)*hsa-miR-6879-5p + (−0.070227)*hsa-miR-940 + (0.218064)*hsa-miR-4750-5p + (−0.067662)*hsa-miR-3154 + (−0.079451)*hsa-miR-3917 + (0.403579)*hsa-miR-3663-3p + (−0.332048)*hsa-miR-4649-5p + (−0.261792)*hsa-miR-4640-5p + (−0.012988)*hsa-miR-6749-5p + (0.173429)*hsa-miR-6869-5p + (−0.717521)*hsa-miR-1343-3p + (−0.094348)*hsa-miR-6771-5p + (−0.177661)*hsa-miR-7108-3p + (0.175484)*hsa-miR-4687-3p + (0.063672)*hsa-miR-1185-2-3p + (−0.225836)*hsa-miR-6088 + (0.889055)*hsa-miR-6785-5p + (0.273289)*hsa-miR-6777-5p + (−0.251561)*hsa-miR-4695-5p + (−0.095305)*hsa-miR-6880-3p + 48.552977 | 0.49 |
| 39 | 91 | (−0.1714341)*hsa-miR-498 + (0.2463315)*hsa-miR-4658 + (0.3041014)*hsa-miR-6717-5p + (−0.123549)*hsa-miR-92a-3p + (−0.0154482)*hsa-miR-342-5p + (−0.0483869)*hsa-miR-6836-3p + (0.6473762)*hsa-miR-4436b-5p + (−0.0229318)*hsa-miR-6812-5p + (0.2948587)*hsa-miR-3648 + (0.0369404)*hsa-miR-4663 + (0.0890896)*hsa-miR-4652-5p + (−0.5085905)*hsa-miR-1343-5p + (0.0309708)*hsa-miR-6780b-5p + (−0.102887)*hsa-miR-4448 + (0.2640522)*hsa-miR-6722-3p + (0.0305644)*hsa-miR-29b-3p + (0.8642005)*hsa-miR-1908-5p + (−0.0148678)*hsa-miR-6840-3p + (−1.3529752)*hsa-miR-3197 + (0.3278804)*hsa-miR-371b-5p + (0.0556899)*hsa-miR-4433a-3p + (−0.2977769)*hsa-miR-4534 + (−0.4677857)*hsa-miR-6800-5p + (−0.2184172)*hsa-miR-150-3p + (−0.2380794)*hsa-miR-296-3p + (0.0634247)*hsa-miR-4771 + (−0.0141326)*hsa-miR-4298 + (0.0254648)*hsa-miR-6782-5p + (0.0577028)*hsa-miR-6510-5p + (−0.025078)*hsa-miR-4741 + (0.6880234)*hsa-miR-1227-5p + (0.2784081)*hsa-miR-1185-1-3p + (0.1796644)*hsa-miR-6765-3p + (0.3870641)*hsa-miR-6741-5p + (−0.1127696)*hsa-miR-5739 + (−0.0761122)*hsa-miR-373-5p + (0.645536)*hsa-miR-663a + (−1.886436)*hsa-miR-1228-5p + (−0.3981721)*hsa-miR-4728-5p + (−0.7314395)*hsa-miR-937-5p + (−0.0764468)*hsa-miR-887-3p + (0.32948)*hsa-miR-6124 + (0.1340597)*hsa-miR-6075 + (−0.1834973)*hsa-miR-6794-5p + (−0.116519)*hsa-miR-6778-5p + (−0.237926)*hsa-miR-4484 + (−3.0932453)*hsa-miR-6087 + (0.074448)*hsa-miR-6760-5p + (0.1941518)*hsa-miR-1237-5p + (−0.0666095)*hsa-miR-711 + (−0.0702674)*hsa-miR-4270 + (−0.2559669)*hsa-miR-4710 + (0.4648048)*hsa-miR-5195-3p + (−0.7575425)*hsa-miR-149-3p + (−0.3350432)*hsa-miR-1914-3p + (0.0006176)*hsa-miR-4763-3p + (0.03025)*hsa-miR-6726-5p + (0.3538286)*hsa-miR-4675 + (0.7209416)*hsa-miR-328-5p + (0.2998346)*hsa-miR-4455 + (0.4944758)*hsa-miR-3619-3p + (0.0378202)*hsa-miR-3160-5p + (1.7012313)*hsa-miR-6724-5p + (−0.1298117)*hsa-miR-423-5p + (−0.2194125)*hsa-miR-4447 + (−0.7956141)*hsa-miR-3621 + (0.1045181)*hsa-miR-4739 + (0.560624)*hsa-miR-6132 + (−0.8742633)*hsa-miR-6791-5p + (−1.1202944)*hsa-miR-4725-3p + (−0.0803233)*hsa-miR-3158-5p + (−0.1336422)*hsa-miR-6766-3p + (−0.0121954)*hsa-miR-6879-5p + (−0.1097786)*hsa-miR-940 + (0.2300339)*hsa-miR-4750-5p + (−0.0722714)*hsa-miR-3154 + (−0.0497431)*hsa-miR-3917 + (0.4532214)*hsa-miR-3663-3p + (−0.4743401)*hsa-miR-4649-5p + (−0.3228496)*hsa-miR-4640-5p + (0.2205531)*hsa-miR-6869-5p + (−0.7541939)*hsa-miR-1343-3p + (−0.1376129)*hsa-miR-6771-5p + | 0.50 |

TABLE 16-2-continued

| No. | Number of miRNA | Discriminant formula | Threshold |
|---|---|---|---|
| | | (−0.1690947)*hsa-miR-7108-3p + (0.2477765)*hsa-miR-4687-3p + (0.0806414)*hsa-miR-1185-2-3p + (−0.261447)*hsa-miR-6088 + (0.9380335)*hsa-miR-6785-5p + (0.2769353)*hsa-miR-6777-5p + (−0.2671711)*hsa-miR-4695-5p + (−0.1020476)*hsa-miR-6880-3p + 47.1759401 | |
| 40 | 92 | (−0.17162)*hsa-miR-498 + (0.25392)*hsa-miR-4658 + (0.31749)*hsa-miR-6717-5p + (−O.14299)*hsamiR-92a-3p + (−0.02031)*hsa-miR-342-5p + (−0.06732)*hsa-miR-6836-3p + (0.68248)*hsa-miR-4436b-5p + (−0.04608)*hsa-miR-6812-5p + (0.23512)*hsa-miR-3648 + (0.03833)*hsa-miR-4663 + (0.09481)*hsa-miR-4652-5p + (−0.5289)*hsa-miR-1343-5p + (−0.1133)*hsa-miR-4448 + (0.32071)*hsa-miR-6722-3p + (0.03138)*hsa-miR-29b-3p + (1.06906)*hsa-miR-1908-5p + (−0.01004)*hsa-miR-6840-3p + (−1.39664)*hsa-miR-3197 + (0.32948)*hsa-miR-371b-5p + (0.06811)*hsa-miR-4433a-3p + (−0.31743)*hsa-miR-4534 + (−0.49913)*hsa-miR-6800-5p + (−0.21824)*hsa-miR-150-3p + (−0.27121)*hsa-miR-296-3p + (0.07165)*hsa-miR-4771 + (−0.01974)*hsa-miR-4298 + (0.02632)*hsa-miR-6782-5p + (0.04795)*hsa-miR-6510-5p + (−0.0424)*hsa-miR-4741 + (0.81323)*hsa-miR-1227-5p + (0.27353)*hsa-miR-1185-1-3p + (0.18259)*hsa-miR-6765-3p + (0.44128)*hsa-miR-6741-5p + (−0.13711)*hsa-miR-5739 + (−0.0791)*hsa-miR-373-5p + (0.66386)*hsa-miR-663a + (−2.0331)*hsa-miR-1228-5p + (0.05132)*hsa-miR-642b-3p + (−0.36336)*hsa-miR-4728-5p + (−0.7776)*hsa-miR-937-5p + (−0.07906)*hsa-miR-887-3p + (0.35931)*hsa-miR-6124 + (0.10676)*hsa-miR-6075 + (−0.12638)*hsa-miR-6794-5p + (−0.12716)*hsa-miR-6778-5p + (−0.25232)*hsa-miR-4484 + (−3.10712)*hsa-miR-6087 + (0.07362)*hsa-miR-6760-5p + (0.22424)*hsa-miR-1237-5p + (−0.06079)*hsa-miR-711 + (−0.10901)*hsa-miR-4270 + (−0.26279)*hsa-miR-4710 + (0.51342)*hsa-miR-5195-3p + (−0.76783)*hsa-miR-149-3p + (−0.34897)*hsa-miR-1914-3p + (0.06333)*hsa-miR-4763-3p + (0.087)*hsa-miR-6726-5p + (0.41177)*hsa-miR-4675 + (0.6519)*hsa-miR-328-5p + (0.30781)*hsa-miR-4455 + (0.52968)*hsa-miR-3619-3p + (0.03472)*hsa-miR-3160-5p + (1.79729)*hsa-miR-6724-5p + (−0.13457)*hsa-miR-423-5p + (−0.23011)*hsa-miR-4447 + (−0.85987)*hsa-miR-3621 + (0.18197)*hsa-miR-4739 + (0.52647)*hsa-miR-6132 + (−1.0189)*hsa-miR-6791-5p + (−1.12745)*hsa-miR-4725-3p + (−0.09467)*hsa-miR-3158-5p + (−0.15787)*hsa-miR-6766-3p + (−0.03789)*hsa-miR-6879-5p + (−0.13591)*hsa-miR-940 + (0.24161)*hsa-miR-4750-5p + (−0.07684)*hsa-miR-3154 + (−0.01999)*hsa-miR-3917 + (0.49788)*hsa-miR-3663-3p + (−0.0175)*hsa-miR-4655-5p + (−0.61636)*hsa-miR-4649-5p + (−0.36528)*hsa-miR-4640-5p + (0.27398)*hsa-miR-6869-5p + (−0.7861)*hsa-miR-1343-3p + (−0.15303)*hsa-miR-6771-5p + (−0.16323)*hsa-miR-7108-3p + (0.31315)*hsa-miR-4687-3p + (0.0902)*hsa-miR-1185-2-3p + (−0.31405)*hsa-miR-6088 + (0.98964)*hsa-miR-6785-5p + (0.27636)*hsa-miR-6777-5p + (−0.28112)*hsa-miR-4695-5p + (−0.10755)*hsa-miR-6880-3p + 46.9107 | 0.50 |
| 41 | 96 | (−0.168327)*hsa-miR-498 + (0.26188)*hsa-miR-4658 + (0.33408)*hsa-miR-6717-5p + (−0.169046)*hsa-miR-92a-3p + (−0.017541)*hsa-miR-342-5p + (−0.005558)*hsa-miR-3652 + (−0.090229)*hsa-miR-6836-3p + (0.720749)*hsa-miR-4436b-5p + (−0.067056)*hsa-miR-6812-5p + (0.176077)*hsa-miR-3648 + (0.040991)*hsa-miR-4663 + (0.100265)*hsa-miR-4652-5p + (−0.551882)*hsa-miR-1343-5p + (0.01134)*hsa-miR-1246 + (−0.124139)*hsa-miR-4448 + (0.372669)*hsa-miR-6722-3p + (−0.024981)*hsa-miR-6826-5p + (0.030499)*hsa-miR-29b-3p + (1.276243)*hsa-miR-1908-5p + (−0.009367)*hsa-miR-6840-3p + (−1.418431)*hsa-miR-3197 + (0.332244)*hsa-miR-371b-5p + (0.076143)*hsa-miR-4433a-3p + (−0.33333)*hsa-miR-4534 + (−0.519439)*hsa-miR-6800-5p + (−0.217395)*hsa-miR-150-3p + (−0.30554)*hsa-miR-296-3p + (0.076408)*hsa-miR-4771 + (−0.029634)*hsa-miR-4298 + (0.026415)*hsa-miR-6782-5p + (0.03805)*hsa-miR-6510-5p + (−0.049401)*hsa-miR-4741 + (0.928068)*hsa-miR-1227-5p + (0.268277)*hsa-miR-1185-1-3p + (0.183168)*hsa-miR-6765-3p + (0.492267)*hsa-miR-6741-5p + (−0.161027)*hsa-miR-5739 + (−0.084522)*hsa-miR-373-5p + (0.660405)*hsa-miR-663a + (−2.186924)*hsa-miR-1228-5p + (0.102916)*hsa-miR-642b-3p + (−0.337328)*hsa-miR-4728-5p + (−0.825603)*hsa-miR-937-5p + (−0.080196)*hsa-miR-887-3p + (0.394368)*hsa-miR-6124 + (0.067784)*hsa-miR-6075 + (−0.074642)*hsa-miR-6794-5p + (−0.139875)*hsa-miR-6778-5p + (−0.271245)*hsa-miR-4484 + (−3.128285)*hsa-miR-6087 + (0.072986)*hsa-miR-6760-5p + (0.24932)*hsa-miR-1237-5p + (−0.053059)*hsa-miR-711 + (−0.142799)*hsa-miR-4270 + (−0.269275)*hsa-miR-4710 + (0.569167)*hsa-miR-5195-3p + (−0.781094)*hsa-miR-149-3p + (−0.365003)*hsa-miR-1914-3p + (0.130811)*hsa-miR-4763-3p + (0.122118)*hsa-miR-6726-5p + (0.467105)*hsa-miR-4675 + (0.585686)*hsa-miR-328-5p + (0.314904)*hsa-miR-4455 + (0.567628)*hsa-miR-3619-3p + (0.031226)*hsa-miR-3160-5p + (1.891636)*hsa-miR-6724-5p + (−0.138551)*hsa-miR-423-5p + (−0.244677)*hsa-miR-4447 + (−0.915858)*hsa-miR-3621 + (0.24268)*hsa-miR-4739 + (0.49819)*hsa-miR-6132 + (−1.160239)*hsa-miR-6791-5p + (−1.14036)*hsa-miR-4725-3p + (−0.105191)*hsa-miR-3158-5p + (−0.177439)*hsa-miR-6766-3p + (−0.073091)*hsa-miR-6879-5p + (−0.164485)*hsa-miR-940 + (0.252274)*hsa-miR-4750-5p + (−0.08018)*hsa-miR-3154 + (0.549568)*hsa-miR-3663-3p + (−0.038808)*hsa-miR-4655-5p + (−0.744936)*hsa-miR-4649-5p + (−0.392245)*hsa-miR-4640-5p + (0.324248)*hsa-miR-6869-5p + (−0.818355)*hsa-miR-1343-3p + (−0.165573)*hsa-miR-6771-5p + (−0.154436)*hsa-miR-7108-3p + (0.38698)*hsa-miR-4687-3p + (0.104229)*hsa-miR- | 0.51 |

TABLE 16-2-continued

| No. | Number of miRNA | Discriminant formula | Threshold |
|---|---|---|---|
| | | 1185-2-3p + (−0.022416)*hsa-miR-1225-5p + (−0.006255)*hsa-miR-4322 + (−0.361259)*hsa-miR-6088 + (1.039438)*hsa-miR-6785-5p + (0.276739)*hsa-miR-6777-5p + (−0.290883)*hsa-miR-4695-5p + (−0.10815)*hsa-miR-6880-3p + 46.950799 | |
| 42 | 101 | (−0.164886)*hsa-miR-498 + (0.271746)*hsa-miR-4658 + (0.342635)*hsa-miR-6717-5p + (−0.195075)*hsa-miR-92a-3p + (−0.005004)*hsa-miR-342-5p + (−0.01172)*hsa-miR-3652 + (−0.095324)*hsa-miR-6836-3p + (0.751026)*hsa-miR-4436b-5p + (−0.089433)*hsa-miR-6812-5p + (0.128132)*hsa-miR-3648 + (0.043433)*hsa-miR-4663 + (0.104041)*hsa-miR-4652-5p + (−0.549339)*hsa-miR-1343-5p + (0.023385)*hsa-miR-1246 + (−0.138751)*hsa-miR-4448 + (0.431639)*hsa-miR-6722-3p + (−0.051407)*hsa-miR-6826-5p + (0.030158)*hsa-miR-29b-3p + (1.522322)*hsa-miR-1908-5p + (−0.020371)*hsa-miR-6840-3p + (−1.446668)*hsa-miR-3197 + (0.331537)*hsa-miR-371b-5p + (0.105015)*hsa-miR-4433a-3p + (−0.356045)*hsa-miR-4534 + (−0.530676)*hsa-miR-6800-5p + (−0.22 miR-296-3p + (0.079662)*hsa-miR-4771 + (−0.04181)*hsa-miR-4298 + (0.023304)*hsa-miR-6782-5p + (0.00421)*hsa-miR-6774-5p + (0.028565)*hsa-miR-6510-5p + (−0.040035)*hsa-miR-4741 + (1.002338)*hsa-miR-1227-5p + (0.258342)*hsa-miR-1185-1-3p + (0.190108)*hsa-miR-6765-3p + (0.547435)*hsa-miR-6741-5p + (−0.192605)*hsa-miR-5739 + (−0.086166)*hsa-miR-373-5p + (0.611532)*hsa-miR-663a + (−2.321989)*hsa-miR-1228-5p + (0.124905)*hsa-miR-642b-3p + (−0.322833)*hsa-miR-4728-5p + (−0.831493)*hsa-miR-937-5p + (−0.07426)*hsa-miR-887-3p + (0.425246)*hsa-miR-6124 + (0.051568)*hsa-miR-6075 + (−0.048001)*hsa-miR-6794-5p + (−0.148839)*hsa-miR-6778-5p + (−0.002104)*hsa-miR-6762-5p + (−0.299278)*hsa-miR-4484 + (−3.147393)*hsa-miR-6087 + (0.075137)*hsa-miR-6760-5p + (0.280394)*hsa-miR-1237-5p + (−0.05035)*hsa-miR-711 + (−0.194744)*hsa-miR-4270 + (−0.271665)*hsa-miR-4710 + (0.618923)*hsa-miR-5195-3p + (0.142587)*hsa-miR-128-2-5p + (−0.749714)*hsa-miR-149-3p + (−0.382437)*hsa-miR-1914-3p + (0.203352)*hsa-miR-4763-3p + (0.129049)*hsa-miR-6726-5p + (−0.007147)*hsa-miR-1207-5p + (0.509897)*hsa-miR-4675 + (0.48708)*hsa-miR-328-5p + (0.324524)*hsa-miR-4455 + (0.606476)*hsa-miR-3619-3p + (0.029777)*hsa-miR-3160-5p + (2.012171)*hsa-miR-6724-5p + (−0.145669)*hsa-miR-423-5p + (−0.263466)*hsa-miR-4447 + (−0.960745)*hsa-miR-3621 + (0.332861)*hsa-miR-4739 + (0.485793)*hsa-miR-6132 + (−1.356838)*hsa-miR-6791-5p + (−1.14425)*hsa-miR-4725-3p + (−0.112144)*hsa-miR-3158-5p + (−0.194603)*hsa-miR-6766-3p + (−0.122519)*hsa-miR-6879-5p + (−0.191731)*hsa-miR-940 + (0.273396)*hsa-miR-4750-5p + (−0.07369)*hsa-miR-3154 + (0.617814)*hsa-miR-3663-3p + (−0.073282)*hsa-miR-4655-5p + (−0.918353)*hsa-miR-4649-5p + (−0.403564)*hsa-miR-4640-5p + (0.345987)*hsa-miR-6869-5p + (−0.831031)*hsa-miR-1343-3p + (−0.173685)*hsa-miR-6771-5p + (−0.142973)*hsa-miR-7108-3p + (−0.07332)*hsa-miR-3195 + (0.474989)*hsa-miR-4687-3p + (0.12152)*hsa-miR-1185-2-3p + (−0.037743)*hsa-miR-1225-5p + (−0.007735)*hsa-miR-4322 + (−0.400051)*hsa-miR-6088 + (1.086969)*hsa-miR-6785-5p + (0.272056)*hsa-miR-6777-5p + (−0.295919)*hsa-miR-4695-5p + (−0.110911)*hsa-miR-6880-3p + 45.893174 | 0.51 |
| 43 | 103 | (−0.1601394)*hsa-miR-498 + (0.2850617)*hsa-miR-4658 + (0.3576893)*hsa-miR-6717-5p + (−0.2212451)*hsa-miR-92a-3p + (−0.0169346)*hsa-miR-3652 + (−0.1033467)*hsa-miR-6836-3p + (0.7803107)*hsa-miR-4436b-5p + (−0.1053903)*hsa-miR-6812-5p + (0.0989707)*hsa-miR-3648 + (0.0452842)*hsa-miR-4663 + (0.1070454)*hsa-miR-4652-5p + (−0.5645943)*hsa-miR-1343-5p + (0.0372825)*hsa-miR-1246 + (−0.1524387)*hsa-miR-4448 + (0.493455)*hsa-miR-6722-3p + (−0.063272)*hsa-miR-6826-5p + (0.0300947)*hsa-miR-29b-3p + (1.7253231)*hsa-miR-1908-5p + (−0.0304343)*hsa-miR-6840-3p + (−1.4718543)*hsa-miR-3197 + (0.3327945)*hsa-miR-371b-5p + (0.1389311)*hsa-miR-4433a-3p + (−0.3786207)*hsa-miR-4534 + (−0.5330388)*hsa-miR-6800-5p + (−0.2281238)*hsa-miR-150-3p + (−0.3571327)*hsa-miR-296-3p + (0.0821236)*hsa-miR-4771 + (−0.000483)*hsa-miR-1908-3p + (−0.0484521)*hsa-miR-4298 + (0.0188425)*hsa-miR-6782-5p + (0.0291535)*hsa-miR-6774-5p + (0.0167763)*hsa-miR-6510-5p + (0.0008741)*hsa-miR-615-5p + (−0.0710587)*hsa-miR-4741 + (1.0816373)*hsa-miR-1227-5p + (0.2452467)*hsa-miR-1185-1-3p + (0.2018208)*hsa-miR-6765-3p + (0.5697991)*hsa-miR-6741-5p + (−0.2300502)*hsa-miR-5739 + (−0.0846453)*hsa-miR-373-5p + (0.5710604)*hsa-miR-663a + (−2.4571022)*hsa-miR-1228-5p + (0.1295403)*hsa-miR-642b-3p + (−0.3104713)*hsa-miR-4728-5p + (−0.8254877)*hsa-miR-937-5p + (−0.0633134)*hsa-miR-887-3p + (0.4501435)*hsa-miR-6124 + (0.0532032)*hsa-miR-6075 + (−0.0167539)*hsa-miR-6794-5p + (−0.159077)*hsa-miR-6778-5p + (−0.0313716)*hsa-miR-6762-5p + (−0.3303255)*hsa-miR-4484 + (−3.1773215)*hsa-miR-6087 + (0.0739993)*hsa-miR-6760-5p + (0.3358439)*hsa-miR-1237-5p + (−0.0440618)*hsa-miR-711 + (−0.2404605)*hsa-miR-4270 + (−0.2751142)*hsa-miR-4710 + (0.6544662)*hsa-miR-5195-3p + (0.295192)*hsa-miR-128-2-5p + (−0.7253273)*hsa-miR-149-3p + (−0.3974438)*hsa-miR-1914-3p + (0.2908112)*hsa-miR-4763-3p + (0.1248389)*hsa-miR-6726-5p + (−0.0067125)*hsa-miR-1207-5p + (0.5368467)*hsa-miR-4675 + (0.4202241)*hsa-miR-328-5p + (−0.007049)*hsa-miR-6716-5p + (0.3352917)*hsa-miR-4455 + (0.6409634)*hsa-miR-3619- | 0.51 |

TABLE 16-2-continued

| No. | Number of miRNA | Discriminant formula | Threshold |
|---|---|---|---|
|  |  | 3p + (0.0309696)*hsa-miR-3160-5p + (2.146443)*hsa-miR-6724-5p + (−0.152149)*hsa-miR-423-5p + (−0.2819543)*hsa-miR-4447 + (−0.9913437)*hsa-miR-3621 + (0.4200105)*hsa-miR-4739 + (0.4525662)*hsa-miR-6132 + (−1.5422233)*hsa-miR-6791-5p + (−1.1506838)*hsa-miR-4725-3p + (−0.1197616)*hsa-miR-3158-5p + (−0.2090465)*hsa-miR-6766-3p + (−0.1497135)*hsa-miR-6879-5p + (−0.2037203)*hsa-miR-940 + (0.2991638)*hsa-miR-4750-5p + (−0.0716387)*hsa-miR-3154 + (0.6954744)*hsa-miR-3663-3p + (−0.1041385)*hsa-miR-4655-5p + (−1.0860398)*hsa-miR-4649-5p + (−0.4193025)*hsa-miR-4640-5p + (0.3758715)*hsa-miR-6869-5p + (−0.8624156)*hsa-miR-1343-3p + (−0.1870276)*hsa-miR-6771-5p + (−0.1372597)*hsa-miR-7108-3p + (−0.1506052)*hsa-miR-3195 + (0.5473537)*hsa-miR-4687-3p + (0.1403362)*hsa-miR-1185-2-3p + (−0.0498392)*hsa-miR-1225-5p + (−0.0090745)*hsa-miR-4322 + (−0.4368464)*hsa-miR-6088 + (1.1299979)*hsa-miR-6785-5p + (0.2718584)*hsa-miR-6777-5p + (−0.3008688)*hsa-miR-4695-5p + (−0.1117853)*hsa-miR-6880-3p + 44.5219553 |  |
| 44 | 104 | (−0.142443)*hsa-miR-498 + (0.343385)*hsa-miR-4658 + (0.431962)*hsa-miR-6717-5p + (0.002511)*hsa-miR-8073 + (−0.337601)*hsa-miR-92a-3p + (−0.029308)*hsa-miR-3652 + (−0.106071)*hsa-miR-6836-3p + (0.006541)*hsa-miR-1193 + (0.875478)*hsa-miR-4436b-5p + (−0.168653)*hsa-miR-6812-5p + (0.053152)*hsa-miR-4663 + (0.1271)*hsa-miR-4652-5p + (−0.591585)*hsa-miR-1343-5p + (0.083892)*hsa-miR-1246 + (−0.216299)*hsa-miR-4448 + (0.733901)*hsa-miR-6722-3p + (−0.137186)*hsa-miR-6826-5p + (0.036726)*hsa-miR-29b-3p + (2.472847)*hsa-miR-1908-5p + (−0.089103)*hsa-miR-6840-3p + (−1.496956)*hsa-miR-3197 + (0.336997)*hsa-miR-371b-5p + (0.239512)*hsa-miR-4433a-3p + (−0.478043)*hsa-miR-4534 + (0.099419)*hsa-miR-6816-5p + (−0.531065)*hsa-miR-6800-5p + (−0.259498)*hsa-miR-150-3p + (−0.449811)*hsa-miR-296-3p + (0.096368)*hsa-miR-4771 + (−0.038915)*hsa-miR-1908-3p + (−0.083576)*hsa-miR-4298 + (0.128277)*hsa-miR-6774-5p + (0.014162)*hsa-miR-615-5p + (−0.162203)*hsa-miR-4741 + (1.37632)*hsa-miR-1227-5p + (0.203311)*hsa-miR-1185-1-3p + (0.2478)*hsa-miR-6765-3p + (0.659776)*hsa-miR-6741-5p + (−0.422742)*hsa-miR-5739 + (−0.062029)*hsa-miR-373-5p + (0.417561)*hsa-miR-663a + (−3.034528)*hsa-miR-1228-5p + (0.156515)*hsa-miR-642b-3p + (−0.296177)*hsa-miR-4728-5p + (−0.798202)*hsa-miR-937-5p + (−0.004472)*hsa-miR-887-3p + (0.524208)*hsa-miR-6124 + (0.169608)*hsa-miR-6075 + (−0.183942)*hsa-miR-6778-5p + (−0.117397)*hsa-miR-6762-5p + (−0.458025)*hsa-miR-4484 + (−3.409511)*hsa-miR-6087 + (0.076078)*hsa-miR-6760-5p + (0.488415)*hsa-miR-1237-5p + (−0.034753)*hsa-miR-711 + (−0.380955)*hsa-miR-4270 + (−0.292588)*hsa-miR-4710 + (0.830594)*hsa-miR-5195-3p + (0.674073)*hsa-miR-128-2-5p + (−0.603804)*hsa-miR-149-3p + (−0.440067)*hsa-miR-1914-3p + (0.573642)*hsa-miR-4763-3p + (0.088688)*hsa-miR-6726-5p + (−0.007254)*hsa-miR-1207-5p + (0.614477)*hsa-miR-4675 + (0.216859)*hsa-miR-328-5p + (−0.069761)*hsa-miR-6716-5p + (0.381322)*hsa-miR-4455 + (0.748721)*hsa-miR-3619-3p + (0.045501)*hsa-miR-3160-5p + (2.573042)*hsa-miR-6724-5p + (−0.17771)*hsa-miR-423-5p + (0.011489)*hsa-miR-92a-2-5p + (−0.344767)*hsa-miR-4447 + (−1.078043)*hsa-miR-3621 + (0.794977)*hsa-miR-4739 + (0.368263)*hsa-miR-6132 + (−2.288217)*hsa-miR-6791-5p + (−1.158644)*hsa-miR-4725-3p + (−0.156604)*hsa-miR-3158-5p + (−0.254161)*hsa-miR-6766-3p + (−0.305986)*hsa-miR-6879-5p + (−0.236762)*hsa-miR-940 + (0.414075)*hsa-miR-4750-5p + (−0.071799)*hsa-miR-3154 + (0.996824)*hsa-miR-3663-3p + (−0.282559)*hsa-miR-4655-5p + (−1.520084)*hsa-miR-4649-5p + (−0.48277)*hsa-miR-4640-5p + (0.064498)*hsa-miR-4783-3p + (0.472275)*hsa-miR-6869-5p + (−0.955611)*hsa-miR-1343-3p + (−0.204386)*hsa-miR-6771-5p + (−0.12549)*hsa-miR-7108-3p + (−0.487461)*hsa-miR-3195 + (0.872821)*hsa-miR-4687-3p + (0.203465)*hsa-miR-1185-2-3p + (−0.087519)*hsa-miR-1225-5p + (−0.01442)*hsa-miR-4322 + (−0.583521)*hsa-miR-6088 + (1.301175)*hsa-miR-6785-5p + (0.27416)*hsa-miR-6777-5p + (−0.307199)*hsa-miR-4695-5p + (−0.11423)*hsa-miR-6880-3p + 39.943135 | 0.65 |

Example 3

<Comparison of miRNA Expression Levels in Serum Between Bladder Cancer Patients and Patients of Cancers Other than Bladder Cancer, Benign Disease Patients, and Healthy Subjects>

In this Example, the miRNA expression levels in serum of bladder cancer patients were compared with those of patients of cancers other than bladder cancer, benign disease patients, and healthy subjects using the training cohort (Table 4) the gene expression levels of which were measured in the above Reference Example. Specifically, first, miRNA expression levels in the training cohort including 261 bladder cancer patients as a positive sample group and including 408 patients of cancers other than bladder cancer, 133 benign disease patients, and 67 healthy subjects as a negative sample group were together normalized in accordance with global normalization, as shown in the above Reference Example. Next, in order to evaluate more reliable diagnostic markers, only genes having a gene expression level of $2^6$ or more in 50% or more samples in either the positive sample group or the negative sample group were selected. Further, to evaluate genes having a statistically significant difference in the gene expression level between the positive sample group and the negative sample group, an equal-variance-assumed two-sided t test was conducted to calculate the P values, which were corrected by Bonferroni correction. Further, in order to evaluate the susceptibility to noise during measurement, the absolute value of the difference (Fold change) in the gene expression levels in the positive sample group or the negative sample group that were logarithmically converted was calculated. Genes with a P value after the correction of 0.01 or less and an absolute value of Fold change of 0.5 or more were extracted as genes with expression varied, to obtain 89 diagnostic markers capable of detecting bladder cancer (Table 17). The mean and SD of the expression levels of the selected genes in the positive sample group and the negative sample group, the P value after Bonferroni correction, and the absolute value of Fold change are shown in Table 17. Among these, genes newly found as markers to examine the presence or absence of bladder cancer are polynucleotides consisting of nucleotide sequences represented by SEQ ID NOs: 1, 2, 3, 4, 5, 11, 12, 15, 17, 19, 20, 21, 26, 27, 28, 31, 35, 36, 41, 44, 45, 47, 48, 49, 50, 53, 59, 65, 67, 72, 73, 74, 76, 80, 82, 83, 85, 88, 89, 95, 96, 98, 99, 104, 107, 108, 119, 120, 121, 125, 126, 128, 130, 132, 133, 135, 136, 137, 138, 142, 146, 148, 149, 150, 152, 154, 155, 156, 161, 164, 169, 172, 174, 176, 179, 182, 198, 201, 204, 209, 219, 222, 223, 224, and 226.

TABLE 17

| No. | Name of miRNA | SEQ ID NO | Bladder cancer | | Negative group | | P value | Fold change |
| --- | --- | --- | --- | --- | --- | --- | --- | --- |
| | | | mean | SD | mean | SD | | |
| 1 | hsa-miR-4652-5p | 104 | 6.30 | 1.78 | 3.01 | 2.53 | 8.49E−65 | 3.30 |
| 2 | hsa-miR-3160-5p | 35 | 9.03 | 2.13 | 6.77 | 2.23 | 1.65E−36 | 2.27 |
| 3 | hsa-miR-4658 | 107 | 5.96 | 1.40 | 3.70 | 2.43 | 5.46E−37 | 2.26 |
| 4 | hsa-miR-4755-3p | 133 | 6.58 | 1.79 | 4.50 | 2.88 | 3.17E−22 | 2.08 |
| 5 | hsa-miR-3194-3p | 41 | 9.28 | 1.43 | 7.25 | 2.35 | 4.76E−32 | 2.03 |
| 6 | hsa-miR-4663 | 108 | 6.42 | 1.76 | 4.41 | 2.48 | 4.95E−27 | 2.02 |
| 7 | hsa-miR-17-3p | 20 | 6.82 | 1.10 | 4.95 | 2.47 | 3.58E−26 | 1.87 |
| 8 | hsa-miR-29b-3p | 31 | 6.00 | 1.48 | 4.14 | 2.86 | 8.95E−19 | 1.86 |
| 9 | hsa-miR-4480 | 88 | 7.18 | 1.61 | 5.43 | 2.55 | 7.73E−20 | 1.75 |
| 10 | hsa-miR-6831-5p | 201 | 6.02 | 1.15 | 4.35 | 2.04 | 4.28E−29 | 1.67 |
| 11 | hsa-miR-4633-3p | 99 | 5.90 | 2.18 | 4.36 | 3.07 | 1.44E−09 | 1.53 |
| 12 | hsa-miR-4727-3p | 125 | 6.85 | 1.17 | 5.33 | 2.00 | 4.13E−25 | 1.52 |
| 13 | hsa-miR-4455 | 83 | 6.19 | 1.48 | 4.67 | 2.20 | 1.43E−19 | 1.51 |
| 14 | hsa-miR-6760-5p | 174 | 6.11 | 1.16 | 4.64 | 2.36 | 2.53E−17 | 1.47 |
| 15 | hsa-miR-4483 | 89 | 6.47 | 1.75 | 5.02 | 1.94 | 1.69E−20 | 1.45 |
| 16 | hsa-miR-2467-3p | 28 | 9.97 | 1.29 | 8.52 | 1.93 | 2.23E−23 | 1.45 |
| 17 | hsa-miR-4771 | 135 | 6.36 | 1.66 | 4.95 | 2.55 | 1.88E−12 | 1.41 |
| 18 | hsa-miR-4718 | 121 | 9.05 | 1.20 | 7.68 | 2.30 | 2.21E−15 | 1.36 |
| 19 | hsa-miR-4525 | 96 | 11.73 | 1.23 | 10.42 | 1.76 | 1.05E−22 | 1.31 |
| 20 | hsa-miR-4740-5p | 130 | 6.99 | 1.32 | 5.69 | 2.02 | 2.83E−17 | 1.30 |
| 21 | hsa-miR-6717-5p | 164 | 8.39 | 0.82 | 7.09 | 1.92 | 4.91E−21 | 1.30 |
| 22 | hsa-miR-1246 | 231 | 8.73 | 1.83 | 7.44 | 3.47 | 4.78E−05 | 1.29 |
| 23 | hsa-miR-4783-5p | 137 | 6.65 | 1.78 | 5.43 | 2.10 | 2.58E−12 | 1.21 |
| 24 | hsa-miR-191-5p | 238 | 6.77 | 1.59 | 5.57 | 2.78 | 2.8E−07 | 1.20 |
| 25 | hsa-miR-4448 | 80 | 9.33 | 1.31 | 8.14 | 1.99 | 1.08E−14 | 1.19 |
| 26 | hsa-miR-371b-5p | 59 | 6.05 | 1.06 | 4.91 | 1.79 | 2.28E−17 | 1.14 |
| 27 | hsa-miR-6777-5p | 182 | 7.19 | 0.84 | 6.07 | 1.75 | 3.14E−18 | 1.12 |
| 28 | hsa-miR-4462 | 85 | 6.06 | 1.29 | 4.95 | 1.91 | 8.34E−14 | 1.12 |
| 29 | hsa-miR-320b | 45 | 6.75 | 0.92 | 5.64 | 1.83 | 4.13E−16 | 1.11 |
| 30 | hsa-miR-4708-3p | 119 | 8.86 | 1.21 | 7.76 | 1.86 | 2.61E−14 | 1.10 |
| 31 | hsa-miR-6131 | 152 | 11.70 | 1.75 | 10.63 | 2.83 | 5.61E−05 | 1.07 |
| 32 | hsa-miR-4515 | 95 | 7.41 | 1.27 | 6.40 | 1.90 | 2.41E−11 | 1.01 |
| 33 | hsa-miR-4436b-5p | 76 | 6.73 | 0.71 | 5.75 | 1.30 | 9.23E−25 | 0.98 |
| 34 | hsa-miR-342-5p | 47 | 7.09 | 0.96 | 6.12 | 1.81 | 2.91E−12 | 0.97 |
| 35 | hsa-miR-8073 | 226 | 8.65 | 0.62 | 7.71 | 1.16 | 9.48E−29 | 0.94 |
| 36 | hsa-miR-5572 | 146 | 6.82 | 0.74 | 5.89 | 1.45 | 2.22E−18 | 0.93 |
| 37 | hsa-miR-4710 | 120 | 8.76 | 1.31 | 7.83 | 1.92 | 4.47E−09 | 0.93 |
| 38 | hsa-miR-615-5p | 155 | 7.01 | 0.60 | 6.09 | 1.20 | 1.48E−26 | 0.93 |
| 39 | hsa-miR-3619-3p | 50 | 9.05 | 0.96 | 8.22 | 0.90 | 2.98E−28 | 0.83 |
| 40 | hsa-miR-4750-5p | 132 | 7.21 | 0.68 | 6.38 | 1.31 | 1.89E−17 | 0.82 |
| 41 | hsa-miR-5010-5p | 142 | 6.30 | 1.94 | 5.50 | 1.79 | 1.25E−05 | 0.80 |
| 42 | hsa-miR-6515-5p | 161 | 5.87 | 1.38 | 5.08 | 2.18 | 0.000249 | 0.79 |
| 43 | hsa-miR-6877-5p | 209 | 8.37 | 0.54 | 7.63 | 0.88 | 4.61E−30 | 0.74 |
| 44 | hsa-miR-3622a-5p | 53 | 6.61 | 1.11 | 5.88 | 1.55 | 1.65E−08 | 0.74 |
| 45 | hsa-miR-4259 | 65 | 5.98 | 1.38 | 5.26 | 2.05 | 0.000472 | 0.73 |
| 46 | hsa-miR-614 | 154 | 10.69 | 0.88 | 9.96 | 1.38 | 2.54E−11 | 0.73 |
| 47 | hsa-miR-6087 | 1 | 11.46 | 0.26 | 12.18 | 0.47 | 3.48E−90 | 0.72 |
| 48 | hsa-miR-4454 | 82 | 11.66 | 0.73 | 10.94 | 1.22 | 1.39E−14 | 0.72 |
| 49 | hsa-miR-4787-3p | 138 | 7.57 | 0.65 | 6.86 | 1.37 | 7.14E−12 | 0.71 |
| 50 | hsa-miR-24-3p | 27 | 6.76 | 1.35 | 6.05 | 1.93 | 0.000223 | 0.71 |
| 51 | hsa-miR-1199-5p | 5 | 5.88 | 1.54 | 5.19 | 1.83 | 0.000313 | 0.69 |
| 52 | hsa-miR-345-3p | 48 | 6.09 | 1.12 | 5.41 | 1.58 | 9.41E−07 | 0.68 |
| 53 | hsa-miR-320a | 44 | 7.29 | 0.80 | 6.61 | 1.28 | 2.05E−11 | 0.68 |
| 54 | hsa-miR-4430 | 74 | 7.07 | 1.01 | 6.39 | 1.44 | 3.51E−08 | 0.67 |
| 55 | hsa-miR-3616-3p | 49 | 5.83 | 1.26 | 5.16 | 1.67 | 2.28E−05 | 0.67 |
| 56 | hsa-miR-4535 | 98 | 5.76 | 1.48 | 5.10 | 1.87 | 0.001443 | 0.66 |
| 57 | hsa-miR-1193 | 4 | 6.63 | 0.83 | 5.97 | 1.31 | 5.18E−10 | 0.66 |
| 58 | hsa-miR-187-5p | 21 | 8.68 | 0.53 | 8.03 | 1.20 | 3.81E−13 | 0.65 |
| 59 | hsa-miR-1343-3p | 17 | 8.49 | 0.60 | 7.84 | 1.27 | 1.91E−11 | 0.65 |
| 60 | hsa-miR-6766-5p | 179 | 7.09 | 0.87 | 6.45 | 1.11 | 8.81E−13 | 0.64 |
| 61 | hsa-miR-4419b | 72 | 7.37 | 0.73 | 6.73 | 1.46 | 8.02E−08 | 0.64 |
| 62 | hsa-miR-1470 | 19 | 5.34 | 1.54 | 5.97 | 1.27 | 1.01E−06 | 0.64 |

TABLE 17-continued

| No. | Name of miRNA | SEQ ID NO | Bladder cancer mean | SD | Negative group mean | SD | P value | Fold change |
|---|---|---|---|---|---|---|---|---|
| 63 | hsa-miR-1238-5p | 11 | 7.95 | 0.59 | 7.33 | 1.28 | 3.53E−10 | 0.62 |
| 64 | hsa-miR-4728-5p | 126 | 6.89 | 0.85 | 7.50 | 0.89 | 1.33E−16 | 0.61 |
| 65 | hsa-miR-1254 | 232 | 6.58 | 0.87 | 5.98 | 1.33 | 7.11E−08 | 0.60 |
| 66 | hsa-miR-3162-5p | 36 | 7.80 | 0.65 | 7.21 | 1.29 | 9.37E−09 | 0.59 |
| 67 | hsa-miR-210-5p | 26 | 5.84 | 1.15 | 5.26 | 1.51 | 8.79E−05 | 0.58 |
| 68 | hsa-miR-4429 | 73 | 7.50 | 0.59 | 6.92 | 1.35 | 1.42E−07 | 0.58 |
| 69 | hsa-miR-6076 | 149 | 8.15 | 0.53 | 7.58 | 0.84 | 8.13E−20 | 0.58 |
| 70 | hsa-miR-7977 | 223 | 9.77 | 0.81 | 9.19 | 1.07 | 4.45E−11 | 0.58 |
| 71 | hsa-miR-4286 | 67 | 7.66 | 0.73 | 7.08 | 1.22 | 8.57E−09 | 0.57 |
| 72 | hsa-miR-619-5p | 156 | 7.85 | 1.28 | 7.28 | 1.78 | 0.008063 | 0.57 |
| 73 | hsa-miR-1185-2-3p | 3 | 8.26 | 1.38 | 7.69 | 1.70 | 0.00471 | 0.57 |
| 74 | hsa-miR-6741-5p | 169 | 8.34 | 0.50 | 7.77 | 0.92 | 8.86E−17 | 0.57 |
| 75 | hsa-miR-6842-5p | 204 | 6.15 | 1.09 | 5.58 | 1.68 | 0.001537 | 0.57 |
| 76 | hsa-miR-6765-3p | 176 | 8.50 | 0.67 | 7.93 | 1.04 | 2.66E−12 | 0.57 |
| 77 | hsa-miR-4783-3p | 136 | 8.37 | 1.20 | 7.80 | 1.51 | 0.00024 | 0.57 |
| 78 | hsa-miR-1273g-3p | 15 | 8.76 | 0.80 | 8.22 | 1.29 | 1.09E−06 | 0.54 |
| 79 | hsa-miR-7975 | 222 | 9.26 | 0.79 | 8.72 | 1.30 | 2.15E−06 | 0.54 |
| 80 | hsa-miR-6819-5p | 198 | 8.49 | 0.43 | 7.96 | 0.69 | 2.07E−25 | 0.54 |
| 81 | hsa-miR-6088 | 150 | 11.01 | 0.32 | 11.55 | 0.61 | 3.53E−33 | 0.53 |
| 82 | hsa-miR-6746-5p | 172 | 7.85 | 0.55 | 7.32 | 1.11 | 1.04E−09 | 0.53 |
| 83 | hsa-miR-8052 | 224 | 6.06 | 1.10 | 5.54 | 1.47 | 0.000729 | 0.52 |
| 84 | hsa-miR-4736 | 128 | 7.21 | 1.03 | 6.69 | 1.20 | 4.11E−06 | 0.52 |
| 85 | hsa-miR-7113-3p | 219 | 6.26 | 0.96 | 5.74 | 1.38 | 0.000112 | 0.52 |
| 86 | hsa-miR-6075 | 148 | 9.16 | 0.46 | 8.65 | 0.63 | 1.54E−26 | 0.51 |
| 87 | hsa-miR-1247-3p | 12 | 7.41 | 0.54 | 6.90 | 1.01 | 1.72E−10 | 0.51 |
| 88 | hsa-miR-1202 | 229 | 7.43 | 0.59 | 6.93 | 1.03 | 8.32E−10 | 0.51 |
| 89 | hsa-miR-1185-1-3p | 2 | 8.79 | 1.19 | 8.29 | 1.43 | 0.001914 | 0.50 |

Example 4

<Discriminant Analysis Between Bladder Cancer Patients of T2 or Higher and Bladder Cancer Patients of Below T2 in TNM Classification>

In this Example, a discriminant formula with one gene marker was created using a training cohort (Table 5) including patients of T2 or higher to be treated by total removal of the bladder and patients of below T2 to be treated by endoscopy or BCG injection in terms of T classification showing the depth of in-wall invasion of the primary tumor in the TNM classification, the discriminant performance was evaluated in the validation cohort (Table 5), and the top 14 genes ranked by the accuracy were extracted from the following group of 398 genes, to obtain gene markers capable of detecting bladder cancer of T2 or higher (Table 18).

Specifically, first, miRNA expression levels in the T2 or higher group and the below T2 group obtained in the above Reference Example were together normalized in accordance with global normalization. Further, in order to acquire more reliable diagnostic markers, only 398 genes with a gene expression level of $2^6$ or larger in 50% or more of the samples were analyzed in either the T2 or higher group or the below T2 group.

Next, Fisher's discriminant analysis was performed on the measured values of the expression levels of the aforementioned 398 genes, to construct discriminant formulas for discriminating the presence or absence of bladder cancer. At this time, discriminant formulas with high discriminant performance were searched for by a modified greedy algorithm. Further, the above-prepared discriminant formulas were used to calculate the accuracy, the sensitivity, and the specificity in the validation cohort. Then, the discriminant performance was validated in independent samples. As a result, the top 14 formulas ranked by the discriminant performance were obtained. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Table 19-1 and 19-2. The genes included in these discriminant formulas were selected as diagnostic markers capable of distinguishing between bladder cancer patients of T2 or higher and bladder cancer patients of below T2. In the validation cohort, the accuracy was 43% to 78%, the sensitivity was 13% to 81%, and the specificity was 36% to 91%, thereby showing a possibility of discrimination with a miRNA marker alone or a combination of miRNA markers according to the priority order of sensitivity and specificity.

TABLE 18

| No. | Name of miRNA | SEQ ID NO |
|---|---|---|
| 1 | hsa-miR-1273g-3p | 15 |
| 2 | hsa-miR-2861 | 29 |
| 3 | hsa-miR-663b | 162 |
| 4 | hsa-miR-128-2-5p | 16 |
| 5 | hsa-miR-4673 | 109 |
| 6 | hsa-miR-4649-5p | 102 |
| 7 | hsa-miR-4436b-5p | 76 |
| 8 | hsa-miR-1915-3p | 25 |
| 9 | hsa-miR-4656 | 106 |
| 10 | hsa-miR-6887-5p | 214 |
| 11 | hsa-miR-6789-5p | 190 |
| 12 | hsa-miR-4634 | 100 |
| 13 | hsa-miR-6885-5p | 213 |
| 14 | hsa-miR-6869-5p | 207 |

TABLE 19-1

| No. | miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| 1 | hsa-miR-1273g-3p | 15 | 0.3103 | 0.8978 | 0.7231 | 0.6232 | 0.2812 | 0.8834 | 0.7846 | 0.5652 |
| 2 | hsa-miR-2861 | 29 | 0.8448 | 0.438 | 0.559 | 0.6369 | 0.8125 | 0.3558 | 0.4308 | 0.5671 |
| 3 | hsa-miR-663b | 162 | 0.2759 | 0.927 | 0.7333 | 0.6204 | 0.125 | 0.908 | 0.7795 | 0.5395 |
| 4 | hsa-miR-128-2-5p | 16 | 0.7931 | 0.438 | 0.5436 | 0.6175 | 0.5 | 0.5399 | 0.5333 | 0.4958 |
| 5 | hsa-miR-4673 | 109 | 0.3103 | 0.8467 | 0.6872 | 0.5882 | 0.1875 | 0.7485 | 0.6564 | 0.5242 |
| 6 | hsa-miR-4649-5p | 102 | 0.6379 | 0.6204 | 0.6256 | 0.6188 | 0.4375 | 0.5951 | 0.5692 | 0.5405 |
| 7 | hsa-miR-4436b-5p | 76 | 0.5517 | 0.5912 | 0.5795 | 0.578 | 0.4375 | 0.5399 | 0.5231 | 0.5067 |
| 8 | hsa-miR-1915-3p | 25 | 0.569 | 0.5985 | 0.5897 | 0.5797 | 0.5625 | 0.5828 | 0.5795 | 0.573 |
| 9 | hsa-miR-4656 | 106 | 0.5172 | 0.6131 | 0.5846 | 0.5563 | 0.4375 | 0.6196 | 0.5897 | 0.5742 |
| 10 | hsa-miR-6887-5p | 214 | 0.3276 | 0.8175 | 0.6718 | 0.5472 | 0.1875 | 0.7975 | 0.6974 | 0.5192 |
| 11 | hsa-miR-6789-5p | 190 | 0.5862 | 0.6496 | 0.6308 | 0.6318 | 0.5 | 0.546 | 0.5385 | 0.5289 |
| 12 | hsa-miR-4634 | 100 | 0.6379 | 0.5766 | 0.5949 | 0.6102 | 0.5938 | 0.5644 | 0.5692 | 0.5828 |
| 13 | hsa-miR-6885-5p | 213 | 0.8448 | 0.3796 | 0.5179 | 0.6114 | 0.7188 | 0.3804 | 0.4359 | 0.5615 |
| 14 | hsa-miR-6869-5p | 207 | 0.6207 | 0.5401 | 0.5641 | 0.5732 | 0.5 | 0.6258 | 0.6051 | 0.5811 |

TABLE 19-2

| No | Discriminant formula | Threshold |
|---|---|---|
| 1 | (1.34571)*hsa-miR-1273g-3p − 11.9051 | 0.9104 |
| 2 | (5.43533)*hsa-miR-2861 − 66.1197 | −0.4464 |
| 3 | (1.2903)*hsa-miR-663b − 11.7566 | 1.07 |
| 4 | (1.5771)*hsa-miR-1282-5p − 17.8517 | −0.3764 |
| 5 | (−0.930503)*hsa-miR-4673 + 5.53046 | 0.3233 |
| 6 | (1.4893)*hsa-miR-4649-5p − 15.8607 | 0.08691 |
| 7 | (−1.32879)*hsa-miR-4436b-5p + 8.9169 | −0.00369 |
| 8 | (2.49604)*hsa-miR-1915-3p − 26.8687 | 0.07825 |
| 9 | (1.90635)*hsa-miR-4656 − 14.7212 | 0.0203 |
| 10 | (−0.926102)*hsa-miR-6887-5p + 6.37662 | 0.4298 |
| 11 | (2.4365)*hsa-miR-6789-5p − 24.9263 | −0.06067 |
| 12 | (2.11662)*hsa-miR-4634 − 19.3942 | −0.1283 |
| 13 | (1.42045)*hsa-miR-6885-5p − 16.331 | −0.5798 |
| 14 | (1.75884)*hsa-miR-6869-5p − 23.1502 | −0.1197 |

Example 5

(Common miRNAs in Examples 1 to 3)

In this Example, genes common in Examples 1 and 2 were extracted from the genes shown in each of Examples 1 to 3 capable of discriminating between bladder cancer patients and subjects without bladder cancer, to obtain 43 gene markers capable of detecting bladder cancer with higher versatility (Table 20). Further, genes common in Examples 1 and 3 were extracted to obtain 62 gene markers capable of detecting bladder cancer with higher versatility (Table 21). Further, genes common in Examples 2 and 3 were extracted to obtain 30 gene markers capable of detecting bladder cancer with higher versatility (Table 22). Further, genes common in all Examples 1 to 3 were extracted to obtain 23 gene markers capable of detecting bladder cancer with higher versatility (Table 23). It can be said that the genes shown in Tables 20 to 23 are markers that can detect bladder cancer with high versatility and can be commonly used in various analytical techniques.

TABLE 20

| No. | Name of miRNA | SEQ ID NO |
|---|---|---|
| 1 | hsa-miR-4658 | 107 |
| 2 | hsa-miR-6717-5p | 164 |
| 3 | hsa-miR-8073 | 226 |
| 4 | hsa-miR-4436b-5p | 76 |
| 5 | hsa-miR-4663 | 108 |
| 6 | hsa-miR-4652-5p | 104 |
| 7 | hsa-miR-1343-5p | 18 |
| 8 | hsa-miR-371b-5p | 59 |
| 9 | hsa-miR-6800-5p | 193 |
| 10 | hsa-miR-4771 | 135 |
| 11 | hsa-miR-615-5p | 155 |
| 12 | hsa-miR-4741 | 131 |
| 13 | hsa-miR-1185-1-3p | 2 |
| 14 | hsa-miR-6741-5p | 169 |
| 15 | hsa-miR-663a | 240 |
| 16 | hsa-miR-1228-5p | 9 |
| 17 | hsa-miR-4728-5p | 126 |
| 18 | hsa-miR-937-5p | 228 |
| 19 | hsa-miR-887-3p | 227 |
| 20 | hsa-miR-6075 | 148 |
| 21 | hsa-miR-6087 | 1 |
| 22 | hsa-miR-6760-5p | 174 |
| 23 | hsa-miR-4763-3p | 134 |
| 24 | hsa-miR-4675 | 110 |
| 25 | hsa-miR-328-5p | 46 |
| 26 | hsa-miR-6716-5p | 163 |
| 27 | hsa-miR-4455 | 83 |
| 28 | hsa-miR-3619-3p | 50 |
| 29 | hsa-miR-3160-5p | 35 |
| 30 | hsa-miR-6724-5p | 166 |
| 31 | hsa-miR-3621 | 52 |
| 32 | hsa-miR-4739 | 129 |
| 33 | hsa-miR-6132 | 153 |
| 34 | hsa-miR-6791-5p | 191 |
| 35 | hsa-miR-4725-3p | 123 |
| 36 | hsa-miR-4750-5p | 132 |
| 37 | hsa-miR-1343-3p | 17 |
| 38 | hsa-miR-7108-3p | 216 |
| 39 | hsa-miR-3195 | 42 |
| 40 | hsa-miR-4687-3p | 111 |
| 41 | hsa-miR-1185-2-3p | 3 |
| 42 | hsa-miR-6088 | 150 |
| 43 | hsa-miR-6777-5p | 182 |

TABLE 21

| No. | Name of miRNA | SEQ ID NO |
|---|---|---|
| 1 | hsa-miR-4652-5p | 104 |
| 2 | hsa-miR-3160-5p | 35 |
| 3 | hsa-miR-4658 | 107 |
| 4 | hsa-miR-4755-3p | 133 |
| 5 | hsa-miR-3194-3p | 41 |
| 6 | hsa-miR-4663 | 108 |
| 7 | hsa-miR-17-3p | 20 |
| 8 | hsa-miR-4480 | 88 |
| 9 | hsa-miR-4727-3p | 125 |
| 10 | hsa-miR-4455 | 83 |
| 11 | hsa-miR-6760-5p | 174 |

TABLE 21-continued

| No. | Name of miRNA | SEQ ID NO |
|---|---|---|
| 12 | hsa-miR-4483 | 89 |
| 13 | hsa-miR-2467-3p | 28 |
| 14 | hsa-miR-4771 | 135 |
| 15 | hsa-miR-4718 | 121 |
| 16 | hsa-miR-4525 | 96 |
| 17 | hsa-miR-4740-5p | 130 |
| 18 | hsa-miR-6717-5p | 164 |
| 19 | hsa-miR-191-5p | 238 |
| 20 | hsa-miR-371b-5p | 59 |
| 21 | hsa-miR-6777-5p | 182 |
| 22 | hsa-miR-4462 | 85 |
| 23 | hsa-miR-320b | 45 |
| 24 | hsa-miR-4708-3p | 119 |
| 25 | hsa-miR-4436b-5p | 76 |
| 26 | hsa-miR-8073 | 226 |
| 27 | hsa-miR-5572 | 146 |
| 28 | hsa-miR-615-5p | 155 |
| 29 | hsa-miR-3619-3p | 50 |
| 30 | hsa-miR-4750-5p | 132 |
| 31 | hsa-miR-5010-5p | 142 |
| 32 | hsa-miR-6877-5p | 209 |
| 33 | hsa-miR-3622a-5p | 53 |
| 34 | hsa-miR-6087 | 1 |
| 35 | hsa-miR-4787-3p | 138 |
| 36 | hsa-miR-345-3p | 48 |
| 37 | hsa-miR-320a | 44 |
| 38 | hsa-miR-4430 | 74 |
| 39 | hsa-miR-3616-3p | 49 |
| 40 | hsa-miR-4535 | 98 |
| 41 | hsa-miR-187-5p | 21 |
| 42 | hsa-miR-1343-3p | 17 |
| 43 | hsa-miR-6766-5p | 179 |
| 44 | hsa-miR-4419b | 72 |
| 45 | hsa-miR-1238-5p | 11 |
| 46 | hsa-miR-4728-5p | 126 |
| 47 | hsa-miR-210-5p | 26 |
| 48 | hsa-miR-6076 | 149 |
| 49 | hsa-miR-619-5p | 156 |
| 50 | hsa-miR-1185-2-3p | 3 |
| 51 | hsa-miR-6741-5p | 169 |
| 52 | hsa-miR-6842-5p | 204 |
| 53 | hsa-miR-1273g-3p | 15 |
| 54 | hsa-miR-7975 | 222 |
| 55 | hsa-miR-6819-5p | 198 |
| 56 | hsa-miR-6088 | 150 |
| 57 | hsa-miR-8052 | 224 |
| 58 | hsa-miR-4736 | 128 |
| 59 | hsa-miR-7113-3p | 219 |
| 60 | hsa-miR-6075 | 148 |
| 61 | hsa-miR-1247-3p | 12 |
| 62 | hsa-miR-1185-1-3p | 2 |

TABLE 22

| No. | Name of miRNA | SEQ ID NO |
|---|---|---|
| 1 | hsa-miR-4652-5p | 104 |
| 2 | hsa-miR-3160-5p | 35 |
| 3 | hsa-miR-4658 | 107 |
| 4 | hsa-miR-4663 | 108 |
| 5 | hsa-miR-29b-3p | 31 |
| 6 | hsa-miR-4455 | 83 |
| 7 | hsa-miR-6760-5p | 174 |
| 8 | hsa-miR-4771 | 135 |
| 9 | hsa-miR-6717-5p | 164 |
| 10 | hsa-miR-1246 | 231 |
| 11 | hsa-miR-4448 | 80 |
| 12 | hsa-miR-371b-5p | 59 |
| 13 | hsa-miR-6777-5p | 182 |
| 14 | hsa-miR-4436b-5p | 76 |
| 15 | hsa-miR-8073 | 226 |
| 16 | hsa-miR-4710 | 120 |
| 17 | hsa-miR-615-5p | 155 |
| 18 | hsa-miR-3619-3p | 50 |
| 19 | hsa-miR-4750-5p | 132 |
| 20 | hsa-miR-6087 | 1 |
| 21 | hsa-miR-1193 | 4 |
| 22 | hsa-miR-1343-3p | 17 |
| 23 | hsa-miR-4728-5p | 126 |
| 24 | hsa-miR-1185-2-3p | 3 |
| 25 | hsa-miR-6741-5p | 169 |
| 26 | hsa-miR-6765-3p | 176 |
| 27 | hsa-miR-4783-3p | 136 |
| 28 | hsa-miR-6088 | 150 |
| 29 | hsa-miR-6075 | 148 |
| 30 | hsa-miR-1185-1-3p | 2 |

TABLE 23

| No. | Name of miRNA | SEQ ID NO |
|---|---|---|
| 1 | hsa-miR-4652-5p | 104 |
| 2 | hsa-miR-3160-5p | 35 |
| 3 | hsa-miR-4658 | 107 |
| 4 | hsa-miR-4663 | 108 |
| 5 | hsa-miR-4455 | 83 |
| 6 | hsa-miR-6760-5p | 174 |
| 7 | hsa-miR-4771 | 135 |
| 8 | hsa-miR-6717-5p | 164 |
| 9 | hsa-miR-371b-5p | 59 |
| 10 | hsa-miR-6777-5p | 182 |
| 11 | hsa-miR-4436b-5p | 76 |
| 12 | hsa-miR-8073 | 226 |
| 13 | hsa-miR-615-5p | 155 |
| 14 | hsa-miR-3619-3p | 50 |
| 15 | hsa-miR-4750-5p | 132 |
| 16 | hsa-miR-6087 | 1 |
| 17 | hsa-miR-1343-3p | 17 |
| 18 | hsa-miR-4728-5p | 126 |
| 19 | hsa-miR-1185-2-3p | 3 |
| 20 | hsa-miR-6741-5p | 169 |
| 21 | hsa-miR-6088 | 150 |
| 22 | hsa-miR-6075 | 148 |
| 23 | hsa-miR-1185-1-3p | 2 |

Example 6

<Discriminant Analysis of Bladder Cancer from Other Cancers>

In this Example, the analysis was performed on sera of 972 people including 392 bladder cancer patients, 40 patients each of the cancers other than the bladder cancer patients shown in the Reference Example, 0 uterine sarcoma patients, and 100 healthy subjects. ½ of the samples of each group were sorted into a training cohort, and rest ½ of the samples were sorted into a validation cohort (Table 24).

In this Example, discriminant formulas with 1 to 9 gene markers were created using a training cohort including bladder cancer patients and subjects without bladder cancer including healthy subjects and patients of cancers other than bladder cancer, the discriminant performance in the validation cohort was evaluated, and genes used for a total of 9 discriminant formulas exhibiting the best discriminant performance in each case of combining 1 to 9 genes were extracted, to obtain 18 gene markers capable of detecting bladder cancer (Table 25).

Figure 20:
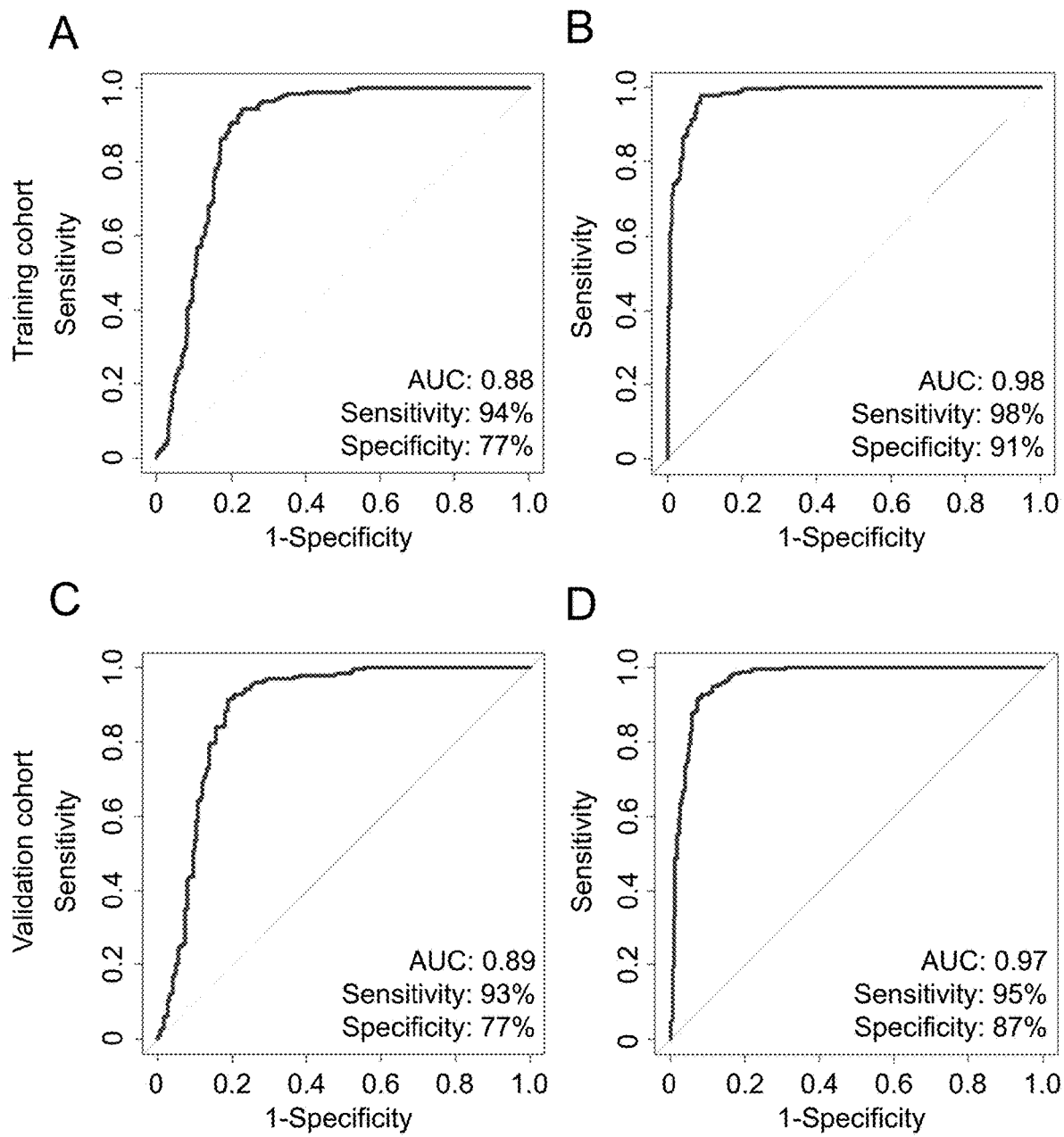
FIG. 20 shows ROC curves for the training cohort (A) and the validation cohort (C) determined with the use of 1 miRNA and ROC curves for the training cohort (B) and the validation cohort (D) determined with the use of 7 miRNAs in combination.
Figure 21:
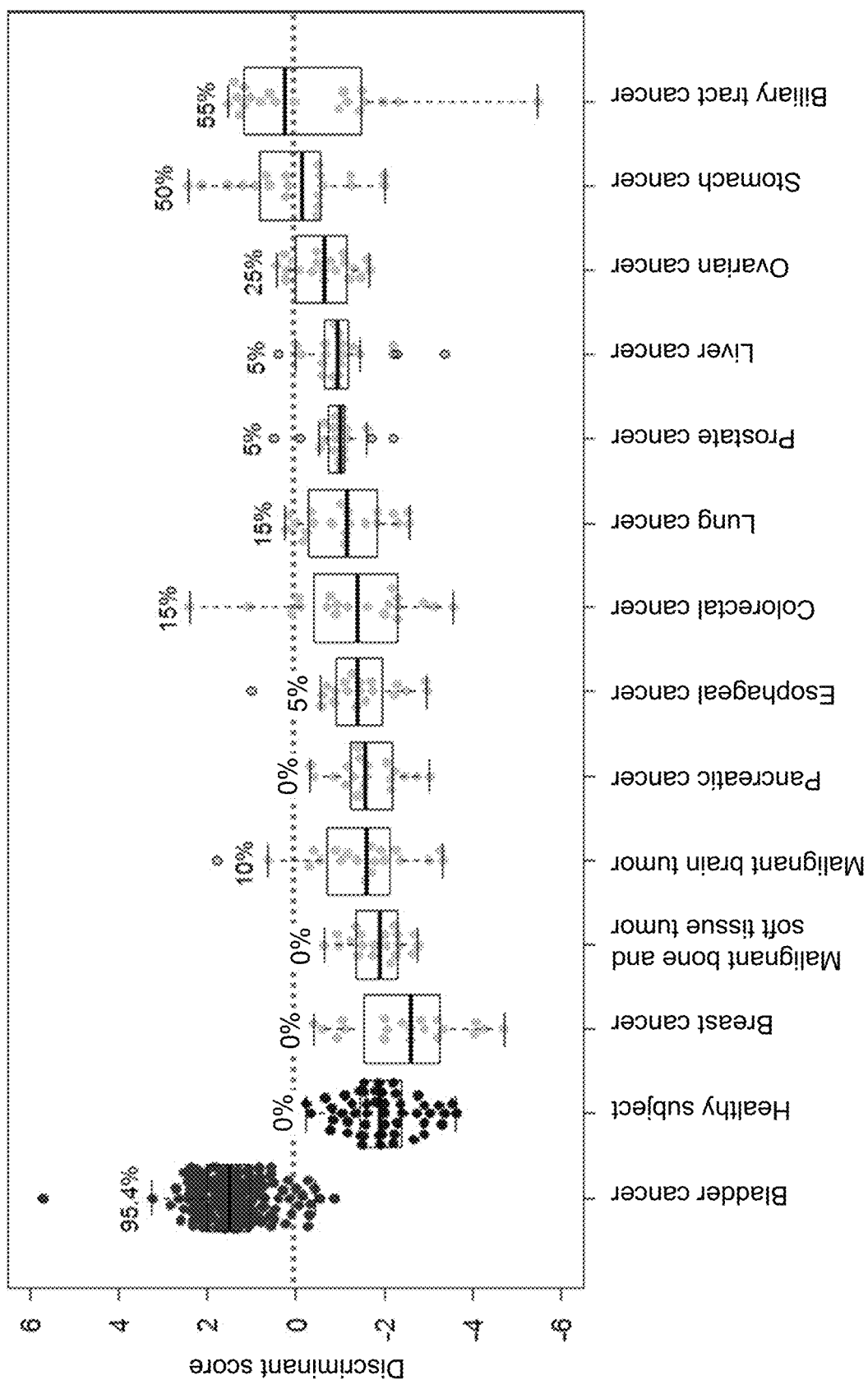
FIG. 21 shows plots of discriminant scores according to the disease type determined with the use of 7 miRNAs in combination.

Specifically, first, miRNA expression levels in the training cohort and the validation cohort obtained as in the above Reference Example were together normalized in accordance with global normalization. Further, in order to acquire more reliable diagnostic markers, only 386 genes with a gene expression level of $2^6$ or larger in 50% or more of the samples were analyzed in either the positive sample group (bladder cancer patients) or the negative sample group (patients of cancers other than bladder cancer, benign disease patients, and healthy subjects). Next, Fisher's discriminant analysis was performed on the measured values of the expression levels of a combination of 1 to 9 genes out of the aforementioned 386 genes, to construct discriminant formulas for discriminating the presence or absence of bladder cancer. At this time, discriminant formulas with high discriminant performance were searched for by a modified greedy algorithm. Further, the above-prepared discriminant formulas were used to calculate the accuracy, the sensitivity, and the specificity in the validation cohort. Then, the discriminant performance was validated in independent samples. The marker, discriminant formula, and the like exhibiting the highest performance is shown for each number of genes used for discrimination (Tables 26-1 and 26-2). Further, the ROC curves of the training cohort and the validation cohort with a combination of 1 or 7 miRNAs are shown in FIG. 20, and the discriminant scores with 7 miRNAs are plotted for each disease type in FIG. 21.

TABLE 24

| Characteristics | Training cohort (n = 546) | Validation cohort (n = 546) |
|---|---|---|
| Bladder cancer | 196 | 196 |
| Median age, yr(range) | 69(60-76) | 68(62-74) |
| Sex, n(%) | | |
| Male | 137(69.9) | 146(74.5) |
| Female | 59(30.1) | 50(25.5) |
| Pathological Tstage, n(%) | | |
| T2 or lower | 150(76.5) | 150(76.5) |
| T2 or higher | 46(23.5) | 44(22.4) |
| Unknown | 0 | 2(1.0) |
| Pathological grade, n(%) | | |
| Low grade | 36(18.4) | 41(20.9) |
| high grade | 160(81.6) | 155(79.1) |

TABLE 24-continued

| Characteristics | Training cohort (n = 546) | Validation cohort (n = 546) |
|---|---|---|
| Healthy | 50 | 50 |
| Median age, yr(range) | 61(51-59) | 68(52-68) |
| Sex, n(%) | | |
| Male | 23(46.0) | 25(50.0) |
| Female | 27(54.0) | 25(50.0) |
| Other cancers | 240 | 240 |
| Median age, yr(range) | 63(56-71) | 63(54-70) |
| Sex, n(%) | | |
| Male | 150(62.5) | 136(56.7) |
| Female | 90(37.5) | 104(43.3) |

TABLE 25

| No. | Name of miRNA | SEQ ID NO |
|---|---|---|
| 1 | hsa-miR-1185-1-3p | 2 |
| 2 | hsa-miR-1185-2-3p | 3 |
| 3 | hsa-miR-1343-5p | 18 |
| 4 | hsa-miR-3184-5p | 39 |
| 5 | hsa-miR-3940-5p | 62 |
| 6 | hsa-miR-3960 | 63 |
| 7 | hsa-miR-4658 | 107 |
| 8 | hsa-miR-4695-5p | 114 |
| 9 | hsa-miR-4728-5p | 126 |
| 10 | hsa-miR-6087 | 1 |
| 11 | hsa-miR-663a | 240 |
| 12 | hsa-miR-6724-5p | 166 |
| 13 | hsa-miR-6781-5p | 185 |
| 14 | hsa-miR-6819-5p | 198 |
| 15 | hsa-miR-6831-5p | 201 |
| 16 | hsa-miR-7108-3p | 216 |
| 17 | hsa-miR-7109-5p | 217 |
| 18 | hsa-miR-744-5p | 221 |

TABLE 26-1

| No. | Number of miRNA | miRNA marker | SEQ ID NO | Validation cohort Sensitivity | Specificity | Accuracy | AUC |
|---|---|---|---|---|---|---|---|
| 1 | 1 | hsa-miR-6087 | 1 | 0.94 | 0.77 | 0.84 | 0.88 |
| 2 | 2 | hsa-miR-6087 | 1 | 0.95 | 0.81 | 0.86 | 0.91 |
| | | hsa-miR-663a | 240 | | | | |
| 3 | 3 | hsa-miR-6087 | 1 | 0.95 | 0.87 | 0.90 | 0.94 |
| | | hsa-miR-6781-5p | 185 | | | | |
| | | hsa-miR-744-5p | 221 | | | | |
| 4 | 4 | hsa-miR-6087 | 1 | 0.97 | 0.86 | 0.91 | 0.95 |
| | | hsa-miR-3940-5p | 62 | | | | |
| | | hsa-miR-4728-5p | 126 | | | | |
| | | hsa-miR-6819-5p | 198 | | | | |
| 5 | 5 | hsa-miR-6087 | 1 | 0.98 | 0.87 | 0.91 | 0.97 |
| | | hsa-miR-6724-5p | 166 | | | | |
| | | hsa-miR-3960 | 63 | | | | |
| | | hsa-miR-1343-5p | 18 | | | | |
| | | hsa-miR-1185-2-3p | 3 | | | | |
| 6 | 6 | hsa-miR-6087 | 1 | 0.97 | 0.90 | 0.93 | 0.97 |
| | | hsa-miR-6724-5p | 166 | | | | |
| | | hsa-miR-3960 | 63 | | | | |
| | | hsa-miR-1343-5p | 18 | | | | |
| | | hsa-miR-1185-2-3p | 3 | | | | |
| | | hsa-miR-4658 | 107 | | | | |
| 7 | 7 | hsa-miR-6087 | 1 | 0.98 | 0.91 | 0.94 | 0.98 |
| | | hsa-miR-6724-5p | 166 | | | | |
| | | hsa-miR-3960 | 63 | | | | |
| | | hsa-miR-1343-5p | 18 | | | | |
| | | hsa-miR-1185-1-3p | 2 | | | | |
| | | hsa-miR-6831-5p | 201 | | | | |
| | | hsa-miR-4695-5p | 114 | | | | |

TABLE 26-1-continued

| No. | Number of miRNA | miRNA marker | SEQ ID NO | Validation cohort Sensitivity | Specificity | Accuracy | AUC |
|---|---|---|---|---|---|---|---|
| 8 | 8 | hsa-miR-6087 | 1 | 0.98 | 0.91 | 0.94 | 0.98 |
|   |   | hsa-miR-6724-5p | 166 |   |   |   |   |
|   |   | hsa-miR-3960 | 63 |   |   |   |   |
|   |   | hsa-miR-1343-5p | 18 |   |   |   |   |
|   |   | hsa-miR-1185-1-3p | 2 |   |   |   |   |
|   |   | hsa-miR-6831-5p | 201 |   |   |   |   |
|   |   | hsa-miR-4695-5p | 114 |   |   |   |   |
|   |   | hsa-miR-7109-5p | 217 |   |   |   |   |
| 9 | 9 | hsa-miR-6087 | 1 | 1.00 | 0.90 | 0.94 | 0.98 |
|   |   | hsa-miR-6724-5p | 166 |   |   |   |   |
|   |   | hsa-miR-3960 | 63 |   |   |   |   |
|   |   | hsa-miR-1343-5p | 18 |   |   |   |   |
|   |   | hsa-miR-1185-1-3p | 2 |   |   |   |   |
|   |   | hsa-miR-6831-5p | 201 |   |   |   |   |
|   |   | hsa-miR-3184-5p | 39 |   |   |   |   |
|   |   | hsa-miR-7108-3p | 216 |   |   |   |   |
|   |   | hsa-miR-4695-5p | 114 |   |   |   |   |

TABLE 26-2

| No. | Number of miRNA | Discriminant formula |
|---|---|---|
| 1 | 1 | (−2.47083)*hsa-miR-6087 + 29.1765 |
| 2 | 2 | (−2.45684)*hsa-miR-6087 + (0.674768)*hsa-miR-663a + 20.7712 |
| 3 | 3 | (−2.47956)*hsa-miR-6087 + (−1.18834)*hsa-miR-6781-5p + (0.662579)*hsa-miR-744-5p + 34.9109 |
| 4 | 4 | (−1.67453)*hsa-miR-6087 + (−1.07965)*hsa-miR-3940-5p + (−0.865343)*hsa-miR-4728-5p + (0.936314)*hsa-miR-6819-5p + 30.2466 |
| 5 | 5 | (−2.33489)*hsa-miR-6087 + (2.1135)*hsa-miR-6724-5p + (−1.28296)*hsa-miR-3960 + (−1.33813)*hsa-miR-1343-5p + (0.211841)*hsa-miR-1185-2-3p + 35.6487 |
| 6 | 6 | (−2.22483)*hsa-miR-6087 + (1.96229)*hsa-miR-6724-5p + (−1.1623)*hsa-miR-3960 + (−1.24909)*hsa-miR-1343-5p + (0.191799)*hsa-miR-1185-2-3p + (0.0988384)*hsa-miR-4658 + 32.9756 |
| 7 | 7 | (−2.21832)*hsa-miR-6087 + (2.17809)*hsa-miR-6724-5p + (−1.04605)*hsa-miR-3960 + (−1.57609)*hsa-miR-1343-5p + (0.202966)*hsa-miR-1185-1-3p + (0.203839)*hsa-miR-6831-5p + (-0.411172)*hsa-miR-4695-5p + 34.7121 |
| 8 | 8 | (−2.23426)*hsa-miR-6087 + (2.10616)*hsa-miR-6724-5p + (−1.09832)*hsa-miR-3960 + (−1.49652)*hsa-miR-1343-5p + (0.233803)*hsa-miR-1185-1-3p + (0.209904)*hsa-miR-6831-5p + (-0.365926)*hsa-miR-4695-5p + (−0.195056)*hsa-miR-7109-5p + 36.4566 |
| 9 | 9 | (−2.18021)*hsa-miR-6087 + (2.14473)*hsa-miR-6724-5p + (−0.990552)*hsa-miR-3960 + (−1.3526)*hsa-miR-1343-5p + (0.201392)*hsa-miR-1185-1-3p + (0.215897)*hsa-miR-6831-5p + (−0.117666)*hsa-miR-3184-5p + (−0.0946823)*hsa-miR-7108-3p + (−0.373914)*hsa-miR-4695-5p + 32.4599 |

INDUSTRIAL APPLICABILITY

The present invention enables bladder cancer of various histological types and stages to be effectively detected by an easy and inexpensive method, thereby enabling detection, diagnosis, and treatment of bladder cancer at an early stage. Further, the method of the present invention enables bladder cancer to be detected minimally invasively using patient blood, thereby enabling bladder cancer to be detected simply and quickly.

All the publications, patents, and patent applications cited herein are incorporated herein by reference.

The invention claimed is:

1. A method for detecting bladder cancer, comprising:
measuring an expression level of miR-1185-1-3p in a sample from a human subject;
determining that the level of miR-1185-1-3p in the sample from the human subject is increased in comparison to a level of miR-1185-1-3p in a control sample from a human subject without bladder cancer;
determining that the human subject has bladder cancer based on the increased expression level of miR-1185-1-3p; and
treating the human subject for the bladder cancer;
wherein the sample is blood, serum, or plasma; and
wherein the treating comprises surgery, radiotherapy, chemotherapy, or a combination thereof.

2. The method according to claim 1, comprising: plugging the gene expression level of miR-1185-1-3p in the sample from the subject into a discriminant formula capable of discriminating the presence or absence of a bladder cancer distinctively, wherein the discriminant formula is created by using gene expression levels in samples from subjects known to have bladder cancer and gene expression levels in samples from subjects having no bladder cancer as training samples.

3. The method according to claim 1, comprising: measuring an expression level of miR-1185-1-3p by using a nucleic acid(s) capable of specifically binding to miR-1185-1-3p or the complement thereof, wherein the nucleic acid(s) is a polynucleotide(s) selected from the group consisting of:
(a) a polynucleotide consisting of SEQ ID NO: 2 or the complement thereof;
(b) a polynucleotide comprising SEQ ID NO: 2 or the complement thereof; and
(c) a polynucleotide derived from SEQ ID NO: 2, wherein the uracils have been replaced with thymines, or a complement thereof.

4. The method according to claim 1, further comprising: measuring an expression level(s) of at least one polynucleotide selected from miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

5. The method according to claim 4, comprising: measuring an expression level of the at least one polynucleotide by using a nucleic acid(s) capable of specifically binding to the at least one polynucleotide or the complement thereof, wherein the nucleic acid(s) is a polynucleotide(s) selected from the group consisting of:
(a) a polynucleotide consisting of any of SEQ ID NOs: 229-243 or the complements thereof;
(b) a polynucleotide comprising any of SEQ ID NOs: 229-243 or the complements thereof; and
(c) a polynucleotide derived from any of SEQ ID NOs: 229-243, wherein the uracils have been replaced with thymines, or the complements thereof.

6. The method according to claim 1, wherein the sample is serum or plasma.

7. The method according to claim 1, wherein the method further comprises measuring an expression level(s) of at least one polynucleotide selected from miR-6087, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-683-1-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p and miR-937-5p in the sample.

8. A method for detecting bladder cancer, comprising:
measuring an expression level of miR-1185-1-3p in a sample from a human subject;
determining that the level of miR-1185-1-3p in the sample from the human subject is increased in comparison to a level of miR-1185-1-3p in a control sample from a human subject without bladder cancer;
determining that the human subject has bladder cancer based on the increased expression level of miR-1185-1-3p; and
treating the human subject for the bladder cancer;
wherein the treating comprises surgery, radiotherapy, chemotherapy, or a combination thereof;
wherein the sample is blood, serum, or plasma; and
wherein the measuring is performed using a kit comprising a nucleic acid(s) capable of specifically binding to miR-1185-1-3p or a complement thereof.

9. The method according to claim 8, wherein the method further comprises measuring an expression level(s) of at least one polynucleotide selected from miR-6087, miR-1185-2-3p, miR-1193, miR-1199-5p, miR-1225-5p, miR- 1227-5p, miR-1228-3p, miR-1228-5p, miR-1237-5p, miR-1238-5p, miR-1247-3p, miR-1268a, miR-1268b, miR-1273¢-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-3p, miR-6800-5p, miR-6802-5p, miR-6803-5p, miR-6812-5p, miR-6816-5p, miR-6819-5p, miR-6821-5p, miR-6826-5p, miR-683-1-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p and miR-937-5p in the sample.

\* \* \* \* \*

SEQUENCE LISTING

<160> NUMBER OF SEQ ID NOS: 766

<210> SEQ ID NO 1
<211> LENGTH: 18
<212> TYPE: RNA
<213> ORGANISM: Homo Sapience

<400> SEQUENCE: 1
ugaggcgggg gggcgagc                                                  18

<210> SEQ ID NO 2
<211> LENGTH: 22

```
<212> TYPE: RNA
<213> ORGANISM: Homo Sapience

<400> SEQUENCE: 2
auauacaggg ggagacucuu au                                    22

<210> SEQ ID NO 3
<211> LENGTH: 22
<212> TYPE: RNA
<213> ORGANISM: Homo Sapience

<400> SEQUENCE: 3
auauacaggg ggagacucuc au                                    22

<210> SEQ ID NO 4
<211> LENGTH: 23
<212> TYPE: RNA
<213> ORGANISM: Homo Sapience

<400> SEQUENCE: 4
gggaugguag accggugacg ugc                                   23

<210> SEQ ID NO 5
<211> LENGTH: 20
<212> TYPE: RNA
<213> ORGANISM: Homo Sapience

<400> SEQUENCE: 5
ccugagcccg ggccgcgcag                                       20

<210> SEQ ID NO 6
<211> LENGTH: 22
<212> TYPE: RNA
<213> ORGANISM: Homo Sapience

<400> SEQUENCE: 6
guggguacgg cccagugggg gg                                    22

<210> SEQ ID NO 7
<211> LENGTH: 17
<212> TYPE: RNA
<213> ORGANISM: Homo Sapience

<400> SEQUENCE: 7
guggggccag gcggugg                                          17

<210> SEQ ID NO 8
<211> LENGTH: 20
<212> TYPE: RNA
<213> ORGANISM: Homo Sapience

<400> SEQUENCE: 8
ucacaccugc cucgccccccc                                      20

<210> SEQ ID NO 9
<211> LENGTH: 21
<212> TYPE: RNA
<213> ORGANISM: Homo Sapience

<400> SEQUENCE: 9
gugggcgggg gcaggugugu g                                     21

<210> SEQ ID NO 10
```

```
<211> LENGTH: 21
<212> TYPE: RNA
<213> ORGANISM: Homo Sapience

<400> SEQUENCE: 10
cgggggcggg gccgaagcgc g                                          21

<210> SEQ ID NO 11
<211> LENGTH: 23
<212> TYPE: RNA
<213> ORGANISM: Homo Sapience

<400> SEQUENCE: 11
gugaguggga gccccagugu gug                                        23

<210> SEQ ID NO 12
<211> LENGTH: 24
<212> TYPE: RNA
<213> ORGANISM: Homo Sapience

<400> SEQUENCE: 12
ccccgggaac gucgagacug gagc                                       24

<210> SEQ ID NO 13
<211> LENGTH: 18
<212> TYPE: RNA
<213> ORGANISM: Homo Sapience

<400> SEQUENCE: 13
cgggcguggu ggugggg                                               18

<210> SEQ ID NO 14
<211> LENGTH: 20
<212> TYPE: RNA
<213> ORGANISM: Homo Sapience

<400> SEQUENCE: 14
cgggcguggu gguggggug                                             20

<210> SEQ ID NO 15
<211> LENGTH: 21
<212> TYPE: RNA
<213> ORGANISM: Homo Sapience

<400> SEQUENCE: 15
accacugcac uccagccuga g                                          21

<210> SEQ ID NO 16
<211> LENGTH: 23
<212> TYPE: RNA
<213> ORGANISM: Homo Sapience

<400> SEQUENCE: 16
gggggccgau acacuguacg aga                                        23

<210> SEQ ID NO 17
<211> LENGTH: 22
<212> TYPE: RNA
<213> ORGANISM: Homo Sapience

<400> SEQUENCE: 17
cuccuggggc ccgcacucuc gc                                         22
```

```
<210> SEQ ID NO 18
<211> LENGTH: 22
<212> TYPE: RNA
<213> ORGANISM: Homo Sapience

<400> SEQUENCE: 18
uggggagcgg cccccgggug gg                                                22

<210> SEQ ID NO 19
<211> LENGTH: 21
<212> TYPE: RNA
<213> ORGANISM: Homo Sapience

<400> SEQUENCE: 19
gcccuccgcc cgugcacccc g                                                 21

<210> SEQ ID NO 20
<211> LENGTH: 22
<212> TYPE: RNA
<213> ORGANISM: Homo Sapience

<400> SEQUENCE: 20
acugcaguga aggcacuugu ag                                                22

<210> SEQ ID NO 21
<211> LENGTH: 22
<212> TYPE: RNA
<213> ORGANISM: Homo Sapience

<400> SEQUENCE: 21
ggcuacaaca caggacccgg gc                                                22

<210> SEQ ID NO 22
<211> LENGTH: 21
<212> TYPE: RNA
<213> ORGANISM: Homo Sapience

<400> SEQUENCE: 22
ccggccgccg gcuccgcccc g                                                 21

<210> SEQ ID NO 23
<211> LENGTH: 21
<212> TYPE: RNA
<213> ORGANISM: Homo Sapience

<400> SEQUENCE: 23
cggcggggac ggcgauuggu c                                                 21

<210> SEQ ID NO 24
<211> LENGTH: 22
<212> TYPE: RNA
<213> ORGANISM: Homo Sapience

<400> SEQUENCE: 24
cgcaggggcc gggugcucac cg                                                22

<210> SEQ ID NO 25
<211> LENGTH: 20
<212> TYPE: RNA
<213> ORGANISM: Homo Sapience

<400> SEQUENCE: 25
ccccagggcg acgcggcggg                                                   20
```

```
<210> SEQ ID NO 26
<211> LENGTH: 22
<212> TYPE: RNA
<213> ORGANISM: Homo Sapience

<400> SEQUENCE: 26
agccccugcc caccgcacac ug                                        22

<210> SEQ ID NO 27
<211> LENGTH: 22
<212> TYPE: RNA
<213> ORGANISM: Homo Sapience

<400> SEQUENCE: 27
uggcucaguu cagcaggaac ag                                        22

<210> SEQ ID NO 28
<211> LENGTH: 22
<212> TYPE: RNA
<213> ORGANISM: Homo Sapience

<400> SEQUENCE: 28
agcagaggca gagaggcuca gg                                        22

<210> SEQ ID NO 29
<211> LENGTH: 19
<212> TYPE: RNA
<213> ORGANISM: Homo Sapience

<400> SEQUENCE: 29
ggggccuggc ggugggcgg                                            19

<210> SEQ ID NO 30
<211> LENGTH: 22
<212> TYPE: RNA
<213> ORGANISM: Homo Sapience

<400> SEQUENCE: 30
gaggguuggg uggaggcucu cc                                        22

<210> SEQ ID NO 31
<211> LENGTH: 23
<212> TYPE: RNA
<213> ORGANISM: Homo Sapience

<400> SEQUENCE: 31
uagcaccauu ugaaaucagu guu                                       23

<210> SEQ ID NO 32
<211> LENGTH: 23
<212> TYPE: RNA
<213> ORGANISM: Homo Sapience

<400> SEQUENCE: 32
ucgaggacug guggaagggc cuu                                       23

<210> SEQ ID NO 33
<211> LENGTH: 22
<212> TYPE: RNA
<213> ORGANISM: Homo Sapience

<400> SEQUENCE: 33
cagaagggga guugggagca ga                                        22
```

<210> SEQ ID NO 34
<211> LENGTH: 21
<212> TYPE: RNA
<213> ORGANISM: Homo Sapience

<400> SEQUENCE: 34
ccugcagaga ggaagcccuu c                                     21

<210> SEQ ID NO 35
<211> LENGTH: 22
<212> TYPE: RNA
<213> ORGANISM: Homo Sapience

<400> SEQUENCE: 35
ggcuuucuag ucucagcucu cc                                    22

<210> SEQ ID NO 36
<211> LENGTH: 23
<212> TYPE: RNA
<213> ORGANISM: Homo Sapience

<400> SEQUENCE: 36
uuagggagua aaggguggg gag                                    23

<210> SEQ ID NO 37
<211> LENGTH: 17
<212> TYPE: RNA
<213> ORGANISM: Homo Sapience

<400> SEQUENCE: 37
ggggcgcggc cggaucg                                          17

<210> SEQ ID NO 38
<211> LENGTH: 22
<212> TYPE: RNA
<213> ORGANISM: Homo Sapience

<400> SEQUENCE: 38 ugggcggag cuuccggagg cc                                     22

<210> SEQ ID NO 39
<211> LENGTH: 24
<212> TYPE: RNA
<213> ORGANISM: Homo Sapience

<400> SEQUENCE: 39
ugaggggccu cagaccgagc uuuu                                  24

<210> SEQ ID NO 40
<211> LENGTH: 23
<212> TYPE: RNA
<213> ORGANISM: Homo Sapience

<400> SEQUENCE: 40
agaagaaggc ggucggucug cgg                                   23

<210> SEQ ID NO 41
<211> LENGTH: 22
<212> TYPE: RNA
<213> ORGANISM: Homo Sapience

<400> SEQUENCE: 41

```
agcucugcug cucacuggca gu                                              22

<210> SEQ ID NO 42
<211> LENGTH: 17
<212> TYPE: RNA
<213> ORGANISM: Homo Sapience

<400> SEQUENCE: 42
cgcgccgggc ccggguu                                                    17

<210> SEQ ID NO 43
<211> LENGTH: 23
<212> TYPE: RNA
<213> ORGANISM: Homo Sapience

<400> SEQUENCE: 43
ggaggcgcag gcucggaaag gcg                                             23

<210> SEQ ID NO 44
<211> LENGTH: 22
<212> TYPE: RNA
<213> ORGANISM: Homo Sapience

<400> SEQUENCE: 44
aaaagcuggg uugagagggc ga                                              22

<210> SEQ ID NO 45
<211> LENGTH: 22
<212> TYPE: RNA
<213> ORGANISM: Homo Sapience

<400> SEQUENCE: 45
aaaagcuggg uugagagggc aa                                              22

<210> SEQ ID NO 46
<211> LENGTH: 23
<212> TYPE: RNA
<213> ORGANISM: Homo Sapience

<400> SEQUENCE: 46
gggggggcag gaggggcuca ggg                                             23

<210> SEQ ID NO 47
<211> LENGTH: 21
<212> TYPE: RNA
<213> ORGANISM: Homo Sapience

<400> SEQUENCE: 47
aggggugcua ucugugauug a                                               21

<210> SEQ ID NO 48
<211> LENGTH: 22
<212> TYPE: RNA
<213> ORGANISM: Homo Sapience

<400> SEQUENCE: 48
gcccugaacg aggggucugg ag                                              22

<210> SEQ ID NO 49
<211> LENGTH: 23
<212> TYPE: RNA
<213> ORGANISM: Homo Sapience

<400> SEQUENCE: 49
```
cgagggcauu ucaugaugca ggc    23

<210> SEQ ID NO 50
<211> LENGTH: 22
<212> TYPE: RNA
<213> ORGANISM: Homo Sapience

<400> SEQUENCE: 50
gggaccaucc ugccugcugu gg    22

<210> SEQ ID NO 51
<211> LENGTH: 22
<212> TYPE: RNA
<213> ORGANISM: Homo Sapience

<400> SEQUENCE: 51
gugggcuggg cugggcuggg cc    22

<210> SEQ ID NO 52
<211> LENGTH: 20
<212> TYPE: RNA
<213> ORGANISM: Homo Sapience

<400> SEQUENCE: 52
cgcgggucgg ggucugcagg    20

<210> SEQ ID NO 53
<211> LENGTH: 22
<212> TYPE: RNA
<213> ORGANISM: Homo Sapience

<400> SEQUENCE: 53
caggcacggg agcucaggug ag    22

<210> SEQ ID NO 54
<211> LENGTH: 21
<212> TYPE: RNA
<213> ORGANISM: Homo Sapience

<400> SEQUENCE: 54
agccgcgggg aucgccgagg g    21

<210> SEQ ID NO 55
<211> LENGTH: 18
<212> TYPE: RNA
<213> ORGANISM: Homo Sapience

<400> SEQUENCE: 55
cggcuggagg ugugagga    18

<210> SEQ ID NO 56
<211> LENGTH: 17
<212> TYPE: RNA
<213> ORGANISM: Homo Sapience

<400> SEQUENCE: 56
ggcgggugcg ggggugg    17

<210> SEQ ID NO 57
<211> LENGTH: 23
<212> TYPE: RNA
<213> ORGANISM: Homo Sapience

```
<400> SEQUENCE: 57
ugagcaccac acaggccggg cgc                                    23

<210> SEQ ID NO 58
<211> LENGTH: 23
<212> TYPE: RNA
<213> ORGANISM: Homo Sapience

<400> SEQUENCE: 58
ugaggauaug gcagggaagg gga                                    23

<210> SEQ ID NO 59
<211> LENGTH: 22
<212> TYPE: RNA
<213> ORGANISM: Homo Sapience

<400> SEQUENCE: 59
acucaaaaga uggcggcacu uu                                     22

<210> SEQ ID NO 60
<211> LENGTH: 22
<212> TYPE: RNA
<213> ORGANISM: Homo Sapience

<400> SEQUENCE: 60
acucaaaaug ggggcgcuuu cc                                     22

<210> SEQ ID NO 61
<211> LENGTH: 20
<212> TYPE: RNA
<213> ORGANISM: Homo Sapience

<400> SEQUENCE: 61
gcucggacug agcagguggg                                        20

<210> SEQ ID NO 62
<211> LENGTH: 20
<212> TYPE: RNA
<213> ORGANISM: Homo Sapience

<400> SEQUENCE: 62
guggguuggg gcgggcucug                                        20

<210> SEQ ID NO 63
<211> LENGTH: 20
<212> TYPE: RNA
<213> ORGANISM: Homo Sapience

<400> SEQUENCE: 63
ggcggcggcg gaggcggggg                                        20

<210> SEQ ID NO 64
<211> LENGTH: 17
<212> TYPE: RNA
<213> ORGANISM: Homo Sapience

<400> SEQUENCE: 64
ccccgccacc gccuugg                                           17

<210> SEQ ID NO 65
<211> LENGTH: 22
<212> TYPE: RNA
<213> ORGANISM: Homo Sapience
```

-continued

```
<400> SEQUENCE: 65
caguuggguc uagggucag ga                                              22

<210> SEQ ID NO 66
<211> LENGTH: 20
<212> TYPE: RNA
<213> ORGANISM: Homo Sapience

<400> SEQUENCE: 66
ucagggaguc aggggagggc                                                20

<210> SEQ ID NO 67
<211> LENGTH: 17
<212> TYPE: RNA
<213> ORGANISM: Homo Sapience

<400> SEQUENCE: 67
accccacucc ugguacc                                                   17

<210> SEQ ID NO 68
<211> LENGTH: 22
<212> TYPE: RNA
<213> ORGANISM: Homo Sapience

<400> SEQUENCE: 68
cugggacagg aggaggaggc ag                                             22

<210> SEQ ID NO 69
<211> LENGTH: 21
<212> TYPE: RNA
<213> ORGANISM: Homo Sapience

<400> SEQUENCE: 69
cugugggcuc agcgcguggg g                                              21

<210> SEQ ID NO 70
<211> LENGTH: 19
<212> TYPE: RNA
<213> ORGANISM: Homo Sapience

<400> SEQUENCE: 70
ggcuugcaug ggggacugg                                                 19

<210> SEQ ID NO 71
<211> LENGTH: 18
<212> TYPE: RNA
<213> ORGANISM: Homo Sapience

<400> SEQUENCE: 71
ggugggcuuc ccggaggg                                                  18

<210> SEQ ID NO 72
<211> LENGTH: 18
<212> TYPE: RNA
<213> ORGANISM: Homo Sapience

<400> SEQUENCE: 72
gaggcugaag gaagaugg                                                  18

<210> SEQ ID NO 73
<211> LENGTH: 20
<212> TYPE: RNA
```

```
<213> ORGANISM: Homo Sapience

<400> SEQUENCE: 73
aaaagcuggg cugagaggcg                                               20

<210> SEQ ID NO 74
<211> LENGTH: 18
<212> TYPE: RNA
<213> ORGANISM: Homo Sapience

<400> SEQUENCE: 74
aggcuggagu gagcggag                                                 18

<210> SEQ ID NO 75
<211> LENGTH: 21
<212> TYPE: RNA
<213> ORGANISM: Homo Sapience

<400> SEQUENCE: 75
acaggagugg ggugggaca u                                              21

<210> SEQ ID NO 76
<211> LENGTH: 22
<212> TYPE: RNA
<213> ORGANISM: Homo Sapience

<400> SEQUENCE: 76
guccacuucu gccugcccug cc                                            22

<210> SEQ ID NO 77
<211> LENGTH: 17
<212> TYPE: RNA
<213> ORGANISM: Homo Sapience

<400> SEQUENCE: 77
uuggaggcgu ggguuuu                                                  17

<210> SEQ ID NO 78
<211> LENGTH: 22
<212> TYPE: RNA
<213> ORGANISM: Homo Sapience

<400> SEQUENCE: 78
cagggcuggc agugacaugg gu                                            22

<210> SEQ ID NO 79
<211> LENGTH: 17
<212> TYPE: RNA
<213> ORGANISM: Homo Sapience

<400> SEQUENCE: 79
ggugggggcu guuguuu                                                  17

<210> SEQ ID NO 80
<211> LENGTH: 20
<212> TYPE: RNA
<213> ORGANISM: Homo Sapience

<400> SEQUENCE: 80
ggcuccuugg ucuagggua                                                20

<210> SEQ ID NO 81
<211> LENGTH: 22
```

<212> TYPE: RNA
<213> ORGANISM: Homo Sapience

<400> SEQUENCE: 81
cgucccgggg cugcgcgagg ca                                    22

<210> SEQ ID NO 82
<211> LENGTH: 20
<212> TYPE: RNA
<213> ORGANISM: Homo Sapience

<400> SEQUENCE: 82
ggauccgagu cacggcacca                                       20

<210> SEQ ID NO 83
<211> LENGTH: 17
<212> TYPE: RNA
<213> ORGANISM: Homo Sapience

<400> SEQUENCE: 83
agggugugug uguuuuu                                          17

<210> SEQ ID NO 84
<211> LENGTH: 22
<212> TYPE: RNA
<213> ORGANISM: Homo Sapience

<400> SEQUENCE: 84
ccaggaggcg gaggaggugg ag                                    22

<210> SEQ ID NO 85
<211> LENGTH: 23
<212> TYPE: RNA
<213> ORGANISM: Homo Sapience

<400> SEQUENCE: 85
ugacacggag gguggcuugg gaa                                   23

<210> SEQ ID NO 86
<211> LENGTH: 18
<212> TYPE: RNA
<213> ORGANISM: Homo Sapience

<400> SEQUENCE: 86
gggugcgggc cggcgggg                                         18

<210> SEQ ID NO 87
<211> LENGTH: 22
<212> TYPE: RNA
<213> ORGANISM: Homo Sapience

<400> SEQUENCE: 87
uggcggcggu aguaugggc uu                                     22

<210> SEQ ID NO 88
<211> LENGTH: 21
<212> TYPE: RNA
<213> ORGANISM: Homo Sapience

<400> SEQUENCE: 88
agccaagugg aaguuacuuu a                                     21

<210> SEQ ID NO 89

```
<211> LENGTH: 17
<212> TYPE: RNA
<213> ORGANISM: Homo Sapience

<400> SEQUENCE: 89
gggguggucu guuguug                                                       17

<210> SEQ ID NO 90
<211> LENGTH: 20
<212> TYPE: RNA
<213> ORGANISM: Homo Sapience

<400> SEQUENCE: 90
aaaaggcggg agaagcccca                                                    20

<210> SEQ ID NO 91
<211> LENGTH: 16
<212> TYPE: RNA
<213> ORGANISM: Homo Sapience

<400> SEQUENCE: 91
accgccugcc caguga                                                        16

<210> SEQ ID NO 92
<211> LENGTH: 18
<212> TYPE: RNA
<213> ORGANISM: Homo Sapience

<400> SEQUENCE: 92 aggggggcggg cuccggcg                                                     18

<210> SEQ ID NO 93
<211> LENGTH: 17
<212> TYPE: RNA
<213> ORGANISM: Homo Sapience

<400> SEQUENCE: 93
ggggcugggc gcgcgcc                                                       17

<210> SEQ ID NO 94
<211> LENGTH: 18
<212> TYPE: RNA
<213> ORGANISM: Homo Sapience

<400> SEQUENCE: 94
aggcugggcu gggacgga                                                      18

<210> SEQ ID NO 95
<211> LENGTH: 22
<212> TYPE: RNA
<213> ORGANISM: Homo Sapience

<400> SEQUENCE: 95
aggacuggac ucccggcagc cc                                                 22

<210> SEQ ID NO 96
<211> LENGTH: 21
<212> TYPE: RNA
<213> ORGANISM: Homo Sapience

<400> SEQUENCE: 96 gggggaugu gcaugcuggu u                                                   21
```

```
<210> SEQ ID NO 97
<211> LENGTH: 17
<212> TYPE: RNA
<213> ORGANISM: Homo Sapience

<400> SEQUENCE: 97
ggauggagga gggucu                                                   17

<210> SEQ ID NO 98
<211> LENGTH: 17
<212> TYPE: RNA
<213> ORGANISM: Homo Sapience

<400> SEQUENCE: 98
guggaccugg cugggac                                                  17

<210> SEQ ID NO 99
<211> LENGTH: 22
<212> TYPE: RNA
<213> ORGANISM: Homo Sapience

<400> SEQUENCE: 99
aggagcuagc caggcauaug ca                                            22

<210> SEQ ID NO 100
<211> LENGTH: 19
<212> TYPE: RNA
<213> ORGANISM: Homo Sapience

<400> SEQUENCE: 100
cggcgcgacc ggcccgggg                                                19

<210> SEQ ID NO 101
<211> LENGTH: 23
<212> TYPE: RNA
<213> ORGANISM: Homo Sapience

<400> SEQUENCE: 101
ugggccaggg agcagcuggu ggg                                           23

<210> SEQ ID NO 102
<211> LENGTH: 24
<212> TYPE: RNA
<213> ORGANISM: Homo Sapience

<400> SEQUENCE: 102
ugggcgaggg gugggcucuc agag                                          24

<210> SEQ ID NO 103
<211> LENGTH: 20
<212> TYPE: RNA
<213> ORGANISM: Homo Sapience

<400> SEQUENCE: 103
cggggugggu gaggucgggc                                               20

<210> SEQ ID NO 104
<211> LENGTH: 22
<212> TYPE: RNA
<213> ORGANISM: Homo Sapience

<400> SEQUENCE: 104
aggggacugg uuaauagaac ua                                            22
```

```
<210> SEQ ID NO 105
<211> LENGTH: 22
<212> TYPE: RNA
<213> ORGANISM: Homo Sapience

<400> SEQUENCE: 105
caccggggau ggcagagggu cg                                              22

<210> SEQ ID NO 106
<211> LENGTH: 23
<212> TYPE: RNA
<213> ORGANISM: Homo Sapience

<400> SEQUENCE: 106
ugggcugagg gcaggaggcc ugu                                             23

<210> SEQ ID NO 107
<211> LENGTH: 23
<212> TYPE: RNA
<213> ORGANISM: Homo Sapience

<400> SEQUENCE: 107
gugagugugg auccuggagg aau                                             23

<210> SEQ ID NO 108
<211> LENGTH: 24
<212> TYPE: RNA
<213> ORGANISM: Homo Sapience

<400> SEQUENCE: 108
agcugagcuc cauggacgug cagu                                            24

<210> SEQ ID NO 109
<211> LENGTH: 22
<212> TYPE: RNA
<213> ORGANISM: Homo Sapience

<400> SEQUENCE: 109
uccaggcagg agccggacug ga                                              22

<210> SEQ ID NO 110
<211> LENGTH: 22
<212> TYPE: RNA
<213> ORGANISM: Homo Sapience

<400> SEQUENCE: 110
ggggcuguga uugaccagca gg                                              22

<210> SEQ ID NO 111
<211> LENGTH: 21
<212> TYPE: RNA
<213> ORGANISM: Homo Sapience

<400> SEQUENCE: 111
uggcuguugg aggggcagg c                                                21

<210> SEQ ID NO 112
<211> LENGTH: 22
<212> TYPE: RNA
<213> ORGANISM: Homo Sapience

<400> SEQUENCE: 112
cagcccuccu cccgcaccca aa                                              22
```

<210> SEQ ID NO 113
<211> LENGTH: 22
<212> TYPE: RNA
<213> ORGANISM: Homo Sapience

<400> SEQUENCE: 113
gagcaggcga ggcugggcug aa                                              22

<210> SEQ ID NO 114
<211> LENGTH: 22
<212> TYPE: RNA
<213> ORGANISM: Homo Sapience

<400> SEQUENCE: 114
caggaggcag ugggcgagca gg                                              22

<210> SEQ ID NO 115
<211> LENGTH: 22
<212> TYPE: RNA
<213> ORGANISM: Homo Sapience

<400> SEQUENCE: 115 aggggcgca gucacugacg ug                                               22

<210> SEQ ID NO 116
<211> LENGTH: 25
<212> TYPE: RNA
<213> ORGANISM: Homo Sapience

<400> SEQUENCE: 116
agcggggagg aagugggcgc ugcuu                                           25

<210> SEQ ID NO 117
<211> LENGTH: 22
<212> TYPE: RNA
<213> ORGANISM: Homo Sapience

<400> SEQUENCE: 117
agcccgcccc agccgagguu cu                                              22

<210> SEQ ID NO 118
<211> LENGTH: 23
<212> TYPE: RNA
<213> ORGANISM: Homo Sapience

<400> SEQUENCE: 118
gccccggcgc gggcggguuc ugg                                             23

<210> SEQ ID NO 119
<211> LENGTH: 22
<212> TYPE: RNA
<213> ORGANISM: Homo Sapience

<400> SEQUENCE: 119
agcaaggcgg caucucucug au                                              22

<210> SEQ ID NO 120
<211> LENGTH: 18
<212> TYPE: RNA
<213> ORGANISM: Homo Sapience

<400> SEQUENCE: 120
gggugagggc aggugguu                                                       18

<210> SEQ ID NO 121
<211> LENGTH: 21
<212> TYPE: RNA
<213> ORGANISM: Homo Sapience

<400> SEQUENCE: 121
agcuguaccu gaaaccaagc a                                                   21

<210> SEQ ID NO 122
<211> LENGTH: 23
<212> TYPE: RNA
<213> ORGANISM: Homo Sapience

<400> SEQUENCE: 122
ggcaggaggg cugugccagg uug                                                 23

<210> SEQ ID NO 123
<211> LENGTH: 22
<212> TYPE: RNA
<213> ORGANISM: Homo Sapience

<400> SEQUENCE: 123 ugggaaggc gucagugucg gg                                                   22

<210> SEQ ID NO 124
<211> LENGTH: 23
<212> TYPE: RNA
<213> ORGANISM: Homo Sapience

<400> SEQUENCE: 124
agggccagag gagccuggag ugg                                                 23

<210> SEQ ID NO 125
<211> LENGTH: 22
<212> TYPE: RNA
<213> ORGANISM: Homo Sapience

<400> SEQUENCE: 125
auagugggaa gcuggcagau uc                                                  22

<210> SEQ ID NO 126
<211> LENGTH: 23
<212> TYPE: RNA
<213> ORGANISM: Homo Sapience

<400> SEQUENCE: 126
ugggagggga gaggcagcaa gca                                                 23

<210> SEQ ID NO 127
<211> LENGTH: 22
<212> TYPE: RNA
<213> ORGANISM: Homo Sapience

<400> SEQUENCE: 127
ugcugggggc cacaugagug ug                                                  22

<210> SEQ ID NO 128
<211> LENGTH: 19
<212> TYPE: RNA
<213> ORGANISM: Homo Sapience

<400> SEQUENCE: 128
aggcagguua ucugggcug    19

<210> SEQ ID NO 129
<211> LENGTH: 25
<212> TYPE: RNA
<213> ORGANISM: Homo Sapience

<400> SEQUENCE: 129
aagggaggag gagcggaggg gcccu    25

<210> SEQ ID NO 130
<211> LENGTH: 22
<212> TYPE: RNA
<213> ORGANISM: Homo Sapience

<400> SEQUENCE: 130
aggacugauc cucucgggca gg    22

<210> SEQ ID NO 131
<211> LENGTH: 23
<212> TYPE: RNA
<213> ORGANISM: Homo Sapience

<400> SEQUENCE: 131
cgggcugucc ggagggucg gcu    23

<210> SEQ ID NO 132
<211> LENGTH: 22
<212> TYPE: RNA
<213> ORGANISM: Homo Sapience

<400> SEQUENCE: 132
cucgggcgga ggugguugag ug    22

<210> SEQ ID NO 133
<211> LENGTH: 22
<212> TYPE: RNA
<213> ORGANISM: Homo Sapience

<400> SEQUENCE: 133
agccaggcuc ugaagggaaa gu    22

<210> SEQ ID NO 134
<211> LENGTH: 24
<212> TYPE: RNA
<213> ORGANISM: Homo Sapience

<400> SEQUENCE: 134
aggcaggggc uggugcuggg cggg    24

<210> SEQ ID NO 135
<211> LENGTH: 21
<212> TYPE: RNA
<213> ORGANISM: Homo Sapience

<400> SEQUENCE: 135
agcagacuug accuacaauu a    21

<210> SEQ ID NO 136
<211> LENGTH: 23
<212> TYPE: RNA
<213> ORGANISM: Homo Sapience

```
<400> SEQUENCE: 136
ccccgguguu ggggcgcguc ugc                                          23

<210> SEQ ID NO 137
<211> LENGTH: 21
<212> TYPE: RNA
<213> ORGANISM: Homo Sapience

<400> SEQUENCE: 137
ggcgcgccca gcucccgggc u                                            21

<210> SEQ ID NO 138
<211> LENGTH: 24
<212> TYPE: RNA
<213> ORGANISM: Homo Sapience

<400> SEQUENCE: 138
gaugcgccgc ccacugcccc gcgc                                         24

<210> SEQ ID NO 139
<211> LENGTH: 18
<212> TYPE: RNA
<213> ORGANISM: Homo Sapience

<400> SEQUENCE: 139
cggugagcgc ucgcuggc                                                18

<210> SEQ ID NO 140
<211> LENGTH: 23
<212> TYPE: RNA
<213> ORGANISM: Homo Sapience

<400> SEQUENCE: 140
uuucaagcca gggggcguuu uuc                                          23

<210> SEQ ID NO 141
<211> LENGTH: 22
<212> TYPE: RNA
<213> ORGANISM: Homo Sapience

<400> SEQUENCE: 141
ugaggcccuu ggggcacagu gg                                           22

<210> SEQ ID NO 142
<211> LENGTH: 22
<212> TYPE: RNA
<213> ORGANISM: Homo Sapience

<400> SEQUENCE: 142 aggggaugg cagagcaaaa uu                                            22

<210> SEQ ID NO 143
<211> LENGTH: 21
<212> TYPE: RNA
<213> ORGANISM: Homo Sapience

<400> SEQUENCE: 143
gggagugcag ggcagggurru c                                           21

<210> SEQ ID NO 144
<211> LENGTH: 21
<212> TYPE: RNA
<213> ORGANISM: Homo Sapience
```

<400> SEQUENCE: 144
auccaguucu cugaggggc u                           21

<210> SEQ ID NO 145
<211> LENGTH: 23
<212> TYPE: RNA
<213> ORGANISM: Homo Sapience

<400> SEQUENCE: 145
agugccugag ggaguaagag ccc                        23

<210> SEQ ID NO 146
<211> LENGTH: 21
<212> TYPE: RNA
<213> ORGANISM: Homo Sapience

<400> SEQUENCE: 146 guugggugc aggggucugc u                           21

<210> SEQ ID NO 147
<211> LENGTH: 20
<212> TYPE: RNA
<213> ORGANISM: Homo Sapience

<400> SEQUENCE: 147
gcggagagag aaugggagc                             20

<210> SEQ ID NO 148
<211> LENGTH: 21
<212> TYPE: RNA
<213> ORGANISM: Homo Sapience

<400> SEQUENCE: 148
acggcccagg cggcauuggu g                          21

<210> SEQ ID NO 149
<211> LENGTH: 21
<212> TYPE: RNA
<213> ORGANISM: Homo Sapience

<400> SEQUENCE: 149
agcaugacag aggagaggug g                          21

<210> SEQ ID NO 150
<211> LENGTH: 20
<212> TYPE: RNA
<213> ORGANISM: Homo Sapience

<400> SEQUENCE: 150
agagaugaag cgggggggcg                            20

<210> SEQ ID NO 151
<211> LENGTH: 20
<212> TYPE: RNA
<213> ORGANISM: Homo Sapience

<400> SEQUENCE: 151
gggaaaagga aggggagga                             20

<210> SEQ ID NO 152
<211> LENGTH: 19
<212> TYPE: RNA

<213> ORGANISM: Homo Sapience

<400> SEQUENCE: 152
ggcuggucag augggagug                                                    19

<210> SEQ ID NO 153
<211> LENGTH: 19
<212> TYPE: RNA
<213> ORGANISM: Homo Sapience

<400> SEQUENCE: 153
agcagggcug gggauugca                                                    19

<210> SEQ ID NO 154
<211> LENGTH: 23
<212> TYPE: RNA
<213> ORGANISM: Homo Sapience

<400> SEQUENCE: 154
gaacgccugu ucuugccagg ugg                                               23

<210> SEQ ID NO 155
<211> LENGTH: 22
<212> TYPE: RNA
<213> ORGANISM: Homo Sapience

<400> SEQUENCE: 155
gggggucccc ggugcucgga uc                                                22

<210> SEQ ID NO 156
<211> LENGTH: 22
<212> TYPE: RNA
<213> ORGANISM: Homo Sapience

<400> SEQUENCE: 156
gcugggauua caggcaugag cc                                                22

<210> SEQ ID NO 157
<211> LENGTH: 22
<212> TYPE: RNA
<213> ORGANISM: Homo Sapience

<400> SEQUENCE: 157
agacacauuu ggagagggac cc                                                22

<210> SEQ ID NO 158
<211> LENGTH: 22
<212> TYPE: RNA
<213> ORGANISM: Homo Sapience

<400> SEQUENCE: 158
cagcagggga gagagaggag uc                                                22

<210> SEQ ID NO 159
<211> LENGTH: 23
<212> TYPE: RNA
<213> ORGANISM: Homo Sapience

<400> SEQUENCE: 159
caggcagaag uggggcugac agg                                               23

<210> SEQ ID NO 160
<211> LENGTH: 20

<212> TYPE: RNA
<213> ORGANISM: Homo Sapience

<400> SEQUENCE: 160
ucucuucauc uacccccag                                              20

<210> SEQ ID NO 161
<211> LENGTH: 21
<212> TYPE: RNA
<213> ORGANISM: Homo Sapience

<400> SEQUENCE: 161
uuggagggug uggaagacau c                                           21

<210> SEQ ID NO 162
<211> LENGTH: 22
<212> TYPE: RNA
<213> ORGANISM: Homo Sapience

<400> SEQUENCE: 162
gguggcccgg ccgugccuga gg                                          22

<210> SEQ ID NO 163
<211> LENGTH: 20
<212> TYPE: RNA
<213> ORGANISM: Homo Sapience

<400> SEQUENCE: 163
ugggaauggg gguaagggcc                                             20

<210> SEQ ID NO 164
<211> LENGTH: 22
<212> TYPE: RNA
<213> ORGANISM: Homo Sapience

<400> SEQUENCE: 164
aggcgaugug gggauguaga ga                                          22

<210> SEQ ID NO 165
<211> LENGTH: 22
<212> TYPE: RNA
<213> ORGANISM: Homo Sapience

<400> SEQUENCE: 165
ugcagggguc ggguggccca gg                                          22

<210> SEQ ID NO 166
<211> LENGTH: 23
<212> TYPE: RNA
<213> ORGANISM: Homo Sapience

<400> SEQUENCE: 166
cugggcccgc ggcgggcgug ggg                                         23

<210> SEQ ID NO 167
<211> LENGTH: 21
<212> TYPE: RNA
<213> ORGANISM: Homo Sapience

<400> SEQUENCE: 167
cgggagcugg ggucugcagg u                                           21

<210> SEQ ID NO 168

```
<211> LENGTH: 21
<212> TYPE: RNA
<213> ORGANISM: Homo Sapience

<400> SEQUENCE: 168 uuggguggu cggcccugga g                                              21

<210> SEQ ID NO 169
<211> LENGTH: 22
<212> TYPE: RNA
<213> ORGANISM: Homo Sapience

<400> SEQUENCE: 169
gugggugcug gugggagccg ug                                            22

<210> SEQ ID NO 170
<211> LENGTH: 22
<212> TYPE: RNA
<213> ORGANISM: Homo Sapience

<400> SEQUENCE: 170 agugggugg gacccagcug uu                                             22

<210> SEQ ID NO 171
<211> LENGTH: 22
<212> TYPE: RNA
<213> ORGANISM: Homo Sapience

<400> SEQUENCE: 171
aaggggcagg gacgggguggc cc                                           22

<210> SEQ ID NO 172
<211> LENGTH: 22
<212> TYPE: RNA
<213> ORGANISM: Homo Sapience

<400> SEQUENCE: 172
ccgggagaag gagguggccu gg                                            22

<210> SEQ ID NO 173
<211> LENGTH: 22
<212> TYPE: RNA
<213> ORGANISM: Homo Sapience

<400> SEQUENCE: 173
ucgggccugg gguuggggga gc                                            22

<210> SEQ ID NO 174
<211> LENGTH: 23
<212> TYPE: RNA
<213> ORGANISM: Homo Sapience

<400> SEQUENCE: 174
cagggagaag guggaagugc aga                                           23

<210> SEQ ID NO 175
<211> LENGTH: 23
<212> TYPE: RNA
<213> ORGANISM: Homo Sapience

<400> SEQUENCE: 175
cggggccaug gagcagccug ugu                                           23
```

```
<210> SEQ ID NO 176
<211> LENGTH: 21
<212> TYPE: RNA
<213> ORGANISM: Homo Sapience

<400> SEQUENCE: 176
ucaccuggcu ggcccgccca g                                          21

<210> SEQ ID NO 177
<211> LENGTH: 25
<212> TYPE: RNA
<213> ORGANISM: Homo Sapience

<400> SEQUENCE: 177
gugaggcggg gccaggaggg ugugu                                      25

<210> SEQ ID NO 178
<211> LENGTH: 22
<212> TYPE: RNA
<213> ORGANISM: Homo Sapience

<400> SEQUENCE: 178
ugauugucuu cccccacccu ca                                         22

<210> SEQ ID NO 179
<211> LENGTH: 24
<212> TYPE: RNA
<213> ORGANISM: Homo Sapience

<400> SEQUENCE: 179 cggugggag cagaucuuau ugag                                        24

<210> SEQ ID NO 180
<211> LENGTH: 22
<212> TYPE: RNA
<213> ORGANISM: Homo Sapience

<400> SEQUENCE: 180
cucgggaggg caugggccag gc                                         22

<210> SEQ ID NO 181
<211> LENGTH: 25
<212> TYPE: RNA
<213> ORGANISM: Homo Sapience

<400> SEQUENCE: 181
acuugggcag gagggacccu guaug                                      25

<210> SEQ ID NO 182
<211> LENGTH: 23
<212> TYPE: RNA
<213> ORGANISM: Homo Sapience

<400> SEQUENCE: 182
acggggaguc aggcaguggu gga                                        23

<210> SEQ ID NO 183
<211> LENGTH: 22
<212> TYPE: RNA
<213> ORGANISM: Homo Sapience

<400> SEQUENCE: 183
agugggagga caggaggcag gu                                         22
```

```
<210> SEQ ID NO 184
<211> LENGTH: 23
<212> TYPE: RNA
<213> ORGANISM: Homo Sapience

<400> SEQUENCE: 184 ugggaaggc uuggcaggga aga                                        23

<210> SEQ ID NO 185
<211> LENGTH: 21
<212> TYPE: RNA
<213> ORGANISM: Homo Sapience

<400> SEQUENCE: 185
cgggccggag gucaagggcg u                                         21

<210> SEQ ID NO 186
<211> LENGTH: 25
<212> TYPE: RNA
<213> ORGANISM: Homo Sapience

<400> SEQUENCE: 186 uaggggugg ggaauucagg ggugu                                      25

<210> SEQ ID NO 187
<211> LENGTH: 20
<212> TYPE: RNA
<213> ORGANISM: Homo Sapience

<400> SEQUENCE: 187
gccggggcuu ugggugaggg                                           20

<210> SEQ ID NO 188
<211> LENGTH: 22
<212> TYPE: RNA
<213> ORGANISM: Homo Sapience

<400> SEQUENCE: 188
ugggagggcg uggaugaugg ug                                        22

<210> SEQ ID NO 189
<211> LENGTH: 22
<212> TYPE: RNA
<213> ORGANISM: Homo Sapience

<400> SEQUENCE: 189 uggcggggu agagcuggcu gc                                         22

<210> SEQ ID NO 190
<211> LENGTH: 24
<212> TYPE: RNA
<213> ORGANISM: Homo Sapience

<400> SEQUENCE: 190 guagggcgu cccgggcgcg cggg                                       24

<210> SEQ ID NO 191
<211> LENGTH: 22
<212> TYPE: RNA
<213> ORGANISM: Homo Sapience

<400> SEQUENCE: 191
ccccuggggc ugggcaggcg ga                                        22
```

```
<210> SEQ ID NO 192
<211> LENGTH: 20
<212> TYPE: RNA
<213> ORGANISM: Homo Sapience

<400> SEQUENCE: 192 caggggacu gggggugagc                                                    20

<210> SEQ ID NO 193
<211> LENGTH: 21
<212> TYPE: RNA
<213> ORGANISM: Homo Sapience

<400> SEQUENCE: 193
guaggugaca gucaggggcg g                                                 21

<210> SEQ ID NO 194
<211> LENGTH: 20
<212> TYPE: RNA
<213> ORGANISM: Homo Sapience

<400> SEQUENCE: 194
cuaggugggg ggcuugaagc                                                   20

<210> SEQ ID NO 195
<211> LENGTH: 22
<212> TYPE: RNA
<213> ORGANISM: Homo Sapience

<400> SEQUENCE: 195 cuggggugg ggggcugggc gu                                                 22

<210> SEQ ID NO 196
<211> LENGTH: 25
<212> TYPE: RNA
<213> ORGANISM: Homo Sapience

<400> SEQUENCE: 196
auggggugag augggagga gcagc                                              25

<210> SEQ ID NO 197
<211> LENGTH: 21
<212> TYPE: RNA
<213> ORGANISM: Homo Sapience

<400> SEQUENCE: 197 ugggcgggg caggucccug c                                                  21

<210> SEQ ID NO 198
<211> LENGTH: 22
<212> TYPE: RNA
<213> ORGANISM: Homo Sapience

<400> SEQUENCE: 198
uuggggugga gggccaagga gc                                                22

<210> SEQ ID NO 199
<211> LENGTH: 23
<212> TYPE: RNA
<213> ORGANISM: Homo Sapience

<400> SEQUENCE: 199
```

```
gugcguggug gcucgaggcg ggg                                               23

<210> SEQ ID NO 200
<211> LENGTH: 23
<212> TYPE: RNA
<213> ORGANISM: Homo Sapience

<400> SEQUENCE: 200
ucaauaggaa agagguggga ccu                                               23

<210> SEQ ID NO 201
<211> LENGTH: 24
<212> TYPE: RNA
<213> ORGANISM: Homo Sapience

<400> SEQUENCE: 201
uagguagagu gugaggagga gguc                                              24

<210> SEQ ID NO 202
<211> LENGTH: 21
<212> TYPE: RNA
<213> ORGANISM: Homo Sapience

<400> SEQUENCE: 202
augccucccc cggccccgca g                                                 21

<210> SEQ ID NO 203
<211> LENGTH: 22
<212> TYPE: RNA
<213> ORGANISM: Homo Sapience

<400> SEQUENCE: 203
gcccaggacu uugugcgggg ug                                                22

<210> SEQ ID NO 204
<211> LENGTH: 22
<212> TYPE: RNA
<213> ORGANISM: Homo Sapience

<400> SEQUENCE: 204
uggggguggu cucuagccaa gg                                                22

<210> SEQ ID NO 205
<211> LENGTH: 22
<212> TYPE: RNA
<213> ORGANISM: Homo Sapience

<400> SEQUENCE: 205
gugcggaacg cuggccgggg cg                                                22

<210> SEQ ID NO 206
<211> LENGTH: 22
<212> TYPE: RNA
<213> ORGANISM: Homo Sapience

<400> SEQUENCE: 206
acuggguagg uggggcucca gg                                                22

<210> SEQ ID NO 207
<211> LENGTH: 22
<212> TYPE: RNA
<213> ORGANISM: Homo Sapience

<400> SEQUENCE: 207
```

-continued

| | |
|---|---|
| gugaguagug gcgcgcggcg gc | 22 |

<210> SEQ ID NO 208
<211> LENGTH: 19
<212> TYPE: RNA
<213> ORGANISM: Homo Sapience

<400> SEQUENCE: 208

| | |
|---|---|
| uggggggagau ggggguuga | 19 |

<210> SEQ ID NO 209
<211> LENGTH: 22
<212> TYPE: RNA
<213> ORGANISM: Homo Sapience

<400> SEQUENCE: 209

| | |
|---|---|
| agggccgaag gguggaagcu gc | 22 |

<210> SEQ ID NO 210
<211> LENGTH: 22
<212> TYPE: RNA
<213> ORGANISM: Homo Sapience

<400> SEQUENCE: 210

| | |
|---|---|
| cagggcaggg aagguggag ag | 22 |

<210> SEQ ID NO 211
<211> LENGTH: 21
<212> TYPE: RNA
<213> ORGANISM: Homo Sapience

<400> SEQUENCE: 211

| | |
|---|---|
| ccgccuucuc uccuccccca g | 21 |

<210> SEQ ID NO 212
<211> LENGTH: 22
<212> TYPE: RNA
<213> ORGANISM: Homo Sapience

<400> SEQUENCE: 212

| | |
|---|---|
| ugguggagga agagggcagc uc | 22 |

<210> SEQ ID NO 213
<211> LENGTH: 25
<212> TYPE: RNA
<213> ORGANISM: Homo Sapience

<400> SEQUENCE: 213

| | |
|---|---|
| aggggggcac ugcgcaagca aagcc | 25 |

<210> SEQ ID NO 214
<211> LENGTH: 23
<212> TYPE: RNA
<213> ORGANISM: Homo Sapience

<400> SEQUENCE: 214

| | |
|---|---|
| uggggggaca gauggagagg aca | 23 |

<210> SEQ ID NO 215
<211> LENGTH: 22
<212> TYPE: RNA
<213> ORGANISM: Homo Sapience

```
<400> SEQUENCE: 215
ucggccuggg gaggaggaag gg                                    22

<210> SEQ ID NO 216
<211> LENGTH: 20
<212> TYPE: RNA
<213> ORGANISM: Homo Sapience

<400> SEQUENCE: 216
acccgcccgu cuccccacag                                       20

<210> SEQ ID NO 217
<211> LENGTH: 21
<212> TYPE: RNA
<213> ORGANISM: Homo Sapience

<400> SEQUENCE: 217
cuggggggag gagacccugc u                                     21

<210> SEQ ID NO 218
<211> LENGTH: 22
<212> TYPE: RNA
<213> ORGANISM: Homo Sapience

<400> SEQUENCE: 218
gggacccagg gagagacgua ag                                    22

<210> SEQ ID NO 219
<211> LENGTH: 23
<212> TYPE: RNA
<213> ORGANISM: Homo Sapience

<400> SEQUENCE: 219
ccucccugcc cgccucucug cag                                   23

<210> SEQ ID NO 220
<211> LENGTH: 18
<212> TYPE: RNA
<213> ORGANISM: Homo Sapience

<400> SEQUENCE: 220
cuggcagggg gagaggua                                         18

<210> SEQ ID NO 221
<211> LENGTH: 22
<212> TYPE: RNA
<213> ORGANISM: Homo Sapience

<400> SEQUENCE: 221
ugcggggcua gggcuaacag ca                                    22

<210> SEQ ID NO 222
<211> LENGTH: 18
<212> TYPE: RNA
<213> ORGANISM: Homo Sapience

<400> SEQUENCE: 222
auccuaguca cggcacca                                         18

<210> SEQ ID NO 223
<211> LENGTH: 18
<212> TYPE: RNA
<213> ORGANISM: Homo Sapience
```

```
<400> SEQUENCE: 223
uucccagcca acgcacca                                                   18

<210> SEQ ID NO 224
<211> LENGTH: 22
<212> TYPE: RNA
<213> ORGANISM: Homo Sapience

<400> SEQUENCE: 224
cgggacugua gagggcauga gc                                              22

<210> SEQ ID NO 225
<211> LENGTH: 23
<212> TYPE: RNA
<213> ORGANISM: Homo Sapience

<400> SEQUENCE: 225
ggaugguugg gggcggucgg cgu                                             23

<210> SEQ ID NO 226
<211> LENGTH: 22
<212> TYPE: RNA
<213> ORGANISM: Homo Sapience

<400> SEQUENCE: 226
accuggcagc agggagcguc gu                                              22

<210> SEQ ID NO 227
<211> LENGTH: 22
<212> TYPE: RNA
<213> ORGANISM: Homo Sapience

<400> SEQUENCE: 227
gugaacgggc gccaucccga gg                                              22

<210> SEQ ID NO 228
<211> LENGTH: 20
<212> TYPE: RNA
<213> ORGANISM: Homo Sapience

<400> SEQUENCE: 228
gugagucagg gugggcugg                                                  20

<210> SEQ ID NO 229
<211> LENGTH: 21
<212> TYPE: RNA
<213> ORGANISM: Homo Sapience

<400> SEQUENCE: 229
gugccagcug cagugggga g                                                21

<210> SEQ ID NO 230
<211> LENGTH: 21
<212> TYPE: RNA
<213> ORGANISM: Homo Sapience

<400> SEQUENCE: 230
uggcagggag gcugggaggg g                                               21

<210> SEQ ID NO 231
<211> LENGTH: 19
<212> TYPE: RNA
```

<213> ORGANISM: Homo Sapience

<400> SEQUENCE: 231
aauggauuuu uggagcagg                                            19

<210> SEQ ID NO 232
<211> LENGTH: 24
<212> TYPE: RNA
<213> ORGANISM: Homo Sapience

<400> SEQUENCE: 232
agccuggaag cuggagccug cagu                                      24

<210> SEQ ID NO 233
<211> LENGTH: 22
<212> TYPE: RNA
<213> ORGANISM: Homo Sapience

<400> SEQUENCE: 233
uauagggauu ggagccgugg cg                                        22

<210> SEQ ID NO 234
<211> LENGTH: 22
<212> TYPE: RNA
<213> ORGANISM: Homo Sapience

<400> SEQUENCE: 234
cucggcgcgg ggcgcgggcu cc                                        22

<210> SEQ ID NO 235
<211> LENGTH: 21
<212> TYPE: RNA
<213> ORGANISM: Homo Sapience

<400> SEQUENCE: 235
agggagggac gggggcugug c                                         21

<210> SEQ ID NO 236
<211> LENGTH: 22
<212> TYPE: RNA
<213> ORGANISM: Homo Sapience

<400> SEQUENCE: 236
cugguacagg ccuggggggac ag                                       22

<210> SEQ ID NO 237
<211> LENGTH: 22
<212> TYPE: RNA
<213> ORGANISM: Homo Sapience

<400> SEQUENCE: 237
ggaggggucc cgcacuggga gg                                        22

<210> SEQ ID NO 238
<211> LENGTH: 23
<212> TYPE: RNA
<213> ORGANISM: Homo Sapience

<400> SEQUENCE: 238
caacggaauc ccaaaagcag cug                                       23

<210> SEQ ID NO 239
<211> LENGTH: 23

```
<212> TYPE: RNA
<213> ORGANISM: Homo Sapience

<400> SEQUENCE: 239
ugaggggcag agagcgagac uuu                                          23

<210> SEQ ID NO 240
<211> LENGTH: 22
<212> TYPE: RNA
<213> ORGANISM: Homo Sapience

<400> SEQUENCE: 240
aggcggggcg ccgcgggacc gc                                           22

<210> SEQ ID NO 241
<211> LENGTH: 22
<212> TYPE: RNA
<213> ORGANISM: Homo Sapience

<400> SEQUENCE: 241 gggugggau uuguugcauu ac                                            22

<210> SEQ ID NO 242
<211> LENGTH: 22
<212> TYPE: RNA
<213> ORGANISM: Homo Sapience

<400> SEQUENCE: 242
uauugcacuu gucccggccu gu                                           22

<210> SEQ ID NO 243
<211> LENGTH: 21
<212> TYPE: RNA
<213> ORGANISM: Homo Sapience

<400> SEQUENCE: 243
aaggcagggc ccccgcuccc c                                            21

<210> SEQ ID NO 244
<211> LENGTH: 49
<212> TYPE: RNA
<213> ORGANISM: Homo Sapience

<400> SEQUENCE: 244
ggugaggcgg gggggcgagc ccugaggggc ucucgcuucu ggcgccaag              49

<210> SEQ ID NO 245
<211> LENGTH: 86
<212> TYPE: RNA
<213> ORGANISM: Homo Sapience

<400> SEQUENCE: 245
uuugguacuu gaagagagga uacccuuugu auguucacuu gauuaauggc gaauauacag  60
ggggagacuc uuauuugcgu aucaaa                                       86

<210> SEQ ID NO 246
<211> LENGTH: 86
<212> TYPE: RNA
<213> ORGANISM: Homo Sapience

<400> SEQUENCE: 246
uuugguacuu aaagagagga uacccuuugu auguucacuu gauuaauggc gaauauacag  60
```

```
ggggagacuc ucauuugcgu aucaaa                                           86
```

<210> SEQ ID NO 247
<211> LENGTH: 78
<212> TYPE: RNA
<213> ORGANISM: Homo Sapience

<400> SEQUENCE: 247

```
guagcugagg ggauggugaga ccggugacgu gcacuucauu uacgauguag gucacccguu    60
ugacuaucca ccagcgcc                                                   78
```

<210> SEQ ID NO 248
<211> LENGTH: 119
<212> TYPE: RNA
<213> ORGANISM: Homo Sapience

<400> SEQUENCE: 248

```
agccugcgcc ggagccgggg ccugagcccg ggccgcgcag gccgugaacu cgucgagcug     60
cgcgugcggc cggugcucaa ccugccgggu ccuggccccg cgcucccgcg cgcccugga    119
```

<210> SEQ ID NO 249
<211> LENGTH: 90
<212> TYPE: RNA
<213> ORGANISM: Homo Sapience

<400> SEQUENCE: 249

```
guggguacgg cccaguggggg gggagaggga cacgcccugg gcucugccca gggugcagcc    60
ggacugacug agcccugug ccgcccccag                                      90
```

<210> SEQ ID NO 250
<211> LENGTH: 88
<212> TYPE: RNA
<213> ORGANISM: Homo Sapience

<400> SEQUENCE: 250

```
guggggccag gcgguggugg gcacugcugg ggugggcaca gcagccaugc agagcgggca     60
uuugaccccg ugccacccuu uuccccag                                       88
```

<210> SEQ ID NO 251
<211> LENGTH: 73
<212> TYPE: RNA
<213> ORGANISM: Homo Sapience

<400> SEQUENCE: 251

```
gugggcgggg gcaggugugu gguggguggu ggccugcggu gagcagggcc cucacaccug     60
ccucgccccc cag                                                       73
```

<210> SEQ ID NO 252
<211> LENGTH: 73
<212> TYPE: RNA
<213> ORGANISM: Homo Sapience

<400> SEQUENCE: 252

```
gugggcgggg gcaggugugu ggugggguggu ggccugcggu gagcagggcc cucacaccug    60
ccucgccccc cag                                                       73
```

<210> SEQ ID NO 253
<211> LENGTH: 102
<212> TYPE: RNA
<213> ORGANISM: Homo Sapience

<400> SEQUENCE: 253
gugggagggc ccaggcgcgg gcagggguge ggguggcaga gcgcuguccc ggggscgggg    60
ccgaagcgcg gcgaccguaa cuccuucuge uccgucccce ag    102

<210> SEQ ID NO 254
<211> LENGTH: 83
<212> TYPE: RNA
<213> ORGANISM: Homo Sapience

<400> SEQUENCE: 254
gugaguggga gccccagugu gugguugggg ccauggcggg uggcagccc agccucugag    60 ccuuccucgu cugucugccc cag    83

<210> SEQ ID NO 255
<211> LENGTH: 136
<212> TYPE: RNA
<213> ORGANISM: Homo Sapience

<400> SEQUENCE: 255
ccgcuugccu cgcccagcgc agcccggcc gcugggcgca cccgucccgu ucgucccgg     60 acguugcucu cuaccccggg aacgucgaga cuggagcgcc cgaacugagc caccuucgcg   120
gaccccgaga gcggcg    136

<210> SEQ ID NO 256
<211> LENGTH: 52
<212> TYPE: RNA
<213> ORGANISM: Homo Sapience

<400> SEQUENCE: 256
uagccgggcg ugguggugg ggccuguggu cccagcuacu uuggaggcug ag    52

<210> SEQ ID NO 257
<211> LENGTH: 50
<212> TYPE: RNA
<213> ORGANISM: Homo Sapience

<400> SEQUENCE: 257
acccgggcgu gguggugggg gugggugccu guaauuccag cuaguuggga    50

<210> SEQ ID NO 258
<211> LENGTH: 100
<212> TYPE: RNA
<213> ORGANISM: Homo Sapience

<400> SEQUENCE: 258
gaggugggag gauugcuuga gucagggugg uugaggcugc aguaaguugu gaucauacca    60
cugcacucca gccugaguga cagagcaaga ccuugucuca    100

<210> SEQ ID NO 259
<211> LENGTH: 84
<212> TYPE: RNA
<213> ORGANISM: Homo Sapience

<400> SEQUENCE: 259
ugugcagugg gaaggggggc cgauacacug uacgagagug aguagcaggu cucacaguga    60
accggucucu uucccuacug uguc    84

<210> SEQ ID NO 260

```
<211> LENGTH: 84
<212> TYPE: RNA
<213> ORGANISM: Homo Sapience

<400> SEQUENCE: 260
gcuggcgucg gugcugggga gcggcccccg gguggccuc ugcucuggcc ccuccugggg    60
cccgcacucu cgcucugggc ccgc                                         84

<210> SEQ ID NO 261
<211> LENGTH: 84
<212> TYPE: RNA
<213> ORGANISM: Homo Sapience

<400> SEQUENCE: 261
gcuggcgucg gugcugggga gcggcccccg gguggccuc ugcucuggcc ccuccugggg    60
cccgcacucu cgcucugggc ccgc                                         84

<210> SEQ ID NO 262
<211> LENGTH: 61
<212> TYPE: RNA
<213> ORGANISM: Homo Sapience

<400> SEQUENCE: 262
gcccuccgcc cgugcacccc ggggcaggag accccgcggg acgcgccgag guaggggga    60 c                                                                  61

<210> SEQ ID NO 263
<211> LENGTH: 84
<212> TYPE: RNA
<213> ORGANISM: Homo Sapience

<400> SEQUENCE: 263
gucagaauaa ugucaaagug cuuacagugc agguagugau augugcaucu acugcaguga   60
aggcacuugu agcauuaugg ugac                                         84

<210> SEQ ID NO 264
<211> LENGTH: 109
<212> TYPE: RNA
<213> ORGANISM: Homo Sapience

<400> SEQUENCE: 264
ggucgggcuc accaugacac agugugagac cucgggcuac aacacaggac ccgggcgcug   60
cucugacccc ucgugucuug uguugcagcc ggagggacgc agguccgca              109

<210> SEQ ID NO 265
<211> LENGTH: 80
<212> TYPE: RNA
<213> ORGANISM: Homo Sapience

<400> SEQUENCE: 265
cgggaaugcc gcggcgggga cggcgauugg uccguaugug uggugccacc ggccgccggc   60
uccgccccgg ccccgcccc                                               80

<210> SEQ ID NO 266
<211> LENGTH: 80
<212> TYPE: RNA
<213> ORGANISM: Homo Sapience

<400> SEQUENCE: 266
cgggaaugcc gcggcgggga cggcgauugg uccguaugug uggugccacc ggccgccggc   60
```

```
uccgccccgg cccccgcccc                                           80

<210> SEQ ID NO 267
<211> LENGTH: 80
<212> TYPE: RNA
<213> ORGANISM: Homo Sapience

<400> SEQUENCE: 267
cauccaggac aauggugagu gccggugccu gcccgggggc cgucccugcg caggggccgg   60
gugcucaccg caucugcccc                                              80

<210> SEQ ID NO 268
<211> LENGTH: 80
<212> TYPE: RNA
<213> ORGANISM: Homo Sapience

<400> SEQUENCE: 268
ugagaggccg caccuugccu ugcugcccgg gccgugcacc cgugggcccc agggcgacgc   60 ggcggggcg gcccuagcga                                               80

<210> SEQ ID NO 269
<211> LENGTH: 110
<212> TYPE: RNA
<213> ORGANISM: Homo Sapience

<400> SEQUENCE: 269
acccggcagu gccuccaggc gcagggcagc cccugcccac cgcacacugc gcugcccag   60 acccacugug cgugugacag cggcugaucu ugccugggc agcgcgaccc             110

<210> SEQ ID NO 270
<211> LENGTH: 81
<212> TYPE: RNA
<213> ORGANISM: Homo Sapience

<400> SEQUENCE: 270
ggacaggcac cugaggcucu guuagccuug gcucgggguc cugcuccuua gagcagaggc   60
agagaggcuc agggucuguc u                                            81

<210> SEQ ID NO 271
<211> LENGTH: 90
<212> TYPE: RNA
<213> ORGANISM: Homo Sapience

<400> SEQUENCE: 271
ggcgccucug cagcuccggc uccccuggc cucucgggaa cuacaaguccc caggggggccu   60 ggcggugggc ggcgggcgga agaggcgggg                                   90

<210> SEQ ID NO 272
<211> LENGTH: 80
<212> TYPE: RNA
<213> ORGANISM: Homo Sapience

<400> SEQUENCE: 272
aggacccuuc cagagggccc ccccucaauc cuguugugcc uaauucagag gguugggugg   60
aggcucuccu gaagggcucu                                              80

<210> SEQ ID NO 273
<211> LENGTH: 63
<212> TYPE: RNA
```

<213> ORGANISM: Homo Sapience

<400> SEQUENCE: 273
gagucgagga cuggggaag ggccuuuccc cucagaccaa ggcccuggcc ccagcuucuu    60
cuc    63

<210> SEQ ID NO 274
<211> LENGTH: 84
<212> TYPE: RNA
<213> ORGANISM: Homo Sapience

<400> SEQUENCE: 274
ggccccuccu ucucagcccc agcucccgcu caccccugcc acgucaaagg aggcagaagg    60
ggaguuggga gcagagaggg gacc    84

<210> SEQ ID NO 275
<211> LENGTH: 82
<212> TYPE: RNA
<213> ORGANISM: Homo Sapience

<400> SEQUENCE: 275
cugacuuuuu uagggaguag aagggugggg agcaugaaca auguuucuca cucccuaccc    60
cuccacuccc caaaaaaguc ag    82

<210> SEQ ID NO 276
<211> LENGTH: 84
<212> TYPE: RNA
<213> ORGANISM: Homo Sapience

<400> SEQUENCE: 276
gaggcugggc ggggcgcggc cggaucgguc gagagcgucc uggcugauga cggucucccg    60
ugcccacgcc ccaaacgcag ucuc    84

<210> SEQ ID NO 277
<211> LENGTH: 75
<212> TYPE: RNA
<213> ORGANISM: Homo Sapience

<400> SEQUENCE: 277
aagcaagacu gagggccuc agaccgagcu uuuggaaaau agaaaagucu cgcucucugc    60
cccucagccu aacuu    75

<210> SEQ ID NO 278
<211> LENGTH: 68
<212> TYPE: RNA
<213> ORGANISM: Homo Sapience

<400> SEQUENCE: 278
gaauggaaga agaaggcggu cggucugcgg gagccaggcc gcagagccau ccgccuucug    60
uccauguc    68

<210> SEQ ID NO 279
<211> LENGTH: 73
<212> TYPE: RNA
<213> ORGANISM: Homo Sapience

<400> SEQUENCE: 279
agguggcagg gccagccacc aggagggcug cgugccaccc gggcagcucu gcugcucacu    60
ggcaguguca ccu    73

```
<210> SEQ ID NO 280
<211> LENGTH: 84
<212> TYPE: RNA
<213> ORGANISM: Homo Sapience

<400> SEQUENCE: 280
ccgcagccgc cgcgccgggc ccggguuggc cgcugacccc cgcggggccc ccggcggccg    60 gggcggggc gggggcugcc ccgg                                           84

<210> SEQ ID NO 281
<211> LENGTH: 73
<212> TYPE: RNA
<213> ORGANISM: Homo Sapience

<400> SEQUENCE: 281
ggcgagggga ggcgcaggcu cggaaaggcg cgcgaggcuc caggcuccuu cccgauccac    60
cgcucuccuc gcu                                                      73

<210> SEQ ID NO 282
<211> LENGTH: 82
<212> TYPE: RNA
<213> ORGANISM: Homo Sapience

<400> SEQUENCE: 282
gcuucgcucc ccuccgccuu cucuucccgg uucuucccgg agucgggaaa agcugggung    60
agagggcgaa aaaggaugag gu                                            82

<210> SEQ ID NO 283
<211> LENGTH: 75
<212> TYPE: RNA
<213> ORGANISM: Homo Sapience

<400> SEQUENCE: 283 uggaguqggg gggcaggagg ggcucaggga gaaagugcau acagccccug gcccucucug    60
cccuuccguc cccug                                                    75

<210> SEQ ID NO 284
<211> LENGTH: 99
<212> TYPE: RNA
<213> ORGANISM: Homo Sapience

<400> SEQUENCE: 284
gaaacugggc ucaaggugag gggugcuauc ugugauugag ggacaugguu aauggaauug    60
ucucacacag aaaucgcacc cgucaccuug gccuacuua                          99

<210> SEQ ID NO 285
<211> LENGTH: 98
<212> TYPE: RNA
<213> ORGANISM: Homo Sapience

<400> SEQUENCE: 285
acccaaaccc uaggucugcu gacuccuagu ccagggcucg ugauggcugg ugggcccuga    60 acgaggggguc uggaggccug gguuugaaua ucgacagc                          98

<210> SEQ ID NO 286
<211> LENGTH: 92
<212> TYPE: RNA
<213> ORGANISM: Homo Sapience
```

```
<400> SEQUENCE: 286 ugcacuccg ccagcaucau gaagugcacu caugauaugu ugccccauc agcgugucac    60 gagggcauuu caugaugcag gcggggugg ca                                92

<210> SEQ ID NO 287
<211> LENGTH: 83
<212> TYPE: RNA
<213> ORGANISM: Homo Sapience

<400> SEQUENCE: 287
acggcaucuu ugcacucagc aggcaggcug gugcagcccg ugguggggga ccauccugcc    60
ugcugugggg uaaggacggc ugu                                          83

<210> SEQ ID NO 288
<211> LENGTH: 79
<212> TYPE: RNA
<213> ORGANISM: Homo Sapience

<400> SEQUENCE: 288 gugaggugg ggccagcagg gaguggcug ggcugggcug ggccaaggua caaggccuca    60
cccugcaucc cgcacccag                                              79

<210> SEQ ID NO 289
<211> LENGTH: 85
<212> TYPE: RNA
<213> ORGANISM: Homo Sapience

<400> SEQUENCE: 289
gugagcugcu ggggacgcgg gucggggucu gcagggcggu gcggcagccg ccaccugacg    60
ccgcgccuuu gucugugucc cacag                                        85

<210> SEQ ID NO 290
<211> LENGTH: 83
<212> TYPE: RNA
<213> ORGANISM: Homo Sapience

<400> SEQUENCE: 290
aauagagggu gcacaggcac gggagcucag gugaggcagg gagcugagcu caccugaccu    60
cccaugccug ugcacccucu auu                                          83

<210> SEQ ID NO 291
<211> LENGTH: 131
<212> TYPE: RNA
<213> ORGANISM: Homo Sapience

<400> SEQUENCE: 291
cggcuggagg ugugaggauc cgaacccagg gguggggggu ggaggcggcu ccugcgaucg    60
aaggggacuu gagacucacc ggccgcacgc caugagggcc cugugggugc ugggccucug   120
cugcguccug c                                                       131

<210> SEQ ID NO 292
<211> LENGTH: 69
<212> TYPE: RNA
<213> ORGANISM: Homo Sapience

<400> SEQUENCE: 292
cuuucggcca gcgggacggc auccgaggug ggcuaggcuc ggcccgugg cgggugcggg    60 gguggagg                                                          69
```

```
<210> SEQ ID NO 293
<211> LENGTH: 97
<212> TYPE: RNA
<213> ORGANISM: Homo Sapience

<400> SEQUENCE: 293
cccgggaccu ugguccaggc gcuggucugc guggugcucg gguggauaag ucgaucuga    60 gcaccacaca ggccgggcgc cgggaccaag ggggcuc                           97

<210> SEQ ID NO 294
<211> LENGTH: 68
<212> TYPE: RNA
<213> ORGANISM: Homo Sapience

<400> SEQUENCE: 294
cguggugagg auauggcagg aaggggagu ucccucuau ucccuucccc ccaguaaucu     60
ucaucaug                                                           68

<210> SEQ ID NO 295
<211> LENGTH: 66
<212> TYPE: RNA
<213> ORGANISM: Homo Sapience

<400> SEQUENCE: 295
gguaacacuc aaaagauggc ggcacuuuca ccagagagca gaaagugccc ccacaguuug   60
agugcc                                                             66

<210> SEQ ID NO 296
<211> LENGTH: 69
<212> TYPE: RNA
<213> ORGANISM: Homo Sapience

<400> SEQUENCE: 296
gggauacuca aaauggggc gcuuccuuu uugucuguac ugggaagugc uucgauuuug     60
ggguguccc                                                          69

<210> SEQ ID NO 297
<211> LENGTH: 93
<212> TYPE: RNA
<213> ORGANISM: Homo Sapience

<400> SEQUENCE: 297
ggcgcuuuug ugcgcgcccg ggucuguugg ugcucagagu guggucaggc ggcucggacu   60
gagcaggugg gugcggggcu cggaggaggc ggc                               93

<210> SEQ ID NO 298
<211> LENGTH: 102
<212> TYPE: RNA
<213> ORGANISM: Homo Sapience

<400> SEQUENCE: 298
gcuuaucgag gaaaagaucg aggugggbuug gggcgggcuc uggggauuug gucucacagc  60
ccggauccca gcccacuuac cuugguuacu cuccuuccuu cu                     102

<210> SEQ ID NO 299
<211> LENGTH: 91
<212> TYPE: RNA
<213> ORGANISM: Homo Sapience
```

```
<400> SEQUENCE: 299
ggcgccccgg cuccccgcgc ccccgaucgg ggccgccgcu aguaguggcg gcggcggagg       60 cggggggcagc ggcggcggcg gcggaggcgc c                                    91

<210> SEQ ID NO 300
<211> LENGTH: 91
<212> TYPE: RNA
<213> ORGANISM: Homo Sapience

<400> SEQUENCE: 300
acgccccccg ccccgccacc gccuuggagg cugaccucuu acuuucgguc ggucuucuuc       60
ccugggcuug guuuggggggc ggggagugu c                                     91

<210> SEQ ID NO 301
<211> LENGTH: 101
<212> TYPE: RNA
<213> ORGANISM: Homo Sapience

<400> SEQUENCE: 301
gaugggcccc uuguguccug aauugggugg gggcucugag uggggaaagu gggggccuag       60
gggaggucac aguugggucu aggggucagg agggcccagg a                         101

<210> SEQ ID NO 302
<211> LENGTH: 70
<212> TYPE: RNA
<213> ORGANISM: Homo Sapience

<400> SEQUENCE: 302
acaaauagcu ucagggaguc aggggagggc agaaauagau ggccuucccc ugcugggaag       60
aaaguggguc                                                             70

<210> SEQ ID NO 303
<211> LENGTH: 93
<212> TYPE: RNA
<213> ORGANISM: Homo Sapience

<400> SEQUENCE: 303
uacuuauggc accccacucc ugguaccaua gucauaaguu aggagauguu agagcuguga       60
guaccaugac uuaagugugg uggcuuaaac aug                                   93

<210> SEQ ID NO 304
<211> LENGTH: 73
<212> TYPE: RNA
<213> ORGANISM: Homo Sapience

<400> SEQUENCE: 304
ggggagguac cuggacagg aggaggaggc agccuugccu cagaaaccaa acugucaaaa        60
guguagguuc cac                                                         73

<210> SEQ ID NO 305
<211> LENGTH: 73
<212> TYPE: RNA
<213> ORGANISM: Homo Sapience

<400> SEQUENCE: 305
accgcgaguu ccgcgccugg ccgugucgcc ccacgagggg gacuggggc ucagcgcgug        60 gggcccggag cau                                                         73
```

```
<210> SEQ ID NO 306
<211> LENGTH: 85
<212> TYPE: RNA
<213> ORGANISM: Homo Sapience

<400> SEQUENCE: 306
ggccugggua ggcuugcaug ggggacuggg aagagaccau gaacagguua guccagggag    60
uucucaucaa gccuuuacuc aguag                                          85

<210> SEQ ID NO 307
<211> LENGTH: 73
<212> TYPE: RNA
<213> ORGANISM: Homo Sapience

<400> SEQUENCE: 307
gaaaacaacc aggugggcuu cccggagggc ggaacaccca gccccagcau ccagggcuca    60
ccuaccacgu uug                                                       73

<210> SEQ ID NO 308
<211> LENGTH: 68
<212> TYPE: RNA
<213> ORGANISM: Homo Sapience

<400> SEQUENCE: 308
cucaggcuca guggugcaug cuuauagucc cagccacucu ggaggcugaa ggaagauggc    60
uugagccu                                                             68

<210> SEQ ID NO 309
<211> LENGTH: 73
<212> TYPE: RNA
<213> ORGANISM: Homo Sapience

<400> SEQUENCE: 309
agggagaaaa gcugggcuga gaggcgacug gugucuaauu guuugucuc uccaacucag     60 acugccuggc cca                                                       73

<210> SEQ ID NO 310
<211> LENGTH: 49
<212> TYPE: RNA
<213> ORGANISM: Homo Sapience

<400> SEQUENCE: 310
gugaggcugg agugagcgga gaucguacca cugcacucca accugguga               49

<210> SEQ ID NO 311
<211> LENGTH: 81
<212> TYPE: RNA
<213> ORGANISM: Homo Sapience

<400> SEQUENCE: 311
cauccuccuu acgucccacc ccccacuccu guuucggug aaauauucaa acaggagugg     60 ggugggaca uaaggaggau a                                               81

<210> SEQ ID NO 312
<211> LENGTH: 53
<212> TYPE: RNA
<213> ORGANISM: Homo Sapience

<400> SEQUENCE: 312
gguggggguu ggaggcgugg guuuuagaac cuaucccuuu cuagcccuga gca           53
```

```
<210> SEQ ID NO 313
<211> LENGTH: 67
<212> TYPE: RNA
<213> ORGANISM: Homo Sapience

<400> SEQUENCE: 313
cugguccauu ucccugccau ucccuuggcu ucaauuuacu cccagggcug gcagugacau      60
gggucaa                                                                67

<210> SEQ ID NO 314
<211> LENGTH: 91
<212> TYPE: RNA
<213> ORGANISM: Homo Sapience

<400> SEQUENCE: 314
guucuagagc augguuucuc aucauuugca cuacugauac uggggucag auaauuguuu       60 guggugggg cuguuguuug cauuguagga u                                      91

<210> SEQ ID NO 315
<211> LENGTH: 86
<212> TYPE: RNA
<213> ORGANISM: Homo Sapience

<400> SEQUENCE: 315
aggagugacc aaaagacaag agugcgagcc uucauuaug cccagacagg gccaccagag       60
ggcuccuugg ucuaggggua augcca                                           86

<210> SEQ ID NO 316
<211> LENGTH: 66
<212> TYPE: RNA
<213> ORGANISM: Homo Sapience

<400> SEQUENCE: 316
agcagcccuc ggcggcccgg ggggcgggcg gcggugcccg ucccggggcu gcgcgaggca      60
caggcg                                                                 66

<210> SEQ ID NO 317
<211> LENGTH: 55
<212> TYPE: RNA
<213> ORGANISM: Homo Sapience

<400> SEQUENCE: 317
ccggauccga gucacggcac caaauuucau gcguguccgu gugaagagac cacca           55

<210> SEQ ID NO 318
<211> LENGTH: 58
<212> TYPE: RNA
<213> ORGANISM: Homo Sapience

<400> SEQUENCE: 318
agaagggugu guguguuuuu ccugagaauaagagaaggaa ggacagccaa auucuuca         58

<210> SEQ ID NO 319
<211> LENGTH: 66
<212> TYPE: RNA
<213> ORGANISM: Homo Sapience

<400> SEQUENCE: 319
acccaggagg cggaggaggu ggagguugca gugagccaag aucguggcac ugacuccagc      60
cugggg                                                                 66
```

<210> SEQ ID NO 320
<211> LENGTH: 58
<212> TYPE: RNA
<213> ORGANISM: Homo Sapience

<400> SEQUENCE: 320
cuucccagcu gcccuaaguc aggaguggcu uuccugacac ggaggguggc uugggaaa    58

<210> SEQ ID NO 321
<211> LENGTH: 54
<212> TYPE: RNA
<213> ORGANISM: Homo Sapience

<400> SEQUENCE: 321
acgcgggugc gggccggcgg gguagaagcc acccggcccg gcccggcccg gcga    54

<210> SEQ ID NO 322
<211> LENGTH: 63
<212> TYPE: RNA
<213> ORGANISM: Homo Sapience

<400> SEQUENCE: 322
ugguggcggc gguaguuaug ggcuucucuu ucucaccagc agccccuggg ccgccgccuc    60
ccu    63

<210> SEQ ID NO 323
<211> LENGTH: 71
<212> TYPE: RNA
<213> ORGANISM: Homo Sapience

<400> SEQUENCE: 323
gcagagguga guugaccucc acagggccac ccagggagua aguagccaag uggaaguuac    60
uuuaccucug u    71

<210> SEQ ID NO 324
<211> LENGTH: 62
<212> TYPE: RNA
<213> ORGANISM: Homo Sapience

<400> SEQUENCE: 324
aaaaaacaac auacuuagug cauacccaua uaauauuagg ggugguucugu uguuguuuuu    60 cu    62

<210> SEQ ID NO 325
<211> LENGTH: 83
<212> TYPE: RNA
<213> ORGANISM: Homo Sapience

<400> SEQUENCE: 325
ggguuuccuc ugccuuuuuu uccaaugaaa auaacgaaac cuguuauuuc ccauugaggg    60
ggaaaaaggc gggagaagcc cca    83

<210> SEQ ID NO 326
<211> LENGTH: 57
<212> TYPE: RNA
<213> ORGANISM: Homo Sapience

<400> SEQUENCE: 326
agaggcaccg ccugcccagu gacaugcguu uaacggccgc gguacccuaa cugugca    57

```
<210> SEQ ID NO 327
<211> LENGTH: 62
<212> TYPE: RNA
<213> ORGANISM: Homo Sapience

<400> SEQUENCE: 327 gguaggggc gggcuccggc gcugggaccc cacuagggug gcgccuuggc cccgccccgc     60
cc                                                                  62

<210> SEQ ID NO 328
<211> LENGTH: 80
<212> TYPE: RNA
<213> ORGANISM: Homo Sapience

<400> SEQUENCE: 328
cugcagcgug cuucuccagg ccccgcgcgc ggacagacac acggacaagu cccgccaggg    60
gcugggcgcg cgccagccgg                                                80

<210> SEQ ID NO 329
<211> LENGTH: 73
<212> TYPE: RNA
<213> ORGANISM: Homo Sapience

<400> SEQUENCE: 329
ggaggcuggg cugggacgga cacccggccu ccacuuucug uggcagguac cuccuccaug    60
ucggcccgcc uug                                                       73

<210> SEQ ID NO 330
<211> LENGTH: 81
<212> TYPE: RNA
<213> ORGANISM: Homo Sapience

<400> SEQUENCE: 330
gcgggaggug uaacaggacu ggacucccgg cagccccagg caggggcgu ggggagcugg     60 uccuagcuca gcgcucccgg a                                              81

<210> SEQ ID NO 331
<211> LENGTH: 75
<212> TYPE: RNA
<213> ORGANISM: Homo Sapience

<400> SEQUENCE: 331
gucagagggg ggaugugcau gcugguuggg gugggcugcc uggaccaa ucagcgugca      60 cuucccacc cugaa                                                      75

<210> SEQ ID NO 332
<211> LENGTH: 60
<212> TYPE: RNA
<213> ORGANISM: Homo Sapience

<400> SEQUENCE: 332
ugugaaugac ccccuuccag agccaaaauc accagggaug gaggagggu cuugggacu      60

<210> SEQ ID NO 333
<211> LENGTH: 59
<212> TYPE: RNA
<213> ORGANISM: Homo Sapience

<400> SEQUENCE: 333
aacugggucc cagucuucac aguugguuuc ugacacgugg accggcugg gacgaugug      59
```

<210> SEQ ID NO 334
<211> LENGTH: 79
<212> TYPE: RNA
<213> ORGANISM: Homo Sapience

<400> SEQUENCE: 334
uggcaagucu ccgcauaugc cuggcuagcu ccuccacaaa ugcgugugga ggagcuagcc    60
aggcauaugc agagcguca                                                79

<210> SEQ ID NO 335
<211> LENGTH: 54
<212> TYPE: RNA
<213> ORGANISM: Homo Sapience

<400> SEQUENCE: 335
ggacaagggc ggcgcgaccg gcccggggcu cuugggcggc cgcguuuccc cucc          54

<210> SEQ ID NO 336
<211> LENGTH: 90
<212> TYPE: RNA
<213> ORGANISM: Homo Sapience

<400> SEQUENCE: 336
cugugggcug ggccagggag cagcuggugg gugggaagua agaucugacc uggacuccau    60
cccacccacc cccuguuucc uggcccacag                                    90

<210> SEQ ID NO 337
<211> LENGTH: 64
<212> TYPE: RNA
<213> ORGANISM: Homo Sapience

<400> SEQUENCE: 337
ucugggcgag ggugggcuc ucagaggggc uggcaguacu gcucugaggc cugccucucc     60
ccag                                                                64

<210> SEQ ID NO 338
<211> LENGTH: 73
<212> TYPE: RNA
<213> ORGANISM: Homo Sapience

<400> SEQUENCE: 338
cggcgacggc ggguggguug aggucgggcc ccaagacucg ggguuugccg ggcgccucag    60
uucaccgcgg ccg                                                      73

<210> SEQ ID NO 339
<211> LENGTH: 78
<212> TYPE: RNA
<213> ORGANISM: Homo Sapience

<400> SEQUENCE: 339
uauuggacga ggggacuggu uaauagaacu aacuaaccag aacuauuuug uucuguuaac    60 ccaucccuc aucuaaua                                                  78

<210> SEQ ID NO 340
<211> LENGTH: 74
<212> TYPE: RNA
<213> ORGANISM: Homo Sapience

<400> SEQUENCE: 340

```
ccaagggcac accggggaug gcagagggug gugggaaagu guugacccuc gucaggcccc    60
cggggagccc cugg                                                     74

<210> SEQ ID NO 341
<211> LENGTH: 75
<212> TYPE: RNA
<213> ORGANISM: Homo Sapience

<400> SEQUENCE: 341
aggcuggcgu gggcugaggg caggaggccu guggccgguc ccaggccucc ugcuuccugg   60
gcucaggcuc gguuu                                                   75

<210> SEQ ID NO 342
<211> LENGTH: 65
<212> TYPE: RNA
<213> ORGANISM: Homo Sapience

<400> SEQUENCE: 342
gcugcccuuc acucagagca ucuacaccca cuaccgguga gugggauccu ggaggaauc   60 guggc                                                              65

<210> SEQ ID NO 343
<211> LENGTH: 76
<212> TYPE: RNA
<213> ORGANISM: Homo Sapience

<400> SEQUENCE: 343
cuguggugga gcugagcucc auggacgugc aguggcaucu ucauugcug ccuuccugga   60 gcucaggccc uugcag                                                  76

<210> SEQ ID NO 344
<211> LENGTH: 59
<212> TYPE: RNA
<213> ORGANISM: Homo Sapience

<400> SEQUENCE: 344
guccaggcag gagccggacu ggaccucagg gaagaggcug acccggcccc ucuugcggc   59

<210> SEQ ID NO 345
<211> LENGTH: 77
<212> TYPE: RNA
<213> ORGANISM: Homo Sapience

<400> SEQUENCE: 345
caugagaaau ccugcggguc aaccauagcc cuggucagac ucuccggggc ugugauugac   60
cagcaggacu ucucaug                                                 77

<210> SEQ ID NO 346
<211> LENGTH: 80
<212> TYPE: RNA
<213> ORGANISM: Homo Sapience

<400> SEQUENCE: 346
accugaggag ccagcccucc ucccgcaccc aaacuuggag cacuugaccu uuggcuguug   60 gaggggcag gcucgcgggu                                               80

<210> SEQ ID NO 347
<211> LENGTH: 80
<212> TYPE: RNA
<213> ORGANISM: Homo Sapience
```

<400> SEQUENCE: 347
accugaggag ccagcccucc ucccgcaccc aaacuuggag cacuugaccu uuggcuguug    60 gaggggcag gcucgcgggu                                                 80

<210> SEQ ID NO 348
<211> LENGTH: 60
<212> TYPE: RNA
<213> ORGANISM: Homo Sapience

<400> SEQUENCE: 348
gagcaggcga ggcugggcug aacccguggg ugaggagugc agcccagcug aggccucugc    60

<210> SEQ ID NO 349
<211> LENGTH: 74
<212> TYPE: RNA
<213> ORGANISM: Homo Sapience

<400> SEQUENCE: 349
ccugcaggag gcagugggcg agcaggcggg gcagcccaau gccaugggcc ugaucucacc    60
gcugccuccu uccc                                                      74

<210> SEQ ID NO 350
<211> LENGTH: 78
<212> TYPE: RNA
<213> ORGANISM: Homo Sapience

<400> SEQUENCE: 350
gggcccagaa gggggcgcag ucacugacgu gaagggacca caucccgcuu caugucagug    60
acuccugccc cuuggucu                                                  78

<210> SEQ ID NO 351
<211> LENGTH: 82
<212> TYPE: RNA
<213> ORGANISM: Homo Sapience

<400> SEQUENCE: 351
gcuacgggga gcgggagga agugggcgcu gcuucugcgu uaucuggaag gagcagccca    60
cuccuguccu gggcucugug gu                                             82

<210> SEQ ID NO 352
<211> LENGTH: 80
<212> TYPE: RNA
<213> ORGANISM: Homo Sapience

<400> SEQUENCE: 352 gguccggag cccggcgcg ggcgguucu ggguguaga cgcugcuggc cagcccgccc       60
cagccgaggu ucucggcacc                                                80

<210> SEQ ID NO 353
<211> LENGTH: 80
<212> TYPE: RNA
<213> ORGANISM: Homo Sapience

<400> SEQUENCE: 353 gguccggag cccggcgcg ggcgguucu ggguguaga cgcugcuggc cagcccgccc       60
cagccgaggu ucucggcacc                                                80

<210> SEQ ID NO 354

```
<211> LENGTH: 67
<212> TYPE: RNA
<213> ORGANISM: Homo Sapience

<400> SEQUENCE: 354
uuuaggagag agaugccgcc uugcuccuug aacaggagga gcaaggcggc aucucucuga      60
uacuaaa                                                                67

<210> SEQ ID NO 355
<211> LENGTH: 56
<212> TYPE: RNA
<213> ORGANISM: Homo Sapience

<400> SEQUENCE: 355
gaccgagugg ggugagggca ggugguucuu cccgaagcag cucucgccuc uucguc         56

<210> SEQ ID NO 356
<211> LENGTH: 51
<212> TYPE: RNA
<213> ORGANISM: Homo Sapience

<400> SEQUENCE: 356
agcuguaccu gaaaccaagc accuguuugu gacuuggcuu caguuacuag c              51

<210> SEQ ID NO 357
<211> LENGTH: 60
<212> TYPE: RNA
<213> ORGANISM: Homo Sapience

<400> SEQUENCE: 357
ggcaggaggg cugugccagg uuggcugggc caggccugac cugccagcac cucccugcag    60

<210> SEQ ID NO 358
<211> LENGTH: 90
<212> TYPE: RNA
<213> ORGANISM: Homo Sapience

<400> SEQUENCE: 358
gugucucucu ggagacccug cagccuuccc acccaccagg gagcuuucca ugggcugugg    60
ggaaggcguc agugucgggu gagggaacac                                      90

<210> SEQ ID NO 359
<211> LENGTH: 58
<212> TYPE: RNA
<213> ORGANISM: Homo Sapience

<400> SEQUENCE: 359
agggccagag gagccuggag uggucggguc gacugaaccc agguucccuc uggccgca      58

<210> SEQ ID NO 360
<211> LENGTH: 55
<212> TYPE: RNA
<213> ORGANISM: Homo Sapience

<400> SEQUENCE: 360
aaucugccag cuuccacagu ggcagauuuu cccauagugg gaagcuggca gauuc         55

<210> SEQ ID NO 361
<211> LENGTH: 67
<212> TYPE: RNA
<213> ORGANISM: Homo Sapience

<400> SEQUENCE: 361
```

```
gugggagggg agaggcagca agcacacagg gccugggacu agcaugcuga ccucccuccu    60
gccccag                                                              67

<210> SEQ ID NO 362
<211> LENGTH: 70
<212> TYPE: RNA
<213> ORGANISM: Homo Sapience

<400> SEQUENCE: 362
cccugccagu gcuggggcc acaugagugu gcagucaucc acacacaagu ggcccccaac     60
acuggcaggg                                                           70

<210> SEQ ID NO 363
<211> LENGTH: 47
<212> TYPE: RNA
<213> ORGANISM: Homo Sapience

<400> SEQUENCE: 363
aggcagguua ucgggcugc caucucccac uggcugcuug ccugccu                   47

<210> SEQ ID NO 364
<211> LENGTH: 74
<212> TYPE: RNA
<213> ORGANISM: Homo Sapience

<400> SEQUENCE: 364
gggaggaaga agggaggagg agcggagggg cccuugucuu cccagagccu cucccuuccu    60
ccccuccccc uccc                                                      74

<210> SEQ ID NO 365
<211> LENGTH: 63
<212> TYPE: RNA
<213> ORGANISM: Homo Sapience

<400> SEQUENCE: 365
gccaaggacu gauccucucg ggcagggagu cagaggggac cgcccgagag gauccguccc    60
ugc                                                                  63

<210> SEQ ID NO 366
<211> LENGTH: 90
<212> TYPE: RNA
<213> ORGANISM: Homo Sapience

<400> SEQUENCE: 366 cgggcgggc gguccggcc gccuccgagc ccggccggca gccccggcc uuaaagcgcg       60 ggcuguccgg agggucggc uuucccaccg                                      90

<210> SEQ ID NO 367
<211> LENGTH: 56
<212> TYPE: RNA
<213> ORGANISM: Homo Sapience

<400> SEQUENCE: 367
cgcucgggcg gagguggung agugccgacu ggcgccugac ccaccccuc ccgcag         56

<210> SEQ ID NO 368
<211> LENGTH: 72
<212> TYPE: RNA
<213> ORGANISM: Homo Sapience
```

<400> SEQUENCE: 368
agauucagcu ucccuucag agccuggcuu uggcaucuau gaaagccagg cucugaaggg     60
aaaguugaau cu                                                        72

<210> SEQ ID NO 369
<211> LENGTH: 92
<212> TYPE: RNA
<213> ORGANISM: Homo Sapience

<400> SEQUENCE: 369
ccugucccuc cugcccugcg ccugcccagc ccuccugcuc uggugacuga ggaccgccag     60
gcaggggcug gugcugggcg ggggcggcg gg                                   92

<210> SEQ ID NO 370
<211> LENGTH: 82
<212> TYPE: RNA
<213> ORGANISM: Homo Sapience

<400> SEQUENCE: 370
gggaaagcgg agggcgcgcc cagcucccgg gcugauugcg cuaacagugg ccccgguguu     60
ggggcgcguc ugccgcugcc cc                                             82

<210> SEQ ID NO 371
<211> LENGTH: 82
<212> TYPE: RNA
<213> ORGANISM: Homo Sapience

<400> SEQUENCE: 371
gggaaagcgg agggcgcgcc cagcucccgg gcugauugcg cuaacagugg ccccgguguu     60
ggggcgcguc ugccgcugcc cc                                             82

<210> SEQ ID NO 372
<211> LENGTH: 84
<212> TYPE: RNA
<213> ORGANISM: Homo Sapience

<400> SEQUENCE: 372
cgguccagac guggcggggg uggcggcggc aucccggacg gccugugagg gaugcgccgc     60
ccacugcccc gcgccgccug accg                                           84

<210> SEQ ID NO 373
<211> LENGTH: 74
<212> TYPE: RNA
<213> ORGANISM: Homo Sapience

<400> SEQUENCE: 373
gcagcccggu gagcgcucgc uggccuggca gucgucgga agaacagggc ggguggggcc      60
gcgcacaucu cugc                                                      74

<210> SEQ ID NO 374
<211> LENGTH: 124
<212> TYPE: RNA
<213> ORGANISM: Homo Sapience

<400> SEQUENCE: 374
aacccuccuu gggaagugaa gcucaggcug ugauuucaag ccaggggcg uuuuucuaua      60 acuggaugaa aagcacccc agagcuugaa gcucacaguu ugagagcaau cgucuaagga    120
aguu                                                                124

<210> SEQ ID NO 375
<211> LENGTH: 94
<212> TYPE: RNA
<213> ORGANISM: Homo Sapience

<400> SEQUENCE: 375
gggcugaccc cuaggucag gugaggcccu uggggcacag uggugccauc uccccugugc    60
ucccagggcc ucgccugucc cuugaggucg gccc                              94

<210> SEQ ID NO 376
<211> LENGTH: 120
<212> TYPE: RNA
<213> ORGANISM: Homo Sapience

<400> SEQUENCE: 376
gauccaggga acccuagagc aggggaugg cagagcaaaa uucauggccu acagcugccu    60
cuugccaaac ugcacuggau uuugucucuc ccauucccca gagcugucug aggugcuuug  120

<210> SEQ ID NO 377
<211> LENGTH: 83
<212> TYPE: RNA
<213> ORGANISM: Homo Sapience

<400> SEQUENCE: 377
gcugcuguug ggagacccug gucugcacuc uaucuguauu cuuacugaag ggagugcagg    60
gcaggguuuc ccauacagag ggc                                           83

<210> SEQ ID NO 378
<211> LENGTH: 115
<212> TYPE: RNA
<213> ORGANISM: Homo Sapience

<400> SEQUENCE: 378
gagcaaaaac cagagaacaa caugggagcg uuccuaaccc cuaaggcaac uggaugggag    60
accugaccca uccaguucuc ugaggggcu cuugugug uu cuacaagguu guuca        115

<210> SEQ ID NO 379
<211> LENGTH: 137
<212> TYPE: RNA
<213> ORGANISM: Homo Sapience

<400> SEQUENCE: 379
agccagacaa gagggucaug gggagucacu gucaacccag agcaggcacu gccccugcga    60
ccagccuggg gcaucgguug gggugcaggg gucugcuggu gaugcuuucc aucucuuugc   120
uuuguccuga uuguagc                                                  137

<210> SEQ ID NO 380
<211> LENGTH: 80
<212> TYPE: RNA
<213> ORGANISM: Homo Sapience

<400> SEQUENCE: 380
gguuggcuau aacuaucauu uccaagguug ugcuuuagg aaauguuggc uguccugcgg     60
agagagaaug gggagccagg                                                80

<210> SEQ ID NO 381
<211> LENGTH: 95
<212> TYPE: RNA

<213> ORGANISM: Homo Sapience

<400> SEQUENCE: 381

```
gacaccacau gcuccuccag gccugccugc ccuccagguc auguccagu gucccacaga      60 ugcagcacca cggcccaggc ggcauuggug ucacc                                95
```

<210> SEQ ID NO 382
<211> LENGTH: 113
<212> TYPE: RNA
<213> ORGANISM: Homo Sapience

<400> SEQUENCE: 382

```
agcaugacag aggagaggug gagguaggcg agaguaauau aauuucucca ggagaacauc      60
ugagagggga aguugcuuuc cugcccuggc ccuuucaccc uccugaguuu ggg            113
```

<210> SEQ ID NO 383
<211> LENGTH: 51
<212> TYPE: RNA
<213> ORGANISM: Homo Sapience

<400> SEQUENCE: 383

```
agagaugaag cgggggggcg gggucuugcu cuauugccua cgcugaucuc a               51
```

<210> SEQ ID NO 384
<211> LENGTH: 85
<212> TYPE: RNA
<213> ORGANISM: Homo Sapience

<400> SEQUENCE: 384

```
ggggagguag ggaaaaggaa gggggaggag aaggugagac caauguccug ggugccacuc      60
cugcccagug ccucccuucc ucguu                                            85
```

<210> SEQ ID NO 385
<211> LENGTH: 109
<212> TYPE: RNA
<213> ORGANISM: Homo Sapience

<400> SEQUENCE: 385

```
ucccgcauuc ccucugcuuu ggucaggugg ugcccuccuu ccauggguag agccagagau      60
gguggguucu ggcuggucag augggagugg acagagaccc ggggguccuc                109
```

<210> SEQ ID NO 386
<211> LENGTH: 109
<212> TYPE: RNA
<213> ORGANISM: Homo Sapience

<400> SEQUENCE: 386

```
ugcuauuguc uuacugcuac agcagggcug gggauugcag uauccgcugu ugcugcugcu      60
cccaguccug ccccugcugc uaccaguccc agccucaccg caucccaga                 109
```

<210> SEQ ID NO 387
<211> LENGTH: 90
<212> TYPE: RNA
<213> ORGANISM: Homo Sapience

<400> SEQUENCE: 387

```
ucuaagaaac gcagugguucu cugaagccug caggggcagg ccagcccugc acugaacgcc     60
uguucuugcc aggugggcaga agguugcugc                                      90
```

```
<210> SEQ ID NO 388
<211> LENGTH: 96
<212> TYPE: RNA
<213> ORGANISM: Homo Sapience

<400> SEQUENCE: 388
cucgggaggg gcgggagggg ggucccoggu gcucggaucu cgagggugcu uauuguucgg    60
uccgagccug ggucucccuc uucccoccaa cccccc                              96

<210> SEQ ID NO 389
<211> LENGTH: 99
<212> TYPE: RNA
<213> ORGANISM: Homo Sapience

<400> SEQUENCE: 389
cgcccaccuc agccucccaa aaugcuggga uuacaggcau gagccacugc ggucgaccau    60
gaccuggaca uguuugugcc caguacuguc aguuugcag                           99

<210> SEQ ID NO 390
<211> LENGTH: 77
<212> TYPE: RNA
<213> ORGANISM: Homo Sapience

<400> SEQUENCE: 390
gaguugggag guucccucuc caaauguguc uugaucccce accccaagac acauuggag    60 agggacccuc ccaacuc                                                    77

<210> SEQ ID NO 391
<211> LENGTH: 54
<212> TYPE: RNA
<213> ORGANISM: Homo Sapience

<400> SEQUENCE: 391
agcagcaggg gagagagagg aguccucuag acaccgacuc ugucuccugc agau          54

<210> SEQ ID NO 392
<211> LENGTH: 57
<212> TYPE: RNA
<213> ORGANISM: Homo Sapience

<400> SEQUENCE: 392
cauuggaggg uguggaagac aucugggcca acucugaucu cuucaucuac cccccag       57

<210> SEQ ID NO 393
<211> LENGTH: 57
<212> TYPE: RNA
<213> ORGANISM: Homo Sapience

<400> SEQUENCE: 393
cauuggaggg uguggaagac aucugggcca acucugaucu cuucaucuac cccccag       57

<210> SEQ ID NO 394
<211> LENGTH: 115
<212> TYPE: RNA
<213> ORGANISM: Homo Sapience

<400> SEQUENCE: 394
ggugccgagg gccguccggc auccuaggcg ggucgcugcg guaccucccu ccugucugug    60
gcggugggau cccguggccg uguuuuccug guggcccggc cgugccgag guuuc          115

<210> SEQ ID NO 395
```

```
<211> LENGTH: 80
<212> TYPE: RNA
<213> ORGANISM: Homo Sapience

<400> SEQUENCE: 395
gagaggccaa gaccuuggga auggggguaa gggccuucug agcccagguc cgaacucucc    60 auccucugc agagcgcucu                                                 80

<210> SEQ ID NO 396
<211> LENGTH: 73
<212> TYPE: RNA
<213> ORGANISM: Homo Sapience

<400> SEQUENCE: 396 cuggguguuug aggcgaugug gggauguaga gacaacuucc cagucucauu uccucauccu   60
gccaggccac cau                                                       73

<210> SEQ ID NO 397
<211> LENGTH: 78
<212> TYPE: RNA
<213> ORGANISM: Homo Sapience

<400> SEQUENCE: 397
ggccucaggc aggcgcaccc gaccacaugc auggcuggug gcggcugca ggggucgggu     60 gggccaggcu gugggcg                                                   78

<210> SEQ ID NO 398
<211> LENGTH: 61
<212> TYPE: RNA
<213> ORGANISM: Homo Sapience

<400> SEQUENCE: 398
gggggcggga gcuggggucu gcagguucgc acugaugccu gcucgcccug ucuccgcua     60 g                                                                    61

<210> SEQ ID NO 399
<211> LENGTH: 70
<212> TYPE: RNA
<213> ORGANISM: Homo Sapience

<400> SEQUENCE: 399
uugggUuggg guggucggcc cuggagggg uuguuugcu uauucccuc ugugcuucac       60 cccuacccag                                                           70

<210> SEQ ID NO 400
<211> LENGTH: 63
<212> TYPE: RNA
<213> ORGANISM: Homo Sapience

<400> SEQUENCE: 400 aaugggugggg ugcugguggg agccgugccc uggccacuca uucggcucuc ucccucaccc   60
uag                                                                  63

<210> SEQ ID NO 401
<211> LENGTH: 62
<212> TYPE: RNA
<213> ORGANISM: Homo Sapience

<400> SEQUENCE: 401
gagggagugg gguggaccc agcuguuggc cauggcgaca acaccugggu uguccccucu     60
```

```
ag                                                               62

<210> SEQ ID NO 402
<211> LENGTH: 71
<212> TYPE: RNA
<213> ORGANISM: Homo Sapience

<400> SEQUENCE: 402
ggguaaaggg gcagggacgg guggcccag gaagaagggc cugguggagc cgcucuucuc    60
ccugcccaca g                                                       71

<210> SEQ ID NO 403
<211> LENGTH: 63
<212> TYPE: RNA
<213> ORGANISM: Homo Sapience

<400> SEQUENCE: 403
cuugcccggg agaaggaggu ggccuggaga gcugcugucu ccagccgccg ccugucucca    60
cag                                                                63

<210> SEQ ID NO 404
<211> LENGTH: 69
<212> TYPE: RNA
<213> ORGANISM: Homo Sapience

<400> SEQUENCE: 404
ggcccucggg ccugggguug ggggagcucu guccugucuc acucauugcu ccuccccugc    60
cuggcccag                                                          69

<210> SEQ ID NO 405
<211> LENGTH: 68
<212> TYPE: RNA
<213> ORGANISM: Homo Sapience

<400> SEQUENCE: 405
cagugcaggg agaaggugga agugcagagu gggcucaccu cucgcccaca cuguccccuu    60
cuccccag                                                           68

<210> SEQ ID NO 406
<211> LENGTH: 86
<212> TYPE: RNA
<213> ORGANISM: Homo Sapience

<400> SEQUENCE: 406
agagccgggg ccauggagca gccuguguag acggggaccu gcccugcaug ggcaccccu     60 cacuggcugc uucccuuggu cuccag                                       86

<210> SEQ ID NO 407
<211> LENGTH: 87
<212> TYPE: RNA
<213> ORGANISM: Homo Sapience

<400> SEQUENCE: 407
gugaggcggg gccaggaggg uguguggcgu gggugcugcg gggccgucag ggugccugcg    60
ggacgcucac cuggcuggcc cgcccag                                      87

<210> SEQ ID NO 408
<211> LENGTH: 87
<212> TYPE: RNA
```

```
<213> ORGANISM: Homo Sapience

<400> SEQUENCE: 408
gugaggcggg gccaggaggg uguguggcgu gggugcugcg gggccgucag ggugccugcg      60
ggacgcucac cuggcuggcc cgcccag                                          87

<210> SEQ ID NO 409
<211> LENGTH: 72
<212> TYPE: RNA
<213> ORGANISM: Homo Sapience

<400> SEQUENCE: 409
augagcgggu gggagcagau cuuauugaga guuccuucuc cugcuccuga uugucuuccc      60
ccacccucac ag                                                          72

<210> SEQ ID NO 410
<211> LENGTH: 72
<212> TYPE: RNA
<213> ORGANISM: Homo Sapience

<400> SEQUENCE: 410
augagcgggu gggagcagau cuuauugaga guuccuucuc cugcuccuga uugucuuccc      60
ccacccucac ag                                                          72

<210> SEQ ID NO 411
<211> LENGTH: 60
<212> TYPE: RNA
<213> ORGANISM: Homo Sapience

<400> SEQUENCE: 411
ggugccucgg gagggcaugg gccaggccac auaaugagcc aaaccccugu cuacccgcag      60

<210> SEQ ID NO 412
<211> LENGTH: 70
<212> TYPE: RNA
<213> ORGANISM: Homo Sapience

<400> SEQUENCE: 412
ugugcacuug ggcaggaggg acccuguaug ucuccccgca gcaccgucau cgugucccuc      60
uuguccacag                                                             70

<210> SEQ ID NO 413
<211> LENGTH: 66
<212> TYPE: RNA
<213> ORGANISM: Homo Sapience

<400> SEQUENCE: 413
ucaagacggg gagucaggca gugguggaga uggagagccc ugagccucca cucuccuggc      60
ccccag                                                                 66

<210> SEQ ID NO 414
<211> LENGTH: 73
<212> TYPE: RNA
<213> ORGANISM: Homo Sapience

<400> SEQUENCE: 414
guucaagugg gaggacagga ggcaggugug guuggaggaa gcagccugaa ccugccuccc      60
ugacauucca cag                                                         73
```

-continued

```
<210> SEQ ID NO 415
<211> LENGTH: 79
<212> TYPE: RNA
<213> ORGANISM: Homo Sapience

<400> SEQUENCE: 415 cagccuggggg aaggcuuggc agggaagaca caugagcagu gccuccacuu cacgccucuc      60 ccugucucc uuucccuag                                                    79

<210> SEQ ID NO 416
<211> LENGTH: 64
<212> TYPE: RNA
<213> ORGANISM: Homo Sapience

<400> SEQUENCE: 416
aaccccgggc cggaggucaa gggcgucgcu ucucccuaau guugccucuu uuccacggcc      60
ucag                                                                   64

<210> SEQ ID NO 417
<211> LENGTH: 69
<212> TYPE: RNA
<213> ORGANISM: Homo Sapience

<400> SEQUENCE: 417 uggggguaggg guggggggaau ucagggggugu cgaacucaug gcugccaccu uugugucccc   60
auccugcag                                                              69

<210> SEQ ID NO 418
<211> LENGTH: 67
<212> TYPE: RNA
<213> ORGANISM: Homo Sapience

<400> SEQUENCE: 418
uacaggccgg ggcuuugggu gagggacccc cggagucugu cacgucuca ccccaacucu      60 gccccag                                                                67

<210> SEQ ID NO 419
<211> LENGTH: 81
<212> TYPE: RNA
<213> ORGANISM: Homo Sapience

<400> SEQUENCE: 419
cucccuggga gggcguggau gaugguggga gaggagcccc acuguggaag ucgaccccc      60 acaucgcccc accuucccca g                                                81

<210> SEQ ID NO 420
<211> LENGTH: 61
<212> TYPE: RNA
<213> ORGANISM: Homo Sapience

<400> SEQUENCE: 420
ucggcuggcg gggguagagc uggcugcagg cccggccccu cucagcugcu gcccucucca     60
g                                                                      61

<210> SEQ ID NO 421
<211> LENGTH: 98
<212> TYPE: RNA
<213> ORGANISM: Homo Sapience

<400> SEQUENCE: 421
```

```
cgagguaggg gcgucccggg cgcgcgggcg gguccaggc ugggcccucu ggaggccggg      60
ugcucacugc cccgucccgg cgccgguguc uccuccag                             98

<210> SEQ ID NO 422
<211> LENGTH: 67
<212> TYPE: RNA
<213> ORGANISM: Homo Sapience

<400> SEQUENCE: 422
ccagaccccu ggggcugggc aggcggaaag aggucugaac ugccucugcc uccuuggucu      60
ccggcag                                                               67

<210> SEQ ID NO 423
<211> LENGTH: 68
<212> TYPE: RNA
<213> ORGANISM: Homo Sapience

<400> SEQUENCE: 423
gggcgcaggg ggacugggg ugagcaggcc cagaacccag cucgugcuca cucucaguccc      60 cucccuag                                                              68

<210> SEQ ID NO 424
<211> LENGTH: 82
<212> TYPE: RNA
<213> ORGANISM: Homo Sapience

<400> SEQUENCE: 424
accuguaggu gacagucagg ggcggggugu ggugggcug ggcuggcccc ccuccucaca       60
ccucuccugg caucgccccc ag                                              82

<210> SEQ ID NO 425
<211> LENGTH: 65
<212> TYPE: RNA
<213> ORGANISM: Homo Sapience

<400> SEQUENCE: 425
gagggcuagg uggggggcuu gaagccccga gaugccucac gucuucaccc cucucaccua      60
agcag                                                                 65

<210> SEQ ID NO 426
<211> LENGTH: 65
<212> TYPE: RNA
<213> ORGANISM: Homo Sapience

<400> SEQUENCE: 426 cucccucuggg gguggggggc ugggcguggu ggacagcgau gcaucccucg ccuucucacc     60
cucag                                                                 65

<210> SEQ ID NO 427
<211> LENGTH: 64
<212> TYPE: RNA
<213> ORGANISM: Homo Sapience

<400> SEQUENCE: 427
ugaggauggg gugagauggg gaggagcagc caguccuguc ucaccgcucu uccccugacc      60
ccag                                                                  64

<210> SEQ ID NO 428
<211> LENGTH: 66
```

<212> TYPE: RNA
<213> ORGANISM: Homo Sapience

<400> SEQUENCE: 428
ccgagugggg cggggcaggu cccugcaggg acugugacac ugaaggaccu gcaccuucgc    60
ccacag                                                              66

<210> SEQ ID NO 429
<211> LENGTH: 61
<212> TYPE: RNA
<213> ORGANISM: Homo Sapience

<400> SEQUENCE: 429
gaggguuggg guggagggcc aaggagcugg gugggguugcc aagccucugu ccccacccca   60
g                                                                   61

<210> SEQ ID NO 430
<211> LENGTH: 74
<212> TYPE: RNA
<213> ORGANISM: Homo Sapience

<400> SEQUENCE: 430
gugcguggug gcucgaggcg ggguggggg ccucgcccug cuuggggcccu cccugaccuc   60 uccgcuccgc acag                                                     74

<210> SEQ ID NO 431
<211> LENGTH: 98
<212> TYPE: RNA
<213> ORGANISM: Homo Sapience

<400> SEQUENCE: 431
cuuggucaau aggaaagagg ugggaccucc uggcuuuucc ucugcagcau ggcucggacc    60
uagugcaaug uuuaagcucc ccucucuuuc cuguucag                            98

<210> SEQ ID NO 432
<211> LENGTH: 81
<212> TYPE: RNA
<213> ORGANISM: Homo Sapience

<400> SEQUENCE: 432
guagguagag ugugaggagg aggucugagc ccaugugugg accuaggucu gcuguuaaac    60
ugacuaacuc ccacucuaca g                                              81

<210> SEQ ID NO 433
<211> LENGTH: 63
<212> TYPE: RNA
<213> ORGANISM: Homo Sapience

<400> SEQUENCE: 433
ggcuccgcag ggcccuggcg caggcaucca gacagcgggc gaaugccucc cccggccccg    60
cag                                                                 63

<210> SEQ ID NO 434
<211> LENGTH: 71
<212> TYPE: RNA
<213> ORGANISM: Homo Sapience

<400> SEQUENCE: 434
ugaccacccc cgggcaaaga ccugcagauc cccuguuaga gacgggccca ggacuuugug    60
cggggugccc a								71

<210> SEQ ID NO 435
<211> LENGTH: 65
<212> TYPE: RNA
<213> ORGANISM: Homo Sapience

<400> SEQUENCE: 435 agcccuggggg guggucucua gccaaggcuc uggggucuca cccuuggcug gucucugcuc		60 cgcag									65

<210> SEQ ID NO 436
<211> LENGTH: 61
<212> TYPE: RNA
<213> ORGANISM: Homo Sapience

<400> SEQUENCE: 436
gugcggaacg cuggccgggg cgggaggggga agggacgccc ggccggaacg ccgcacucac		60 g									61

<210> SEQ ID NO 437
<211> LENGTH: 64
<212> TYPE: RNA
<213> ORGANISM: Homo Sapience

<400> SEQUENCE: 437
gaggcacugg guaggugggg cuccagggcu ccugacaccu ggaccucucc uccccaggcc		60 caca									64

<210> SEQ ID NO 438
<211> LENGTH: 62
<212> TYPE: RNA
<213> ORGANISM: Homo Sapience

<400> SEQUENCE: 438
gugaguagug gcgcgcggcg gcucggaguac ccucugccgc cgcgcgcauc ggcucagcau		60 gc									62

<210> SEQ ID NO 439
<211> LENGTH: 60
<212> TYPE: RNA
<213> ORGANISM: Homo Sapience

<400> SEQUENCE: 439
caaggugggg gagauggggg uugaacuuca uuucucaugc ucauccccau cuccuuucag		60

<210> SEQ ID NO 440
<211> LENGTH: 64
<212> TYPE: RNA
<213> ORGANISM: Homo Sapience

<400> SEQUENCE: 440
aguucagggc cgaagggugg aagcugcugg ugcucaucuc agccucugcc cuuggccucc		60 ccag									64

<210> SEQ ID NO 441
<211> LENGTH: 66
<212> TYPE: RNA
<213> ORGANISM: Homo Sapience

<400> SEQUENCE: 441

```
cagagcaggg cagggaaggu gggagagggg cccagcugac ccuccuguca cccgcuccuu    60
gcccag                                                              66

<210> SEQ ID NO 442
<211> LENGTH: 62
<212> TYPE: RNA
<213> ORGANISM: Homo Sapience

<400> SEQUENCE: 442
gaggguggug gaggaagagg gcagcuccca ugacugccug accgccuucu cuccuccccc    60
ag                                                                  62

<210> SEQ ID NO 443
<211> LENGTH: 62
<212> TYPE: RNA
<213> ORGANISM: Homo Sapience

<400> SEQUENCE: 443
gaggguggug gaggaagagg gcagcuccca ugacugccug accgccuucu cuccuccccc    60
ag                                                                  62

<210> SEQ ID NO 444
<211> LENGTH: 66
<212> TYPE: RNA
<213> ORGANISM: Homo Sapience

<400> SEQUENCE: 444
ccuggagggg ggcacugcgc aagcaaagcc agggacccug agaggcuuug cuuccugcuc    60
cccuag                                                              66

<210> SEQ ID NO 445
<211> LENGTH: 65
<212> TYPE: RNA
<213> ORGANISM: Homo Sapience

<400> SEQUENCE: 445
gagaaugggg ggacagaugg agaggacaca ggcuggcacu gaggucsccu ccacuuuccu    60
ccuag                                                               65

<210> SEQ ID NO 446
<211> LENGTH: 80
<212> TYPE: RNA
<213> ORGANISM: Homo Sapience

<400> SEQUENCE: 446
ugccgucggc cugggagga ggaagggcaa guccaaaggu auacaguugg ucguucauu     60 cucucuuuuu ggccuacaag                                               80

<210> SEQ ID NO 447
<211> LENGTH: 87
<212> TYPE: RNA
<213> ORGANISM: Homo Sapience

<400> SEQUENCE: 447
guguggccgg caggcgggug ggcggggcg gccgguggga accccgcccc gccccgcgcc     60
cgcacucacc cgcccgucuc cccacag                                       87

<210> SEQ ID NO 448
```

```
<211> LENGTH: 65
<212> TYPE: RNA
<213> ORGANISM: Homo Sapience

<400> SEQUENCE: 448
gucuccuggg gggaggagac ccugcucucc cuggcagcaa gccucuccug cccuuccaga    60
uuagc                                                                65

<210> SEQ ID NO 449
<211> LENGTH: 76
<212> TYPE: RNA
<213> ORGANISM: Homo Sapience

<400> SEQUENCE: 449
acugacuuug agucucuccu cagggugcug caggcaaagc uggggaccca gggagagacg    60
uaagugaggg gagaug                                                    76

<210> SEQ ID NO 450
<211> LENGTH: 59
<212> TYPE: RNA
<213> ORGANISM: Homo Sapience

<400> SEQUENCE: 450
cuccagggag acagugugug aggccucuug ccauggccuc ccugcccgcc ucucugcag     59

<210> SEQ ID NO 451
<211> LENGTH: 94
<212> TYPE: RNA
<213> ORGANISM: Homo Sapience

<400> SEQUENCE: 451
cacgguguuc ccugguggaa ccuggcaggg ggagagguaa ggucuuucag ccucuccaaa    60
gcccaugguc agguacucag gugggggagc ccug                                94

<210> SEQ ID NO 452
<211> LENGTH: 98
<212> TYPE: RNA
<213> ORGANISM: Homo Sapience

<400> SEQUENCE: 452
uugggcaagg ugcggggcua gggcuaacag cagucuuacu gaagguuucc uggaaaccac    60
gcacaugcug uugccacuaa ccucaaccuu acucgguc                            98

<210> SEQ ID NO 453
<211> LENGTH: 68
<212> TYPE: RNA
<213> ORGANISM: Homo Sapience

<400> SEQUENCE: 453
gugcaaagag caggaggaca ggggauuuau cucccaaggg agguccccug auccaguca    60 cggcacca                                                             68

<210> SEQ ID NO 454
<211> LENGTH: 49
<212> TYPE: RNA
<213> ORGANISM: Homo Sapience

<400> SEQUENCE: 454
uucccagcca acgcaccaaa aaugauaugg gucuguuguc uggagaaac                49
```

```
<210> SEQ ID NO 455
<211> LENGTH: 69
<212> TYPE: RNA
<213> ORGANISM: Homo Sapience

<400> SEQUENCE: 455
uggagggcug  cgggacugua  gagggcauga  gcucaggagc  ucaggccagc  ucauggugca    60
aggccucug                                                                 69

<210> SEQ ID NO 456
<211> LENGTH: 72
<212> TYPE: RNA
<213> ORGANISM: Homo Sapience

<400> SEQUENCE: 456
gauuucagug  accuggcagc  agggagcguc  gucaguguuu  gacuguuuau  gguaugucag    60
ggagcugguu  cc                                                            72

<210> SEQ ID NO 457
<211> LENGTH: 79
<212> TYPE: RNA
<213> ORGANISM: Homo Sapience

<400> SEQUENCE: 457
gugcagaucc  uugggagccc  uguuagacuc  uggauuuuac  acuuggagug  aacgggcgcc    60
aucccgaggc  uuugcacag                                                     79

<210> SEQ ID NO 458
<211> LENGTH: 86
<212> TYPE: RNA
<213> ORGANISM: Homo Sapience

<400> SEQUENCE: 458
agcacugccc  ccggugaguc  agggugggc  uggcccccug  cuucgugccc  auccgcgcuc     60
ugacucucug  cccaccugca  ggagcu                                            86

<210> SEQ ID NO 459
<211> LENGTH: 83
<212> TYPE: RNA
<213> ORGANISM: Homo Sapience

<400> SEQUENCE: 459
ccugcugcag  aggugccagc  ugcaguggggg  gaggcacugc  cagggcugcc  cacucugcuu   60
agccagcagg  ugccaagaac  agg                                               83

<210> SEQ ID NO 460
<211> LENGTH: 87
<212> TYPE: RNA
<213> ORGANISM: Homo Sapience

<400> SEQUENCE: 460
gcagggcugg  cagggaggcu  gggagggggcu  ggcugggucu  gguagugggc  aucagcuggc   60
ccucauuucu  uaagacagca  cuucugu                                           87

<210> SEQ ID NO 461
<211> LENGTH: 73
<212> TYPE: RNA
<213> ORGANISM: Homo Sapience

<400> SEQUENCE: 461
```

```
uguauccuug aauggauuuu uggagcagga guggacaccu gacccaaagg aaaucaaucc    60
auaggcuagc aau                                                      73

<210> SEQ ID NO 462
<211> LENGTH: 90
<212> TYPE: RNA
<213> ORGANISM: Homo Sapience

<400> SEQUENCE: 462
aggccucgcu guucucuaug gcuuuuauu ccuaugugau ucuacugcuc acucauauag     60
ggauuggagc cguggcgcac ggcggggaca                                    90

<210> SEQ ID NO 463
<211> LENGTH: 47
<212> TYPE: RNA
<213> ORGANISM: Homo Sapience

<400> SEQUENCE: 463
cucggcgcgg ggcgcgggcu ccgguuggg gcgagccaac gccgggg                  47

<210> SEQ ID NO 464
<211> LENGTH: 89
<212> TYPE: RNA
<213> ORGANISM: Homo Sapience

<400> SEQUENCE: 464
gccggcgccc gagcucuggc uccgugucuu cacucccgug cuuguccgag gagggaggga   60
gggacggggg cugugcuggg gcagcugga                                     89

<210> SEQ ID NO 465
<211> LENGTH: 84
<212> TYPE: RNA
<213> ORGANISM: Homo Sapience

<400> SEQUENCE: 465
cuccccaugg cccugucucc caacccuugu accagugcug ggcucagacc cugguacagg   60 ccuggggac agggaccugg ggac                                           84

<210> SEQ ID NO 466
<211> LENGTH: 80
<212> TYPE: RNA
<213> ORGANISM: Homo Sapience

<400> SEQUENCE: 466
cgugugagcc cgcccugugc ccggcccacu ucugcuuccu cuuagcgcag gagggguccc   60
gcacugggag gggcccucac                                               80

<210> SEQ ID NO 467
<211> LENGTH: 92
<212> TYPE: RNA
<213> ORGANISM: Homo Sapience

<400> SEQUENCE: 467
cggcuggaca gcgggcaacg gaaucccaaa agcagcuguu gucccagag cauuccagcu    60 gcgcuuggau uucgucccu gcucuccugc cu                                  92

<210> SEQ ID NO 468
<211> LENGTH: 94
<212> TYPE: RNA
<213> ORGANISM: Homo Sapience
```

<400> SEQUENCE: 468
auaaaggaag uuaggcugag gggcagagag cgagacuuuu cuauuuucca aaagcucggu    60
cugaggcccc ucagucuugc uuccuaaccc gcgc    94

<210> SEQ ID NO 469
<211> LENGTH: 93
<212> TYPE: RNA
<213> ORGANISM: Homo Sapience

<400> SEQUENCE: 469
ccuuccggcg ucccaggcgg ggcgccgcgg gaccgcccuc gugucugugg cgguggggauc    60 ccgcggccgu guuuuccugg uggcccggcc aug    93

<210> SEQ ID NO 470
<211> LENGTH: 75
<212> TYPE: RNA
<213> ORGANISM: Homo Sapience

<400> SEQUENCE: 470
ucaucccugg gugggauuuu guugcauuac uuguguucua auaaaguau ugcacuuguc    60 ccggccugug gaaga    75

<210> SEQ ID NO 471
<211> LENGTH: 94
<212> TYPE: RNA
<213> ORGANISM: Homo Sapience

<400> SEQUENCE: 471
gugaggugug ggcccggccc caggagcggg gccugggcag ccccgugugu ugaggaagga    60
aggcagggcc cccgcucccc gggccugacc ccac    94

<210> SEQ ID NO 472
<211> LENGTH: 68
<212> TYPE: RNA
<213> ORGANISM: Homo Sapience

<400> SEQUENCE: 472
cuccggugcc uacugagcug auaucaguuc ucauuuaca cacuggcuca guucagcagg    60
aacaggag    68

<210> SEQ ID NO 473
<211> LENGTH: 81
<212> TYPE: RNA
<213> ORGANISM: Homo Sapience

<400> SEQUENCE: 473
cuucaggaag cugguuucau auggugguuu agauuuaaau agugauuguc uagcaccauu    60
ugaaaucagu guucuugggg g    81

<210> SEQ ID NO 474
<211> LENGTH: 81
<212> TYPE: RNA
<213> ORGANISM: Homo Sapience

<400> SEQUENCE: 474
auucaggccg guccugcaga gaggaagccc uucugcuuac agguauugga agggcuuccu    60
cucugcagga ccggccugaa u    81

```
<210> SEQ ID NO 475
<211> LENGTH: 85
<212> TYPE: RNA
<213> ORGANISM: Homo Sapience

<400> SEQUENCE: 475
ggaccugccc ugggcuuucu agucucagcu cuccuccagc ucagcgguc aggagagcug    60 agacuagaaa gcccagggca gguuc                                         85

<210> SEQ ID NO 476
<211> LENGTH: 79
<212> TYPE: RNA
<213> ORGANISM: Homo Sapience

<400> SEQUENCE: 476
aauuaauccc ucucuuucua guucuuccua gagugaggaa aagcugggu gagagggcaa    60 acaaauuaac uaauuaauu                                                79

<210> SEQ ID NO 477
<211> LENGTH: 180
<212> TYPE: RNA
<213> ORGANISM: Homo Sapience

<400> SEQUENCE: 477
cgcgacugcg gcggcggugg uggggggagc cgcggggauc gccgagggcc ggucggccgc    60
cccgggugcc gcgcggugcc gccggcggcg gugaggcccc gcgcgugugu cccggcugcg   120
gucggccgcg cucgagggu ccccguggcg uccccuuccc gccggccgc cuuucucgcg    180

<210> SEQ ID NO 478
<211> LENGTH: 91
<212> TYPE: RNA
<213> ORGANISM: Homo Sapience

<400> SEQUENCE: 478
guguccucac uuguccacuu cugccugccc ugcccaaaug guggagcaga uucgaggggc    60
agggcaggaa gaaguggaca agugaggcca u                                  91

<210> SEQ ID NO 479
<211> LENGTH: 74
<212> TYPE: RNA
<213> ORGANISM: Homo Sapience

<400> SEQUENCE: 479
gcucuagccu aauuuagau cggucugcu ucaguuucac uccaagcaga cuugaccuac    60
aauuagccua gagc                                                     74

<210> SEQ ID NO 480
<211> LENGTH: 97
<212> TYPE: RNA
<213> ORGANISM: Homo Sapience

<400> SEQUENCE: 480
ugaugcuuug cuggcuggug cagugccuga gggaguaaga gcccuguugu uguaagauag    60
ugucuuacuc ccucaggcac aucccaaca agucucu                             97

<210> SEQ ID NO 481
<211> LENGTH: 86
<212> TYPE: RNA
<213> ORGANISM: Homo Sapience
```

```
<400> SEQUENCE: 481
cgccugagcg ugcagcagga caucuuccug accugguaau aauuagguga gaaggauggu    60 uggggcggu cggcguaacu caggga                                          86

<210> SEQ ID NO 482
<211> LENGTH: 97
<212> TYPE: RNA
<213> ORGANISM: Homo Sapience

<400> SEQUENCE: 482
ggugggagga uugcuugagc cuggaagcug gagccugcag ugaacuauca uugugccacu    60
guacuccagc cuaggcaaca aaaugaaauc cugucua                             97

<210> SEQ ID NO 483
<211> LENGTH: 78
<212> TYPE: RNA
<213> ORGANISM: Homo Sapience

<400> SEQUENCE: 483
cuuucuacac agguugggau cgguugcaau gcuguguuuc uguauggau ugcacuuguc     60 ccggccuguu gaguuugg                                                  78

<210> SEQ ID NO 484
<211> LENGTH: 73
<212> TYPE: RNA
<213> ORGANISM: Homo Sapience

<400> SEQUENCE: 484
cucugccucc cgugccuacu gagcugaaac acaguugguu uguguacacu ggcucaguuc    60
agcaggaaca ggg                                                       73

<210> SEQ ID NO 485
<211> LENGTH: 81
<212> TYPE: RNA
<213> ORGANISM: Homo Sapience

<400> SEQUENCE: 485
cuucuggaag cugguuucac augguggcuu agauuuuucc aucuuuguau cuagcaccau    60
uugaaaucag uguuuuagga g                                              81

<210> SEQ ID NO 486
<211> LENGTH: 81
<212> TYPE: RNA
<213> ORGANISM: Homo Sapience

<400> SEQUENCE: 486
auucaggccg guccugcaga gaggaagccc uuccaauacc uguaagcaga agggcuuccu    60
cucugcagga ccggccugaa u                                              81

<210> SEQ ID NO 487
<211> LENGTH: 81
<212> TYPE: RNA
<213> ORGANISM: Homo Sapience

<400> SEQUENCE: 487
accugcccug ggcuuucuag ucucagcucu ccugaccagc ugagcuggag gagagcugag    60
acuagaaagc ccagggcagg u                                              81
```

<210> SEQ ID NO 488
<211> LENGTH: 138
<212> TYPE: RNA
<213> ORGANISM: Homo Sapience

<400> SEQUENCE: 488
uguuauuuuu ugucuucuac cuaagaauuc ugucucuuag gcuuucucuu cccagauuuc      60
ccaaaguugg gaaaagcugg guugagaggg caaaaggaaa aaaaaagaau ucugucucug     120
acauaauuag auagggaa                                                  138

<210> SEQ ID NO 489
<211> LENGTH: 180
<212> TYPE: RNA
<213> ORGANISM: Homo Sapience

<400> SEQUENCE: 489
cgcgacugcg gcggcggugg uggggggagc cgcggggauc gccgagggcc ggucggccgc      60
cccgggugcc gcgcggugcc gccggcggcg gugaggcccc gcgcgugugu cccggcugcg     120
gucggccgcg cucgagggu ccccguggcg ucccuuccc cgccggccgc cuuucucgcg      180

<210> SEQ ID NO 490
<211> LENGTH: 91
<212> TYPE: RNA
<213> ORGANISM: Homo Sapience

<400> SEQUENCE: 490
guguccucac uuguccacuu cugccugccc ugcccaaaug guggagcaga uucgaggggc      60
agggcaggaa gaaguggaca agugaggcca u                                    91

<210> SEQ ID NO 491
<211> LENGTH: 74
<212> TYPE: RNA
<213> ORGANISM: Homo Sapience

<400> SEQUENCE: 491
gcucuagccu aauuuuagau cuggucugcu ucaguuucac uccaagcaga cuugaccuac      60
aauuagccua gagc                                                       74

<210> SEQ ID NO 492
<211> LENGTH: 97
<212> TYPE: RNA
<213> ORGANISM: Homo Sapience

<400> SEQUENCE: 492
ugaugcuuug cuggcuggug cagugccuga gggaguaaga gcccuguugu ugucagauag      60
ugucuuacuc cccucaggcac aucuccagcg agucucu                             97

<210> SEQ ID NO 493
<211> LENGTH: 86
<212> TYPE: RNA
<213> ORGANISM: Homo Sapience

<400> SEQUENCE: 493
cgccugagcg ugcagcagga caucuuccug accugguaau aauuagguga gaaggauggu      60 uggggcggu cggcguaacu caggga                                           86

<210> SEQ ID NO 494
<211> LENGTH: 63

```
<212> TYPE: RNA
<213> ORGANISM: Homo Sapience

<400> SEQUENCE: 494
cugagccugg aagcuggagc cugcagugag cuaugaucau gucccuguac ucuagccugg      60
gca                                                                   63

<210> SEQ ID NO 495
<211> LENGTH: 75
<212> TYPE: RNA
<213> ORGANISM: Homo Sapience

<400> SEQUENCE: 495
ucaucccugg gugggggauuu guugcauuac uuguguucua uauaaaguau ugcacuuguc    60
ccggccugug gaaga                                                      75

<210> SEQ ID NO 496
<211> LENGTH: 94
<212> TYPE: RNA
<213> ORGANISM: Homo Sapience

<400> SEQUENCE: 496
cagugcgacg ggcggagcuu ccagacgcuc cgccccacgu cgcaugcgcc ccgggaaagc    60
guggggcgga gcuuccggag gccccgcccu gcug                                 94

<210> SEQ ID NO 497
<211> LENGTH: 88
<212> TYPE: RNA
<213> ORGANISM: Homo Sapience

<400> SEQUENCE: 497
gcgacgggcg gagcuuccag acgcuccgcc ccacgucgca ugcgcccggg aaagcgugg     60 ggcggagcuu ccggaggccc cgcccugc                                        88

<210> SEQ ID NO 498
<211> LENGTH: 94
<212> TYPE: RNA
<213> ORGANISM: Homo Sapience

<400> SEQUENCE: 498
cagugcgacg ggcggagcuu ccagacgcuc cgccccacgu cgcaugcgcc ccgggaaagc    60
guggggcgga gcuuccggag gccccgcccu gcug                                 94

<210> SEQ ID NO 499
<211> LENGTH: 67
<212> TYPE: RNA
<213> ORGANISM: Homo Sapience

<400> SEQUENCE: 499
ccugcaggca gaaguggggc ugacagggca gagggguugcg ccccucacc aucccuucug    60 ccugcag                                                               67

<210> SEQ ID NO 500
<211> LENGTH: 92
<212> TYPE: RNA
<213> ORGANISM: Homo Sapience

<400> SEQUENCE: 500
cgcugcgcuu cugggcccgc ggcgggcgug gggcugcccg ggccggucga ccagcgcgcc    60
```

```
guagcucccg aggcccgagc cgcgacccgc gg                                  92

<210> SEQ ID NO 501
<211> LENGTH: 67
<212> TYPE: RNA
<213> ORGANISM: Homo Sapience

<400> SEQUENCE: 501
ccugcaggca aagugggggc ugacagggca gaggguugcg cccccucacc aucccuucug    60
ccugcag                                                              67

<210> SEQ ID NO 502
<211> LENGTH: 92
<212> TYPE: RNA
<213> ORGANISM: Homo Sapience

<400> SEQUENCE: 502
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 503
<211> LENGTH: 67
<212> TYPE: RNA
<213> ORGANISM: Homo Sapience

<400> SEQUENCE: 503
ccugcaggca aagugggggc ugacagggca gaggguugcg cccccucacc aucccuucug    60
ccugcag                                                              67

<210> SEQ ID NO 504
<211> LENGTH: 92
<212> TYPE: RNA
<213> ORGANISM: Homo Sapience

<400> SEQUENCE: 504
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 505
<211> LENGTH: 67
<212> TYPE: RNA
<213> ORGANISM: Homo Sapience

<400> SEQUENCE: 505
ccugcaggca aagugggggc ugacagggca gaggguugcg cccccucacc aucccuucug    60
ccugcag                                                              67

<210> SEQ ID NO 506
<211> LENGTH: 92
<212> TYPE: RNA
<213> ORGANISM: Homo Sapience

<400> SEQUENCE: 506
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 507
<211> LENGTH: 26
<212> TYPE: RNA
<213> ORGANISM: Homo Sapience
```

```
<400> SEQUENCE: 507
gaggggcucu cgcuucuggc gccaag                                  26

<210> SEQ ID NO 508
<211> LENGTH: 23
<212> TYPE: RNA
<213> ORGANISM: Homo Sapience

<400> SEQUENCE: 508
aauauacagg gggagacucu uau                                     23

<210> SEQ ID NO 509
<211> LENGTH: 24
<212> TYPE: RNA
<213> ORGANISM: Homo Sapience

<400> SEQUENCE: 509
auauacaggg ggagacucuc auuu                                    24

<210> SEQ ID NO 510
<211> LENGTH: 22
<212> TYPE: RNA
<213> ORGANISM: Homo Sapience

<400> SEQUENCE: 510
ccucacaccu gccucgcccc cc                                      22

<210> SEQ ID NO 511
<211> LENGTH: 22
<212> TYPE: RNA
<213> ORGANISM: Homo Sapience

<400> SEQUENCE: 511
gugggcgggg gcaggugugu gg                                      22

<210> SEQ ID NO 512
<211> LENGTH: 15
<212> TYPE: RNA
<213> ORGANISM: Homo Sapience

<400> SEQUENCE: 512
uggcagagcg cuguc                                              15

<210> SEQ ID NO 513
<211> LENGTH: 22
<212> TYPE: RNA
<213> ORGANISM: Homo Sapience

<400> SEQUENCE: 513
ccgggaacgu cgagacugga gc                                      22

<210> SEQ ID NO 514
<211> LENGTH: 21
<212> TYPE: RNA
<213> ORGANISM: Homo Sapience

<400> SEQUENCE: 514
gccgggcgug guggugggggg c                                      21

<210> SEQ ID NO 515
<211> LENGTH: 24
<212> TYPE: RNA
```

```
<213> ORGANISM: Homo Sapience

<400> SEQUENCE: 515
cgggcguggu gguggggug ggug                                        24

<210> SEQ ID NO 516
<211> LENGTH: 19
<212> TYPE: RNA
<213> ORGANISM: Homo Sapience

<400> SEQUENCE: 516
cuccagccug agugacaga                                             19

<210> SEQ ID NO 517
<211> LENGTH: 23
<212> TYPE: RNA
<213> ORGANISM: Homo Sapience

<400> SEQUENCE: 517
gggggccgau acacuguacg aga                                        23

<210> SEQ ID NO 518
<211> LENGTH: 23
<212> TYPE: RNA
<213> ORGANISM: Homo Sapience

<400> SEQUENCE: 518
cuccuggggc ccgcacucuc gcu                                        23

<210> SEQ ID NO 519
<211> LENGTH: 25
<212> TYPE: RNA
<213> ORGANISM: Homo Sapience

<400> SEQUENCE: 519
acugcaguga aggcacuugu agcau                                      25

<210> SEQ ID NO 520
<211> LENGTH: 22
<212> TYPE: RNA
<213> ORGANISM: Homo Sapience

<400> SEQUENCE: 520
gggcuacaac acaggacccg gg                                         22

<210> SEQ ID NO 521
<211> LENGTH: 20
<212> TYPE: RNA
<213> ORGANISM: Homo Sapience

<400> SEQUENCE: 521
accggccgcc ggcuccgccc                                            20

<210> SEQ ID NO 522
<211> LENGTH: 23
<212> TYPE: RNA
<213> ORGANISM: Homo Sapience

<400> SEQUENCE: 522
ugcgcagggg ccgggugcuc acc                                        23

<210> SEQ ID NO 523
<211> LENGTH: 20
```

<212> TYPE: RNA
<213> ORGANISM: Homo Sapience

<400> SEQUENCE: 523
ccccagggcg acgcggcggg					20

<210> SEQ ID NO 524
<211> LENGTH: 23
<212> TYPE: RNA
<213> ORGANISM: Homo Sapience

<400> SEQUENCE: 524
agccccugcc caccgcacac ugc				23

<210> SEQ ID NO 525
<211> LENGTH: 48
<212> TYPE: RNA
<213> ORGANISM: Homo Sapience

<400> SEQUENCE: 525
uggcucaguu cagcaggaac aggacuggcu caguucagca ggaacagg	48

<210> SEQ ID NO 526
<211> LENGTH: 23
<212> TYPE: RNA
<213> ORGANISM: Homo Sapience

<400> SEQUENCE: 526
agcagaggca gagaggcuca ggg				23

<210> SEQ ID NO 527
<211> LENGTH: 16
<212> TYPE: RNA
<213> ORGANISM: Homo Sapience

<400> SEQUENCE: 527 ggcgguggc ggcggg					16

<210> SEQ ID NO 528
<211> LENGTH: 22
<212> TYPE: RNA
<213> ORGANISM: Homo Sapience

<400> SEQUENCE: 528
gaggguuggg uggaggcucu cc				22

<210> SEQ ID NO 529
<211> LENGTH: 26
<212> TYPE: RNA
<213> ORGANISM: Homo Sapience

<400> SEQUENCE: 529
uagcaccauu ugaaucagu guucuu				26

<210> SEQ ID NO 530
<211> LENGTH: 24
<212> TYPE: RNA
<213> ORGANISM: Homo Sapience

<400> SEQUENCE: 530
ucgaggacug guggaagggc cuuu				24

<210> SEQ ID NO 531

-continued

```
<211> LENGTH: 22
<212> TYPE: RNA
<213> ORGANISM: Homo Sapience

<400> SEQUENCE: 531
cagaagggga guugggagca ga                                              22

<210> SEQ ID NO 532
<211> LENGTH: 22
<212> TYPE: RNA
<213> ORGANISM: Homo Sapience

<400> SEQUENCE: 532
uccugcagag aggaagcccu uc                                              22

<210> SEQ ID NO 533
<211> LENGTH: 23
<212> TYPE: RNA
<213> ORGANISM: Homo Sapience

<400> SEQUENCE: 533
agggaguaga agguugggga gca                                             23

<210> SEQ ID NO 534
<211> LENGTH: 24
<212> TYPE: RNA
<213> ORGANISM: Homo Sapience

<400> SEQUENCE: 534
gaucggucga gagcguccug gcug                                            24

<210> SEQ ID NO 535
<211> LENGTH: 23
<212> TYPE: RNA
<213> ORGANISM: Homo Sapience

<400> SEQUENCE: 535
uggggcggag cuuccggagg ccc                                             23

<210> SEQ ID NO 536
<211> LENGTH: 17
<212> TYPE: RNA
<213> ORGANISM: Homo Sapience

<400> SEQUENCE: 536
ggggcggggg cgggggc                                                    17

<210> SEQ ID NO 537
<211> LENGTH: 23
<212> TYPE: RNA
<213> ORGANISM: Homo Sapience

<400> SEQUENCE: 537
ggaggcgcag gcucggaaag gcg                                             23

<210> SEQ ID NO 538
<211> LENGTH: 27
<212> TYPE: RNA
<213> ORGANISM: Homo Sapience

<400> SEQUENCE: 538
gaaaagcugg guugagaggg cgaaaaa                                         27
```

```
<210> SEQ ID NO 539
<211> LENGTH: 24
<212> TYPE: RNA
<213> ORGANISM: Homo Sapience

<400> SEQUENCE: 539
gaaaagcugg guugagaggg caaa                                          24

<210> SEQ ID NO 540
<211> LENGTH: 16
<212> TYPE: RNA
<213> ORGANISM: Homo Sapience

<400> SEQUENCE: 540 guggggggc aggagg                                                    16

<210> SEQ ID NO 541
<211> LENGTH: 28
<212> TYPE: RNA
<213> ORGANISM: Homo Sapience

<400> SEQUENCE: 541
aggggugcua ucugugauug agggacau                                      28

<210> SEQ ID NO 542
<211> LENGTH: 58
<212> TYPE: RNA
<213> ORGANISM: Homo Sapience

<400> SEQUENCE: 542
gcugacuccu aguccagggc ucgugauggc uggugggccc ugaacgaggg gucuggag     58

<210> SEQ ID NO 543
<211> LENGTH: 22
<212> TYPE: RNA
<213> ORGANISM: Homo Sapience

<400> SEQUENCE: 543
cgagggcauu ucaugaugca gg                                            22

<210> SEQ ID NO 544
<211> LENGTH: 23
<212> TYPE: RNA
<213> ORGANISM: Homo Sapience

<400> SEQUENCE: 544
gugggcuggg cugggcuggg cca                                           23

<210> SEQ ID NO 545
<211> LENGTH: 29
<212> TYPE: RNA
<213> ORGANISM: Homo Sapience

<400> SEQUENCE: 545
gggagccgcg gggaucgccg agggccggu                                     29

<210> SEQ ID NO 546
<211> LENGTH: 22
<212> TYPE: RNA
<213> ORGANISM: Homo Sapience

<400> SEQUENCE: 546
cggcuggagg ugugaggauc cg                                            22
```

-continued

<210> SEQ ID NO 547
<211> LENGTH: 19
<212> TYPE: RNA
<213> ORGANISM: Homo Sapience

<400> SEQUENCE: 547
uggcgggugc ggggguggg                                                      19

<210> SEQ ID NO 548
<211> LENGTH: 23
<212> TYPE: RNA
<213> ORGANISM: Homo Sapience

<400> SEQUENCE: 548
ugaggauaug gcagggaagg gga                                                 23

<210> SEQ ID NO 549
<211> LENGTH: 29
<212> TYPE: RNA
<213> ORGANISM: Homo Sapience

<400> SEQUENCE: 549
ggucaggcgg cucggacuga gcagguggg                                           29

<210> SEQ ID NO 550
<211> LENGTH: 19
<212> TYPE: RNA
<213> ORGANISM: Homo Sapience

<400> SEQUENCE: 550
guggguuggg gcgggcucu                                                      19

<210> SEQ ID NO 551
<211> LENGTH: 18
<212> TYPE: RNA
<213> ORGANISM: Homo Sapience

<400> SEQUENCE: 551
ggcagcggcg gcggcggc                                                       18

<210> SEQ ID NO 552
<211> LENGTH: 20
<212> TYPE: RNA
<213> ORGANISM: Homo Sapience

<400> SEQUENCE: 552
caccccacuc cugguaccau                                                     20

<210> SEQ ID NO 553
<211> LENGTH: 15
<212> TYPE: RNA
<213> ORGANISM: Homo Sapience

<400> SEQUENCE: 553
aggaggagga ggcag                                                          15

<210> SEQ ID NO 554
<211> LENGTH: 17
<212> TYPE: RNA
<213> ORGANISM: Homo Sapience

<400> SEQUENCE: 554 gcgugggggcc cggagca                                                       17

-continued

```
<210> SEQ ID NO 555
<211> LENGTH: 18
<212> TYPE: RNA
<213> ORGANISM: Homo Sapience

<400> SEQUENCE: 555
ggugggcuuc ccggaggg                                                       18

<210> SEQ ID NO 556
<211> LENGTH: 18
<212> TYPE: RNA
<213> ORGANISM: Homo Sapience

<400> SEQUENCE: 556
gaggcugaag gaagaugg                                                       18

<210> SEQ ID NO 557
<211> LENGTH: 22
<212> TYPE: RNA
<213> ORGANISM: Homo Sapience

<400> SEQUENCE: 557
aaaagcuggg cugagaggcg ac                                                  22

<210> SEQ ID NO 558
<211> LENGTH: 19
<212> TYPE: RNA
<213> ORGANISM: Homo Sapience

<400> SEQUENCE: 558
gaggcuggag ugagcggag                                                      19

<210> SEQ ID NO 559
<211> LENGTH: 23
<212> TYPE: RNA
<213> ORGANISM: Homo Sapience

<400> SEQUENCE: 559
acaggagugg ggugggaca uaa                                                  23

<210> SEQ ID NO 560
<211> LENGTH: 21
<212> TYPE: RNA
<213> ORGANISM: Homo Sapience

<400> SEQUENCE: 560
guuggaggcg uggguuuuag a                                                   21

<210> SEQ ID NO 561
<211> LENGTH: 23
<212> TYPE: RNA
<213> ORGANISM: Homo Sapience

<400> SEQUENCE: 561
ccagggcugg cagugacaug ggu                                                 23

<210> SEQ ID NO 562
<211> LENGTH: 20
<212> TYPE: RNA
<213> ORGANISM: Homo Sapience

<400> SEQUENCE: 562
```

| | |
|---|---|
| ggcuccuugg ucuagggggua | 20 |

<210> SEQ ID NO 563
<211> LENGTH: 24
<212> TYPE: RNA
<213> ORGANISM: Homo Sapience

<400> SEQUENCE: 563

| | |
|---|---|
| gugcccgucc cggggcugcg cgag | 24 |

<210> SEQ ID NO 564
<211> LENGTH: 21
<212> TYPE: RNA
<213> ORGANISM: Homo Sapience

<400> SEQUENCE: 564

| | |
|---|---|
| cggauccgag ucacggcacc a | 21 |

<210> SEQ ID NO 565
<211> LENGTH: 23
<212> TYPE: RNA
<213> ORGANISM: Homo Sapience

<400> SEQUENCE: 565

| | |
|---|---|
| ccaggaggcg gaggaggugg agg | 23 |

<210> SEQ ID NO 566
<211> LENGTH: 19
<212> TYPE: RNA
<213> ORGANISM: Homo Sapience

<400> SEQUENCE: 566

| | |
|---|---|
| gggugcgggc cggcggggu | 19 |

<210> SEQ ID NO 567
<211> LENGTH: 25
<212> TYPE: RNA
<213> ORGANISM: Homo Sapience

<400> SEQUENCE: 567

| | |
|---|---|
| uggcggcggu aguuaugggc uucuc | 25 |

<210> SEQ ID NO 568
<211> LENGTH: 16
<212> TYPE: RNA
<213> ORGANISM: Homo Sapience

<400> SEQUENCE: 568

| | |
|---|---|
| ggggugucu guuguu | 16 |

<210> SEQ ID NO 569
<211> LENGTH: 20
<212> TYPE: RNA
<213> ORGANISM: Homo Sapience

<400> SEQUENCE: 569

| | |
|---|---|
| ggaaaaaggc gggagaagcc | 20 |

<210> SEQ ID NO 570
<211> LENGTH: 24
<212> TYPE: RNA
<213> ORGANISM: Homo Sapience

<400> SEQUENCE: 570

| | |
|---|---|
| agaggcaccg ccugcccagu gaca | 24 |

<210> SEQ ID NO 571
<211> LENGTH: 19
<212> TYPE: RNA
<213> ORGANISM: Homo Sapience

<400> SEQUENCE: 571

| | |
|---|---|
| aggggcggg cuccggcgc | 19 |

<210> SEQ ID NO 572
<211> LENGTH: 17
<212> TYPE: RNA
<213> ORGANISM: Homo Sapience

<400> SEQUENCE: 572

| | |
|---|---|
| aggggcuggg cgcgcgc | 17 |

<210> SEQ ID NO 573
<211> LENGTH: 30
<212> TYPE: RNA
<213> ORGANISM: Homo Sapience

<400> SEQUENCE: 573

| | |
|---|---|
| gcugggcugg gacggacacc cggccuccac | 30 |

<210> SEQ ID NO 574
<211> LENGTH: 23
<212> TYPE: RNA
<213> ORGANISM: Homo Sapience

<400> SEQUENCE: 574

| | |
|---|---|
| aggacuggac ucccggcagc ccc | 23 |

<210> SEQ ID NO 575
<211> LENGTH: 23
<212> TYPE: RNA
<213> ORGANISM: Homo Sapience

<400> SEQUENCE: 575

| | |
|---|---|
| gggggaugu gcaugcuggu ugg | 23 |

<210> SEQ ID NO 576
<211> LENGTH: 25
<212> TYPE: RNA
<213> ORGANISM: Homo Sapience

<400> SEQUENCE: 576

| | |
|---|---|
| cugggccagg gagcagcugg ugggu | 25 |

<210> SEQ ID NO 577
<211> LENGTH: 23
<212> TYPE: RNA
<213> ORGANISM: Homo Sapience

<400> SEQUENCE: 577

| | |
|---|---|
| ggugggugag gucgggcccc aag | 23 |

<210> SEQ ID NO 578
<211> LENGTH: 22
<212> TYPE: RNA
<213> ORGANISM: Homo Sapience

```
<400> SEQUENCE: 578
acaccgggga uggcagaggg uc                                              22

<210> SEQ ID NO 579
<211> LENGTH: 24
<212> TYPE: RNA
<213> ORGANISM: Homo Sapience

<400> SEQUENCE: 579
caggcaggag ccggacugga ccuc                                            24

<210> SEQ ID NO 580
<211> LENGTH: 20
<212> TYPE: RNA
<213> ORGANISM: Homo Sapience

<400> SEQUENCE: 580
uggcuguugg aggggggcagg                                                20

<210> SEQ ID NO 581
<211> LENGTH: 19
<212> TYPE: RNA
<213> ORGANISM: Homo Sapience

<400> SEQUENCE: 581
gcaggcgagg cugggcuga                                                  19

<210> SEQ ID NO 582
<211> LENGTH: 21
<212> TYPE: RNA
<213> ORGANISM: Homo Sapience

<400> SEQUENCE: 582
aggaggcagu gggcgagcag g                                               21

<210> SEQ ID NO 583
<211> LENGTH: 25
<212> TYPE: RNA
<213> ORGANISM: Homo Sapience

<400> SEQUENCE: 583
agcggggagg aagugggcgc ugcuu                                           25

<210> SEQ ID NO 584
<211> LENGTH: 23
<212> TYPE: RNA
<213> ORGANISM: Homo Sapience

<400> SEQUENCE: 584
cagcccgccc cagccgaggu ucu                                             23

<210> SEQ ID NO 585
<211> LENGTH: 23
<212> TYPE: RNA
<213> ORGANISM: Homo Sapience

<400> SEQUENCE: 585
gccccggcgc gggcggguuc ugg                                             23

<210> SEQ ID NO 586
<211> LENGTH: 22
<212> TYPE: RNA
<213> ORGANISM: Homo Sapience
```

```
<400> SEQUENCE: 586
aggagcaagg cggcaucucu cu                                        22

<210> SEQ ID NO 587
<211> LENGTH: 23
<212> TYPE: RNA
<213> ORGANISM: Homo Sapience

<400> SEQUENCE: 587
uggggaaggc gucagugucg ggu                                       23

<210> SEQ ID NO 588
<211> LENGTH: 27
<212> TYPE: RNA
<213> ORGANISM: Homo Sapience

<400> SEQUENCE: 588
agggccagag gagccuggag ggucgg                                    27

<210> SEQ ID NO 589
<211> LENGTH: 22
<212> TYPE: RNA
<213> ORGANISM: Homo Sapience

<400> SEQUENCE: 589
ugggagggga gaggcagcaa gc                                        22

<210> SEQ ID NO 590
<211> LENGTH: 21
<212> TYPE: RNA
<213> ORGANISM: Homo Sapience

<400> SEQUENCE: 590 ugcuggggc cacaugagug u                                          21

<210> SEQ ID NO 591
<211> LENGTH: 23
<212> TYPE: RNA
<213> ORGANISM: Homo Sapience

<400> SEQUENCE: 591
aagggaggag gagcggaggg gcc                                       23

<210> SEQ ID NO 592
<211> LENGTH: 26
<212> TYPE: RNA
<213> ORGANISM: Homo Sapience

<400> SEQUENCE: 592
gcgggcuguc cggaggggucg ggcuuu                                   26

<210> SEQ ID NO 593
<211> LENGTH: 24
<212> TYPE: RNA
<213> ORGANISM: Homo Sapience

<400> SEQUENCE: 593
cgcucgggcg gaggugguug agug                                      24

<210> SEQ ID NO 594
<211> LENGTH: 22
<212> TYPE: RNA
```

-continued

```
<213> ORGANISM: Homo Sapience

<400> SEQUENCE: 594
agccaggcuc ugaagggaaa gu                                    22

<210> SEQ ID NO 595
<211> LENGTH: 24
<212> TYPE: RNA
<213> ORGANISM: Homo Sapience

<400> SEQUENCE: 595
aggcaggggc uggugcuggg cggg                                  24

<210> SEQ ID NO 596
<211> LENGTH: 22
<212> TYPE: RNA
<213> ORGANISM: Homo Sapience

<400> SEQUENCE: 596
uaauuuuaga ucuggucugc uu                                    22

<210> SEQ ID NO 597
<211> LENGTH: 22
<212> TYPE: RNA
<213> ORGANISM: Homo Sapience

<400> SEQUENCE: 597
ccccgguguu ggggcgcguc ug                                    22

<210> SEQ ID NO 598
<211> LENGTH: 15
<212> TYPE: RNA
<213> ORGANISM: Homo Sapience

<400> SEQUENCE: 598
gagcgcucgc uggcc                                            15

<210> SEQ ID NO 599
<211> LENGTH: 26
<212> TYPE: RNA
<213> ORGANISM: Homo Sapience

<400> SEQUENCE: 599
gaggggcucu cgcuucuggc gccaag                                26

<210> SEQ ID NO 600
<211> LENGTH: 22
<212> TYPE: RNA
<213> ORGANISM: Homo Sapience

<400> SEQUENCE: 600
gggagugcag ggcagggulu cc                                    22

<210> SEQ ID NO 601
<211> LENGTH: 16
<212> TYPE: RNA
<213> ORGANISM: Homo Sapience

<400> SEQUENCE: 601
ugcuggugau gcuuuc                                           16

<210> SEQ ID NO 602
<211> LENGTH: 15
```

```
<212> TYPE: RNA
<213> ORGANISM: Homo Sapience

<400> SEQUENCE: 602
ugaagcgggg gggcg                                                    15

<210> SEQ ID NO 603
<211> LENGTH: 18
<212> TYPE: RNA
<213> ORGANISM: Homo Sapience

<400> SEQUENCE: 603
aaaaggaagg gggaggag                                                 18

<210> SEQ ID NO 604
<211> LENGTH: 20
<212> TYPE: RNA
<213> ORGANISM: Homo Sapience

<400> SEQUENCE: 604
ggcuggucag augggagugg                                               20

<210> SEQ ID NO 605
<211> LENGTH: 23
<212> TYPE: RNA
<213> ORGANISM: Homo Sapience

<400> SEQUENCE: 605
acagcagggc uggggauugc agu                                           23

<210> SEQ ID NO 606
<211> LENGTH: 17
<212> TYPE: RNA
<213> ORGANISM: Homo Sapience

<400> SEQUENCE: 606
ugcaggggca ggccagc                                                  17

<210> SEQ ID NO 607
<211> LENGTH: 23
<212> TYPE: RNA
<213> ORGANISM: Homo Sapience

<400> SEQUENCE: 607
gggggucccc ggugcucgga ucu                                           23

<210> SEQ ID NO 608
<211> LENGTH: 22
<212> TYPE: RNA
<213> ORGANISM: Homo Sapience

<400> SEQUENCE: 608
gcugggauua caggcaugag cc                                            22

<210> SEQ ID NO 609
<211> LENGTH: 20
<212> TYPE: RNA
<213> ORGANISM: Homo Sapience

<400> SEQUENCE: 609
aagacacauu uggagaggga                                               20

<210> SEQ ID NO 610
```

```
<211> LENGTH: 21
<212> TYPE: RNA
<213> ORGANISM: Homo Sapience

<400> SEQUENCE: 610
cagcagggga gagagaggag u                                              21

<210> SEQ ID NO 611
<211> LENGTH: 25
<212> TYPE: RNA
<213> ORGANISM: Homo Sapience

<400> SEQUENCE: 611
ugcaggcaga agugggcug acagg                                           25

<210> SEQ ID NO 612
<211> LENGTH: 22
<212> TYPE: RNA
<213> ORGANISM: Homo Sapience

<400> SEQUENCE: 612
auuggagggu guggaagaca uc                                             22

<210> SEQ ID NO 613
<211> LENGTH: 23
<212> TYPE: RNA
<213> ORGANISM: Homo Sapience

<400> SEQUENCE: 613
ggcccggccg ugccugaggu uuc                                            23

<210> SEQ ID NO 614
<211> LENGTH: 21
<212> TYPE: RNA
<213> ORGANISM: Homo Sapience

<400> SEQUENCE: 614
ugggaauggg gguaagggcc u                                              21

<210> SEQ ID NO 615
<211> LENGTH: 21
<212> TYPE: RNA
<213> ORGANISM: Homo Sapience

<400> SEQUENCE: 615
gaggcgaugu ggggauguag a                                              21

<210> SEQ ID NO 616
<211> LENGTH: 25
<212> TYPE: RNA
<213> ORGANISM: Homo Sapience

<400> SEQUENCE: 616
uucugggccc gcggcgggcg ugggg                                          25

<210> SEQ ID NO 617
<211> LENGTH: 16
<212> TYPE: RNA
<213> ORGANISM: Homo Sapience

<400> SEQUENCE: 617
ggacccaggg agagac                                                    16
```

```
<210> SEQ ID NO 618
<211> LENGTH: 25
<212> TYPE: RNA
<213> ORGANISM: Homo Sapience

<400> SEQUENCE: 618
ugcggggcua gggcuaacag caguc                                          25

<210> SEQ ID NO 619
<211> LENGTH: 27
<212> TYPE: RNA
<213> ORGANISM: Homo Sapience

<400> SEQUENCE: 619
gugaacgggc gccaucccga ggcuuug                                        27

<210> SEQ ID NO 620
<211> LENGTH: 21
<212> TYPE: RNA
<213> ORGANISM: Homo Sapience

<400> SEQUENCE: 620
gugagucagg gugggcugg c                                               21

<210> SEQ ID NO 621
<211> LENGTH: 21
<212> TYPE: RNA
<213> ORGANISM: Homo Sapience

<400> SEQUENCE: 621
gaauggauuu uuggagcagg a                                              21

<210> SEQ ID NO 622
<211> LENGTH: 27
<212> TYPE: RNA
<213> ORGANISM: Homo Sapience

<400> SEQUENCE: 622
agccuggaag cuggagccug cagugaa                                        27

<210> SEQ ID NO 623
<211> LENGTH: 22
<212> TYPE: RNA
<213> ORGANISM: Homo Sapience

<400> SEQUENCE: 623
auauagggau uggagccgug gc                                             22

<210> SEQ ID NO 624
<211> LENGTH: 23
<212> TYPE: RNA
<213> ORGANISM: Homo Sapience

<400> SEQUENCE: 624
gagggaggga cggggcugu gcu                                             23

<210> SEQ ID NO 625
<211> LENGTH: 24
<212> TYPE: RNA
<213> ORGANISM: Homo Sapience

<400> SEQUENCE: 625
ugguacaggc cugggggaca ggga                                           24
```

<210> SEQ ID NO 626
<211> LENGTH: 23
<212> TYPE: RNA
<213> ORGANISM: Homo Sapience

<400> SEQUENCE: 626 aggaggggguc ccgcacuggg agg                                              23

<210> SEQ ID NO 627
<211> LENGTH: 29
<212> TYPE: RNA
<213> ORGANISM: Homo Sapience

<400> SEQUENCE: 627
caacggaauc ccaaaagcag cguugucu                                          29

<210> SEQ ID NO 628
<211> LENGTH: 30
<212> TYPE: RNA
<213> ORGANISM: Homo Sapience

<400> SEQUENCE: 628
ugaggggcag agagcgagac uuuucuauuu                                        30

<210> SEQ ID NO 629
<211> LENGTH: 22
<212> TYPE: RNA
<213> ORGANISM: Homo Sapience

<400> SEQUENCE: 629
ggcgucccag gcggggcgcc gc                                                22

<210> SEQ ID NO 630
<211> LENGTH: 25
<212> TYPE: RNA
<213> ORGANISM: Homo Sapience

<400> SEQUENCE: 630
ggguggggau uuguugcauu acuug                                             25

<210> SEQ ID NO 631
<211> LENGTH: 28
<212> TYPE: RNA
<213> ORGANISM: Homo Sapience

<400> SEQUENCE: 631
guaugguauu gcacuugucc cggccugu                                          28

<210> SEQ ID NO 632
<211> LENGTH: 23
<212> TYPE: RNA
<213> ORGANISM: Homo Sapience

<400> SEQUENCE: 632
aggaaggaag gcagggcccc cgc                                               23

<210> SEQ ID NO 633
<211> LENGTH: 15
<212> TYPE: RNA
<213> ORGANISM: Homo Sapience

<400> SEQUENCE: 633
ggugaggcgg ggggg                                                        15

```
<210> SEQ ID NO 634
<211> LENGTH: 15
<212> TYPE: RNA
<213> ORGANISM: Homo Sapience

<400> SEQUENCE: 634
auauacaggg ggaga                                        15

<210> SEQ ID NO 635
<211> LENGTH: 15
<212> TYPE: RNA
<213> ORGANISM: Homo Sapience

<400> SEQUENCE: 635
auauacaggg ggaga                                        15

<210> SEQ ID NO 636
<211> LENGTH: 21
<212> TYPE: RNA
<213> ORGANISM: Homo Sapience

<400> SEQUENCE: 636
uaggucaccc guuugacuau c                                 21

<210> SEQ ID NO 637
<211> LENGTH: 15
<212> TYPE: RNA
<213> ORGANISM: Homo Sapience

<400> SEQUENCE: 637
ucacaccugc cucgc                                        15

<210> SEQ ID NO 638
<211> LENGTH: 15
<212> TYPE: RNA
<213> ORGANISM: Homo Sapience

<400> SEQUENCE: 638
cgggggcagg ugugu                                        15

<210> SEQ ID NO 639
<211> LENGTH: 15
<212> TYPE: RNA
<213> ORGANISM: Homo Sapience

<400> SEQUENCE: 639
uggcagagcg cuguc                                        15

<210> SEQ ID NO 640
<211> LENGTH: 15
<212> TYPE: RNA
<213> ORGANISM: Homo Sapience

<400> SEQUENCE: 640
cgggaacguc gagac                                        15

<210> SEQ ID NO 641
<211> LENGTH: 15
<212> TYPE: RNA
<213> ORGANISM: Homo Sapience

<400> SEQUENCE: 641
```

```
uagccgggcg uggug                                              15

<210> SEQ ID NO 642
<211> LENGTH: 15
<212> TYPE: RNA
<213> ORGANISM: Homo Sapience

<400> SEQUENCE: 642
cgggcguggu ggugg                                              15

<210> SEQ ID NO 643
<211> LENGTH: 15
<212> TYPE: RNA
<213> ORGANISM: Homo Sapience

<400> SEQUENCE: 643
acugcacucc agccu                                              15

<210> SEQ ID NO 644
<211> LENGTH: 20
<212> TYPE: RNA
<213> ORGANISM: Homo Sapience

<400> SEQUENCE: 644
gggggccgau acacuguacg                                         20

<210> SEQ ID NO 645
<211> LENGTH: 18
<212> TYPE: RNA
<213> ORGANISM: Homo Sapience

<400> SEQUENCE: 645
cuccuggggc ccgcacuc                                           18

<210> SEQ ID NO 646
<211> LENGTH: 15
<212> TYPE: RNA
<213> ORGANISM: Homo Sapience

<400> SEQUENCE: 646
cccgcgggac gcgcc                                              15

<210> SEQ ID NO 647
<211> LENGTH: 15
<212> TYPE: RNA
<213> ORGANISM: Homo Sapience

<400> SEQUENCE: 647
acugcaguga aggca                                              15

<210> SEQ ID NO 648
<211> LENGTH: 22
<212> TYPE: RNA
<213> ORGANISM: Homo Sapience

<400> SEQUENCE: 648
gcuacaacac aggacccggg cg                                      22

<210> SEQ ID NO 649
<211> LENGTH: 17
<212> TYPE: RNA
<213> ORGANISM: Homo Sapience

<400> SEQUENCE: 649
```

```
ccggccgccg gcuccgc                                                    17

<210> SEQ ID NO 650
<211> LENGTH: 19
<212> TYPE: RNA
<213> ORGANISM: Homo Sapience

<400> SEQUENCE: 650
cgcaggggcc gggugcuca                                                  19

<210> SEQ ID NO 651
<211> LENGTH: 15
<212> TYPE: RNA
<213> ORGANISM: Homo Sapience

<400> SEQUENCE: 651
cgcggcgggg gcggc                                                      15

<210> SEQ ID NO 652
<211> LENGTH: 16
<212> TYPE: RNA
<213> ORGANISM: Homo Sapience

<400> SEQUENCE: 652
agccccugcc caccgc                                                     16

<210> SEQ ID NO 653
<211> LENGTH: 15
<212> TYPE: RNA
<213> ORGANISM: Homo Sapience

<400> SEQUENCE: 653
aguucagcag gaaca                                                      15

<210> SEQ ID NO 654
<211> LENGTH: 15
<212> TYPE: RNA
<213> ORGANISM: Homo Sapience

<400> SEQUENCE: 654
agcagaggca gagag                                                      15

<210> SEQ ID NO 655
<211> LENGTH: 15
<212> TYPE: RNA
<213> ORGANISM: Homo Sapience

<400> SEQUENCE: 655
ggccucucgg gaacu                                                      15

<210> SEQ ID NO 656
<211> LENGTH: 15
<212> TYPE: RNA
<213> ORGANISM: Homo Sapience

<400> SEQUENCE: 656
gaggguuggg uggag                                                      15

<210> SEQ ID NO 657
<211> LENGTH: 15
<212> TYPE: RNA
<213> ORGANISM: Homo Sapience
```

```
<400> SEQUENCE: 657
cuagcaccau uugaa                                              15

<210> SEQ ID NO 658
<211> LENGTH: 17
<212> TYPE: RNA
<213> ORGANISM: Homo Sapience

<400> SEQUENCE: 658
acugguggaa gggccuu                                            17

<210> SEQ ID NO 659
<211> LENGTH: 16
<212> TYPE: RNA
<213> ORGANISM: Homo Sapience

<400> SEQUENCE: 659 gaagggagu ugggag                                              16

<210> SEQ ID NO 660
<211> LENGTH: 18
<212> TYPE: RNA
<213> ORGANISM: Homo Sapience

<400> SEQUENCE: 660
ccugcagaga ggaagccc                                           18

<210> SEQ ID NO 661
<211> LENGTH: 16
<212> TYPE: RNA
<213> ORGANISM: Homo Sapience

<400> SEQUENCE: 661
uagggaguag aagggu                                             16

<210> SEQ ID NO 662
<211> LENGTH: 15
<212> TYPE: RNA
<213> ORGANISM: Homo Sapience

<400> SEQUENCE: 662
gcugggcggg gcgcg                                              15

<210> SEQ ID NO 663
<211> LENGTH: 15
<212> TYPE: RNA
<213> ORGANISM: Homo Sapience

<400> SEQUENCE: 663
gccccgggaa agcgu                                              15

<210> SEQ ID NO 664
<211> LENGTH: 21
<212> TYPE: RNA
<213> ORGANISM: Homo Sapience

<400> SEQUENCE: 664
aagaaggcgg ucggucugcg g                                       21

<210> SEQ ID NO 665
<211> LENGTH: 20
<212> TYPE: RNA
<213> ORGANISM: Homo Sapience
```

-continued

<400> SEQUENCE: 665
agcucugcug cucacuggca                    20

<210> SEQ ID NO 666
<211> LENGTH: 15
<212> TYPE: RNA
<213> ORGANISM: Homo Sapience

<400> SEQUENCE: 666
cgcgccgggc ccggg                          15

<210> SEQ ID NO 667
<211> LENGTH: 15
<212> TYPE: RNA
<213> ORGANISM: Homo Sapience

<400> SEQUENCE: 667
gcaggcucgg aaagg                          15

<210> SEQ ID NO 668
<211> LENGTH: 15
<212> TYPE: RNA
<213> ORGANISM: Homo Sapience

<400> SEQUENCE: 668
cuucucuucc cgguu                          15

<210> SEQ ID NO 669
<211> LENGTH: 15
<212> TYPE: RNA
<213> ORGANISM: Homo Sapience

<400> SEQUENCE: 669
gaaaagcugg guuga                          15

<210> SEQ ID NO 670
<211> LENGTH: 19
<212> TYPE: RNA
<213> ORGANISM: Homo Sapience

<400> SEQUENCE: 670 gggggggcagg aggggcuca                     19

<210> SEQ ID NO 671
<211> LENGTH: 15
<212> TYPE: RNA
<213> ORGANISM: Homo Sapience

<400> SEQUENCE: 671
gcuaucugug auuga                          15

<210> SEQ ID NO 672
<211> LENGTH: 17
<212> TYPE: RNA
<213> ORGANISM: Homo Sapience

<400> SEQUENCE: 672
gcccugaacg aggguc                         17

<210> SEQ ID NO 673
<211> LENGTH: 16
<212> TYPE: RNA

```
<213> ORGANISM: Homo Sapience

<400> SEQUENCE: 673
gggcauuuca ugaugc                                          16

<210> SEQ ID NO 674
<211> LENGTH: 15
<212> TYPE: RNA
<213> ORGANISM: Homo Sapience

<400> SEQUENCE: 674
gggcugggcu gggcu                                           15

<210> SEQ ID NO 675
<211> LENGTH: 18
<212> TYPE: RNA
<213> ORGANISM: Homo Sapience

<400> SEQUENCE: 675
gcacgggagc ucagguga                                        18

<210> SEQ ID NO 676
<211> LENGTH: 15
<212> TYPE: RNA
<213> ORGANISM: Homo Sapience

<400> SEQUENCE: 676
ggcggcggug guggg                                           15

<210> SEQ ID NO 677
<211> LENGTH: 16
<212> TYPE: RNA
<213> ORGANISM: Homo Sapience

<400> SEQUENCE: 677
gcuggaggug ugagga                                          16

<210> SEQ ID NO 678
<211> LENGTH: 15
<212> TYPE: RNA
<213> ORGANISM: Homo Sapience

<400> SEQUENCE: 678
uggcgggugc ggggg                                           15

<210> SEQ ID NO 679
<211> LENGTH: 19
<212> TYPE: RNA
<213> ORGANISM: Homo Sapience

<400> SEQUENCE: 679
ugaggauaug gcagggaag                                       19

<210> SEQ ID NO 680
<211> LENGTH: 15
<212> TYPE: RNA
<213> ORGANISM: Homo Sapience

<400> SEQUENCE: 680
agaguguggu caggc                                           15

<210> SEQ ID NO 681
<211> LENGTH: 19
```

```
<212> TYPE: RNA
<213> ORGANISM: Homo Sapience

<400> SEQUENCE: 681
guggguuggg gcgggcucu                                              19

<210> SEQ ID NO 682
<211> LENGTH: 15
<212> TYPE: RNA
<213> ORGANISM: Homo Sapience

<400> SEQUENCE: 682
gcuccccgcg ccccc                                                  15

<210> SEQ ID NO 683
<211> LENGTH: 15
<212> TYPE: RNA
<213> ORGANISM: Homo Sapience

<400> SEQUENCE: 683
ccccacuccu gguac                                                  15

<210> SEQ ID NO 684
<211> LENGTH: 15
<212> TYPE: RNA
<213> ORGANISM: Homo Sapience

<400> SEQUENCE: 684
aggaggagga ggcag                                                  15

<210> SEQ ID NO 685
<211> LENGTH: 15
<212> TYPE: RNA
<213> ORGANISM: Homo Sapience

<400> SEQUENCE: 685
ggugggcuuc ccgga                                                  15

<210> SEQ ID NO 686
<211> LENGTH: 15
<212> TYPE: RNA
<213> ORGANISM: Homo Sapience

<400> SEQUENCE: 686
gaggcugaag gaaga                                                  15

<210> SEQ ID NO 687
<211> LENGTH: 15
<212> TYPE: RNA
<213> ORGANISM: Homo Sapience

<400> SEQUENCE: 687
aaagcugggc ugaga                                                  15

<210> SEQ ID NO 688
<211> LENGTH: 15
<212> TYPE: RNA
<213> ORGANISM: Homo Sapience

<400> SEQUENCE: 688
aggcuggagu gagcg                                                  15

<210> SEQ ID NO 689
```

```
<211> LENGTH: 20
<212> TYPE: RNA
<213> ORGANISM: Homo Sapience

<400> SEQUENCE: 689
acaggagugg ggguggaca                                            20

<210> SEQ ID NO 690
<211> LENGTH: 15
<212> TYPE: RNA
<213> ORGANISM: Homo Sapience

<400> SEQUENCE: 690
guuggaggcg ugggu                                                15

<210> SEQ ID NO 691
<211> LENGTH: 19
<212> TYPE: RNA
<213> ORGANISM: Homo Sapience

<400> SEQUENCE: 691
cagggcuggc agugacaug                                            19

<210> SEQ ID NO 692
<211> LENGTH: 15
<212> TYPE: RNA
<213> ORGANISM: Homo Sapience

<400> SEQUENCE: 692
cuuggucuag gggua                                                15

<210> SEQ ID NO 693
<211> LENGTH: 17
<212> TYPE: RNA
<213> ORGANISM: Homo Sapience

<400> SEQUENCE: 693
ccggggcugc gcgaggc                                              17

<210> SEQ ID NO 694
<211> LENGTH: 15
<212> TYPE: RNA
<213> ORGANISM: Homo Sapience

<400> SEQUENCE: 694
uccgagucac ggcac                                                15

<210> SEQ ID NO 695
<211> LENGTH: 15
<212> TYPE: RNA
<213> ORGANISM: Homo Sapience

<400> SEQUENCE: 695
acccaggagg cggag                                                15

<210> SEQ ID NO 696
<211> LENGTH: 15
<212> TYPE: RNA
<213> ORGANISM: Homo Sapience

<400> SEQUENCE: 696
ugcgggccgg cgggg                                                15
```

```
<210> SEQ ID NO 697
<211> LENGTH: 15
<212> TYPE: RNA
<213> ORGANISM: Homo Sapience

<400> SEQUENCE: 697
ggcgggagaa gcccc                                                    15

<210> SEQ ID NO 698
<211> LENGTH: 15
<212> TYPE: RNA
<213> ORGANISM: Homo Sapience

<400> SEQUENCE: 698
gaggcaccgc cugcc                                                    15

<210> SEQ ID NO 699
<211> LENGTH: 15
<212> TYPE: RNA
<213> ORGANISM: Homo Sapience

<400> SEQUENCE: 699 guaggggcg ggcuc                                                     15

<210> SEQ ID NO 700
<211> LENGTH: 15
<212> TYPE: RNA
<213> ORGANISM: Homo Sapience

<400> SEQUENCE: 700 cagggcugg gcgcg                                                     15

<210> SEQ ID NO 701
<211> LENGTH: 18
<212> TYPE: RNA
<213> ORGANISM: Homo Sapience

<400> SEQUENCE: 701 gcgugggag cugguccu                                                  18

<210> SEQ ID NO 702
<211> LENGTH: 15
<212> TYPE: RNA
<213> ORGANISM: Homo Sapience

<400> SEQUENCE: 702
aucagcgugc acuuc                                                    15

<210> SEQ ID NO 703
<211> LENGTH: 20
<212> TYPE: RNA
<213> ORGANISM: Homo Sapience

<400> SEQUENCE: 703
ugggccaggg agcagcuggu                                               20

<210> SEQ ID NO 704
<211> LENGTH: 20
<212> TYPE: RNA
<213> ORGANISM: Homo Sapience

<400> SEQUENCE: 704
caccggggau ggcagagggu                                               20
```

```
<210> SEQ ID NO 705
<211> LENGTH: 17
<212> TYPE: RNA
<213> ORGANISM: Homo Sapience

<400> SEQUENCE: 705
gugagugugg auccugg                                                17

<210> SEQ ID NO 706
<211> LENGTH: 21
<212> TYPE: RNA
<213> ORGANISM: Homo Sapience

<400> SEQUENCE: 706
uccaggcagg agccggacug g                                           21

<210> SEQ ID NO 707
<211> LENGTH: 15
<212> TYPE: RNA
<213> ORGANISM: Homo Sapience

<400> SEQUENCE: 707 ggaggggca ggcuc                                                   15

<210> SEQ ID NO 708
<211> LENGTH: 21
<212> TYPE: RNA
<213> ORGANISM: Homo Sapience

<400> SEQUENCE: 708
cagcccuccu cccgcaccca a                                           21

<210> SEQ ID NO 709
<211> LENGTH: 16
<212> TYPE: RNA
<213> ORGANISM: Homo Sapience

<400> SEQUENCE: 709
aggcgaggcu gggcug                                                 16

<210> SEQ ID NO 710
<211> LENGTH: 21
<212> TYPE: RNA
<213> ORGANISM: Homo Sapience

<400> SEQUENCE: 710
aggaggcagu gggcgagcag g                                           21

<210> SEQ ID NO 711
<211> LENGTH: 21
<212> TYPE: RNA
<213> ORGANISM: Homo Sapience

<400> SEQUENCE: 711
agcggggagg aagugggcgc u                                           21

<210> SEQ ID NO 712
<211> LENGTH: 17
<212> TYPE: RNA
<213> ORGANISM: Homo Sapience

<400> SEQUENCE: 712
agcccgcccc agccgag                                                17
```

```
<210> SEQ ID NO 713
<211> LENGTH: 16
<212> TYPE: RNA
<213> ORGANISM: Homo Sapience

<400> SEQUENCE: 713
ggagccccgg cgcggg                                                        16

<210> SEQ ID NO 714
<211> LENGTH: 18
<212> TYPE: RNA
<213> ORGANISM: Homo Sapience

<400> SEQUENCE: 714
gagcaaggcg gcaucucu                                                      18

<210> SEQ ID NO 715
<211> LENGTH: 15
<212> TYPE: RNA
<213> ORGANISM: Homo Sapience

<400> SEQUENCE: 715
gggugagggc aggug                                                         15

<210> SEQ ID NO 716
<211> LENGTH: 17
<212> TYPE: RNA
<213> ORGANISM: Homo Sapience

<400> SEQUENCE: 716
ggcaggaggg cugugcc                                                       17

<210> SEQ ID NO 717
<211> LENGTH: 16
<212> TYPE: RNA
<213> ORGANISM: Homo Sapience

<400> SEQUENCE: 717
uggggaaggc gucagu                                                        16

<210> SEQ ID NO 718
<211> LENGTH: 23
<212> TYPE: RNA
<213> ORGANISM: Homo Sapience

<400> SEQUENCE: 718
agggccagag gagccuggag ugg                                                23

<210> SEQ ID NO 719
<211> LENGTH: 19
<212> TYPE: RNA
<213> ORGANISM: Homo Sapience

<400> SEQUENCE: 719
auagugggaa gcuggcaga                                                     19

<210> SEQ ID NO 720
<211> LENGTH: 22
<212> TYPE: RNA
<213> ORGANISM: Homo Sapience

<400> SEQUENCE: 720
```

```
ugggagggga gaggcagcaa gc                                         22

<210> SEQ ID NO 721
<211> LENGTH: 20
<212> TYPE: RNA
<213> ORGANISM: Homo Sapience

<400> SEQUENCE: 721 gcuggggcc acaugagugu                                             20

<210> SEQ ID NO 722
<211> LENGTH: 15
<212> TYPE: RNA
<213> ORGANISM: Homo Sapience

<400> SEQUENCE: 722
gggaggagga gcgga                                                 15

<210> SEQ ID NO 723
<211> LENGTH: 16
<212> TYPE: RNA
<213> ORGANISM: Homo Sapience

<400> SEQUENCE: 723
gcuguccgga gggguc                                                16

<210> SEQ ID NO 724
<211> LENGTH: 17
<212> TYPE: RNA
<213> ORGANISM: Homo Sapience

<400> SEQUENCE: 724
ucgggcggag gugguug                                               17

<210> SEQ ID NO 725
<211> LENGTH: 15
<212> TYPE: RNA
<213> ORGANISM: Homo Sapience

<400> SEQUENCE: 725
gaagggaaag uugaa                                                 15

<210> SEQ ID NO 726
<211> LENGTH: 15
<212> TYPE: RNA
<213> ORGANISM: Homo Sapience

<400> SEQUENCE: 726 gggcggggg cggcg                                                  15

<210> SEQ ID NO 727
<211> LENGTH: 19
<212> TYPE: RNA
<213> ORGANISM: Homo Sapience

<400> SEQUENCE: 727
aauuuuagau cuggucugc                                             19

<210> SEQ ID NO 728
<211> LENGTH: 21
<212> TYPE: RNA
<213> ORGANISM: Homo Sapience

<400> SEQUENCE: 728
```
cccgguguug gggcgcgucu g               21

<210> SEQ ID NO 729
<211> LENGTH: 15
<212> TYPE: RNA
<213> ORGANISM: Homo Sapience

<400> SEQUENCE: 729
gcccacugcc ccgcg                      15

<210> SEQ ID NO 730
<211> LENGTH: 15
<212> TYPE: RNA
<213> ORGANISM: Homo Sapience

<400> SEQUENCE: 730
cggugagcgc ucgcu                      15

<210> SEQ ID NO 731
<211> LENGTH: 15
<212> TYPE: RNA
<213> ORGANISM: Homo Sapience

<400> SEQUENCE: 731
ggugaggcgg ggggg                      15

<210> SEQ ID NO 732
<211> LENGTH: 18
<212> TYPE: RNA
<213> ORGANISM: Homo Sapience

<400> SEQUENCE: 732
agggagugca gggcaggg                   18

<210> SEQ ID NO 733
<211> LENGTH: 15
<212> TYPE: RNA
<213> ORGANISM: Homo Sapience

<400> SEQUENCE: 733
gagggaguaa gagcc                      15

<210> SEQ ID NO 734
<211> LENGTH: 16
<212> TYPE: RNA
<213> ORGANISM: Homo Sapience

<400> SEQUENCE: 734
ugcuggugau gcuuuc                     16

<210> SEQ ID NO 735
<211> LENGTH: 15
<212> TYPE: RNA
<213> ORGANISM: Homo Sapience

<400> SEQUENCE: 735
ugaagcgggg gggcg                      15

<210> SEQ ID NO 736
<211> LENGTH: 16
<212> TYPE: RNA
<213> ORGANISM: Homo Sapience

```
<400> SEQUENCE: 736
aaggaagggg gaggag                                                    16

<210> SEQ ID NO 737
<211> LENGTH: 20
<212> TYPE: RNA
<213> ORGANISM: Homo Sapience

<400> SEQUENCE: 737
ggcuggucag augggagugg                                                20

<210> SEQ ID NO 738
<211> LENGTH: 17
<212> TYPE: RNA
<213> ORGANISM: Homo Sapience

<400> SEQUENCE: 738
ugcaggggca ggccagc                                                   17

<210> SEQ ID NO 739
<211> LENGTH: 20
<212> TYPE: RNA
<213> ORGANISM: Homo Sapience

<400> SEQUENCE: 739
gggggucccc ggugcucgga                                                20

<210> SEQ ID NO 740
<211> LENGTH: 15
<212> TYPE: RNA
<213> ORGANISM: Homo Sapience

<400> SEQUENCE: 740
gauuacaggc augag                                                     15

<210> SEQ ID NO 741
<211> LENGTH: 16
<212> TYPE: RNA
<213> ORGANISM: Homo Sapience

<400> SEQUENCE: 741
agacacauuu ggagag                                                    16

<210> SEQ ID NO 742
<211> LENGTH: 20
<212> TYPE: RNA
<213> ORGANISM: Homo Sapience

<400> SEQUENCE: 742
cagcagggga gagagaggag                                                20

<210> SEQ ID NO 743
<211> LENGTH: 20
<212> TYPE: RNA
<213> ORGANISM: Homo Sapience

<400> SEQUENCE: 743
cugcaggcag aagugggggcu                                               20

<210> SEQ ID NO 744
<211> LENGTH: 16
<212> TYPE: RNA
<213> ORGANISM: Homo Sapience
```

```
<400> SEQUENCE: 744
uuggagggug uggaag                                              16

<210> SEQ ID NO 745
<211> LENGTH: 15
<212> TYPE: RNA
<213> ORGANISM: Homo Sapience

<400> SEQUENCE: 745 uguuuccug guggc                                                15

<210> SEQ ID NO 746
<211> LENGTH: 15
<212> TYPE: RNA
<213> ORGANISM: Homo Sapience

<400> SEQUENCE: 746
cuucugagcc caggu                                               15

<210> SEQ ID NO 747
<211> LENGTH: 20
<212> TYPE: RNA
<213> ORGANISM: Homo Sapience

<400> SEQUENCE: 747
cccagucuca uuccucauc                                           20

<210> SEQ ID NO 748
<211> LENGTH: 15
<212> TYPE: RNA
<213> ORGANISM: Homo Sapience

<400> SEQUENCE: 748
cgcggcgggc guggg                                               15

<210> SEQ ID NO 749
<211> LENGTH: 16
<212> TYPE: RNA
<213> ORGANISM: Homo Sapience

<400> SEQUENCE: 749
ggacccaggg agagac                                              16

<210> SEQ ID NO 750
<211> LENGTH: 15
<212> TYPE: RNA
<213> ORGANISM: Homo Sapience

<400> SEQUENCE: 750
ugcggggcua gggcu                                               15

<210> SEQ ID NO 751
<211> LENGTH: 17
<212> TYPE: RNA
<213> ORGANISM: Homo Sapience

<400> SEQUENCE: 751
uccuagucac ggcacca                                             17

<210> SEQ ID NO 752
<211> LENGTH: 16
<212> TYPE: RNA
```

<213> ORGANISM: Homo Sapience

<400> SEQUENCE: 752
gugaacgggc gccauc                                                    16

<210> SEQ ID NO 753
<211> LENGTH: 21
<212> TYPE: RNA
<213> ORGANISM: Homo Sapience

<400> SEQUENCE: 753
gugagucagg guggggcugg c                                              21

<210> SEQ ID NO 754
<211> LENGTH: 15
<212> TYPE: RNA
<213> ORGANISM: Homo Sapience

<400> SEQUENCE: 754
gcugcagugg gggag                                                     15

<210> SEQ ID NO 755
<211> LENGTH: 15
<212> TYPE: RNA
<213> ORGANISM: Homo Sapience

<400> SEQUENCE: 755
ggauuuuugg agcag                                                     15

<210> SEQ ID NO 756
<211> LENGTH: 15
<212> TYPE: RNA
<213> ORGANISM: Homo Sapience

<400> SEQUENCE: 756
ggugggagga uugcu                                                     15

<210> SEQ ID NO 757
<211> LENGTH: 20
<212> TYPE: RNA
<213> ORGANISM: Homo Sapience

<400> SEQUENCE: 757
auauagggau uggagccgug                                                20

<210> SEQ ID NO 758
<211> LENGTH: 15
<212> TYPE: RNA
<213> ORGANISM: Homo Sapience

<400> SEQUENCE: 758
gaggagggag ggagg                                                     15

<210> SEQ ID NO 759
<211> LENGTH: 19
<212> TYPE: RNA
<213> ORGANISM: Homo Sapience

<400> SEQUENCE: 759
gguacaggcc uggggaca                                                  19

<210> SEQ ID NO 760
<211> LENGTH: 15

```
<212> TYPE: RNA
<213> ORGANISM: Homo Sapience

<400> SEQUENCE: 760
ugggaggggc ccuca                                              15

<210> SEQ ID NO 761
<211> LENGTH: 15
<212> TYPE: RNA
<213> ORGANISM: Homo Sapience

<400> SEQUENCE: 761
caacggaauc ccaaa                                              15

<210> SEQ ID NO 762
<211> LENGTH: 15
<212> TYPE: RNA
<213> ORGANISM: Homo Sapience

<400> SEQUENCE: 762
cagagagcga gacuu                                              15

<210> SEQ ID NO 763
<211> LENGTH: 15
<212> TYPE: RNA
<213> ORGANISM: Homo Sapience

<400> SEQUENCE: 763
gcgccgcggg accgc                                              15

<210> SEQ ID NO 764
<211> LENGTH: 20
<212> TYPE: RNA
<213> ORGANISM: Homo Sapience

<400> SEQUENCE: 764 gggugggggau uuguugcauu                                        20

<210> SEQ ID NO 765
<211> LENGTH: 15
<212> TYPE: RNA
<213> ORGANISM: Homo Sapience

<400> SEQUENCE: 765
uauugcacuu guccc                                              15

<210> SEQ ID NO 766
<211> LENGTH: 15
<212> TYPE: RNA
<213> ORGANISM: Homo Sapience

<400> SEQUENCE: 766
gggcccccgc ucccc                                              15
```